US012233118B2

(12) United States Patent
Poolman et al.

(10) Patent No.: US 12,233,118 B2
(45) Date of Patent: Feb. 25, 2025

(54) MULTIVALENT VACCINE COMPOSITIONS AND USES THEREOF

(71) Applicant: Janssen Pharmaceuticals, Inc., Titusville, NJ (US)

(72) Inventors: Jan Theunis Poolman, Vogelenzang (NL); Kellen Cristhina Fae, Oegstgeest (NL); Michal Sarnecki, Basel (CH); Jeroen Geurtsen, Vleuten (NL); Darren Robert Abbanat, Cornwall, NY (US); Bart Gustaaf M. Spiessens, Bierbeek (BE); Frank Germaine F. Struyf, Bierbeek (BE)

(73) Assignee: Janssen Pharmaceuticals, Inc., Titusville, NJ (US)

( * ) Notice: Subject to any disclaimer, the term of this patent is extended or adjusted under 35 U.S.C. 154(b) by 311 days.

(21) Appl. No.: 17/478,584

(22) Filed: Sep. 17, 2021

(65) Prior Publication Data

US 2022/0088165 A1 Mar. 24, 2022

Related U.S. Application Data

(60) Provisional application No. 63/079,734, filed on Sep. 17, 2020, provisional application No. 63/191,471, filed on May 21, 2021.

(30) Foreign Application Priority Data

Feb. 2, 2021 (EP) .................................... 21154782

(51) Int. Cl.

| | |
|---|---|
| *A61K 47/64* | (2017.01) |
| *A61K 31/739* | (2006.01) |
| *A61K 39/00* | (2006.01) |
| *A61K 39/108* | (2006.01) |

(52) U.S. Cl.

CPC ........ *A61K 39/0258* (2013.01); *A61K 31/739* (2013.01); *A61K 47/6415* (2017.08); *A61K 47/646* (2017.08); *A61K 2039/55583* (2013.01); *A61K 2039/70* (2013.01)

(58) Field of Classification Search

None

See application file for complete search history.

(56) References Cited

U.S. PATENT DOCUMENTS

| | | | | |
|---|---|---|---|---|
| 3,700,612 | A | 10/1972 | Fath | |
| 5,057,540 | A | 10/1991 | Kensil | |
| 5,370,872 | A | 12/1994 | Cryz | |
| 6,331,415 | B1 | 12/2001 | Cabilly | |
| 6,858,211 | B1 | 2/2005 | Szu | |
| 9,700,612 | B2 | 7/2017 | Kowarik | |
| 9,849,169 | B2 | 12/2017 | Nagy | |
| 10,150,952 | B2 | 12/2018 | Haas | |
| 10,159,751 | B2 | 12/2018 | Labovitiadi | |
| 10,206,992 | B2 | 2/2019 | Nagy | |
| 10,441,647 | B2 | 10/2019 | Kowarik | |
| 10,525,145 | B2 | 1/2020 | Labovitiadi | |
| 10,577,592 | B2 | 3/2020 | Haas | |
| 10,583,185 | B2 | 3/2020 | Poolman | |
| 10,940,191 | B2 | 3/2021 | Nagy | |
| 10,940,192 | B2 | 3/2021 | Kowarik | |
| 11,015,177 | B2 | 5/2021 | Haas | |
| 11,033,633 | B2 | 6/2021 | Labovitiadi | |
| 11,446,370 | B2 | 9/2022 | Geurtsen | |
| 2014/0038296 | A1 | 2/2014 | Palsson | |
| 2015/0238588 | A1 | 8/2015 | Kowarik | |
| 2018/0002679 | A1 | 1/2018 | Haas | |
| 2019/0078064 | A1 | 3/2019 | Haas | |
| 2020/0181586 | A1 | 6/2020 | Haas | |
| 2020/0316184 | A1 | 10/2020 | Geurtsen | |
| 2020/0353073 | A1 | 11/2020 | Geurtsen | |
| 2021/0004617 | A1 | 1/2021 | Gouraud | |
| 2021/0154286 | A1 | 5/2021 | Kowarik | |
| 2021/0275681 | A1* | 9/2021 | Labovitiadi | A61K 47/646 |
| 2022/0323576 | A1* | 10/2022 | Geurtsen | A61P 37/04 |
| 2023/0118878 | A1 | 4/2023 | Geurtsen | |

FOREIGN PATENT DOCUMENTS

| | | | |
|---|---|---|---|
| CN | 1554759 | | 12/2004 |
| CN | 101983070 | | 3/2011 |
| CN | 105008539 | | 10/2015 |
| CN | 105828839 | | 8/2016 |
| EP | 2289911 | | 3/2011 |
| EP | 3941516 | A1 | 1/2022 |
| GB | 2220211 | A | 1/1990 |

(Continued)

OTHER PUBLICATIONS

DebRoy et al., "Comparison of O-Antigen Gene Clusters of All O-Serogroups of *Escherichia coli* and Proposal for Adopting a New Nomenclature for O-Typing," PLoS ONE 11(1): e0147434, Jan. 29, 2016, 13 pages.

Office Action issued Feb. 3, 2023 in corresponding Korean Patent Application No. 10-2019-7011812, 8 pages, with English Translation.

DebRoy C, Fratamico PM, Yan X, Baranzoni G, Liu Y, et al. (2016) Correction: Comparison of O-Antigen Gene Clusters of All O-Serogroups of *Escherichia coli* and Proposal for Adopting a New Nomenclature for O-Typing. PLOS ONE 11(4): e0154551, Published: Apr. 27, 2016, 5 pages.

Office Action issued Apr. 22, 2021 in corresponding Russian Patent Application No. 2019144146/10(085375), 9 pages, with English Translation.

Pinayev et al., "The Cell Cultures", Information Gazette, 2010, Issue 26, St. Petersburg, 61 pages.

(Continued)

*Primary Examiner* — S. Devi

(74) *Attorney, Agent, or Firm* — Ice Miller, LLP

(57) ABSTRACT

Compositions and methods are described for inducing an immune response against extra-intestinal pathogenic *Escherichia coli* (ExPEC) to thereby provide immune protection against diseases associated with ExPEC. In particular, compositions and methods are described for using conjugates of *E. coli* polysaccharide antigen O75 covalently bound to a carrier protein for the prevention of invasive ExPEC disease.

25 Claims, 10 Drawing Sheets

Specification includes a Sequence Listing.

(56) References Cited

FOREIGN PATENT DOCUMENTS

| | | | |
|---|---|---|---|
| JP | S62500173 | | 1/1987 |
| JP | H10500102 | A | 1/1998 |
| JP | 2004515450 | A | 5/2004 |
| JP | 2007256214 | | 10/2007 |
| JP | 2008539743 | A | 11/2008 |
| JP | 2011514155 | | 5/2011 |
| JP | 4791866 | B2 | 10/2011 |
| JP | 2012525376 | A | 10/2012 |
| JP | 2017507178 | | 3/2017 |
| JP | 2018525423 | A | 9/2018 |
| RU | 2189253 | C1 | 9/2002 |
| WO | 8601806 | A1 | 3/1986 |
| WO | 86001806 | | 3/1986 |
| WO | 9303765 | A1 | 3/1993 |
| WO | 9522563 | | 8/1995 |
| WO | 9522563 | A1 | 8/1995 |
| WO | 9523256 | | 8/1995 |
| WO | 2001078787 | A2 | 10/2001 |
| WO | 2003074679 | | 9/2003 |
| WO | 2003074687 | A1 | 9/2003 |
| WO | 2004078209 | A1 | 9/2004 |
| WO | 2006119987 | A2 | 11/2006 |
| WO | 2007109812 | A2 | 9/2007 |
| WO | 2007109813 | A1 | 9/2007 |
| WO | 2009036379 | | 3/2009 |
| WO | 2009089396 | A2 | 7/2009 |
| WO | 2009104074 | A2 | 8/2009 |
| WO | 2010105256 | | 9/2010 |
| WO | 2010125565 | A2 | 11/2010 |
| WO | 2011062615 | | 5/2011 |
| WO | 2012009568 | | 1/2012 |
| WO | 2012078482 | A1 | 6/2012 |
| WO | 2013034664 | A1 | 3/2013 |
| WO | 2014037585 | A1 | 3/2014 |
| WO | 2014057109 | A1 | 4/2014 |
| WO | 2014072405 | | 5/2014 |
| WO | 2014102265 | A1 | 7/2014 |
| WO | 2014111516 | A1 | 7/2014 |
| WO | 2015052344 | | 4/2015 |
| WO | 2015068129 | | 5/2015 |
| WO | 2015117711 | A1 | 8/2015 |
| WO | 2015124769 | A1 | 8/2015 |
| WO | 2016107818 | A1 | 7/2016 |
| WO | 2016107819 | A1 | 7/2016 |
| WO | 2017035181 | A1 | 3/2017 |
| WO | 2018077853 | A1 | 5/2018 |
| WO | 2019016187 | A1 | 1/2019 |
| WO | 2020039359 | | 2/2020 |
| WO | 2020191082 | | 9/2020 |
| WO | 2020191088 | | 9/2020 |

OTHER PUBLICATIONS

Yakubke et al., "Amino acids, peptides, proteins", MTR Publishers, 1985, 456 pages.
Wacker, M., et al., "Substrate specificity of bacterial oliogsaccharyltransferase suggests a common transfer mechanism for the bacterial and eukaryotic systems," PNAS, vol. 103, No. 18, pp. 7088-7093, May 2, 2006.
International Search Report issued Jun. 12, 2020 in PCT/US2020/023404, 5 pages.
Written Opinion issued Jun. 12, 2020 in PCT/US2020/023404, 6 pages.
Van Den Dobbelsteen Germie P J M et al, "Immunogenicity and safety of a tetravalent*E. coli*O-antigen bioconjugate vaccine in animal models", Vaccine, Elsevier, Amsterdam, NL, (Jul. 6, 2016), vol. 34, No. 35, doi:10.1016/J.Vaccine.2016.06.067, ISSN 0264-410X, pp. 4152-4160, XP029644969.
Ihssen Julian et al, "Production of glycoprotein vaccines in *Escherichia coli*", Microbial Cell Factories,, (Aug. 11, 2010), vol. 9, No. 1, doi:10.1186/1475-2859-9-61, ISSN 1475-2859, p. 61, XP021077209.
Roland Stenutz et al, "The structures of*Escherichia coli* O-polysaccharide antigens", FEMS Microbiology Reviews, Elsevier, Amsterdam; NL, vol. 30, doi:10.1111/J.1574-6976.2006.00016.X, ISSN 0168-6445, (Jan. 1, 2006), pp. 382-403, (Feb. 9, 2006), XP007921666.
ClinicalTrials.gov archive, "History of Changes for Study: NCT03819049, A Study of Three Different Doses of VAC52416 (ExPEC10V) in Adults Aged 60 to 85 Years in Stable Health", https://clinicaltrials.gov/ct2/history/NCT03819049, Aug. 6, 2019 (v6), 6 pages.
Jansson et al., "Sturctural Studies of the O-Antigen Polysaccharide of *Escherichia coli* O4", Carbohydrate Research, 134 (1984) 283-291.
"Typhoid Vi Polysaccharide Vaccine Typhim VI," Sanofi Pasteur Inc., vol. 3., pp. 1-26 (Mar. 2014).
A. Cross et al, "Safety and Immunogenicity of a Polyvalent *Escherichia coli* Vaccine in Human Volunteers", Journal of Infectious Diseases. JID, Chicago, IL., (Oct. 1, 1994), vol. 170, No. 4, doi:10.1093/infdis/170.4.834, ISSN 0022-1899, pp. 834-840, XP055311603.
Amor et al., "Distribution of core oligosaccharide types in lipopolysaccharides from *Escherichia coli*," Infect. Immun., vol. 68, No. 3, pp. 1116-1124 (2000).
Banerjee et al., "A new clone sweeps clean: the enigmatic emergence of *Escherichia coli* sequence type 131," Antimicrob Agents Chemother. vol. 58, No. 9, pp. 4997-5004 (2014).
Blanco et al., "Virulence factors and 0 groups of *Escherichia coli* isolates from patients with acute pyelonephritis, cystitis and asymptomatic bacteriuria," Eur. J. Epidemiol., vol. 12, No. 2, pp. 191-198 (1996).
Blanco et al., "Molecular epidemiology of *Escherichia coli* producing extended-spectrum {beta}-lactamases in Lugo (Spain): dissemination of clone O25b:H4-ST131 producing CTX-M-15," J. Antimicrob. Chemother., vol. 63, pp. 1135-1141 (2009).
Bowie etal. (Science, 1990, 247:1306-1310).
Burgess et al. (J. Cell Biol. 111:2129-2138, 1990).
Clermont et al, "The CTX-M-15-producing *Escherichia coli* diffusing clone belongs to a highly virulent B2 phylogenetic subgroup," J. Antimicrob. Chemother., vol. 61, No. 5, pp. 1024-1028 (2008).
Clermont et al., "Rapid Detection of the O25b-ST131 clone of *Escherichia coil* encompassing the CTX-M-15-producing strains," Journal of Antimicrobial Chemotherapy, vol. 64, No. 2, pp. 274-277 (2009).
Cryz Jr. et al., "Synthesis and Characterization of *Escherichia coli* O18 O-Polysaccharide Conjugate Vaccines," Infection and Immunity, vol. 58, No. 2, pp. 373-377 (1990).
Cryz S J et al, "Synthesis and characterization of a polyvalent *Escherichia coli* O-polysaccharide-toxin A conjugate vaccine", Vaccine, Elsevier Ltd, GB, (Jan. 1, 1995), vol. 13, No. 5, doi:10.1016/0264-410X(94)00009-C, ISSN 0264-410X, pp. 449-453, XP004057719.
Datsenko et al., "One-step inactivation of chromosomal genes in *Escherichia coli* K-12 using PCR products," PNAS, vol. 97, No. 12, pp. 6640-6645 (2000).
Debroy et al., "Detection of O antigens in *Escherichia coli*," Animal Health Research Reviews, vol. 12, No. 2, pp. 169-185 (2011).
Extended Search Report dated Sep. 10, 2021 in EP Application No. 21154782.3.
Extended Search Report dated Apr. 12, 2017 in EP Application No. 16195256.9, 8 pages.
Foxman, "Epidemiology of Urinary Tract Infections: Incidence, morbidity, and Economic Costs", The American Journal of Medicine, vol. 113(1A), 5S-13S, Jul. 2002.
Fratamico et al., "*Escherichia coli* serogroup O2 and O28ac O-antigen gene cluster sequences and detection of pathogenic *Escherichia coil* O2 and O28ac by PCR," Canadian Journal of Microbiology, vol. 56, No. 4, pp. 308-316 (2010).
Frenck, et al., "Safety and Immunogenicity of a vaccine for extra-intestinal pathogenic *Escherichia coli* (ESTELLA): a phase 2 randomised controlled trial," Lancet Infect. Dis. vol. 1, No. 6, pp. 631-640 (2019).
Fundin et al., "NMR analysis of the O-antigen polysaccharide from *Escherichia coli* strain F171," Magnetic Resonance in Chemistry, vol. 41, No. 3, pp. 202-205 (2003).

(56) References Cited

OTHER PUBLICATIONS

Glover et al., "Chemoenzymatic synthesis of Glycopeptides with PgIB, a bacterial oligosaccharyl transferase from Campylobacter jejuni," Chemistry and Biology, Current Biology, vol. 12, No. 12, pp. 1311-1316 (2005).
Ho et al., Preclinical Laboratory Evaluation of a Bivalent *Staphylococcus aureus* Saccharide-Exotoxin A Protein Conjugate Vaccine, Human vaccines, 2:3, pp. 89-98, May/Jun. 2006.
Ihssen et al., "Production of glycoprotein vaccines in *Escherichia coli*," Microbial Cell Factories, vol. 9, No. 61, pp. 1-13 (2010).
Int'l Preminary Report on Patentability dated Feb. 14, 2019 in Int'l Application No. PCT/EP2017/077123, 16 pages.
Int'l Search Report and Written Opinion dated Jul. 20, 2017 in Int'l Application No. PCT/US2016/048278, 9 pages.
Int'l Search Report and Written Opinion issued Jun. 15, 2015 in Int'l Application No. PCT/EP2015/053739, 10 pages.
Int'l Search Report and Written Opinion issued Oct. 27, 2016 in Int'l Application No. PCT/US2016/048278, 16 pages.
Int'l Search Report issued Jan. 24, 2018 in Int'l Application No. PCT/EP2017/077123, 6 pages.
International Search Report and Written Opinion for App. No. PCT/US2020/023415, dated Jun. 12, 2020, 21 pages.
Jadhav et al., "Virulence characteristics and genetic affinities of multiple drug resistant uropathogenic *Escherichia coli* from a Semi Urban Locality in India," PLOS One, vol. 6, No. 3, (2011), 7 pages.
Jann et al., "Structural Comparison of the O6 Specific Polysaccharides From *Escherichia coli* O6:K2:H1, *Escherichia coli* O6:K13:H1, and *Escherichia coli* O6:K54:H10," Carbohydrate Research, vol. 263, No. 2, pp. 217-225 (1994).
Jansson et al., "Structural studies of the *Escherichia coli* O-antigen 6," Carbohydrate Research, vol. 131, No. 2, pp. 277-283 (1984).
Jansson et al., "Structural studies of the O-specific side-chains of the *Escherichia coli* O2 lipopolysaccharide," Carbohydrate Res., vol. 161, pp. 273-279 (1987).
Jiang et al., "Tungsten-Induced Protein Aggregation: Solution Behavior," Wiley InterScience, vol. 98, No. 12, pp. 4695-4710 (2009).
Johnson et al., "*Escherichia coli* sequence type ST131 as an emerging fluoroquinolone-resistant uropathogen among renal transplant recipients," Antimicrob Agents Chemother. vol. 54, No. 1, pp. 546-550 (2010).
Johnson et al., Extraintestinal Pathogenic *Escherichi coli*: "The other bad *E coli*", J Lab Clin Med., 139(3), pp. 155-162, 2002.
Kenne et al., "Structural studies of the *Escherichia coli* O-antigen 25," Carbohydrate Research, vol. 122, No. 2, pp. 249-256 (1983).
Kim et al., "Efficiency of a pneumococal Opsonophagocytic Killing Assay Improved by Multiplexing and by Colloring Colonies", Clinical and Dianostic laboratory Immunology, pp. 616-621, Jul. 2003.
Kohler et al., "What defines extraintestinal pathogenic *Escherichia coli*", Elsevier, International journal of Medical Microbiology 301, pp. 642-647, 2011.
Laurentin et al., "A Microtiter Modification of the anthrone-sulfuric acid colorimetric assay for glucose-based carbohydrates", Analytical Biochemistry, 315, pp. 143-145, 2003.
Lazar et al. (Mol. Cell. Biol., 8:1247-1252, 1988).
Lipsitch, "Bacterial vaccines and Serotype Replacement: Lessons from Haemophilus Influenzae and Prospects for *Streptococcus pneumoniae*", Emerging Infectious Diseases, vol. 5, No. 3, May/Jun. 1999, 10 pages.
Lukac et al., "Toxoid of Pseudomonas aeruginosa exotoxin A generated by deletion of an active-site residue," Infect Immun, vol. 56, No. 12, pp. 3095-3098 (1988).
Mario F Feldman et al, "Engineering N-linked protein glycosylation with diverse O antigen lipopolysaccharide structures in *Escherichia coli*", Proceedings of the National Academy of Sciences, vol. 102, No. 8, pp. 3016-3021, (Feb. 9, 2005).
Molina-Lopez et al., "Drug resistance, serotypes, and phylogenetic groups among uropathogenic *Escherichia coli* including O25-ST131 in Mexico City," J Infect Dev Ctries, vol. 5, No. 12, pp. 840-849 (2011).
Mora et al, "Emergence of clonal groups 01:HNM-D-ST59, 015:H1-D-ST393, O20:H34/HNM-D-ST354, O25b:H4-B2-ST131 and ONT:H21,42-B1-ST101 among CTX-M-14-producing *Escherichia coli* clinical isolates in Galicia, northwest Spain," International J. of Antimicrob. Agents, vol. 37, No. 1, pp. 16-21 (2011).
Phan et al., "The serum resistome of a globally disseminated multidrug resistant uropathogenic *Escherichia coil* clone," PLOS Genetics, vol. 9, No. 10, pp. 1-18 (2013).
Pitout et al., "Extraintestinal Pathogenic *Escherichia coli*: An Update on Antimicrobial Resistance, Laboratory Diagnosis and Treatment," Expert Rev. Anti. Infect. Then, vol. 10, No. 10, pp. 1165-1176 (2012).
Poolman et al., "Extraintestinal Pathogenic *Escherichia coli*, a Common Human Pathogen: Challenges for Vaccine Development and Progress in the Field," Journal of Infectious Diseases, vol. 213, pp. 6-13 (2016).
Rogers B.A. et al., "*Escherichia coli* O25b-ST131: a pandemic, multiresistant, community-associated strain", Journal of Antimicrobial Chemotherapy, 2011, vol. 66, No. 1, pp. 1-14.
Russo et al., "A killed, genetically engineered derivative of a wild-type extraintestinal pathogenic *E coli* strain is a caccine candidate", Elsevier, Vaccine 25, pp. 3859-3870, 2007.
Russo et al., "Medical and Exonomic impact of extraintestinal infections due to *Escherichia coli*: focus on an Increasingly important endemic problem", Elsevier, Microbes and Infection 5, pp. 449-456, 2003.
Saade, Elie, et al., "Characertization of *Escherichia coli* isolates potentially covered by ExPEC4V and ExPEC10V, that were collected from post-transrectal ultrasound-guided prostate needle biopsy," Vasccine, Elsevier, Amsterdam, NL, vol. 38, No. 33, Jun. 16, 2020 pp. 5100-5104.
Schito et al., "The ARESC study: an international survey on the antimicrobial resistance of pathogens involved in uncomplicated urinary tract infections", Elsevier, International Journal of Antimicrobial Agents 34, pp. 407-413, 2009.
Seidl et al., "Tungsten-Induced Denaturation and Aggregation of Epoetin Alfa During Primary Packaging as a Cause of Immunogenicity," Pharm. Res., vol. 29, pp. 1454-1467 (2012).
Stenutz R et al, "The structures of *Escherichia coli* O-polysaccharide antigens.", FEMS Microbiol Rev. May 2006;30(3):382-403.
Stevenson et al., "Structure of the O antigen of *Escherichia coli* K-12 and the sequence of its rfb gene cluster," J. Bacteriol., vol. 176, No. 13, pp. 4144-4156 (1994).
Stoute et al., "A Preliminary Evaluation of a Recombinant Circumsporozoite Protein Vaccine Against Plasmodium Falciparum Malaria," New England Journal of Medicine, vol. 336, pp. 86-91 (1997).
Szijarto et al. "The rapidly emerging ESBL-producing *Escherichia coil* O25-ST131 clone carries LPS core synthesis genes of the K-12 type," FEMS Microbiol. Lett., vol. 332, pp. 131-136 (2012).
Terai et al., "*Escherichia coli* Virulence Factors and Serotypes in Acute Bacterial Prostatitis," Int. Journal of Urology, vol. 4, No. 3, pp. 289-294 (1997).
V. Szijarto et al, "Diagnostic Potential of Monoclonal Antibodies Specific to the Unique O-Antigen of Multidrug-Resistant Epidemic *Escherichia coli* Clone ST131-O25b:H4", Clinical and Vaccine Immunology, (Apr. 30, 2014), vol. 21, No. 7, doi:10.1128/CVI.00685-13, ISSN 1556-6811, pp. 930-939, XP055179667.
Van Den Dobbelsteen et al., "Immunogenicity and safety of tetravalent *Escherichia coli* O-antigen bioconjugate vaccine in animal models," Vaccine, vol. 34, No. 35, pp. 4152-4160 (2016).
Wacker et al., "N-linked glycosylation in Campylobacter jejuni and its functional transfer into *Escherichia coli*," Science, vol. 298, No. 5599, pp. 1790-1793 (2002).
Written Opinion dated Dec. 21, 2018 in Int'l Application No. PCT/EP2017/077123, 8 pages.
Written opinion of the Int'l Searching Authority dated Jan. 24, 2018 in Int'l Application No. PCT/EP2017/077123, 6 pages.
Written Opinion of the International Preliminary Examining Authority dated Sep. 11, 2018 in PCT/EP2017/077123, 8 pages.
International Search Report issued in International Application No. PCT/EP2014/050895 dated Mar. 14, 2014. 2 pages.

(56) References Cited

OTHER PUBLICATIONS

Written Opinion of the International Searching Authority dated Mar. 14, 2014, in connection with corresponding International Application No. PCT/EP2014/050895. 8 pages.
European Search Report issued in International Application No. 13151627.0 dated Mar. 28, 2013. 7 pages.
B.R. Brodeur et al., "Mouse-Human Myelome Partners for the Production of Heterohybridomas", Monoclonal Antibody Production Techniques and Applications, Marcel Dekker, Inc., 1987, pp. 51-63.
J. Wibbenmeyer et al., "Cloning, expression, and characterization of the Fab fragment of the anti-lysozyme antibody HyHEL-5", Biochimica et Biophysica Acta, 1999, vol. 1430, No. 2, pp. 191-202.
N. Woodford et al., "Multiresistant Gram-negative bacteria: the role of high-risk clones in the dissemination of antibiotic resistance", FEMS Microbiol Rev, 2011, vol. 35, No. 5, pp. 736-755.
Duda et al., "The lipopolysaccharide of the mastitis isolate *Escherichia coli* strain 1303 comprises a novel O-antigen and the rare K-12 core type," Microbiology (2011), 157, 1750-1760, doi: 10.1099/mic.0.046912-0.
G. Kohler et al., "Continuous cultures of fused cells secreting antibody of predefined specificity", Nature, Aug. 7, 1975, vol. 256, pp. 495-497.
D. Kozbor et al., "A Human Hybrid Myeloma for Production of Human Monoclonal Antibodies", The Journal of Immunology, Dec. 1984, vol. 133, No. 6, pp. 3001-3005.
Myung-Hoon Lee, et al., "Expression and functional reconstitution of a recombinant antibody (Fab') specific for human apolipoprotein B-100", Journal of Biotechnology, 2003, vol. 101, pp. 189-198.
S. Muller-Loennies, et al., "Structural Analysis of Oligosaccharides from Lipopolysaccharide (LPS) of *Escherichia coli* K12 Strain W3100 Reveals a Link between Inner and Outer Core LPS Biosynthesis", The Journal of Biological Chemistry, Sep. 5, 2003, vol. 278, No. 36, pp. 34090-34101.
G. Peirano, et al., "Molecular characteristics of extended-spectrum β-lactamase-producing *Escherichia coli* from the Chicago area: high prevalence of ST131 producing CTX-M-15 in community hospitals", International Journal of Antimicrobial Agents, 2010, vol. 36, pp. 19-23.
Extended European Search Report dated Mar. 14, 2017, including the European Search Report and the European Search Opinion, in connection with corresponding EP Application No. 16201732.1 (10 pgs.).
European Office Action dated Mar. 7, 2017, in connection with corresponding EP Application No. 14703783.2 (7 pgs.).
Szijarto et al., "Bactericidal Monoclonal Antibodies Specific to the Lipopolysaccharide 0 Antigen from Multidrug-Resistant *Escherichia coli* Clone ST131-025b:H4 Elicit Protection in Mice," Antimicrobial Agents and Chemotherapy, Jun. 2015, vol. 59, No. 6, pp. 3109-3116, XP009187151.
Nagy, Gábor and Pál, Tibor. "Lipopolysaccharide: a tool and target in enterobacterial vaccine development", Biological Chemistry 389(5):513-20.
Simone Cagnacci, et al., "European Emergence of Ciprofloxacin-Resistant *Escherichia coli* Clonal Groups O25:H4-ST 131 and O15:K52:H1 Causing Community-Acquired Uncomplicated Cystitis", in the Journal of Clinical Microbiology, Aug. 2008, vol. 46, No. 8, pp. 2605-2612 (8 pgs.).
Vajdos et al., "Comprehensive Functional Maps of the Antigen-binding Site of an Anti-ErbB2 Antibody Obtained with Shotgun Scanning Mutagenesis," J Mol. Biol. 2002, vol. 320(2), pp. 415-428.
Brown et al., "Tolerance to Single, but Not Multiple, Amino Acid Replacements in Antibody Vh CDR2," The Journal of Immunology, 1996, 156: 3285-3291.
Notification Concerning Transmittal of International Preliminary Report on Patentability dated Aug. 18, 2016, in connection with corresponding international Application No. PCT/EP2014/078709 (7 pgs.).
International Search Report and Written Opinion issued in International Application No. PCT/EP2014/078709 dated May 12, 2015, 4 pages.
Extended European Search Report dated Jul. 16, 2014, in connection with corresponding EP Application No. 14154158.1 (5 pgs.).
Denka Seiken Co. Ltd.(Catalogue), Bacterial Antisera "Seiken", [Denka Seiken Co.,Ltd, MSDS No. 200000-01, Feb. 16, 2010. 13 pages.
G. Peirano, et al., "Molecular epidemiology of *Escherichia coli* producing CTX-M beta-lactamases: the worldwide emergence of clone ST131 O25:H4", in International Journal of Antimicrobial Agents, vol. 35, 2010, pp. 316-321 (7 pgs.).
Cristina Caldas, et al., "Humanization of the anti-CD18 antibody 6.7: an unexpected effect of a framework residue in binding to antigen", in Molecular Immunology, vol. 39, 2003, pp. 941-952 (12 pgs.).
Arturo Casadevall, et al., "Immunoglobulin isotype influences affinity and specificity", in PNAS, vol. 109, No. 31, Jul. 31, 2012, pp. 12272-12273 (2 pgs.).
Nadine C. Chien, et al., "Significant structural and functional change of an antigen-binding site by a distant amino acid substitution: Proposal of a structural mechanism", in Proc. Natl. Acad. Sci., vol. 86, Jul. 1989, pp. 5532-5536 (5 pgs.).
Chris Galanos, et al., "Galactosamine-induced sensitization to the lethal effects of endotoxin", in Proc. Natl. Acad. Sci., vol. 76, No. 11, Nov. 1979, pp. 599-5943 (5 pgs.).
Angela M. Giusti, et al., "Somatic diversification of S107 from an antiphosphocholine to an anti-DNA autoantibody is due to a single base change in its heavy chain variable region", in Proc. Natl. Acad. Sci., vol. 84, May 1987, pp. 2926-2930 (5 pgs.).
Neil S. Greenspan, et al., "Defining epitopes: It's not as easy as it seems", in Nature Biotechnology, vol. 17, Oct. 1999, pp. 936-937 (2 pgs.).
Marie-Paule Lefranc, et al., "IMGT, the international ImMunoGeneTics database", in Nucleic Acids Research, vol. 27, No. 1, 1999, pp. 209-212 (4 pgs.).
Helen Miajlovic, et al., "Response of Extraintestinal Pathogenic *Escherichia coli* to Human Serum Reveals a Protective Role for Rcs-Regulated Exopolysaccharide", in Infection and Immunity, vol. 82, No. 1, Jan. 2014, pp. 298-305 (8 pgs.).
Angela Novais, et al., "Contribution of IncFII and Broad-Host IncA/C and IncN Plasmids to the Local Expansion and Diversification of Phylogroup B2 *Escherichia coli* ST131 Clones Carrying blaCTX-M-15 and qnrS1 Genes", in Antimicrobial Agents and Chemotherapy, vol. 56, No. 5, May 2012, pp. 2763-2766 (4 pgs.).
Gisele Peirano, et al., "Characteristics of *Escherichia coli* Sequence Type 131 Isolates That Produce Extended-Spectrum B-Lactamases: Global Distribution of the H30-Rx Sublineage", in Antimicrobial Agents and Chemotherapy, vol. 58, No. 7, Jul. 2014, pp. 3762-3767 (6 pgs.).
Josef Prassler, et al., "In vitro affinity maturation of HuCAL antibodies: complementarity determining region exchange and RapMat technology", in Immunotherapy, vol. 1, No. 4, 2009, pp. 571-583 (13 pgs.).
Jeffrey Skolnick, et al., "From genes to protein structure and function: novel applications of computational approaches in the genomic era", in Tibtech, vol. 18, Jan. 2000, pp. 34-39 (6 pgs.).
Claudia Sheedy, et al., "Isolation and affinity maturation of hapten-specific antibodies", in Biotechnolgy Advances 25, 2007, pp. 333-352 (20 pgs.).
Pablo Umaña, et al., "Engineeredglycoforms of an antineuroblastoma IgG1 with optimized antibody-dependent cellular cyto9toxic activity", in Nature Biotechnology, vol. 17, Feb. 1999, pp. 176-180 (5 pgs.).
Russian Office Action dated Dec. 27, 2017, in connection with corresponding RU Application No. 2015134413/10 (052839) (18 pgs., including English translation).
Russian Office Action dated Apr. 24, 2018, in connection with corresponding RU Application No. 2016135962/10 (056446) (5 pgs.).
Office Action issued on Aug. 23, 2018 in corresponding Russian Application No. 2016135962, 17 pages including English-language translation.

(56) References Cited

OTHER PUBLICATIONS

Reschedko, G.K. et al, "*Escherichia coli* as a Nosocomial Pathogen in ICUs", Clinical microbiology and antimicrobial chemotherapy, 2011, vol. 13, No. 4, pp. 314-321.
Office Action issued on Oct. 4, 2018 in corresponding Japanese Application No. 2016-550556; 9 pages including English-language translation.
Office Action issued on Aug. 28, 2018 in corresponding Japanese Application No. 2015-553093; 12 pages including English-language translation.
Royt A et al., "Hypervariable sequences of antigen-recognition centers enable binding of various antigens by antibodies", Immunology, Moscow, "Mir" Publishers 2000, 4 pages including English-language translation, abstract only.
Office Action dated Oct. 17, 2018 in corresponding Russian Application No. 2015134413/10(052839), 17 pages including English-language translation.
Office Action dated Mar. 29, 2018 in Russian Patent Application No. 2015134413, with English translation. 12 pages.
Response to Austrian Office Action dated Mar. 12, 2019 in Austrian Patent Application No. 2018204437. 6 pages.
Abbanat et al., Poster presented at ASM's Interscience Conference of Antimicrobial Agents and Chemotherapy (ICAAC), Jun. 16-20, 2016, Boston, 1 page.
Huttner et al., "Safety, immunogenicity, and preliminary clinical efficacy of a vaccine against extraintestinal pathogenic *Escherichia coli* in women with a history of recurrent urinary tract infection: a randomised, single-blind, placebo-controlled phase 1b trial", Lancet Infect Dis., 2017, vol. 17, No. 5, pp. 528-537.

* cited by examiner

SEQUENCE LISTING

```
<160> NUMBER OF SEQ ID NOS: 20

<210> SEQ ID NO 1
<211> LENGTH: 3
<212> TYPE: PRT
<213> ORGANISM: Artificial Sequence
<220> FEATURE:
<223> OTHER INFORMATION: Glycosylation consensus sequence
<220> FEATURE:
<221> NAME/KEY: VARIANT
<222> LOCATION: (2)..(2)
<223> OTHER INFORMATION: Any amino acid residue except Pro
<220> FEATURE:
<221> NAME/KEY: VARIANT
<222> LOCATION: (3)..(3)
<223> OTHER INFORMATION: Ser or Thr

<400> SEQUENCE: 1

Asn Xaa Xaa
1


<210> SEQ ID NO 2
<211> LENGTH: 5
<212> TYPE: PRT
<213> ORGANISM: Artificial Sequence
<220> FEATURE:
<223> OTHER INFORMATION: Optimized glycosylation consensus sequence
<220> FEATURE:
<221> NAME/KEY: VARIANT
<222> LOCATION: (1)..(1)
<223> OTHER INFORMATION: Asp or Glu
<220> FEATURE:
<221> NAME/KEY: VARIANT
<222> LOCATION: (2)..(2)
<223> OTHER INFORMATION: Any amino acid residue except Pro
<220> FEATURE:
<221> NAME/KEY: VARIANT
<222> LOCATION: (4)..(4)
<223> OTHER INFORMATION: Any amino acid residue except Pro
<220> FEATURE:
<221> NAME/KEY: VARIANT
<222> LOCATION: (5)..(5)
<223> OTHER INFORMATION: Ser or Thr

<400> SEQUENCE: 2
```

```
Xaa Xaa Asn Xaa Xaa
1               5


<210> SEQ ID NO 3
<211> LENGTH: 652
<212> TYPE: PRT
<213> ORGANISM: Artificial Sequence
<220> FEATURE:
<223> OTHER INFORMATION: EPA carrier protein comprising 4 glycosylation
      consensus sequences (EPA-4)

<400> SEQUENCE: 3

Gly Ser Gly Gly Gly Asp Gln Asn Ala Thr Gly Ser Gly Gly Gly Lys
1               5                   10                  15

Leu Ala Glu Glu Ala Phe Asp Leu Trp Asn Glu Cys Ala Lys Ala Cys
            20                  25                  30

Val Leu Asp Leu Lys Asp Gly Val Arg Ser Ser Arg Met Ser Val Asp
        35                  40                  45

Pro Ala Ile Ala Asp Thr Asn Gly Gln Gly Val Leu His Tyr Ser Met
    50                  55                  60

Val Leu Glu Gly Gly Asn Asp Ala Leu Lys Leu Ala Ile Asp Asn Ala
65                  70                  75                  80

Leu Ser Ile Thr Ser Asp Gly Leu Thr Ile Arg Leu Glu Gly Gly Val
                85                  90                  95

Glu Pro Asn Lys Pro Val Arg Tyr Ser Tyr Thr Arg Gln Ala Arg Gly
            100                 105                 110

Ser Trp Ser Leu Asn Trp Leu Val Pro Ile Gly His Glu Lys Pro Ser
        115                 120                 125

Asn Ile Lys Val Phe Ile His Glu Leu Asn Ala Gly Asn Gln Leu Ser
    130                 135                 140

His Met Ser Pro Ile Tyr Thr Ile Glu Met Gly Asp Glu Leu Leu Ala
145                 150                 155                 160

Lys Leu Ala Arg Asp Ala Thr Phe Phe Val Arg Ala His Glu Ser Asn
                165                 170                 175

Glu Met Gln Pro Thr Leu Ala Ile Ser His Ala Gly Val Ser Val Val
            180                 185                 190

Met Ala Gln Ala Gln Pro Arg Arg Glu Lys Arg Trp Ser Glu Trp Ala
        195                 200                 205

Ser Gly Lys Val Leu Cys Leu Leu Asp Pro Leu Asp Gly Val Tyr Asn
    210                 215                 220

Tyr Leu Ala Gln Gln Arg Cys Asn Leu Asp Asp Thr Trp Glu Gly Lys
225                 230                 235                 240

Ile Tyr Arg Val Leu Ala Gly Asn Pro Ala Lys His Asp Leu Asp Ile
                245                 250                 255

Lys Asp Asn Asn Asn Ser Thr Pro Thr Val Ile Ser His Arg Leu His
            260                 265                 270

Phe Pro Glu Gly Gly Ser Leu Ala Ala Leu Thr Ala His Gln Ala Cys
        275                 280                 285

His Leu Pro Leu Glu Ala Phe Thr Arg His Arg Gln Pro Arg Gly Trp
    290                 295                 300

Glu Gln Leu Glu Gln Cys Gly Tyr Pro Val Gln Arg Leu Val Ala Leu
305                 310                 315                 320

Tyr Leu Ala Ala Arg Leu Ser Trp Asn Gln Val Asp Gln Val Ile Arg
                325                 330                 335

Asn Ala Leu Ala Ser Pro Gly Ser Gly Gly Asp Leu Gly Glu Ala Ile
```

```
            340                 345                 350

Arg Glu Gln Pro Glu Gln Ala Arg Leu Ala Leu Thr Leu Ala Ala Ala
        355                 360                 365

Glu Ser Glu Arg Phe Val Arg Gln Gly Thr Gly Asn Asp Glu Ala Gly
    370                 375                 380

Ala Ala Ser Ala Asp Val Val Ser Leu Thr Cys Pro Val Ala Lys Asp
385                 390                 395                 400

Gln Asn Arg Thr Lys Gly Glu Cys Ala Gly Pro Ala Asp Ser Gly Asp
                405                 410                 415

Ala Leu Leu Glu Arg Asn Tyr Pro Thr Gly Ala Glu Phe Leu Gly Asp
            420                 425                 430

Gly Gly Asp Val Ser Phe Ser Thr Arg Gly Thr Gln Asn Trp Thr Val
        435                 440                 445

Glu Arg Leu Leu Gln Ala His Arg Gln Leu Glu Glu Arg Gly Tyr Val
    450                 455                 460

Phe Val Gly Tyr His Gly Thr Phe Leu Glu Ala Ala Gln Ser Ile Val
465                 470                 475                 480

Phe Gly Gly Val Arg Ala Arg Ser Gln Asp Leu Asp Ala Ile Trp Arg
                485                 490                 495

Gly Phe Tyr Ile Ala Gly Asp Pro Ala Leu Ala Tyr Gly Tyr Ala Gln
            500                 505                 510

Asp Gln Glu Pro Asp Ala Arg Gly Arg Ile Arg Asn Gly Ala Leu Leu
        515                 520                 525

Arg Val Tyr Val Pro Arg Trp Ser Leu Pro Gly Phe Tyr Arg Thr Gly
    530                 535                 540

Leu Thr Leu Ala Ala Pro Glu Ala Ala Gly Glu Val Glu Arg Leu Ile
545                 550                 555                 560

Gly His Pro Leu Pro Leu Arg Leu Asp Ala Ile Thr Gly Pro Glu Glu
                565                 570                 575

Glu Gly Gly Arg Val Thr Ile Leu Gly Trp Pro Leu Ala Glu Arg Thr
            580                 585                 590

Val Val Ile Pro Ser Ala Ile Pro Thr Asp Pro Arg Asn Val Gly Gly
        595                 600                 605

Asp Leu Asp Pro Ser Ser Ile Pro Asp Lys Glu Gln Ala Ile Ser Ala
    610                 615                 620

Leu Pro Asp Tyr Ala Ser Gln Pro Gly Lys Pro Pro Arg Glu Asp Leu
625                 630                 635                 640

Lys Leu Gly Ser Gly Gly Gly Asp Gln Asn Ala Thr
                645                 650


<210> SEQ ID NO 4
<211> LENGTH: 421
<212> TYPE: PRT
<213> ORGANISM: Artificial Sequence
<220> FEATURE:
<223> OTHER INFORMATION: O4 GtrS amino acid sequence

<400> SEQUENCE: 4

Met Asn Asn Leu Ile Met Asn Asn Trp Cys Lys Leu Ser Ile Phe Ile
1               5                   10                  15

Ile Ala Phe Ile Leu Leu Trp Leu Arg Arg Pro Asp Ile Leu Thr Asn
            20                  25                  30

Ala Gln Phe Trp Ala Glu Asp Ser Val Phe Trp Tyr Lys Asp Ala Tyr
        35                  40                  45

Glu Asn Gly Phe Leu Ser Ser Leu Thr Thr Pro Arg Asn Gly Tyr Phe
```

```
    50                  55                  60

Gln Thr Val Ser Thr Phe Ile Val Gly Leu Thr Ala Leu Leu Asn Pro
65                  70                  75                  80

Asp Tyr Ala Pro Phe Val Ser Asn Phe Phe Gly Ile Met Ile Arg Ser
                85                  90                  95

Val Ile Ile Trp Phe Leu Phe Thr Glu Arg Phe Asn Phe Leu Thr Leu
            100                 105                 110

Thr Thr Arg Ile Phe Leu Ser Ile Tyr Phe Leu Cys Met Pro Gly Leu
        115                 120                 125

Asp Glu Val His Ala Asn Ile Thr Asn Ala His Trp Tyr Leu Ser Leu
    130                 135                 140

Tyr Val Ser Met Ile Leu Ile Ala Arg Asn Pro Ser Ser Lys Ser Trp
145                 150                 155                 160

Arg Phe His Asp Ile Phe Phe Ile Leu Leu Ser Gly Leu Ser Gly Pro
                165                 170                 175

Phe Ile Ile Phe Ile Leu Ala Ala Ser Cys Phe Lys Phe Ile Asn Asn
            180                 185                 190

Cys Lys Asp His Ile Ser Val Arg Ser Phe Ile Asn Phe Tyr Leu Arg
        195                 200                 205

Gln Pro Tyr Ala Leu Met Ile Val Cys Ala Leu Ile Gln Gly Thr Ser
    210                 215                 220

Ile Ile Leu Thr Phe Asn Gly Thr Arg Ser Ser Ala Pro Leu Gly Phe
225                 230                 235                 240

Ser Phe Asp Val Ile Ser Ser Ile Ile Ser Ser Asn Ile Phe Leu Phe
                245                 250                 255

Thr Phe Val Pro Trp Asp Ile Ala Lys Ala Gly Trp Asp Asn Leu Leu
            260                 265                 270

Leu Ser Tyr Phe Leu Ser Val Ser Ile Leu Ser Cys Ala Ala Phe Val
        275                 280                 285

Phe Val Lys Gly Thr Trp Arg Met Lys Val Phe Ala Thr Leu Pro Leu
    290                 295                 300

Leu Ile Ile Ile Phe Ser Met Ala Lys Pro Gln Leu Thr Asp Ser Ala
305                 310                 315                 320

Pro Gln Leu Pro Thr Leu Ile Asn Gly Gln Gly Ser Arg Tyr Phe Val
                325                 330                 335

Asn Ile His Ile Ala Ile Phe Ser Leu Leu Cys Val Tyr Leu Leu Glu
            340                 345                 350

Cys Val Arg Gly Lys Val Ala Thr Leu Phe Ser Lys Ile Tyr Leu Thr
        355                 360                 365

Ile Leu Leu Phe Val Met Gly Cys Leu Asn Phe Val Ile Thr Pro Leu
    370                 375                 380

Pro Asn Met Asn Trp Arg Glu Gly Ala Thr Leu Ile Asn Asn Ala Lys
385                 390                 395                 400

Thr Gly Asp Val Ile Ser Ile Gln Val Leu Pro Pro Gly Leu Thr Leu
                405                 410                 415

Glu Leu Arg Lys Lys
            420
```

<210> SEQ ID NO 5
<211> LENGTH: 1266
<212> TYPE: PRT
<213> ORGANISM: Artificial Sequence
<220> FEATURE:
<223> OTHER INFORMATION: Example O4 gtrS nucleic acid sequence

<400> SEQUENCE: 5

Ala Thr Gly Ala Ala Thr Ala Ala Thr Thr Thr Ala Ala Thr Thr Ala
1               5                   10                  15

Thr Gly Ala Ala Thr Ala Ala Cys Thr Gly Gly Thr Gly Thr Ala Ala
            20                  25                  30

Ala Thr Thr Ala Thr Cys Thr Ala Thr Ala Thr Thr Thr Ala Thr Thr
        35                  40                  45

Ala Thr Thr Gly Cys Ala Thr Thr Thr Ala Thr Thr Thr Thr Gly Cys
    50                  55                  60

Thr Ala Thr Gly Gly Cys Thr Thr Ala Gly Ala Ala Gly Gly Cys Cys
65                  70                  75                  80

Gly Gly Ala Thr Ala Thr Ala Cys Thr Cys Ala Cys Ala Ala Ala Cys
                85                  90                  95

Gly Cys Ala Cys Ala Ala Thr Thr Thr Thr Gly Gly Gly Cys Ala Gly
            100                 105                 110

Ala Ala Gly Ala Thr Thr Cys Cys Gly Thr Thr Thr Thr Cys Thr Gly
        115                 120                 125

Gly Thr Ala Thr Ala Ala Gly Gly Ala Cys Gly Cys Cys Thr Ala Thr
    130                 135                 140

Gly Ala Gly Ala Ala Cys Gly Gly Ala Thr Thr Cys Thr Thr Ala Ala
145                 150                 155                 160

Gly Thr Thr Cys Ala Cys Thr Ala Ala Cys Ala Ala Cys Gly Cys Cys
                165                 170                 175

Thr Ala Gly Gly Ala Ala Thr Gly Gly Gly Thr Ala Thr Thr Thr Cys
            180                 185                 190

Cys Ala Gly Ala Cys Thr Gly Thr Thr Thr Cys Thr Ala Cys Ala Thr
        195                 200                 205

Thr Thr Ala Thr Ala Gly Thr Thr Gly Gly Thr Cys Thr Gly Ala Cys
    210                 215                 220

Thr Gly Cys Thr Thr Thr Ala Thr Thr Ala Ala Ala Thr Cys Cys Ala
225                 230                 235                 240

Gly Ala Thr Thr Ala Thr Gly Cys Ala Cys Cys Thr Thr Thr Thr Gly
                245                 250                 255

Thr Thr Thr Cys Thr Ala Ala Thr Thr Thr Thr Thr Thr Thr Gly Gly
            260                 265                 270

Cys Ala Thr Ala Ala Thr Gly Ala Thr Thr Cys Gly Cys Thr Cys Ala
        275                 280                 285

Gly Thr Ala Ala Thr Thr Ala Thr Ala Thr Gly Gly Thr Thr Thr Thr
    290                 295                 300

Thr Ala Thr Thr Thr Ala Cys Ala Gly Ala Ala Ala Gly Ala Thr Thr
305                 310                 315                 320

Cys Ala Ala Cys Thr Thr Cys Cys Thr Cys Ala Cys Ala Thr Thr Gly
                325                 330                 335

Ala Cys Thr Ala Cys Thr Ala Gly Gly Ala Thr Thr Thr Thr Cys Thr
            340                 345                 350

Thr Ala Thr Cys Thr Ala Thr Thr Thr Ala Thr Thr Thr Thr Cys Thr
        355                 360                 365

Ala Thr Gly Cys Ala Thr Gly Cys Cys Thr Gly Gly Ala Thr Thr Gly
    370                 375                 380

Gly Ala Thr Gly Ala Ala Gly Thr Thr Cys Ala Thr Gly Cys Ala Ala
385                 390                 395                 400

Ala Thr Ala Thr Ala Ala Cys Ala Ala Ala Thr Gly Cys Ala Cys Ala
                405                 410                 415

-continued

```
Thr Thr Gly Gly Thr Ala Thr Thr Thr Gly Thr Cys Ala Thr Thr Ala
            420                 425                 430

Thr Ala Thr Gly Thr Ala Thr Cys Ala Ala Thr Gly Ala Thr Cys Cys
        435                 440                 445

Thr Gly Ala Thr Ala Gly Cys Thr Cys Gly Cys Ala Ala Thr Cys Cys
    450                 455                 460

Ala Ala Gly Thr Thr Cys Ala Ala Ala Ala Thr Cys Ala Thr Gly Gly
465                 470                 475                 480

Ala Gly Gly Thr Thr Thr Cys Ala Thr Gly Ala Thr Ala Thr Ala Thr
                485                 490                 495

Thr Cys Thr Thr Thr Ala Thr Cys Thr Thr Gly Cys Thr Ala Thr Cys
            500                 505                 510

Cys Gly Gly Gly Cys Thr Cys Ala Gly Thr Gly Gly Cys Cys Cys Ala
        515                 520                 525

Thr Thr Thr Ala Thr Ala Ala Thr Thr Thr Thr Cys Ala Thr Thr Thr
    530                 535                 540

Thr Ala Gly Cys Ala Gly Cys Thr Thr Cys Ala Thr Gly Cys Thr Thr
545                 550                 555                 560

Thr Ala Ala Ala Thr Thr Thr Ala Thr Ala Ala Ala Thr Ala Ala Thr
                565                 570                 575

Thr Gly Thr Ala Ala Ala Gly Ala Thr Cys Ala Thr Ala Thr Thr Ala
            580                 585                 590

Gly Thr Gly Thr Ala Ala Gly Ala Thr Cys Thr Thr Thr Cys Ala Thr
        595                 600                 605

Ala Ala Ala Thr Thr Thr Cys Thr Ala Cys Thr Thr Gly Cys Gly Thr
    610                 615                 620

Cys Ala Gly Cys Cys Ala Thr Ala Cys Gly Cys Ala Thr Thr Ala Ala
625                 630                 635                 640

Thr Gly Ala Thr Thr Gly Thr Thr Thr Gly Cys Gly Cys Thr Thr Thr
                645                 650                 655

Ala Ala Thr Thr Cys Ala Ala Gly Gly Ala Ala Cys Thr Thr Cys Thr
            660                 665                 670

Ala Thr Ala Ala Thr Thr Cys Thr Ala Ala Cys Thr Thr Thr Cys Ala
        675                 680                 685

Ala Thr Gly Gly Cys Ala Cys Ala Cys Gly Thr Thr Cys Cys Thr Cys
    690                 695                 700

Ala Gly Cys Ala Cys Cys Gly Cys Thr Ala Gly Gly Ala Thr Thr Cys
705                 710                 715                 720

Ala Gly Thr Thr Thr Thr Gly Ala Thr Gly Thr Gly Ala Thr Thr Thr
                725                 730                 735

Cys Gly Thr Cys Thr Ala Thr Thr Ala Thr Ala Thr Cys Ala Thr Cys
            740                 745                 750

Gly Ala Ala Thr Ala Thr Thr Thr Thr Thr Thr Thr Ala Thr Thr Thr
        755                 760                 765

Ala Cys Ala Thr Thr Thr Gly Thr Cys Cys Cys Ala Thr Gly Gly Gly
    770                 775                 780

Ala Thr Ala Thr Thr Gly Cys Ala Ala Ala Gly Gly Cys Thr Gly Gly
785                 790                 795                 800

Gly Thr Gly Gly Gly Ala Thr Ala Ala Thr Thr Thr Ala Cys Thr Gly
                805                 810                 815

Thr Thr Ala Thr Cys Thr Thr Ala Thr Thr Thr Thr Thr Thr Gly Thr
            820                 825                 830
```

-continued

```
Cys Thr Gly Thr Thr Thr Cys Gly Ala Thr Thr Thr Thr Gly Thr Cys
        835                 840                 845

Gly Thr Gly Thr Gly Cys Gly Gly Cys Cys Thr Thr Thr Gly Thr Thr
    850                 855                 860

Thr Thr Thr Gly Thr Thr Ala Ala Ala Gly Gly Thr Ala Cys Gly Thr
865                 870                 875                 880

Gly Gly Cys Gly Ala Ala Thr Gly Ala Ala Ala Gly Thr Ala Thr Thr
                885                 890                 895

Thr Gly Cys Ala Ala Cys Thr Thr Thr Ala Cys Cys Ala Thr Thr Gly
            900                 905                 910

Cys Thr Ala Ala Thr Thr Ala Thr Ala Ala Thr Ala Thr Thr Thr Thr
        915                 920                 925

Cys Ala Ala Thr Gly Gly Cys Ala Ala Ala Ala Cys Cys Ala Cys Ala
    930                 935                 940

Ala Thr Thr Gly Ala Cys Ala Gly Ala Cys Thr Cys Gly Gly Cys Ala
945                 950                 955                 960

Cys Cys Thr Cys Ala Ala Thr Thr Gly Cys Cys Ala Ala Cys Ala Cys
                965                 970                 975

Thr Thr Ala Thr Thr Ala Ala Thr Gly Gly Gly Cys Ala Ala Gly Gly
            980                 985                 990

Thr Thr Cys Ala Ala Gly Ala Thr  Ala Cys Thr Thr Cys  Gly Thr Ala
        995                  1000                1005

Ala Ala  Thr Ala Thr Ala Cys  Ala Thr Ala Thr Thr  Gly Cys Gly
    1010                 1015                 1020

Ala Thr  Ala Thr Thr Cys Thr  Cys Thr Thr Thr Gly  Cys Thr Ala
    1025                 1030                 1035

Thr Gly  Thr Gly Thr Thr Thr  Ala Cys Thr Thr Ala  Cys Thr Thr
    1040                 1045                 1050

Gly Ala  Gly Thr Gly Cys Gly  Thr Cys Ala Gly Gly  Gly Gly Gly
    1055                 1060                 1065

Ala Ala  Ala Gly Thr Gly Gly  Cys Ala Ala Cys Thr  Thr Thr Ala
    1070                 1075                 1080

Thr Thr  Thr Thr Cys Cys Ala  Ala Ala Ala Thr Ala  Thr Ala Cys
    1085                 1090                 1095

Thr Thr  Ala Ala Cys Ala Ala  Thr Thr Thr Thr Gly  Cys Thr Ala
    1100                 1105                 1110

Thr Thr  Cys Gly Thr Gly Ala  Thr Gly Gly Gly Ala  Thr Gly Thr
    1115                 1120                 1125

Thr Thr  Gly Ala Ala Thr Thr  Thr Thr Gly Thr Thr  Ala Thr Cys
    1130                 1135                 1140

Ala Cys  Cys Cys Cys Ala Cys  Thr Cys Cys Cys Ala  Ala Ala Cys
    1145                 1150                 1155

Ala Thr  Gly Ala Ala Cys Thr  Gly Gly Ala Gly Gly  Gly Ala Ala
    1160                 1165                 1170

Gly Gly  Thr Gly Cys Thr Ala  Cys Thr Thr Thr Gly  Ala Thr Thr
    1175                 1180                 1185

Ala Ala  Thr Ala Ala Thr Gly  Cys Ala Ala Ala Ala  Ala Cys Thr
    1190                 1195                 1200

Gly Gly  Thr Gly Ala Thr Gly  Thr Cys Ala Thr Thr  Thr Cys Gly
    1205                 1210                 1215

Ala Thr  Thr Cys Ala Ala Gly  Thr Gly Cys Thr Ala  Cys Cys Ala
    1220                 1225                 1230

Cys Cys  Thr Gly Gly Cys Cys  Thr Ala Ala Cys Ala  Cys Thr Thr
```

```
    1235                1240                1245

Gly Ala  Ala Cys Thr Ala Ala  Gly Gly Ala Ala Ala  Ala Ala Ala
    1250                1255                1260

Thr Ala  Ala
    1265


<210> SEQ ID NO 6
<211> LENGTH: 713
<212> TYPE: PRT
<213> ORGANISM: Artificial Sequence
<220> FEATURE:
<223> OTHER INFORMATION: Example PglB sequence ('wild-type')

<400> SEQUENCE: 6

Met Leu Lys Lys Glu Tyr Leu Lys Asn Pro Tyr Leu Val Leu Phe Ala
1               5                   10                  15

Met Ile Ile Leu Ala Tyr Val Phe Ser Val Phe Cys Arg Phe Tyr Trp
            20                  25                  30

Val Trp Trp Ala Ser Glu Phe Asn Glu Tyr Phe Phe Asn Asn Gln Leu
        35                  40                  45

Met Ile Ile Ser Asn Asp Gly Tyr Ala Phe Ala Glu Gly Ala Arg Asp
    50                  55                  60

Met Ile Ala Gly Phe His Gln Pro Asn Asp Leu Ser Tyr Tyr Gly Ser
65                  70                  75                  80

Ser Leu Ser Ala Leu Thr Tyr Trp Leu Tyr Lys Ile Thr Pro Phe Ser
                85                  90                  95

Phe Glu Ser Ile Ile Leu Tyr Met Ser Thr Phe Leu Ser Ser Leu Val
            100                 105                 110

Val Ile Pro Thr Ile Leu Leu Ala Asn Glu Tyr Lys Arg Pro Leu Met
        115                 120                 125

Gly Phe Val Ala Ala Leu Leu Ala Ser Ile Ala Asn Ser Tyr Tyr Asn
    130                 135                 140

Arg Thr Met Ser Gly Tyr Tyr Asp Thr Asp Met Leu Val Ile Val Leu
145                 150                 155                 160

Pro Met Phe Ile Leu Phe Phe Met Val Arg Met Ile Leu Lys Lys Asp
                165                 170                 175

Phe Phe Ser Leu Ile Ala Leu Pro Leu Phe Ile Gly Ile Tyr Leu Trp
            180                 185                 190

Trp Tyr Pro Ser Ser Tyr Thr Leu Asn Val Ala Leu Ile Gly Leu Phe
        195                 200                 205

Leu Ile Tyr Thr Leu Ile Phe His Arg Lys Glu Lys Ile Phe Tyr Ile
    210                 215                 220

Ala Val Ile Leu Ser Ser Leu Thr Leu Ser Asn Ile Ala Trp Phe Tyr
225                 230                 235                 240

Gln Ser Ala Ile Ile Val Ile Leu Phe Ala Leu Phe Ala Leu Glu Gln
                245                 250                 255

Lys Arg Leu Asn Phe Met Ile Ile Gly Ile Leu Gly Ser Ala Thr Leu
            260                 265                 270

Ile Phe Leu Ile Leu Ser Gly Gly Val Asp Pro Ile Leu Tyr Gln Leu
        275                 280                 285

Lys Phe Tyr Ile Phe Arg Ser Asp Glu Ser Ala Asn Leu Thr Gln Gly
    290                 295                 300

Phe Met Tyr Phe Asn Val Asn Gln Thr Ile Gln Glu Val Glu Asn Val
305                 310                 315                 320

Asp Leu Ser Glu Phe Met Arg Arg Ile Ser Gly Ser Glu Ile Val Phe
```

-continued

```
                325                 330                 335

Leu Phe Ser Leu Phe Gly Phe Val Trp Leu Leu Arg Lys His Lys Ser
            340                 345                 350

Met Ile Met Ala Leu Pro Ile Leu Val Leu Gly Phe Leu Ala Leu Lys
        355                 360                 365

Gly Gly Leu Arg Phe Thr Ile Tyr Ser Val Pro Val Met Ala Leu Gly
    370                 375                 380

Phe Gly Phe Leu Leu Ser Glu Phe Lys Ala Ile Met Val Lys Lys Tyr
385                 390                 395                 400

Ser Gln Leu Thr Ser Asn Val Cys Ile Val Phe Ala Thr Ile Leu Thr
                405                 410                 415

Leu Ala Pro Val Phe Ile His Ile Tyr Asn Tyr Lys Ala Pro Thr Val
            420                 425                 430

Phe Ser Gln Asn Glu Ala Ser Leu Leu Asn Gln Leu Lys Asn Ile Ala
        435                 440                 445

Asn Arg Glu Asp Tyr Val Val Thr Trp Trp Asp Tyr Gly Tyr Pro Val
    450                 455                 460

Arg Tyr Tyr Ser Asp Val Lys Thr Leu Val Asp Gly Gly Lys His Leu
465                 470                 475                 480

Gly Lys Asp Asn Phe Phe Pro Ser Phe Ala Leu Ser Lys Asp Glu Gln
                485                 490                 495

Ala Ala Ala Asn Met Ala Arg Leu Ser Val Glu Tyr Thr Glu Lys Ser
            500                 505                 510

Phe Tyr Ala Pro Gln Asn Asp Ile Leu Lys Thr Asp Ile Leu Gln Ala
        515                 520                 525

Met Met Lys Asp Tyr Asn Gln Ser Asn Val Asp Leu Phe Leu Ala Ser
    530                 535                 540

Leu Ser Lys Pro Asp Phe Lys Ile Asp Thr Pro Lys Thr Arg Asp Ile
545                 550                 555                 560

Tyr Leu Tyr Met Pro Ala Arg Met Ser Leu Ile Phe Ser Thr Val Ala
                565                 570                 575

Ser Phe Ser Phe Ile Asn Leu Asp Thr Gly Val Leu Asp Lys Pro Phe
            580                 585                 590

Thr Phe Ser Thr Ala Tyr Pro Leu Asp Val Lys Asn Gly Glu Ile Tyr
        595                 600                 605

Leu Ser Asn Gly Val Val Leu Ser Asp Asp Phe Arg Ser Phe Lys Ile
    610                 615                 620

Gly Asp Asn Val Val Ser Val Asn Ser Ile Val Glu Ile Asn Ser Ile
625                 630                 635                 640

Lys Gln Gly Glu Tyr Lys Ile Thr Pro Ile Asp Asp Lys Ala Gln Phe
                645                 650                 655

Tyr Ile Phe Tyr Leu Lys Asp Ser Ala Ile Pro Tyr Ala Gln Phe Ile
            660                 665                 670

Leu Met Asp Lys Thr Met Phe Asn Ser Ala Tyr Val Gln Met Phe Phe
        675                 680                 685

Leu Gly Asn Tyr Asp Lys Asn Leu Phe Asp Leu Val Ile Asn Ser Arg
    690                 695                 700

Asp Ala Lys Val Phe Lys Leu Lys Ile
705                 710
```

<210> SEQ ID NO 7
<211> LENGTH: 120
<212> TYPE: PRT
<213> ORGANISM: Escherichia coli

<400> SEQUENCE: 7

Met Leu Lys Leu Phe Ala Lys Tyr Thr Ser Ile Gly Val Leu Asn Thr
1               5                   10                  15

Leu Ile His Trp Val Val Phe Gly Val Cys Ile Tyr Val Ala His Thr
            20                  25                  30

Asn Gln Ala Leu Ala Asn Phe Ala Gly Phe Val Val Ala Val Ser Phe
        35                  40                  45

Ser Phe Phe Ala Asn Ala Lys Phe Thr Phe Lys Ala Ser Thr Thr Thr
    50                  55                  60

Met Arg Tyr Met Leu Tyr Val Gly Phe Met Gly Thr Leu Ser Ala Thr
65                  70                  75                  80

Val Gly Trp Ala Ala Asp Arg Cys Ala Leu Pro Pro Met Ile Thr Leu
                85                  90                  95

Val Thr Phe Ser Ala Ile Ser Leu Val Cys Gly Phe Val Tyr Ser Lys
            100                 105                 110

Phe Ile Val Phe Arg Asp Ala Lys
        115                 120

<210> SEQ ID NO 8
<211> LENGTH: 306
<212> TYPE: PRT
<213> ORGANISM: Escherichia coli

<400> SEQUENCE: 8

Met Lys Ile Ser Leu Val Val Pro Val Phe Asn Glu Glu Glu Ala Ile
1               5                   10                  15

Pro Ile Phe Tyr Lys Thr Val Arg Glu Phe Glu Glu Leu Lys Ser Tyr
            20                  25                  30

Glu Val Glu Ile Val Phe Ile Asn Asp Gly Ser Lys Asp Ala Thr Glu
        35                  40                  45

Ser Ile Ile Asn Ala Leu Ala Val Ser Asp Pro Leu Val Val Pro Leu
    50                  55                  60

Ser Phe Thr Arg Asn Phe Gly Lys Glu Pro Ala Leu Phe Ala Gly Leu
65                  70                  75                  80

Asp His Ala Thr Gly Asp Ala Ile Ile Pro Ile Asp Val Asp Leu Gln
                85                  90                  95

Asp Pro Ile Glu Val Ile Pro His Leu Ile Glu Lys Trp Gln Ala Gly
            100                 105                 110

Ala Asp Met Val Leu Ala Lys Arg Ser Asp Arg Ser Thr Asp Gly Arg
        115                 120                 125

Leu Lys Arg Lys Thr Ala Glu Trp Phe Tyr Lys Leu His Asn Lys Ile
    130                 135                 140

Ser Asn Pro Lys Ile Glu Glu Asn Val Gly Asp Phe Arg Leu Met Ser
145                 150                 155                 160

Arg Asp Val Val Glu Asn Ile Lys Leu Met Pro Glu Arg Asn Leu Phe
                165                 170                 175

Met Lys Gly Ile Leu Ser Trp Val Gly Gly Lys Thr Asp Ile Val Glu
            180                 185                 190

Tyr Val Arg Ala Glu Arg Ile Ala Gly Asp Thr Lys Phe Asn Gly Trp
        195                 200                 205

Lys Leu Trp Asn Leu Ala Leu Glu Gly Ile Thr Ser Phe Ser Thr Phe
    210                 215                 220

Pro Leu Arg Ile Trp Thr Tyr Ile Gly Leu Val Val Ala Ser Val Ala
225                 230                 235                 240

-continued

```
Phe Ile Tyr Gly Ala Trp Met Ile Leu Asp Thr Ile Ile Phe Gly Asn
                245                 250                 255

Ala Val Arg Gly Tyr Pro Ser Leu Leu Val Ser Ile Leu Phe Leu Gly
            260                 265                 270

Gly Ile Gln Met Ile Gly Ile Gly Val Leu Gly Glu Tyr Ile Gly Arg
        275                 280                 285

Thr Tyr Ile Glu Thr Lys Lys Arg Pro Lys Tyr Ile Ile Lys Arg Val
    290                 295                 300

Lys Lys
305


<210> SEQ ID NO 9
<211> LENGTH: 14440
<212> TYPE: DNA
<213> ORGANISM: Artificial Sequence
<220> FEATURE:
<223> OTHER INFORMATION: example O4 rfb locus nucleotide sequence -
      O4-EPA production strain BVEC-L-00684f

<400> SEQUENCE: 9

atgacgaatt taaaagcagt tattcctgta gcgggtctcg ggatgcatat gttgcctgcc     60

actaaggcga tacccaaaga gatgctacca atcgtcgaca agccaatgat tcagtacatt    120

gttgacgaga ttgtggctgc agggatcaaa gaaatcctcc tggtaactca cgcgtccaag    180

aacgcggtcg aaaaccactt cgacacctct tatgagttag aatcactcct tgagcagcgc    240

gtgaagcgtc aactgctggc ggaagtacag tccatctgtc cgccgggcgt gaccattatg    300

aacgtgcgtc agggcgaacc tttaggttta ggccactcca ttttgtgtgc gcgacctgcc    360

attggtgaca acccatttgt cgtggtactg ccagacgttg tgatcgacga tgccagcgcc    420

gacccgctac gttacaacct tgctgccatg attgcacgtt tcaacgaaac gggccgcagc    480

caggtgctgg caaaacgtat gccgggtgac ctctctgaat actccgtcat ccagactaaa    540

gagccgctgg accgtgaggg taaagtcagc cgcattgttg aatttatcga aaaaccggat    600

cagccgcaga cgctggactc agacatcatg gccgtaggtc gctatgtgct ttctgccgat    660

atttggccgg aactggaacg tactcagcct ggtgcatggg gacgtattca gctgactgat    720

gctattgccg agctggcgaa aaaacaatcc gttgatgcaa tgctgatgac cggcgacagt    780

tacgactgcg gcaaaaaaat gggctatatg caggcgtttg tgaagtatgg cctacgcaac    840

ctgaaagaag ggcgaagtt ccgtaaaggt attgagaagc tgttaagcga ataatgaaaa    900

tctgaccgga tgtaacggtt gataagaaaa ttataacggc agtgaaaatt cgcagcaaaa    960

gtaatttgtt gcgaatcttc ctgccgttgt tttatataaa ccatcagaat aacaacgagt   1020

tagcagtagg gttttattca aagttttcca ggattttcct tgtttccaga gcggattggt   1080

aagacaatta gcgtttgaat ttttcgggtt tagcgcgagt gggtaacgct cgtcacatca   1140

taggcatgca tgcagtgctc tggtagctgt aaagccaggg gcggtagcgt gcattaatac   1200

ctctattaat caaactgaga gccgcttatt tcacagcatg ctctgaagta atatggaata   1260

aattaagtga aaatacttgt tactggtggc gcaggattta ttggttcagc tgtagttcgt   1320

cacattataa ataatacgca ggatagtgtt gttaatgtcg ataaattaac gtacgccgga   1380

aaccgggaat cacttgctga tgtttctgat tctgaacgct atgtttttga acatgcggat   1440

atttgcgatg cacctgcaat ggcacggatt tttgctcagc atcagccgga tgcagtgatg   1500

cacctggctg ctgaaagcca tgttgaccgt tcaattacag gccctgcggc atttattgaa   1560
```

```
accaatattg ttggtactta tgtccttttg gaagccgctc gcaattactg gtctgctctt   1620
gatagcgaca agaaaaatag cttccgtttt catcatattt ctactgacga agtatatggt   1680
gatttgcctc atcctgacga ggtaaataat acagaagaat tacccttatt tactgagaca   1740
acagcttacg cgccaagcag cccttattcc gcatccaaag catccagcga tcatttagtc   1800
cgcgcgtgga aacgtaccta tggtttaccg accattgtga ctaattgctc taacaattat   1860
ggtccttatc atttcccgga aaaattgatt ccattggtta ttctcaatgc tctggaaggt   1920
aaagcattac ctatttatgg taaaggggat caaattcgcg actggctgta tgttgaagat   1980
catgcgcgtg cgttatatac cgtcgtaacc gaaggtaaag cgggtgaaac ttataacatt   2040
ggtgggcaca acgaaaagaa aaacatagat gtagtgctca ctatttgtga tttgctggat   2100
gagattgtac cgaaagagaa atcttatcgt gagcaaatca cttatgttgc cgatcgtccg   2160
ggacacgatc gccgttatgc gattgatgct gagaatattg gtcgcgaatt gggatggaaa   2220
ccacaggaaa cgtttgagag cgggattcgg aagacagtgg aatggtatct gtccaataca   2280
aaatgggttg ataatgtgaa aagtggtgcc tatcaatcgt ggattgaaga gaactatgag   2340
ggccgccagt aatgaatatc ctcctttttg gcaaaacagg gcaggtaggt tgggaactac   2400
agcgtgctct ggcacctctg ggtaacttga ttgctcttga tgttcattcc actgattatt   2460
gtggcgattt cagtaacccc gaaggtgtgg ctgaaaccgt caaaaaaatt cgcccagatg   2520
ttattgttaa tgctgctgct cataccgcgg tagataaggc tgagtcagaa ccagaatttg   2580
cacaattact caatgcgacc agcgttgaag caattgcaaa agcggctaat gaagttgggg   2640
cttgggtaat tcattactca actgactacg tcttccctgg aaatggcgac atgccatggc   2700
tcgagactga tgtaaccgct ccgctcaatg tttatggcaa aaccaaattg gctggagaaa   2760
gagcattaca agaacattgc gcaaagcatc ttattttccg taccagctgg gtatatgcag   2820
gtaaaggaaa taactttgcc aaaacaatgt tacgtctggc aaaagagcgc gaagaactgg   2880
ctgtgataaa cgatcagttt ggcgcaccaa caggtgctga attgctggct gattgcaccg   2940
ctcatgccat tcgcgtggca ttaaaaaaac cagaagttgc tggcttgtac catctggtag   3000
caaatggcac aacaacctgg cacgattacg ccgcgctagt attcgaagaa gcccgtaaag   3060
cagggattga ccttgcactt aacaaactca acgccgtacc aacaacggct tatcctactc   3120
cagcccgccg tcctcataat tctcgcctca ataccgaaaa gtttcagcag aactttgcgc   3180
ttgtcttgcc tgactggcag gtgggcgtga aacgtatgct caacgaatta tttacgacta   3240
cggcaattta acaaattttt gcatctcgct catgatgcca gagcgggatg aattaaaagg   3300
aatggtgaaa tgaaaacgcg taaaggtatt attctggctg gtggttccgg cactcgtctt   3360
tatcctgtga cgatggcagt gagtaaacaa ctgctgccga tttatgataa gccgatgatt   3420
tattatccgc tttcaacgct tatgttagcg ggtattcgcg atattcttat tatcagtacg   3480
ccacaggata caccgcgttt ccaacaattg ttgggggacg ggagtcagtg gggcttaat    3540
ctacagtata aagtacaacc gagtccggat ggcctggcgc aagcgtttat tattggtgaa   3600
gactttattg gtggtgatga ttgtgcactc gtacttggcg ataatatctt ctatggacac   3660
gacttgccga aattaatgga agctgctgtt aacaaagaaa tcggtgcaac ggtatttgct   3720
tatcacgtca atgatcctga acgttatggt gtcgtggagt ttgataataa cggtactgca   3780
attagcctgg aagaaaaacc gctggaacca aaaagtaact atgcggttac tgggctttat   3840
ttctatgaca atgatgttgt agaaatggcg aaaaacctta agccttctgc ccgtggcgaa   3900
ctggaaatta ccgatattaa ccgtatttat atggagcagg gacgtttgtc tgtcgctatg   3960
```

```
atggggcgtg gttatgcctg gttggatact ggtacacatc aaagtcttat tgaagcaagt   4020
aacttcattg ccaccattga agagcgtcag ggattaaagg tatcttgccc ggaagagatt   4080
gcttaccgta aagggtttat tgatgctgag caggtgaaag tattagccga accgctgaag   4140
aaaaatgatt atggtcagta tctgctaaaa atgattaaag gttattaata aaatgaacgt   4200
aattaaaact gaaattcctg atgtgctgat ttttgaacca aaagtttttg gtgatgaacg   4260
tggcttcttt tttgagagtt ttaaccagaa agtatttgaa gaagctgtag gacggaaggt   4320
tgaatttgtt caggataacc attctaagtc taaaataaat gtattgcgtg ggatgcatta   4380
tcaaacacaa aatactcaag gaaaactggt tcgggtaatt tctggttcag tatatgatgt   4440
tgccgtagat ttaagagaaa aatcaaagac atttggcaaa tgggtgggtg tagaattatc   4500
tgggaataat aaaagacaat tgtggatccc cgaaggtttt gcccatggtt tttatgtgtt   4560
ggaggagaat accgaatttg tttataaatg taccgatact tataaccctg ctcatgaaca   4620
cacattgcta tggaatgatc caactatcaa tataagttgg ccaatcatac aaaactgcaa   4680
gccaattatt tctgaaaaag atgctaatgg acatcttttt tcacataaaa cctatttctg   4740
aaatgcaata ttatgagttt aattagaaac agtttctata atattgctgg ttttgctgtg   4800
ccgacattag ttgcagtccc tgctttgggg attcttgcca ggctgcttgg accggagaat   4860
tttggacttt tcacactagc attcgctttg ataggatatg caagtatttt cgacgccggg   4920
attagtcgag ctgtaatcag agaaatcgct ctttatcgag aaagtgaaaa agagcaaata   4980
caaattattt cgacagcaag tgtaatcgta ctattcttag ggtggttgc agctttgtta   5040
ctttatttta gtagtaataa agttgttgag ttattgaatg ttagttccgt ttatattgaa   5100
acagcagtgc gtgcattctc tgttatttca tttataatac ctgtgtatct gattaaccag   5160
atttggcttg gttatctgga agggctagaa aaatttgcaa atataaatgt tcagagaatg   5220
atttctagca caagcttggc tatattacca gtgatatttt gttattacaa tccctcgttg   5280
ctttatgcta tgtatgggtt ggtggttggg cgtgtgattt catttttgat tagcgcaata   5340
atttgtcgag atattattct taaaagtaaa ctttacttta atgtggcaac ttgcaatcgt   5400
cttatctctt ttggtggatg gataacagtt agtaatatca taagcccaat catggcatat   5460
ttcgaccgct ttatcatctc tcatattatg ggggcttcga gaattgcatt ttatacagcg   5520
ccctcagagg gtgtatcaag gttaattaat atcccatatg ctttggcaag agctctattt   5580
cctaaattgg catatagcaa taatgatgat gaacgaaaaa aattacaact acagagctac   5640
gcaattataa gcattgtatg tctacccata gttgttattg gtgtcatttt tgcctcattc   5700
ataatgacaa catggatggg acctgattat gccttagaag cagcaactat catgaaaata   5760
cttcttgctg gtttttcttt taactcttta gcgcaaatac cttatgcata cttgcaatct   5820
atcggaaagt caaaaattac cgcatttgtg catctcatag aacttgcgcc atacttatta   5880
ttattgtatt acttcacaat gcatttcggc ataattggca cggcaatcgc ttggtcactt   5940
agaacatttt gtgattttgt tatactactt tcgatatcga gaagaaaatg attgcggttg   6000
atattgcgct tgcaacctac aatggtgcta attttattcg gcaacagatt gaatctatcc   6060
agaaacaaac ttatagaaat tggcgtctta taataagtga tgataactcg agtgatgata   6120
ctgttgatat tattaaggat atgatgtcta acgacagtcg tatctatttg gtaggaaata   6180
aaagacaagg aggggttatt cagaacttta attatgctct ttcacaaact acatctgaaa   6240
ttgtgttact atgtgaccag gatgacattt ggccggagga gcgtctggaa attcttatag   6300
```

-continued

```
ataaatttaa ggccttgcag cgtaatgatt ttgttccggc aatgatgttt actgatttga   6360
aattagtaga cgaaaataat tgtttgattg cagaaagttt ttatcgaacg aataatatta   6420
atccacaaga taatctgaaa aataataatc ttctctggcg ttcaacggta tatggctgta   6480
cttgcatcat gaataagaaa cttgttgata ttgcattgcc tatacctaca tatgcacata   6540
tgcatgatca atggttggca ttattagcga agcaatatgg taacattttt tatttcgact   6600
atgcgtctgt tcgttatagg caacattcta caaatgttgt tggtggtaga aataaaacgc   6660
catttcaaaa atttaattcc atacaaaaaa acctaaaaag gattaatttg ctagtggata   6720
gaactgttgc tttaattaaa tcaaataacg atttctatcc agggaataaa atggaaaata   6780
aaattgatta cttaaaattt ggagtgaatg aagtattacc ttatcttttt aaaggaaaca   6840
agaaagtttt ttcactttgt gtattaatta gtttggcatt acaaaaatga tatatttatt   6900
attttttttt gcactgttta tgatctgtac gtttttaaca cacaggcgac aggcattata   6960
tgttgtatct gcgttagtat ttcttttttt ggctttaacc tatccatcag gaggggactg   7020
gataggttat tttctccatt atgactgcat ggttaatgag cagtgtaata atggttttat   7080
aatgtttgaa cctggatatg aattaattgt ttccttattt ggatatttgg gatttcagac   7140
aattattatt tttatagccg ctgtaaatgt aattctaata ttaaattttg caaagcattt   7200
tgaaaacgga agttttgtta ttgttgcgat aatgtgcatg ttcctttgga gtgtttatgt   7260
tgaggcgatt agacaggctc tggccttatc tatagttata tttgggattc attctctttt   7320
tttgggtaga aaaaggaaat ttataacatt agtattattt gcgtcaactt tccatataac   7380
tgctttgatt tgttttcttc taatgactcc tctattttca aagaaattaa gcaagataat   7440
aagttatagc ctattaattt tcagtagctt ctttttcgct ttttctgaaa ccatattaag   7500
tgcactcctt gcaattttgc cagaaggatc cattgccagt gaaaaattaa gtttttactt   7560
agcaaccgag caatacaggc cacagttatc tattgggagt ggcactattc ttgacattat   7620
acttattttt ctgatatgtg taagttttaa acgaataaag aaatatatgc tcgctaatta   7680
taatgctgca aatgagatat tgcttattgg ttgctgtctt tatatttctt tcggtatttt   7740
tatcgggaaa atgatgccag ttatgactcg cattggttgg tatggttttc catttgttat   7800
agtacttctt tatattaact tgggttattc agaatatttt aagaggtata taaataaaag   7860
agggtgtggg tatagcaaat tattaattgc tttttatttt ttgctacaaa ttttgcgacc   7920
attaacatat gattatagct attataatat aatgcaccag gatactttgc tgaataggtt   7980
tgatgcatta gatgatgcat cattaagaca atcagcgaag agaaaatgtt tcgatttggg   8040
aaagatagga tatggtttct tatgtagtat ataatatcct gcattcattc ggataatttc   8100
ctatggaagt gtcctttgct ctgtctgtcc tcatttgttg aaattttatg ttaataagaa   8160
gctttagata accacttagg aactgtatgt ttgatctgtc caaaaattat attattgtaa   8220
gtgcgacggc gctggcttcc ggaggtgcat taactatatt aaagcaattt ataaaacatg   8280
catcacaaaa ttcaaatgac tatattatgt ttgtatctgc gggattggag ttgccggtct   8340
gtgataacat catttacata gaaaacacac caaaaggatg gttgaaaaga atatattggg   8400
attggttcgg ttgtcggaag tttatctcgg aacataagat taacgttaag aaagtaattt   8460
ctctacaaaa ttccagtttg aatgttcctt acgaacagat tatttacttg caccagccaa   8520
ttccttttag taaagttgat tcttttttaa aaaatatcac atccgataac gtaaagcttt   8580
ttttatataa aaagttttat tcctatttta tatttaaata tgtgaatgcc aatacaacca   8640
tcgtagtgca aacgaattgg atgaaaaaag gagtgctgga gcaatgtgat aaaattagta   8700
```

-continued ccgaaagggt ccttgttata aaacctgata tcaaagcatt taataatact aattttgatg 8760
tagatatgga tgtatctgca aaaacactct tatatccagc gacaccactt acctataaaa 8820
atcatttggt cattctgaag gcgttggtta ttttaaagaa aaagtatttt atagatgatc 8880
tgaaattcca agtgactttt gaaaagaata ggtacaaaaa ttttgataag tttgtgcaat 8940
taaataactt aagcaaaaac gttgattatc tcggcgttct ttcatactcg aacttgcaaa 9000
aaaaatatat ggcggcatct ttaatcgttt ttcctagcta tatcgaatca tatgggttac 9060
cactcatcga agctgctagt ttaggaaaaa aaatcattag tagtgatctt ccttatgccc 9120
gggatgtttt aaaggattat agcggcgtag attttgtaat ttacaataat gaagatggct 9180
gggctaaggc gttgtttaat gttttaaatg gcaattcgaa gctcaatttt aggccttatg 9240
aaaaagatag tcgttcatct tggccacagt tcttctctat tttgaaataa ggtgtattat 9300
gtttaatggt aaaatattgt taattactgg tggtacgggg tctttcggta atgctgttct 9360
aagacgtttt cttgacactg atatcaaaga aatacgtatt ttttcccggg atgaaaaaaa 9420
acaagatgac atgaggaaaa aatataataa tccgaaactt aagttctata taggtgatgt 9480
tcgcgactat tcgagtatcc tcaatgcttc tcgaggtgtt gattttattt atcatgctgc 9540
agctctgaag caagtacctt cctgcgaatt ccacccaatg gaagctgtaa aaacgaatgt 9600
tttaggtacg gaaaacgtac tggaagcggc aatagctaat ggagttaggc gaattgtatg 9660
tttgagtaca gataaagctg tatatcctat caatgcaatg ggtatttcca aagcgatgat 9720
ggaaaaagta atggtagcaa aatcgcgcaa tgttgactgc tctaaaacgg ttatttgcgg 9780
tacacgttat ggcaatgtaa tggcatctcg tggttcagtt atcccattat ttgtcgatct 9840
gattaaatca ggtagaccaa tgacgataac agaccctaat atgactcgtt tcatgatgac 9900
tctcgaagac gctgttgatt tggttcttta cgcatttgaa catggcaata atggtgatat 9960
ttttgtccaa aaggcacctg cggctaccat cgaaacgttg gctattgcac tcaaagaatt 10020
acttaatgta aaccaacacc ctgtaaatat aatcggcacc cgacacgggg aaaaactgta 10080
cgaagcgtta ttgagccgag aggaaatgat tgcagcggag gatatgggtg attattatcg 10140
tgttccacca gatctccgcg atttgaacta tggaaaatat gtggaacatg gtgaccgtcg 10200
tatctcggaa gtggaagatt ataactctca taatactgat aggttagatg ttgagggaat 10260
gaaaaaatta ctgctaaaac ttccttttat ccgggcactt cggtctggtg aagattatga 10320
gttggattca taatatgaaa attttagtta ctggcgctgc agggtttatc ggtcgaaatt 10380
tggtattccg gcttaaggaa gctggatata acgaactcat tacgatagat cgtaactctt 10440
ctttggcgga tttagagcag ggacttaagc aggcagattt tatttttcac cttgctgggg 10500
taaatcgtcc cgtgaaggag tgtgaatttg aagagggaaa tagtaatcta actcaacaga 10560
ttgttgatat cctgaaaaaa aacaataaaa atactcctat catgctgagt tcttccatcc 10620
aggctgaatg tgataacgct tatggaaaga gtaaagcagc tgcggaaaaa atcattcagc 10680
agtatgggga aacgacaaac gctaaatatt atatttatcg cttgccgaat gtattcggta 10740
agtggtgtcg accaaattat aactccttta tagcaacttt ctgccatcgc attgcaaatg 10800
atgaagctat tacaattaat gatccttcag cagttgtaaa tctggtgtat atagatgact 10860
tttgttctga catattaaag ctattagaag gagcgaacga aactggttac aggacatttg 10920
gtccaattta ttctgttact gttggtgaag tggcacaatt aatttaccgg tttaaagaaa 10980
gtcgccaaac attaatcacc gaagatgtag gtaatggatt tacacgtgca ttgtactcaa 11040

-continued

```
catggttaag ttacctgtct cctgaacagt ttgcgtatac ggttccttct tatagtgatg  11100
acagaggggt attctgtgaa gtattgaaaa cgaaaaacgc gggccagttt tcgttcttta  11160
ctgcgcatcc aggaattact cggggtggtc attatcatca ttccaaaaat gagaaattta  11220
ttgtcatccg aggaagtgct tgtttcaaat ttgaaaatat tgtcacgagt gaacgatatg  11280
aacttaatgt ttcctctgat gattttaaaa ttgttgaaac agttccggga tggacgcata  11340
acattactaa taatggctcg gatgagctag ttgttatgct ttgggcaaat gaaatattta  11400
atcgttctga accagatact atagcgagag ttttatcgtg aaaaaattga aagtcatgtc  11460
ggttgttggg actcgtccag aaattattcg actctcgcgt gtccttgcaa aattagatga  11520
atattgtgac caccttattg ttcataccgg gcaaaactac gattatgaac tgaatgaagt  11580
tttttcaaa gatttgggtg ttcgcaaacc tgattatttt cttaatgccg caggtaaaaa  11640
tgcagcagag actattggac aagttatcat taaagttgat gaggtccttg aacaggaaaa  11700
accagaagcc atgttagtac ttggcgatac taactcctgt atttcagcaa taccagcaaa  11760
gcgtcgaaga attccgatct tccatatgga ggctgggaat cgttgttttg accaacgcgt  11820
accggaagaa actaacagaa aaatagttga tcataccgct gatatcaata tgacatatag  11880
tgatatcgcg cgtgaatatc ttctggctga aggtgtacca gccgatagaa ttattaaaac  11940
cggtagccca atgtttgaag tactcactca ttatatgccg cagattgatg gttccgatgt  12000
actttctcgc ctgaatttaa cacctgggaa tttctttgtg gtaagtgccc acagagaaga  12060
aaatgttgat acccctaaac aacttgtgaa actggcgaat atacttaata ccgtggctga  12120
aaaatatgat gtcccggtag ttgtttctac tcatcctcgc actcgtaacc gcatcaacga  12180
aaacggtatt caattccata aaaatatctt gcttcttaag ccattaggat ttcacgatta  12240
caaccatctg caaaaaaatg cacgtgctgt tttatcggat agtgggacta ttacagaaga  12300
gtcctccatt atgaacttcc ctgcactcaa tatacgagaa gcgcacgaac gcccggaagg  12360
cttcgaagaa ggggcagtaa tgatggtcgg tcttgaatct gatcgcgttt tacaggcatt  12420
agaaattatt gcaacacagc ctcgtggaga agtacgctta cttcgtcagg ttagtgacta  12480
tagcatgcca aatgtttcag ataaagttct gcgtattatc cattcatata ctgactacgt  12540
taaacgggtt gtctggaagc aatactaatg aaacttgcat taatcattga tgattatttg  12600
ccccatagca cacgcgttgg ggctaaaatg tttcatgagt taggccttga attactgagc  12660
agaggccatg atgtaactgt aattacgcct gacatctcat tacaagcaat ttattctatt  12720
agtatgattg atggtataaa ggtttggcgt ttcaaaagtg gacctttaaa ggatgtaggt  12780
aaggctaaac gtgccataaa tgaaactctt ttatcttttc gcgcatggcg cgcatttaag  12840
cacctcattc aacatgatac atttgatggt atcgtttatt attcccccctc tattttttgg  12900
ggcgacttgg ttaaaaaaat aaaacaacga tgccagtgcc caagctatct gatcctaagg  12960
gatatgtttc cacagtgggt cattgatgca ggtatgttga aagccggttc accaattgaa  13020
aaatatttta ggtattttga aaaaaagtca tatcagcagg ctggccggat aggggtaatg  13080
tctgataaga atcttgagat atttcgccag accaataaag gttatccgtg tgaagtttta  13140
cgtaattggg cctcaatgac tcctgtgtct gccagcgatg attatcattc acttcgtcaa  13200
aaatacgatc taaaagataa agtcattttt ttctatggcg gtaatattgg gcatgctcag  13260
gatatggcaa acttaatgcg ccttgcgcgt aatatgatgc gttatcatga tgctcatttc  13320
ctgtttatag ggcagggtga tgaagttgag ctgataaaat ctcttgctgc agaatggaat  13380
ttaactaatt tcactcatct accttcagtg aaccaggaag agtttaaatt aattttatct  13440
```

gaagttgatg tcggcctgtt ctccctttca tctcgccatt cttcacataa tttccccgga 13500
aaattactag ggtatatggt tcaatcaatc ccgatccttg ggagtgtgaa tggcggcaat 13560
gatttaatgg atgtaattaa taagcacaga gccggtttca ttcatgttaa tggtgaagat 13620
gataaactgt ttgaatctgc acaattgctt cttagtgatt cagttttaag aaaacagcta 13680
ggtcagaacg ctaatgtgtt gttaaagtct caattttcgg ttgaatcggc ggcacatact 13740
atcgaagtcc gactggaggc tggagaatgc gtttagttga tgacaatatt ctggatgaac 13800
tttttcgcac tgcagcaaat tctgaacgtt tgcgcgctca ttatttattg cacgcatctc 13860
atcaggagaa ggttcaacgt ttacttattg catttgtacg cgacagctat gttgaacccc 13920
attggcatga gttaccgcat cagtgggaaa tgtttgtcgt catgcaaggg caattagaag 13980
tttgtttgta tgagcaaaat ggtgagatcc aaaaacagtt tgttgttgga gacggtacgg 14040
gaataagcgt cgtggaattt tccccaggag atatacatag tgtcaaatgc ctgtcaccaa 14100
aagcccttat gttggagata aaggaggggc catttgaccc actcaaagct aaggcttttt 14160
ctaagtggtt atagggcgat acaccaccgt ttattcttct atcttattct atacatgctg 14220
ggttaccatc ttagcttctt caagccgcgc aaccccgcgg tgaccacccc tgacaggagt 14280
agctagcatt tgaccacccc tgacaggatt agctagcata tgagctcgag gatatctact 14340
gtgggtaccc gggatccgtg taggctggag ctgcttcgaa gttcctatac tttctagaga 14400
ataggaactt cggaatagga actaaggagg atattcatat 14440

<210> SEQ ID NO 10
<211> LENGTH: 19
<212> TYPE: PRT
<213> ORGANISM: Artificial Sequence
<220> FEATURE:
<223> OTHER INFORMATION: example signal sequence for EPA carrier protein

<400> SEQUENCE: 10

Met Lys Lys Ile Trp Leu Ala Leu Ala Gly Leu Val Leu Ala Phe Ser
1 5 10 15

Ala Ser Ala

<210> SEQ ID NO 11
<211> LENGTH: 13043
<212> TYPE: DNA
<213> ORGANISM: Artificial Sequence
<220> FEATURE:
<223> OTHER INFORMATION: example O1A rfb locus nucleotide sequence -
O1A-EPA production strain stGVXN4411 and stLMTB10217

<400> SEQUENCE: 11
atgacgaatt taaaagcagt tattcctgta gcgggtctcg ggatgcatat gttgcctgcc 60
actaaggcga tacccaaaga gatgctacca atcgtcgaca agccaatgat tcagtacatt 120
gttgacgaga ttgtggctgc agggatcaaa gaaatcctcc tggtaactca cgcgtccaag 180
aacgcggtcg aaaaccactt cgacacctct tatgagttag aatcactcct tgagcagcgc 240
gtgaagcgtc aactgctggc ggaagtacag tccatctgtc cgccgggcgt gaccattatg 300
aacgtgcgtc agggcgaacc tttaggttta ggccactcca ttttgtgtgc gcgacctgcc 360
attggtgaca acccatttgt cgtggtactg ccagacgttg tgatcgacga tgccagcgcc 420
gacccgctac gttacaacct tgctgccatg attgcacgtt tcaacgaaac gggccgcagc 480
caggtgctgg caaaacgtat gccgggtgac ctctctgaat actccgtcat ccagactaaa 540

-continued

```
gagccgctgg accgtgaggg taaagtcagc cgcattgttg aatttatcga aaaaccggat    600
cagccgcaga cgctggactc agacatcatg gccgtaggtc gctatgtgct ttctgccgat    660
atttggccgg aactggaacg tactcagcct ggtgcatggg gacgtattca gctgactgat    720
gctattgccg agctggcgaa aaaacaatcc gttgatgcaa tgctgatgac cggcgacagt    780
tacgactgcg gcaaaaaaat gggctatatg caggcgtttg tgaagtatgg cctacgcaac    840
ctgaaagaag gggcgaagtt ccgtaaaggt attgagaagc tgttaagcga ataatgaaaa    900
tctgaccgga tgtaacggtt gataagaaaa ttataacggc agtgaaaatt cgcagcaaaa    960
gtaatttgtt gcgaatcttc ctgccgttgt tttatataaa ccatcagaat aacaacgagt   1020
tagcagtagg gttttattca aagttttcca ggattttcct tgtttccaga gcggattggt   1080
aagacaatta gcgtttgaat ttttcgggtt tagcgcgagt gggtaacgct cgtcacatca   1140
taggcatgca tgcagtgctc tggtagctgt aaagccaggg gcggtagcgt gcattaatac   1200
ctctattaat caaactgaga gccgcttatt tcacagcatg ctctgaagta atatggaata   1260
aattaagcta gcgtgaagat acttgttact aggggcgcag gatttattgg ttctgctgta   1320
gttcgtcaca ttataaataa tacgcaggat agtgttgtta atgtcgataa attaacgtac   1380
gccggaaacc tggaatcact tgctgatgtt tctgactctg aacgctatgt ttttgaacat   1440
gcggatattt gcgatgctgc tgcaatggcg cggatttttg ctcagcatca gccggatgca   1500
gtgatgcacc tggctgctga aagccatgtg gatcgttcaa ttacaggccc tgcggcattt   1560
attgaaacca atattgttgg tacttatgtc cttttggaag cggctcgcaa ttactggtct   1620
gctcttgatg gcgacaagaa aaatagcttc cgttttcatc atatttctac tgacgaagtc   1680
tatggtgatt tgcctcatcc tgacgaagta aataataaag aacaattacc cctctttact   1740
gagacgacag cttacgcgcc tagtagtcct tattccgcat caaaagcatc cagcgatcat   1800
ttagtccgcg cgtggaaacg tacctatggt ttaccgacta ttgtgactaa ctgttcgaat   1860
aactacggtc cttatcactt tccggaaaaa ttgattccac tagtaattct taatgctctg   1920
gaaggtaagg cattacctat ttatggcaaa ggggatcaaa ttcgtgactg gctgtatgtt   1980
gaagatcatg cgcgtgcgtt atataccgta gttactgaag gtcaagcggg tgaaacctat   2040
aacattggcg gacacaacga aaagaaaaac atcgatgttg tgctgactat ttgtgatttg   2100
ttggacgaga tagtcccgaa agagaaatct tatcgtgagc aaattactta tgttgctgat   2160
cgcccagggc atgatcgccg ttatgcgatt gatgctgaga agattggtcg cgaattggga   2220
tggaaaccac aggaaacgtt tgagagtggg attcgtaaaa cggtggaatg gtatttggct   2280
aatgcaaaat gggttgataa tgtgaaaagt ggtgcctatc aatcgtggat tgaacagaac   2340
tatgagggcc gccagtaatg aatatcctcc tttttggcaa aacagggcag gtaggttggg   2400
aactacagcg tgctctggca cctctgggta atttgattgc tcttgatgtt cactccactg   2460
attactgtgg tgattttagt aaccctgaag gtgtggctga aacagtcaaa agaattcgac   2520
ctgatgttat tgttaatgct gcggctcaca ccgcagtaga taaggctgag tcagaacccg   2580
aatttgcaca attactcaat gcgactagcg ttgaatcaat tgcaaaagcg gcaaatgaag   2640
ttggggcttg ggtaattcat tactcaactg actacgtatt ccctggaaat ggcgacacgc   2700
catggctgga gatggatgca accgcaccgc taaatgttta cggtgaaacc aagttagctg   2760
gagaaaaagc attacaagag cattgtgcga agcacctaat tttccgtacc agctgggtct   2820
atgcaggtaa aggaaataat ttcgccaaaa cgatgttgcg tctggcaaaa gagcgtgaag   2880
aactagccgt tattaatgat cagtttggtg cgccaacagg tgctgaactg ctggctgatt   2940
```

gtacggcaca tgccattcgt gtcgcactga ataaaccgga tgtcgcaggc ttgtaccatt 3000
tggtagccag tggtaccaca acctggtacg attatgctgc gctggttttt gaagaggcgc 3060
gcaatgcagg cattcctctt gcactcaaca agctcaacgc agtaccaaca actgcctatc 3120
ctacaccagc tcgtcgtcca cataactctc gccttaatac agaaaaattt cagcagaatt 3180
ttgcgcttgt attgcctgac tggcaggttg gtgtgaaacg catgctcaac gaattattta 3240
cgactacagc aatttaatag tttttgcatc ttgttcgtga tggtggagca agatgaatta 3300
aaaggaatga tgaaatgaaa acgcgtaaag gtattatttt agcgggtggt tctggtactc 3360
gtctttatcc tgtgactatg gtcgtcagta aacagctatt acctatatat gataaaccga 3420
tgatctatta tccgctttct acactgatgt tagcgggtat tcgcgatatt ctgattatta 3480
gtacgccaca ggatactcct cgttttcaac aactgctggg tgacggtagc cagtggggcc 3540
tgaatcttca gtacaaagtg caaccgagtc cggatggtct tgcgcaggca tttattatcg 3600
gtgaagagtt tattggtggt gatgattgtg ctttggtact tggtgataat atcttctacg 3660
gtcacgacct gcctaagtta atggatgccg ctgttaacaa agaaagtggt gcaacggtat 3720
ttgcctatca cgttaatgat cctgaacgct atggtgtcgt tgagtttgat aaaaacggta 3780
cggcgatcag cctggaagaa aaaccgctac aaccaaaaag taattatgcg gtaaccgggc 3840
tttattttta tgataacgac gttgtcgaaa tggcgaaaaa tcttaagcct tctgcccgcg 3900
gtgaactgga aattaccgat attaaccgta tctatatgga acaagggcgt ttatctgttg 3960
ccatgatggg gcgtggttat gcgtggttag acacggggac acatcagagc ctgattgagg 4020
caagcaactt tattgcaaca attgaagagc gtcaggggct gaaagtttcc tgcccggaag 4080
aaattgctta ccgtaaaggg tttgttgatg ctgagcaggt gaaagtatta gctgaacctc 4140
tgaaaaaaaa tgcttatggt cagtatctgc tgaaaatgat taaaggttat taataaaatg 4200
aacgtaatta aaacagaaat tcctgatgta ctgatttttg aaccgaaagt ttttggtgat 4260
gagcgtggtt tctttttga gagctttaac cagaaggttt ttgaggaagc tgtaggccgc 4320
aaagttgaat ttgttcagga taaccattcg aagtctagta aaggtgtttt acgcgggctg 4380
cattatcagt tggaacctta tgcacaagga aaattggtgc gttgcgttgt cggtgaagtt 4440
tttgacgtag ctgttgatat tcgtaaatcg tcatcgactt ttggcaaatg ggttggggtg 4500
aatttatctg ctgagaataa gcggcaattg tggattcctg agggatttgc acatggtttt 4560
ttagtgctga gtgagacggc ggagtttttg tataagacga caaattatta tcatcctcag 4620
agtgatagag gaataaaatg ggatgatcca agcatcaata tttcatggcc agtcgattca 4680
caagtgctgc tatcagctaa agataataag catcctccat taacaaagat tgaaatgtat 4740
agttaagatc acgataaatc ttggaagggt tgcaaaattg aataaaatag tgagcaaaag 4800
tgaaataagg aacgtaatcc acaatgctgg ctatatgatg attactcaga tagctttata 4860
tgttgcacca ttatttatac tgagttatct gttaaaaaca ctgggggttg cacagtttgg 4920
taattatgcc ttaatactat caatcgttgc atatttacag attataacgg attatggttt 4980
ttcttttagt gcaagtcgtg cgatctcaca gaatagagag gacaaagaat atatatcaaa 5040
aatttatctg tcaactatga ctatcaagtt ggcgatatgc gctttcttat tcttattgct 5100
catgctattt ttaaatcttt tgcctgtgca agctgaatta aaacaaggaa tattatatgg 5160
atatcttctt gtaataggaa atactttcca accacaatgg tttttccaag gtatcgaaaa 5220
attaaaaatc atagcccttt ctaatgttat atcaagatgc gccgcgtgtt tacttgtatt 5280

```
tatctatgtg aggaatagcg aggatttaca aaaagcactt ttagtacagt cacttccatt   5340
agtaatttct gcgattggat taaatatatt tatattgaaa tatatcaata ttatttttcc   5400
ggaaaaaaaa ttatttaagg taattttaaa agaaggtaag gatttttttc ttgcatcact   5460
ttattctgtt attctcaata atagtggcat ttttctatta gggattttta ctaatcctgt   5520
tattgttggt gtatatgccg ccgctgaaaa gatagtcaag gccgtattgt cgctatttac   5580
accactgacg caagctatat atccttataa ttgtcgtaag ttttcactat ccgtatttga   5640
cggcattgag gcagcaaaaa aaactggtat accaattata attttagcat ttatagctgc   5700
tgttatcgtt gcaattacct tacctgttgc aatcgactat cttaattttc caaaagaaac   5760
aatttttgta ggtcaaatat taagtgcatg gatctttttt ggtgttctta ataatgtatt   5820
cggcattcag atattgagtg catcaggaag aagtaaaata tatagtagga tggtattcgt   5880
atcagcgctt ataacattac ttttgattac tctattattg cagttttgta acgccactgg   5940
agtggcatgt gcaatattat tgggtgaaat gttcttatca atattgttac ttaagcgata   6000
taaaaaaata atttaaggaa tagttatgaa gaagttatta ttagtgttcg gtactaggcc   6060
tgaagcaata aagatggcct ctatcattga attattaaaa aaagattgta gattcgaata   6120
taaaatatgt gtgacaggcc aacataaaga gatgcttgat caagttatgc aagtatttga   6180
tgttaaacct gattataatt tacggattat gcagcctggg caaacattag tatctatagc   6240
aacaaatata ctctcacggt taagtgaagt tttaattata gaaaagccag atattatact   6300
tgtgcatggg gatacaacga ctacccttgc tgctacttta gctgggtatt accaccaaat   6360
aaaagtttgt catgtggaag caggattaag aacaggggat atttactctc cttggcctga   6420
agagggcaat cgtaaagtta caggggcatt agcatgtatt catttcgccc caacagagag   6480
atcaaaagat aatctcctga gggagggggt caaagtaaat aatatatttg taacgggtaa   6540
taccgtcatc gactctttat ttattgcaaa agatatcata gataatgacc ctaatataaa   6600
gaacgcttta cataataaat ttaattttct tgataaaagc cgacgagtag tacttataac   6660
aggtcatcga agagaaaatt tcgggaaagg ttttgaagat atatgctttg caataaagga   6720
attagctttc atttatccta atgtagattt tatttatccg gtgcatctta atcccaatgt   6780
aatggaacca gtacatcgta tattagataa tatatgtaat atttacctta ttgagccctt   6840
ggattatttg ccttttgttt atttaatgaa tgagtcatat ttaatattga ctgattcagg   6900
ggggatacaa gaagaagcgc cttcgttagg taaaccggtt ttggttatgc gtgatactac   6960
tgaacgccct gaggcggttg aggctggtac tgttgtatta gtggggactt ctaagataaa   7020
aatagtaaat aaagtaacgg agctattaaa caatgctgat atctacaatg ctatgtctct   7080
gttacataat ccatatggcg atggaacagc tgctcaaaaa attcttaatg tgctcgccca   7140
agagctaatt taatttaagc taaaaatatg ttattaatta ttgctgatta tccaaacgaa   7200
atgaatatgc gcgagggagc tatgcaacga atagatgcga tagactctct cattcgagat   7260
cgcaagcgag tgtatttgaa tatttcattc aaaaagcatc tagttcgctc aaatagttcc   7320
tttaataatg ttatagttga aaatctaaat gcaattattc acagaaacat cataaaacag   7380
tacatgcaaa aatcaacaac tatatatgtt cattctgttt ataatttatt aaaggttata   7440
acgctcattg atctaaaaaa aacaattctt gatatacatg gtgttgtacc ggaagaactt   7500
ttggcagata ataaaaaatt acttagtaaa gtatataaca tggtggaaaa aaaaggtgtc   7560
cttggatgca aaaaattaat acacgtcagt acagaaatgc aaaaacacta tgaagcaaaa   7620
tatggagtaa acttggctga aaggtcaata gtgctcccga tttttgaata taaaaatata   7680
```

acccaatcgc aaaacaaatg gacagaaaat aaaatacgaa gtatctatct tggaggatta 7740
caaacatggc aaaatattga taaaatgatt caagtttgtg atgacacagt gataaacaat 7800
gaagcaggta agtatgaatt caactttttc atcccacaga gtaacttgga agggtttata 7860
gataaatatt cgttaaaatt acataatatc aatgctaatg catctacgct atcacgtgat 7920
gaagtaattc cctttctaaa agaatgtcat attggttttg tattgcgcga tgatataata 7980
gtaaacagag ttgcgtgccc tacaaaattg gttgaatatt tagagtgtgg tgtcgttcca 8040
gttgtgctct ccccacttat aggtgatttt tattcgatgg gatatcaata cattactaca 8100
gaggaaatgg ctaacagaag tataagtttg ttggatcttg aaaaaatggc tgcacataat 8160
ttacaaattt tgacttctta tcagaagaga acctacaagg cacagaaaga acttattgct 8220
caactgtgct gaatttttta catatataaa attatgtaag catatcgcgg gtcaggtaat 8280
tgtatgcgta tcaaatataa agataacggt tatatattat gttttctatt atgtttcatt 8340
ttgagctact tagttttact caaatctgac tactttcctg ctgattttct gccatataca 8400
gaaatatacg atgggacata cggagaaatc aataatattg agcctgcctt tttatattta 8460
acacggttgt ttcattattt aaatttcccc tatatatttt ttgcaatgtt agtttgtgcc 8520
ttatgtttaa gttggaaaat aaaatatgca agaaaaataa ttaaagatag ttatatatat 8580
ttgttcttgt atgtatatgt atcattttat gtgtttttgc atgaaatgac tcaattgcgc 8640
atagcaattg cagtcactat gtgctatgtg tcggtttatt attactttta taaaaattgt 8700
attaaacatg cactgccatg gatggtgttg gctattttgt ttcattacag cgccttgctt 8760
ttatttatgt cattatttat atacagttat aggaggttat taatagtaat tatagggttt 8820
gtaatatgta tgagcttttt aaacgtgtat gcagatacaa ttgcactata tttgccaaat 8880
gaaaaaatag taaattattt atatagtatt tcatcatcat tagacaatag aaatgatttg 8940
gcaatattca acctgaataa tataatattt ttatcaatat ttattttgat cttttatctt 9000
agccgatata taaaattaaa tgataatgag gcgaagttta ttaagtatgt gcaatgttca 9060
ggaatattag cctttttgtat tttctttctg gctagtggag tcccggtcat tgcttatcga 9120
actgcagagt tgctgcgaat attttatccg atggctttag tattaatcct ttcgcatata 9180
aaaaataata atatgcgtta ttttattgca gtcattatag ttatcctttc aggcttaatg 9240
ttgtttataa cactaagggc tgtatcaata gttggtcaag gattataaaa tgaatgttgc 9300
tattttgttg tctacgtata atggcgaaaa atatttagag gaacaactgg attcattgct 9360
gcttcaaagt tatcaggatt ttgtagtgta tatccgtgat gacggatcat ctgatagaac 9420
tgtaaatata ataaaccaat acgtaatgaa agataacaga tttattaacg tgggtaattc 9480
agaaaatctt ggttgtgctg cttcgtttat taatttatta agaaatgctt cagccgatat 9540
ttatatgttt tgtgaccaag atgattattg gcttccgaat aaattacagc gtgctgtgga 9600
ttatttttcg gctattgatc ctttacaacc taccttgtat cattgcgatc taagcgttgt 9660
tgatgaaaaa cttaatatta tacaaaattc atttttgcag catcagaaaa tgtcagcgta 9720
tgattcaatg agaaaaaata atcttttcat acaaaatttt gttgttggtt gttcatgtgc 9780
tgttaatgct tcacttgcgg aatttgttct ttcgcgaatt ggagagcagc atgtaaaaat 9840
gatagctatg catgactggt ggttagccgt gactgcaaaa ctttttggtc gaatccattt 9900
tgataatact caaacgattc tttatcgaca acatcagggc aatgtattag gtgcaaaatc 9960
atcaggtatg atgcgtttta ttcgattagg attaaatggg caagggattt cgcgagtagt 10020

-continued

```
atcttttaga aaaaaagttt gtgcgcaaaa taagcttctt ttagatgtct atgataaaga  10080
tttaaatctt gagcaaaaaa aatctatcag gcttgtaatt gagggcctta aagagaactc  10140
ttcaattgct gacctttttaa aatgtttcta tcatggtagc tatatgcaag gttttaaacg  10200
taatcttgcc ttaatatatt cagttcttta cacaaaaaaa agaagatagt gtatccttat  10260
gaaaaaaatt gctattatcg gtactgttgg cataccagca tcatatggcg gatttgaaac  10320
attagttgaa aatttaacaa gatacaattc ctcgggagtt gaatataatg tttttgttc  10380
atcgtttcac tacaaatccc accaaaaaaa acataatggg gcccgtttaa tttatattcc  10440
gcttaaagcc aatggatggc agagcattgc gtatgacata atttcgttag catattctat  10500
tttttgaag cctgatgtga ttctgatttt aggggtttct ggttgttcat ttttgccttt  10560
cttcaaactc ttaacacgcg ctaagtttat tactaatatt gatggcctgg aatggcgaag  10620
agataaatgg aattcaaaag tgaaacgttt cttaaaattt tcagaaaaaa tcgcagttca  10680
atattcggat gtcgttatta cggataatga ggcaatttct gagtacgttt ttaacgagta  10740
taataaagat agccgagtta ttgcctatgg aggggatcat gcatggttaa atactgagga  10800
tgtatttaca acaagaaatt ataaaagcga ttactacctt tctgtatgtc gtatcgaacc  10860
cgaaaacaat gtagaattaa ttttaaaaac attttcaaag ctaaaatata aaataaaatt  10920
tattggaaat tggaatggca gcgagtttgg aaagaaactt aggctgcatt attctaacta  10980
tccaaatatt gaaatgattg atccgattta tgatcttcaa caattatttc acttacgaaa  11040
taattgcata ggatatatac atggtcattc ggctggagga acaaaccctt ctttagtcga  11100
ggcaatgcat tttagtaaac ctatatttgc atatgattgt aagtttaata ggtacactac  11160
tgaaaatgaa gcatgttatt tttctaatga atctgacctc gcagagaaaa tcataatgca  11220
ttgtgagcta tcattaggtg tctctggcac gaaaatgaaa gaaattgcta accagaaata  11280
cacttggaga cgaatagcag aaatgtatga ggattgctat taactctgtt aaacttcaaa  11340
tcttttacaa tatatggcat gactataagc gcattaattg tttttcaagc cgctctcgcg  11400
gtgaccaccc cctgacaggg gatccgtgta ggctggagct gcttcgaagt tcctatactt  11460
tctagagaat aggaacttcg gaataggaac taaggaggat attcatatgg ataaagccgt  11520
aagcatataa gcatggataa gctatttata ctttaataag tactttgtat acttatttgc  11580
gaacattcca ggccgcgagc attcagcgcg gtgatcacac ctgacaggag tatgtaatgt  11640
ccaagcaaca gatcggcgta gtcggtatgg cagtgatggg acgcaacctt gcgctcaaca  11700
tcgaaagccg tggttatacc gtctctattt tcaaccgttc ccgtgagaag acggaagaag  11760
tgattgccga aaatccaggc aagaaactgg ttccttacta tacggtgaaa gagtttgtcg  11820
aatctctgga aacgcctcgt cgcatcctgt taatggtgaa agcaggtgca ggcacggatg  11880
ctgctattga ttccctcaaa ccatatctcg ataaaggaga catcatcatt gatggtggta  11940
acaccttctt ccaggacact attcgtcgta atcgtgagct ttcagcagag ggctttaact  12000
tcatcggtac cggtgtttct ggcggtgaag agggggcgct gaaaggtcct tctattatgc  12060
ctggtggcca gaaagaagcc tatgaattgg tagcaccgat cctgaccaaa atcgccgccg  12120
tagctgaaga cggtgaacca tgcgttacct atattggtgc cgatggcgca ggtcactatg  12180
tgaagatggt tcacaacggt attgaatacg gcgatatgca gctgattgct gaagcctatt  12240
ctctgcttaa aggtggcctg aacctcacca acgaagaact ggcgcagacc tttaccgagt  12300
ggaataacgg tgaactgagc agttacctga tcgacatcac caaagatatc ttcaccaaaa  12360
aagatgaaga cggtaactac ctggttgatg tgatcctgga tgaagcggct aacaaaggta  12420
```

ccggtaaatg gaccagccag agcgcgctgg atctcggcga accgctgtcg ctgattaccg 12480
agtctgtgtt tgcacgttat atctcttctc tgaaagatca gcgtgttgcc gcatctaaag 12540
ttctctctgg tccgcaagca cagccagcag gcgacaaggc tgagttcatc gaaaaagttc 12600
gtcgtgcgct gtatctgggc aaaatcgttt cttacgccca gggcttctct cagctgcgtg 12660
ctgcgtctga agagtacaac tgggatctga actacggcga aatcgcgaag attttccgtg 12720
ctggctgcat catccgtgcg cagttcctgc agaaaatcac cgatgcttat gccgaaaatc 12780
cacagatcgc taacctgttg ctggctccgt acttcaagca aattgccgat gactaccagc 12840
aggcgctgcg tgatgtcgtt gcttatgcag tacagaacgg tattccggtt ccgaccttct 12900
ccgcagcggt tgcctattac gacagctacc gtgctgctgt tctgcctgcg aacctgatcc 12960
aggcacagcg tgactatttt ggtgcgcata cttataagcg tatcgataaa gaaggtgtgt 13020
tccataccga atggctggat taa 13043

<210> SEQ ID NO 12
<211> LENGTH: 13790
<212> TYPE: DNA
<213> ORGANISM: Artificial Sequence
<220> FEATURE:
<223> OTHER INFORMATION: example O2 rfb locus nucleotide sequence - O2-EPA production strain stGVXN4906

<400> SEQUENCE: 12
atgacgaatt taaaagcagt tattcctgta gcgggtctcg ggatgcatat gttgcctgcc 60
actaaggcga tacccaaaga gatgctacca atcgtcgaca agccaatgat tcagtacatt 120
gttgacgaga ttgtggctgc agggatcaaa gaaatcctcc tggtaactca cgcgtccaag 180
aacgcggtcg aaaaccactt cgacacctct tatgagttag aatcactcct tgagcagcgc 240
gtgaagcgtc aactgctggc ggaagtacag tccatctgtc cgccgggcgt gaccattatg 300
aacgtgcgtc agggcgaacc tttaggttta ggccactcca ttttgtgtgc gcgacctgcc 360
attggtgaca acccatttgt cgtggtactg ccagacgttg tgatcgacga tgccagcgcc 420
gacccgctac gttacaacct tgctgccatg attgcacgtt tcaacgaaac gggccgcagc 480
caggtgctgg caaaacgtat gccgggtgac ctctctgaat actccgtcat ccagactaaa 540
gagccgctgg accgtgaggg taaagtcagc cgcattgttg aatttatcga aaaaccggat 600
cagccgcaga cgctggactc agacatcatg gccgtaggtc gctatgtgct ttctgccgat 660
atttggccgg aactggaacg tactcagcct ggtgcatggg gacgtattca gctgactgat 720
gctattgccg agctggcgaa aaaacaatcc gttgatgcaa tgctgatgac cggcgacagt 780
tacgactgcg gcaaaaaaat gggctatatg caggcgtttg tgaagtatgg cctacgcaac 840
ctgaaagaag ggcgaagtt ccgtaaaggt attgagaagc tgttaagcga ataatgaaaa 900
tctgaccgga tgtaacggtt gataagaaaa ttataacggc agtgaaaatt cgcagcaaaa 960
gtaatttgtt gcgaatcttc ctgccgttgt tttatataaa ccatcagaat aacaacgagt 1020
tagcagtagg gttttattca aagttttcca ggattttcct tgtttccaga gcggattggt 1080
aagacaatta gcgtttgaat ttttcgggtt tagcgcgagt gggtaacgct cgtcacatca 1140
taggcatgca tgcagtgctc tggtagctgt aaagccaggg gcggtagcgt gcattaatac 1200
ctctattaat caaactgaga gccgcttatt tcacagcatg ctctgaagta atatggaata 1260
aattaagtga aaatacttgt tactggtggc gcaggattta ttggttcagc tgtagttcgt 1320
cacattataa ataatacgca ggatagtgtt gttaatgtcg ataaattaac gtacgccgga 1380
aaccgggaat cacttgctga tgtttctgat tctgaacgct atgtttttga acatgcggat 1440
atttgcgatg cacctgcaat ggcacggatt tttgctcagc atcagccgga tgcagtgatg 1500
cacctggctg ctgaaagcca tgttgaccgt tcaattacag gccctgcggc atttattgaa 1560
accaatattg ttggtactta tgtccttttg gaagccgctc gcaattactg gtctgctctt 1620
gatagcgaca agaaaaatag cttccgtttt catcatattt ctactgacga agtctatggt 1680
gatttgcctc atccagatga agtaaataat acagaagaat tacccttatt tactgagacg 1740
acagcttacg cgccaagcag cccttattcc gcatccaaag catccagcga tcatttagtc 1800
cgcgcatgga aacgtacgta tggtttaccg accattgtga ctaattgctc gaacaactat 1860
ggtccgtatc acttcccgga aaagcttatt ccattggtta ttcttaatgc actggaaggt 1920
aaggcattac ctatttatgg caaaggggat caaattcgcg actggttgta tgtagaggat 1980
catgctcgtg cgttatatac cgtcgtaacc gaaggtaaag cgggtgaaac ttataacatt 2040
ggcggacaca acgaaaagaa aaacatcgat gttgtgctga ctatttgtga tttgttggat 2100
gagattgtac cgaaagagaa atcttatcgt gagcaaatta cttatgttgc tgatcgccca 2160
gggcatgatc gccgttatgc aattgatgcc gataaaatta gccgcgaatt gggctggaaa 2220
ccacaggaaa cgtttgagag cgggattcgc aaaacggtgg aatggtatct ggctaataca 2280
aattgggttg agaatgtgaa aagcggtgct tatcagtcat ggatcgaaca aaactatgag 2340
ggccgtcagt aatgaatatc ctgcttttcg gcaaaacagg gcaggtgggt tgggaactgc 2400
agcgtgctct ggcgccgctg ggtaatctga tcgctcttga tgttcactcc actaattatt 2460
gtggagattt cagcaacccc gaaggtgtgg cagaaaccgt caaaaaaatt cgtcctgacg 2520
ttattgttaa tgctgctgct cacactgcag tagataaagc agaatcagaa ccggatttcg 2580
cacaattact taacgcgaca agcgtcgaag cgattgcaaa agctgctaat gaagtcgggg 2640
cctgggttat acactactct actgattatg ttttcccagg cagtggtgac gcgccatggc 2700
tggaaacgga tgcaacagca ccgctaaatg tttacggtga aacaaaatta gctggggaaa 2760
aggcattaca agaacattgc gcaaagcatc ttattttccg taccagctgg gtatacgctg 2820
gtaaaggaaa taactttgct aaaacgatgt tgcgtttggc aaaagaacgc gaagaactgg 2880
ctgtgataaa cgatcagttt ggcgcaccaa caggtgctga attgctggct gattgcaccg 2940
ctcatgccat tcgcgtggca ttaaaaaaac cagaagtcgc tggcttgtac catctggtag 3000
caagtggcac aacaacctgg cacgattatg ctgcgctggt tttgaagag gcgcgcaaag 3060
cagggattaa tcttgcactt aacaaactta acgccgtgcc aacaacggcc tatcccacac 3120
cagcccgtcg accccataac tctcgcctca atacagaaaa gtttcagcag aactttgcgc 3180
ttgtcttgcc tgactggcag gtgggcgtga aacgtatgct caacgaatta tttacgacta 3240
cggcaattta acaaattttt gcatctcgct catgatgcca gagcgggatg aattaaaagg 3300
aatggtgaaa tgaaaacgcg taaaggtatt attctggctg gtggttccgg cactcgtctt 3360
tatcctgtga cgatggcagt gagtaaacaa ttgctgccga tttatgataa gccgatgatt 3420
tattatccgc tttcaacgct tatgttagcg ggtattcgcg atattcttat tattagtacg 3480
ccacaggata caccgcgttt ccaacaatta ttgggggacg ggagccagtg ggtcttaat 3540
ctacagtata aagtacaacc gagtccggat ggcctggcgc aagcgtttat tattggcgaa 3600
gactttattg gtggtgatga ttgtgcactc gtacttggcg ataatatctt ctatggacac 3660
gacttgccga aattgatgga agctgctgtt aacaaagaaa gcggtgcaac ggtatttgct 3720

-continued

```
tatcacgtta atgatcctga acgctatggt gtcgtggagt ttgataataa cggtacggca   3780
attagcctgg aagaaaaacc gctggagcca aaaagcaact atgcggttac tgggctttat   3840
ttctatgaca atgacgttgt ggaaatggct aaaaacctta agccttctgc ccgtggcgaa   3900
ctggaaatta ccgatattaa ccgtatttat atggaacaag gacgtttgtc tgtagccatg   3960
atggggcgtg gctatgcatg gttggataca gggacgcatc aaagccttat tgaagcaagt   4020
aacttcattg caacaattga agagcgtcag ggattaaagg tatcttgccc ggaagagatt   4080
gcttaccgta aagggtttat tgatgccgag caggtgaaag tattagccga accgcttatc   4140
aagaatcaat atggtcaata tttgctgaaa atgatcagcg aatagtatat gggaactcaa   4200
tgatggatat taaattaatc tctttgcaaa aacatgggga tgagcgcggt gcattaattg   4260
ctcttgaaga gcaacgaaat ataccttttcg aagtcaaaag aatatattac atacttgaga   4320
ctcttaatgg agtaagacgc ggatttcatg cgcacaaggt tactcgtcag ttagctattg   4380
tagtcaaggg agcttgtaaa tttcatctgg ataatggtaa agaaacaaag caggtggaac   4440
ttaatgatcc aacaattgcg ttgctgatag aaccctatat atggcatgaa atgtatgatt   4500
ttagtgatga ttgtgtgctg cttgtaattg cggatgattt ctataaagag tctgattata   4560
tccgcaatta tgatgatttt attagaagag taaattcaat tgagaattca taagctaagt   4620
gacgtccaga caacatcaat tggtgatgga acaactatct ggcagtttgt tgtgatacta   4680
aaaggtgctg taattggtaa taattgcaac atctgtgcaa ataccttaat tgaaaataac   4740
gttgtaattg gtaacaatgt cacagtcaaa agcggtgtgt atatttggga tggcgttaaa   4800
atagaggata atgtttttat tggtccttgt gtagcattta caaatgataa gtatcctcgc   4860
tctaaagtct atcctgatga atttttgcaa acaataatac gcaaaggagc atcaataggt   4920
gctaacgcaa ccatcctgcc aggaattgaa attggtgaaa aagcaatcgt tggtgcgggg   4980
agtgttgtaa ccaaaaatgt accgccatgc gcaatagtag taggtaatcc agctcgattt   5040
attaaatggg tagaggataa tgaataaaat tgattttttta gatcttttttg caattaacca   5100
gcgacagcac aaagaattag tctctgcgtt tagtagggtg ctagattctg gttggtatat   5160
catgggcgaa gaacttgagc agttcgagaa agagttcgca gaatactgtg gagttaagta   5220
ttgcattggt gtagcaaatg gccttgatgc gttgatacta gtattgaggg catggaaaga   5280
acttggctat cttgaagacg gtgacgaggt attagtaccg gcaaatacat atattgcttc   5340
tattcttgct ataacagaga acaaacttgt tcctgttctt gttgaaccag atatagaaac   5400
ttataatatt aatcctgctt taattgaaaa ttacattacg gaaaaaacta aagcaatatt   5460
accggttcac ttatatggtc tattgtgcaa tatgccagaa attagtgcaa tcgccagaaa   5520
atataatctg ttgattcttg aagattgtgc acaagcacat ggtgcaatac gtgatggtcg   5580
caaagctgga gcttgggggg atgctgcagg atttagtttt tatccaggaa aaaaccttgg   5640
agctttgggg gatgcgggag ctgttactac aaataatgca gaattatcct caactataaa   5700
agctttgcga aattatgggt cacataagaa atatgaaaat atttatcagg gattgaatag   5760
tcgattggat gaactgcaag cagccttatt gcgtgtaaaa atccatacat taccggaaga   5820
tactgcgatt cggcaaagga ttgctgaaaa atatattcgt gaaataaaaa accctgcgat   5880
tacgttacca gtgtacgaag gccaaggtgc gcatgtttgg catttatttg tagtaagaat   5940
cgctaatcgt gaaaaattcc agtcatactt attagagaag ggtatcaaaa ccttaattca   6000
ctatccatta ccaccccata agcagcaagc atatcaaaat atgtctagcc ttagccttcc   6060
aattactgag caaattcatg atgaagtcat ttctttacct ataagtccgg taatgagtga   6120
```

agatgatgtc aattatgtaa tcaaaatggt caatgattac aagtaatgaa aaaatttctt 6180
caggtaacta tattatccgc tatctataca ttcattaaaa tgattgcggg ttttatcatc 6240
ggtaaggtag tagcaattta tacagggcca tcaggggtag caatgcttgg ccaagtgcaa 6300
agtttaatca caatagttgc aggtactacc tctgcacctg taagcacagg ccttgttcga 6360
tatactgcgg aaaattggca agaaggacaa gaagcatgcg cgccatggtg gcgcgcatgc 6420
ttaagggtta ctctgttttt attcttgctt attattcccg ttgttattat attgtcgaaa 6480
aatattagtg agttactttt tagcgatgga caatacacat ggttaatcat tttcgcatgt 6540
tgtatattgc cattctccat tataaataca ttgatcgctt cagttttaaa tggtcaacaa 6600
ttttataagc aatatatatt ggttgggatg ttttctgtat tcatttctac tatgtttatg 6660
attttgttga ttgtagctta taatcttaaa ggtgcattga ttgccacagc tataaatagt 6720
gctattgctg gtcttgtatt ggttttattt tgtctcaata aatcttggtt tagatttaaa 6780
tattggtggg gtaaaacgga taaagacaaa attataaaaa ttattcatta tactctgatg 6840
gctctggttt ctgttatctc catgcctaca gcattgatgt gtattagaaa aatattgatt 6900
gctaaaactg gttgggagga tgcagggcaa tggcaggccg tatggaagat atctgaggtt 6960
tatcttggtg ttgtgacaat tgctttgtca acatatttct taccaagatt gacaattata 7020
aaaacaagtt tccttataaa aaaagaagta aatagtacta tattatacat aatatctatt 7080
acttcattca tggcgttgag tatctattta ttccgcgatt tggtaataac agttttattt 7140
actgaacagt ttcgctcagc tcgtgaatta tttttattac aacttatagg ggatgtaata 7200
aaaattgctg ggtttcttta tgcataccct cttcaaagtc aggggcatac taaactattc 7260
atcagttcag aagtgatttt ttctatgctc tttatcatta ccacctatat ttttgttgta 7320
aattatggag tacatggtgc taacataagt tatgtcatta catatagttt atattttgtg 7380
tttgcatttg tgtttactaa ttttattaat gttagaagaa ataattaaaa acagaggttg 7440
aattttgaaa ataattatac ctgtcttagg atttggcagg gctggtggtg aaagagttct 7500
ttctaagctg gcaactgaat tgatgaatta tggacatgat gtaagttttg ttgttccaga 7560
taatagaact aatccatatt atgctaccac agcaaaaatt gtcacgagta aatctagtca 7620
aaaccgtgta aaaatattga gaatcattaa aaattactat aatctgtggc gtaaatgcat 7680
agagttaaat cctgatgctg tagttgctag ttttcatttg actgcctatc ttgtcgcatt 7740
attaccaatc acccgtcgta agaaatatta ttatattcag gcgtatgaag ttaatttttt 7800
tgataatata atatggaaat taatagcggg tttaacatat tatttaccgc ttaaaaaaat 7860
actaaatagt cctaatttgc ttcctcataa acatgatgat tttataggag tagttcctgc 7920
aggagtagat ttaaacgttt tctatccgaa accatcaaat aggttattaa atggtcacac 7980
atcaataggg attattggta gaaaagagaa gcacaaagga actagcgaaa ttatttcagt 8040
attgtgttca ctggaaaata aagctggaat tataatcaat attgcgatct atcttgaaga 8100
agttgataag cagcgtttaa tcgctgccgg gtttcaggtt aattttttc cgattacttc 8160
tgatttagaa ttggcatcct tttatcgaag caatgacatc atgattgctg ttgggttaat 8220
tgaagatggc gctttccatt atccttgtgc tgaatcaatg gcttgtggtt gtcttgttat 8280
ttcaaattat gcgccactta ctgaaactaa cagtgtactt aaattagtca agtttgatgc 8340
ttgcaaactt ggtgaagcaa ttaatctttg tctcaatctt gacctagaag aaaaaagcaa 8400
agaaatccaa tctaatattt ctgtgttgaa taaatatgac tggaaaattg ttggtgaaac 8460

```
tttcaatagt ttattgttag atgcaaataa atagtatacg ttgatgggga aaatatgaat   8520
attgttaaaa ctgatattcc agatctgatc gttcttgaac caaaagtgtt tagtgatgaa   8580
cgcggctttt ttatggagag ttataatcag attgaatttg agaaggcaat aggaaggcac   8640
gtaaattttg ttcaggataa tcattcaaaa tctagtaaag gcgtactacg tgggttgcat   8700
tatcaattag caccgtatgc acaggctaaa ttagttcgat gtgttgtagg tcaggtattt   8760
gatgttgctg ttgatcttag aaaaaattca ccaacgttca aaaaatggtt tggaataacc   8820
ctttccgcag aaaataaacg acaattatgg atacccgaag gatttgctca tggtttcttg   8880
gtgaccagtg atgaagctga gttcatttat aagacaacta actactatgc tcctggtcat   8940
cagcaagcaa ttatttacaa tgatcctatt ttaaacatcg attggccttt ctgcagtagt   9000
gctctgtcat tatcacaaaa agatcaagaa gcaaaattat tttcagaatt attggacagt   9060
gaactgttct aataaagtgt gccaccttat ccgtctgaag gataggtggt tgcttatatt   9120
tttttgagta tgtttgtata atgacagaaa atagtccgaa atataaacac gataaaagct   9180
taataagttt tatctactta ttttttatat ttacacttat tgtaggcttt attatcgcaa   9240
atacccagtt tttggggcga agtagagact atgataatta tatacagatc ttttctggta   9300
aagaagggga gggggttctt gaattatttt atcgcggatt gatgttaata acgaccagct   9360
atgaaactat catttttata attttaacat gttctttttt tataaaggca aggtttctcg   9420
ctaactattc gcgtaatttt tcaggcttga ccttattctt tatttattat gcaagcgttg   9480
cactttgggt tttagattat actcaattca gaaatggtct atgtatttcc attttaatgt   9540
tttccgtata ctatttattt ataaataaac cgacttattt ttatttctcg gtattatgtg   9600
caattgcaac tcattggtct gctttgcctt ttttgctttt atatcctttt gtctattcaa   9660
caaaaataag acgccttggt tatttttgtt tcagtattct tgttttgatt gcgatctcag   9720
gagaaggaaa agagatcata tcttttataa gaaattttgg agtgggacaa aaaataggaa   9780
atgaagctgg tgtaaattta ataaattcat tatcccttac cgctatttcc tggtttatta   9840
ttagttacat atcaagcatt ggaaatgaaa ggagaaattt aaggcttttc ttttgttatg   9900
gtgtcatgca atacgtgact tttagccttt tctctctacc tgttatggct ttccgtattt   9960
tggaaatgta ttttttcctt atgctaacca ttggggtgtt tattaagcaa aaaaagaatt  10020
attattttat tttttgcaaa gtgttaattt tattgtatct aacatactat tatcatatgg  10080
tctttggagt gattaatgtg taaggctaag gtgttggcta taattgttac ttacaacccg  10140
gaaattattc gattgacgga atgtattaac tctttagccc cacaagttga gagaataatt  10200
cttgtagata atggctcaaa taatagtgat ttgataaaaa atatcagtat taataacctt  10260
gaaattattt tactttcgga aaacaaaggc attgcatttg ctcagaacca tggtgttaag  10320
aagggcctgg aagcaaaaga gtttgactat ttatttttct cagatcagga tacttgcttt  10380
cctagcgatg ttattgaaaa acttaagagt acatttacga aaaataataa aaaaggtaaa  10440
aatgttgctt gtgcttctcc tttttttaaa gaccatcgtt caaattatat gcatccgtca  10500
gtcagcctaa atatttttac gagtacaaaa gttatatgta gtgaagtaga cgatgatctt  10560
tatccctcgc atgttattgc ttctgggatg ttaatgtctc gtgaagcatg gcgcgtcgtc  10620
ggaccatttt gtgaaaaact ctttatagac tgggttgata cagaatggtg ttggcgtgca  10680
ttagctaata atatgattat tgttcagaca ccatcagtca tcatttctca tgaacttggg  10740
tatgggcaga aaatttttgc tggtcgatct gttacaatac ataattcttt cagaaatttt  10800
tataaaatac gcaatgcaat atacttaatg ctgcattcaa attatagctt caagtatcgt  10860
```

```
tatcatgctt tttttcatgc gacaaagaat gttgtatttg aaattttata ttcgaaagaa  10920
aaattaaatt cactgaaggt ttgttttaaa gctgtacgtg atggtatgtt caataatttt  10980
taatacgaaa atagttaggc tcaaggtgtt taaatggaag aaaataatat gaagacggtc  11040
gctgtagttg gcacagtggg tgttcctgct tgttatggtg ggttcgaatc acttgttcag  11100
aatctaattg attatcaatc tgatggtata caatatcaga tattttgctc ttcaaaaaaa  11160
tatgataaaa aatttaaaaa ttataaaaat gcagaattaa tctatttgcc gataaatgcc  11220
aatggcgtct ctagcataat ttatgatatt atgtgtttaa ttatttgttt attcaaaagg  11280
ccagatgttg ttttaatatt gggggtgtct ggttgtttat ttctaccaat ttataaacta  11340
ttttcaaaat caaagattat tgtcaatatt gatgggcttg aatggcgtag aaataaatgg  11400
ggaacgtttg ctaagaaatt tcttaaaata tctgaggcga tatctattag aatagctgat  11460
attatcattt cagataatca agcaatagct gattatgtgg aaaataagta caagaaaaaa  11520
agtgtagtta tagcttatgg cggagatcat gccactaatc ttagtacacc gatagacaat  11580
gatcaaaaaa aagaaggtta ttatttgggg ctttgtagga tagagcctga gaataatata  11640
gaaatgattc tgaatgcctt cattaataca gataaaaaaa ttaaatttat gggtaattgg  11700
gataacagcg agtatggacg ccagctaaaa aaatattatt caaactatcc aaatatcacc  11760
ctactagaac ctaactataa tattgaagag ctttataaac taagaaaaaa ttgtcttgca  11820
tacattcatg gacactcggc tggtggaaca aacccttctt tagttgaagc gatgcatttt  11880
aatattccta tttttgcttt cgattgtgac tttaatcgtt acacaactaa caatttagct  11940
cattacttta atgattctga acaacttagc ttattagcag aaagtttgtc ttttggaaat  12000
cttaaatgtc gagtattaga tttaaaaaat tatgctgaag atatgtataa ctggaggcat  12060
atagctgcta tgtatgaatc tatttattaa acgcattaac aataatataa ttgaccttat  12120
atagcaggga aagatcacgt aacgctgcgg cgcgccgatc cccatatgaa tatcctcctt  12180
agttcctatt ccgaagttcc tattctttct agagaatagg aacttcggaa taggaactaa  12240
ggaggatatt catatggata aagccgtaag catataagca tggataagct atttatactt  12300
taataagtac tttgtatact tatttgcgaa cattccaggc cgcgagcatt cagcgcggtg  12360
atcacacctg acaggagtat gtaatgtcca agcaacagat cggcgtagtc ggtatggcag  12420
tgatgggacg caaccttgcg ctcaacatcg aaagccgtgg ttataccgtc tctattttca  12480
accgttcccg tgagaagacg gaagaagtga ttgccgaaaa tccaggcaag aaactggttc  12540
cttactatac ggtgaaagag tttgtcgaat ctctggaaac gcctcgtcgc atcctgttaa  12600
tggtgaaagc aggtgcaggc acggatgctg ctattgattc cctcaaacca tatctcgata  12660
aaggagacat catcattgat ggtggtaaca ccttcttcca ggacactatt cgtcgtaatc  12720
gtgagctttc agcagagggc tttaacttca tcggtaccgg tgtttctggc ggtgaagagg  12780
gggcgctgaa aggtccttct attatgcctg gtggccagaa agaagcctat gaattggtag  12840
caccgatcct gaccaaaatc gccgccgtag ctgaagacgg tgaaccatgc gttacctata  12900
ttggtgccga tggcgcaggt cactatgtga agatggttca caacggtatt gaatacggcg  12960
atatgcagct gattgctgaa gcctattctc tgcttaaagg tggcctgaac ctcaccaacg  13020
aagaactggc gcagaccttt accgagtgga ataacggtga actgagcagt tacctgatcg  13080
acatcaccaa agatatcttc accaaaaaag atgaagacgg taactacctg gttgatgtga  13140
tcctggatga agcggctaac aaaggtaccg gtaaatggac cagccagagc gcgctggatc  13200
```

```
tcggcgaacc gctgtcgctg attaccgagt ctgtgtttgc acgttatatc tcttctctga  13260

aagatcagcg tgttgccgca tctaaagttc tctctggtcc gcaagcacag ccagcaggcg  13320

acaaggctga gttcatcgaa aaagttcgtc gtgcgctgta tctgggcaaa atcgtttctt  13380

acgcccaggg cttctctcag ctgcgtgctg cgtctgaaga gtacaactgg gatctgaact  13440

acggcgaaat cgcgaagatt ttccgtgctg gctgcatcat ccgtgcgcag ttcctgcaga  13500

aaatcaccga tgcttatgcc gaaaatccac agatcgctaa cctgttgctg gctccgtact  13560

tcaagcaaat tgccgatgac taccagcagg cgctgcgtga tgtcgttgct tatgcagtac  13620

agaacggtat tccggttccg accttctccg cagcggttgc ctattacgac agctaccgtg  13680

ctgctgttct gcctgcgaac ctgatccagg cacagcgtga ctattttggt gcgcatactt  13740

ataagcgtat cgataaagaa ggtgtgttcc ataccgaatg gctggattaa             13790
```

<210> SEQ ID NO 13
<211> LENGTH: 13777
<212> TYPE: DNA
<213> ORGANISM: Artificial Sequence
<220> FEATURE:
<223> OTHER INFORMATION: example O6A rfb locus nucleotide sequence - O6A-EPA production strain stGVXN4112 and stLMTB10923

<400> SEQUENCE: 13

```
atgacgaatt taaaagcagt tattcctgta gcgggtctcg ggatgcatat gttgcctgcc     60

actaaggcga tacccaaaga gatgctacca atcgtcgaca agccaatgat tcagtacatt    120

gttgacgaga ttgtggctgc agggatcaaa gaaatcctcc tggtaactca cgcgtccaag    180

aacgcggtcg aaaaccactt cgacacctct tatgagttag aatcactcct tgagcagcgc    240

gtgaagcgtc aactgctggc ggaagtacag tccatttgcc cgccgggcgt gacaattatg    300

aacgtgcgtc agggcgaacc tttaggtttg ggccactcca ttttatgtgc acgacctgcc    360

attggtgaca atccatttgt cgtggtgctg ccagacgttg tgatcgacga cgccagcgcc    420

gacccgctgc gctacaacct tgctgccatg attgcgcgct tcaacgaaac gggccgcagc    480

caggtgctgg caaaacgtat gccgggtgac ctctctgaat actctgtcat ccagaccaaa    540

gagccgctgg accgcgaagg taaagtcagc cgcattgttg aattcatcga aaaaccggat    600

cagccgcaga cgctggactc agacatcatg gccgttggtc gctatgtgct ttctgccgat    660

atttggccgg aacttgaacg cactcagcct ggtgcatggg ggcgtattca gctgactgat    720

gccattgccg aactggcgaa aaaacagtcc gttgatgcca tgctgatgac cggcgacagc    780

tacgactgcg gtaaaaaaat gggttatatg caagcgttcg tgaagtatgg actacgcaac    840

ctcaaagaag ggcgaagtt ccgtaaaggg attgagaagc tgttaagcga ataatgaaaa    900

tctgaccgga tgtaacggtt gataagaaaa ttataacggc agtgaagatt agcggcgaaa    960

gtaatttgtt gcgaattttc ctgccgttgt tttatataaa caatcagaat aacaacgact   1020

tagcaatagg attttcgtca aagttttcca ggattttcct tgtttccaga gcggattggt   1080

aagacaatta gcatttgaat tttacgggtt tagcgcgagt gggtaacgct cgtcacatcg   1140

tagacatgca tgcagtgctc tggtagctgt aaagccaggg gcggtagcgt gctgaaatta   1200

taaagtcatt cttatagaac atcgcatttc aataatataa ttacacctaa atgaatagga   1260

tacaacgtgt gcacaattat ttaaggctta aagataaaat aaaaaacgta tttttagggt   1320

tgtatatatt gcagttattt aattatatcg cgccattggt aattatccct atcctgataa   1380

aatatattgg gttgggggaa tatggggaat tggtctatat tacatctatt tatcaaatag   1440
```

-continued

```
tggctttgat tattgatttt ggctttactt acacaggacc tgtggttgct gcgagacata   1500
gatgtgagac ccaaaattta cagcgctatt actcaatagt tgttctttta aaatcattgc   1560
tttttataat tgcattaaca tgtgtatttt tattgtgcag attaaatata gtccacttgt   1620
catttttgg gtttttgtca atttttctat gcactattgg taatatatta tcgcccaatt   1680
ggtttttgca ggggattggt gattttaaaa aactttcata ctcacaagta atagtgagaa   1740
taacattgtt tatcatactt cttgtttatg tctgtagtgg cggagataat gtttttatcc   1800
taagtttttt gcaaaatgca acattactca tatgctgtat atacttatgg ccaaatattc   1860
atattagcca tgttgttcat cttaaaccta atgaatgcat tgtggaattt aagaaggcag   1920
gaaatgtttt tattggcgta ataggtacga ttggttacaa tggtctaatt cctgtgttaa   1980
ttggaaacct ttgcggtaat acgagtcttg gtgtttttc aatcgttcaa aaaatgacaa   2040
cagcatgtca aagtctaatt aatccaatat cacagtatat gttatctcaa gtttcagaaa   2100
ttaaacctca agataaactg ttttattata gaattaaaaa aagtttttt gtgcatttaa   2160
caattagcat aattgcatgt ttatgttata tggggttagg gcaatatgtg gcgactttta   2220
taggtaaagt tgacgtttca tttgttatta ttttatttgc gtcaataatt accatttttt   2280
catctttaaa taatgtcctt ggtatacagt ttcttatacc gacagataat gtaaaaatac   2340
tacgaagtat aaatgttatg gcgggaatta ttgttgttag tttgtcctgg ctgttaatat   2400
cacgctttga cattctgggg ggggttttat taaacctaat tggtgagttt cttgtattca   2460
gtatgctagc ttttattgcc catcgaaagt ggggagcgag agtataatga aagtgaaggc   2520
ggttcctgct attacattct atttaagttt aatgctgaca attttagtgt tactgtttgg   2580
taatgaacca aataaatcac aatatatcct tgttatagca acgataacag tttttatat   2640
cgcatatatc actaataaaa taacttctcc ggccagcctt ctcgttatat catcttttgt   2700
gtttttaggt tgtcgccctt tattatcttt gtttgcaaac tatgattata ggattgccga   2760
ttggtttatt gaaggatata tggatgacga tgtgattttg gctaactatg ctataacact   2820
aatgtattat ggttatacat tgggactaat tctatgcaaa aatactgaaa aattttatcc   2880
gcatggtcct tatcctgaaa aacaattgct aaaaataaag tttcttttga ctttattttt   2940
tctgggttcg ataggtatgg ttgtaaaagg gatattcttt tttaacttta tagaatctaa   3000
tagttatgtt gatatttatc aatcaaatat aacaacgcca ataggttatg attttctatc   3060
ttatttattt tattgttctt ttttccttat atgtgcgttt catatacagt tcagaacaaa   3120
taaaaaattt ctttttattg cgatatgcat tgctgcattt agcaccttga agggtagtcg   3180
tagtgaagct ataacgtttc ttttaacggt tacatgtata tattttaatg aagtaaagac   3240
aagaaactta cgtctgctga ttacaatgat ttttgttttt agcgtcattt ttgtgattag   3300
tgaatttatc tcaatgtggc gcactggagg gagttttttt caattaatgc agggtaataa   3360
tcctgttata aactttgtat acggcatggg agtatcatat ctttccattt atcaatcagt   3420
aaaactacaa ctattgtcag gggatataa tgttacctat ctattcagcc agttaataat   3480
aacttgctcg tcaatattta atgtcaaatt gagcttgccg gaaataagct atagccattt   3540
ggcctcatac acagcaaacc cagaactata taatcttggg ttcggacttg gggggagtta   3600
tttagcagaa tcgtttttag catttggtct gattggatgt ttcattatac cctttttact   3660
tttacttaat ttaaatgtat tggaaaaata tacaaaaaac aaaccaatta tatattttgt   3720
ttattatagt gtgttgccac ctatattatt cacaccaaga gagactttgt tctatttctt   3780
cccctatctt gtcaaaagta tatttgttgc ttttttagtt acattataca tccagtataa   3840
```

```
aaaggattga ccaaaatgtc agaaaaaaat gtcagcataa taatcccaag ttataacagg   3900
gctcatattc ttaaggaggt cataccaagt tattttcagg atgagacttt agaggttata   3960
gttatcaatg atggatcaac agataataca aatagtgtat tagctgaact gaaggaaaaa   4020
tattctcagt tagttatttt agaaaatgaa acgaataaaa aacagatgta ttctaaaaac   4080
cgagggattg aaatagccaa agggaaatat atttttttg gtgatgatga ctcttacctc   4140
ttacccggtg ttatatctcg gttattggct acaaaatatg agacaggcgc tgatgtaatc   4200
ggcgcaagaa tactttatat gaataataac gagaaaacaa ttgaagattg cataaatcga   4260
cataaaaaag aggggcgttt tgttagtgat ctaaatagat tggattttag ttatacatgt   4320
gatttggacc atccgattga atgtttttat gcacagcctt ttgttctagc tgaaagggaa   4380
ctaatatcga aatatcgatt tgatatatct tatacgggaa actgctatcg tgaggaaact   4440
gatttcatgc tatctctatt tattaaaaat aaaaaattta tatatgattc aaaggctttg   4500
ttaataaatt tacctccaag aaaagcgacg ggaggggcaa gaacagctaa tcgattaaaa   4560
tatcattacg aaagttgcat aaataattat agatttttaa aaaaatataa tgataatttg   4620
aatcttcttt caggacaaaa gcatgctata ttttaccgac agtgtcaatt cgttctgcta   4680
aaaatgaagt cgtttatcgg gaagttttta aaatgattat atatatcgcc gcgtataatg   4740
gttcaggagg gcaaggtggg gtggaaaggg ttgttgccca acaatgtaac attcttaaaa   4800
atttgggggt taaagtcatt atacttgata aaacatactt caaaatttct aacaaaattc   4860
gtaacaaaaa aatacaagta gcactttatc caatattagt ttctctttat ttaaccttac   4920
aaaaattacg tggcgtgacg tttaaagtta ttgcacatgg ctattgttct cctttttata   4980
ggaatgacat cttaatagct catggcaata tgaaatgtta ttttcaaaca gtcatgaata   5040
aaaaacctaa tcggttgtct ggcagtggtc ttttatcttt ctatgagcgt tgggctggag   5100
cattttcaaa aaatatctgg gctgtttcaa ataaggttaa aagtgaatgg aatgagcttt   5160
acaatattaa ttcacataaa atcaaagttg ttcgaaattt tataaatctt gcacaatttg   5220
attacactga tgttaatgaa gcagaatatg tgacatttgt cgggcgattg gaaaaaggaa   5280
aaggaataga tgatctgtat tacatatgta aaaatctgcc agatacttcc ttccatttag   5340
tttcaagtat tcccgcccca caaaattttg cttcgctaaa taatgttctg accagcattg   5400
ctgtccccta tgcgaaaatg ccagaaatat ttaagaaatc cagagtactt attttaccgt   5460
cctattatga aggatatgag ctggttacta ttgaagcgct atgctgtggt tgccctgtga   5520
taggctataa tgttggtgca attagagagt tgtatgcaga aagttttcct ggcgtattta   5580
ttgccaataa taaagaagat ttagcacaag tagcctacaa attaattagt cttgataatg   5640
aaaaatatta tcatttgaga caaactattt atagcaagcg tgagcttttt tctgaagaga   5700
gatatgcgga aattttaacg gcggcattta atgaaaaaaa ataagaaact ctgtctcatt   5760
tcaattaact catataatga acttaccgga ggaggagtat atttacgtac gcttgttagt   5820
tttctacaaa aacagaatgt taatttaaca cttattgata aaaaatcctc aggtaaacta   5880
ttcgaagaca atacttttca acatatatca tttattaaag gtaaacgtca ggatataata   5940
tccaggcttt tttttatacc atcattttat gtcccttata ttttctcaat aattaaaatt   6000
ttacggaagc aagatattct tgcttttcac aactctcggc ttggattgtt atgtctgctt   6060
tttagaatac tcatgcccca caaaaagatc atattgttta cggataactt cgaatatgac   6120
ttaataagac aaaaagataa aaacataact acttttattg aaaaattaat tgtttatctc   6180
```

aatgaattta tcgggcttaa gaattcagat ttagttagct atattacccg gcaagataaa 6240
aatgcaatgg ataaatttta tgggattaaa aaaagcagaa atttaattct ccctgtgata 6300
tttagtagag aaaaaccaac tgatgtattg tcagctcact ttattaatga gtataatcga 6360
ttgaataatg ataataggaa aaaagtagta tttactgcat cttttgattt ttttccaaat 6420
atagatgctg ccaactatgt tttaaatgca gcaaagtcta ataatgatta ttgctatatt 6480
ttggcaggta ggaaaagtac tactttgaat cttcctgatt tggataattt attttttttc 6540
gataatctat ctaatagtga aatgtcatat ttattatctg cttgtgatgt tttttattct 6600
cctatagttt taggaagtgg aatgaaaaca aaaattgcag aagcactatc atatggatta 6660
tatatttatg cgacagagca ttccttaatc ggctatgatg aaattataca caataaggag 6720
tgtgttaaaa aatctcaca tttggatgag gaatttccta aagatttcaa gatgaaaagt 6780
atcaataaac agctaataat gtcttatcag caaaaatatt attcacatta tcggtttaat 6840
ggccatgaac ttgatataat aaattttgac gattagttag tggagatata atatgaacat 6900
attagtaact ggtggtgctg gatatatcgg atctcatacg gctattgaat tactgaatgc 6960
aggtcatgag attatcgttc tggacaattt cagtaatgct tcatacaagt gtatcgaaaa 7020
aataaaagaa attactcgac gtgattttat aacaattact ggagatgctg ggtgtaggaa 7080
gacactctcc gctattttcg agaaacacgc catagatata gttattcatt ttgctggctt 7140
taaatctgtt tcagagtcta aaagtgaacc cttaaagtat taccagaata atgttggagt 7200
gaccattact ttattacagg taatggaaga gtacagaatt aaaaaattta tctttagttc 7260
atctgcgaca gtctatggtg aaccagagat aattccaatt ccagaaacag ctaaaattgg 7320
aggaactacg aatccatatg gcacatcgaa gtattttgtt gaaaaaattc tagaggatgt 7380
tagttccacg ggaaaactgg atataatttg cttgagatat tttaatcctg tcggtgctca 7440
ttctagtggt aaaataggtg aggctccatc tggtatccct aataatcttg ttccttattt 7500
attggatgtt gcgagtggta aacgtgataa attatttatt tatggcaatg attaccctac 7560
taatgatgga acaggtgtaa gggattttat tcatgttgtt gacttagcga aaggtcattt 7620
ggctgcaatg aattatttaa gtatcaattc gggatataat atctttaatc ttggtacagg 7680
aaaaggttat tcggtacttg aattaatcac tacatttgaa aaattaacaa acattaaggt 7740
caataaatct tttatagaga gaagggcagg ggatgttgcg tcttgttggg ctgatgcaga 7800
taaagctaat tctttattgg actggcaagc cgaacaaact ctagaacaga tgttattgga 7860
ctcgtggcgt tggaaaaaaa attatccaga cggattctga atataaaagg tttcagtttt 7920
atgaatcaat cagagcagag aaaaaaaata ctggttctta cacctcgctt tccctaccct 7980
gtcattggag gggatagatt aagagtctat atgttatgta aagaactttc caaaaaatat 8040
gatcttattc ttctgagctt atgtgatcaa ccactagaac ttgaaataaa tataaatgac 8100
tcggtcttca aagaaattca tcgtgtctat ctaccaaaat ataaatcata ttataatgta 8160
ttaaaagctt tggttacgca aaaaccgttg caaattgctt attatcaatc ggacacattt 8220
aagaataaat acaataaatt aattaaacaa tgcgatgcag tattttgtca tctgataaga 8280
gttgctgatt atgttaagga tacagacaag ttcaaaattc ttgatatgac agatgcaata 8340
tctttgaatt acagtcgcgt taaaaaatta gcaagtaaaa aaagtttgcg tgcaattatt 8400
tattctctgg aacaaaaaag attagaatca tatgaacgtt ctgtggcgaa tctttttgat 8460
ttgaccactt ttatttcatc cgtagaccgt gactatctct accctaatct gggcagtaat 8520
atccatatag tcaataatgg ggttgataca tcagccttga gatatataaa aagagaaata 8580

```
aaaatcgata agcctgtgga acttatattt atcggaaata tgtattcttt acaaaatatg   8640
gatgctgcaa aacattttgc taagaatatt ttaccttgct tgtatgatga gtttaatatt   8700
atttttaaag tgattggtaa gatctcagaa actaataaaa atatattaaa ttcatttaaa   8760
aatacaattg ctttaggtac tgttgatgat atcaattctt ccgcttctac agggcatata   8820
ggtatatgtc ctgttcgtct tggagcaggc gtacaaaata aaattcttga atacatggct   8880
ttaggtttac catgtattac atctagcatt ggttatgaag gtattaatgc aaaatcaggt   8940
agcgaaattt ttgttgcaga tacagtagag caatataaaa acgtactaag agaaataatt   9000
tacgattata atcgttatac tgaagtggct gaaaatgccc gtagttttgt agaaaataat   9060
ttttcttggg aatcaaaagt tgccaattta atgaatacat tagatgagaa attatatgaa   9120
caataataaa attattacac ctatcattat ggctggtggt tcaggcagtc ggttgtggcc   9180
actatcaaga attctctatc cgaaacaatt tcttagccta atcggtagtc ataccatgct   9240
tcaaacaacg gctaatcgtc tggatggttt ggattgtacc aacccttatg tcatttgtaa   9300
tgaacaatac cgctttatag ttgctgaaca gcttagaaaa atcgatagat tgacttcaaa   9360
gaatatcatc cttgagcctg ttgggcgtaa cactgcccct gcaattgcat tagcggcgtt   9420
gctgatgtct aagtctgata aaagtgcaga tgatcttatg ctcgtactgg ctgcagatca   9480
cgttatacac gatgaagaaa aattttgtaa cgctgttaga tcggcaattc catacgctgc   9540
tgatgggaaa ttggtaacat ttggtataat tccagacaaa gcagaaactg gttatggtta   9600
tatacatcga ggacaatata ttaatcagga agattcggat gcatttatag tgtcatcatt   9660
tgttgaaaag ccaaatcatg agacagccac taaatatctt gcttccggtg agtattattg   9720
gaatagcggt atgtttttgt ttagtgcaaa tcgttatata gaggaactta aacaatttcg   9780
gcctgatatt ttatccgctt gtgaaaaagc aattgcttca gcgaactttg accttgattt   9840
tgtgcgttta gatgaaagtt ctttctctaa gtgccctgaa gaatcaattg attacgctgt   9900
aatggaaaaa acaaaagacg caattgttat tccaatggat gctggctgga gtgatgtcgg   9960
ttcatggtct tctctttggg aaattaatga taaagactca gacggcaacg taatagttgg  10020
ggatattttc tctcatgaaa caaagaattc tttcatatat gccgaatcgg gaattgttgc  10080
tacagttgga gtggaaaatt tagttgttgt ccaaacaaag gatgctgttc ttgtctcaga  10140
gagaaataaa gttcaggatg taaagaaaat agtagaacaa attaaaaatt caggtcgtag  10200
cgagcattat gttcatcgcg aagtatatcg tccttggggt aaatatgatt ccattgacac  10260
aggggagcgt tatcaggtca aacgtataac agtaaatcct ggtgaaggac tttctttaca  10320
aatgcaccat catagggcag aacattggat catagtttct ggaactgcaa gggtgactat  10380
aggttctgaa actaagattc ttagcgaaaa tgaatctgtt tacatacctc ttggtgtaat  10440
acactgcttg gaaaatccag ggaaaattcc tcttgattta attgaagttc gttctggatc  10500
ttatttagaa gaagacgatg ttatccgttt tcaggaccga tatggtcgta gctaaatttt  10560
tgataatgta acgttagtag aagagcgcta atatttttag ttaatctgta ataagtatta  10620
tttgtttaag gtatatcatg tcgagtttac cctgctttaa agcctatgat attcgcggga  10680
aattaggcga agaactgaat gaagatattg cctggcgcat tggtcgcgct tatggcgaat  10740
ttctcaaacc gaaaaccatt gtgttaggcg gtgacgtccg actcaccagc gaaaccttaa  10800
aactggcgct ggcgaagggg ttacaggatg cgggcgtcga tgtgctggat attggcatgt  10860
ccggcaccga agagatctat ttcgccacgt tccatctcgg cgtggatggc ggcatcgaag  10920
```

-continued

```
ttaccgccag ccataacccg atggattaca acggcatgaa actggtgcgc gaaggggctc  10980
gcccgatcag cggtgatacc ggactgcgcg acatccagcg tctggcagaa gccaacgact  11040
ttcctcccgt tgatgaaacc aaacgcggtc gctatcagca aatcaatctg cgtgacgctt  11100
acgttgatca cctgttcggt tatatcaacg tcaaaaacct cacgccgctc aagctggtga  11160
ttaactccgg gaacggcgcg gcgggtccgg tggtggacgc cattgaagcc cgctttaaag  11220
ccctcggcgc acccgtggaa ttaatcaaag tgcacaacac gccggacggc aatttcccca  11280
acggtattcc taacccgcta ctgccggaat gtcgcgacga cacccgcaat gcggtcatca  11340
aacacggcgc ggatatgggc attgcctttg atggcgattt tgaccgctgt ttcctgtttg  11400
acgaaaaagg gcagtttatt gagggctact acattgtcgg cctgctggca gaagcgttcc  11460
tcgaaaaaaa tcccggcgcg aagatcatcc acgatccacg tctctcctgg aacaccgttg  11520
atgtggtgac tgccgcaggc ggcaccccgg taatgtcgaa aaccggacac gcctttatta  11580
aagaacgtat gcgcaaggaa gacgctatct acggtggcga aatgagcgcc caccattact  11640
tccgtgattt cgcttactgc gacagcggca tgatcccgtg gctgctggtc gccgaactgg  11700
tgtgcctgaa aggaaaaacg ctgggcgaac tggtgcgcga ccggatggca gcgtttccgg  11760
caagcggtga gatcaacagc aaactggcac accccgttga ggcgattaac cgcgtggaac  11820
agcactttag ccgcgaggcg ctggcggtgg atcgcaccga tggcatcagc atgacctttg  11880
ccgactggcg ctttaacctg cgctcctcta acaccgaacc ggtggtgcgg ttgaatgtgg  11940
aatcgcgcgg cgatgtaccg ctgatggaag aaaagacaaa acttatcctt gagttactga  12000
acaagtaatt cagtaatttc atataaatgg gttttaaaaa acggaaaaga tgagatatcc  12060
ggtgtggtat atccaaggta atgctattca gtatctctat gagtgagtta acatctatac  12120
cacatttaag ccgcacactt cgggatcccc atatgaatat cctccttagt tcctattccg  12180
aagttcctat tctttctaga gaataggaac ttcggaatag gaactaagga ggatattcat  12240
atggataaag ccgtaagcat ataagcatgg ataagctatt tatactttaa taagtacttt  12300
gtatacttat ttgcgaacat tccaggccgc gagcattcag cgcggtgatc acacctgaca  12360
ggagtatgta atgtccaagc aacagatcgg cgtagtcggt atggcagtga tgggacgcaa  12420
ccttgcgctc aacatcgaaa gccgtggtta taccgtctct attttcaacc gttcccgtga  12480
gaagacggaa gaagtgattg ccgaaaatcc aggcaagaaa ctggttcctt actatacggt  12540
gaaagagttt gtcgaatctc tggaaacgcc tcgtcgcatc ctgttaatgg tgaaagcagg  12600
tgcaggcacg gatgctgcta ttgattccct caaaccatat ctcgataaag gagacatcat  12660
cattgatggt ggtaacacct tcttccagga cactattcgt cgtaatcgtg agctttcagc  12720
agagggcttt aacttcatcg gtaccggtgt ttctggcggt gaagaggggg cgctgaaagg  12780
tccttctatt atgcctggtg gccagaaaga agcctatgaa ttggtagcac cgatcctgac  12840
caaaatcgcc gccgtagctg aagacggtga accatgcgtt acctatattg gtgccgatgg  12900
cgcaggtcac tatgtgaaga tggttcacaa cggtattgaa tacggcgata tgcagctgat  12960
tgctgaagcc tattctctgc ttaaaggtgg cctgaacctc accaacgaag aactggcgca  13020
gacctttacc gagtggaata acggtgaact gagcagttac ctgatcgaca tcaccaaaga  13080
tatcttcacc aaaaaagatg aagacggtaa ctacctggtt gatgtgatcc tggatgaagc  13140
ggctaacaaa ggtaccggta aatggaccag ccagagcgcg ctggatctcg gcgaaccgct  13200
gtcgctgatt accgagtctg tgtttgcacg ttatatctct tctctgaaag atcagcgtgt  13260
tgccgcatct aaagttctct ctggtccgca agcacagcca gcaggcgaca aggctgagtt  13320
```

catcgaaaaa gttcgtcgtg cgctgtatct gggcaaaatc gtttcttacg cccagggctt 13380
ctctcagctg cgtgctgcgt ctgaagagta caactgggat ctgaactacg gcgaaatcgc 13440
gaagattttc cgtgctggct gcatcatccg tgcgcagttc ctgcagaaaa tcaccgatgc 13500
ttatgccgaa aatccacaga tcgctaacct gttgctggct ccgtacttca agcaaattgc 13560
cgatgactac cagcaggcgc tgcgtgatgt cgttgcttat gcagtacaga acggtattcc 13620
ggttccgacc ttctccgcag cggttgccta ttacgacagc taccgtgctg ctgttctgcc 13680
tgcgaacctg atccaggcac agcgtgacta ttttggtgcg catacttata agcgtatcga 13740
taaagaaggt gtgttccata ccgaatggct ggattaa 13777

<210> SEQ ID NO 14
<211> LENGTH: 15027
<212> TYPE: DNA
<213> ORGANISM: Artificial Sequence
<220> FEATURE:
<223> OTHER INFORMATION: example O8 rfb locus nucleotide sequence - O8-EPA production strain stLMTB11734

<400> SEQUENCE: 14
atgacgaatt taaaagcagt tattcctgta gcgggtctcg ggatgcatat gttgcctgcc 60
actaaggcga tacccaaaga gatgctacca atcgtcgaca agccaatgat tcagtacatt 120
gttgacgaga ttgtggctgc agggatcaaa gaaatcctcc tggtaactca cgcgtccaag 180
aacgcggtcg aaaaccactt cgacacctct tatgagttag aatcactcct tgagcagcgc 240
gtgaagcgtc aactgctggc ggaagtacag tccatctgtc cgccgggcgt gaccattatg 300
aacgtgcgtc agggcgaacc tttaggttta ggccactcca ttttgtgtgc gcgacctgcc 360
attggtgaca acccatttgt cgtggtactg ccagacgttg tgatcgacga tgccagcgcc 420
gacccgctac gttacaacct tgctgccatg attgcacgtt tcaacgaaac gggccgcagc 480
caggtgctgg caaaacgtat gccgggtgac ctctctgaat actccgtcat ccagactaaa 540
gagccgctgg accgtgaggg taaagtcagc cgcattgttg aatttatcga aaaaccggat 600
cagccgcaga cgctggactc agacatcatg gccgtaggtc gctatgtgct ttctgccgat 660
atttggccgg aactggaacg tactcagcct ggtgcatggg gacgtattca gctgactgat 720
gctattgccg agctggcgaa aaaacaatcc gttgatgcaa tgctgatgac cggcgacagt 780
tacgactgcg gcaaaaaaat gggctatatg caggcgtttg tgaagtatgg cctacgcaac 840
ctgaaagaag ggcgaagtt ccgtaaaggt attgagaagc tgttaagcga ataatgaaaa 900
tctgaccgga tgtaacggtt gataagaaaa ttataacggc agtgaaaatt cgcagcaaaa 960
gtaatttgtt gcgaatcttc ctgccgttgt tttatataaa ccatcagaat aacaacgagt 1020
tagcagtagg gttttattca aagttttcca ggattttcct tgtttccaga gcggattggt 1080
aagacaatta gcgtttgaat ttttcgggtt tagcgcgagt gggtaacgct cgtcacatca 1140
taggcatgca tgcagtgctc tggtagctgt aaagccaggg gcggtagcgt gcattaatac 1200
ctctattaat caaactgaga gccgcttatt tcacagcatg ctctgaagta atatggaata 1260
aattaagcta gcgatcgctt aagatctagg atttcattat gttacttcct gtaattatgg 1320
ctggtggtac cggcagtcgt ctctggccga tgtcacgcga gctttatccg aaacagttcc 1380
tccgcctgtt cgggcagaac tccatgctgc aggaaaccat cacccgactc tcgggccttg 1440
aaatccatga accgatggtc atctgtaacg aagagcaccg cttcctggtg gctgaacagc 1500
tacgccagct caataagctg tcgaataata ttattcttga gccggtcggg cgcaacaccg 1560

```
ccccggccat cgccctggca gcccttcagg ccacccgcga cggcgacgac ccgctgatgc   1620
tggttctcgc cgctgaccat atcatcaata accagtcggc cttccacgac gccatccggg   1680
tcgccgagca gtatgctgat gaaggtcatc tggtcacctt cggtatcgtg ccgaatgccc   1740
cggaaactgg ctacggttac attcagcgcg gcgtggcgct caccgatagt gcccattccg   1800
cgtaccaggt ggcccgcttt gtggagaagc cggatcgcga gcgcgccgag gcttacctcg   1860
cctccgggga gtactactgg aacagcggca tgtttatgtt ccgcgccaag aaatacctca   1920
tcgagctggc caaataccgt ccggatatcc tggaagcctg ccaggctgcg gtgaatgccg   1980
ccgataatgg cagcgatttc atcaatatcc cgcatgatat tttctgcgag tgcccggatg   2040
agtccgtgga ctatgccgtt atggagaaaa ccgccgatgc ggtggtggtc ggtctcgatg   2100
ctgactggag cgacgtcggc tcctggtccg cactatggga ggtcagcccg aaagacgagc   2160
agggcaatgt cctcagcggt gacgcgtggg tacacaacag cgaaaactgc tacatcaaca   2220
gcgacgagaa gctagtggcg gccattggcg tagagaatct ggtgattgtc agcactaagg   2280
acgccgtgct ggtgatgaat cgcgagcgtt cccaggacgt gaagaaggcg gtcgagttcc   2340
tcaagcagaa ccagcgcagc gagtacaagc gccaccgtga gatttaccgc ccctggggcc   2400
gttgcgacgt agtggtccag accccgcgct tcaacgtcaa ccgcatcacg gtgaaaccag   2460
gcggtgcctt ctcgatgcag atgcaccacc atcgcgccga gcattgggtt attctcgccg   2520
gcaccggtca ggtgactgtc aacggtaagc agttcctgtt gtccgagaac cagtccacct   2580
ttattccgat tggcgccgag cactgcctgg aaaaccctgg ctgtattccg ctggaagtgc   2640
tggagatcca gtcgggggcg taccttggcg aggacgacat tattcgtatt aaagaccagt   2700
atggtcgttg ctaattattt tcgggacaag acgcagaatg acacagttaa cttgttttaa   2760
agcttatgac atccgtggtg aactgggtga ggaactgaac gaggacatcg cctaccgtat   2820
cggtcgcgcc tacggcgaat ttctgaaacc cgggaagata gtggtggggg gcgatgtgcg   2880
cctcacaagc gagtcgctga agctggcgct ggcccgcggg ttaatggacg ccggtaccga   2940
cgtgctggac atcggcctga gcggtaccga agagatttac tttgccacct tccaccttgg   3000
ggtagatggt ggcatcgagg tgaccgcgag ccacaatcct atgaactaca acggcatgaa   3060
gctggtgcgc gagaatgcga agcccatcag cggcgacacc ggcctgcggg atatccagcg   3120
cctggcggag gaaaaccagt tcccgccagt ggacccggcg cgtcgcggga ccctgagcaa   3180
gatatcggta ctgaaggagt atgttgacca tctgatgagc tacgtggact tctcgaactt   3240
cacccgtcca ctgaagttgg tggtgaactc cggaaacggg gctgcggggc acgtgattga   3300
tgaggtggag aaacgcttcg cggcggctgg ggtgccggta acctttatca aggtgcatca   3360
ccagccggat ggccatttcc ctaacggtat cccgaatccg ctgctgccgg agtgccgcca   3420
ggataccgcc gacgcggtgc gcgagcatca ggccgacatg gggattgcct ttgacggcga   3480
cttcgatcgc tgcttcctgt tcgatgacga agcttcgttt atcgaggggt attacattgt   3540
cggcctgctg gctgaggcgt tcctgcagaa gcagccggga gcgaaaatca ttcacgaccc   3600
gcgcttgacg tggaacacgg tagacatcgt gacccgcaac ggcggccagc cggtgatgtc   3660
gaagacgggg catgcgttca tcaaggagcg gatgcgtcag gaagacgcta tctacggcgg   3720
ggagatgagt gcgcaccatt acttccgcga tttcgcctac tgcgatagcg ggatgatccc   3780
gtggctgctg gtggcggagc tgctgtgtct gaagaacagc tcgctgaaat cgctggtggc   3840
ggaccgccag aaggcgttcc ctgcgtcggg agagatcaac cgcaagctaa gtaatgctgc   3900
```

tgaggcgatc gcccgcatcc gggcgcagta tgagccggcg gctgcacaca tcgacacaac 3960
ggacgggatc agtattgaat accctgaatg gcgctttaac ctgcgcacgt ctaacaccga 4020
gccggtggtg cgtctgaacg ttgagtccag agctgatgtg gcgcttatga atgaaaaaac 4080
gaccgagctg ttacacctgt taagcgggga ataaggtgag agatttacta acgacgattt 4140
atcgttatcg gggatttatc tggagcagtg ttaaacgtga ttttcaggca cgctatcaaa 4200
ctagtatgct gggcgcacta tggctcgttt tacaaccgct ctctatgatt ctggtctata 4260
ccctggtttt ttccgaggtg atgaaggcaa gaatgcccga taataccggg tcgtttgcct 4320
atagtattta tctctgttcc ggggtactga cctggggatt atttactgag atgctggata 4380
aaggtcagag cgtatttatt aacaatgcta atctgatcaa gaaactcagt tttccgaaaa 4440
tctgtctgcc gatcatcgtg acgttatcgg cggtgctaaa tttcgcgatt attttcagtc 4500
tgtttctaat ttttatcatt gtcaccggta acttccccgg ctggctcttt ctctcggtga 4560
taccggtcct gcttttgcag atcctgtttg ccggtgggct ggggatgatc cttggtgtca 4620
tgaacgtctt tttcagggat gtggggcaac tggttggcgt tgcgctgcaa ttctggtttt 4680
ggttcacacc cattgtttat gtactgaatt cattacctgc atgggcaaaa aatctgatga 4740
tgtataaccc gatgactcgg atcatgcaat cttatcagtc catcttcgcc tatcatctgg 4800
cccccaactg gtattcgcta tggccagtat tggctctcgc cattattttc tgcgtcatcg 4860
gtttcaggat gttccgcaag catgcggcgg atatggtgga tgaattataa tgagttatat 4920
cagagtaaat aatgtcggta aggcgtatcg ccagtatcac tcaaagaccg ggagactgat 4980
cgaatggtta tcccctctga ataccaaacg ccataatttg aaatggatcc tccgcgatat 5040
taatttcgaa gtcgctccgg gcgaggctgt cggtattatc ggtatcaacg gtgcaggcaa 5100
gagtaccctg cttaaactca taaccgggac gtccaggccg acgactggag aaattgaaat 5160
ctccggacgt gtcgctgcat tactcgaatt ggggatgggg tttcattctg atttcactgg 5220
tcggcagaat gtttatatgt ctgggcaact gttggggtta tcgtcagaga aaataactga 5280
actgatgccg caaattgaag agtttgctga gattggggac tatatcgatc aacctgtgcg 5340
cgtctactcc agtgggatgc aagttcgatt agcttttagt gtagcgacgg ctatccgtcc 5400
tgatgtgcta attatcgatg aggcattatc tgttggggat gcatatttcc agcataaaag 5460
ctttgagcgt attcgaaaat ttcgtcagga agggaccacg ctgttgctgg tatcccatga 5520
taaacaagcg atccaaagca tttgcgaccg ggccatttta ttgaataaag gccaaattga 5580
aatggaaggt gaacctgaag cagtgatgga ttattacaat gctcttctgg ccgataaaca 5640
aaatcagtcc attaaacaag ttgagcataa tggtaaaacg caaactgttt caggcactgg 5700
tgaggtgact atctctgagg ttcatcttct cgatgaacag ggcaatgtga ctgaatttgt 5760
ttcggtaggg catcgtgtca gcttgcaggt caacgttgag gtcaaggacg atattcctga 5820
gcttgttgtc ggatatatga ttaaggatcg acttgggcag ccgattttcg ggaccaatac 5880
gtaccatctc aatcagacac tcacctccct gaaaaaagga gaaaagcgtt cgttcttatt 5940
ttctttcgat gcgagattgg gggttggctc ctattctgtc gctgtcgcgt tgcatacttc 6000
cagtacgcac ctcggcaaaa actatgaatg gcgcgatctg gccgtggtat tcaacgtcgt 6060
taacacggaa caacaagagt ttgtcggcgt gtcctggttg ccgcctgaac tggagatttc 6120
ttaatgggtt cgtcgtttta tcgttcattt gaagaacgac acagaggttc ggttgaagaa 6180
atcaagcgcc gcttgagttt ttatttacct tttcttgcag gtctgaagga catttatcct 6240
gatggcgtga ttgcggatat tggttgcgga cgtggcgaat ggttggagat cctgactgaa 6300

-continued

```
aatggcattg cgaacatcgg cgtcgatctc gatgatggca tgctggcgcg cgccagggag   6360
gccggactga atgtgcagaa aatggattgt ctgcagtttt tgcaaagtca ggcggatcag   6420
agcctgatag cgttgaccgg ttttcatatt gctgagcatt tgccgtttga ggtcctgcag   6480
caactcgcca tgcataccct acgggtgctg aaaccaggtg gtttgctgat cctcgaaacg   6540
ccgaacccgg agaatgtaag cgtcggcacc tgttcatttt atatggatcc aacgcataat   6600
catcctctgc caccgccact gcttgagttt ttacctattc attatggttt tacccgagca   6660
attaccgttc gtctgcagga aaaagaggtt cttcaatctc cggatgcagc cgttaatttg   6720
gtcgatgtac tcaaaggggt gagccccgac tacagcatca ttgctcagaa agcagcgcca   6780
acagatattc ttgaacgctt tgacaccctg tttacccagc agtacggtct gacgctggat   6840
gctctgagca accgttacga tgcgattttg cgccaacagt tttcgtccgt tgtctcacgg   6900
ctggagacgt tgaaccaaac ctatatgcaa cagataagcc aaatgtcaga gactattcag   6960
acgttgcaag gtgaggttga cgatctgagt catgtcatcg atcagaacca tcagcttcat   7020
cagcaaatgg cggatttaca taacagtcgt tcatggcgta ttactcaacc actacgctgg   7080
ttgtctttgc aacgtcaatt attacgtcag gaaggggcta aagtgcgagc ccgtagggct   7140
gggaaaaaaa tattgcgcaa agggatggcg ctctcgctgg tctttttcca tcgttaccct   7200
aagtctaagg tttatctgtt taaggttctg agaaaaactg gctgctatac attgctacaa   7260
cgtttgttcc aacgcgtaat gctggtgcaa tctgacacga tgatgatgca gtccagaaga   7320
tatgatgtgg gtactgaaga aatgacaagt cgcgcgatga gtatttataa cgaattaaaa   7380
aataaaaata cggagaaata acgatgcgta ttgtcataga tttacaaggc gcacagacgg   7440
aaagccgctt tcgtggcatc ggtcgttata gtatcgcaat cgccagaggc ataatcagaa   7500
ataacagccg gcatgagatt ttcatcgcgc tatccgccat gctggatgag tcgattgcaa   7560
atattaaggc gcaatttgcc gatctcctgc cggcagaaaa tatagtcgta tggcatgccg   7620
taggccctgt tcgtgcgatg gaccaaggta atgaatggcg tcgggagagc gcagaactga   7680
ttcgggaagc gtttcttgaa tcattgtgtc cagatgtcgt tttcattacg agtttgtttg   7740
aaggtcatgt cgacgatgcg gctacatcgg tacacaaatt tagtcgtcag tataaagtag   7800
ccgtactgca ccacgatctt atccccctcg tgcaggcgga aacctatctg caggacgatg   7860
tatacaaacc ctactattta cagaaagttg agtggttaaa aaacgctgac cttttgttga   7920
ctaactctgc ttataccgca caggaagcga tcgagcatct gcatttacag ggcgatcatg   7980
tgcagaatat tgcagccgca gtcgattctc agttttgtat ggcggaggtg gcagcgagcg   8040
aaaaagagac cgtccttggc cattacggta ttcagcgcga gttcatgttg tatgcgcccg   8100
gaggatttga ctcaaggaaa aactttaaac ggttgattga ggcctatgcc gggctcagtg   8160
atgccttacg tcgcagtcat caactggtca tcgtcagtaa gctttccatc ggtgatcgtc   8220
agtatctgga atcccttgcg tcaggtaatg gtttacagca gggcgaactg gtactcactg   8280
gttatgtgcc ggaagatgag ctgatccagc tctatcgcct atgtaagctg ttcatctttg   8340
cttcactaca tgaaggtttt gggttgccgg ttctggaagc aatgtcgtgc ggtgcgccgg   8400
tgattggctc aaatgtcacc agtattcctg aagtcatcgg taatcctgag gcattattcg   8460
acccgtattc tgtctcttcc atgagggata agatcgcgca atgtttgact gatgatacct   8520
tcctcgcgcg tctgaaagaa atggcgcagc agcaagcgcg taatttctct tgggataaag   8580
ctgcggtgac tgctctggaa gctttcgaaa agatcgcggt agaagacacc ggtactgcgc   8640
```

aggttttgcc tgaagctttg attcagaaga tccttgctat ctcacaaggg cagccagatg 8700
accgcgatct gcgcttgtgc gcaacggcca ttgattacaa tctgaaaacg gcagaacttt 8760
atcaaatcga cgataaatcg ctgaactggc gtgtggaagg cccattcgat agctcatata 8820
gtctggcgtt ggtcaaccgc gaatttgccc gggcactctc agccgatggt gtagaggttt 8880
tattgcattc cactgaagga ccaggtgatt ttgccccaga tgcctcgttt atggcacagt 8940
cggaaaatag tgatcttctg gcattttata atcaatgtca gacccgcaag agtaacgaaa 9000
agatagatat tattagcaga aatatctatc caccgcgggt taccaaaatg gatgccaaag 9060
taaaattcct tcattgttat gcttgggaag aaacgggctt tccgcaaccg tggatcaatg 9120
aatttaatcg ggaacttgac ggagtgctgt gtacttcgga acatgttcgt aaaatactga 9180
ttgataacgg actgaatgtg cccgcatttg ttgttggcaa tggctgtgac cattggctca 9240
atatcccagc cgagacgaca aaagatgtgg atcacggaac attccgtttc ctgcacgtct 9300
cttcttgttt cccacgcaaa gggatacagg caatgcttca ggcttggggg aaggcgttca 9360
ctcgtcgtga caatgttatc ttaatcatta agacttttaa caatccgcac aatgaaattg 9420
acgcatggct ggctcaggcc caggctcaat tcatagacta tcccaaagtt gaagtgatca 9480
aagaggatat gtcagccacc gagcttaaag ggctttatga aagctgtgat gttttggttg 9540
ctccaggttg cgctgaaggc tttggtttac ctattgctga agcaatgctg agtgggctac 9600
cggctatcgt caccaattgg agcgggcaac ttgattttgt taattcacaa aattcatggc 9660
tggttgacta tcagttcact cgggtaaaaa cgcactttgg tctgttttcc tcagcctggg 9720
ccagtgtgga tattgacaac ttaacagatg cattaaaagc ggcagcctca accgataaat 9780
cagtgctgcg tgacatggcc aatgctggtc gcgagcttct tctgcagcag tttacctgga 9840
aagcggtggc tgatcgttct tgccaggcgg tcaagactct gcgtgcgcat attgatattg 9900
cacagcatcg ggcgcgcatt ggctgggtga cgacctggaa cacgaaatgt gggatcgcaa 9960
cctattccca gcatctggtg gaaagcgcac ctcatggcgc ggatgttgtt tttgctcccc 10020
aggtcagcgc tggcgatctt gtgtgtgcag acgaagagtt tgtacttcgc aactggattg 10080
taggtaaaga gagcaactat ctggaaaacc tccagccaca cattgatgct ctgagactcg 10140
atgtcattgt gatccaattc aactatggat tctttaatca tcgagaactg tcggcgttta 10200
ttcgtcgcca gcatgacgcc ggtcgttcag ttgttatgac gatgcactca actgtggatc 10260
cgctggaaaa agagccgagc tggaatttcc gtcttgctga aatgaaagag gcgctggcac 10320
tttgcgaccg gttgttggtg cattcgattg ccgatatgaa ccgccttaaa gatttaggct 10380
taactgcgaa tgttgcttta ttcccgcacg gtgttatcaa ctactccgca gcgagcgtca 10440
cacgtcaaca gcagtcttta ccgctaattg cgagctatgg cttctgctta ccgcataagg 10500
gcctgatgga actagtagaa tccgtccata gactcaagca agccggtaaa ccggttcgtt 10560
tacgactggt gaacgcagag tatcctgttg gggagtcacg cgatctggtg gcagagctta 10620
aagctgctgc tcagcggtta ggtgttaccg atctgattga gatgcataat gatttcctac 10680
ctgatgcgga gagtctgcgg ttgctttcag aagccgatct tctgattttt gcttatcaga 10740
atactgggga gtctgctagc ggggcggtac gttatggtat ggcgactcaa aaacctgttg 10800
cggtaacgcc cctggcgata tttgatgatt tggacgatgc cgtctttaaa tttgatggat 10860
gcagcgtcga tgatatcagt caggggattg accggatcct gaattccatc cgtgaacaga 10920
actcttgggc aaccaggact caacaacgtg ccgatgcatg gcgggaacaa catgattatc 10980
aagctgtttc acgccgtctg gttaatatgt gtcaaggctt agctaaagct aaatatttta 11040

-continued aataaaaata tctctcttgt attttttgcc tttgaataca agaggggtta gataatgtgt 11100
catttattat gaaaattatt tttgctactg agccaattaa atacccatta acgggcatcg 11160
gtcggtattc cctggagctg gttaagcggc tggcggtcgc ccgcgaaatt gaagaattaa 11220
agctatttca cggtgcgtcg tttatagaac agatcccttt ggtggagaat aaaagcgata 11280
ccaaagccag caatcatggt cgtctgtcgg cgtttctacg ccgacagacg ctgttgattg 11340
aggcttatcg cttgctgcat ccgcggcgcc aggcgtgggc attgcgcgac tataaggatt 11400
atatctacca tggccccaat ttttatctgc cgcataaact ggaacgcgcc gtgaccacgt 11460
ttcatgacat atccattttt acctgcccgg aatatcatcc aaaagatcgg gttcgctata 11520
tggagaagtc cctgcatgag agtctggatt cggcaaagct gatcctgacc gtttctgatt 11580
tctcgcgcag tgaaattatc cgcttgttca actatccggc ggagcggatc gtaaccacca 11640
agctagcctg cagcagtgac tatatcccac gcagcccggc agagtgtctg ccggtactgc 11700
agaaatatca gctggcgtgg caggcctacg cgctatatat cggcactatg gagccacgta 11760
aaaatatccg aggcctgctg catgcctatc agctgctacc gatggagatc cgcatgcgct 11820
atccgctaat ccttagcggc tatcgcggct gggaagacga tgtgctgtgg cagttagtcg 11880
agcgcggtac tcgggaaggc tggatccgtt acctcggata tgttccggat gaagacctgc 11940
cgtatctgta cgcagcggcc agagtctttg tttatccctc cttctacgag ggattcggtt 12000
tacctattct tgaagcgatg tcttgcggtg tgccggtagt atgctccaat gtcacctctt 12060
tgcctgaggt tgttggcgat gccggcctcg ttgccgatcc taatgatata gacgcgatta 12120
gcgcgcaaat tttgcagagc ctgcaagatg atagctggcg ggaaatcgcc accgcgcgcg 12180
gtcttgctca ggcgaaacag ttttcgtggg agaactgtgc gacacagacc attaacgcct 12240
ataaattact ctaagggtgt cagttgagag ttctacacgt ctataagact tactatcccg 12300
atacctacgg cggtattgag caggtcattt atcagctaag tcagggctgc gcccgccggg 12360
gaatcgcagc cgatgttttc acttttagcc cggacaaaga tacaggtcct gtcgcttacg 12420
aagatcatcg ggtcatttat aataaacagc tttttgaaat tgcctccacg ccgttttcgc 12480
tgaaagcgtt aaagcgtttt aagctgatta aagatgacta cgatatcatc aactaccatt 12540
ttccgtttcc ctttatggat atgctgcatc tttcggcgcg gcctgacgcc aggactgtgg 12600
tgacctatca ctctgatata gtgaaacaaa aacggttaat gaagctgtac cagccgctgc 12660
aggagcgatt tctcagcggc gtagattgca tcgttgcctc gtcgcccaat tacgtggctt 12720
ccagccagac cctgaaaaaa tatctggata aaacggtggt gatcccgttt ggtctggagc 12780
agcaggacgt gcagcacgat ccgcagaggg tcgcgcactg gcgggaaact gtcggcgata 12840
agttctttct cttcgtcggc actttccgct actacaaagg gctgcatatt ctgatggatg 12900
ccgctgagcg tagccgactg ccagtggtgg ttgtaggggg cgggccgctg gaatcggaag 12960
tgcggcgtga agcgcagcag cgcgggctga gcaatgtgat gtttaccggc atgctcaacg 13020
acgaagataa gtacattctc ttccagctct gccggggcgt ggtattcccc tcgcatctgc 13080
gctctgaggc gtttggcatt acgttattgg aaggcgcacg ctttgcaagg ccgctgatct 13140
cttgcgagat cggtacaggt acctctttca ttaaccagga caaagtgagt ggttgcgtga 13200
ttccgccgaa tgatagccag gcgctggtgg aggcgatgaa tgagctctgg aataacgagg 13260
aaacctccaa ccgctatggc gaaaactcgc gtcgtcgttt tgaagagatg tttactgccg 13320
accatatgat tgacgcctat gtcaatctct acactacatt gctggaaagc aaatcctgag 13380
cggccgcgag ctcgtcgact cgaggatccg tgtaggctgg agctgcttcg aagttcctat 13440
actttctaga gaataggaac ttcggaatag gaactaagga ggatattcat atggataaag 13500
ccgtaagcat ataagcatgg ataagctatt tatactttaa taagtacttt gtatacttat 13560
ttgcgaacat tccaggccgc gagcattcag cgcggtgatc acacctgaca ggagtatgta 13620
atgtccaagc aacagatcgg cgtagtcggt atggcagtga tgggacgcaa ccttgcgctc 13680
aacatcgaaa gccgtggtta taccgtctct attttcaacc gttcccgtga gaagacggaa 13740
gaagtgattg ccgaaaatcc aggcaagaaa ctggttcctt actatacggt gaaagagttt 13800
gtcgaatctc tggaaacgcc tcgtcgcatc ctgttaatgg tgaaagcagg tgcaggcacg 13860
gatgctgcta ttgattccct caaaccatat ctcgataaag gagacatcat cattgatggt 13920
ggtaacacct tcttccagga cactattcgt cgtaatcgtg agctttcagc agagggcttt 13980
aacttcatcg gtaccggtgt ttctggcggt gaagaggggg cgctgaaagg tccttctatt 14040
atgcctggtg gccagaaaga agcctatgaa ttggtagcac cgatcctgac caaaatcgcc 14100
gccgtagctg aagacggtga accatgcgtt acctatattg gtgccgatgg cgcaggtcac 14160
tatgtgaaga tggttcacaa cggtattgaa tacggcgata tgcagctgat tgctgaagcc 14220
tattctctgc ttaaaggtgg cctgaacctc accaacgaag aactggcgca gacctttacc 14280
gagtggaata acggtgaact gagcagttac ctgatcgaca tcaccaaaga tatcttcacc 14340
aaaaaagatg aagacggtaa ctacctggtt gatgtgatcc tggatgaagc ggctaacaaa 14400
ggtaccggta aatggaccag ccagagcgcg ctggatctcg gcgaaccgct gtcgctgatt 14460
accgagtctg tgtttgcacg ttatatctct tctctgaaag atcagcgtgt tgccgcatct 14520
aaagttctct ctggtccgca agcacagcca gcaggcgaca aggctgagtt catcgaaaaa 14580
gttcgtcgtg cgctgtatct gggcaaaatc gtttcttacg cccagggctt ctctcagctg 14640
cgtgctgcgt ctgaagagta caactgggat ctgaactacg gcgaaatcgc gaagattttc 14700
cgtgctggct gcatcatccg tgcgcagttc ctgcagaaaa tcaccgatgc ttatgccgaa 14760
aatccacaga tcgctaacct gttgctggct ccgtacttca agcaaattgc cgatgactac 14820
cagcaggcgc tgcgtgatgt cgttgcttat gcagtacaga acggtattcc ggttccgacc 14880
ttctccgcag cggttgccta ttacgacagc taccgtgctg ctgttctgcc tgcgaacctg 14940
atccaggcac agcgtgacta ttttggtgcg catacttata agcgtattga taaagaaggt 15000
gtgttccata ccgaatggct ggattaa 15027

<210> SEQ ID NO 15
<211> LENGTH: 11283
<212> TYPE: DNA
<213> ORGANISM: Artificial Sequence
<220> FEATURE:
<223> OTHER INFORMATION: example O15 rfb locus nucleotide sequence - O15-EPA production strain stLMTB11738

<400> SEQUENCE: 15
atgacgaatt taaaagcagt tattcctgta gcgggtctcg ggatgcatat gttgcctgcc 60
actaaggcga tacccaaaga gatgctacca atcgtcgaca agccaatgat tcagtacatt 120
gttgacgaga ttgtggctgc agggatcaaa gaaatcctcc tggtaactca cgcgtccaag 180
aacgcggtcg aaaaccactt cgacacctct tatgagttag aatcactcct tgagcagcgc 240
gtgaagcgtc aactgctggc ggaagtacag tccatctgtc cgccgggcgt gaccattatg 300
aacgtgcgtc agggcgaacc tttaggttta ggccactcca ttttgtgtgc gcgacctgcc 360

```
attggtgaca acccatttgt cgtggtactg ccagacgttg tgatcgacga tgccagcgcc    420
gacccgctac gttacaacct tgctgccatg attgcacgtt tcaacgaaac gggccgcagc    480
caggtgctgg caaaacgtat gccgggtgac ctctctgaat actccgtcat ccagactaaa    540
gagccgctgg accgtgaggg taaagtcagc cgcattgttg aatttatcga aaaaccggat    600
cagccgcaga cgctggactc agacatcatg gccgtaggtc gctatgtgct ttctgccgat    660
atttggccgg aactggaacg tactcagcct ggtgcatggg gacgtattca gctgactgat    720
gctattgccg agctggcgaa aaaacaatcc gttgatgcaa tgctgatgac cggcgacagt    780
tacgactgcg gcaaaaaaat gggctatatg caggcgtttg tgaagtatgg cctacgcaac    840
ctgaaagaag gggcgaagtt ccgtaaaggt attgagaagc tgttaagcga ataatgaaaa    900
tctgaccgga tgtaacggtt gataagaaaa ttataacggc agtgaaaatt cgcagcaaaa    960
gtaatttgtt gcgaatcttc ctgccgttgt tttatataaa ccatcagaat aacaacgagt   1020
tagcagtagg gttttattca aagttttcca ggattttcct tgtttccaga gcggattggt   1080
aagacaatta gcgtttgaat ttttcgggtt tagcgcgagt gggtaacgct cgtcacatca   1140
taggcatgca tgcagtgctc tggtagctgt aaagccaggg gcggtagcgt gcattaatac   1200
ctctattaat caaactgaga gccgcttatt tcacagcatg ctctgaagta atatggaata   1260
aattaagcta gcatgagcaa aactaaacta aatgttcttt accttgcaat aagtcagggt   1320
gccaattacc tactgccatt attaattttt ccttatcttg ttagagtcat tggtgtatcg   1380
aattttggtg atctgagttt ttcattgata actatacaag tgttgttaat ggttgttgaa   1440
tatggttttg gatatagtgg gacaagagaa atagcactaa ataacgataa aaaataccat   1500
tctgaatttt tttgcggtgt ggtgcttgct cgttttatat taatgctaat tgcagctata   1560
atactcataa tactctgttt tttttatgtt tttaacgacg ttaagtcttt gttatgtgtt   1620
ggttttctgt ccgtaattgc aggtgttttc aatccaaatt ggtttttgca aggtaaggaa   1680
atgatgagtg tgatggctgt gctgtcacta ttttcacgag gcatagcagt cgttgcagtt   1740
tatctaatta taaaacccgc aacgccgatg tacatcagtg ccttattatt gagcatgcca   1800
tatattttgt attcattctg tggcgttgcc tacttactta ttatcaagga gattttttta   1860
tgtaggccac cgataaagaa aattcaagta attttaaaaa atggatttca tttttttttgt  1920
tcaacacttg cgactagtgc atacacaatg ttgacccctc ttgtattggg tggcgtatct   1980
ggaaagtttg atgtaggcat ctttaactca gctaacatga tcaaacaagg tttggctgga   2040
cttgcatcac cattagtcca agctttttat ccaagaatta acatttgca aagagagaat   2100
ccatatattg caaacttaaa atctagaatg attcttaaat acttgcttgt tttttacatg   2160
gctttagcaa taccattttt acttttgcc aaccaattat cattattaat attcggcatg    2220
aaaggtgaag taattgcagg tgcaatgcaa ttaatgacat tgcttcctat attcataggt   2280
tttaatacag ttgtcgggtt acttgtatta gtacctaatg ggatgcaaaa acagtatttc   2340
aaatctattt tcctaggaac tattacttgt ttaagcatag tttatccagc atgtaaatat   2400
tatggagcaa cgggtgcgat tgtgagtctt attgtagctg aaattttcgt tggcatggga   2460
atgcttaaac aattcattaa agtaaataaa accgtatgta ggcctcataa attatgaata   2520
tctcggtaat aatatctgtt tggaaacgcc cagttcaatt agaattgatt ctctctgagc   2580
tcgattctca ggctaaagac aatagtctac acctagaagt aattgtttcc gatagtcata   2640
gtggtaaaga aattgatgat gtagttgctg ataatattca taaaaagaaa aatattaata   2700
ttatccatca acatactaaa aatatactct ccgctaagcg caatttcgga gcatccctag   2760
```

```
cccatgggga ttatttaata tttcttgatg atgattgtat acccgcaagt ggatatatat   2820
catcgttgct gaactattta aaaaaaatga atagtaaaag cgttttatgt ggggaagtta   2880
gattcgaaaa tgaactcatt gagaccagca attactatcg ctacaggaac tctttacacc   2940
ctaagtttag tgatagtcct gatatctcta tgaatgcctg gacttttgtc gcaatgaatt   3000
gtgttcttga tagaaaggca ttttcatcag gtatagtttc atataatgaa aattttattg   3060
gttatggttg tgaagatcat gagtttgggt ggcaacttga aaaaaatgac ttcaaaatta   3120
tttttgctga ttttaaaata ttacatcacg aatacagtgg cgatatagaa ggatatacaa   3180
aaaaaattcg tgctacagca cgtgatggta tgaatgtatt aagcaaagta aggcctgaaa   3240
tgttttctac taataaaaaa ttattcctag ttgagaaaat atttagtaaa cacaaaacgt   3300
ttagtaaaat atgccaatca atatttttca ataaatttat ttttaaaaaa ataatacaat   3360
ttttaaaaaa aacagatgca aataaaaaac tctatttccc aattctttac agatatgtgt   3420
tgatttcggc atatatacat ggtattggag agcgtggcac ctcaaaaaca gatgatttgc   3480
ttaagaactg gtatatatag atgatgctat cttcatttat taagacattt gtatggaagg   3540
taaaaaacaa tgaagtataa tgcattgatg gctttttat tattttttgt tgttttttt    3600
agattgtcgc tgataatacc tttcttatat ttggcattta ttcctgcatt ttttggtatt   3660
atgtatttag tgcgtaattt tatgattact atgggcaatg gattggtatc tatagatcgt   3720
aaaaatttgt tgctgttatc tatattcata attattttt tattttgttt ggttttcgat    3780
ttgtttcaaa aaagccattc ttttcaaagt tattttaccg ttagattatt tatgttgttt   3840
ttattttcat ttgttcctgc gtattattta gtaaatagat tcataaaggg tgacttgaaa   3900
ttaatggagc gaatattagt gtattctctc tgggttcaaa tagttatttt ttttggtatg   3960
tatataagtc cagagttaaa aagattgtta tatactttct ttggtatgtc tgactctgtt   4020
aatctttggg aacaaaatgc taaagtaaga ggatttgggt tgtcgggtga aataaatttc   4080
atgacaccat tttgatgat ctatatgtca ttttttatga tgaaaaggcg ttatgcttta    4140
attactttaa tttgtctgac tcaaatcgta aattctaaca tggctgtgat tgcagccatt   4200
attggtatcg gttgctctag acttaatatt aatataaaaa ttgcaacagt attgattttg   4260
ggagttttag tttatagctt aggagcggtg ttctttcctc gattttatga tgagttcgtt   4320
tctggagatg gcacaagaac tctggatatc ttattacagc aacatgtgtt tgttgtaggt   4380
aatttagatt tttttaatat tatatttgga ttacagcaaa acatatcttc atcaatcccc   4440
gatattaaac aaagttcgga tatgggctgg gttatactgt ttaattacgg tgggttaaca   4500
tttattacac tctttttatt tttaatcttt actatttcta ttgcgacatt tggaatgaca   4560
tatcaagcaa ttatatggat gttaattggg ataattttca ataccaaagg tttagtttta   4620
ggatctaacg gctatttctt tctatctttt atatatatgt ttttgaatag agtaacactt   4680
agtggacaga gttcaattac taataagtta ggtcaagtaa gtaaatagct tccagagtat   4740
atttgtcaat gatttgaggt tcggttatta tgttttcatc taaaacactg ttaattactg   4800
gtggtactgg ctctttcggg aatgctgtat taaatagatt tcttgataca gatattgcag   4860
aaatccgtat atttagtcgt gatgaaaaaa aacaagatga tatgcggaaa aaatacaata   4920
atcaaaaatt aaagttctat attggtgatg tcagagatta ccgtagtatt ttgaatgcga   4980
ctcgcggtgt tgattttata tatcatgcag cggcacttaa gcaagttcca tcatgtgaat   5040
ttcatcctat ggaagccgtt aaaactaata tccttggtac ggaaaatgtt cttgaagcag   5100
```

```
ctatagcgaa tgaagtgaag agggttgtat gcctaagtac tgataaagct gtatacccga   5160
ttaacgcaat gggtatttca aaagctatga tggaaaaggt catggtcgcg aaatcccgta   5220
atgttgatcg caataaaaca gtaatatgtg gtacccgtta tgggaatgtt atggcatctc   5280
gcggttcagt tattccatta tttgttgatc ttattagagc gggcaagcca ctcacaataa   5340
ctgatcctaa tatgacccgc tttatgatga ctcttgagga tgcggtagat ttagttcttt   5400
atgcgtttga acatggtaat aatggtgata tctttgtgca aaaagcacct gcagcaacta   5460
ttgacacatt agctattgct ttaaaggaat tactaaatgt tcctgaccat ccggtaaatg   5520
tcattggaac gcgtcatggc gagaaattat atgaagctct acttagtcgt gaggaaatga   5580
tcgctgctat agatatgggc gattattacc gtgtcccgcc agatcttcgt gaccttaatt   5640
atggcaaata tgttgagcaa ggtgatagcc gaatatctga aatagaagat tataactctc   5700
ataatactca acggttagat gttgaaggca tgaaagagct cttgctaaaa ttagccttta   5760
ttcgagcaat tcgtgctggt gaaaaatata atctggattc atgatatgaa aatattagtt   5820
actggtgcaa atggttttat tggtcgtaat ttatgtttga ggcttgagga acttggttat   5880
aaagatctta ttagaattga tcgagaatca acgaagcaag atcttgaaca aggcttacag   5940
gatgccgatt ttatttatca cttagctggt atcaatagac ctaagactga tgatgagttt   6000
atttctggaa acagtgattt aacaaagcat atagttgagt atctcctttc tattggtaag   6060
aatacaccaa ttatgctaag ttcttcgata caagctgaac ttaataatgc ttatggggtt   6120
agcaaagctg tagctgaaag ctatgtcgaa aaatatgctg ctgctagtgg ttcttcgtat   6180
tatattttca gatatccaaa cgtttttggt aaatggtgta agccaaacta taattctttt   6240
atagcaactt tttgctacaa tatttccaat gatattgaga ttactatcaa tgatgcagca   6300
gcgccagtca atctggtcta tattgatgat gtttgtactg atgctatagc tcttctctct   6360
gggacggttg aaagtggata taaagttgtt gcaccaattt attcaacaac agttggtgaa   6420
gttgcagaat taatttatag cttcaaaaat agccgttcca ccctgatcac agaggctgtc   6480
ggggcgggat ttacccgtgc attgtattct acatggctga gttatttacc agcagagaag   6540
tttgcgtaca aggtaccttt ttatggggat gcccgcggag tcttttgtga gatgttgaaa   6600
acgccttcag cggggcagtt ttcatttttt actgctcacc ctggtattac gcgtggcgga   6660
cattaccatc acagtaaaaa tgagaagttt ttggtcattc gaggtcaggc atgctttaaa   6720
tttgaacatg tgattaccgg tgagcgatat gaactgaaag tttcatcggg tgagtttaag   6780
attgttgaaa cagttcctgg ttggacacat gacattacaa atattggaac tgatgaatta   6840
atagtcatgc tctgggcaaa tgaaattttc aaccgtgatg agcccgatac tattgcgaga   6900
cctctataat gaaaaaatta aaagttatgt ctgttgttgg aacccgtcct gagattatcc   6960
gtttgtcgag ggttcttgct aagtttgatg aatactgcga gcatattatt gtccatactg   7020
gtcaaaatta tgattacgaa ttaaatgaag tgttcttcaa tgacttgggt gttcgaaaac   7080
ctgattattt tttaaatgca gcgggtaaaa atgcggcgga aaccattggt caggttatta   7140
ttaaggtaga tgaagtatta gaaatcgaaa aacctgaagc aatactggta ttgggcgata   7200
cgaattcatg tatttctgcc attccggcca aacgccgtaa agtgcctata tttcatatgg   7260
aagcaggtaa ccgttgtttc gatcaacgcg tgcctgaaga aaccaacaga cgtattgttg   7320
accatacggc tgatatcaat atgacctaca gtgatattgc tcgtgaatat ctcttggctg   7380
aaggtatccc agctgatcgg atcataaaaa ctggtagccc tatgtttgag gttctttcat   7440
attatatgcc ccaaattgat ggttcagatg tgctatcgcg tttgaatcta cagtctggtg   7500
```

-continued

```
agttttttgt agtaagtgcg catcgtgaag agaatgttga ttctccaaaa cagctcgtaa   7560
agcttgcgaa cattctaaat actgttgctg aaaaatataa tcttccagtt attgtctcca   7620
cacacccaag gacacgtaac cgaatccgtg agcaaggaat tgaatttcat tcaaatataa   7680
atctactgaa accattgggt ttccatgatt ataaccactt gcagaagaac tcacgagctg   7740
tgctttcaga tagcggtact atcactgaag agtcatccat catgaatttc ccagcggtaa   7800
acatccggga agcgcatgag cgtccggaag gctttgagga agcatccgtc atgatggtgg   7860
ggttagagtg tgaacgcgta ttacaagcgc tggatattct ggcaacacaa ccgcgaggtg   7920
aagtccgtct tttacgtcag gttagtgatt acagcatgcc aaatgtgtcg gataaagttg   7980
tcagaattgt tcactcttac acagattatg ttaagagagt cgtctggaaa gaatattgat   8040
gaaacttgct ttaatcatag atgattacct gcccaacagt actcgtgttg gtgcaaaaat   8100
gtttcatgaa cttgctcaag aatttatcca gcgtgggcac gatgttacgg taattactcc   8160
tggtacgggc atgcaagaag agatttcttt tgataccttt caggggggtaa aaacatggcg   8220
ttttaaaagc gggccgctca aggatgtaag taaaattcag cgagcggtca atgaaacgct   8280
tttgtcctat cgggcgtgga aagccatcaa aaaatgggta aaaaaagaga cctttgaggg   8340
ggtgatttat tattcacctt ccatattctg gggccttta gttaaaaaaa ttaaagctcg   8400
ttgccaatgt cctgcttatc ttattttaag agatatgttt ccacaatggg taattgatgc   8460
aggaatgctt aatgctggtt ccccaataga acgctacttt cgtctttttg aaaaaatatc   8520
ttatcgtcag gcaaatcgta ttggacttat gtctgataag aatcttgatg tttttcggaa   8580
agataataaa ggctatccgt gcgaagtttt gcgtaattgg gcatccctaa caccaacgat   8640
catacccaag gattatatac cactacgtaa gcgacttggc ctagaggata aaaccatttt   8700
cttctatggt ggaaacatag gtcatgcaca ggacatgaca aacttgatgc gacttgtgag   8760
aaacatggca gcatatcctc aagctcattt cctatttatt ggccaggggg atgaagttga   8820
attaattaat tcattagcat ctgagtgggc attgacgaat ttcacctatt tgccctcggt   8880
taaccaagat gaatttaagt tcattttgtc ggaaatggat atcggcttgt tttctctttc   8940
cgctagacac tcttcccata attttcctgg taagttatta ggctatatgg ttcagtcgct   9000
acctatttta ggtagcgtaa atgccggaaa tgatttgctc gacattgtca atcaaaataa   9060
tgcgggatta atccatgtca atggtgagga cgataaatta tgtcaatctg cgctattaat   9120
gttgcatgat attgatgtgc gccggcaact tggttcgggg gcgaatatat tgttgaaaga   9180
acaattctcc gttgagtctg cggcacagac gatagaaatg aggttggagg catgcaatgc   9240
gattaattga taatgaccaa ctcgacgaat tatatgatca agccgggcaa tcggaacgtt   9300
tacgttccca ccttatgatg cacggctcgc atcaagaaaa ggtacagcgt ttacttattg   9360
cattagtaaa gggcagctat gttgaaccgc attatcacga acttcctcat cagtgggaaa   9420
tgttcattgt tatggagggg caacttcagg tttgtttgta tggtagaaat ggtgaggtta   9480
taaagcaatt tatagcagga gataatactg gaatgagcat tgtggagttt tctccgggcg   9540
atatacacag tgtcgaatgc ctatctccgc gtgctcttat ggtggaagtt aaggaggggc   9600
catttgaccc ttcttttgca aaatcgttcg tgtgagcggc cgcgagctcg tcgactcgag   9660
gatccgtgta ggctggagct gcttcgaagt tcctatactt tctagagaat aggaacttcg   9720
gaataggaac taaggaggat attcatatgg ataaagccgt aagcatataa gcatggataa   9780
gctatttata ctttaataag tactttgtat acttatttgc gaacattcca ggccgcgagc   9840
```

```
attcagcgcg gtgatcacac ctgacaggag tatgtaatgt ccaagcaaca gatcggcgta   9900
gtcggtatgg cagtgatggg acgcaacctt gcgctcaaca tcgaaagccg tggttatacc   9960
gtctctattt tcaaccgttc ccgtgagaag acggaagaag tgattgccga aaatccaggc  10020
aagaaactgg ttccttacta tacggtgaaa gagtttgtcg aatctctgga aacgcctcgt  10080
cgcatcctgt taatggtgaa agcaggtgca ggcacggatg ctgctattga ttccctcaaa  10140
ccatatctcg ataaaggaga catcatcatt gatggtggta acaccttctt ccaggacact  10200
attcgtcgta atcgtgagct ttcagcagag ggctttaact tcatcggtac cggtgtttct  10260
ggcggtgaag agggggcgct gaaaggtcct tctattatgc ctggtggcca gaaagaagcc  10320
tatgaattgg tagcaccgat cctgaccaaa atcgccgccg tagctgaaga cggtgaacca  10380
tgcgttacct atattggtgc cgatggcgca ggtcactatg tgaagatggt tcacaacggt  10440
attgaatacg gcgatatgca gctgattgct gaagcctatt ctctgcttaa aggtggcctg  10500
aacctcacca acgaagaact ggcgcagacc tttaccgagt ggaataacgg tgaactgagc  10560
agttacctga tcgacatcac caaagatatc ttcaccaaaa aagatgaaga cggtaactac  10620
ctggttgatg tgatcctgga tgaagcggct aacaaaggta ccggtaaatg gaccagccag  10680
agcgcgctgg atctcggcga accgctgtcg ctgattaccg agtctgtgtt tgcacgttat  10740
atctcttctc tgaaagatca gcgtgttgcc gcatctaaag ttctctctgg tccgcaagca  10800
cagccagcag gcgacaaggc tgagttcatc gaaaaagttc gtcgtgcgct gtatctgggc  10860
aaaatcgttt cttacgccca gggcttctct cagctgcgtg ctgcgtctga agagtacaac  10920
tgggatctga actacggcga aatcgcgaag atttccgtg ctggctgcat catccgtgcg  10980
cagttcctgc agaaaatcac cgatgcttat gccgaaaatc cacagatcgc taacctgttg  11040
ctggctccgt acttcaagca aattgccgat gactaccagc aggcgctgcg tgatgtcgtt  11100
gcttatgcag tacagaacgg tattccggtt ccgaccttct ccgcagcggt tgcctattac  11160
gacagctacc gtgctgctgt tctgcctgcg aacctgatcc aggcacagcg tgactatttt  11220
ggtgcgcata cttataagcg tattgataaa gaaggtgtgt tccataccga atggctggat  11280
taa                                                                11283
```

<210> SEQ ID NO 16
<211> LENGTH: 13435
<212> TYPE: DNA
<213> ORGANISM: Artificial Sequence
<220> FEATURE:
<223> OTHER INFORMATION: example O16 rfb locus nucleotide sequence - O16-EPA production strain stLMTB11739

<400> SEQUENCE: 16

```
atgacgaatt taaaagcagt tattcctgta gcgggtctcg ggatgcatat gttgcctgcc     60
actaaggcga tacccaaaga gatgctacca atcgtcgaca agccaatgat tcagtacatt    120
gttgacgaga ttgtggctgc agggatcaaa gaaatcctcc tggtaactca cgcgtccaag    180
aacgcggtcg aaaaccactt cgacacctct tatgagttag aatcactcct tgagcagcgc    240
gtgaagcgtc aactgctggc ggaagtacag tccatctgtc cgccgggcgt gaccattatg    300
aacgtgcgtc agggcgaacc tttaggttta ggccactcca ttttgtgtgc gcgacctgcc    360
attggtgaca acccatttgt cgtggtactg ccagacgttg tgatcgacga tgccagcgcc    420
gacccgctac gttacaacct tgctgccatg attgcacgtt tcaacgaaac gggccgcagc    480
caggtgctgg caaaacgtat gccgggtgac ctctctgaat actccgtcat ccagactaaa    540
```

gagccgctgg accgtgaggg taaagtcagc cgcattgttg aatttatcga aaaaccggat 600
cagccgcaga cgctggactc agacatcatg gccgtaggtc gctatgtgct ttctgccgat 660
atttggccgg aactggaacg tactcagcct ggtgcatggg gacgtattca gctgactgat 720
gctattgccg agctggcgaa aaaacaatcc gttgatgcaa tgctgatgac cggcgacagt 780
tacgactgcg gcaaaaaaat gggctatatg caggcgtttg tgaagtatgg cctacgcaac 840
ctgaaagaag gggcgaagtt ccgtaaaggt attgagaagc tgttaagcga ataatgaaaa 900
tctgaccgga tgtaacggtt gataagaaaa ttataacggc agtgaaaatt cgcagcaaaa 960
gtaatttgtt gcgaatcttc ctgccgttgt tttatataaa ccatcagaat aacaacgagt 1020
tagcagtagg gttttattca aagttttcca ggattttcct tgtttccaga gcggattggt 1080
aagacaatta gcgtttgaat ttttcgggtt tagcgcgagt gggtaacgct cgtcacatca 1140
taggcatgca tgcagtgctc tggtagctgt aaagccaggg gcggtagcgt gcattaatac 1200
ctctattaat caaactgaga gccgcttatt tcacagcatg ctctgaagta atatggaata 1260
aattaagtga aaatacttgt tactggtggc gcaggattta ttggttcagc tgtagttcgt 1320
cacattataa ataatacgca ggatagtgtt gttaatgtcg ataaattaac gtacgccgga 1380
aaccgggaat cacttgctga tgtttctgat tctgaacgct atgtttttga acatgcggat 1440
atttgcgatg cacctgcaat ggcacggatt tttgctcagc atcagccgga tgcagtgatg 1500
cacctggctg ctgaaagcca tgttgaccgt tcaattacag gccctgcggc atttattgaa 1560
accaatattg ttggtactta tgtccttttg gaagccgctc gcaattactg gtctgctctt 1620
gatagcgaca agaaaaatag cttccgtttt catcatattt ctactgacga agtctatggt 1680
gatttgcctc atccagatga agtaaataat acagaagaat tacccttatt tactgagacg 1740
acagcttacg cgccaagcag cccttattcc gcatccaaag catccagcga tcatttagtc 1800
cgcgcgtgga aacgtacata tggtttaccg acaattgtga ctaattgctc gaacaactat 1860
ggtccttatc atttcccgga aaagcttatt ccactggtta ttcttaatgc actggaaggt 1920
aaggcattac ctatttatgg caaaggagat cagatccgcg actggttgta tgttgaagat 1980
catgcgcgtg cgttatatac cgtcgtaacc gaaggtaaag cgggtgaaac ttataacatt 2040
ggtgggcaca acgaaaagaa aaacatcgat gtagtgctca ctatttgtga tttgctggat 2100
gagattgtac cgaaagagaa atcttatcgt gagcaaatca cttatgttgc tgatcgtccg 2160
ggacacgatc gccgctatgc tattgatgct gagaagattg gtcgcgcatt gggatggaaa 2220
ccacaggaaa cgtttgagag cgggattcgt aaaacggtgg aatggtacct gtccaataca 2280
aaatgggttg ataatgtgaa aagtggtgcc tatcaatcgt ggattgaaca gaactatgag 2340
ggccgccagt aatgaatatc ctcctttttg gcaaaacagg gcaggtaggt tgggaactac 2400
agcgtgctct ggcacctttg ggtaatttga ttgcttttga tgttcactct actgattatt 2460
gcggtgattt tagtaatcct gaaggtgtag ctgaaaccgt aagaagcatt cggccggata 2520
ttattgtcaa tgcagccgct cacaccgcag tagacaaagc agaatcagaa ccggagtttg 2580
cacaattaat taacgcaaca agtgtcgaag cgattgcgaa agcagcaaat gaagttggag 2640
cctgggttat ccattactcg actgattacg tcttccctgg aaatggcgat atgccatggc 2700
tggagacgga tgcaaccgca ccactaaatg tttacggtga aaccaagtta gccggagaaa 2760
aagcgttaca ggaatattgc gcgaagcatc ttattttccg gaccagctgg gtctatgcag 2820
gaaaaggaaa taacttcgcc aaaacgatgt tacgtctggc aaaagagcgt gaagaattag 2880
cggttattaa cgatcagttt ggtgcgccaa caggtgctga actgctggct gattgtacag 2940

```
cacatgccat tcgtgtcgca ctgaataaac cggatgtcgc aggcttgtac catttggtag   3000
ccagtggtac cacaacctgg tacgattatg ctgcgctggt tttgaagag gcgcgcaaag   3060
caggcattcc ccttgcactc aacaagctca acgcagtacc aacaacagcc tatcctacac   3120
cagctcgtcg tccacataac tctcgcctta atacagaaaa atttcagcag aactttgcgc   3180
ttgtcttgcc tgactggcag gttggcgtga aacgaatgct caatgaatta tttacgacta   3240
cagcaattta atagtttttg catcttgttc gtgatggtgg agcaagatga attaaaagga   3300
atgatgaaat gaaaatgcgt aaaggtatta ttttagcggg tggttctggt acacgtcttt   3360
atcctgtgac tatggctgtc agtaaacagc tattacctat ttatgataaa ccgatgatct   3420
attacccgct ctctacactg atgttggcgg gtattcgcga tattttgatt atcagtacac   3480
ctcaggatac tcctcgtttt caacaattgc tgggtgacgg tagccagtgg ggcctgaatc   3540
ttcagtacaa agtgcaacct agcccagatg gcctcgcgca ggcatttatc atcggtgaag   3600
agtttattgg tggtgatgat tgtgctttgg ttcttggtga taatatcttt tacggtcacg   3660
atctgccgaa gctaatggag gccgctgtta acaaagaaag tggtgcaacg gtatttgcct   3720
atcacgttaa tgatccagaa cgctatggtg tcgttgagtt tgataaaaac ggtacggcaa   3780
tcagtctgga agaaaaaccg ttagaaccaa agagtaatta cgccgttaca ggtctgtact   3840
tttatgataa cgacgtggtt cagatggcga aaaacttgaa gccgtctgca cgtggtgagt   3900
tagaaattac agatattaac cgtatttatc ttgagcaggg acgtctgtct gtcgcgatga   3960
tggggcgtgg ctacgcgtgg ctggacacgg ggactcatca gagtctgata gaagcaagta   4020
attttattgc gacaattgaa gagcgccagg gattgaaggt ttcctgtcct gaagagattg   4080
catttcgtaa aggttttatt gatgttgagc aagtaagaaa attagctgta ccactaataa   4140
agaataatta tgggcagtat ctttataaaa tgacgaagga ttcaaattaa tgaatgtgat   4200
tagaactgaa attgaagatg tgctaattct ggagccaaga gtatttggtg atgatagagg   4260
tttcttttat gagagcttta atcaatcagc atttgaacat attctaggct atccggtcag   4320
ctttgttcaa gacaatcact cacgttcatc aaaaaatgta ctcagaggcc ttcactttca   4380
acgcggcgag tacgcacaag ataaacttgt acgctgcact catggagcag tttttgatgt   4440
tgctgttgat attcgaccca attcggtatc ctttggtaaa tgggttggtg ttctgctttc   4500
agctgataat aagcagcagt tgtggatacc aaaagggttt gctcatggct tttggttct   4560
gtctgatatc gctgaatttc aatataaaac tacaaactat tatcatcctg aaagcgattg   4620
tggaatatgt tggaatgatg aacgcattgc aattgattgg ccccaaacat cagggttaat   4680
cctttcgcca aaagatgaaa ggctctttac gttagatgag cttatcagat taaaattaat   4740
tgcatgaata cgaataaatt atctttaaga agaaacgtta tatatctggc tgtcgttcaa   4800
ggtagcaatt atcttttacc attgcttaca tttccatatc ttgtaagaac acttggtcct   4860
gaaaatttcg gtatattcgg tttttgccaa gcgactatgc tatatatgat aatgtttgtt   4920
gaatatggtt tcaatctcac agcaactcag agtattgcca aagcagcaga tagtaaagat   4980
aaagtaacgt ctattttttg ggcggtgata ttttcaaaaa tagttcttat cgtcattaca   5040
ttgattttct taacgtcgat gaccttgctt gttcctgaat ataacaagca tgccgtaatt   5100
atatggtcgt ttgttcctgc attagtcggg aatttaatct accctatctg gctgtttcag   5160
ggaaaagaaa aaatgaaatg gctgacttta agtagtattt tatcccgctt ggctattatc   5220
cctctaacat ttatttttgt gaacacaaag tcagatatag caattgccgg ttttattcag   5280
```

```
tcaagtgcaa atctggttgc tggaattatt gcactagcta tcgttgttca tgaaggttgg   5340
attggtaaag ttacgctatc attacataat gtgcgtcgat ctttagcaga cggttttcat   5400
gtttttattt ccacatctgc tattagttta tattctacgg gaatagttat tatcctggga   5460
tttatatctg gaccaacgtc cgtagggaat tttaatgcgg ccaatactat aagaaacgcg   5520
cttcaagggc tattaaatcc tatcacccaa gcaatatacc caagaatatc aagtacgctt   5580
gttcttaatc gtgtgaaggg tgtgatttta attaaaaaat cattgacctg cttgagtttg   5640
attggtggtg ctttttcatt aattctgctc ttgggtgcat ctatactagt aaaaataagt   5700
atagggccgg gatatgataa tgcagtgatt gtgctaatga ttatatcgcc tctgcctttt   5760
cttatttcat taagtaatgt ctatggcatt caagttatgc tgacccataa ttataagaaa   5820
gaattcagta agattttaat cgctgcgggt ttgttgagtt tgttgttgat ttttccgcta   5880
acaactcttt ttaaagagat tggtgcagca ataacattgc ttgcaacaga gtgcttagtt   5940
acgtcactca tgctgatgtt cgtaagaaat aataaattac tggtttgctg aggattttat   6000
gtacgattat atcattgttg gttctggttt gtttggtgcc gtttgtgcga atgagttaaa   6060
aaagctaaac aaaaaagttt tagtgattga gaaaagaaat catatcggtg gaaatgcgta   6120
cacagaggac tgtgagggta tccagattca taaatatggt gcacatattt ttcataccaa   6180
tgataaatat atatgggatt acgttaatga tttagtagaa tttaatcgtt ttactaattc   6240
tccactggcg atttataaag acaaattatt caaccttcct tttaatatga atactttcca   6300
ccaaatgtgg ggagttaaag atcctcaaga agctcaaaat atcattaatg ctcagaaaaa   6360
aaagtatggt gacaaggtac ctgaaaattt ggaggagcag gcgatttcat tagttgggga   6420
ggacttatac caagcattga taaagggtta tacggagaag cagtggggaa gaagtgcaaa   6480
agaattgcct gcatttatta ttaagcgaat cccagtgaga tttacgtttg ataacaatta   6540
tttttccgat cgctatcaag gtattccggt gggaggctac actaagctta ttgaaaaaat   6600
gcttgaaggt gtggacgtaa aattaggcat tgatttttttg aaagacaaag attctctagc   6660
gagtaaagcc catagaatca tctacactgg acccattgat cagtacttcg actataggtt   6720
tggagcgtta gaatatcgct ctttaaaatt tgagacggaa cgccatgaat ttccaaactt   6780
ccaagggaat gcagtaataa atttcactga tgctaatgta ccatatacca gaataattga   6840
gcataaacat tttgactatg ttgagacaaa gcatacggtt gttacaaaag aatatccatt   6900
agagtggaaa gttggcgacg aaccctacta tccagttaat gataataaaa acatggagct   6960
ttttaagaaa tatagagagt tagctagcag agaagacaag gttatatttg gcgggcgttt   7020
ggccgagtat aaatattatg atatgcatca agtgatatct gccgctcttt atcaagtgaa   7080
aaatataatg agtacggatt aatgatctat cttgtaatta gtgtctttct cattacagca   7140
tttatctgtt tatatcttaa gaaggatata ttttatccag ccgtatgcgt taatatcatc   7200
ttcgcactgg tcttattggg atatgaaata acgtcagata tatatgcttt tcagttaaat   7260
gacgctacgt tgatttttct actttgcaat gttttgacat ttaccctgtc atgtttattg   7320
acggaaagtg tattagatct aaatatcaga aaagtcaata atgctattta tagcatacca   7380
tcgaagaaag tgcataatgt aggcttgtta gttatttctt tttcgatgat atatatatgc   7440
atgaggttaa gtaactacca gttcgggact agcttactta gctatatgaa tttgataaga   7500
gatgctgatg ttgaagacac atcaagaaat ttctcagcat acatgcagcc aatcattcta   7560
actacttttg ctttatttat ttggtctaaa aaatttacta atacaaaggt aagtaaaaca   7620
tttactttac ttgtttttat tgtattcatc tttgcaatta tactgaatac tggtaagcaa   7680
```

```
attgtcttta tggttatcat ctcttatgca ttcatcgtag gtgttaatag agtaaaacat   7740
tatgtttatc ttattacagc tgtaggtgtt ctattctcct tgtatatgct ctttttacgt   7800
ggactgcctg gggggatggc atattatcta tccatgtatt tggtcagccc tataatcgcg   7860
tttcaggagt tttattttca gcaagtatct aactctgcca gttctcatgt cttttggttt   7920
tttgaaaggc tgatggggct attaacaggt ggagtctcta tgtcgttgca taaagaattt   7980
gtgtgggtgg gtttgccaac aaatgtttat actgcttttt cggattatgt ttatatttcc   8040
gcggagctaa gctatttgat gatggttatt catggctgta tttcaggtgt tttatggaga   8100
ttgtctcgaa attacatatc tgtgaaaata ttttattcat attttattta taccttttct   8160
ttcatttttt atcatgaaag cttcatgact aatattagca gttggataca aataactctt   8220
tgtatcatag tattctctca atttcttaag gcccagaaaa taaagtgaaa atgtattttt   8280
tgaatgattt aaatttctct agacgcgatg ctggatttaa agcaagaaaa gatgcactgg   8340
acattgcttc agattatgaa aacatttctg ttgttaacat tcctctatgg ggtggagtag   8400
tccagagaat tattagttct gttaagctta gtacatttct ctgcggtctt gaaaataaag   8460
atgttttaat tttcaatttc ccgatggcca aaccattttg gcatatattg tcattctttc   8520
accgccttct aaaatttaga atagtacctc tgattcatga tattgatgaa ttaagaggag   8580
gagggggtag tgattctgtg cggcttgcta cctgtgatat ggtcataagt cacaatccac   8640
aaatgacaaa gtaccttagt aaatatatgt ctcaggataa aatcaaagac ataaaaatat   8700
ttgattacct cgtctcatct gatgtggagc atcgagatgt tacggataag caacgagggg   8760
tcatatatgc tggcaacctt tctaggcata aatgttcttt catatatact gaaggatgcg   8820
attttactct ctttggtgtc aactatgaaa ataaagataa tcctaaatat cttggaagtt   8880
ttgatgctca atctccggaa aagattaacc tcccaggcat gcaatttgga ctcatttggg   8940
atggagattc tgtcgaaacc tgtagtggtg cctttggcga ctatttaaag tttaataacc   9000
ctcataagac atctctttat ctttcaatgg aacttccagt atttatatgg gataaagccg   9060
cccttgcgga tttcattgta gataatagaa taggatatgc agtgggatca atcaaagaaa   9120
tgcaagagat tgttgactcc atgacaatag aaacttataa gcaaattagt gagaatacaa   9180
aaattatttc tcagaaaatt cgaacaggaa gttacttcag ggatgttctt gaagaggtga   9240
tcgatgatct taaaactcgc taaacgatat ggtctctgtg gttttattcg gcttgttaga   9300
gatgtcttat tgactcgtgt attttaccgg aactgtagaa ttattcgatt tccctgctat   9360
attcgcaatg atggtagcat taattttggt gaaaatttca caagtggagt cggtctcagg   9420
ctggatgcat ttggacgtgg cgtgattttt ttttccgata atgtgcaagt taacgactat   9480
gttcatatcg cctcaattga gagcgttacg ataggtcggg atacgcttat tgcaagtaaa   9540
gtatttatta ccgatcataa tcacggttcc tttaagcact ctgatccaat gagttcgcca   9600
aatatacctc cagacatgcg cacgttggaa tcttcagctg ttgtaattgg ccagagggtt   9660
tggttgggtg agaatgtgac ggttttgcct ggaacaatta ttggtaatgg agtcgtagtc   9720
ggcgccaatt ctgttgttag aggttctatt cccgaaaata ctgtcattgc gggagtacca   9780
gcaaaaatca taaagaaata caatcatgag accaaattat gggaaaaagc atagtcgttg   9840
tttctgcggt caattttacc actggcggtc catttaccat tttgaaaaaa tttttggcag   9900
caactaataa taaagaaaat gtcagtttta tcgcattagt ccattctgct aaagagttaa   9960
aagaaagtta tccatgggtt aaattcattg agtttcctga ggttaaaggg tcgtggctaa  10020
```

-continued

```
aacgtttgca ctttgaatat gtagtttgta aaaaactttc aaaagagctg aatgctacgc  10080
attggatttg tctgcatgat attacggcca atgtcgtcac taaaaaaaga tatgtgtatt  10140
gtcataaccc tgccccttt tataaaggaa ttttattccg tgaaattctt atggagccta  10200
gctttttctt atttaaaatg ctatacgggc tgatatataa aataaacatt aaaaaaaata  10260
ctgcagtgtt tgttcaacaa ttctggatga aagaaaaatt tatcaagaaa tattctataa  10320
ataacatcat tgtcagtcgg ccagaaatta aattatctga taaaagccaa cttactgatg  10380
atgattctca atttaagaat aacccttctg agttgacaat attttaccct gctgttccac  10440
gagtatttaa aaattacgag cttattatta gtgcagcaag gaaattgaaa gaacaatcca  10500
atattaaatt tctgcttact atcagtggta cagaaaatgc gtatgcaaaa tatattatca  10560
gtcttgcaga aggactggat aatgttcatt tcctcgggta cttggataaa gaaaaaatcg  10620
atcattgtta taatatttca gatatagttt gttttccctc taggttagaa acatggggat  10680
tgccgttgtc tgaggctaaa gagcgaggta agtgggtatt agcatcagat ttcccattta  10740
ctagagaaac tcttggtagt tatgaaaaga aagctttttt tgattctaat aacgatgaca  10800
tgttagttaa acttattatt gacttcaaaa aaggtaacct caaaaaagat atctctgatg  10860
caaatttcat ttatcgtaat gaaaatgtat tagttgggtt tgatgaacta gttaatttta  10920
ttactgaaga acattgaaat ggtatatata ataatcgttt cccacggaca tgaagactac  10980
atcaaaaaat tactcgaaaa tcttaatgct gacgatgagc actacaagat tatcgtacgc  11040
gacaacaaag actctctatt attgaaacaa atatgccagc attatgcagg cctggactat  11100
attagtggag gtgtatacgg ctttggtcat aataataata ttgcggtggc gtatgtaaag  11160
gaaaaatata gacccgcaga tgatgattac attttgtttt tgaatcccga tatcatcatg  11220
aagcatgatg atttgctgac atatattaaa tatgtcgaaa gtaagcgtta tgcttttagt  11280
acattatgcc tgttccgaga tgaagcgaaa tctttacatg attattccgt aagaaaattt  11340
cctgtgcttt ctgattttat tgtgtcattt atgttaggga ttaataaaac aaaaattcct  11400
aaagaaagta tctattctga tacggttgtt gattggtgcg caggatcatt tatgctggta  11460
cgtttttcag attttgtgcg tgtaaatggc ttcgatcaag gttactttat gtactgtgaa  11520
gatattgacc tgtgcttgag gcttagcctg gctggtgtca gacttcatta tgttcccgct  11580
tttcatgcga tacattatgc tcatcatgac aatcgaagtt ttttttcaaa agccttcaga  11640
tggcacttaa aaagtacttt tagatattta gccagaaaac gtattttatc aaatcgcaac  11700
tttgatcgaa tttcatcagt tttcacccg taagagctcg gtacccgggc ctagggtgta  11760
ggctggagct gcttcgaagt tcctatactt tctagagaat aggaacttcg gaataggaac  11820
taaggaggat attcatatcc gtcgacggcg gccgccctgc aggcatgcaa gcttgatcca  11880
tatggatcgc tagcttaatt aaataaagcc gtaagcatat aagcatggat aagctattta  11940
tactttaata agtactttgt atacttattt gcgaacattc caggccgcga gcattcagcg  12000
cggtgatcac acctgacagg agtatgtaat gtccaagcaa cagatcggcg tagtcggtat  12060
ggcagtgatg ggacgcaacc ttgcgctcaa catcgaaagc cgtggttata ccgtctctat  12120
tttcaaccgt tcccgtgaga agacggaaga agtgattgcc gaaaatccag gcaagaaact  12180
ggttccttac tatacggtga aagagtttgt cgaatctctg gaaacgcctc gtcgcatcct  12240
gttaatggtg aaagcaggtg caggcacgga tgctgctatt gattccctca aaccatatct  12300
cgataaagga gacatcatca ttgatggtgg taacaccttc ttccaggaca ctattcgtcg  12360
taatcgtgag ctttcagcag agggctttaa cttcatcggt acgggtgttt ctggcggtga  12420
```

```
agagggggcg ctgaaaggtc cttctattat gcctggtggc cagaaagaag cctatgaatt  12480

ggtagcaccg atcctgacca aaatcgccgc cgtagctgaa gacggtgaac catgcgttac  12540

ctatattggt gccgatggcg caggtcacta tgtgaagatg gttcacaacg gtattgaata  12600

cggcgatatg cagctgattg ctgaagccta ttctctgctt aaaggtggcc tgaacctcac  12660

caacgaagaa ctggcgcaga cctttaccga gtggaataac ggtgaactga gcagttacct  12720

gatcgacatc accaaagata tcttcaccaa aaaagatgaa gacggtaact acctggttga  12780

tgtgatcctg gatgaagcgg ctaacaaagg tacgggtaaa tggaccagcc agagcgcgct  12840

ggatctcggc gaaccgctgt cgctgattac cgagtctgtg tttgcacgtt atatctcttc  12900

tctgaaagat cagcgtgttg ccgcatctaa agttctctct ggtccgcaag cacagccagc  12960

aggcgacaag gctgagttca tcgaaaaagt tcgtcgtgcg ctgtatctgg gcaaaatcgt  13020

ttcttacgcc cagggcttct ctcagctgcg tgctgcgtct gaagagtaca actgggatct  13080

gaactacggc gaaatcgcga agattttccg tgctggctgc atcatccgtg cgcagttcct  13140

gcaaaaaatc accgatgctt atgccgaaaa tccacagatc gctaacctgt tgctggctcc  13200

gtacttcaag caaattgccg atgactacca gcaggcgctg cgtgatgtcg ttgcttatgc  13260

agtacagaac ggtattccgg ttccgacctt ctccgcagcg gttgcctatt acgacagcta  13320

ccgtgctgct gttctgcctg cgaacctgat ccaggcacag cgtgactatt ttggtgcgca  13380

tacttataag cgtattgata aagaaggtgt gttccatacc gaatggctgg attaa       13435
```

<210> SEQ ID NO 17
<211> LENGTH: 13228
<212> TYPE: DNA
<213> ORGANISM: Artificial Sequence
<220> FEATURE:
<223> OTHER INFORMATION: example O18A rfb locus nucleotide sequence - O18A-EPA production strain BVEC-L-00559

<400> SEQUENCE: 17

```
atgacgaatt taaaagcagt tattcctgta gcgggtctcg ggatgcatat gttgcctgcc     60

actaaggcga tacccaaaga gatgctacca atcgtcgaca agccaatgat tcagtacatt    120

gttgacgaga ttgtggctgc agggatcaaa gaaatcctcc tggtaactca cgcgtccaag    180

aacgcggtcg aaaaccactt cgacacctct tatgagttag aatcactcct tgagcagcgc    240

gtgaagcgtc aactgctggc ggaagtacag tccatctgtc cgccgggcgt gaccattatg    300

aacgtgcgtc agggcgaacc tttaggttta ggccactcca ttttgtgtgc gcgacctgcc    360

attggtgaca acccatttgt cgtggtactg ccagacgttg tgatcgacga tgccagcgcc    420

gacccgctac gttacaacct tgctgccatg attgcacgtt tcaacgaaac gggccgcagc    480

caggtgctgg caaaacgtat gccgggtgac ctctctgaat actccgtcat ccagactaaa    540

gagccgctgg accgtgaggg taaagtcagc cgcattgttg aatttatcga aaaaccggat    600

cagccgcaga cgctggactc agacatcatg gccgtaggtc gctatgtgct ttctgccgat    660

atttggccgg aactggaacg tactcagcct ggtgcatggg gacgtattca gctgactgat    720

gctattgccg agctggcgaa aaaacaatcc gttgatgcaa tgctgatgac cggcgacagt    780

tacgactgcg gcaaaaaaat gggctatatg caggcgtttg tgaagtatgg cctacgcaac    840

ctgaaagaag ggcgaagtt ccgtaaaggt attgagaagc tgttaagcga ataatgaaaa    900

tctgaccgga tgtaacggtt gataagaaaa ttataacggc agtgaaaatt cgcagcaaaa    960

gtaatttgtt gcgaatcttc ctgccgttgt tttatataaa ccatcagaat aacaacgagt   1020
```

```
tagcagtagg gttttattca aagttttcca ggattttcct tgtttccaga gcggattggt   1080
aagacaatta gcgtttgaat ttttcgggtt tagcgcgagt gggtaacgct cgtcacatca   1140
taggcatgca tgcagtgctc tggtagctgt aaagccaggg gcggtagcgt gcattaatac   1200
ctctattaat caaactgaga gccgcttatt tcacagcatg ctctgaagta atatggaata   1260
aattaagtga aaatacttgt tactggtggc gcaggattta ttggttcagc tgtagttcgt   1320
cacattataa ataatacgca ggatagtgtt gttaatgtcg ataaattaac gtacgccgga   1380
aaccgggaat cacttgctga tgtttctgat tctgaacgct atgtttttga acatgcggat   1440
atttgcgatg cacctgcaat ggcacggatt tttgctcagc atcagccgga tgcagtgatg   1500
cacctggctg ctgaaagcca tgttgaccgt tcaattacag gccctgcggc atttattgaa   1560
accaatattg ttggtactta tgtccttttg gaagccgctc gcaattactg gtctgctctt   1620
gatagcgaca agaaaaatag cttccgtttt catcatattt ctactgacga agtctatggt   1680
gatttgcctc atccagatga agtaaataat acagaagaat taccccttatt tactgagacg   1740
acagcttacg cgccaagcag cccttattcc gcatccaaag catccagcga tcatttagtc   1800
cgcgcgtgga aacgtacata tggtttaccg acaattgtga ctaattgctc gaacaactat   1860
ggtccttatc atttcccgga aaagcttatt ccactggtta ttcttaatgc actggaaggt   1920
aaggcattac ctatttatgg caaaggagat cagatccgcg actggttgta tgttgaagat   1980
catgcgcgtg cgttatatac cgtcgtaacc gaaggtaaag cgggtgaaac ttataacatt   2040
ggtgggcaca acgaaaagaa aaacatcgat gtagtgctca ctatttgtga tttgctggat   2100
gagattgtac cgaaagagaa atcttatcgt gagcaaatca cttatgttgc tgatcgtccg   2160
ggacacgatc gccgctatgc tattgatgct gagaagattg gtcgcgcatt gggatggaaa   2220
ccacaggaaa cgtttgagag cgggattcgt aaaacggtgg aatggtacct gtccaataca   2280
aaatgggttg ataatgtgaa aagtggtgcc tatcaatcgt ggattgaaca gaactatgag   2340
ggccgccagt aatgaatatc ctcctttttg gcaaaacagg gcaggtaggt tgggaactac   2400
agcgtgctct ggcacctttg ggtaatttga ttgcttttga tgttcactct actgattatt   2460
gcggtgattt tagtaatcct gaaggtgtag ctgaaaccgt aagaagcatt cggccggata   2520
ttattgtcaa tgcagccgct cacaccgcag tagacaaagc agaatcagaa ccggagtttg   2580
cacaattaat taacgcaaca agtgtcgaag cgattgcgaa agcagcaaat gaagttggag   2640
cctgggttat ccattactcg actgattacg tcttccctgg aaatggcgat atgccatggc   2700
tggagacgga tgcaaccgca ccactaaatg tttacggtga aaccaagtta gccggagaaa   2760
aagcgttaca ggaatattgc gcgaagcatc ttattttccg gaccagctgg gtctatgcag   2820
gaaaaggaaa taacttcgcc aaaacgatgt tacgtctggc aaaagagcgt gaagaattag   2880
cggttattaa cgatcagttt ggtgcgccaa caggtgctga actgctggct gattgtacag   2940
cacatgccat tcgtgtcgca ctgaataaac cggatgtcgc aggcttgtac catttggtag   3000
ccagtggtac cacaacctgg tacgattatg ctgcgctggt ttttgaagag gcgcgcaaag   3060
caggcattcc ccttgcactc aacaagctca acgcagtacc aacaacagcc tatcctacac   3120
cagctcgtcg tccacataac tctcgcctta atacagaaaa atttcagcag aactttgcgc   3180
ttgtcttgcc tgactggcag gttggcgtga aacgaatgct caatgaatta tttacgacta   3240
cagcaattta atagtttttg catcttgttc gtgatggtgg agcaagatga attaaaagga   3300
atgatgaaat gaaaatgcgt aaaggtatta ttttagcggg tggttctggt acacgtcttt   3360
```

-continued

```
atcctgtgac tatggctgtc agtaaacagc tattacctat ttatgataaa ccgatgatct   3420
attacccgct ctctacactg atgttggcgg gtattcgcga tattttgatt atcagtacac   3480
ctcaggatac tcctcgtttt caacaattgc tgggtgacgg tagccagtgg ggcctgaatc   3540
ttcagtacaa agtgcaacct agcccagatg gcctcgcgca ggcatttatc atcggtgaag   3600
agtttattgg tggtgatgat tgtgctttgg ttcttggtga taatatcttt tacggtcacg   3660
atctgccgaa gctaatggag gccgctgtta acaaagaaag tggtgcaacg gtatttgcct   3720
atcacgttaa tgatccagaa cgctatggtg tcgttgagtt tgataaaaac ggtacggcaa   3780
tcagtctgga agaaaaaccg ttagaaccaa agagtaatta cgccgttaca ggtctgtact   3840
tttatgataa cgacgtggtt cagatggcga aaaacttgaa gccgtctgca cgtggtgagt   3900
tagaaattac agatattaac cgtatttatc ttgagcaggg acgtctgtct gtcgcgatga   3960
tggggcgtgg ctacgcgtgg ctggacacgg ggactcatca gagtctgata gaagcaagta   4020
attttattgc gacaattgaa gagcgccagg gattgaaggt ttcctgtcct gaagagattg   4080
catttcgtaa aggttttatt gatgttgagc aagtaagaaa attagctgta ccactaataa   4140
agaataatta tgggcagtat ctttataaaa tgacgaagga ttcaaattaa tgaatgtgat   4200
tagaactgaa attgaagatg tgctaattct ggagccaaga gtatttggtg atgatagagg   4260
tttcttttat gagagcttta atcaatcagc atttgaacat attctaggct atccggtcag   4320
ctttgttcaa gacaatcact cacgttcatc aaaaaatgta ctcagaggcc ttcactttca   4380
acgcggcgag tacgcacaag ataaacttgt acgctgcact catggagcag tttttgatgt   4440
tgctgttgat attcgaccca attcggtatc ctttggtaaa tgggttggtg ttctgctttc   4500
agctgataat aagcagcagt tgtggatacc aaaagggttt gctcatggct tttggttct   4560
gtctgatatc gctgaatttc aatataaaac tacaaactat tatcatcctg aaagcgattg   4620
tggaatatgt tggaatgatg aacgcattgc aattgattgg ccccaaacat cagggttaat   4680
cctttcgcca aaagatgaaa ggctctttac gttagatgag cttatcagat taaaattaat   4740
tgcatgaggc cggccttaag gaggactagt cccggcgcgc catgagttta atcaaaaaca   4800
gtttttggaa cctttgcggg tatgtacttc cagctattgt gacactacca gctttgggta   4860
ttatggggcg aaaattaggc ccagaattat ttggtgtatt cactttggca ttagctgttg   4920
tgggttatgc aagcattttt gatgcaggcc ttactcgcgc agtgatacga gaagtcgcaa   4980
ttgaaaaaga taatgaagaa aataagttga aaattatttc ttcagcgaca gttgtaatta   5040
tttatttgag tttggccgcc tcactcttat tattttttt tagtggtcat atcgcattgc   5100
tactgaacat tagtgagact ttttttcata atgtaagtgt ctcgcttaaa attctcgcag   5160
catccatacc attattttg attactcaaa tatggttgtc aattttagaa ggtgaagaaa   5220
gatttggttt acttaatatc tacaaatcaa ttacgggagt gatattagca atctcaccgg   5280
cattatttat acttattaaa ccctctttga tgtatgcgat aataggctta gttctagcaa   5340
ggttttatg ttttatttg gcttttataa tttgtcacga taaagtgctt aaagctaaac   5400
taacaatcga tataccaaca attaaaagat tgtttatgtt cggtggttgg attacagtaa   5460
gtaatatcat cagccctgtg ctatcatatt ttgataggtt tattgtttca aatcaacttg   5520
gggctgctaa tgttgctttt tatactgcac catcagaaat tatttctcgg cttagtataa   5580
ttccaggtgc gttttcaaga gccttatttc caagattagc taatgcaaat aattccgctg   5640
aaagatataa aacgaaaaga ttaattacaa tttcactttt aataatcatc acccctattt   5700
tttgtattgg cgtgttattt tcagagaaga taatggtttt atggatgggg gcatcatttt   5760
```

ttggtgagcc tggtttggta ttatcaatat tactgattgg ctttattttt aatggattgg 5820
cacaagtacc atttgccagt attcaatccc gaggtcatgc taagataact gcatttgttc 5880
atctcttaga gttgtttcct tatttattac ttttatttta cctcataaaa gcacatgggg 5940
ttgttggcgc gggtattgcg tggtcagtga ggatgatagt agattatata gcattaagtc 6000
ttttggacgg taagtatatt aataaataaa attcaaaatg caagttaata actcatggct 6060
ttatttgggt aggtgacaat ttataatgat atatatatta actttaactc ttcttctagt 6120
tatagccata atgttttctc ttctcggcac aaaaagtagg atcacatctc cattaccttt 6180
gcattttta ccatggttac taactttaat tgtcgggata agtaattacg atcaatttta 6240
cgagtttaat gaaagaagct tttactcttt gttgatttgg tttacagtta tttttatatt 6300
ttatttcata ggggaactgg ttaattataa acgtgaaaat ataaatgttt attatggtct 6360
ttcacatatt aaatatgaat gtaaaaaata ttggatcatt gtcatcccaa tttcattata 6420
taccattttc gaaatatata tggttggtat ggggggagca gatggattct ttctcaattt 6480
acgtcttgca aatacattgg agggctatac gggtaaaaaa tttatcttaa tgcctgctgt 6540
atatcctcta atgatggcta tgttcgcaat tgtttgtcta acaaaaactt ccaaattaaa 6600
taaatactcc atttatttct ggatgttttt gtattgtatt ggcacaatgg gaaaattttc 6660
aatattaacg ccaatattga catatttaat tatttatgac ttcaaacata gattaaaagt 6720
aaaaaaaaca ataaagttta cattgttgat aattatatta gctttaactt tgcattttac 6780
acgtatggct gagaatgacc actcaacatt tttatctatt ttagggctct atatttattc 6840
accaataatt gctttaggcc agttgaatga agtaaatagt agtcattttg gtgagtatac 6900
gtttagattc atatatgcta taactaataa aattggcctt attaaagaat tgccagtaaa 6960
tactattctt gactattcat acgttcctgt accaacaaat gtatatactg cacttcaacc 7020
attttaccag gattttggtt atactggcat catatttgga gcagtattat acggactaat 7080
atatgtgagt ttatacacgg ccggtgttcg tggaaataat acacaggcat tactgattta 7140
cgcattgttt tcagttagca gtgcaacggc tttcttcgct gaaacgctag taacgaattt 7200
agctggaaat gtgatgttag tattatgtac catcttacta tggcgattta cagtaatatg 7260
caaaccagta cagtaaccat tctaatggcc acctacaatg gcgaggcctt catcaaaaat 7320
cagattttgt cactacaaca acaaacattt tctaactggc ggttatttat tcaggatgat 7380
gggtctacag acaatactat atctataata aaaaacttcc aaaaatctga ctccagaatt 7440
cggctagttg atgataattt gaaaggtcaa ggtgcaggaa aaaatttttt atcgctgata 7500
aagtacagcg agacagatta tacaatttat tgtgaccaag atgatatttg gttagaaaac 7560
aaaatatttg aattagtaaa gtatgcaaat gaaattaaat tgaatgtatc agatgcgcct 7620
tcgctagttt atgctgatgg ctatgcttat atggatggtg agggtacaat cgattttct 7680
gggatatcta acaatcatgc tgatcaatta aaggattttc tttttttaa tggtggatac 7740
caaggatgtt ctattatgtt caatcgtgca atgaccaaat ttcttctgaa ttatcgagga 7800
tttgtatatc tacatgacga tatcacaaca ttagctgcat acgctcttgg taaagtttat 7860
tttctcccga aataccttat gttatataga cagcacacga atgcggtaac tggtatcaaa 7920
acattccgca atggattgac ttctaaattt aaatcaccag taaactatct tttatcacga 7980
aaacattatc aggtaaaaaa atcttttttt gaatgtaaca gctctatctt atcagagacg 8040
aataaaaaag tttttttgga ttttatttca ttttgtgaat caaataataa atttacagat 8100

```
tttttaagt tatggcgagg tgggtttaga ttaaataaca gtagaactaa attattatta   8160
aaattcttaa tacggagaaa atttagcgaa tgatttcaat acttacacct acttttaatc   8220
ggcaacatac tttatcaagg ctattcaatt ctcttatatt acaaactgat aaagattttg   8280
agtggataat aattgatgat ggtagtatag atgcaacagc ggtacttgta gaagatttta   8340
gaaaaaaatg tgattttgac ttgatttatt gctatcagga aaataatggt aagcccatgg   8400
ctttaaacgc tggtgttaaa gcttgtagag gcgattatat ctttattgtt gacagtgatg   8460
atgcactaac tcccgatgcc ataaaattaa ttaaagaatc aatacatgat tgcttatctg   8520
agaaggaaag tttcagcgga gtcggtttta gaaaagcata tataaaaggg gggattattg   8580
gtaatgattt aaataattct tcagaacata tatactattt aaatgcgact gagattagca   8640
atttaataaa tggtgatgtt gcatattgtt ttaaaaaaga aagtttggta aaaaatccat   8700
tcccccgtat agaagatgaa aaatttgttc cagaattata tatttggaat aaaataactg   8760
acaaggcgaa gattcgattt aacataagca aagttatata tctttgtgag tatcttgatg   8820
atggtctttc taaaaatttc cataaccagc ttaaaaaata cccaaagggg tttaagattt   8880
attacaaaga tcaaagaaaa cgagagaaaa cttatataaa aaaaacaaag atgctaatta   8940
gatatttgca atgttgttat tatgagaaaa taaaatgaaa atactatttg tcattacagg   9000
tttaggcctt ggaggtgctg agaagcaggt ttgtctttta gctgataaat taagtttaag   9060
cgggcaccat gtaaagatta tttcacttgg acatatgtct aataataaag tctttcctag   9120
cgaaaataat gttaatgtca ttaatgtaaa tatgtcaaaa aacatttctg gagttataaa   9180
aggttgtgtc agaattagag atgttatagc taatttcaaa ccagacattg tacacagtca   9240
tatgtttcat gcaaacatta tcactagatt gtctgtaatt ggaatcaaaa acagacctgg   9300
tattatatca actgcacata ataaaaatga aggtgggtat ttcagaatgc tcacatatag   9360
aataaccgat tgtttaagtg attgttgtac aaatgttagc aaagaagcag tggatgagtt   9420
tttacggata aaagccttta atcccgctaa agcaattact atgtataatg ggatagatac   9480
caataaattt aaatttgatt tattggcaag gagggaaatt cgagacggta ttaatataaa   9540
aaatgatgat atattattac ttgctgcagg tcgtttaacg ttagctaaag attatcctaa   9600
tttattgaat gcaatgactc tgcttcctga acactttaaa cttattatta ttggtgatgg   9660
tgaattgcgt gacgaaatta atatgcttat aaaaaaattg caattatcta atagggtgtc   9720
cttgttggga gttaaaaaaa atattgctcc ctatttttct gcatgtgata tttttgttct   9780
ctcttctcgt tgggaaggat ttggattagt cgtggcagaa gctatgtcat gtgagcgaat   9840
tgttgttggc acggattcag ggggagtaag agaagttatt ggtgacgatg attttcttgt   9900
acccatatct gattcaacac aacttgcaag caaaattgaa aaattgtctt tgagccagat   9960
acgtgatcac attggttttc ggaatcgtga gcgtatttta aaaaatttct caatagatac  10020
tattattatg cagtggcaag aactctatgg aactataatt tgctcaaaac atgaaaggta  10080
gatttatatt tggaacgtgt cttttgtttg aatttaattc aatctcaatt gagattttttg  10140
tatttcaaaa ataccatcat agctaacgat gattggtatt tattttaaga tgctttctat  10200
aaatatattg acgtttttaa tgcgccgaaa cgattgggct gggaacagag aagtaaaact  10260
gttttgagaa tgaagagttt ttgagatgtt tatggatatt aaaaattgat ccagtgaatt  10320
aattatttat aataaatcaa gatttaatgt taataaatga taatcttttc tgacactcat  10380
attaattatg agtggtacgt ttggtaaacg gtaaactatt atatgacagc tagaacaact  10440
aaagttttgc acttacaatt actcccactc ttaagtggcg ttcaaagggt aacattaaac  10500
```

```
gaaattagtg cgttatatac tgattatgat tatacactag tttgctcaaa aaaaggtcca  10560
ctaacaaaag cattgctgga atatgatgtc gattgtcatt gtatccccga acttacgaga  10620
gaaattaccg taaagaatga ttttaaagca ttgttcaagc tttataagtt cataaaaaaa  10680
gaaaaatttg acattgtgca tacacattct tcaaaaacag gtattttggg gcgagttgct  10740
gccaaattag cacgtgttgg aaaggtgatc cacactgtac atggtttttc ttttccagcc  10800
gcatctagta aaaaaagtta ttacctttat tttttcatgg aatggatagc aaagttcttt  10860
acggataagt taatcgtctt gaatgtagat gatgaatata tagcaataaa caaattaaaa  10920
ttcaagcggg ataaagtttt tttaattcct aatggagtag acactgataa gttttctcct  10980
ttagaaaata aaatttatag tagcaccttg aatctagtaa tggttggtag attatccaag  11040
caaaaagatc ctgagacatt attgcttgct gttgaaaaac tgctgaatga aaatgttaat  11100
gttaagctga cacttgtagg agatggtgaa ctaaaagaac agttagaaag caggttcaaa  11160
cggcaagatg gacgtataat ttttcatgga tggtcagata acattgttaa tattttaaaa  11220
gttaatgatc tttttatatt accttctctt tgggagggta tgccattagc aattttagaa  11280
gcattgagct gtggacttcc atgtatagtc actaatattc caggtaataa tagcttaata  11340
gaagatggct ataatggttg tttgtttgaa attagagatt gtcagttatt atctcaaaaa  11400
atcatgtcat atgttggtaa gccagaactg attgcacagc aatctaccaa tgcacgatca  11460
tttattctga aaaattatgg attagttaaa agaaataata aggtcagaca gctatatgat  11520
aattaagagc tcggtacccg ggcctagggt gtaggctgga gctgcttcga agttcctata  11580
ctttctagag aataggaact tcggaatagg aactaaggag gatattcata tccgtcgacg  11640
gcggccgccc tgcaggcatg caagcttgat ccatatggat cgctagctta attaaataaa  11700
gccgtaagca tataagcatg gataagctat ttatacttta ataagtactt tgtatactta  11760
tttgcgaaca ttccaggccg cgagcattca gcgcggtgat cacacctgac aggagtatgt  11820
aatgtccaag caacagatcg gcgtagtcgg tatggcagtg atgggacgca accttgcgct  11880
caacatcgaa agccgtggtt ataccgtctc tattttcaac cgttcccgtg agaagacgga  11940
agaagtgatt gccgaaaatc caggcaagaa actggttcct tactatacgg tgaaagagtt  12000
tgtcgaatct ctggaaacgc ctcgtcgcat cctgttaatg gtgaaagcag gtgcaggcac  12060
ggatgctgct attgattccc tcaaaccata tctcgataaa ggagacatca tcattgatgg  12120
tggtaacacc ttcttccagg acactattcg tcgtaatcgt gagctttcag cagagggctt  12180
taacttcatc ggtaccggtg tttctggcgg tgaagagggg gcgctgaaag gtccttctat  12240
tatgcctggt ggccagaaag aagcctatga attggtagca ccgatcctga ccaaaatcgc  12300
cgccgtagct gaagacggtg aaccatgcgt tacctatatt ggtgccgatg gcgcaggtca  12360
ctatgtgaag atggttcaca acggtattga atacggcgat atgcagctga ttgctgaagc  12420
ctattctctg cttaaaggtg gcctgaacct caccaacgaa gaactggcgc agacctttac  12480
cgagtggaat aacggtgaac tgagcagtta cctgatcgac atcaccaaag atatcttcac  12540
caaaaaagat gaagacggta actacctggt tgatgtgatc ctggatgaag cggctaacaa  12600
aggtacgggt aaatggacca gccagagcgc gctggatctc ggcgaaccgc tgtcgctgat  12660
taccgagtct gtgtttgcac gttatatctc ttctctgaaa gatcagcgtg ttgccgcatc  12720
taaagttctc tctggtccgc aagcacagcc agcaggcgac aaggctgagt tcatcgaaaa  12780
agttcgtcgt gcgctgtatc tgggcaaaat cgtttcttac gcccagggct tctctcagct  12840
```

gcgtgctgcg tctgaagagt acaactggga tctgaactac ggcgaaatcg cgaagatttt 12900
ccgtgctggc tgcatcatcc gtgcgcagtt cctgcaaaaa atcaccgatg cttatgccga 12960
aaatccacag atcgctaacc tgttgctggc tccgtacttc aagcaaattg ccgatgacta 13020
ccagcaggcg ctgcgtgatg tcgttgctta tgcagtacag aacggtattc cggttccgac 13080
cttctccgca gcggttgcct attacgacag ctaccgtgct gctgttctgc ctgcgaacct 13140
gatccaggca cagcgtgact attttggtgc gcatacttat aagcgtattg ataaagaagg 13200
tgtgttccat accgaatggc tggattaa 13228

<210> SEQ ID NO 18
<211> LENGTH: 13554
<212> TYPE: DNA
<213> ORGANISM: Artificial Sequence
<220> FEATURE:
<223> OTHER INFORMATION: example O25B rfb locus nucleotide sequence - O25B-EPA production strain stGVXN4459

<400> SEQUENCE: 18
atgacgaatt taaaagcagt tattcctgta gcgggtctcg ggatgcatat gttgcctgcc 60
actaaggcga tacccaaaga gatgctacca atcgtcgaca agccaatgat tcagtacatt 120
gttgacgaga ttgtggctgc agggatcaaa gaaatcctcc tggtaactca cgcgtccaag 180
aacgcggtcg aaaaccactt cgacacctct tatgagttag aatcactcct tgagcagcgc 240
gtgaagcgtc aactgctggc ggaagtacag tccatctgtc cgccgggcgt gaccattatg 300
aacgtgcgtc agggcgaacc tttaggttta ggccactcca ttttgtgtgc gcgacctgcc 360
attggtgaca acccatttgt cgtggtactg ccagacgttg tgatcgacga tgccagcgcc 420
gacccgctac gttacaacct tgctgccatg attgcacgtt tcaacgaaac gggccgcagc 480
caggtgctgg caaaacgtat gccgggtgac ctctctgaat actccgtcat ccagactaaa 540
gagccgctgg accgtgaggg taaagtcagc cgcattgttg aatttatcga aaaaccggat 600
cagccgcaga cgctggactc agacatcatg gccgtaggtc gctatgtgct ttctgccgat 660
atttggccgg aactggaacg tactcagcct ggtgcatggg gacgtattca gctgactgat 720
gctattgccg agctggcgaa aaaacaatcc gttgatgcaa tgctgatgac cggcgacagt 780
tacgactgcg gcaaaaaaat gggctatatg caggcgtttg tgaagtatgg cctacgcaac 840
ctgaaagaag ggcgaagtt ccgtaaaggt attgagaagc tgttaagcga ataatgaaaa 900
tctgaccgga tgtaacggtt gataagaaaa ttataacggc agtgaaaatt cgcagcaaaa 960
gtaatttgtt gcgaatcttc ctgccgttgt tttatataaa ccatcagaat aacaacgagt 1020
tagcagtagg gttttattca aagttttcca ggattttcct tgtttccaga gcggattggt 1080
aagacaatta gcgtttgaat ttttcgggtt tagcgcgagt gggtaacgct cgtcacatca 1140
taggcatgca tgcagtgctc tggtagctgt aaagccaggg gcggtagcgt gcattaatac 1200
ctctattaat caaactgaga gccgcttatt tcacagcatg ctctgaagta atatggaata 1260
aattaagcta gcagtgaaga tacttgttac tggtggcgca ggatttattg gttctgctgt 1320
tgttcgtcac ataataaata atacgcaaga tagtgttgtt aatgtcgata aattaacata 1380
cgccggaaac ctggaatcac ttgcagatgt ttctgattct gaacgctatt tctttgaaca 1440
tgcggatatt tgtgatgcag ctgcaatggc acggattttt gctcagcatc agccggatgc 1500
agtgatgcac ctggcagctg aaagccatgt tgaccgttca attacaggcc ctgcggcatt 1560
tattgaaacc aatattgtgg gtacttatgt ccttttagaa gcggctcgga attattggtc 1620

-continued

```
tggtctggat gatgaaaaga aaaaaaactt ccgttttcat catatttcta ctgatgaggt   1680
gtatggtgac ttaccccatc cggatgaagt aaatagcaat gaaacgttgc cgctatttac   1740
ggaaacgaca gcatacgcgc caagtagtcc atattctgct tctaaagctt ccagcgatca   1800
tttggttcgc gcatggaaac gtacttatgg tttaccgacc attgtgacta attgctcgaa   1860
caactatggt ccttatcatt tcccggaaaa gcttattcca ctggttattc ttaattcact   1920
ggaaggtaag gcattaccta tttatggcaa aggagatcag atccgcgact ggttgtatgt   1980
agaggatcat gctcgagcgt tatataccgt cgtaaccgaa ggtaaagcgg gcgaaactta   2040
taacattggt ggacacaacg aaaagaaaaa catcgacgta gtgttcacta tttgtgattt   2100
gttggatgag atagtcccga aagagaaatc ttaccgcgag caaattactt atgttaccga   2160
tcgtccggga cacgatcgcc gttatgcgat tgatgctgag aagattggtc gcgaattggg   2220
atggaaacca caggaaacgt ttgagagtgg gattcgtaaa acggtggaat ggtacctgtc   2280
caatacaaaa tgggttgata atgtgaaaag tggtgcctat caatcgtgga ttgaacagaa   2340
ctatgagggc cgccagtaat gaatatcctc ctttttggca aaacagggca ggtaggttgg   2400
gaactacagc gtgctctggc acctctgggt aatttgattg ctcttgatgt tcactccact   2460
gattactgtg gtgattttag taatcctgaa ggtgtagctg aaaccgtaag aagcattcgg   2520
cctgatatta ttgtcaacgc agccgctcac accgcagtag acaaagcaga atcagaaccg   2580
aagtttgcac aattactgaa cgcgacgagt gtcgaagcga tcgcgaaagc agccaatgaa   2640
gtcggcgcct gggttattca ctactctact gactacgtat ttccggggac cggtgaaata   2700
ccatggcagg aggaggatgc aaccgcaccg ctaaatgttt acggtgaaac caagttagcg   2760
ggagaaaaag cattacaaga gcattgtgcg aagcacctta ttttccggac cagctgggtc   2820
tatgcaggta aaggaaataa cttcgccaaa acaatgttgc gtctggcaaa agagcgtgaa   2880
gaattagccg ttattaatga tcagtttggt gcgccaactg gcgcagagtt actggctgat   2940
tgtacggcac atgctattcg tgtggcactg aataaaccgg aagtcgcagg cttgtaccat   3000
ctggtagcta gtggtaccac aacgtggcac gattatgctg cgctggtttt tgaagaggcg   3060
cgcaaagcag gcattcccct tgcactcaac aagctcaacg cagtaccaac aacagcctat   3120
cctacaccag ctcgtcgtcc acataactct cgccttaata cagaaaaatt tcagcagaac   3180
tttgcgcttg tcttgcctga ctggcaggtt ggcgtgaaac gaatgcttaa cgaattattt   3240
acgactacag caatttaata gtttttgcat cttgttcgta atggtggagc aagatgtatt   3300
aaaaggaatg atgaaatgaa aacgcgtaaa ggtattattt tggcgggtgg ttctggtact   3360
cgtctttatc ctgtgacgat ggccgtcagt aaacagctgt taccgattta tgataaaccg   3420
atgatctatt acccgctctc tacactgatg ttagcgggta ttcgcgatat tctgattatc   3480
agtacaccac aggatactcc tcgttttcaa caactgctgg gtgacgggag ccagtggggc   3540
ctgaatcttc agtacaaagt gcaaccgagt ccggatggtc ttgcgcaggc gtttattatc   3600
ggtgaagagt ttattggtgg tgatgattgt gctttggtac ttggtgataa tatcttctac   3660
ggccacgacc tgccgaagtt aatggacgta gctgttaaca aagaaagtgg tgcaacggta   3720
tttgcctatc acgttaatga tcctgaacgt tatggtgtcg tggagtttga taataacggt   3780
actgcaatta gcctggaaga aaaaccgctg gaaccaaaaa gtaactatgc ggttactggg   3840
ctttatttct atgacaatga cgttgtggaa atggcgaaaa accttaagcc ttctgcccga   3900
ggtgaactgg aaattaccga tattaaccgt atttatatgg aacaaggacg tttgtctgtc   3960
gctatgatgg ggcgtggcta tgcatggctg gatacaggga cgcatcaaag tcttattgaa   4020
```

-continued gcaagcaact tcattgccac cattgaagag cgccagggac taaaggtttc ctgtccggaa 4080
gaaattgctt atcgtaaagg gtttattgat gctgagcagg taaaagtatt agccgaaccg 4140
ttgaagaaaa atgcttatgg tcagtatctg ctcaaaatga ttaaaggtta ttaataagat 4200
gaacgtaatt aaaactgaaa ttcctgatgt gctgattttt gaaccaaaag tttttgggga 4260
tgaacgtggc ttcttttttg agagttttaa tcagaggatt tttgaagaag cagtaggtcg 4320
taaggttgag tttgttcagg ataaccattc taagtccagt aaaggtgttt tacgtggtct 4380
tcattatcag ttagaacctt atgctcaagg aaaactggtg cgctgtgttg ttggcgaggt 4440
ttttgatgtt gcggttgata ttcgtaaatc gtcacctaca tttgggaaat gggttggggt 4500
gaatttgtct gctgagaata agcgtcagtt gtggattcct gagggatttg cacatggttt 4560
tttggtgctg agtgatttag cagaagtttt atataaaacg aatcaatatt atgctccatc 4620
acatgaaaaa aatattatat ggaatgacct cttgcttaat attaaatggc cgagcacagc 4680
actgatcact ctgtctgata aggatgcaaa tggggaaaga tttgaactaa gtgagttttg 4740
aaatgtctct cttaaaacat agtatatgga atgttgcggg ctactttata ccaacattaa 4800
ttgcaattcc cgcctttgga ttaattgcga ggaaaattgg tgtagaacta tttggtttgt 4860
atacgttagc aatgattttt atagggtatg caagtatatt tgatgctggg ttaacaagag 4920
ctgttgtgcg tgaaatagca ttactaaaaa acagagtgga cgattgtaat acgataatag 4980
taacttctat tatcgctgtg atatttttag ggtttatcgg aggcgggga gtgtttctgc 5040
ttaaaggcga tattattgaa ctgttaaata tctcaccaat atattacgcc gattcgataa 5100
agtctctagt attattatca tctctgatac ctgtattctt agtcacgcaa atactattag 5160
cagagcttga gggtcgggaa tattttggga ttctaaatat acaaaaaagt gtagggaatt 5220
ctttaattgc agggttacct gcattatttg ttttaattaa tcaaacgctt ttttctgcaa 5280
ttattggtgt agcgattgca agagttatat gcttgtggtt aagctacatt atgagcaggg 5340
aaagaataac tatcgatatc tcattttttt caataactgt tttaaagcgg ttatttagat 5400
atggcgggtg ggtaactata agtaacataa tatctcctat attagcgagt atggatagat 5460
ttattctatc ccatatccag ggagcatcaa aaatatcatt ctatacagtc cctaatgagc 5520
tggtaactag gcttggaata gttccaggct ctcttgggaa agctgttttt ccaaaattaa 5580
gtcatgcaag gaattttaca gcgtcatatg cagagcaaaa aaaagcttat atattaatga 5640
ctgtcattgt aatgcctttg gttttatttg tatattatta cgcaaagttt attttaacat 5700
tgtggatggg ggctgagtat gcagggattt cggtcgaaat attacggatt atgcttatag 5760
ggtatatttt taactgttat tcacaaatct cttttgccaa catacaggcc tttggaaaag 5820
caaaatacac tgcatacatc catatgatgg aatttattcc ttatttgata atgttatata 5880
taatttcaaa ggaatatggg gttattggtg ttgcgtggtt atggacaatt cgagtaataa 5940
ttgatttttt gatgctttta tatatgagtt atcgttgtaa taatcttatg aaaaaagggt 6000
agcctgatga tatatattgt ggtattaaat tggaatgggg ctatagatac cattaattgt 6060
gttaaaagtt taatggattt aaatgttagc gattataaaa ttatcattgt tgataactgt 6120
tctatggata actcatatga tactataaaa gaaaatctta attcattata tattgctgat 6180
aaaagtatca ttgaggtgaa gtatgaggat agaaataaat ataaaacctt agaaaacgat 6240
aaaatcatat taatacaatc tccgcaaaat aatgggtacg caagtggtaa taatattggc 6300
atagagttcg ctcttaatca ggagaatatg aaatacgtct gggttctgaa taatgatact 6360
gaagtggata aagaggcttt aactcattta attagtaaat gtgattcaga taaaagtata 6420
gggatttgcg gttctcgttt agtctatttt gccgacagag agatgcagca aggactaggt 6480
ggggtgcata acaaatggtt atgcactaca aaaaattatg aaatgggaag attagtttcc 6540
aaaaaatatg atgatgaagt cattagtaat gatatagatt atataattgg cgcatcgatg 6600
tttttctcta gagaatgttt ggaaacagtt ggattgatga atgaagaata ttttttatac 6660
tatgaagagt tagatatttg cctcagagca aaagcaaaga actttaaatt aggtatttgc 6720
tcagaaagtt tggtttatca taaaataggt gcaagtactg atgggggaaa gagcatgatg 6780
gctgatcttt gctcaataaa aaataggctg gtcattacag aaaggtttta tccccaatat 6840
tattggacgg tatggttgtc actttttgtt gtagcattta accgtgctag aagaggtgag 6900
tttaataaga tgaaaagatg tttgaatgtt atgtttaact tcaaacgaaa caaaggtagc 6960
aaatgccatt agaatatgca cttaatcatg gtgttaataa atctatagtt tgatatgtta 7020
ttaaagggta tttaatgaaa gtggcttttt tatctgctta tgatccacta tctacatcca 7080
gttggtctgg cacaccttat tatatgctaa aggcattatc gaagagaaat atttccattg 7140
aaatattagg accggtaaat agctatatga tatacatgtt aaaagtatat aaattaatat 7200
taaggtgttt cggaaaagaa tatgattata gtcattcgaa gttgctttcc aggtattacg 7260
gtagaatatt cggtaggaaa ttaaaaaaaa ttgatggttt ggattttatt atcgcacctg 7320
caggttcctc acaaattgct tttttaaaaa caaccatacc aataatatat ctatcggata 7380
caacatatga tcaattaaaa agctattatc cgaatttaaa taaaaaaaca attataaatg 7440
atgaggatgc aagtttaatc gaacgcaagg ctattgaaaa agcaacagta gtatctttcc 7500
catctaaatg ggcaatggat ttttgcagga attattacag attagatttt gataaattag 7560
ttgaaatacc atggggggct aatttatttg atgatattca ctttgctaat aaaaatataa 7620
ttcaaaagaa tagttatact tgtcttttct tgggagttga ttgggaaaga aaaggtggga 7680
aaacagcctt gaaagcaatt gaatatgtaa ggcagttata tgggatcgat gttagactaa 7740
aaatttgtgg atgtactccg aatcaaaaga ttttacctac ttgggttgaa ttaattgata 7800
aagtagataa aaataacgtt gacgaatatc agaaattcat cgatgtgtta tctaacgctg 7860
atatacttct tttaccaacc attgctgaat gttatggaat ggtattttgt gaagctgctg 7920
cttttggatt gcctgttgtc gctacagata caggtggagt cagttctata gttatcaacg 7980
aaaggacggg gatattaatt aaagacccgt tagactataa gcactttgga aatgcaattc 8040
ataaaataat tagttccgta gagacttatc aaaactactc ccaaaacgca agaattagat 8100
ataataatat attgcattgg gacaattggg ctaaaaagat aattgagatt atgtatgagc 8160
ataagaatag aagaatcaaa tagcacaaaa agaattatat gtttatttat acttttttctt 8220
gttttccctg attttttgtt ttatacatta ggggttgata attttagcat ttcaacgata 8280
atctcaatta cattgctttt tgttttttta agagctaaaa atatttgcaa agataatttt 8340
ctaataatag tagcgttatt catattgttg tgttttaact gtttgttaag tatgctattt 8400
aatattgaac aggctttaac atttaaagtt gtactttcaa tatatagcat cttaataatg 8460
gcatacgtct cctcttgtta tgcacagacg ttgtggttat gttctgaaga aatacttaag 8520
agatccgtct tttatttgtt cgcatttctt tgccttattg gcattataag tattctttta 8580
cagaagactg agattataca tgataaaagt atgattcttt ttcctgaacc atcagcattt 8640
gcattggttt ttatacctat cttttcattt tgtttatact atacaagagg ggggggcta 8700
ctattgctct atatattatc tttgggtatt gcgttaggta tccagaattt aacaatgttg 8760

```
gtaggcattg tgattagtgt ttttgtgatg aaaaaaataa ctataaggca aactattgtt   8820
atacttttgg gggcatggat tttttccatg atattaagtg atttagacat ttcttactat   8880
acatcgcggc ttgattttaa aaatactacg aacctatcag tgcttgtata tctttcagga   8940
attgaaagag ctttcttgaa ttttattaca agttatggtc ttggtattgg ttttcaacaa   9000
atgggagtga atggggagat aggaatatat caacaaattt tagctgaact tgatgcccct   9060
atgttaaata tatacgatgg ctcatttatt tcttctaagt taatatctga gtttggggtt   9120
attggtgcat taatgtgtat tttctatttt ttttattttt cccgatttta tctgcgtttc   9180
aaaaaaagta agagatattc accgcagtat attttagcat atagcttcta catgtgtttc   9240
ttcatccctc tttttatacg tggtgctggt tatataaacc cctatgtgtt tatgttattt   9300
tcatcaatat ttttgtgcaa atatcacgct aaaaatatct tgatgaaatc taatgtccag   9360
atagctatat aatagtagat tatattatca ttatcacgta aattacatat taatagcata   9420
tatgataact aggacataaa taatgtgcat taaaaaaaaa cttaagttaa ttaaacgata   9480
tggcctttat ggtggtctta ggcttcttaa agatatattc ttaacaaaat ttttattttg   9540
ttcaaatgtt aggattatta gatttccatg ttatattaga aaagatggaa gtgttagttt   9600
tggaaaaggt tttacatcag gtgtaggatt acgagttgat gcatttatgg atgccgtagt   9660
ttccattgga gaaaatgttc aaattaatga ctatgttcac atcgcggcta ttaataatgt   9720
cattattggt agagatacat taatagcaag taaagtattt attagtgatc ataatcatgg   9780
tattttttct aaatccgata tccatagttc accaactatt attccttcgt ctaggcccct   9840
tgaatctgca cctgtgtata ttggagagcg tgtgtggatt ggcgaaaatg tgacaatatt   9900
accaggtgcg tgtataggta atggtgtagt tattggcgca aacagtgttg ttcgtggtga   9960
gattcctaat aatgtgatca ttgctggtgt tccagctaaa attgttaaaa aatataacta  10020
tgagcgtatg caatgggaaa gaatatagtt gtaatatcgg ctgttaattt tacaaccgga  10080
ggcccccttta ccgtactaaa aaatgtgctt acagcaacta aagatagagc cgaatgtaaa  10140
tttattgcac tggttcatag ctctgctgaa ctaatggaat tatttccgtg ggttgaattt  10200
atagagtatc cagaagtcaa gtcttcgtgg gttaaaagat tatatttcga atatataact  10260
tgcaatagat tatctaaggt gattaaggca actcattggg tatgcttaca tgatattaca  10320
gcaaatgtta gtgtacccta tagatttgtt tattgccaca atcctgcacc gttctataaa  10380
tatttaagct atcgagatat tataggagaa cctaaatttt atcttttttta tcttttttat  10440
gggcttttat acaatatcaa tataaaaaag aacacagcag tttttgttca gcagcagtgg  10500
ctaaaaaaag aattcgaaaa aaaatataag ttaaagaatg ttgttgttag tcgccctgaa  10560
gatatttgcc cttttgaaag tgatggtttg gtaagaaata ataataaaaa ggatgtgagg  10620
atattttacc cagcagtgcc ccgtatattt aaaaactttg aagttatcat acgtgctgca  10680
caaatattac aagataaaaa tattcatttt tatcttactt ttgatggtac tgaaaataag  10740
tatgcaaaaa gaatatataa attagcttcc gaactgaaaa atgtacattt cctcggttac  10800
cttaatgcaa ccgagatggt taacttttat caagattcag atattatttg tttcccatcg  10860
aaactagaaa cgtggggatt accattatca gaagctaaaa catacaaaaa atggatattt  10920
gcggcagact taccttatgc tcatgaagtt ttatataact attcaaaaac tagatatttt  10980
ccatttgacg atgagaaaat acttgttcgc tacatattag agtacacaag taaaaatatg  11040
catgaagata taaaaaatag tagggtgaat tttaataatg atgcattgac tggttttgaa  11100
```

-continued

```
cagtttattg aatatatcct caaggggaac tgacgtggtt tatattataa tcgtttcaca  11160
tggccatgat gactatatag aaaatctttt attaaattta aagttgccct ctggaagatt  11220
taaaataata gttcgtgata acaaaagttc aatggtttta aaaaaaacat gcgaaaaaaa  11280
ttgcgtaacc tatttgcatg gagggcaata tggatttgga cataataata acatagcagt  11340
gtcatatata attaataact tcatgattat gaataatgat tattttctct ttcttaaccc  11400
cgatgtattc ataaccagtg aaagtttgat taattatgtt gattatataa ttagtaatga  11460
ttataagttt agcacattat gtctttatcg agattttact aaaagcaaac atgattattc  11520
aatacggagt tttccaactt tatatgattt tctttgttct tttttattgg gggtgaataa  11580
aagtaaaatt aagaaggaaa atatactttc tgatactgta gttgattggt gtgctggctc  11640
atttatgctt attcatgctt taagtttctt aaatgtgaat ggttttgatc aaaaatattt  11700
tatgtattgt gaagatattg acctttgtat gcgtttaaaa ttaagtggag tagatcttta  11760
ctatactccc cattttgatg ctattcatta tgcgcagcat gaaaatagaa gaatatttac  11820
taaagcattt cgatggcata taaggagtat tacgcgctac atattacgga aaccaattct  11880
ttcttataaa aactatagaa aaattacatc cgaactggta aagtgattaa ggatccgtgt  11940
aggctggagc tgcttcgaag ttcctatact ttctagagaa taggaacttc ggaataggaa  12000
ctaaggagga tattcatatg gataaagccg taagcatata agcatggata agctatttat  12060
actttaataa gtactttgta tacttatttg cgaacattcc aggccgcgag cattcagcgc  12120
ggtgatcaca cctgacagga gtatgtaatg tccaagcaac agatcggcgt agtcggtatg  12180
gcagtgatgg gacgcaacct tgcgctcaac atcgaaagcc gtggttatac cgtctctatt  12240
ttcaaccgtt cccgtgagaa gacggaagaa gtgattgccg aaaatccagg caagaaactg  12300
gttccttact atacggtgaa agagtttgtc gaatctctgg aaacgcctcg tcgcatcctg  12360
ttaatggtga aagcaggtgc aggcacggat gctgctattg attccctcaa accatatctc  12420
gataaaggag acatcatcat tgatggtggt aacaccttct tccaggacac tattcgtcgt  12480
aatcgtgagc tttcagcaga gggctttaac ttcatcggta ccggtgtttc tggcggtgaa  12540
gagggggcgc tgaaaggtcc ttctattatg cctggtggcc agaaagaagc ctatgaattg  12600
gtagcaccga tcctgaccaa aatcgccgcc gtagctgaag acggtgaacc atgcgttacc  12660
tatattggtg ccgatggcgc aggtcactat gtgaagatgg ttcacaacgg tattgaatac  12720
ggcgatatgc agctgattgc tgaagcctat tctctgctta aaggtggcct gaacctcacc  12780
aacgaagaac tggcgcagac ctttaccgag tggaataacg gtgaactgag cagttacctg  12840
atcgacatca ccaaagatat cttcaccaaa aaagatgaag acggtaacta cctggttgat  12900
gtgatcctgg atgaagcggc taacaaaggt accggtaaat ggaccagcca gagcgcgctg  12960
gatctcggcg aaccgctgtc gctgattacc gagtctgtgt ttgcacgtta tatctcttct  13020
ctgaaagatc agcgtgttgc cgcatctaaa gttctctctg gtccgcaagc acagccagca  13080
ggcgacaagg ctgagttcat cgaaaaagtt cgtcgtgcgc tgtatctggg caaaatcgtt  13140
tcttacgccc agggcttctc tcagctgcgt gctgcgtctg aagagtacaa ctgggatctg  13200
aactacggcg aaatcgcgaa gattttccgt gctggctgca tcatccgtgc gcagttcctg  13260
cagaaaatca ccgatgctta tgccgaaaat ccacagatcg ctaacctgtt gctggctccg  13320
tacttcaagc aaattgccga tgactaccag caggcgctgc gtgatgtcgt tgcttatgca  13380
gtacagaacg gtattccggt tccgaccttc tccgcagcgg ttgcctatta cgacagctac  13440
cgtgctgctg ttctgcctgc gaacctgatc caggcacagc gtgactattt tggtgcgcat  13500
```

acttataagc gtattgataa agaaggtgtg ttccataccg aatggctgga ttaa 13554

<210> SEQ ID NO 19
<211> LENGTH: 15197
<212> TYPE: DNA
<213> ORGANISM: Artificial Sequence
<220> FEATURE:
<223> OTHER INFORMATION: example O75 rfb locus nucleotide sequence - O75-EPA production strain stLMTB11737

<400> SEQUENCE: 19
atgacgaatt taaaagcagt tattcctgta gcgggtctcg ggatgcatat gttgcctgcc 60
actaaggcga tacccaaaga gatgctacca atcgtcgaca agccaatgat tcagtacatt 120
gttgacgaga ttgtggctgc agggatcaaa gaaatcctcc tggtaactca cgcgtccaag 180
aacgcggtcg aaaaccactt cgacacctct tatgagttag aatcactcct tgagcagcgc 240
gtgaagcgtc aactgctggc ggaagtacag tccatctgtc cgccgggcgt gaccattatg 300
aacgtgcgtc agggcgaacc tttaggttta ggccactcca ttttgtgtgc gcgacctgcc 360
attggtgaca acccatttgt cgtggtactg ccagacgttg tgatcgacga tgccagcgcc 420
gacccgctac gttacaacct tgctgccatg attgcacgtt tcaacgaaac gggccgcagc 480
caggtgctgg caaaacgtat gccgggtgac ctctctgaat actccgtcat ccagactaaa 540
gagccgctgg accgtgaggg taaagtcagc cgcattgttg aatttatcga aaaaccggat 600
cagccgcaga cgctggactc agacatcatg gccgtaggtc gctatgtgct ttctgccgat 660
atttggccgg aactggaacg tactcagcct ggtgcatggg gacgtattca gctgactgat 720
gctattgccg agctggcgaa aaaacaatcc gttgatgcaa tgctgatgac cggcgacagt 780
tacgactgcg gcaaaaaaat gggctatatg caggcgtttg tgaagtatgg cctacgcaac 840
ctgaaagaag ggcgaagtt ccgtaaaggt attgagaagc tgttaagcga ataatgaaaa 900
tctgaccgga tgtaacggtt gataagaaaa ttataacggc agtgaaaatt cgcagcaaaa 960
gtaatttgtt gcgaatcttc ctgccgttgt tttatataaa ccatcagaat aacaacgagt 1020
tagcagtagg gttttattca aagttttcca ggattttcct tgtttccaga gcggattggt 1080
aagacaatta gcgtttgaat ttttcgggtt tagcgcgagt gggtaacgct cgtcacatca 1140
taggcatgca tgcagtgctc tggtagctgt aaagccaggg gcggtagcgt gcattaatac 1200
ctctattaat caaactgaga gccgcttatt tcacagcatg ctctgaagta atatggaata 1260
aattaagcta gcagtgaaga tacttgttac tggtggcgca ggatttattg gttctgctgt 1320
tgttcgtcac ataataaata atacgcaaga tagtgttgtt aatgtcgata aattaacata 1380
cgccggaaac ctggaatcgc tcgctgaaat ttctgattct gaacgttatt catttgagca 1440
tgcagatatc tgcgatgccg aagcgatggc tcgtattttc gcacagcacc agccagacgc 1500
ggtgatgcac ctggcagcag agagccacgt tgaccgctca ataactggcc ctgcggcatt 1560
tattgaaacc aatattgtgg gtacttatgt tcttttagaa gcggcgcgca attattggtc 1620
tggtctggat gatgaaaaga aaaaaaactt ccgctttcat catatttcta ctgatgaggt 1680
gtatggtgac ttaccccatc cggatgaagt aaatagcaat gaaacgttgc cgctatttac 1740
ggaaatgaca gcatacgcgc caagtagtcc atattctgct tctaaagctt ccagcgatca 1800
tttggttcgc gcatggaaac gtacttatgg tttaccgacc attgtgacta attgctcgaa 1860
caactatggt ccttatcatt tcccggaaaa gcttattcca ctggttattc ttaatgcact 1920
ggaaggtaag gcattaccta tttatggcaa aggagatcag atccgcgact ggttgtatgt 1980
agaggatcat gctcgagcgt tatataccgt cgtaaccgaa ggtaaagcgg gcgaaactta 2040
taacattggt ggacacaacg aaaagaaaaa catcgacgta gtgttcacta tttgtgattt 2100
gttggatgag atagtcccga aagagaaatc ttatcgtgag caaattacct atgttgctga 2160
tcgcccaggg catgatcgcc gttatgcaat tgatgccgat aaaattagcc gcgaattggg 2220
ctggaaacca caggaaacgt ttgagagcgg gattcgtaaa actgtggaat ggtatctgtc 2280
caatacaaaa tgggttgata atgtgaaaag tggtgcctat caatcgtgga ttgaacagaa 2340
ctatgggggc cgccactaat gaatatcctc ctttttggca aaacagggca ggttggttgg 2400
gaactacagc gtgctctggc acctctgggt aatttgattg ctcttgatgt tcactccact 2460
gattactgtg gtgattttag taaccctgaa ggtgtggctg aaaccgttag aagcattcgg 2520
cctgatatta ttgtcaacgc agccgctcac accgcagtag acaaagcaga atcagaaccg 2580
gagtttgcac aattactgaa cgcgacgagt gtcgaagcga tcgcgaaagc agccaatgaa 2640
gtcggcgctt gggttattca ctactctact gactacgtat ttccggggac cggtgaaata 2700
ccatggcagg aggaggatgc aaccgcaccg ctaaatgttt acggtgaaac caagttagca 2760
ggagaaaaag cattacaaga gcattgtgcg aagcacctta ttttccggac cagctgggtc 2820
tatgcaggta aaggaaataa cttcgccaaa acgatgttgc gtctggcaaa agagcgtgaa 2880
gaattagccg ttattaatga tcagtttggt gcgccaactg gcgcagagtt gctggctgat 2940
tgtacggcac atgccattcg tgtggcactg aataaaccgg aagtcgcagg tttgtaccat 3000
ctggtagcca gtggtaccac aacctggcac gattatgctg cgctggtttt tgaagaggcg 3060
cgcaaagcag gcattcccct tgcactcaac aagctcaacg cagtaccaac aacagtctat 3120
cctacaccag ctcgtcgtcc acataactct cgccttaata cagaaaaatt tcagcagaac 3180
tttgcgcttg tcttgcctga ctggcaggtt ggtgtgaaac gcatgctcaa cgaattattt 3240
acgactacag caatttaata gtttttgcat cttgttcgtg atggtggaac aagatgaatt 3300
aaaaggaatg atggaatgaa tacgcgtaaa ggtattattt tagcgggtgg ttctggtaca 3360
cgtctttatc ctgtgactat ggctgtcagt aaacagctgt taccgattta tgataaaccg 3420
atgatctatt acccgctctc tacactgatg ttggcgggta ttcgcgatat tttgattatc 3480
agcacgccac aggatactcc tcgttttcaa caactgctgg gtgatgggag ccagtggggg 3540
ctaaatcttc actacaaagt gcaaccgagt ccggatggtc ttgcgcaggc atttatcatc 3600
ggtgaagagt ttatcggtgg tgatgattgt gctttggtac ttggtgataa tatcttctac 3660
ggtcacgacc tgcctaagtt aatggatgcc gctgttaaca aagaaagtgg tgcaacggta 3720
tttgcctatc acgttaatga tcctgaacgc tatggtgtcg ttgagtttga taaaaacggt 3780
actgcaatca gcctggaaga aaaaccgtta caaccaaaaa gtaattatgc ggtaaccggg 3840
ctttatttct atgataacta cgttgtggaa atggcgaaaa atcttaagcc ttctgcccgc 3900
ggtgaactgg aaattaccga tattaaccgt atctatatgg aacaggggca tttatctgtt 3960
gccatgatgg gacgtggata tgcctggctg gacacgggga cacatcaaag tcttattgaa 4020
gcaagcaact tcattgccac cattgaagag cgccagggct tgaaagtttc ctgcccggaa 4080
gaaattgctt accgtaaagg gtttattgat gctgagcagg tgaaagtatt agctaaaccg 4140
ctgaaaaaaa atgcttatgg tcagtatctg ctaaaaatga ttaaaggtta ttaataaaat 4200
gaatgttatt aaaacagaaa ttccagatgt actgattttt gaaccgaaag tttttggtga 4260
tgagcgtggt ttctttatgg aaagctttaa tcagaaagtt ttcgaagagg ctgtagggcg 4320
gaaggttgaa tttgttcagg ataatcattc taaatcgtgt aaaggtgtac ttagaggttt 4380
acactttcag cttcctccct ttgagcaggc aaaattagta aggtgtatag ttggcgaggt 4440
atttgatgtt gcagtagaca ttagacctaa ttctgaaaca tttggttcat gggttggagt 4500
aactctttcg tcagaaaata aaaggcagct atggattcca gaaggattcg cccatggttt 4560
tttaacttta agtgatattg cagagtttgt ttataaaact aacaactatt attctttaaa 4620
tcatgaaagg ggagtcattt ggaacgatga ggaaattaac attgcctggc cctctcaatc 4680
agagaagatt ctgtcacaga aagatattaa tttaccatca tttagatttg ttcaaatgtt 4740
tagcaagtag tgttatcttt acactgcaca tagtcatcat tttttatgct ttaagtaaat 4800
tatattgcac atctataaca caaagcgcaa taatatttcg acctgatgaa ggtttgtggt 4860
tatttatctt tctaggcgtt ttttatgact aaaatagttg tggtttctac agctccaata 4920
ttcccgacaa ataatgggta caaaagttct gtattaggaa gaattgatga gttattaaat 4980
gaggataatg aggtcgtttt gattgaaata aaccttgaaa atgttacgga aaagaaagat 5040
gaattaatac caacaagatt taataatatt caaagatatg aagtaaaaaa aatatctaga 5100
tcatttattg ccgagttaca aatattattt gatatcagaa ctcggtatga acaattattt 5160
tcttctgctg acattagaga taacataaaa aagataattg atttagaaaa accttctatt 5220
attattgctg agtctatatg ggcgttgcaa gcattgccta ttgaaattag tgcgagaata 5280
cactgtgtta ttcatgatgt ggcaactgat ttctttaaag aaatgtttgt atctcataat 5340
gaggttgtac gaaaaatttt gttttttaat gattacctaa agttgaaaat tactgaagaa 5400
aatattatca aacgtttgag agttgagcaa tttatctttc tgacagaaga agataaatgt 5460
tggtataaaa caagatacaa tattgatgag ggttgttgtt ccttagcgag caatcatctt 5520
tatgtagaaa agattaagag aactatcaat ttccaaaccc ctttcctgct tattcccggt 5580
agcattgaat tttcacaaaa tttttacggc ttaaattggt ttataaaaaa tatatatcct 5640
ggattaaata ggaaaataag aatagttgta acaggaaagg catcagataa aaaaataaag 5700
atgttaaact gtggagagga aattaccttt acgggagagc ttgacttttc cacatataat 5760
aaacttagct caacatgctt gtgtgttatt gcaccgatta caacgggcac tggaattaaa 5820
ataaaaatat tagaagctgt acaaaaaggt attcctgtac ttacaacaaa atttgcttca 5880
aaaggaatat gttccgattt atgtttttat tgcgaggagg atactgacac aaactttgtc 5940
aatttaatta acagttttct tgaaacgaca ttaagagtcc aagaatgaat ttattgcttt 6000
tttcagtcct tgcgtttggt ttaatattgg ctttggccca taataataaa agtggagata 6060
ttaacgcata cttaatgttt tttctcgtgg tcctaatggt attaatatca gggctgcgta 6120
tgaatgatag tgattatatc gaatacagga aaatgtataa tgaagtgcct attttatgtg 6180
actttagtct cgcatctata agagatatac atggggaggt aggctatcta ttcttatcat 6240
caatctttaa aactttatgc ttgccatttc aattatttct ttttttttatt gctttttttat 6300 cactcctgct tacatatttt tcattcagaa aaataagttt aataccgata ctatcgttag 6360 tttttttattt aagccatgct tttatagtta gagatttgat tcaaattagg gcaggattag 6420
ctgttagcat atcattatat tcaataatta aatttaaagg aaataaaagt ataattacag 6480
gagttttatt tgcttctttg attcattctg ggcgcttat tattgctctt tgttatcctt 6540
ttttcaaaaa aaaatacata acattaaaaa tgatgttgtt tttatttttta gtgtcaatta 6600 tttttttctta tttgaatggg cttaatttat cgatacaact cttatctcaa tatagtttgc 6660
ttccaactgc aatttcgaat tatgttggtt gggaagaata tgattatcgg gtgagtatat 6720

-continued

```
ttactaatcc ggtttttatt aaaggtgttt ttttaattgt cttaatgcac aaatatgtac   6780
tttcagatat taaaaatgag aaaattatag tgctttataa cttatatgtt ttaggtgtat   6840
tagctatggt tgcattgagt gggatggcta ttctttcagg ccgtctttca tcctttctga   6900
cactaggtga aagcatttta attgtatatg ctctgttcta caaaagaaat acacctctgg   6960
cgtttctaat tttttctttt ttaacaattg tgcaattagg atatgatcta tttatttcta   7020
atgtgcatcc tgagcttact ctgattatat ttgggtgaat ctaagtgaaa aataataaaa   7080
taggcatact tatctctaaa atacaaaatc ttggacctgt gaatgtagta cgaggattga   7140
taaaagaaaa taaaaaatat gcttttactg tttttttgttt aacaaatagc gtagataaaa   7200
atatatatga tgagttatgc tgtttaggag ccaaggttat attaatacca gatggtactt   7260
ggttcagcaa aattttattt gtgagaagtt ttttaaagga acatccacat aatatcttac   7320
attcacatgg gatcacggcc gatatgtttt cttactttct gaatggcgtg aaaatatcta   7380
ctattcacaa tagactagat gaggattata tcccattatt tggcgcggtt aaagggaatg   7440
ctatatatta tcttcatcgt tttatattac gaagatttaa tcatatcgtt gcttgctcag   7500
cagcggtcca atcaaaactg aaacaatcga aagtaaaaac taaaataacc accatccaga   7560
atgggattga tataactagg tttaagacac ttgagtctga taaaaaaaaa ttattgaggg   7620
aaaaacacgg atttgatagt gaaaaaagaa tatttatata ttgtggctcg ttatcattaa   7680
ggaaaaatat tgcttacctc ttggaacact tagccatcga agaaaatgat atatttttaa   7740
ttctaggtga tggtgaactt tttagatatt gtaaggataa atattctaaa gatttacggt   7800
atatatttat ggggaaagtt gaatgccctc ttgaatatta tcaattatca gatatttttg   7860
tttccgcttc tttatcggaa gggctcccct tggcactatt agaagctgcc tctactgggt   7920
gctatttata tgttagcgat atagagcccc atagagaaat tgcatctcta ttaggagagg   7980
aaaatatttc tatgtttaaa attaaggatg gatcatataa ttatttgcaa cctaaaataa   8040
aaaaagctga ctataacgct ctttctgacg ataaacttta caatatatcc gataaaaaaa   8100
tgtcaaatct ttatgacaaa ctttttgttt ctttattaga gcagaggcac taatataatg   8160
atttatgttt cggtaatttc tcatggtcat ttcaaaactc ttaaggaatt aggagcagta   8220
tcaaaattaa ataatcacag cagaattaaa gttatcatca aagataattt aggagagagc   8280
gagcttttgg atttttgtca ggaaaacaaa ataacttatt taaggtctaa agagaaaaaa   8340
ggatttggag agaataataa tgaagttttt tcctctatat cctccttaat tactaaggaa   8400
gatttttttg tggttatgaa tcctgatata tatattgagt gctctgatct attagatgtc   8460
gtagatgagt gtggttcagc gaatgttaat ctagcaacga taaatttata cagggatttt   8520
gataaaaaaa catatgataa ctcagtaagg aaatttccct cggcaattga ttttttttatg   8580
tcatttttat ttaagaaaaa tgactgtgta gtaaataaga acaaaataac gaaaccaaca   8640
tatgttgatt gggctgcagg ttcttttcta atatttaatg ccttctttta ttcaaaactc   8700
aacggattca acgaaaagta ttttatgtat tgcgaagata ttgatatatg ttggcgagct   8760
aaaaaacact tcaatacttc agttttatac tatccatgct atgcagcaat tcatttggca   8820
caatttaaca atcgtaggat ttttagtaga catttcattt ggcatataaa aagtattatc   8880
ctttttttat tatataaaaa tggtatgctg cgttctagta agttgcttta atgctaatat   8940
tcttttaaga ggtgagaatg atacctgtta ttttggctgg tggttcggga agtcgcttgt   9000
ggccactttc acgagaaaag ttccccaagc agtttttaaa gttgactggc agtttgacaa   9060
```

-continued

```
tgttgcagtc aacattgtca cgtcttaata atttaaatgc tgatgattca atagttatat   9120
gcaacgaaga gcatagattt attgttgcag aacaattaag agagttaggc aaactttcaa   9180
ataacattat tcttgaaccc aaaggtcgta atacagcccc tgctataaca ctcgcagcat   9240
tagcagcaaa aagaaaattc gctgatgaag atccattgat tcttatttta gctgcagatc   9300
acaacatcca agacgaacat gttttctgtg aggcaattaa taaggcgtca tctttagcta   9360
gttatggaaa actagtgact tttggtatcg ttccattcaa acctgaaact gggtatggct   9420
atattcgtcg cggtgatgaa gtgcctgtag atgagcagca tgcggtggcc tttgaagtgg   9480
cgcagtttgt cgaaaaaccg aatctggaaa ccgcgcaggc ctatgtggca agcggcgaat   9540
attactggaa cagcggtatg ttcctgttcc gtgccggacg ctatctcgaa gaactgaaaa   9600
agtatcgtcc ggatattctc gatgcctgtg aaaaagcgat gagcgccgtc gatccggatc   9660
tcgattttat tcgtgtggat gaagaggcgt ttctcgcttg tccggaagag tcggtggatt   9720
acgcggtcat ggaatgcacg gcagatgccg ttgtggtgcc gatggatgcg ggctggagcg   9780
atgtcggttc ctggtcttca ttatgggaga tcagcgccca caccgccgag ggcaacgttt   9840
gccacggcga tgtgattaat cacaaaactg aaaacagcta tgtgtacgcc gaatctggcc   9900
tggtcaccac cgtcggggtg aaagatttgg tggtagtgca gaccaaagat gcagtgctga   9960
ttgccgaccg taatgcggtg caggatgtga agaaagtggt cgagcagatc aaagctgatg  10020
gtcgccatga gcatcgggtg catcgcgaag tgtatcgtcc gtggggcaaa tatgactcta  10080
tcgacgcggg cgaccgctac caggtgaaac gcatcaccgt gaaaccgggc gaaggtttgt  10140
cggtacagat gcattatcat cgcgcggaac actgggtggt tgtcgcggga acggcaaaag  10200
tcactatcaa cggtgatatc aaactgcttg gtgaaaacga gtccatttat attccgctgg  10260
gggcgatgca ctgcctggaa aacccgggga aaatagattt agaattaatt gaagttcgct  10320
ctggtgcata tcttgaagaa gatgatgtta ttagatgtta tgatcgctat ggacgaaagt  10380
aatatataat aattatttca gaattagaaa tgataattat aagttttcgt ctggataaac  10440
aatagatagt atgggttgga aatatgagt  tctttaactt gttttaaagc ttacgacatt  10500
cgcgggaaat taggtgaaga actgaatgaa gatatcgcct ggcgcattgg tcgcgcctat  10560
ggcgaatttc tcaaaccgaa aaccattgtg ttaggcggtg atgtccgtct caccagcgaa  10620
accttaaaac tggcgctggc aaaaggttta caggatgcgg gcgtcgatgt gctggatatt  10680
ggcatgtccg gcaccgaaga gatttatttc gccacgttcc atctcggcgt ggatggcggc  10740
attgaagtta ccgccagcca taatccgatg gattacaacg gcatgaagct ggtgcgcgaa  10800
ggggctcgcc cgatcagcgg tgataccgga ctgcgcgacg tccagcgtct ggcagaagct  10860
aacgactttc ctcccgtcga tgaaaccaaa cgcggtcgct atcagcaaat caatctgcgt  10920
gacgcttacg ttgatcacct gttcggttat atcaatgtca aaaaccttac gccgctcaag  10980
ctggtgatca actccgggaa tggcgcagcg ggtccggtgg tggacgctat cgaagcccgc  11040
tttaaagccc tcggcgcacc ggtggagtta atcaaagtgc ataacacgcc ggacggcaat  11100
ttccccaacg gtattcctaa cccgttgctg ccggaatgtc gcgacgacac ccgcaatgcg  11160
gtcatcaaac acggcgcgga tatgggcatt gcctttgatg gcgattttga ccgctgtttc  11220
ctgtttgacg aaaaagggca gtttattgag ggctactaca ttgtcggcct gctggcagaa  11280
gcgttcctcg aaaaaaatcc cggcgcgaag atcatccacg atccacgtct ctcctggaac  11340
accattgatg tggtgacggc cgcgggcggc acgccggtga tgtcgaaaac aggacacgcc  11400
tttattaaag aacgtatgcg caaggaagac gccatctacg gtggcgaaat gagcgctcac  11460
```

```
cattacttcc gcgatttcgc ttactgtgac agcggcatga tcccgtggct gctggtcgcc  11520
gaactggtgt gcctgaaagg aaaaacgctg ggcgaactgg tgcgcgaccg gatggcggcg  11580
tttccggcaa gcggtgagat caacagaaaa ctggcgcacc ctgttgaggc gattaaccgc  11640
gtggaacagc attttagccg tgaggtgctg gcggtggatc gcaccgatgg catcagcatg  11700
acctttgccg actggcgctt taacctgcgc tcttccaaca ccgaaccggt ggtgcgcctg  11760
aatgtggaat ctcgcggtga tgttcaggtt atggtaatcc atactcaaga aatattatca  11820
attttgacgt cataaagaat aagccctgac aagttagggc ttaattaata tatatttttt  11880
ttgaattggg gatttgtggt aagattttta atatgttatt taatgtggtt gaattaatgt  11940
tgactggaaa ataataatga gaacgaaaaa agcattacac aactttaaag ttgatttatt  12000
aattactttt ttattggttt tgctagggtt ttatattcga actgtttttg tttcaaaaat  12060
gggaagtgat attactggag tgatgttact attcacacag ttgacagcat atctcaattt  12120
ggcagaatta ggtattggaa ttgcagctgc cagcgtatta tataaaccgc tcagcgagaa  12180
tgaatacaat aaaataactt acataatatc tttgctctca gtcatataca aatatatatt  12240
tgtgtttgtt ttgattcttg gcgttgttat aggtatctgt atttattact ttattgattc  12300
tgtaaaggtt gtaaatggcg tttttttata ttgggctttg ttcgttttta atacatcgtt  12360
gacatatagt tatgctaaat actccacatt attaactgct aatcagcggt actcagcagt  12420
aagaaaaatt caaggtggcg gaaaagttat aataattgta tttcagatat taattttgtg  12480
ctttacgcaa agtttcatac tttatttgtt agttgagact ttaggtattt tttctcaata  12540
tttgattttt aaaaaaataa ttgggaacgg aaatcaatat ctcagtaatg aggttttact  12600
tattgaaagc gataaacttt tgataaaaaa agaattaaaa ataagaataa aaaatatgtt  12660
cttccataaa ataggtgctg tgcttgtcct taatacagac tacctgcttg tatcaaagtt  12720
tctgacatta agttatgtga caatttttgg cagctatatg atggtatttc agatagtaac  12780
tgttttgatg tcaagttttg ttaatgctat tactgcagga atgggtaatt acttaattaa  12840
taaaagtaat ttagaaatta aggaaattac acgtcaattt tatgtgatat ttatcgcctt  12900
tgcaacattc atatcactaa atatgttttt tcttgttaat gattttatcg caaaatggat  12960
aggtgttaat tatacattaa gtaacaccct agttgcatta atgattgtta acgtattcat  13020
tagtgttgtc agggtacctt ctgatatatt aaaaaacgca agtggacatt ttggtgatat  13080
ttattatcca ttattagaag gtgtgctgaa tattacgata tccatcattt tggctatcat  13140
tattggatta cctggcatta ttatagggac aatagtatct aacttaatag taataatgct  13200
tgcgaaacca ttatatcttt actctaagtt atttaatctt agaaatccga cgagggttta  13260
ttttgaattt atttctcggc ctatgttata ttcattatgt gtgattgggg tgagctattt  13320
attgcgcgat gaaatatatt catttaaagt aagtacatgg ttggatttta ttaacaagct  13380
actcttagtc tctactccta gcatattggt aatatgtgct attttctcta cggatagtga  13440
ctttagatta tttttcagaa aaattatata tgtgattatg aagaaataaa aatttcgaaa  13500
atgtattaat cgaaattatg caacgagctt tatttttata aatgatatgt gatcttttcg  13560
cgaataggag taaggatccg tgtaggctgg agctgcttcg aagttcctat actttctaga  13620
gaataggaac ttcggaatag gaactaagga ggatattcat atggataaag ccgtaagcat  13680
ataagcatgg ataagctatt tatactttaa taagtacttt gtatacttat ttgcgaacat  13740
tccaggccgc gagcattcag cgcggtgatc acacctgaca ggagtatgta atgtccaagc  13800
```

-continued

```
aacagatcgg cgtagtcggt atggcagtga tgggacgcaa ccttgcgctc aacatcgaaa  13860
gccgtggtta taccgtctct attttcaacc gttcccgtga gaagacggaa gaagtgattg  13920
ccgaaaatcc aggcaagaaa ctggttcctt actatacggt gaaagagttt gtcgaatctc  13980
tggaaacgcc tcgtcgcatc ctgttaatgg tgaaagcagg tgcaggcacg gatgctgcta  14040
ttgattccct caaaccatat ctcgataaag gagacatcat cattgatggt ggtaacacct  14100
tcttccagga cactattcgt cgtaatcgtg agctttcagc agagggcttt aacttcatcg  14160
gtaccggtgt ttctggcggt gaagaggggg cgctgaaagg tccttctatt atgcctggtg  14220
gccagaaaga agcctatgaa ttggtagcac cgatcctgac caaaatcgcc gccgtagctg  14280
aagacggtga accatgcgtt acctatattg gtgccgatgg cgcaggtcac tatgtgaaga  14340
tggttcacaa cggtattgaa tacggcgata tgcagctgat tgctgaagcc tattctctgc  14400
ttaaaggtgg cctgaacctc accaacgaag aactggcgca gacctttacc gagtggaata  14460
acggtgaact gagcagttac ctgatcgaca tcaccaaaga tatcttcacc aaaaaagatg  14520
aagacggtaa ctacctggtt gatgtgatcc tggatgaagc ggctaacaaa ggtaccggta  14580
aatggaccag ccagagcgcg ctggatctcg gcgaaccgct gtcgctgatt accgagtctg  14640
tgtttgcacg ttatatctct tctctgaaag atcagcgtgt tgccgcatct aaagttctct  14700
ctggtccgca agcacagcca gcaggcgaca aggctgagtt catcgaaaaa gttcgtcgtg  14760
cgctgtatct gggcaaaatc gtttcttacg cccagggctt ctctcagctg cgtgctgcgt  14820
ctgaagagta caactgggat ctgaactacg gcgaaatcgc gaagattttc cgtgctggct  14880
gcatcatccg tgcgcagttc ctgcagaaaa tcaccgatgc ttatgccgaa aatccacaga  14940
tcgctaacct gttgctggct ccgtacttca agcaaattgc cgatgactac cagcaggcgc  15000
tgcgtgatgt cgttgcttat gcagtacaga acggtattcc ggttccgacc ttctccgcag  15060
cggttgccta ttacgacagc taccgtgctg ctgttctgcc tgcgaacctg atccaggcac  15120
agcgtgacta ttttggtgcg catacttata agcgtattga taaagaaggt gtgttccata  15180
ccgaatggct ggattaa                                                 15197
```

<210> SEQ ID NO 20
<211> LENGTH: 535
<212> TYPE: PRT
<213> ORGANISM: Artificial Sequence
<220> FEATURE:
<223> OTHER INFORMATION: Example CRM197 sequence

<400> SEQUENCE: 20

```
Gly Ala Asp Asp Val Val Asp Ser Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Glu Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110
```

-continued

```
Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
    370                 375                 380

Lys Thr Gln Pro Phe Leu His Asp Gly Tyr Ala Val Ser Trp Asn Thr
385                 390                 395                 400

Val Glu Asp Ser Ile Ile Arg Thr Gly Phe Gln Gly Glu Ser Gly His
                405                 410                 415

Asp Ile Lys Ile Thr Ala Glu Asn Thr Pro Leu Pro Ile Ala Gly Val
            420                 425                 430

Leu Leu Pro Thr Ile Pro Gly Lys Leu Asp Val Asn Lys Ser Lys Thr
        435                 440                 445

His Ile Ser Val Asn Gly Arg Lys Ile Arg Met Arg Cys Arg Ala Ile
    450                 455                 460

Asp Gly Asp Val Thr Phe Cys Arg Pro Lys Ser Pro Val Tyr Val Gly
465                 470                 475                 480

Asn Gly Val His Ala Asn Leu His Val Ala Phe His Arg Ser Ser Ser
                485                 490                 495
```

-continued

```
Glu Lys Ile His Ser Asn Glu Ile Ser Ser Asp Ser Ile Gly Val Leu
            500                 505                 510

Gly Tyr Gln Lys Thr Val Asp His Thr Lys Val Asn Ser Lys Leu Ser
        515                 520                 525

Leu Phe Phe Glu Ile Lys Ser
    530                 535
```

MULTIVALENT VACCINE COMPOSITIONS AND USES THEREOF

BACKGROUND OF THE INVENTION

Extraintestinal pathogenic *Escherichia coli* (ExPEC) are normally harmless inhabitants of human gut, alongside commensal *E. coli* strains. However, ExPEC strains can possess virulence factors for the colonization and infection of sites outside of the gastrointestinal tract to cause diverse and serious invasive diseases, resulting in significant morbidity, mortality, and costs annually (see, e.g., Johnson et al., *J Lab Clin Med.* 2002; 139(3):155-162; Kohler et al., *Int J Med Microbiol.* 2011; 301(8):642-647; Foxman, *Am J Med.* 2002; 113 Suppl 1A:5S-13S; and Russo et al., *Microbes Infect.* 2003; 5(5):449-456). ExPEC strains are the most common cause of urinary tract infection (UTI). They are also a contributor to surgical site infections and neonatal meningitis (Johnson et al., 2002; and Russo et al., 2003), associated with abdominal and pelvic infections and nosocomial pneumonia, and are occasionally involved in other extra-intestinal infections such as osteomyelitis, cellulitis, and wound infections. All these primary sites of infection can result in ExPEC bacteremia (Russo et al., 2003). Neonates, the elderly, and immunocompromised patients are particularly susceptible to ExPEC infection, including invasive ExPEC disease (IED).

Bacterial resistance to antibiotics is a major concern in the fight against bacterial infection, and multi-drug resistant (MDR) *E. coli* strains are becoming more and more prevalent (see, e.g., Schito et al., 2009, Int. J. Antimicrob. Agents 34(5):407-413; and Pitout et al., 2012, Expert Rev. Anti. Infect. Ther. 10(10):1165-1176). The emergence and rapid global dissemination of ExPEC sequence type 131 (ST131) is considered the main driver of increased drug resistance, including multi-drug resistance (Johnson et al., Antimicrob Agents Chemother. 2010; 54(1):546-550; Rogers et al., J Antimicrob Chemother. 2011; 66(1):1-14). This clone is found in 12.5% to 30% of all ExPEC clinical isolates, mostly exhibits serotype O25B:H4, and shows high levels of fluoroquinolone resistance, which is often accompanied by trimethoprim/sulfamethoxazole resistance and extended-spectrum beta-lactamases conferring resistance to cephalosporins (Rogers et al, 2011, and Banerjee et al., Antimicrob Agents Chemother. 2014; 58(9):4997-5004).

The O-antigen serotype is based on the chemical structure of the O polysaccharide antigen, the outer membrane portion of the lipopolysaccharide (LPS) in a Gram-negative bacterium. More than 180 serologically unique *E. coli* O-antigens have been reported (Stenutz et al., FEMS Microbial Rev. 2006; 30: 382-403), although the vast majority of ExPEC isolates are classified within less than 20 O-antigen serotypes. Full-length *E. coli* O-antigens are typically comprised of about 10 to 25 repeating sugar units attached to the highly conserved LPS core structure, with each component synthesized separately by enzymes encoded predominantly in the rfb and rfa gene clusters, respectively. Following polymerization of the O-antigen, the O-antigen polysaccharide backbone may be modified, typically through the addition of acetyl or glucose residues. These modifications effectively increase serotype diversity by creating antigenically distinct serotypes that share a common polysaccharide backbone, but differ in side branches. Genes encoding O-antigen modifying enzymes typically reside outside of the rfb cluster on the chromosome, and in some cases, these genes are found within lysogenic bacteriophages.

ExPEC infection can be caused by any serotype. Although there is an overrepresentation of certain serotypes in ExPEC infection, surface polysaccharides from ExPEC isolates nonetheless exhibit considerable antigenic diversity, which makes the development of an ExPEC vaccine based on surface polysaccharides extremely challenging (Russo et al., Vaccine. 2007; 25: 3859-3870). Also, certain O-antigens may be poorly immunogenic. Furthermore, based on studies from Pneumococcal conjugate vaccines, when a number of serotypes can cause a disease, the vaccine composition, such as the choice of serotypes for inclusion in a vaccine and the dosage levels of the included serotypes, can be critical, since use of a vaccine against certain serotypes may potentially increase carriage of and disease from serotypes not included in the vaccine, or even a serotype that is included in the vaccine but only weakly effective in immunizing against the serotype (Lipsitch, Emerging Infectious Diseases; 1999, 5:336-345). Ideally, a vaccine should maximize its beneficial effects in the prevention of disease caused by serotypes included in the vaccine, while minimizing the risk of added disease from increased carriage of non-vaccine serotypes.

Efforts toward the development of a vaccine to prevent ExPEC infections have focused on O-antigen polysaccharide conjugates. A 12-valent O-antigen conjugate vaccine was synthesized through extraction and purification of O-antigen polysaccharide and chemical conjugation to detoxified *Pseudomonas aeruginosa* exotoxin A and tested for safety and immunogenicity in a Phase 1 clinical study (Cross et al., *J. Infect. Dis.* (1994) v.170, pp. 834-40). This candidate vaccine was never licensed for clinical use. A bioconjugation system in *E. coli* has been developed recently, in which the polysaccharide antigen and the carrier protein are both synthesized in vivo and subsequently conjugated in vivo through the activities of the oligosaccharyl transferase PglB, a *Campylobacter jejuni* enzyme, expressed in *E. coli* (Wacker et al., *Proc. Nat. Acad. Sci.* (2006) v. 103, pp. 7088-93). This N-linked protein glycosylation system is capable of the transfer of diverse polysaccharides to a carrier protein, allowing for straightforward methods to purify the conjugate.

Bioconjugation has been used successfully to produce conjugate polysaccharide for an *E. coli* four-valent O-antigen candidate vaccine (Poolman and Wacker, *J. Infect. Dis.* (2016) v.213(1), pp. 6-13). However, the development of a successful ExPEC vaccine requires coverage of predominant serotypes, and the presence of further O-antigen modifications in subsets of ExPEC isolates presents a further challenge in covering isolates displaying unmodified and modified LPS. Moreover, immune responses to vaccine compositions comprising O-antigens from multiple serotypes may differ between the serotypes. Accordingly, there is a continued need in the art for vaccines against ExPEC. In particular, there exists a need for an ExPEC vaccine based on surface polysaccharides that can be used to provide effective immune protection against ExPEC O75 serotype and other serotypes prevalent among ExPEC.

BRIEF SUMMARY OF THE INVENTION

It has been surprisingly discovered that *E. coli* O75 antigen appears less immunogenic than other *E. coli* O-antigens (e.g., O1, O2, and O6) when tested as conjugates of the O-antigens each covalently bound to a carrier protein in a composition with such other O-antigens at the same concentrations in a clinical trial. Vaccination with a composition containing conjugates of *E. coli* O75 antigen and conjugates of one or more additional *E. coli* O-antigens at an appropriate dose and ratio provides an improved immune response against the ExPEC O75 serotype and the one or more additional ExPEC O-serotypes.

Accordingly, in a first general aspect provided herein is a composition comprising *E. coli* O1, O2, O4, O15, O16, O18, O25, O75 and O6 antigen polysaccharides, wherein each of the antigen polysaccharides is independently covalently linked to a carrier protein, and wherein the concentration of each of O75 and O25 antigen polysaccharides is independently increased relative to the concentration of each of O1, O2, O4, O15, O16, O18 and O6 antigen polysaccharides.

In certain embodiments, the weight ratio of concentrations of O75 antigen polysaccharide independently to each of O1, O2, O4, O15, O16, O18 and O6 antigen polysaccharides is about 1.5:1 to about 2.5:1.

In certain embodiments, the weight ratio of concentrations of O75 antigen polysaccharide independently to each of O1, O2, O4, O15, O16, O18 and O6 antigen polysaccharides is about 2:1.

In a second general aspect, provided herein is a composition comprising *E. coli* O1, O2, O4, O15, O16, O18, O25, O75 and O6 antigen polysaccharides, wherein each of the antigen polysaccharides is independently covalently linked to a carrier protein, and wherein the weight ratio of concentrations of O75 antigen polysaccharide to O1, O2, and/or O6 antigen polysaccharide is about 1.5:1 to about 4:1. Preferably wherein the weight ratio of concentrations of O75 antigen polysaccharide to O1, O2, and/or O6 is about 2:1.

In certain embodiments, the weight ratio of concentrations of O75 antigen polysaccharide to O4, O15, O16 and/or O18 antigen polysaccharide is about 1.5:1 to about 4:1. Preferably the weight ratio of concentrations of O75 antigen polysaccharide to O4, O15, O16 and/or O18 antigen polysaccharide is about 2:1.

In a third general aspect, provided herein is a composition comprising *E. coli* O1, O2, O4, O15, O16, O18, O25, O75 and O6 antigen polysaccharides, wherein each of the antigen polysaccharides is independently covalently linked to a carrier protein, and wherein the concentration of each of O75 and O25 antigen polysaccharides is independently increased relative to the concentration of each of O1, O2, O4, O15, O16, O18 and O6 antigen polysaccharides, wherein the weight ratio of concentrations of O75 antigen polysaccharide to O1, O2, and/or O6 antigen polysaccharide is about 1.5:1 to about 4:1. Preferably, preferably the weight ratio of concentrations of O75 antigen polysaccharide to O1, O2, and/or O6 antigen polysaccharide is about 2:1.

Certain embodiments of the first, second and third general aspect are now described.

In certain embodiments, the weight ratio of concentrations of O75 antigen polysaccharide to O25 antigen polysaccharide in the composition is about 1:1.

In certain embodiments, the weight ratio of concentrations of the *E. coli* antigen polysaccharides O1:O2:O4:O6:O15:O16:O18:O25:O75 is 1:1:1:1:1:1:1:2:2.

In certain embodiments, the O1 antigen is O1A, the O4 is glucosylated, the O6 antigen is O6A, the O18 antigen is O18A, and the O25 antigen is O25B, wherein:

(i) the *E. coli* O1 antigen polysaccharide comprises the structure of Formula (O1A) shown in Table 1, (ii) the *E. coli* O2 antigen polysaccharide comprises the structure of Formula (O2): shown in Table 1, (iii) the *E. coli* O4 antigen polysaccharide comprises the structure of Formula (O4-Glc+) shown in Table 1, (iv) the *E. coli* O6 antigen polysaccharide comprises the structure of Formula (O6A) shown in Table 1, (v) the *E. coli* O15 antigen polysaccharide comprises the structure of Formula (O15) shown in Table 1, (vi) the *E. coli* O16 antigen polysaccharide comprises the structure of Formula (O16) shown in Table 1, (vii) the *E. coli* O18 antigen polysaccharide comprises the structure of Formula (O18A) shown in Table 1, (viii) the *E. coli* O25 antigen polysaccharide comprises the structure of Formula (O25B) shown in Table 1, and (ix) the *E. coli* O75 antigen polysaccharide comprises the structure of Formula (O75) shown in Table 1, wherein each n is independently an integer of 1 to 100, preferably of 3 to 50, for example 5 to 40, preferably of 5 to 30, for example 7 to 25, for example 10 to 20.

In certain embodiments, the concentration of the O75 antigen polysaccharide is from about 8 to about 64 μg/mL, preferably about 8 to about 50 μg/mL, preferably about 12 to about 40 μg/mL, preferably about 16 to about 32 μg/mL, preferably about 28 to about 36 μg/mL, preferably about 32 μg/mL.

In certain embodiments, the *E. coli* O antigen polysaccharides present in the composition consist of O1, O2, O4, O15, O16, O18, O25, O75 and O6.

In certain embodiments, the composition further comprises at least one additional *E. coli* antigen polysaccharide covalently linked to a carrier protein, preferably wherein the at least one additional *E. coli* antigen polysaccharide comprises O8 antigen polysaccharide with Formula (O8) shown in Table 1, wherein n is an integer of 1 to 100, preferably of 3 to 50, for example 5 to 40, preferably of 5 to 30, for example 7 to 25, for example 10 to 20.

In certain embodiments, the carrier protein is detoxified exotoxin A of *Pseudomonas aeruginosa* (EPA) or $CRM_{197}$, preferably EPA. Preferably the carrier protein comprises 1 to 20, such as 1 to 10, or 2 to 4, glycosylation consensus sequences having the amino acid sequence of SEQ ID NO: 1, such as the consensus sequences having the amino acid sequence of SEQ ID NO: 2. More preferably the carrier protein comprises four of the glycosylation consensus sequences. Most preferably each carrier protein is EPA comprising the amino acid sequence of SEQ ID NO: 3.

In certain embodiments, the *E. coli* antigen polysaccharides are covalently linked to the carrier protein by bioconjugation or by chemical conjugation, preferably the *E. coli* antigen polysaccharides are covalently linked to the carrier protein by bioconjugation, preferably the polysaccharide is covalently linked to an Asn residue in a glycosylation site in the carrier protein.

In another aspect, there is provided a method of inducing an immune response to *E. coli*, preferably extra-intestinal pathogenic *E. coli* (ExPEC), in a subject, comprising administering to the subject the composition of the invention.

In a further aspect there is provided a method of inducing an immune response to *E. coli*, preferably extra-intestinal pathogenic *E. coli* (ExPEC), in a subject, comprising administering to the subject an effective amount of each of *E. coli* O1, O2, O4, O15, O16, O18, O25, O75 and O6 antigen polysaccharides, wherein each of the antigen polysaccharides is independently covalently linked to a carrier protein, wherein the effective amount of each of O75 and O25 antigen polysaccharides is independently increased relative to each of O1, O2, O4, O15, O16, O18 and O6 antigen polysaccharides.

In certain embodiments according to a method of the invention, the effective amount of O75 antigen polysaccharide is administered at a weight ratio of independently about 1.5:1 to about 2.5:1, preferably about 2:1, to each of O1, O2, O4, O15, O16, O18 and O6 antigen polysaccharides.

In certain embodiments according to a method of the invention, the effective amount of O75 antigen polysaccharide is administered at a weight ratio of independently about 1.5:1 to about 4:1, preferably about 2:1, to O1, O2, and/or O6 antigen polysaccharide, preferably further wherein the effective amount of O75 antigen polysaccharide is administered at a weight ratio of about 1:1 to O25 antigen polysaccharide.

In another aspect, there is provided a method of inducing an immune response to *E. coli*, preferably extra-intestinal pathogenic *E. coli* (ExPEC), in a subject, comprising administering to the subject an effective amount of each of *E. coli O*1, O2, O4, O15, O16, O18, O25, O75 and O6 antigen polysaccharides, wherein each of the antigen polysaccharides is independently covalently linked to a carrier protein, the effective amount of O75 antigen polysaccharide is administered at a weight ratio of independently about 1.5:1 to about 4:1, to O1, O2, and/or O6 antigen polysaccharide. The effective amount of O75 antigen polysaccharide may preferably be administered at a weight ratio of about 1:1 to O25 antigen polysaccharide. Preferably, the effective amount of O75 antigen polysaccharide is administered at a weight ratio of independently about 2:1, to O1, O2, and/or O6 antigen polysaccharide.

Provided below are embodiments of any method aspect of the invention.

In certain embodiments according to a method of the invention, the immune response limits the severity of or prevents an invasive ExPEC disease in the subject, preferably wherein the invasive ExPEC disease comprises sepsis and/or bacteremia.

In certain embodiments according to a method of the invention, the O1 antigen is O1A, the O4 is glucosylated, the O6 antigen is O6A, the O18 antigen is O18A, and the O25 antigen is O25B. Preferably the O1A, O2, glucosylated O4, O6A, O15, O16, O18A, O25B, and O75 antigen polysaccharides comprise the structures of Formulas (O1A), (O2), (O4-Glc+), (O6A), (O15), (O16), (O18A), (O25B), and (O75), respectively, as shown in Table 1, wherein each n is independently an integer of 1 to 100, preferably of 3 to 50, for example 5 to 40, preferably of 5 to 30, for example 7 to 25, for example 10 to 20, wherein the weight ratio of O75 antigen polysaccharide to O6 antigen polysaccharide is about 1.5:1 to about 4:1, more preferably about 2:1.

In certain embodiments according to a method of the invention, the *E. coli* O antigen polysaccharides administered to the subject consist of O1, O2, O4, O15, O16, O18, O25, O75 and O6.

In certain embodiments according to a method of the invention, the *E. coli* O antigen polysaccharides administered to the subject further comprise from 1 to 15 additional *E. coli* O antigen polysaccharides, each independently covalently linked to a carrier protein.

In certain embodiments according to a method of the invention, the subject is a human having or at risk of having an *E. coli* (preferably ExPEC) infection, preferably an invasive ExPEC disease.

In certain embodiments according to a method of the invention, 8-16 μg, preferably about 16 μg, of the O75 antigen polysaccharide is administered per administration.

In certain embodiments according to a method of the invention, the effective amount of the administered *E. coli* antigen polysaccharides of O1:O2:O4:O6:O15:O16:O18:O25:O75 is administered at a weight ratio of 1:1:1:1:1:1:1:2:2.

BRIEF DESCRIPTION OF THE DRAWINGS

The foregoing summary, as well as the following detailed description of the invention, will be better understood when read in conjunction with the appended drawings. It should be understood that the invention is not limited to the precise embodiments shown in the drawings.

FIG. 3A shows the overall study design for Cohort 1, and FIG. 3B shows the overall study design for Cohort 2. See Example 7 for details.

DETAILED DESCRIPTION OF THE INVENTION

Figure 1A:
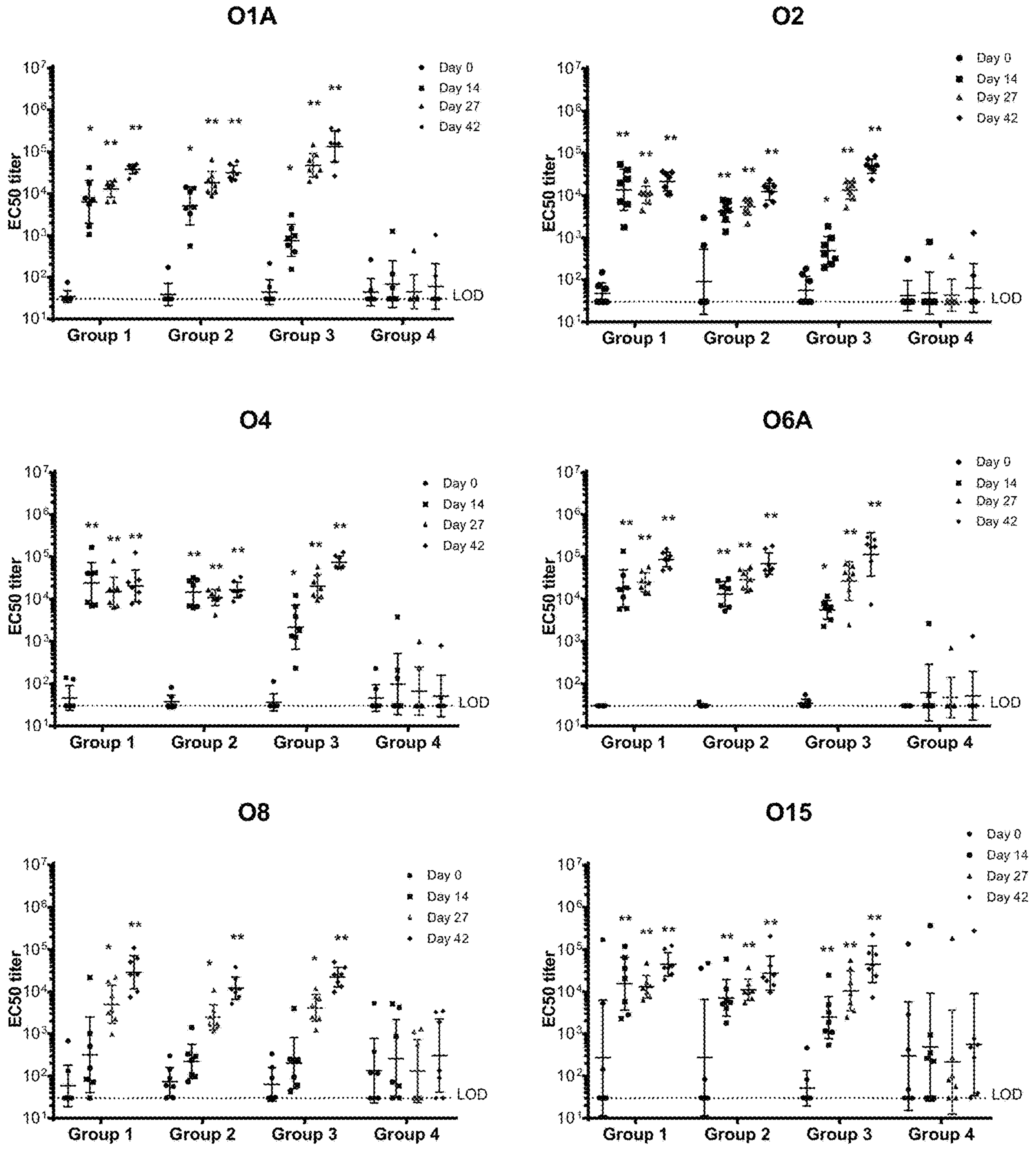
FIG. 1A-1B shows antibody responses induced by ExPEC10V vaccine in New Zealand White rabbits. Animals received 3 intramuscular immunizations with ExPEC10V or saline administered 2 weeks apart. ExPEC10V vaccine was administered at 3 different concentrations (group 1: high dose, group 2: medium dose and group 3: low dose, Table 11) and a control group received only saline (group 4, 0.9% (w/v) sodium chloride solution). Antibody levels were measured by ELISA at day 0 (pre-vaccination) and days 14, 27 and 42 (post-vaccination). Individual titers (EC50 titer) and geometric mean titers (GMT)+95% CI are shown. Wilcoxon Rank Sum test with Bonferroni correction for multiple comparisons. Comparisons ExPEC10V vaccinated animals (group 1, 2 and 3) versus saline control (group 4). * $p \leq 0.05$,  $p \leq 0.01$; *$p \leq 0.001$; **** $p \leq 0.0001$. LOD: limit of detection.

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

Unless defined otherwise, all technical and scientific terms used herein have the same meaning commonly understood to one of ordinary skill in the art to which this invention pertains. Otherwise, certain terms cited herein have the meanings as set in the specification. It must be noted that as used herein and in the appended claims, the singular forms "a," "an," and "the" include plural reference unless the context clearly dictates otherwise.

Unless otherwise indicated, the term "at least" preceding a series of elements is to be understood to refer to every element in the series.

The term "about," when used in conjunction with a number, refers to any number within ±10%, e.g. ±5%, or ±1%, of the referenced number.

Those skilled in the art will recognize or be able to ascertain using no more than routine experimentation, many equivalents to the specific embodiments of the invention described herein. Such equivalents are intended to be encompassed by the invention.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having".

When used herein "consisting of" excludes any element, step, or ingredient not specified in the claim element. When used herein, "consisting essentially of" does not exclude materials or steps that do not materially affect the basic and novel characteristics of the claim. Any of the aforementioned terms of "comprising," "containing," "including," and "having," whenever used herein in the context of an aspect or embodiment of the invention can be replaced with the term "consisting of" or "consisting essentially of" to vary scopes of the disclosure.

As used herein, the conjunctive term "and/or" between multiple recited elements is understood as encompassing both individual and combined options. For instance, where two elements are conjoined by "and/or," a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or."

As used herein, the terms "O polysaccharide," "O-antigen", "O-antigen", "O-antigen polysaccharide," "O-polysaccharide antigen" and the abbreviation "OPS", all refer to the O-antigen of Gram-negative bacteria, which is a component of the lipopolysaccharide (LPS) and is specific for each serotype or sero(sub)type of the Gram-negative bacteria. The O-antigen usually contains repeating units (RUs) of two to seven sugar residues. As used herein, the RU is set equal to the biological repeat unit (BRU). The BRU describes the RU of an O-antigen as it is synthesized in vivo. Different serotypes of *E. coli* express different O-antigens. In *E. coli*, the gene products involved in O-antigen biogenesis are encoded by the rfb gene cluster. Whenever referring to an O-antigen polysaccharide herein, the O-antigen polysaccharide of the respective *E. coli* serotype and any existing subserotypes thereof are meant unless indicated otherwise, e.g. when referring to O1 antigen polysaccharide, this can be O-antigen polysaccharide of *E. coli* subserotypes O1A, O1A1, O1B, or O1C, while O25 antigen polysaccharide can mean O25A or O25B antigen polysaccharide, etc. Many *E. coli* serotypes and subserotypes as well as the corresponding structure of a RU (moiety structure, or O-unit) of the O-antigen polysaccharides thereof are provided in Table 1 of WO 2020/039359, incorporated by reference herein.

As used herein, "rfb cluster" and "rfb gene cluster" refer to a gene cluster that encodes enzymatic machinery capable of synthesizing an O-antigen backbone structure. The term rfb cluster can apply to any O-antigen biosynthetic cluster, and preferably refers to a gene cluster from the genus *Escherichia*, particularly *E. coli*.

As used herein, the term "O1A" refers to the O1A antigen of *E. coli* (a subserotype of *E. coli* serotype O1). The term "O2" refers to the O2 antigen of *E. coli* (*E. coli* serotype O2). The term "O4" refers to the O4 antigen of *E. coli* (*E. coli* serotype O4). The term "O6A" refers to the O6A antigen of *E. coli* (a subserotype of *E. coli* serotype O6). The term "O8" refers to the O8 antigen of *E. coli* (*E. coli* serotype O8). The term "O15" refers to the O15 antigen of *E. coli* (*E. coli* serotype O15). The term "O16" refers to the O16 antigen of *E. coli* (*E. coli* serotype O16). The term "O18A" refers to the O18A antigen of *E. coli* (a subserotype of *E. coli* serotype O18). The term "O25B" refers to the O25B antigen from *E. coli* (a subserotype of *E. coli* serotype O25). The term "O75" refers to the O75 antigen of *E. coli* (*E. coli* serotype O75). As used herein, the terms "glucosylated O4", "glucose-branched O4", "O4 Glc+" and "Glc+O4" O-antigen refer to O4 O-antigen of *E. coli* (*E. coli* serotype O4) with a glucose side-branch, while "non-glucosylated O4," "O4 Glc-," and "Glc-O4" refer to an O4 antigen without a glucose side-branch.

The structures of several *E. coli* O-antigen polysaccharides referred to throughout this application are shown below in Table 1. A single repeating unit for each *E. coli* O-antigen polysaccharide is shown.

TABLE 1

Structures of *E. coli* O-antigen Polysaccharides

| *E. coli* O-antigen Polysaccharide | Structure of Repeating Unit[1] |
|---|---|
| O1A antigen polysaccharide (O1A) | [→3)-α-L-Rhap-(1→3)-α-L-Rhap-(1→3)-β-L-Rhap-(1→4)-β-D-GlcpNac-(1→]$_n$<br>2<br>↑<br>1<br>β-D-ManpNAc |
| O2 antigen polysaccharide (O2) | [→3)-α-L-Rhap-(1→2)-α-L-Rhap-(1→3)-β-L-Rhap-(1→4)-β-D-GlcpNac-(1→]$_n$<br>2<br>↑<br>1<br>α-D-Fucp3NAc |
| Non-glucosylated O4 antigen polysaccharide (O4-Glc−) | [→2)-α-L-Rhap-(1→6)-α-D-Glcp-(1→3)-α-L-FucpNAc-(1→3)-β-D-GlcpNac-(1→]$_n$ |
| Glucosylated O4 antigen polysaccharide (O4-Glc+) | α-D-Glcp<br>1<br>↓<br>3<br>[→2)-α-L-Rhap-(1→6)-α-D-Glcp-(1→3)-α-L-FucpNAc-(1→3)-β-D-GlcpNac-(1→]$_n$ |
| O6A antigen polysaccharide (O6A) | [→4)-α-D-GalpNAc-(1→3)-β-D-Manp-(1→4)-β-D-Manp-(1→3)-α-D-GlcpNac-(1→]$_n$<br>2<br>↑<br>1<br>β-D-Glcp |
| O8 antigen polysaccharide (O8) | α-D-Manp3Me-(1→[3)-β-D-Manp-(1→2)-α-D-Manp-(1→2)-α-D-Manp-(1→]$_n$ |
| O15 antigen polysaccharide (O15) | [→2)-β-D-Galp-(1→3)-α-L-FucpNAc-(1→3)-β-D-GlcpNAc-(1→]$_n$ |
| O16 antigen polysaccharide (O16) | [→2)-β-D-Galf-(1→6)-α-D-Glcp-(1→3)-α-L-Rhap-(1→3)-α-D-GlcpNac-(1→]$_n$<br>2<br>↑<br>Ac |
| O18A antigen polysaccharide (O18A) | [→2)-α-L-Rhap-(1→6)-α-D-Glcp-(1→4)-α-D-Galp-(1→3)-α-D-GlcpNac-(1→]$_n$<br>3<br>↑<br>1<br>β-D-GlcpNAc |
| O25B antigen polysaccharide (O25B) | β-D-Glcp<br>1<br>↓<br>6<br>[→4)-α-D-Glcp-(1→3)-α-L-Rhap-(1→3)-β-D-GlcpNAc-(1→]$_n$<br>3 2<br>↑ ↑<br>1 Ac<br>α-L-Rhap |

TABLE 1-continued

| Structures of *E. coli* O-antigen Polysaccharides | |
|---|---|
| *E. coli* O-antigen Polysaccharide | Structure of Repeating Unit[1] |
| O75 antigen polysaccharide (O75) | β-D-Manp<br>1<br>↓<br>4<br>[→3)-α-D-Galp-(1→4)-α-L-Rhap-(1→3)-β-D-GlcpNAc-(1→]$_n$ |

[1]Each n is independently an integer of 1 to 100, such as 1-50, 1-40, 1-30, 1-20, and 1-10, 3-50, 3-40, 5-30, e.g. at least 5, such as 5-40, e.g. 7-30, e.g. 7 to 25, e.g. 10 to 20, but in some instances can be 1-2.

All monosaccharides described herein have their common meaning known in the art. Monosaccharides can have the D or L configuration. If D or L is not specified, the sugar is understood to have the D configuration. Monosaccharides are typically referred to by abbreviations commonly known and used in the art. For example, Glc refers to glucose; D-Glc refers to D-glucose; and L-Glc refers to L-glucose. Other common abbreviations for monosaccharides include: Rha, rhamnose; GlcNAc, N-acetylglucosamine; GalNAc, N-acetylgalactosamine; Fuc, fucose; Man, mannose; Man3Me, 3-O-methyl-mannose; Gal, galactose; FucNAc, N-acetylfucosamine; and Rib, ribose. The suffix “f” refers to furanose and the suffix “p” refers to pyranose.

The terms “RU,” “repeat unit,” and “repeating unit” as used with respect to an O-antigen refer to the biological repeat unit (BRU) of an O-antigen as it is synthesized in vivo by cellular machinery (e.g., glycosyltransferases). The number of RUs of an O-antigen may vary per serotype, and in embodiments of the invention typically varies from about 1-100 RUs, preferably about 1 to 50 RUs, such as 1-50 RUs, 1-40 RUs, 1-30 RUs, 1-20 RUs, and 1-10 RUs, and more preferably at least 3 RUs, at least 4 RUs, at least 5 RUs, such as 3-50 RUs, preferably 5-40 RUs, preferably 5-30 RUs, e.g. 7-25 RUs, e.g. 10-20 RUs. However, in some instances, the number of RUs of an O-antigen can be 1-2. The structure of each O-antigen that is specifically described herein is shown containing one RU with the variable “n” designating the number of RUs. In each O-antigen polysaccharide in a bioconjugate of the invention, n is independently an integer of 1-100, such as 1-50, 1-40, 1-30, 1-20, 1-10, preferably at least 3, more preferably at least 5, such as 3-50, preferably 5-40 (e.g. 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40), more preferably 5-30, but in some instances can be 1-2. In some embodiments n is independently an integer of about 7-25, e.g. about 10-20. The values may vary between individual O-antigen polysaccharides in a composition, and are provided here as average values, i.e. if a bioconjugate is described herein as having an n that is independently an integer of 5-40, the composition contains a majority of O-antigen polysaccharides with 5-40 repeat units, but may also contain some O-antigen polysaccharides that have less than 5 repeat units or more than 40 repeat units.

As used herein, the terms “conjugate” and “glycoconjugate” refer to a sugar or saccharide antigen (e.g., oligo- and polysaccharide)-protein conjugate linked to another chemical species, including but not limited to proteins, peptides, lipids, etc. Glycoconjugates can be prepared chemically, e.g., by chemical (synthetic) linkage of the protein and sugar or saccharide antigen. The term glycoconjugate also includes bioconjugates.

As used herein, the term “effective amount” in the context of administering an O-antigen to a subject in methods according to embodiments of the invention refers to the amount of the O-antigen that is sufficient to induce a desired immune effect or immune response in the subject. In certain embodiments, an “effective amount” refers to the amount of an O-antigen which is sufficient to produce immunity in a subject to achieve one or more of the following effects in the subject: (i) prevent the development or onset of an ExPEC infection, preferably an invasive ExPEC disease, or symptom associated therewith; (ii) prevent the recurrence of an ExPEC infection, preferably an invasive ExPEC disease, or symptom associated therewith; (iii) prevent, reduce or ameliorate the severity of an ExPEC infection, preferably an invasive ExPEC disease, or symptom associated therewith; (iv) reduce the duration of an ExPEC infection, preferably an invasive ExPEC disease, or symptom associated therewith; (v) prevent the progression of an ExPEC infection, preferably an invasive ExPEC disease, or symptom associated therewith; (vi) cause regression of an ExPEC infection or symptom associated therewith; (vii) prevent or reduce organ failure associated with an ExPEC infection; (viii) reduce the chance or frequency of hospitalization of a subject having an ExPEC infection; (ix) reduce hospitalization length of a subject having an ExPEC infection; (x) increase the survival of a subject with an ExPEC infection, preferably an invasive ExPEC disease; (xi) eliminate an ExPEC infection, preferably an invasive ExPEC disease; (xii) inhibit or reduce ExPEC replication; and/or (xiii) enhance or improve the prophylactic or therapeutic effect(s) of another therapy.

An “effective amount” can vary depending upon a variety of factors, such as the physical condition of the subject, age, weight, health, etc.; route of administration, such as oral or parenteral; the composition administered, such as the target O-antigen, the other co-administered O-antigens, adjuvant, etc.; and the particular disease for which immunity is desired. When the O-antigen is covalently bound to a protein carrier, the effective amount for the O-antigen is calculated based on only the O-antigen polysaccharide moiety in the conjugate. All concentrations, amounts, and ratios of conjugates, including bioconjugates, as described herein, are also calculated based only on the weight of the O-antigen polysaccharide moieties in the conjugates, regardless of the concentration, amount, or ratio of any conjugated carrier proteins, unless indicated otherwise. For example, administration of 16 μg of a particular bioconjugate means that the administered bioconjugate comprises 16 μg of the particular O-antigen polysaccharide, and the amount of the conjugated carrier protein is not included in this number. For another example, if a composition is said to comprise conjugates of O-antigen polysaccharides from serotypes A and B in a ratio of 2:1, it indicates that there is two times the concentration or amount of the conjugated O-antigen polysaccharide A than that of the conjugated O-antigen polysaccharide B based on the weight of the conjugated O-antigen polysaccharides, disregarding the weight of the conjugated carrier proteins, in the composition.

The term "Invasive Extraintestinal pathogenic *Escherichia coli* (ExPEC) disease (IED)" as used herein is an acute illness consistent with systemic bacterial infection, which is microbiologically confirmed either by the isolation and identification of *E. coli* from blood or other normally sterile body sites, or by the isolation and identification of *E. coli* from urine in a patient with presence of signs and symptoms of invasive disease (systemic inflammatory response syndrome (SIRS), sepsis or septic shock) and no other identifiable source of infection. In certain embodiments, IED is an acute illness consistent with systemic bacterial infection, which is microbiologically confirmed either by (i) the isolation and identification of *E. coli* from blood or other normally sterile body sites, or by (ii) the isolation and identification of *E. coli* from urine in a patient with life threatening organ dysfunction due to dysregulated host response to infection originating from the urinary tract and/or male genital organs and no other identifiable source of infection.

IED may include, but is not necessarily limited to, urinary tract infection (UTI), a surgical-site infection, an abdominal or pelvic infection, pneumonia, osteomyelitis, cellulitis, sepsis, bacteremia, a wound infection, pyelonephritis, prostate biopsy-related infection (such as transrectal ultrasound-guided prostate needle biopsy [TRUS-PNB] related infection), urosepsis, meningitis, peritonitis, cholangitis, soft-tissue infections, pyomyositis, septic arthritis, endophthalmitis, suppurative thyroiditis, sinusitis, endocarditis, neutropenic fever, and prostatitis (including but not limited to acute bacterial prostatitis [ABP]).

In certain preferred embodiments, IED comprises sepsis. In certain preferred embodiments, IED comprises bacteremia. The invention in certain embodiments provides a composition according to the invention for preventing sepsis caused by *E. coli*. The invention in certain embodiments provides a composition according to the invention for preventing bacteremia caused by *E. coli*.

The term "IED event meeting criteria for sepsis" indicates an IED case including evidence of life-threatening organ dysfunction due to dysregulated host response to infection. A case of IED is meeting criteria for sepsis if there is an acute change in total Sequential Organ Failure Assessment (SOFA) score of 2 points or greater from baseline and deemed secondary to the IED. The invention in certain embodiments provides a composition according to the invention for preventing IED meeting the criteria for sepsis. The term "urosepsis" as used herein is sepsis caused by an infection originating from the urogenital tract and/or male genital organs.

The term "bacteremic IED" is an IED case which includes isolation and identification of *E. coli* from blood. The invention in certain embodiments provides a composition according to the invention for preventing bacteremic IED.

As used herein, an "immunological response" or "immune response" to an antigen or composition refers to the development in a subject of a humoral and/or a cellular immune response to the antigen or an antigen present in the composition.

As used herein, a "composition" comprising more than one *E. coli* antigen polysaccharide can be a single pharmaceutical composition that comprises the more than one *E. coli* antigen polysaccharide in the same pharmaceutical composition, or a combination of more than one pharmaceutical composition that comprises the more than one *E. coli* antigen polysaccharide in separate pharmaceutical compositions. In preferred embodiments, a composition is a single pharmaceutical composition. In a method of inducing an immune response to *E. coli*, a "composition" comprising more than one *E. coli* antigen polysaccharide can be administered to a subject in need thereof together in a single pharmaceutical composition that comprises the more than one *E. coli* antigen polysaccharide, or can be administered to the subject in combination in separate pharmaceutical compositions. In preferred embodiments, a single pharmaceutical composition is administered to the subject.

As used herein, the terms "in combination," or "a combination of" in the context of the administration of two or more O-antigens or compositions to a subject, does not restrict the order in which O-antigens or compositions are administered to a subject. For example, a first composition can be administered prior to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second composition to a subject. Preferably the two or more O-antigens are administered to a subject essentially simultaneously, e.g. within five minutes of each other, and more preferably the two or more O-antigens are administered simultaneously via administration of at least two compositions at the same time, most preferably via administration of a single composition that comprises the two or more O-antigens.

As used herein, "subject" means any animal, preferably a mammal, most preferably a human, to who will be or has been vaccinated by a method or composition according to an embodiment of the invention. The term "mammal" as used herein, encompasses any mammal. Examples of mammals include, but are not limited to, cows, horses, sheep, pigs, cats, dogs, mice, rats, rabbits, guinea pigs, monkeys, humans, etc., most preferably a human. The terms "subject" and "patient" may be used herein interchangeably.

The term "percent (%) sequence identity" or "% identity" describes the number of matches ("hits") of identical amino acids of two or more aligned amino acid sequences as compared to the number of amino acid residues making up the overall length of the amino acid sequences. In other terms, using an alignment, for two or more sequences the percentage of amino acid residues that are the same (e.g. 90%, 95%, 97% or 98% identity) may be determined, when the sequences are compared and aligned for maximum correspondence as measured using a sequence comparison algorithm as known in the art, or when manually aligned and visually inspected. The sequences which are compared to determine sequence identity may thus differ by substitution(s), addition(s) or deletion(s) of amino acids. Suitable programs for aligning protein sequences are known to the skilled person. The percentage sequence identity of protein sequences can, for example, be determined with programs such as CLUSTALW, Clustal Omega, FASTA or BLAST, e.g using the NCBI BLAST algorithm (Altschul S F, et al (1997), Nucleic Acids Res. 25:3389-3402).

For example, for amino acid sequences, sequence identity and/or similarity can be determined by using standard techniques known in the art, including, but not limited to, the local sequence identity algorithm of Smith and Waterman, 1981, Adv. Appl. Math. 2:482, the sequence identity alignment algorithm of Needleman and Wunsch, 1970, J. Mol. Biol. 48:443, the search for similarity method of Pearson and Lipman, 1988, Proc. Nat. Acad. Sci. U.S.A. 85:2444, computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al, 1984, Nucl. Acid Res. 12:387-395, preferably using the default settings, or by inspection. In certain embodiments, percent identity is calculated by FastDB based upon the following parameters: mismatch penalty of 1; gap penalty of 1; gap size penalty of 0.33; and joining penalty of 30, "Current Methods in Sequence Comparison and Analysis," Macromolecule Sequencing and Synthesis, Selected Methods and Applications, pp 127-149 (1988), Alan R. Liss, Inc.

Another example of a useful algorithm is the BLAST algorithm, described in: Altschul et al, 1990, J. Mol. Biol. 215:403-410; Altschul et al, 1997, Nucleic Acids Res. 25:3389-3402; and Karin et al, 1993, Proc. Natl. Acad. Sci. U.S.A. 90:5873-5787. A particularly useful BLAST program is the WU-BLAST-2 program which was obtained from Altschul et al, 1996, Methods in Enzymology 266:460-480. WU-BLAST-2 uses several search parameters, most of which are set to the default values.

An additional useful algorithm is gapped BLAST as reported by Altschul et al, 1993, Nucl. Acids Res. 25:3389-3402.

*E. coli* O-Antigens

It has been surprisingly discovered in the invention that *E. coli* O75 antigen conjugated to a carrier protein appears to be less immunogenic than other *E. coli* O-antigens (e.g., O1A, O2, O4, O6A, O15, O16 and O18A) conjugated to the carrier protein at the same polysaccharide concentration in a multivalent vaccine composition. This discovery led to further investigation into the dosage of *E. coli* O75 antigen and the dosage ratios of various *E. coli* O-antigens within a multivalent vaccine, thus the development of multivalent vaccines and immunization methods based on *E. coli* O-antigens for improved immune responses against the O75 serotype and other serotypes of ExPEC.

Embodiments of the invention relate to compositions and methods relating to *E. coli* O75 antigen polysaccharide and one or more additional *E. coli* O-antigens polysaccharides. Preferably, the one or more additional O-antigens are prevalent among the clinical isolates of *E. coli*. Examples of such *E. coli* antigens that can be used in the invention include, but are not limited to, the *E. coli* O1, O2, O4, O6, O8, O15, O16, O18, and O25 antigens. Depending on the need, the composition can include more than one additional *E. coli* O antigens, such as two, three, four, five, six, seven, eight, nine, ten, eleven, twelve, thirteen, fourteen or fifteen additional *E. coli* O antigens, to provide immune protection against multiple *E. coli* serotypes in addition to the *E. coli* O75 serotype. In some embodiments, the additional *E. coli* O-antigen is selected from the group consisting of *E. coli* O1, O2, O4, O6, O15, O16, O18 and O25 antigens. In preferred embodiments, the additional *E. coli* O-antigen is selected from the group consisting of O1A, O2, glucosylated O4, O6A, O15, O16, O18A and O25B. More preferably, the composition includes all of O1A, O2, glucosylated O4, O6A, O15, O16, O18A and O25B *E. coli* O-antigens. In a particular embodiment, the *E. coli* O-antigens comprise the structures as shown in Table 1, wherein n is an integer of 1 to 100. In some embodiments, n is an integer of 3 to 50, e.g. 5 to 40, preferably of 5 to 30, e.g. 7 to 25, e.g. 10 to 20.

In one embodiment, a composition of the invention comprises *E. coli* O75 and O6 antigen polysaccharides, wherein each of the antigen polysaccharides is independently covalently linked to a carrier protein, and wherein the ratio of concentrations of O75 antigen polysaccharide to O6 antigen polysaccharide is about 1.2:1 to about 8:1, preferably about 1.5:1 to about 4:1, more preferably about 2:1, e.g. about 1:5:1, 1.6:1, 1.7:1, 1.8:1, 1.9:1, 2.0:1, 2.1:1, 2.2:1, 2.3:1, 2.4:1 or 2.5:1. In some embodiments, the composition further comprises one or more, preferably all, of *E. coli O*1, O2, O4, O15, O16, O18, O25 antigen polysaccharides, wherein each of the antigen polysaccharides is independently covalently linked to a carrier protein, preferably the O1 antigen is O1A, the O4 is glucosylated, the O6 antigen is O6A, the O18 antigen is O18A, and the O25 antigen is O25B.

An *E. coli* O-antigen useful in the invention can be produced by methods known in the art in view of the present disclosure. For example, they can be produced from a cell, preferably a recombinant cell that is optimized for the biosynthesis of the O-antigen. See, e.g., relevant disclosure on the nucleic acids, proteins, host cells, production methods, etc., for *E. coli* O-antigen biosynthesis in WO 2006/119987, WO 2009/104074, International Patent Application No. PCT/EP2015/053739, Ihssen et al., 2010, *Microbial Cell Factories* 9, 61, the disclosures of which are herein incorporated by reference in their entirety.

Carrier Proteins

According to embodiments of the invention, each *E. coli* O-antigen is covalently bound to a carrier protein, preferably by a glycosidic linkage. Any carrier protein known to those skilled in the art in view of the present disclosure can be used. Suitable carrier proteins include, but are not limited to, detoxified Exotoxin A of *P. aeruginosa* (EPA), $CRM_{197}$, *E. coli* flagellin (FliC), maltose binding protein (MBP), Diphtheria toxoid, Tetanus toxoid, detoxified hemolysin A of *S. aureus*, clumping factor A, clumping factor B, *E. coli* heat labile enterotoxin, detoxified variants of *E. coli* heat labile enterotoxin, Cholera toxin B subunit (CTB), cholera toxin, detoxified variants of cholera toxin, *E. coli* Sat protein, the passenger domain of *E. coli* Sat protein, *Streptococcus pneumoniae* Pneumolysin, Keyhole limpet hemocyanin (KLH), *P. aeruginosa* PcrV, outer membrane protein of *Neisseria meningitidis* (OMPC), and protein D from non-typeable *Haemophilus influenzae*. Bioconjugation with various different carrier proteins containing the required consensus glycosylation sequence has been described, showing that a wide range of proteins can be glycosylated using this technology (see, e.g. WO 06/119987, WO 2015/124769, WO 2015/158403, WO 2015/82571, WO 2017/216286, and WO 2017/67964, together showing a wide variety of carrier proteins that were successfully used in bioconjugation).

In certain embodiments a carrier protein is modified, e.g., modified in such a way that the protein is less toxic and/or more susceptible to glycosylation. In a specific embodiment, the carrier proteins used herein are modified such that the number of glycosylation sites in the carrier proteins is maximized in a manner that allows for lower concentrations of the protein to be administered, e.g., in an immunogenic composition, particularly in its bioconjugate form.

Thus, in certain embodiments, the carrier proteins described herein are modified to include 1, 2, 3, 4, 5, 6, 7, 8, 9, 10 or more glycosylation sites than would normally be associated with the carrier protein (e.g., relative to the number of glycosylation sites associated with the carrier protein in its native/natural, i.e., "wild-type" state). Introduction of glycosylation sites into a carrier protein can be accomplished by insertion of a glycosylation consensus sequence anywhere in the primary structure of the protein by, e.g., adding new amino acids to the primary structure of the protein such that a glycosylation site is added in full or in part, or by mutating existing amino acids in the protein in order to generate a glycosylation site. One of ordinary skill in the art will recognize that the amino acid sequence of a protein can be readily modified using approaches known in the art, e.g., recombinant approaches that include modification of the nucleic acid sequence encoding the protein. In specific embodiments, glycosylation consensus sequences are introduced into specific regions of the carrier protein, e.g., surface structures of the protein, at the N or C termini of the protein, and/or in loops that are stabilized by disulfide bridges at the base of the protein. In some embodiments, a glycosylation consensus sequence can be extended by addition of lysine residues for more efficient glycosylation.

Exemplary examples of glycosylation consensus sequences that can be inserted into or generated in a carrier protein include Asn-X-Ser(Thr), wherein X can be any amino acid except Pro (SEQ ID NO: 1); and preferably Asp(Glu)-X-Asn-Z-Ser(Thr), wherein X and Z are independently selected from any amino acid except Pro (SEQ ID NO: 2).

In some embodiments, the *E. coli* O-antigen polysaccharide is covalently linked to an asparagine (Asn) residue in the carrier protein (e.g., N-linked), wherein the Asn residue is present in a glycosylation site comprising a glycosylation consensus sequence having SEQ ID NO: 1, more preferably having SEQ ID NO: 2. Typically, a carrier protein comprises 1-10 glycosylation sites, preferably 2 to 4 glycosylation sites, most preferably 4 glycosylation sites, such as 1-10, preferably 2-4, and more preferably 4 glycosylation sites each comprising a glycosylation consensus sequences having the amino acid sequence of SEQ ID NO: 1, and more preferably the amino acid sequence of SEQ ID NO: 2.

In particular embodiments, a carrier protein is a detoxified Exotoxin A of *P. aeruginosa*. For EPA, various detoxified protein variants have been described in literature and could be used as carrier proteins. For example, detoxification can be achieved by mutating and deleting the catalytically essential residues L552V and ΔE553 according to Lukac et al., 1988, *Infect Immun,* 56: 3095-3098, and Ho et al., 2006, *Hum Vaccin,* 2:89-98. As used herein, "EPA" refers to a detoxified Exotoxin A of *P. aeruginosa*. In those embodiments wherein the carrier protein is EPA, an *E. coli* antigen polysaccharide can be covalently linked to an Asn residue in a glycosylation site comprising a glycosylation consensus sequence having SEQ ID NO: 1, and preferably covalently linked to an Asn residue in a glycosylation site comprising a glycosylation consensus sequence having SEQ ID NO: 2. Preferably, the EPA carrier protein comprises 1-10 glycosylation sites, preferably 2 to 4 glycosylation sites, most preferably 4 glycosylation sites, such as 1-10, preferably 2-4, and more preferably 4 glycosylation sites each comprising a glycosylation consensus sequence having the amino acid sequence of SEQ ID NO: 1, and more preferably the amino acid sequence of SEQ ID NO: 2.

In some embodiments, the EPA carrier protein comprises four glycosylation sites each comprising a glycosylation consensus sequence, for instance a glycosylation site comprising a glycosylation consensus sequence having SEQ ID NO: 2. As used herein, "EPA-4 carrier protein" and "EPA-4" refer to a detoxified Exotoxin A of *P. aeruginosa* carrier protein comprising four glycosylation sites each comprising a glycosylation consensus sequences having SEQ ID NO: 2. An exemplary preferred example of an EPA-4 carrier protein is EPA carrier protein comprising the amino acid sequence of SEQ ID NO: 3.

In certain embodiments, the EPA carrier protein can be produced together with a signal sequence (such as a signal peptide for *E. coli* DsbA, *E. coli* outer membrane porin A (OmpA), *E. coli* maltose binding protein (MalE), etc.) that targets the carrier protein to the periplasmic space of the host cell that expresses the carrier protein. The EPA carrier protein can also be modified to a "tag," i.e., a sequence of amino acids that allows for the isolation and/or identification of the carrier protein.

An EPA carrier protein useful in the invention can be produced by methods known in the art in view of the present disclosure. See, e.g., relevant disclosure in e.g., Ihssen et al., 2010, Microbial Cell Factories 9, 61, and in WO 2006/119987, WO 2009/104074, and WO 2015/124769, the disclosures of which are herein incorporated by reference in their entireties.

In other embodiments, a carrier protein is $CRM_{197}$. The $CRM_{197}$ protein is a nontoxic form of diphtheria toxin but is immunologically indistinguishable from the diphtheria toxin. $CRM_{197}$ is produced by *Corynebacterium diphtheriae* infected by the nontoxigenic phage $\beta 197^{tox-}$ created by nitrosoguanidine mutagenesis of the toxigenic corynephage beta (Uchida et al. (1971) Nature New Biology 233:8-11). The $CRM_{197}$ protein has the same molecular weight as the diphtheria toxin but differs therefrom by a single base change (guanine to adenine) in the structural gene. This single base change causes an amino acid substitution (glutamic acid for glycine) in the mature protein and eliminates the toxic properties of diphtheria toxin. The $CRM_{197}$ protein is a safe and effective T-cell dependent carrier for saccharides. The amino acid sequence of a $CRM_{197}$ protein is shown in SEQ ID NO: 20. Further details about $CRM_{197}$ and production thereof can be found, e.g., in U.S. Pat. No. 5,614,382. In an embodiment, an O-antigen polysaccharide of the invention is conjugated to $CRM_{197}$ protein or the A chain of $CRM_{197}$ (see CN103495161). In an embodiment, an O-antigen polysaccharide of the invention is conjugated the A chain of $CRM_{197}$ obtained via expression by genetically recombinant *E. coli* (see CN103495161). In an embodiment, the O-antigen polysaccharides of the invention are each independently conjugated to $CRM_{197}$. In an embodiment, the O-antigen polysaccharides of the invention are each independently conjugated to the A chain of $CRM_{197}$.

Conjugates

The term "bioconjugate" refers to a conjugate between a protein (e.g., a carrier protein) and a sugar or saccharide antigen (e.g., oligo- and polysaccharide) prepared in a host cell background, preferably a bacterial host cell, e.g. an *E. coli* host cell, wherein host cell machinery links the antigen to the protein (e.g., N-links). Preferably, the term "bioconjugate" refers to a conjugate between a protein (e.g., carrier protein) and an O-antigen, preferably an *E. coli* O-antigen (e.g., O1A, O2, O4, O6A, O8, O15, O16, O18A, O25B, O75, etc.) prepared in a host cell background, wherein host cell machinery links the antigen to the protein (e.g., N-links). Because bioconjugates are prepared in host cells by host cell machinery, the antigen and protein are covalently linked via a glycosidic linkage or bond in a bioconjugate. Bioconjugates can be prepared in recombinant host cells engineered to express the cellular machinery needed to synthesize the O-antigen and/or link the O-antigen to the target protein. Bioconjugates, as described herein, have advantageous properties over chemically prepared glycoconjugates where the glycans are purified from bacterial cell walls and subsequently chemically coupled to a carrier protein, e.g., bioconjugates require fewer chemicals in manufacture and are more consistent in terms of the final product generated, and contain less or no free (i.e. unbound to carrier protein) glycan. Purification of O-antigen free from lipid A and subsequent chemical conjugation to a carrier protein is a lengthy and laborious process. Additionally, the purification, lipid A detoxification and chemical conjugation processes can result in loss of epitopes, antigen heterogeneity and reduced immunogenicity of the conjugated polysaccharide. Synthesis of glycoconjugates by bioconjugation can overcome these limitations of classical purification and chemical conjugation. Thus, in typical embodiments, bioconjugates are preferred over chemically produced glycoconjugates.

In certain embodiments, a host cell can produce an *E. coli* O-antigen and an EPA carrier protein, and covalently bind the O-antigen to the EPA carrier protein to form a bioconjugate useful in the invention. See, e.g., relevant disclosure in e.g., Ihssen et al., 2010*, Microbial Cell Factories* 9, 61, and in WO 2006/119987, WO 2009/104074, and WO 2015/124769, the disclosures of which are herein incorporated by reference in their entirety.

In a specific embodiment, the carrier protein is N-linked to an *E. coli* O-antigen useful in the invention. For example, the *E. coli* O-antigen is linked to the Asn residue in a glycosylation sequence of a carrier protein, such as Asn-X-Ser(Thr), wherein X can be any amino acid except Pro (SEQ ID NO: 2), preferably Asp(Glu)-X-Asn-Z-Ser(Thr), wherein X and Z are independently selected from any natural amino acid except Pro (SEQ ID NO: 3).

Alternatively, the glycoconjugates can be prepared by chemical synthesis, i.e., prepared outside of host cells (in vitro). For example, the *E. coli* O-antigens described herein, e.g., O75 antigen, can be conjugated to carrier proteins using methods known to those of skill in the art, including by means of using activation reactive groups in the polysaccharide/oligosaccharide as well as the protein carrier. See, e.g., Pawlowski et al., 2000, Vaccine 18:1873-1885; and Robbins et al., 2009, Proc Natl Acad Sci USA 106:7974-7978, the disclosures of which are herein incorporated by reference. Such approaches comprise extraction of antigenic polysaccharides/oligosaccharides from host cells, purifying the polysaccharides/oligosaccharides, chemically activating the polysaccharides/oligosaccharides, and conjugating the polysaccharides/oligosaccharides to a carrier protein. Methods to make glycoconjugates of *E. coli* O-antigens conjugated to carrier proteins using chemical conjugation to carrier protein, and compositions comprising such glycoconjugates, have also been described in WO 2020/039359.

For example, conjugates can be prepared using CDAP chemistry. In these embodiments, the polysaccharides are activated with 1-cyano-4-dimethylamino pyridinium tetrafluoroborate (CDAP) to form a cyanate ester. The activated polysaccharide is then coupled directly or via a spacer (linker) group to an amino group on the carrier protein (e.g., EPA or $CRM_{197}$). For example, the spacer could be cystamine or cysteamine to give a thiolated polysaccharide which could be coupled to the carrier via a thioether linkage obtained after reaction with a maleimide-activated carrier protein (for example using N-[7-maleimidobutyrloxy]succinimide ester (GMBS)) or a haloacetylated carrier protein (for example using iodoacetimide, N-succinimidyl bromoacetate (SBA; SIB), N-succinimidyl(4-iodoacetyl)aminobenzoate (SIAB), sulfosuccinimidyl(4-iodoacetyl)aminobenzoate (sulfo-SIAB), N-succinimidyl iodoacetate (SIA), or succinimidyl 3-[bromoacetamido]proprionate (SBAP)). Preferably, the cyanate ester (optionally made by CDAP chemistry) is coupled with hexane diamine or adipic acid dihydrazide (ADH) and the amino-derivatised saccharide is conjugated to the carrier protein (e.g., EPA or $CRM_{197}$) using carbodiimide (e.g., EDAC or EDC) chemistry via a carboxyl group on the protein carrier. Such conjugates are described for example in WO 93/15760, WO 95/08348 and WO 96/129094.

Other suitable techniques for conjugation use carbodiimides, hydrazides, active esters, norborane, p-nitrobenzoic acid, N-hydroxysuccinimide, S-NHS, EDC, TSTU. Many are described in WO 98/42721. Conjugation may involve a carbonyl linker which may be formed by reaction of a free hydroxyl group of the saccharide with CDI (see Bethell et al. (1979) 1. Biol. Chem. 254:2572-2574; Hearn et al. (1981) J. Chromatogr. 218:509-518) followed by reaction with a protein to form a carbamate linkage. This may involve reduction of the anomeric terminus to a primary hydroxyl group, optional protection/deprotection of the primary hydroxyl group, reaction of the primary hydroxyl group with CDI to form a CDI carbamate intermediate and coupling the CDI carbamate intermediate with an amino group on a protein.

In other embodiments, conjugates are prepared using reductive amination. Reductive amination involves two steps, (1) oxidation of the polysaccharide, (2) reduction of the activated polysaccharide and a carrier protein to form a conjugate. Before oxidation, the polysaccharide is optionally hydrolyzed. Mechanical or chemical hydrolysis maybe employed. Chemical hydrolysis can be conducted using acetic acid.

The oxidation step can involve reaction with periodate. For the purpose of the present invention, the term "periodate" includes both periodate and periodic acid; the term also includes both metaperiodate ($IO_4^-$) and orthoperiodate ($IO_6^{5-}$) and includes the various salts of periodate (e.g., sodium periodate and potassium periodate). In an embodiment, the capsular polysaccharide is oxidized in the presence of metaperiodate, preferably in the presence of sodium periodate ($NaIO_4$). In another embodiment the capsular polysaccharide is oxidized in the presence of orthoperiodate, preferably in the presence of periodic acid.

In an embodiment, the oxidizing agent is a stable nitroxyl or nitroxide radical compound, such as piperidine-N-oxy or pyrrolidine-N-oxy compounds, in the presence of an oxidant to selectively oxidize primary hydroxyls (as described in WO 2014/097099). In said reaction, the actual oxidant is the N-oxoammonium salt, in a catalytic cycle. In an aspect, said stable nitroxyl or nitroxide radical compound are piperidine-N-oxy or pyrrolidine-N-oxy compounds. In an aspect, said stable nitroxyl or nitroxide radical compound bears a TEMPO (2,2,6,6-tetramethyl-1-piperidinyloxy) or a PROXYL (2,2,5,5-tetramethyl-1-pyrrolidinyloxy) moiety. In an aspect, said stable nitroxyl radical compound is TEMPO or a derivative thereof. In an aspect, said oxidant is a molecule bearing a N-halo moiety. In an aspect, said oxidant is selected from the group consisting of N-Chloro-Succinimide, N-Bromosuccinimide, N-Iodosuccinimide, Dichloroisocyanuric acid, 1,3,5-trichloro-1,3,5-triazinane-2, 4,6-trione, Dibromoisocyanuric acid, 1,3,5-tribromo-1,3,5-triazinane-2,4,6-trione, Diiodoisocyanuric acid and 1,3,5-triiodo-1,3,5-triazinane-2,4,6-trione. Preferably said oxidant is N-Chlorosuccinimide.

Optionally the oxidation reaction is quenched by addition of a quenching agent. The quenching agent is selected from vicinal diols, 1,2-aminoalcohols, amino acids, glutathione, sulfite, bisulfate, dithionite, metabisulfite, thiosulfate, phosphites, hypophosphites or phosphorous acid (such as glycerol, ethylene glycol, propan-1,2-diol, butan-1,2-diol or butan-2,3-diol, ascorbic acid).

Following the oxidation step of the polysaccharide, the polysaccharide is said to be activated and is referred to an "activated polysaccharide" here below. The activated polysaccharide and the carrier protein may be lyophilised (freeze-dried), either independently (discrete lyophilization) or together (co-lyophilized). In one embodiment the activated polysaccharide and the carrier protein are co-lyophilized. In another embodiment the activated polysaccharide and the carrier protein are lyophilized independently.

In one embodiment the lyophilization takes place in the presence of a non-reducing sugar, possible non-reducing sugars include sucrose, trehalose, raffinose, stachyose, melezitose, dextran, mannitol, lactitol and palatinit.

The second step of the conjugation process is the reduction of the activated polysaccharide and a carrier protein to form a conjugate (so-called reductive amination), using a reducing agent. Reducing agents which are suitable include the cyanoborohydrides (such as sodium cyanoborohydride, sodium triacetoxyborohydride or sodium or zinc borohydride in the presence of Bronsted or Lewis acids), amine boranes such as pyridine borane, 2-Picoline Borane, 2,6-diborane-methanol, dimethylamine-borane, t-BuMe$^i$PrN—$BH_3$, benzylamine-$BH_3$ or 5-ethyl-2-methylpyridine borane (PEMB) or borohydride exchange resin. In one embodiment the reducing agent is sodium cyanoborohydride.

In an embodiment, the reduction reaction is carried out in aqueous solvent (e.g., selected from PBS, MES, HEPES, Bis-tris, ADA, PIPES, MOPSO, BES, MOPS, DIPSO, MOBS, HEPPSO, POPSO, TEA, EPPS, Bicine or HEPB, at a pH between 6.0 and 8.5, 7.0 and 8.0, or 7.0 and 7.5), in another embodiment the reaction is carried out in aprotic solvent. In an embodiment, the reduction reaction is carried out in DMSO (dimethylsulfoxide) or in DMF (dimethylformamide) solvent. The DMSO or DMF solvent may be used to reconstitute the activated polysaccharide and carrier protein which has been lyophilized.

At the end of the reduction reaction, there may be unreacted aldehyde groups remaining in the conjugates, these may be capped using a suitable capping agent. In one embodiment this capping agent is sodium borohydride ($NaBH_4$).

In other embodiments, conjugates are prepared using eTEC conjugation, such as described in WO 2014/027302. Said glycoconjugates comprise a saccharide covalently conjugated to a carrier protein through one or more eTEC spacers, wherein the saccharide is covalently conjugated to the eTEC spacer through a carbamate linkage, and wherein the carrier protein is covalently conjugated to the eTEC spacer through an amide linkage. The eTEC linked glycoconjugates of the invention may be represented by the general formula (I):

(I)

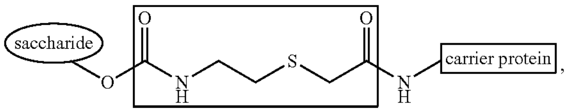

where the atoms that comprise the eTEC spacer are contained in the central box.

The eTEC spacer includes seven linear atoms (i.e., —$C(O)NH(CH_2)_2SCH_2C(O)$—) and provides stable thioether and amide bonds between the saccharide and carrier protein. Synthesis of the eTEC linked glycoconjugate involves reaction of an activated hydroxyl group of the saccharide with the amino group of a thioalkylamine reagent, e.g., cystamine or cysteinamine or a salt thereof, forming a carbamate linkage to the saccharide to provide a thiolated saccharide. Generation of one or more free sulfhydryl groups is accomplished by reaction with a reducing agent to provide an activated thiolated saccharide. Reaction of the free sulfhydryl groups of the activated thiolated saccharide with an activated carrier protein having one or more α-haloacetamide groups on amine containing residues generates a thioether bond to form the conjugate, wherein the carrier protein is attached to the eTEC spacer through an amide bond.

The conjugates described herein can be purified by any method known in the art for purification of a protein, for example, by chromatography (e.g., ion exchange, anionic exchange, affinity, and sizing column chromatography), centrifugation, differential solubility, or by any other standard technique for the purification of proteins. See, e.g., Saraswat et al., 2013, *Biomed. Res. Int.* ID #312709 (p. 1-18); see also the methods described in WO 2009/104074. The actual conditions used to purify a particular conjugate will depend, in part, on the synthesis strategy (e.g., synthetic production vs. recombinant production) and on factors such as net charge, hydrophobicity, and/or hydrophilicity of the bioconjugate, and will be apparent to those having skill in the art.

Host Cells

Described herein are host cells, e.g., prokaryotic host cells, capable of producing *E. coli* O antigens and bioconjugates comprising such *E. coli* O antigens. The host cells described herein preferably are modified to comprise (e.g., through genetic engineering) one or more of the nucleic acids encoding host cell machinery (e.g., glycosyltransferases) used to produce *E. coli* O-antigen polysaccharides and/or bioconjugates thereof.

Any host cells known to those of skill in the art can be used to produce the *E. coli* O antigen polysaccharides described herein (e.g., *E. coli* O75 polysaccharide) and bioconjugates comprising the *E. coli* O antigen polysaccharides described herein (e.g., a bioconjugate of *E. coli* O75 antigen polysaccharide) including archaea, prokaryotic host cells, and eukaryotic host cells. In a preferred embodiment, a host cell is a prokaryotic host cell. Exemplary prokaryotic host cells for use in production of the *E. coli* O antigen polysaccharides described herein and bioconjugates comprising the *E. coli* O antigen polysaccharides described herein include, but are not limited to, *Escherichia* species, *Shigella* species, *Klebsiella* species, *Xhantomonas* species, *Salmonella* species, *Yersinia* species, *Lactococcus* species, *Lactobacillus* species, *Pseudomonas* species, *Corynebacte-*

*rium* species, *Streptomyces* species, *Streptococcus* species, *Staphylococcus* species, *Bacillus* species, and *Clostridium* species.

In a specific embodiment, the host cell used to produce the *E. coli* O antigen polysaccharides described herein and bioconjugates comprising the *E. coli* O antigen polysaccharides described herein is a prokaryotic host cell, and is preferably *E. coli*.

In certain embodiments, the host cells used to produce the *E. coli* O antigen polysaccharides and bioconjugates described herein are engineered to comprise heterologous nucleic acids, e.g., heterologous nucleic acids comprising rfb gene clusters of a desired O antigen serotype, heterologous nucleic acids that encode one or more carrier proteins and/or glycosyltransferases. In a specific embodiment, heterologous rfb genes, and/or heterologous nucleic acids that encode proteins involved in glycosylation pathways (e.g., prokaryotic and/or eukaryotic glycosylation pathways) can be introduced into the host cells described herein. Such nucleic acids can encode proteins including, but not limited to, oligosaccharyl transferases and/or glycosyltransferases.

Sequences of various genes and gene clusters encoding glycosyltransferases useful in making recombinant host cells that can, e.g., be used to prepare *E. coli* O antigen polysaccharides and bioconjugates thereof are described herein. Those skilled in the art will appreciate that due to the degeneracy of the genetic code, a protein having a specific amino acid sequence can be encoded by multiple different nucleic acids. Thus, those skilled in the art will understand that a nucleic acid provided herein can be altered in such a way that its sequence differs from a sequence provided herein, without affecting the amino acid sequence of the protein encoded by the nucleic acid.

Described herein are host cells (e.g., recombinant host cells) for producing a bioconjugate of an *E. coli* O75 antigen polysaccharide, O1A antigen polysaccharide, O2 antigen polysaccharide, glucosylated or non-glucosylated O4 antigen polysaccharide, O6A antigen polysaccharide, O8 antigen polysaccharide, O15 antigen polysaccharide, O16 antigen polysaccharide, O18A antigen polysaccharide, or O25B antigen polysaccharide. The host cells described herein comprise nucleic acids encoding enzymes (e.g., glycosyltransferases) capable of producing the *E. coli* O antigen polysaccharide. The host cells described herein can naturally express nucleic acids capable of producing an O antigen of interest, or the host cells can be made to express such nucleic acids. In certain embodiments the nucleic acids are heterologous to the host cells and introduced into the host cells using genetic approaches known in the art. For example, the nucleic acids can be introduced into the host cell by genetic manipulation (e.g., the gene cluster is expressed on a plasmid or plasmids or integrated into the host cell genome (see, e.g., WO 2014/037585, WO 2014/057109, WO 2015/052344).

Also described herein are host cells (e.g., recombinant host cells) capable of producing a bioconjugate of an *E. coli* O1A, O2, glucosylated or non-glucosylated O4, O6A, O8, O15, O16, O18A, O25B, or O75 antigen polysaccharide covalently linked to a carrier protein. Such host cells (e.g., recombinant host cells) comprise nucleotide sequence of an rfb gene cluster specific to the O-antigen polysaccharide. The rfb gene clusters can be isolated from wild-type *E. coli* strains, and combined with nucleic acids encoding an oligosaccharyl transferase (e.g., PglB) and carrier protein (e.g., EPA) within one host cell to obtain a recombinant host cell that produces the *E. coli* O-antigen of interest or bioconjugate thereof. For example, such host cells can be engineered using recombinant approaches to comprise one or more plasmids comprising the rfb gene cluster, oligosaccharyl transferase (e.g., PglB) and carrier protein (e.g., EPA) using bioconjugation technology such as that described in WO 2015/124769, WO 2014/037585, WO 2009/104074, and WO 2009/089396. Preferably the host cells comprise the rfb gene clusters integrated into their genome. The nucleic acids encoding oligosaccharyl transferase, carrier protein, and where applicable gtrS gene, are in certain embodiments also integrated into the genome of the host cell. Heterologous or homologous gtrA and gtrB genes are in certain embodiments also integrated into the genome of the host cell.

Preparation of bioconjugates for O1A, O2, O6A and O25B antigens has been described in detail in WO 2015/124769 and WO 2017/035181. Exemplary gene clusters for each *E. coli* O antigen (rfb loci) have been described in Iguchi A, et al, DNA Research, 2014, 1-7, and in DebRoy C, et al, PLoS One. 2016, 11(1):e0147434; correction in: Plos One. 2016, 11(4):e0154551). Nucleic acid sequences for the rfb clusters and amino acid sequences for proteins encoded therein can also be found in public databases, such as GenBank. Exemplary sequences for rfb clusters that can be used in production strains for bioconjugates with polysaccharide antigens of the serotypes disclosed herein, are also provided in SEQ ID NOs: 9 and 11-19. Thus, for each of the desired bioconjugates mentioned above, the respective rfb cluster can be introduced into a host cell, to obtain host cells with the specific rfb cluster for the desired O-antigen, as well as containing nucleic acid encoding oligosaccharyltransferase and carrier protein. For reasons indicated above, preferably the host cells are recombinant host cells, and preferably are derived from strains with relatively well-known characteristics, such as *E. coli* laboratory or production strains, e.g. *E. coli* K12 or *E. coli* BL21, etc. Preferably, the rfb clusters are heterologous to the host cell, e.g. introduced into a precursor cell of the host cell, and preferably integrated into the genome thereof. Preferably an original rfb gene cluster, if such was present in a precursor cell, has been replaced by the rfb gene cluster for the O-antigen of interest in the host cell, to enable production of bioconjugate of the O-antigen of interest. Preferably the oligosaccharyltransferase is heterologous to the host cell, and in certain embodiments nucleic acid encoding such oligosaccharyltransferase is integrated into the genome of the host cell.

Any of the host cells described herein (e.g., recombinant host cells, preferably recombinant prokaryotic host cells) comprise nucleic acids encoding additional enzymes active in the N-glycosylation of proteins, e.g., the host cell described herein can further comprise a nucleic acid encoding an oligosaccharyl transferase or nucleic acids encoding other glycosyltransferases.

The host cells described herein typically comprise a nucleic acid that encodes an oligosaccharyl transferase. Such oligosaccharyl transferases transfer lipid-linked oligosaccharides to asparagine residues of nascent polypeptide chains that comprise an N-glycosylation consensus motif. The nucleic acid that encodes an oligosaccharyl transferase can be native to the host cell, or can be introduced into the host cell using genetic approaches. In preferred embodiments, the oligosaccharyl transferase is heterologous to the host cell. *E. coli* does not naturally comprise an oligosaccharyl transferase, and hence if *E. coli* is used as a host cell for production of bioconjugates, a heterologous oligosaccharyl transferase is comprised in such host cell, e.g. upon introduction by genetic engineering. The oligosaccharyl transferase can be from any source known in the art in view of the present disclosure.

In certain embodiments, an alternative to an oligosaccharyl transferase with N-glycosyltransferase activity, such as an O-glycosyltransferase, e.g. as a non-limiting example PglL, can be used, in conjunction with its own, different, glycosylation consensus sequence in the carrier protein, as for instance described in WO 2016/82597 and WO 2020/120569. Other glycosyltransferases, such as O-glycosyltransferases, can thus also be used as an oligosaccharyltransferase according to the invention.

In certain preferred embodiments, the oligosaccharyl transferase is an oligosaccharyl transferase from *Campylobacter*. For example, in one embodiment, the oligosaccharyl transferase is an oligosaccharyl transferase from *Campylobacter jejuni* (i.e., pglB; see, e.g., Wacker et al., 2002, Science 298:1790-1793; see also, e.g., NCBI Gene ID: 3231775, UniProt Accession No. O86154). In another embodiment, the oligosaccharyl transferase is an oligosaccharyl transferase from *Campylobacter lari* (see, e.g., NCBI Gene ID: 7410986).

In specific embodiments, the oligosaccharyl transferase is PglB oligosaccharyl transferase from *Campylobacter jejuni*, including the natural (wild-type) protein or any variant thereof, such as those described in WO 2016/107818 and WO 2016/107819. PglB can transfer lipid-linked oligosaccharides to asparagine residues in the consensus sequences SEQ ID NO: 1 and SEQ ID NO: 2. In particular embodiments, the PglB oligosaccharyl transferase comprises SEQ ID NO: 6, or a variant thereof. In certain embodiments one or more endogenous glycosylation consensus sequences in a wild-type PglB have been mutated to avoid PglB autoglycosylation, e.g. SEQ ID NO: 6 comprising the mutation N534Q. Examples of variant PglB oligosaccharyl transferases suitable for use in the recombinant host cells provided herein include the PglB oligosaccharyl transferase of SEQ ID NO: 6 comprising at least one mutation selected from the group consisting of N311V, K482R, D483H, A669V, Y77H, S80R, Q287P, and K289R. In one particular embodiment, a variant PglB oligosaccharyl transferase has SEQ ID NO: 6 comprising the mutation N311V. In another particular embodiment, a variant PglB oligosaccharyl transferase has SEQ ID NO: 6 comprising the mutations Y77H and N311V. In another particular embodiment, a variant PglB oligosaccharyl transferase has SEQ ID NO: 6 comprising the mutations N311V, K482R, D483H, and A669V. In another particular embodiment, a variant PglB oligosaccharyl transferase has SEQ ID NO: 6 comprising the mutations Y77H, S80R, Q287P, K289R, and N311V. It was found and described in PCT/US20/23415, filed on 18 Mar. 2020, that certain PglB oligosaccharyl transferase variants give surprisingly improved yields in production of *E. coli* O-antigen bioconjugates of specific serotypes. The improved or optimal PglB variant for a given *E. coli* O-antigen was not predictable. The invention in certain aspects therefore also discloses methods for producing bioconjugates of specific *E. coli* O-antigens, using specific PglB variants as the oligosaccharyl transferase. Further variants of PglB that are at least 80%, 85%, 90%, 91%, 92%, 93%, 94%, 95%, 96%, 97%, 98%, 99% identical to SEQ ID NO: 6 and still have oligosaccharyl transferase activity, preferably having one or more of the specific amino acids on the indicated positions disclosed in combination herein (e.g. 77Y, 80S, 287Q, 289K, 311N, 482K, 483D, 669A; or 311V; or 311V, 482R, 483H, 669V; or 77H, 80R, 287P, 289R, 311V; or 77H, 311V; etc) can also be used for production of bioconjugates.

In a specific embodiment, a host cell (e.g., recombinant host cell) capable of producing a bioconjugate of an *E. coli* O75 antigen polysaccharide covalently linked to a carrier protein further comprises a nucleotide sequence encoding PglB oligosaccharyl transferase from *Campylobacter jejuni* having the amino acid sequence of SEQ ID NO: 6, or preferably SEQ ID NO: 6 comprising the mutation N311V.

In other specific embodiments, a host cell (e.g., recombinant host cell) capable of producing a bioconjugate of an *E. coli* O1A, O6A, or O15 antigen polysaccharide covalently linked to a carrier protein further comprises a nucleotide sequence encoding PglB oligosaccharyl transferase from *Campylobacter jejuni* having the amino acid sequence of SEQ ID NO: 6, or preferably SEQ ID NO: 6 comprising the mutations N311V, K482R, D483H, and A669V.

In a specific embodiment, a host cell (e.g., recombinant host cell) capable of producing a bioconjugate of an *E. coli* glucosylated O4 antigen polysaccharide covalently linked to a carrier protein further comprises a nucleotide sequence encoding PglB oligosaccharyl transferase from *Campylobacter jejuni* having the amino acid sequence of SEQ ID NO: 6, or preferably SEQ ID NO: 6 comprising the mutation N311V, or more preferably SEQ ID NO: 6 comprising the mutations Y77H and N311V. Preferably, the recombinant host cell for production of a bioconjugate of an *E. coli* glucosylated O4 antigen polysaccharide covalently linked to a carrier protein further comprises a sequence encoding a glucosyltransferase GtrS having the amino acid sequence of SEQ ID NO: 4 (or a variant thereof that is at least 80%, 85%, 90%, 91%, 92%, 93%, 94%, 95%, 96%, 97%, 98%, 99% identical to SEQ ID NO: 4) and being capable of modifying an *E. coli* O4 antigen polysaccharide by addition of glucose to produce the *E. coli* glucosylated O4 antigen polysaccharide, and nucleotide sequences encoding a translocase GtrA and a glycosyltransferase GtrB having the amino acid sequences of SEQ ID NOs: 7 and 8 respectively (or variants thereof with amino acid sequences that are at least 80%, 85%, 90%, 91%, 92%, 93%, 94%, 95%, 96%, 97%, 98%, 99% identical to SEQ ID NOs: 7 and 8 respectively), wherein the translocase is capable of translocating bactoprenol linked glucose and the glycosyltransferase is capable of glucosylating bactoprenol. For production of a bioconjugate of an *E. coli* non-glucosylated O4 antigen polysaccharide covalently linked to a carrier protein the cell does not require such sequences encoding GtrS, GtrA, and GtrB proteins. Production of bioconjugates of an *E. coli* glucosylated O4 antigen polysaccharide covalently linked to a carrier protein, using a novel GtrS specific for glucosylation of *E. coli* O4 antigen polysaccharide, is described in PCT/US20/23404, filed on 18 Mar. 2020, incorporated in its entirety by reference herein.

In a specific embodiment, a host cell (e.g., recombinant host cell) capable of producing a bioconjugate of an *E. coli* O16 antigen polysaccharide covalently linked to a carrier protein further comprises a nucleotide sequence encoding PglB oligosaccharyl transferase from *Campylobacter jejuni* having the amino acid sequence of SEQ ID NO: 6, or preferably SEQ ID NO: 6 comprising the mutations Y77H, S80R, Q287P, K289R, and N311V.

In a specific embodiment, a host cell (e.g., recombinant host cell) capable of producing a bioconjugate of an *E. coli* O8, O18A, O25B, or O2 antigen polysaccharide covalently linked to a carrier protein further comprises a nucleotide sequence encoding PglB oligosaccharyl transferase from *Campylobacter jejuni* having the amino acid sequence of SEQ ID NO: 6, preferably wherein SEQ ID NO: 6 comprises no amino acid mutations at positions 77, 80, 287, 289, 311, 482, 483, and 669.

In some embodiments, any of the host cells described herein comprise a nucleic acid encoding a carrier protein, e.g., a protein to which the O-antigen polysaccharide(s) produced by the host cell glycosylation machinery can be attached to form a bioconjugate. The host cell can comprise a nucleic acid encoding any carrier protein known to those skilled in the art in view of the present disclosure including, but not limited to, detoxified Exotoxin A of *P. aeruginosa* (EPA), *E. coli* flagellin (FliC), $CRM_{197}$, maltose binding protein (MBP), Diphtheria toxoid, Tetanus toxoid, detoxified hemolysin A of *S. aureus*, clumping factor A, clumping factor B, *E. coli* heat labile enterotoxin, detoxified variants of *E. coli* heat labile enterotoxin, Cholera toxin B subunit (CTB), cholera toxin, detoxified variants of cholera toxin, *E. coli* Sat protein, the passenger domain of *E. coli* Sat protein, *Streptococcus pneumoniae* Pneumolysin, Keyhole limpet hemocyanin (KLH), *P. aeruginosa* PcrV, outer membrane protein of *Neisseria meningitidis* (OMPC), and protein D from non-typeable *Haemophilus influenzae*.

In preferred embodiments, a host cell further comprises a nucleic acid encoding detoxified Exotoxin A of *P. aeruginosa* (EPA). Preferably, the EPA carrier protein comprises 1-10 glycosylation sites, preferably 2 to 4 glycosylation sites, most preferably 4 glycosylation sites, such as 1-10, preferably 2-4, and more preferably 4 glycosylation sites each comprising a glycosylation consensus sequence having the amino acid sequence of SEQ ID NO: 1, and more preferably having the amino acid sequence of SEQ ID NO: 2. In a specific embodiment, a host cell further comprises a nucleic acid encoding EPA-4 carrier protein comprising SEQ ID NO: 3.

In certain embodiments, the carrier proteins used in the generation of the bioconjugates by the host cells described herein comprise a "tag," i.e., a sequence of amino acids that allows for the isolation and/or identification of the carrier protein. For example, adding a tag to a carrier protein can be useful in the purification of that protein and, hence, the purification of conjugate vaccines comprising the tagged carrier protein. Exemplary tags that can be used herein include, without limitation, histidine (HIS) tags (e.g., hexahistidine-tag, or 6×His-Tag), FLAG-TAG, and HA tags. In certain embodiments, the tags used herein are removable, e.g., removal by chemical agents or by enzymatic means, once they are no longer needed, e.g., after the protein has been purified. In other embodiments, the carrier protein does not comprise a tag.

In certain embodiments, the carrier proteins described herein comprise a signal sequence that targets the carrier protein to the periplasmic space of the host cell that expresses the carrier protein. In a specific embodiment, the signal sequence is from *E. coli* DsbA, *E. coli* outer membrane porin A (OmpA), *E. coli* maltose binding protein (MalE), *Erwinia carotovorans* pectate lyase (PelB), FlgI, NikA, or *Bacillus* sp. endoxylanase (XynA), heat labile *E. coli* enterotoxin LTIIb, *Bacillus* endoxylanase XynA, or *E. coli* flagellin (FlgI). In one embodiment, the signal sequence comprises SEQ ID NO: 10. A signal sequence may be cleaved off after translocation of the protein to the periplasm and may thus no longer be present in the final carrier protein of a bioconjugate.

In certain embodiments, additional modifications can be introduced (e.g., using recombinant techniques) into the host cells described herein. For example, host cell nucleic acids (e.g., genes) that encode proteins that form part of a possibly competing or interfering glycosylation pathway (e.g., compete or interfere with one or more heterologous genes involved in glycosylation that are recombinantly introduced into the host cell) can be deleted or modified in the host cell background (genome) in a manner that makes them inactive/dysfunctional (i.e., the host cell nucleic acids that are deleted/modified do not encode a functional protein). In certain embodiments, when nucleic acids are deleted from the genome of the host cells provided herein, they are replaced by a desirable sequence, e.g., a sequence that is useful for production of an O antigen polysaccharide or bioconjugate thereof.

Exemplary genes or gene clusters that can be deleted in host cells (and, in some cases, replaced with other desired nucleic acid sequences) include genes or gene clusters of host cells involved in glycolipid biosynthesis, such as waaL (see, e.g., Feldman et al., 2005, PNAS USA 102:3016-3021), the lipid A core biosynthesis cluster (waa), galactose cluster (gal), arabinose cluster (ara), colonic acid cluster (wc), capsular polysaccharide cluster, undecaprenol-p biosynthesis genes (e.g. uppS, uppP), und-P recycling genes, metabolic enzymes involved in nucleotide activated sugar biosynthesis, enterobacterial common antigen cluster (eca), and prophage O antigen modification clusters like the gtrABS cluster or regions thereof. In a specific embodiment, the host cells described herein are modified such that they do not produce any O antigen polysaccharide other than a desired O antigen polysaccharide, e.g., glucosylated O4 antigen polysaccharide.

In a specific embodiment, the waaL gene is deleted or functionally inactivated from the genome of a host cell (e.g., recombinant host cell) provided herein. The terms "waaL" and "waaL gene" refer to the O-antigen ligase gene encoding a membrane bound enzyme with an active site located in the periplasm. The encoded enzyme transfers undecaprenylphosphate (UPP)-bound O antigen to the lipid A core, forming lipopolysaccharide. Deletion or disruption of the endogenous waaL gene (e.g., ΔwaaL strains) disrupts transfer of the O-antigen to lipid A, and can instead enhance transfer of the O-antigen to another biomolecule, such as a carrier protein.

In another specific embodiment, one or more of the waaL gene, gtrA gene, gtrB gene, gtrS gene, and the rfb gene cluster is deleted or functionally inactivated from the original genome of a prokaryotic host cell provided herein.

In one embodiment, a host cell used herein is *E. coli* that produces a bioconjugate of glucosylated O4 antigen polysaccharide, wherein the waaL gene is deleted or functionally inactivated from the genome of the host cell, and a gtrS gene specific to *E. coli* O4 antigen polysaccharide is inserted. In certain embodiments for production strains for bioconjugates of the glucosylated O4 O-antigen, a gtrS gene encoding a glucosyl transferase having at least 80% sequence identity to SEQ ID NO: 4 is inserted in the place of a gtrS gene of the parent strain, so as to replace the gtrS gene in that parent strain with the one that is responsible for glucosylation of the O4 antigen. An example of such a parent strain is *E. coli* K-12 strain W3110. The gtrA and gtrB genes can be homologous to the parent strain, or alternatively one or both of these genes can be heterologous to the parent strain. Typically, and unlike the gtrS gene, these gtrA and gtrB genes are not specific for the O-antigen structure.

Also described herein are methods of making recombinant host cells. Recombinant host cells produced by the methods described herein can be used to produce bioconjugates of *E. coli* O antigens. The methods comprise introducing one or more recombinant nucleic acid molecules into a cell to produce the recombinant host cell. Typically, the recombinant nucleic acid molecules are heterologous. Any method known in the art in view of the present disclosure can be used to introduce recombinant nucleic acid molecules into a host cell. Recombinant nucleic acids can be introduced into the host cells described herein using any methods known to those of ordinary skill in the art, e.g., electroporation, chemical transformation, by heat shock, natural transformation, phage transduction, and conjugation. In specific embodiments, recombinant nucleic acids are introduced into the host cells described herein using a plasmid. For example, the heterologous nucleic acids can be expressed in the host cells by a plasmid (e.g., an expression vector). In another specific embodiment, heterologous nucleic acids are introduced into the host cells described herein using the method of insertion into the genome as for instance described in WO 2014/037585, WO 2014/057109, or WO 2015/052344.

*E. coli* strains that are used routinely in molecular biology as both a tool and a model organism can for instance be used as parents for host cells in certain embodiments. Non-limiting examples include *E. coli* K12 strains (for example, such as W1485, W2637, W3110, MG1655, DH1, DH5α, DH10, etc.), B strains (e.g. BL-21, REL606, etc.), C strains, or W strains. In one particular embodiment, the host strain is derived from parent strain W3110. This strain can for instance be obtained from the *E. coli* Genetic Stock Center at Yale. For more information on *E. coli*, see e.g. Ecoliwiki.net.

In some embodiments, the host cells described herein can be used to produce bioconjugates comprising an *E. coli* O antigen polysaccharide covalently linked to a carrier protein. Methods of producing such bioconjugates using host cells are known in the art. See, e.g., WO 2003/074687 and WO 2006/119987. Such methods comprise culturing any of the recombinant host cells described herein under conditions for production of the bioconjugate. Bioconjugates can be isolated, separated, and/or purified from recombinant host cells using any method known in the art in view of the present disclosure. For example, bioconjugates can be purified by any method known in the art for purification of a protein, for instance, by chromatography (e.g., ion exchange, anionic exchange, affinity, and sizing column chromatography), centrifugation, differential solubility, or by any other standard technique for the purification of proteins. See, e.g., methods described in WO 2009/104074. Further, the bioconjugates can be fused to heterologous polypeptide sequences to facilitate purification. The actual conditions used to purify a particular bioconjugate will depend, in part, on factors such as net charge, hydrophobicity, and/or hydrophilicity of the bioconjugate, and will be apparent to those skilled in the art. Preparation of bioconjugates for O1A, O2, O6A, and O25B, as well as vaccine compositions comprising these, have for instance been described in WO 2015/124769 and in WO 2017/035181.

Also provided are bioconjugates produced by the methods described herein, i.e., using the recombinant host cells described herein.

In some embodiments, a method of preparing a bioconjugate of an *E. coli* O-antigen polysaccharide covalently linked to a carrier protein comprises: (i) providing a recombinant host cell comprising (a) nucleotide sequence of an rfb gene cluster for the O-antigen polysaccharide; (b) a nucleotide sequence encoding a carrier protein, preferably EPA, comprising at least one glycosylation site comprising a glycosylation consensus sequence having SEQ ID NO: 1, preferably SEQ ID NO: 2, and more preferably comprising four glycosylation sites each comprising a glycosylation consensus sequence having SEQ ID NO: 2; and (c) nucleotide sequence encoding an oligosaccharyl transferase, for instance PglB oligosaccharyl transferase or variant thereof.

In certain embodiments, *E. coli* O-antigen polysaccharides are covalently bound to the carrier protein at a particular polysaccharide to protein ratio by weight (w/w). This ratio of amount of O-antigen polysaccharide by weight covalently bound to the carrier protein by weight is referred to as the "glycan/protein ratio" or "polysaccharide/protein ratio" or "PS/protein ratio". In some embodiments, the O-antigen polysaccharide is covalently bound to the carrier protein at a polysaccharide to protein (w/w) ratio of about 1:20 to 20:1, preferably 1:10 to 10:1, more preferably 1:3 to 3:1. In certain non-limiting embodiments for bioconjugates described herein, glycan/protein ratio is about 0.1 to 0.5, such as 0.1, 0.15, 0.2, 0.25, 0.3, 0.35, 0.4, 0.45, or 0.5. In such embodiments, the weight ratio of the O-antigen polysaccharide: protein is about 1:10 to 1:2, such as 1:10: 1:9: 1:8, 1:7, 1:6, 1:5, 1:4, 1:3, or 1:2, depending on the particular O-antigen serotype. In certain embodiments the glycan/protein ratio is from about 0.15 to about 0.45. In general, a higher glycan/protein ratio of O-antigen polysaccharide to carrier protein is preferred, because a high amount of carrier protein can lead to immunological interference in some instances. Also, a higher glycan/protein ratio would help getting sufficient O-antigen polysaccharide dosed in the form of bioconjugate, while keeping the amount of carrier protein relatively low, which is especially beneficial for multivalent compositions where multiple serotypes are to be covered by the composition, e.g. compositions comprising bioconjugates from at least 4 different O-antigens, at least 5 different O-antigens, at least 6 different O-antigens, at least 7 different O-antigens, at least 8 different O-antigens, at least 9 different O-antigens, at least 10 different O-antigens, etc.

A glycan/protein ratio of a conjugate according to the invention can be determined by determining the protein amount and the glycan amount. Protein amount can be determined by measurement of UV absorbance at 280 nm (A280). Glycan amount can be determined based on ion chromatography with pulsed amperometric detection (IC-PAD) of a sugar in the repeat unit (e.g. of Man for O8 in Table 1, and of GlcNAc for the other glycans in Table 1), after which the structural information of the repeat unit can be used to calculate the total glycan amount (e.g. the repeat unit of O1A has a molar mass of 845 Da and one mole of such a repeat unit contains one mole of GlcNAc, enabling calculation of the total glycan amount when the amount of GlcNAc has been determined by IC-PAD).

In some embodiments, a bioconjugate of an *E. coli* O25B antigen polysaccharide covalently linked to a carrier protein as described herein has a certain degree of acetylation at position 2 of the L-Rh sugar. The degree of O-acetylation of O25B antigen polysaccharide in a (bio)conjugate is preferably at least 30%, preferably at least 50%, such as at least 50%, 55%, 60%, 65%, 70%, 75%, 80%, 85%, 90%, 95%, or 100%.

Similarly, the degree of O-acetylation of an *E. coli* O16 antigen polysaccharide in a (bio)conjugate is preferably at least 30%, preferably at least 50%, such as at least 50%, 55%, 60%, 65%, 70%, 75%, 80%, 85%, 90%, 95%, or 100%.

In specific embodiments, a method of preparing a bioconjugate of an O-antigen polysaccharide comprises providing a recombinant host cell comprising nucleic acid sequence encoding a particular oligosaccharyl transferase enzyme, particularly a PglB oligosaccharyl transferase or variant thereof, depending on the O-antigen polysaccharide bioconjugate to be produced. The particular oligosaccharyl transferase enzyme variant may impact the yield of bioconjugate produced by the host cell. Typically, a higher yield is preferred, since the yield will impact the costs for producing a specific bioconjugate, which is especially important for multivalent compositions comprising several different bioconjugates.

In one particular embodiment, when the O-antigen is O75 antigen polysaccharide, the PglB oligosaccharyl transferase comprises the amino acid mutation of N311V, wherein the amino acid mutations are relative to the wild-type PglB having the amino acid sequence of SEQ ID NO: 6.

In another particular embodiment, when the O-antigen is O1A, O6A, or O15 antigen polysaccharide, the PglB oligosaccharyl transferase comprises the amino acid mutations of N311V, K482R, D483H, and A669V, wherein the amino acid mutations are relative to the wild-type PglB having the amino acid sequence of SEQ ID NO: 6.

In another particular embodiment, when the O-antigen is glucosylated O4 antigen polysaccharide, the PglB oligosaccharyl transferase comprises the amino acid mutation N311V, or the amino acid mutations of Y77H and N311V, wherein the amino acid mutations are relative to the wild-type PglB having the amino acid sequence of SEQ ID NO: 6.

In another particular, embodiment, when the O-antigen is O16 antigen polysaccharide, the PglB oligosaccharyl transferase comprises the amino acid mutations of Y77H, S80R, Q287P, K289R, and N311V, wherein the amino acid mutations are relative to the wild-type PglB having the amino acid sequence of SEQ ID NO: 6.

In another particular embodiment, when the O-antigen is O8, O18A, O25B, or O2 antigen polysaccharide, the PglB oligosaccharyl transferase comprises the amino acid sequence of SEQ ID NO: 6, wherein SEQ ID NO: 6 comprises no amino acid mutations at positions 77, 80, 287, 289, 311, 482, 483, and 669. In certain embodiments thereof, the PglB oligosaccharyl transferase comprises the amino acid sequence of SEQ ID NO: 6.

In some embodiments, bioconjugates of O-antigen polysaccharides produced by recombinant host cells encoding the oligosaccharyl transferase enzymes per the O-antigen/PglB oligosaccharyl transferase pairings indicated above preferably have one or more of the preferred attributes described herein, e.g., glycan/protein ratio and/or percent of multi-glycosylated carrier protein.

Compositions and Combinations

Provided herein are compositions and combinations comprising *E. coli* O75 and O6 antigen polysaccharides, wherein each of the antigen polysaccharides is independently covalently linked to a carrier protein, and optionally further comprising one or more, preferably all, of *E. coli* O1, O2, O4, O15, O16, O18, O25 antigen polysaccharides, wherein each of the antigen polysaccharides is independently covalently linked to a carrier protein. A combination of O-antigen polysaccharides or conjugates, e.g., bioconjugates, can comprise multiple compositions, but it is preferred if a combination of O-antigen polysaccharides or conjugates, e.g., bioconjugates, is present in the same composition.

The compositions and combinations described herein are useful in the treatment and prevention of infection of subjects (e.g., human subjects) with *E. coli*, preferably prevention of invasive ExPEC disease. In some embodiments, a composition is an immunogenic composition. As used herein, an "immunogenic composition" refers to a composition that can elicit an immune response in a host or subject to whom the composition is administered. Compositions and immunogenic compositions can further comprise a pharmaceutically acceptable carrier. As used herein, the term "pharmaceutically acceptable" means approved by a regulatory agency of a Federal or a state government or listed in the U.S. Pharmacopeia or other generally recognized pharmacopeia for use in animals, and more particularly in humans. The term "carrier," as used herein in the context of a pharmaceutically acceptable carrier, refers to a diluent, adjuvant, excipient, or vehicle with which the pharmaceutical composition is administered. Saline solutions and aqueous dextrose and glycerol solutions can also be employed as liquid carriers, particularly for injectable solutions. Suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Examples of suitable pharmaceutical carriers are described in "Remington's Pharmaceutical Sciences" by E. W. Martin.

In one embodiment, a composition of the invention comprises the (bio)conjugates as described herein in a Tris-buffered saline (TBS) pH 7.4 (e.g. containing Tris, NaCl and KCl, e.g. at 25 mM, 137 mM and 2.7 mM, respectively). In other embodiments, the compositions of the invention comprise (bio)conjugates as described herein in about 10 mM $KH_2PO_4/Na_2HPO_4$ buffer at pH of about 7.0, about 5% (w/v) sorbitol, about 10 mM methionine, and about 0.02% (w/v) polysorbate 80. In other embodiments, the compositions of the invention comprise (bio)conjugates as described herein in about 10 mM $KH_2PO_4/Na_2HPO_4$ buffer at pH of about 7.0, about 8% (w/v) sucrose, about 1 mM EDTA, and about 0.02% (w/v) polysorbate 80 (see e.g. WO 2018/077853 for suitable buffers for bioconjugates of *E. coli* O-antigens covalently bound to EPA carrier protein). In other embodiments, the compositions of the invention comprise (bio)conjugates as described herein in about 5 mM succinate/0.9% NaCl, pH 6.0.

Provided herein are compositions (e.g., pharmaceutical and/or immunogenic compositions) that are multivalent compositions, e.g., bivalent, trivalent, tetravalent, etc. compositions. For example, a multivalent composition comprises more than one antigen, such as an *E. coli* O-antigen, glycoconjugate, or bioconjugate thereof. In particular embodiments, multivalent compositions provided herein comprise a bioconjugate of an *E. coli* O75 antigen polysaccharide and a bioconjugate of an *E. coli* O6A antigen polysaccharide. In some embodiments, multivalent compositions provided herein comprise at least one additional antigen or bioconjugate.

Typically the compositions of the invention can be prepared by first obtaining individual glycoconjugates for each of the *E. coli* O-antigen polysaccharides as described herein by independently covalently linking these O-antigen polysaccharides to a carrier protein e.g. by chemical conjugation or bioconjugation, and subsequently mixing the individual glycoconjugates in amounts and ratios as described herein to obtain compositions according to the invention.

In one embodiment, a composition (e.g., pharmaceutical and/or immunogenic composition) is a multivalent composition comprising an *E. coli* O75 antigen polysaccharide covalently linked to a carrier protein as described herein, and at least one additional antigen.

In some embodiments, the additional antigen is antigen saccharide or polysaccharide, more preferably an *E. coli* O-antigen polysaccharide, such as *E. coli* O-antigens of one or more of the O1, O2, O4, O6, O8, O15, O16, O18, and O25 serotypes and subserotypes thereof, preferably each individually conjugated to a carrier protein, wherein the carrier protein for each serotype may be the same or may differ between some or all serotypes. Preferably, a multivalent composition comprising a (bio)conjugate of an *E. coli* O75 polysaccharide further comprises *E. coli* O-antigens of each of the O1, O2, O4, O6, O15, O16, O18, and O25 serotypes or subserotypes thereof. In some embodiments, each of the additional *E. coli* O-antigen polysaccharides is a glycoconjugate, meaning that the *E. coli* O-antigen polysaccharide is covalently linked to another chemical species, e.g., protein, peptide, lipid, etc., most preferably a carrier protein, such as by chemical or enzymatic methods. In preferred embodiments, each of the additional *E. coli* O-antigen polysaccharides is a bioconjugate in which the O-antigen polysaccharide is covalently linked to, e.g. a carrier protein, via a glycosidic bond enzymatically by host cell machinery. In certain embodiments, the multivalent composition further comprises *E. coli* O-antigen of the O8 serotype, preferably in the form of a glycoconjugate, preferably a bioconjugate. Compositions provided herein in certain embodiments can comprise 1-20 additional glycoconjugates, more preferably bioconjugates of *E. coli* O-antigen polysaccharides, such as 1, 2, 3, 4, 5, 6, 7, 8, 9, 10, 11, 12, 13, 14, 15, 16, 17, 18, 19 or 20 additional glycoconjugates or preferably bioconjugates of *E. coli* O-antigen polysaccharides. Other antigens can be included in the compositions provided herein, such as peptide, protein, or lipid antigens, etc.

In some embodiments, a composition (e.g., pharmaceutical and/or immunogenic composition) comprises a (bio) conjugate of an *E. coli* O75 antigen polysaccharide and a (bio)conjugate of an *E. coli* O6 antigen polysaccharide, and at least one additional antigen polysaccharide selected from the group consisting of an *E. coli* O1 antigen polysaccharide, *E. coli* O2 antigen polysaccharide, *E. coli* glucosylated O4 antigen polysaccharide, *E. coli* O8 antigen polysaccharide, *E. coli* O15 antigen polysaccharide, *E. coli* O16 antigen polysaccharide, *E. coli* O18 antigen polysaccharide, and *E. coli* O25 antigen polysaccharide, preferably at least *E. coli* O1 antigen polysaccharide, *E. coli* O2 antigen polysaccharide and *E. coli* O25 antigen polysaccharide, more preferably at least *E. coli* O1 antigen polysaccharide, *E. coli* O2 antigen polysaccharide, *E. coli* O25 antigen polysaccharide, *E. coli* O4 antigen polysaccharide, *E. coli* O15 antigen polysaccharide, *E. coli* O16 antigen polysaccharide and *E. coli* O18 antigen polysaccharide. Preferably the O1 antigen polysaccharide is an O1A antigen polysaccharide, the O6 antigen polysaccharide is an O6A antigen polysaccharide, the O4 antigen polysaccharide is a glucosylated O4 antigen polysaccharide, the O18 antigen polysaccharide is an O18A antigen polysaccharide, and the O25 antigen polysaccharide is an O25B antigen polysaccharide. Preferably, each of the additional O-antigen polysaccharides is covalently linked to a carrier protein, and is more preferably a bioconjugate.

In some embodiments, a composition comprises *E. coli* O75 and at least one of *E. coli* O1, O2, or O6 antigen polysaccharides, preferably at least one of *E. coli* O1 or O6 antigen polysaccharides, wherein each of the antigen polysaccharides is independently covalently linked to a carrier protein, and wherein the ratio of concentrations of O75 antigen polysaccharide to O1, O2, and/or O6 antigen polysaccharide is about 1.2:1 to about 8:1, preferably about 1.5:1 to about 4:1, more preferably about 2:1, e.g. about 1.5:1, 1.6:1, 1.7:1, 1.8:1, 1.9:1, 2.0:1, 2.1:1, 2.2:1, 2.3:1, 2.4:1, or 2.5:1. In preferred embodiments, the composition further comprises *E. coli* O25 antigen polysaccharide, preferably *E. coli* O25B antigen polysaccharide, covalently linked to a carrier protein, and wherein the ratio of concentrations of O25 antigen polysaccharide to O1, O2, and/or O6 antigen polysaccharide is about 1.5:1 to about 4:1, preferably about 2:1. In such embodiments, preferably the ratio of concentrations of O25 antigen polysaccharide to O75 antigen polysaccharide is about 2:1 to about 1:1, preferably about 1.5:1, more preferably about 1:1. In certain embodiments thereof, the ratio of concentrations of O25 antigen polysaccharide to O2 antigen polysaccharide is about 4:1 to about 2:1. In certain embodiments, the composition comprises *E. coli* O75, O1, O2, O6 and O25 antigen polysaccharides, preferably wherein the O1, O6 and O25 antigen polysaccharides respectively are O1A, O6A and O25B polysaccharides, wherein each of the antigen polysaccharides is independently covalently linked to a carrier protein, and wherein the ratio of concentrations of antigen polysaccharides O75:O1:O2:O6:O25 is about 2:1:1:1:2. In certain embodiments, the O-antigens are covalently linked to a carrier protein by bioconjugation, e.g. via N-links to Asn-residues in the carrier protein. In certain embodiments, the concentration of O75 antigen polysaccharide in the composition is about 8-64 μg/mL, preferably about 16-32 μg/mL, preferably about 28-36 μg/mL, e.g. about 32 μg/mL. In certain embodiments, the composition further comprises one or more, preferably all, of *E. coli* O4, O15, O16, O18 antigen polysaccharides, wherein each of the antigen polysaccharides is independently covalently linked to a carrier protein, preferably wherein the O4 is glucosylated, and the O18 antigen is O18A. In certain embodiments, the composition further comprises *E. coli* O8 antigen polysaccharide covalently linked to a carrier protein. In certain embodiments, the ratio of concentrations of antigen polysaccharides O75:O4:O15:O16:O18:O8 in as far as each of these is present in the composition is about 2:1:1:1:1:1. In additional embodiments, the composition can comprise one or more further *E. coli* O antigen polysaccharides, wherein each of the antigen polysaccharides is independently covalently linked to a carrier protein.

In one embodiment, an O1 antigen polysaccharide (e.g., in isolated form or as part of a glycoconjugate or bioconjugate) is used in a composition provided herein (e.g., in combination with an O75 antigen polysaccharide or bioconjugate thereof). In a specific embodiment, the O1 antigen polysaccharide comprises the structure of formula (O1A) as shown in Table 1, wherein n is an integer of 1-100, preferably 3-50, e.g. 5-40, preferably 5-30, e.g. 7 to 25, e.g. 10 to 20. Preferably, the O1 antigen polysaccharide is part of a bioconjugate and is covalently linked to a carrier protein, e.g., EPA or $CRM_{197}$. In certain embodiments the weight ratio between O75:O1 antigen polysaccharides in the composition and/or as administered to a subject is between about 1.2:1 and 8:1, preferably between about 1.5:1 and 4:1, more preferably about 2:1, e.g. about 1.5:1, 1.6:1, 1.7:1, 1.8:1, 1.9:1, 2.0:1, 2.1:1, 2.2:1, 2.3:1, 2.4:1, or 2.5:1.

In one embodiment, an O2 antigen polysaccharide (e.g., in isolated form or as part of a glycoconjugate or bioconjugate) is used in a composition provided herein (e.g., in combination with an O75 antigen polysaccharide or bioconjugate thereof). In a specific embodiment, the O2 antigen polysaccharide comprises the structure of formula (O2) as shown in Table 1, wherein n is an integer of 1-100, preferably 3-50, e.g. 5-40, preferably 5-30, e.g. 7 to 25, e.g. 10 to 20. Preferably, the O2 antigen polysaccharide is part of a bioconjugate and is covalently linked to a carrier protein, e.g., EPA or $CRM_{197}$. In certain embodiments the weight ratio between O75:02 antigen polysaccharides in the composition and/or as administered to a subject is between about 1.2:1 and 8:1, preferably between about 1.5:1 and 4:1, more preferably about 2:1, e.g. about 1.5:1, 1.6:1, 1.7:1, 1.8:1, 1.9:1, 2.0:1, 2.1:1, 2.2:1, 2.3:1, 2.4:1, or 2.5:1.

In one embodiment, an O4 antigen polysaccharide (e.g., in isolated form or as part of a glycoconjugate or bioconjugate) is used in a composition provided herein (e.g., in combination with an O75 antigen polysaccharide or bioconjugate thereof). In a specific embodiment, the O4 antigen polysaccharide is a glucosylated O4 antigen polysaccharide, and in a specific embodiment comprises the structure of formula (O4-Glc+) as shown in Table 1, wherein n is an integer of 1-100, preferably 3-50, e.g. 5-40, preferably 5-30, e.g. 7 to 25, e.g. 10 to 20. Preferably, the O4 antigen polysaccharide is part of a bioconjugate and is covalently linked to a carrier protein, e.g., EPA or $CRM_{197}$. In certain embodiments the weight ratio between O75:04 antigen polysaccharides in the composition and/or as administered to a subject is between about 1.2:1 and 8:1, preferably between about 1.5:1 and 4:1, more preferably about 2:1, e.g. about 1.5:1, 1.6:1, 1.7:1, 1.8:1, 1.9:1, 2.0:1, 2.1:1, 2.2:1, 2.3:1, 2.4:1, or 2.5:1.

In one embodiment, an O6 antigen polysaccharide (e.g., in isolated form or as part of a glycoconjugate or bioconjugate) is used in a composition provided herein (e.g., in combination with an O75 antigen polysaccharide or bioconjugate thereof). In a specific embodiment, the O6 antigen polysaccharide comprises the structure of formula (O6A) as shown in Table 1, wherein n is an integer of 1-100, preferably 3-50, e.g. 5-40, preferably 5-30, e.g. 7 to 25, e.g. 10 to 20. Preferably, the O6 antigen polysaccharide is part of a bioconjugate and is covalently linked to a carrier protein, e.g., EPA or $CRM_{197}$. In certain embodiments the weight ratio between O75:O6 antigen polysaccharides in the composition and/or as administered to a subject is between about 1.2:1 and 8:1, preferably between about 1.5:1 and 4:1, more preferably about 2:1, e.g. about 1.5:1, 1.6:1, 1.7:1, 1.8:1, 1.9:1, 2.0:1, 2.1:1, 2.2:1, 2.3:1, 2.4:1, or 2.5:1.

In one embodiment, an O8 antigen polysaccharide (e.g., in isolated form or as part of a glycoconjugate or bioconjugate) is used in a composition provided herein (e.g., in combination with an O75 antigen polysaccharide or bioconjugate thereof). In a specific embodiment, the O8 antigen polysaccharide comprises the structure of formula (O8) as shown in Table 1, wherein n is an integer of 1-100, preferably 3-50, e.g. 5-40, preferably 5-30, e.g. 7 to 25, e.g. 10 to 20. Preferably, the O8 antigen polysaccharide is part of a bioconjugate and is covalently linked to a carrier protein, e.g., EPA or $CRM_{197}$. In certain embodiments the weight ratio between O75:O8 antigen polysaccharides in the composition and/or as administered to a subject is between about 1.2:1 and 8:1, preferably between about 1.5:1 and 4:1, more preferably about 2:1, e.g. about 1.5:1, 1.6:1, 1.7:1, 1.8:1, 1.9:1, 2.0:1, 2.1:1, 2.2:1, 2.3:1, 2.4:1, or 2.5:1.

In one embodiment, an O15 antigen polysaccharide (e.g., in isolated form or as part of a glycoconjugate or bioconjugate) is used in a composition provided herein (e.g., in combination with an O75 antigen polysaccharide or bioconjugate thereof). In a specific embodiment, the O15 antigen polysaccharide comprises the structure of formula (O15) as shown in Table 1, wherein n is an integer of 1-100, preferably 3-50, e.g. 5-40, preferably 5-30, e.g. 7 to 25, e.g. 10 to 20. Preferably, the O15 antigen polysaccharide is part of a bioconjugate and is covalently linked to a carrier protein, e.g., EPA or $CRM_{197}$. In certain embodiments the weight ratio between O75:O15 antigen polysaccharides in the composition and/or as administered to a subject is between about 1.2:1 and 8:1, preferably between about 1.5:1 and 4:1, more preferably about 2:1, e.g. about 1.5:1, 1.6:1, 1.7:1, 1.8:1, 1.9:1, 2.0:1, 2.1:1, 2.2:1, 2.3:1, 2.4:1, or 2.5:1.

In one embodiment, an O16 antigen polysaccharide (e.g., in isolated form or as part of a glycoconjugate or bioconjugate) is used in a composition provided herein (e.g., in combination with an O75 antigen polysaccharide or bioconjugate thereof). In a specific embodiment, the O16 antigen polysaccharide comprises the structure of formula (O16) as shown in Table 1, wherein n is an integer of 1-100, preferably 3-50, e.g. 5-40, preferably 5-30, e.g. 7 to 25, e.g. 10 to 20. Preferably, the O16 antigen polysaccharide is part of a bioconjugate and is covalently linked to a carrier protein, e.g., EPA or $CRM_{197}$. In certain embodiments the weight ratio between O75:O16 antigen polysaccharides in the composition and/or as administered to a subject is between about 1.2:1 and 8:1, preferably between about 1.5:1 and 4:1, more preferably about 2:1, e.g. about 1.5:1, 1.6:1, 1.7:1, 1.8:1, 1.9:1, 2.0:1, 2.1:1, 2.2:1, 2.3:1, 2.4:1, or 2.5:1.

In one embodiment, an O18 antigen polysaccharide (e.g., in isolated form or as part of a glycoconjugate or bioconjugate) is used in a composition provided herein (e.g., in combination with an O75 antigen polysaccharide or bioconjugate thereof). In a specific embodiment, the O18 antigen polysaccharide comprises the structure of formula (O18A) as shown in Table 1, wherein n is an integer of 1-100, preferably 3-50, e.g. 5-40, preferably 5-30, e.g. 7 to 25, e.g. 10 to 20. Preferably, the O18 antigen polysaccharide is part of a bioconjugate and is covalently linked to a carrier protein, e.g., EPA or $CRM_{197}$. In certain embodiments the weight ratio between O75:O18 antigen polysaccharides in the composition and/or as administered to a subject is between about 1.2:1 and 8:1, preferably between about 1.5:1 and 4:1, more preferably about 2:1, e.g. about 1.5:1, 1.6:1, 1.7:1, 1.8:1, 1.9:1, 2.0:1, 2.1:1, 2.2:1, 2.3:1, 2.4:1, or 2.5:1.

In one embodiment, an O25 antigen polysaccharide (e.g., in isolated form or as part of a glycoconjugate or bioconjugate) is used in a composition provided herein (e.g., in combination with an O75 antigen polysaccharide or bioconjugate thereof). In a specific embodiment, the O25 antigen polysaccharide comprises an O25B antigen polysaccharide, and in a specific embodiment comprises the structure of formula (O25B) as shown in Table 1, wherein n is an integer of 1-100, preferably 3-50, e.g. 5-40, preferably 5-30, e.g. 7 to 25, e.g. 10 to 20. Preferably, the O25 antigen polysaccharide is part of a bioconjugate and is covalently linked to a carrier protein, e.g., EPA or $CRM_{197}$. In certain embodiments the weight ratio between O75:O25 antigen polysaccharides in the composition and/or as administered to a subject is between about 1:4 and 1:0.5, preferably between about 1:2 and 1:1, more preferably about 1:1, e.g. about 1:1.5, 1:1.4, 1:1.3, 1:1.2, 1:1.1, 1:1.0, 1:0.9, 1:0.8, 1:0.7, 1:0.6, or 1:0.5.

In another embodiment, a composition (e.g., a pharmaceutical and/or immunogenic composition) comprises at least the *E. coli* O75, O1, O2, O4, O6 and O25 antigen polysaccharides conjugated to carrier protein, preferably bioconjugates of the O75, O1A, O2, glucosylated O4, O6A and O25B antigen polysaccharides covalently linked to a carrier protein, e.g., EPA or $CRM_{197}$ (i.e., an at least hexavalent composition). In one embodiment the weight ratio between O75:O1:O2:O4:O6:O25 antigen polysaccharides in the composition and/or as administered to a subject is about 2:1:1:1:1:2.

In a preferred embodiment, a composition (e.g., a pharmaceutical and/or immunogenic composition) comprises at least the *E. coli* O1, O2, O4, O6, O15, O16, O18, O25 and O75 antigen polysaccharides conjugated to carrier protein, preferably bioconjugates of the O1A, O2, glucosylated O4, O6A, O15, O16, O18A, O25B and O75 antigen polysaccharides covalently linked to a carrier protein, e.g., EPA or $CRM_{197}$ (i.e., an at least 9-valent composition). In one embodiment the weight ratio between O75:O1:O2:O4:O6:

O15:O16:O18:O25 antigen polysaccharides in the composition and/or as administered to a subject is about 2:1:1:1:1:1:1:1:2.

In another preferred embodiment, a composition (e.g., a pharmaceutical and/or immunogenic composition) comprises at least the *E. coli* O1, O2, O4, O6, O8, O15, O16, O18, O25 and O75 antigen polysaccharides conjugated to carrier protein, preferably bioconjugates of the O1A, O2, glucosylated O4, O6A, O8, O15, O16, O18A, O25B and O75 antigen polysaccharides covalently linked to a carrier protein, e.g., EPA or $CRM_{197}$ (i.e., an at least 10-valent composition). In one embodiment the weight ratio between O75:O1:O2:O4:O6:O8:O15:O16:O18:O25 antigen polysaccharides in the composition and/or as administered to a subject is about 2:1:1:1:1:1:1:1:1:2.

Also contemplated herein are compositions which optionally further comprise additional O-antigens (e.g., in isolated form, or as part of a glycoconjugate or bioconjugate) from other *E. coli* serotypes. In some embodiments, a composition (e.g., a pharmaceutical and/or immunogenic composition) comprises at least the 6-, 9- or 10-valent compositions as described above, and further comprises from 1 to 15 additional *E. coli* antigen polysaccharides, preferably (bio) conjugates of the antigen polysaccharides covalently linked to a carrier protein, e.g., EPA or $CRM_{197}$, such as 1, 2, 3, 4, 5, 6, 7, 8, 9, 10, 11, 12, 13, 14, or 15 additional *E. coli* antigen polysaccharides. In certain embodiments, the 6-, 9- or 10-valent compositions as described above do not comprise additional *E. coli* antigen polysaccharides or conjugates thereof, i.e. such compositions include 6, 9, or 10 but not more *E. coli* antigen polysaccharides, respectively, preferably in the form of conjugates, preferably bioconjugates. It is thus an embodiment to provide a composition that comprises 9 conjugates, in particular *E. coli* O1, O2, O4, O6, O15, O16, O18, O25 and O75 antigen polysaccharides conjugated to carrier protein, preferably bioconjugates of the O1A, O2, glucosylated O4, O6A, O15, O16, O18A, O25B and O75 antigen polysaccharides covalently linked to a carrier protein, e.g., EPA or $CRM_{197}$ (i.e., a 9-valent composition), and no additional conjugates of *E. coli* O-antigen polysaccharides covalently linked to a carrier protein. It is thus another embodiment to provide a composition that comprises 10 conjugates, in particular *E. coli* O1, O2, O4, O6, O8, O15, O16, O18, O25 and O75 antigen polysaccharides conjugated to carrier protein, preferably bioconjugates of the O1A, O2, glucosylated O4, O6A, O8, O15, O16, O18A, O25B and O75 antigen polysaccharides covalently linked to a carrier protein, e.g., EPA or $CRM_{197}$ (i.e., a 10-valent composition), and no additional conjugates of *E. coli* O-antigen polysaccharides covalently linked to a carrier protein.

In some preferred embodiments, each of the additional *E. coli* O1, O2, O4, O6, O15, O16, O18, and/or O25 antigen polysaccharides is covalently linked to a carrier protein. The O-antigen polysaccharide can be linked to a carrier protein by chemical or other synthetic methods, or the O-antigen polysaccharide can be part of a bioconjugate, and is preferably part of a bioconjugate. Preferably the O-antigens per serotype covered by the composition are each separately coupled to a carrier protein, i.e., each glycoconjugate or bioconjugate covering a specific serotype can be produced separately before being mixed in a composition according to the invention. The carrier protein preferably can be the same for each glycoconjugate or bioconjugate in the composition, or alternatively can differ for some or all of the *E. coli* O-antigens, e.g. O-antigens of different serotypes can also be conjugated to different carrier proteins. Any carrier protein known to those skilled in the art in view of the present disclosure can be used. Suitable carrier proteins include, but are not limited to, detoxified Exotoxin A of *P. aeruginosa* (EPA), *E. coli* flagellin (FliC), $CRM_{197}$, maltose binding protein (MBP), Diphtheria toxoid, Tetanus toxoid, detoxified hemolysin A of *S. aureus*, clumping factor A, clumping factor B, *E. coli* heat labile enterotoxin, detoxified variants of *E. coli* heat labile enterotoxin, Cholera toxin B subunit (CTB), cholera toxin, detoxified variants of cholera toxin, *E. coli* Sat protein, the passenger domain of *E. coli* Sat protein, *Streptococcus pneumoniae* Pneumolysin, Keyhole limpet hemocyanin (KLH), *P. aeruginosa* PcrV, outer membrane protein of *Neisseria meningitidis* (OMPC), and protein D from non-typeable *Haemophilus influenzae*. Preferably, the carrier protein is EPA or $CRM_{197}$.

In some embodiments, each of the additional *E. coli* O1(A), O2, (glucosylated) O4, O6(A), O15, O16, O18(A), and/or O25(B) antigen polysaccharides, particularly when part of a bioconjugate, is covalently linked to an asparagine (Asn) residue in the carrier protein, wherein the Asn residue is present in a glycosylation site comprising a glycosylation consensus sequence Asn-X-Ser(Thr), wherein X can be any amino acid except Pro (SEQ ID NO: 1), preferably wherein the Asn residue is present in a glycosylation site comprising a glycosylation consensus sequence Asp(Glu)-X-Asn-Z-Ser (Thr), wherein X and Z are independently selected from any amino acid except Pro (SEQ ID NO: 2). The carrier protein can comprise 1-10 glycosylation sites, preferably 2 to 4 glycosylation sites, most preferably 4 glycosylation sites, each comprising a glycosylation consensus sequence. In a particular embodiment, the carrier protein is EPA-4 carrier protein, for instance EPA-4 carrier protein comprising the amino acid sequence of SEQ ID NO: 3.

In a particular embodiment, provided herein is a composition (e.g., pharmaceutical and/or immunogenic composition) comprising: (i) a bioconjugate of an *E. coli* O75 antigen polysaccharide covalently linked to a detoxified Exotoxin A of *P. aeruginosa* carrier protein comprising SEQ ID NO: 3 (EPA-4 carrier protein), wherein the *E. coli* O75 antigen polysaccharide comprises the structure of Formula (O75); (ii) a bioconjugate of an *E. coli* O1A antigen polysaccharide covalently linked to an EPA-4 carrier protein, wherein the *E. coli* O1A antigen polysaccharide comprises the structure of Formula (O1A); (iii) a bioconjugate of an *E. coli* O2 antigen polysaccharide covalently linked to an EPA-4 carrier protein, wherein the *E. coli* O2 antigen polysaccharide comprises the structure of Formula (O2); (iv) a bioconjugate of an *E. coli* O6A antigen polysaccharide covalently linked to an EPA-4 carrier protein, wherein the *E. coli* O6A antigen polysaccharide comprises the structure of Formula (O6A); (v) a bioconjugate of an *E. coli* O15 antigen polysaccharide covalently linked to an EPA-4 carrier protein, wherein the *E. coli* O15 antigen polysaccharide comprises the structure of Formula (O15); (vi) a bioconjugate of an *E. coli* O16 antigen polysaccharide covalently linked to an EPA-4 carrier protein, wherein the *E. coli* O16 antigen polysaccharide comprises the structure of Formula (O16); (vii) a bioconjugate of an *E. coli* O18A antigen polysaccharide covalently linked to an EPA-4 carrier protein, wherein the *E. coli* O18A antigen polysaccharide comprises the structure of Formula (O18A); (viii) a bioconjugate of an *E. coli* O25B antigen polysaccharide covalently linked to an EPA-4 carrier protein, wherein the *E. coli* O25B antigen polysaccharide comprises the structure of Formula (O25B); and (ix) a bioconjugate of an *E. coli* glucosylated O4 antigen polysaccharide covalently linked to an EPA-4 carrier protein, wherein the *E. coli* glucosylated O4 antigen polysaccharide comprises the structure of Formula (O4-Glc+), wherein each of the Formulas is provided in Table 1, and for each of the Formulas independently n is an integer of 1 to 100, e.g. 1 to 50, preferably 3 to 50, e.g. 5 to 40, preferably 5-30, e.g. 7 to 25, e.g. 10 to 20.

In a particular embodiment, said composition (e.g. pharmaceutical and/or immunogenic composition) further comprises: (x) a bioconjugate of an *E. coli* O8 antigen polysaccharide covalently linked to an EPA-4 carrier protein, wherein the *E. coli* O8 antigen polysaccharide comprises the structure of Formula (O8) as shown in Table 1, wherein n for this structure is an integer of 1 to 100, e.g. 1 to 50, preferably 3 to 50, e.g. 5 to 40, preferably 5-30, e.g. 7 to 25, e.g. 10 to 20.

In some embodiments, a composition provided herein comprises a conjugate of an *E. coli* O75 antigen polysaccharide, and at least a conjugate of an *E. coli* O6 antigen polysaccharide, preferably O6A antigen polysaccharide, wherein the conjugate of the *E. coli* O75 antigen polysaccharide is present in the composition at a concentration that is about 1.2 to 8 times, e.g. about 2 to 4 times higher, such as 1.3, 1.4, 1.5, 1.6, 1.7, 1.8, 1.9, 2.0, 2.1, 2.2, 2.3, 2.4, 2.5, 3, 4, 5, 6, 7, or 8 times higher than the concentration of the O6 antigen polysaccharide present in the composition (all concentrations based on weight of the O-antigen polysaccharides). Preferably the *E. coli* O75 antigen polysaccharide in the composition is present at a concentration that is about 1.5 to 2.5 times, such as 1.5, 1.6, 1.7, 1.8, 1.9, 2.0, 2.1, 2.2, 2.3, 2.4, or 2.5 times, the concentration of the O6 antigen polysaccharide in the composition.

In particular embodiments, a composition comprises bioconjugates of *E. coli* O1A, O2, glucosylated O4, O6A, O15, O16, O18, O25B, and O75 antigen polysaccharides, wherein the bioconjugates of O1A:O2:glucosylated O4:O6A:O15:O16:O18:O25B:O75 are present in a ratio (by weight of O-antigen polysaccharide) of 1:1:1:1:1:1:1:2:2, 1:1:1:1:1:1:1:2:1.5, 2:1:1:2:1:1:1:4:3, 2:1:1:2:1:1:1:4:4, 2:1:2:2:2:2:2:4:4, preferably about 1:1:1:1:1:1:1:2:2.

In particular embodiments, a composition comprises bioconjugates of *E. coli* O1A, O2, glucosylated O4, O6A, O8, O15, O16, O18A, O25B, and O75 antigen polysaccharides, wherein the bioconjugates of O1A:O2:glucosylated O4:O6A:O8:O15:O16:O18A:O25B:O75 are present in a ratio (by weight of O-antigen polysaccharide) of 1:1:1:1:1:1:1:1:2:2, 2:1:2:2:2:2:2:2:4:4, 2:1:1:2:1:1:1:1:4:3, or 2:1:1:2:1:1:1:1:4:4, preferably about 1:1:1:1:1:1:1:1:2:2.

In some embodiments, a composition provided herein comprises a bioconjugate of an *E. coli* O75 antigen polysaccharide, and at least a bioconjugate of an *E. coli* O6 antigen polysaccharide, wherein the bioconjugate of the *E. coli* O75 antigen polysaccharide is present in the composition at a concentration of about 8 to about 50 μg/mL, preferably about 12 to about 40 μg/mL, more preferably about 16 to about 32 μg/mL, such as 16, 18, 20, 22, 24, 26, 28, 30, or 32 μg/mL, preferably about 32 μg/mL. The concentration of the bioconjugate of the *E. coli* O75 antigen polysaccharide is preferably about 1.2 to about 8 times, e.g., about 2 to 4 times higher, such as 1.5, 2, 3, 4, 5, 6, 7, or 8 times higher than the concentration of the O6 bioconjugate present in the composition.

In one particular embodiment, a pharmaceutical composition is provided, which composition comprises:

(i) a bioconjugate of an *E. coli* O1A antigen polysaccharide covalently linked to an EPA-4 carrier protein, at a polysaccharide concentration of about 12 to 20, preferably about 16 μg/mL;

(ii) a bioconjugate of an *E. coli* O2 antigen polysaccharide covalently linked to an EPA-4 carrier protein, at a polysaccharide concentration of about 12 to 20, preferably about 16 μg/mL;

(iii) a bioconjugate of an *E. coli* O4 antigen polysaccharide covalently linked to an EPA-4 carrier protein, at a polysaccharide concentration of about 12 to 20, preferably about 16 μg/mL;

(iv) a bioconjugate of an *E. coli* O6A antigen polysaccharide covalently linked to an EPA-4 carrier protein, at a polysaccharide concentration of about 12 to 20, preferably about 16 μg/mL;

(v) a bioconjugate of an *E. coli* O15 antigen polysaccharide covalently linked to an EPA-4 carrier protein, at a polysaccharide concentration of about 12 to 20, preferably about 16 μg/mL;

(vi) a bioconjugate of an *E. coli* O16 antigen polysaccharide covalently linked to an EPA-4 carrier protein, at a polysaccharide concentration of about 12 to 20, preferably about 16 μg/mL;

(vii) a bioconjugate of an *E. coli* O18A antigen polysaccharide covalently linked to an EPA-4 carrier protein, at a polysaccharide concentration of about 12 to 20, preferably about 16 μg/mL;

(viii) a bioconjugate of an *E. coli* O25B antigen polysaccharide covalently linked to an EPA-4 carrier protein, at a polysaccharide concentration of about 28 to 36, preferably about 32 μg/mL; and (ix) a bioconjugate of an *E. coli* O75 antigen polysaccharide covalently linked to an EPA-4 carrier protein, at a polysaccharide concentration of about 28 to 36, preferably about 32 μg/mL; wherein the EPA-4 carrier protein comprises the amino acid sequence of SEQ ID NO: 3, and wherein the O1A, O2, O4, O6A, O15, O16, O18A, O25B, and O75 antigen polysaccharides comprise the structures of Formulas (O1A), (O2), (O4-Glc+), (O6A), (O15), (O16), (O18A), (O25B), and (O75), respectively, as shown in Table 1, wherein each n is independently an integer of 1 to 100, preferably of 3 to 50, for example 5 to 40, more preferably of 5 to 30, for example 7 to 25, for example 10 to 20.

In certain embodiments, such a composition further comprises:

(x) a bioconjugate of an *E. coli* O75 antigen polysaccharide covalently linked to an EPA-4 carrier protein, at a polysaccharide concentration of about 12 to 20, preferably about 16 μg/mL; wherein the O8 antigen polysaccharide comprises the structure of Formula (O8) as shown in Table 1, wherein n is an integer of 1 to 100, preferably of 3 to 50, for example 5 to 40, more preferably of 5 to 30, for example 7 to 25, for example 10 to 20.

In one embodiment, there is provided a composition comprising a bioconjugate of *E. coli* O75 antigen polysaccharide covalently linked to a carrier protein, wherein the O75 antigen polysaccharide is at a concentration of at least about 32 μg/mL.

In one embodiment, there is provided a composition comprising:

(i) a bioconjugate of an *E. coli* O1A antigen polysaccharide covalently linked to a carrier protein, wherein the *E. coli* O1A antigen polysaccharide comprises the structure of Formula (O1A);

(ii) a bioconjugate of an *E. coli* O2 antigen polysaccharide covalently linked to a carrier protein, wherein the *E. coli* O2 antigen polysaccharide comprises the structure of Formula (O2);

(iii) a bioconjugate of an *E. coli* glucosylated O4 antigen polysaccharide covalently linked to a carrier protein, wherein the *E. coli* glucosylated O4 antigen polysaccharide comprises the structure of Formula (O4-Glc+);

(iv) a bioconjugate of an *E. coli* O6A antigen polysaccharide covalently linked to a carrier protein, wherein the *E. coli* O6A antigen polysaccharide comprises the structure of Formula (O6A);

(v) a bioconjugate of an *E. coli* O15 antigen polysaccharide covalently linked to a carrier protein, wherein the *E. coli* O15 antigen polysaccharide comprises the structure of Formula (O15);

(vi) a bioconjugate of an *E. coli* O16 antigen polysaccharide covalently linked to a carrier protein, wherein the *E. coli* O16 antigen polysaccharide comprises the structure of Formula (O16);

(vii) a bioconjugate of an *E. coli* O18A antigen polysaccharide covalently linked to a carrier protein, wherein the *E. coli* O18A antigen polysaccharide comprises the structure of Formula (O18A);

(viii) a bioconjugate of an *E. coli* O25B antigen polysaccharide covalently linked to a carrier protein, wherein the *E. coli* O25B antigen polysaccharide comprises the structure of Formula (O25B); and (ix) a bioconjugate of an *E. coli* O75 antigen polysaccharide covalently linked to a carrier protein, wherein the *E. coli* O75 antigen polysaccharide comprises the structure of Formula (O75);

wherein each of the structures of Formulas (O1A), (O2), (O4-Glc+), (O6A), (O15), (O16), (O18A), (O25B), and (O75) is shown in Table 1, wherein each n is independently an integer of 1 to 100, preferably of 3 to 50, for example 5 to 40, more preferably of 5 to 30, for example 7 to 25, for example 10 to 20, wherein the *E. coli* antigen polysaccharides present in the composition consist of O1A, O2, O4-Glc+, O6A, O15, O16, O18A, O25B, and O75. Preferably, the carrier protein is detoxified Exotoxin A of *P. aeruginosa* (EPA-4), more preferably the EPA-4 comprises the amino acid sequence of SEQ ID NO: 3. Preferably, the ratio of concentrations of O75 antigen polysaccharide to O1A, O2, and/or O6A antigen polysaccharide is about 1.2:1 to about 8:1, preferably about 1.5:1 to about 4:1, more preferably about 2:1. Preferably the *E. coli* antigen polysaccharides present in the composition consist of O1A, O2, O4-Glc+, O6A, O15, O16, O18A, O25B, and O75 at a ratio of 1:1:1:1:1:1:1:2:2.

In one general aspect, provided herein is a composition comprising *E. coli* O75 and O6 antigen polysaccharides, wherein each of the antigen polysaccharides is independently covalently linked to a carrier protein, and wherein the ratio of concentrations of O75 antigen polysaccharide to O6 antigen polysaccharide is about 1.2:1 to about 8:1, preferably about 1.5:1 to about 4:1, preferably about 1.5:1 to about 2.5:1, more preferably about 2:1.

In certain embodiments, the composition further comprises one or more, preferably all, of *E. coli O*1, O2, O4, O15, O16, O18, O25 antigen polysaccharides, wherein each of the antigen polysaccharides is independently covalently linked to a carrier protein, preferably wherein the O1 antigen is O1A, the O4 is glucosylated, the O6 antigen is O6A, the O18 antigen is O18A, and the O25 antigen is O25B.

In certain embodiments, the *E. coli* O1 antigen polysaccharide comprises the structure of Formula (O1A) shown in Table 1, the *E. coli* O2 antigen polysaccharide comprises the structure of Formula (O2) shown in Table 1, the *E. coli* O4 antigen polysaccharide comprises the structure of Formula (O4-Glc+) shown in Table 1, the *E. coli* O6 antigen polysaccharide comprises the structure of Formula (O6A) shown in Table 1, the *E. coli* O15 antigen polysaccharide comprises the structure of Formula (O15) shown in Table 1, the *E. coli* O16 antigen polysaccharide comprises the structure of Formula (O16) shown in Table 1, the *E. coli* O18 antigen polysaccharide comprises the structure of Formula (O18A) shown in Table 1, the *E. coli* O25 antigen polysaccharide comprises the structure of Formula (O25B) shown in Table 1, and the *E. coli* O75 antigen polysaccharide comprises the structure of Formula (O75) shown in Table 1, wherein each n is independently an integer of 1 to 100, preferably of 3 to 50, for example 5 to 40, preferably of 5 to 30, for example 7 to 25, for example 10 to 20.

In certain embodiments, the weight ratio of the *E. coli* antigen polysaccharides of O1:O2:O4:O6:O15:O16:O18:O25:O75 is 1:1:1:1:1:1:1:2:2.

In certain embodiments, the concentration of the O75 antigen polysaccharide is from about 8 to about 50 μg/mL, preferably 12 to 40 μg/mL, e.g. 16-32 μg/mL, preferably about 32 μg/mL.

In certain embodiments, the composition further comprises at least one additional *E. coli* antigen polysaccharide covalently linked to a carrier protein.

In a particular embodiment, the at least one additional *E. coli* antigen polysaccharide comprises O8 antigen polysaccharide with Formula (O8) shown in Table 1, wherein n is an integer of 1 to 100, preferably of 3 to 50, for example 5 to 40, preferably of 5 to 30, for example 7 to 25, for example 10 to 20.

In certain embodiments, each carrier protein is independently selected from the group consisting of detoxified Exotoxin A of *P. aeruginosa* (EPA), *E. coli* flagellin (FliC), $CRM_{197}$, maltose binding protein (MBP), Diphtheria toxoid, Tetanus toxoid, detoxified hemolysin A of *S. aureus*, clumping factor A, clumping factor B, *E. coli* heat labile enterotoxin, detoxified variants of *E. coli* heat labile enterotoxin, Cholera toxin B subunit (CTB), cholera toxin, detoxified variants of cholera toxin, *E. coli* Sat protein, the passenger domain of *E. coli* Sat protein, *Streptococcus pneumoniae* Pneumolysin, Keyhole limpet hemocyanin (KLH), *P. aeruginosa* PcrV, outer membrane protein of *Neisseria meningitidis* (OMPC), and protein D from non-typeable *Haemophilus influenzae.*

In a particular embodiment, the carrier protein is detoxified exotoxin A of *Pseudomonas aeruginosa* (EPA) or $CRM_{197}$.

In certain embodiments, the carrier protein comprises 1 to 20, such as 1 to 10, or 2 to 4, glycosylation consensus sequences having the amino acid sequence of SEQ ID NO: 1, preferably the consensus sequences having the amino acid sequence of SEQ ID NO: 2, most preferably the carrier protein comprises four of the glycosylation consensus sequences.

In a particular embodiment, each carrier protein is EPA comprising the amino acid sequence of SEQ ID NO: 3.

In certain embodiments, the *E. coli* antigen polysaccharides are covalently linked to the carrier protein by bioconjugation or by chemical conjugation. Chemical conjugation can, for example, include reductive amination chemistry (RAC), single-end conjugation, conjugation with a (2-((2-oxoethyl)thio)ethyl) carbamate (eTEC) spacer, cyanylation chemistry (CNBr, CDAP) with or without ADH spacer, thioether chemistry (maleimide/bromoacetyl linker based), or EDC-N-Hydroxy succinimide zero linker chemistry.

In certain embodiments, the *E. coli* antigen polysaccharides are covalently linked to the carrier protein by bioconjugation, preferably the polysaccharide is covalently linked to an Asn residue in a glycosylation site in the carrier protein.

In another aspect, provided herein is a composition comprising a bioconjugate of an *E. coli* O1A antigen polysaccharide covalently linked to a detoxified Exotoxin A of *P. aeruginosa* (EPA-4) carrier protein, wherein the *E. coli* O1A antigen polysaccharide comprises the structure of Formula (O1A);

a bioconjugate of an *E. coli* O2 antigen polysaccharide covalently linked to an EPA-4 carrier protein, wherein the *E. coli* O2 antigen polysaccharide comprises the structure of Formula (O2);

a bioconjugate of an *E. coli* glucosylated O4 antigen polysaccharide covalently linked to an EPA-4 carrier protein, wherein the *E. coli* glucosylated O4 antigen polysaccharide comprises the structure of Formula (O4-Glc+);

a bioconjugate of an *E. coli* O6A antigen polysaccharide covalently linked to an EPA-4 carrier protein, wherein the *E. coli* O6A antigen polysaccharide comprises the structure of Formula (O6A);

a bioconjugate of an *E. coli* O15 antigen polysaccharide covalently linked to an EPA-4 carrier protein, wherein the *E. coli* O15 antigen polysaccharide comprises the structure of Formula (O15);

a bioconjugate of an *E. coli* O16 antigen polysaccharide covalently linked to an EPA-4 carrier protein, wherein the *E. coli* O16 antigen polysaccharide comprises the structure of Formula (O16);

a bioconjugate of an *E. coli* O18A antigen polysaccharide covalently linked to an EPA-4 carrier protein, wherein the *E. coli* O18A antigen polysaccharide comprises the structure of Formula (O18A);

a bioconjugate of an *E. coli* O25B antigen polysaccharide covalently linked to an EPA-4 carrier protein, wherein the *E. coli* O25B antigen polysaccharide comprises the structure of Formula (O25B); and a bioconjugate of an *E. coli* O75 antigen polysaccharide covalently linked to an EPA-4 carrier protein, wherein the *E. coli* O75 antigen polysaccharide comprises the structure of Formula (O75);

wherein the EPA-4 comprises the amino acid sequence of SEQ ID NO: 3, wherein each of the structures of Formulas (O1A), (O2), (O4-Glc+), (O6A), (O15), (O16), (O18A), (O25B), and (O75) is shown in Table 1, wherein each n is independently an integer of 1 to 100, preferably of 3 to 50, for example 5 to 40, more preferably of 5 to 30, for example 7 to 25, for example 10 to 20, and wherein the ratio of O75 antigen polysaccharide to O6A antigen polysaccharide is about 1.2:1 to about 8:1, preferably about 1.5:1 to about 4:1, more preferably about 2:1.

In certain embodiments, the composition further comprises from 1 to 15 additional *E. coli* antigen polysaccharides each independently covalently linked to a carrier protein.

In certain embodiments, the composition comprises a bioconjugate of an *E. coli* glucosylated O4 antigen polysaccharide covalently linked to a carrier protein, wherein the *E. coli* glucosylated O4 antigen polysaccharide comprises the structure of Formula (O4-Glc+) shown in Table 1, wherein n is an integer of 3 to 50, for example 5 to 40, preferably of 5 to 30, for example 7 to 25, for example 10 to 20, wherein the bioconjugate of an *E. coli* glucosylated O4 antigen polysaccharide covalently linked to a carrier protein has been produced in an *E. coli* cell that comprises:

(i) a nucleotide sequence of an rfb gene cluster for the *E. coli* O4 antigen polysaccharide;

(ii) a nucleotide sequence encoding a glucosyl transferase having at least 80%, preferably at least 90%, preferably at least 95% sequence identity to SEQ ID NO: 4, wherein the glucosyl transferase is capable of modifying the *E. coli* O4 antigen polysaccharide to produce the *E. coli* glucosylated O4 antigen polysaccharide;

(iii) nucleotide sequences encoding a translocase and a glycosyltransferase having at least 80%, preferably at least 90%, preferably at least 95% sequence identity to SEQ ID NOs: 7 and 8 respectively, wherein the translocase is capable of translocating bactoprenol-linked glucose and the glycosyltransferase is capable of glucosylating bactoprenol;

(iv) a nucleotide sequence encoding the carrier protein; and (v) a nucleotide sequence encoding an oligosaccharyl transferase capable of covalently linking the *E. coli* glucosylated O4 antigen polysaccharide to the carrier protein, preferably wherein the oligosaccharyl transferase is PglB from *Campylobacter jejuni*.

In certain embodiments, the compositions described herein additionally comprise a preservative, such as the mercury derivative thimerosal. In a specific embodiment, the pharmaceutical compositions described herein comprise 0.001% to 0.01% thimerosal. In other embodiments, the pharmaceutical compositions described herein do not comprise a preservative.

In certain embodiments, the compositions described herein (e.g., the immunogenic compositions) comprise, or are administered in combination with, an adjuvant. The adjuvant for administration in combination with a composition described herein may be administered before (e.g. within 72 hours, 48 hours, 24 hours, 12 hours, 6 hours, 2 hours, 1 hour, 10 minutes), concomitantly with, or after (e.g. within 72 hours, 48 hours, 24 hours, 12 hours, 6 hours, 2 hours, 1 hour, 10 minutes) administration of said composition. In some embodiments, the term "adjuvant" refers to a compound that when administered in conjunction with or as part of a composition described herein augments, enhances and/or boosts the immune response to a bioconjugate, but when the adjuvant compound is administered alone does not generate an immune response to the bioconjugate. In some embodiments, the adjuvant generates an immune response to the bioconjugate peptide and does not produce an allergy or other adverse reaction. Adjuvants can enhance an immune response by several mechanisms including, e.g., lymphocyte recruitment, stimulation of B and/or T cells, and stimulation of macrophages. In certain preferred embodiments, the compositions described herein do not comprise an adjuvant besides the bioconjugates, and/or are not administered in combination with an adjuvant besides the bioconjugates (in case the bioconjugates would comprise some intrinsic adjuvant properties, these would be disregarded and no extrinsic adjuvant would be added in these embodiments).

Examples of suitable adjuvants include, but are not limited to, aluminum salts (alum) (such as aluminum hydroxide, aluminum phosphate, aluminum sulfate and aluminum oxide, including nanoparticles comprising alum or nanoalum formulations), calcium phosphate, monophosphoryl lipid A (MPL) or 3-de-O-acylated monophosphoryl lipid A (3D-MPL) (see e.g., GB2220211, EP0971739, EP1194166, U.S. Pat. No. 6,491,919), AS01, AS02, AS03 and AS04 (all GlaxoSmithKline; see e.g. EP1126876, U.S. Pat. No. 7,357,936 for AS04, EP0671948, EP0761231, U.S. Pat. No. 5,750,110 for AS02), MF59 (Novartis), imidazopyridine compounds (see WO2007/109812), imidazoquinoxaline compounds (see WO2007/109813), delta-inulin, STING-activating synthetic cyclic-di-nucleotides (e.g. US20150056224), combinations of lecithin and carbomer homopolymers (e.g. U.S. Pat. No. 6,676,958), and saponins, such as QuilA and QS21 (see e.g. Zhu D and W Tuo, 2016, Nat Prod Chem Res 3: e113, Matrix M, Iscoms, Iscomatrix, etc, optionally in combination with QS7 (see Kensil et al., in Vaccine Design: The Subunit and Adjuvant Approach (eds. Powell & Newman, Plenum Press, N Y, 1995); U.S. Pat. No. 5,057,540). In some embodiments, the adjuvant is Freund's adjuvant (complete or incomplete). Other adjuvants are oil in water emulsions (such as squalene or peanut oil), optionally in combination with immune stimulants, such as monophosphoryl lipid A (see Stoute et al., N. Engl. J. Med. 336, 86-91 (1997)). Another adjuvant is CpG. Further examples of adjuvants are liposomes containing immune stimulants such as MPL and QS21 such as in AS01E and AS01B (e.g. US 2011/0206758). Other examples of adjuvants are imidazoquinolines (such as imiquimod and R848). See, e.g., Reed G, et al., 2013, *Nature Med*, 19: 1597-1608. In certain embodiments, the adjuvant contains a toll-like receptor 4 (TLR4) agonist. TLR4 agonists are well known in the art, see e.g. Ireton GC and SG Reed, 2013, Expert Rev Vaccines 12: 793-807. In certain embodiments, the adjuvant comprises a TLR4 agonist comprising lipid A, or an analog or derivative thereof, such as MPL, 3D-MPL, RC529 (e.g. EP1385541), PET-lipid A, GLA (glycopyranosyl lipid adjuvant, a synthetic disaccharide glycolipid; e.g. US20100310602, U.S. Pat. No. 8,722,064), SLA (e.g. Carter D et al, 2016, Clin Transl Immunology 5: e108 (doi: 10.1038/cti.2016.63), which describes a structure-function approach to optimize TLR4 ligands for human vaccines), PHAD (phosphorylated hexaacyl disaccharide), 3D-PHAD (the structure of which is the same as that of GLA), 3D-(6-acyl)-PHAD (3D(6A)-PHAD) (PHAD, 3D-PHAD, and 3D(6A)PHAD are synthetic lipid A variants, see e.g. avantilipids.com/divisions/adjuvants, which also provide structures of these molecules), E6020 (CAS Number 287180-63-6), ON04007, OM-174, and the like.

In certain embodiments, the compositions described herein do not comprise, and are not administered in combination with, an adjuvant.

In certain embodiments, the compositions described herein are formulated to be suitable for the intended route of administration to a subject. For example, the compositions described herein may be formulated to be suitable for subcutaneous, parenteral, oral, intradermal, transdermal, colorectal, intraperitoneal, and rectal administration. In a specific embodiment, the pharmaceutical composition may be formulated for intravenous, oral, intraperitoneal, intranasal, intratracheal, subcutaneous, intramuscular, topical, intradermal, transdermal or pulmonary administration. In certain embodiments, the compositions described herein are administered by intramuscular injection.

In certain embodiments, the compositions described herein additionally comprise one or more buffers, e.g., Tris-buffered saline, phosphate buffer, or sucrose phosphate glutamate buffer.

In certain embodiments, the compositions described herein additionally comprise one or more salts, e.g., Tris-hydrochloride, sodium chloride, calcium chloride, potassium chloride, sodium phosphate, monosodium glutamate, or aluminum salts (e.g., aluminum hydroxide, aluminum phosphate, alum (potassium aluminum sulfate), or a mixture of such aluminum salts).

The compositions described herein can be included in a container, pack, or dispenser together with instructions for administration.

The compositions described herein can be stored before use, e.g., the compositions can be stored frozen (e.g., at about −20° C. or at about −70° C.); stored in refrigerated conditions (e.g., at about 4° C.); or stored at room temperature.

In one aspect the invention also provides methods to prepare compositions according to the invention, comprising providing each of the required O-antigen conjugates (e.g., by obtaining or manufacturing these, e.g., in the form of drug substances), and mixing them in the desired ratios and/or amounts to obtain a composition of the invention (e.g., a multivalent *E. coli*, particularly ExPEC, vaccine composition, sometimes referred to as drug product).

Methods of Inducing an Immunological Response

Bioconjugates and compositions provided herein can be used to induce antibodies against an *E. coli* O-antigen in a subject, or to vaccinate a subject against *E. coli*. The methods of inducing an immune response in a subject described herein result in vaccination of the subject against infection by the ExPEC strains whose O-antigens are present in the composition(s). When an O-antigen subtype is used, a method of the invention can also induce immune response to another O-antigen subtype having similar antigenicity. Examples are cross-reactivity between subserotypes, e.g. immunization with O25B antigen induces antibodies that recognize O-LPS of both O25B and O25A serotypes, and immunization with glucosylated O4 induces antibodies that recognize O-LPS of both glucosylated O4 and non-glucosylated O4 serotypes, and in other examples there can also be cross-immunization towards other serotypes that have different O-antigens but still share some similarity in the antigenic structures (e.g., some sera appear to cross-react in serotyping studies).

In some embodiments, the subject is human. In some embodiments, the subject is a human having or at risk of having an ExPEC infection or an invasive ExPEC disease.

In some embodiments, the invasive ExPEC disease comprises sepsis. In some embodiments, the invasive ExPEC disease comprises bacteremia. In some embodiments, the invasive ExPEC disease comprises one or more of urinary tract infection, a surgical-site infection, an abdominal or pelvic infection, pneumonia, osteomyelitis, cellulitis, sepsis, bacteremia, a wound infection, pyelonephritis, meningitis, peritonitis, cholangitis, soft-tissue infections, pyomyositis, septic arthritis, endophthalmitis, suppurative thyroiditis, sinusitis, endocarditis, and prostatitis.

In certain embodiments, the immune response induced in a subject following administration of a composition described herein limits the severity of or prevents an invasive ExPEC disease in the subject. In one embodiment, the subject has an *E. coli* (e.g., ExPEC) infection at the time of administration. In a preferred embodiment, the subject does not have an *E. coli* (e.g., ExPEC) infection at the time of administration.

In certain embodiments, the immune response induced in a subject following administration of a composition described herein is effective to prevent or reduce a symptom resulting from an ExPEC infection, preferably in at least 30%, more preferably at least 40%, such as at least 50%, of the subjects administered with the composition. Symptoms of ExPEC infection may vary depending on the nature of the infection and may include, but are not limited to: dysuria, increased urinary frequency or urgency, pyuria, hematuria, back pain, pelvic pain, pain while urinating, fever, chills, and/or nausea (e.g., in subjects having a urinary tract infection caused by ExPEC); high fever, headache, stiff neck, nausea, vomiting, seizures, sleepiness, and/or light sensitivity (e.g., in subjects having meningitis caused by ExPEC); fever, increased heart rate, increased respiratory rate, decreased urine output, decreased platelet count, abdominal pain, difficulty breathing, and/or abnormal heart function (e.g., in subjects having sepsis caused by ExPEC).

In certain embodiments, the immune response induced in a subject following administration of a composition described herein is effective to reduce the likelihood of hospitalization of a subject suffering from an ExPEC infection. In some embodiments, the immune response induced in a subject following administration of a composition described herein is effective to reduce the duration of hospitalization of a subject suffering from an ExPEC infection.

In certain embodiments, vaccination with a composition of the invention is for preventing an invasive ExPEC disease (IED), e.g., urosepsis, bacteremia, sepsis, etc. In certain embodiments, vaccination is to prevent or reduce the occurrence or severity of urinary tract infections. In certain embodiments, an IED can be hospital-acquired, e.g. in patients undergoing urogenital and/or abdominal procedures or surgeries. In certain embodiments, an IED can be healthcare-associated, e.g. in patients receiving health care for another condition, for instance via central lines, catheters, etc, e.g. in a hospital, ambulatory surgical center, end-stage renal disease facility, long-term care facility, etc. In certain embodiments, the IED can be community-acquired, e.g. in a patient that was not recently exposed to healthcare risks.

In some embodiments, a method of inducing an immune response to extra-intestinal pathogenic *E. coli* (ExPEC) in a subject comprises administering to the subject a composition described herein.

In some embodiments, a method of inducing an immune response to extra-intestinal pathogenic *E. coli* (ExPEC) in a subject comprises administering to the subject a first effective amount of *E. coli* O75 antigen polysaccharide, and a second effective amount of *E. coli* O6 antigen polysaccharide, wherein each of the antigen polysaccharides is independently covalently linked to a carrier protein, and wherein the ratio of the first effective amount to the second effective amount is about 1.2:1 to about 8:1, preferably about 1.5:1 to about 4:1, e.g. about 1.5:1, 1.6:1, 1.7:1, 1.8:1, 1.9:1, 2.0:1, 2.1:1, 2.2:1, 2.3:1, 2.4:1, 2.5:1, more preferably about 2:1. In some preferred embodiments, the O75 antigen polysaccharide covalently linked to a carrier protein and the O6 antigen polysaccharide covalently linked to a carrier protein are administered as one composition. In some alternative embodiments, the O75 antigen polysaccharide covalently linked to a carrier protein and the O6 antigen polysaccharide covalently linked to a carrier protein are administered as a combination of separate compositions.

In some embodiments, a method of inducing an immune response to extra-intestinal pathogenic *E. coli* (ExPEC) in a subject further comprises administering to the subject one or more, preferably all, of *E. coli O*1, O2, O4, O15, O16, O18, O25 antigen polysaccharides, wherein each of the antigen polysaccharides is independently covalently linked to a carrier protein. Preferably the O1 antigen is O1A, the O4 antigen is glucosylated O4 antigen polysaccharide, the O6 antigen is O6A, the O18 antigen is O18A, and the O25 antigen is O25B. Preferably the O1-, O2-, O4-, O6-, O15-, O16-, O18-, O25-, and O75-antigens respectively have the structures of Formulas (O1A), (O2), (O4-Glc+), (O6A), (O15), (O16), (O18A), (O25B), and (O75) as shown in Table 1, wherein each n is independently an integer of 1 to 100, preferably of 3 to 50, for example 5 to 40, preferably of 5 to 30, for example 7 to 25, for example 10 to 20. According to the invention, the ratio of O75 antigen polysaccharide to O6 antigen polysaccharide is about 1.2:1 to about 8:1, preferably about 1.5:1 to about 4:1, more preferably about 2:1. In some embodiments, the method further comprises administering to the subject from 1 to 15 additional *E. coli* antigen polysaccharides, each independently covalently linked to a carrier protein. In certain embodiments such additional *E. coli* antigens comprise O8 antigen polysaccharide, preferably having the structure of Formula (O8) as shown in Table 1, wherein n is an integer of 1 to 100, preferably of 3 to 50, for example 5 to 40, preferably of 5 to 30, for example 7 to 25, for example 10 to 20. Preferably, each *E. coli* antigen polysaccharide covalently linked to a carrier protein is a bioconjugate. In some embodiments, the bioconjugates are administered as one composition. In some embodiments, the bioconjugates are administered as a combination of two or more separate compositions. It is preferred to limit the number of separate administrations, so use of single compositions comprising most or all of the antigens is preferred.

In one embodiment is a method of administering a composition for inducing an immune response to *E. coli*, preferably extra-intestinal pathogenic *E. coli* (ExPEC), wherein the composition comprises a bioconjugate of *E. coli* O75 antigen polysaccharide covalently linked to a carrier protein, and wherein the concentration of O75 antigen polysaccharide administered is at least 16 μg per dose.

In some embodiments, a method of inducing an immune response to extra-intestinal pathogenic *E. coli* (ExPEC) in a subject comprises administering to the subject a first effective amount of *E. coli* O75 antigen polysaccharide, and a second effective amount of *E. coli* O1 antigen polysaccharide, wherein each of the antigen polysaccharides is independently covalently linked to a carrier protein, and wherein the ratio of the first effective amount to the second effective amount is between about 1.2:1 to about 8:1, preferably between about 1.5:1 to about 4:1, e.g. about 1.5:1, 1.6:1, 1.7:1, 1.8:1, 1.9:1, 2.0:1, 2.1:1, 2.2:1, 2.3:1, 2.4:1, 2.5:1, more preferably about 2:1. In some preferred embodiments, the O75 antigen polysaccharide covalently linked to a carrier protein and the O1 antigen polysaccharide covalently linked to a carrier protein are administered as one composition. In some alternative embodiments, the O75 antigen polysaccharide covalently linked to a carrier protein and the O1 antigen polysaccharide covalently linked to a carrier protein are administered as a combination of compositions. In some embodiments, the method further comprises administering to the subject one or more, preferably all, of *E. coli* O2, O4, O6, O15, O16, O18, O25 antigen polysaccharides, wherein each of the antigen polysaccharides is independently covalently linked to a carrier protein. Preferably the O1 antigen is O1A, the O4 antigen is glucosylated O4 antigen polysaccharide, the O6 antigen is O6A, the O18 antigen is O18A, and the O25 antigen is O25B. Preferably the O1-, O2-, O4-, O6-, O15-, O16-, O18-, O25-, and O75-antigens respectively have the structures of Formulas (O1A), (O2), (O4-Glc+), (O6A), (O15), (O16), (O18A), (O25B), and (O75) as shown in Table 1, wherein each n is independently an integer of 1 to 100, preferably of 3 to 50, for example 5 to 40, preferably of 5 to 30, for example 7 to 25, for example 10 to 20. According to the invention, the ratio of O75 antigen polysaccharide to O1 antigen polysaccharide is about 1.2:1 to about 8:1, preferably about 1.5:1 to about 4:1, more preferably about 2:1. In some embodiments, the method further comprises administering to the subject from 1 to 15 additional *E. coli* antigen polysaccharides, each independently covalently linked to a carrier protein. In certain embodiments such additional *E. coli* antigens comprise O8 antigen polysaccharide, preferably having the structure of Formula (O8) as shown in Table 1, wherein n is an integer of 1 to 100, preferably of 3 to 50, for example 5 to 40, preferably of 5 to 30, for example 7 to 25, for example 10 to 20. Preferably, each *E. coli* antigen polysaccharide covalently linked to a carrier protein is a bioconjugate. In some embodiments, the bioconjugates are administered as one composition. In some embodiments, the bioconjugates are administered as a combination of two or more separate compositions. It is preferred to limit the number of separate administrations, so use of single compositions comprising most or all of the antigens is preferred.

In some embodiments, a method of inducing an immune response to extra-intestinal pathogenic *E. coli* (ExPEC) in a subject comprises administering to the subject a first effective amount of *E. coli* O75 antigen polysaccharide, and a second effective amount of *E. coli* O2 antigen polysaccharide, wherein each of the antigen polysaccharides is independently covalently linked to a carrier protein, and wherein the ratio of the first effective amount to the second effective amount is about 1.2:1 to about 8:1, preferably about 1.5:1 to about 4:1, e.g. about 1.5:1, 1.6:1, 1.7:1, 1.8:1, 1.9:1, 2.0:1, 2.1:1, 2.2:1, 2.3:1, 2.4:1, 2.5:1, more preferably about 2:1. In some preferred embodiments, the O75 antigen polysaccharide covalently linked to a carrier protein and the O2 antigen polysaccharide covalently linked to a carrier protein are administered as one composition. In some alternative embodiments, the O75 antigen polysaccharide covalently linked to a carrier protein and the O2 antigen polysaccharide covalently linked to a carrier protein are administered as a combination of compositions. In some embodiments, the method further comprises administering to the subject one or more, preferably all, of *E. coli* O1, O4, O6, O15, O16, O18, O25 antigen polysaccharides, wherein each of the antigen polysaccharides is independently covalently linked to a carrier protein. Preferably the O1 antigen is O1A, the O4 antigen is glucosylated O4 antigen polysaccharide, the O6 antigen is O6A, the O18 antigen is O18A, and the O25 antigen is O25B. Preferably the O1-, O2-, O4-, O6-, O15-, O16-, O18-, O25-, and O75-antigens respectively have the structures of Formulas (O1A), (O2), (O4-Glc+), (O6A), (O15), (O16), (O18A), (O25B), and (O75) as shown in Table 1, wherein each n is independently an integer of 1 to 100, preferably of 3 to 50, for example 5 to 40, preferably of 5 to 30, for example 7 to 25, for example 10 to 20. According to the invention, the ratio of O75 antigen polysaccharide to O2 antigen polysaccharide is about 1.2:1 to about 8:1, preferably about 1.5:1 to about 4:1, more preferably about 2:1. In some embodiments, the method further comprises administering to the subject from 1 to 15 additional *E. coli* antigen polysaccharides, each independently covalently linked to a carrier protein. Preferably, each *E. coli* antigen polysaccharide covalently linked to a carrier protein is a bioconjugate. In some embodiments, the bioconjugates are administered as one composition. In some embodiments, the bioconjugates are administered as a combination of two or more separate compositions. It is preferred to limit the number of separate administrations, so use of single compositions comprising most or all of the antigens are preferred.

In some embodiments, a method of inducing an immune response to extra-intestinal pathogenic *E. coli* (ExPEC) in a subject comprises administering to the subject a first effective amount of *E. coli* O75 antigen polysaccharide, and a second effective amount of *E. coli* O25 antigen polysaccharide, wherein each of the antigen polysaccharides is independently covalently linked to a carrier protein, and wherein the ratio of the first effective amount to the second effective amount is about 1:4 and 1:0.5, preferably between about 1:2 and 1:1, more preferably about 1:1, e.g. about 1:1.5, 1:1.4, 1:1.3, 1:1.2, 1:1.1, 1:1.0, 1:0.9, 1:0.8, 1:0.7, 1:0.6, or 1:0.5. In some preferred embodiments, the O75 antigen polysaccharide covalently linked to a carrier protein and the O25 antigen polysaccharide covalently linked to a carrier protein are administered as one composition. In some alternative embodiments, the O75 antigen polysaccharide covalently linked to a carrier protein and the O25 antigen polysaccharide covalently linked to a carrier protein are administered as a combination of compositions. In some embodiments, the method further comprises administering to the subject one or more, preferably all, of *E. coli* O1, O2, O4, O6, O15, O16, O18 antigen polysaccharides, wherein each of the antigen polysaccharides is independently covalently linked to a carrier protein. Preferably the O1 antigen is O1A, the O4 antigen is glucosylated O4 antigen polysaccharide, the O6 antigen is O6A, the O18 antigen is O18A, and the O25 antigen is O25B. Preferably the O1-, O2-, O4-, O6-, O15-, O16-, O18-, O25-, and O75-antigens respectively have the structures of Formulas (O1A), (O2), (O4-Glc+), (O6A), (O15), (O16), (O18A), (O25B), and (O75) as shown in Table 1, wherein each n is independently an integer of 1 to 100, preferably of 3 to 50, for example 5 to 40, preferably of 5 to 30, for example 7 to 25, for example 10 to 20. According to the invention, the ratio of O75 antigen polysaccharide to O25 antigen polysaccharide is about 1:4 to about 1:0.5, preferably between about 1:2 and 1:1, more preferably about 1:1. In some embodiments, the method further comprises administering to the subject from 1 to 15 additional *E. coli* antigen polysaccharides, each independently covalently linked to a carrier protein. In certain embodiments such additional *E. coli* antigens comprise O8 antigen polysaccharide, preferably having the structure of Formula (O8) as shown in Table 1, wherein n is an integer of 1 to 100, preferably of 3 to 50, for example 5 to 40, preferably of 5 to 30, for example 7 to 25, for example 10 to 20. Preferably, each *E. coli* antigen polysaccharide covalently linked to a carrier protein is a bioconjugate. In some embodiments, the bioconjugates are administered as one composition. In some embodiments, the bioconjugates are administered as a combination of two or more separate compositions. It is preferred to limit the number of separate administrations, so use of single compositions comprising most or all of the antigens are preferred.

In certain embodiments, the compositions, combinations, and bioconjugates described herein can be administered to a subject to induce an immune response that includes the production of antibodies, preferably antibodies having opsonophagocytic activity. Such antibodies can be isolated using techniques known to one of skill in the art (e.g., immunoaffinity chromatography, centrifugation, precipitation, etc.).

The ability of the bioconjugates and compositions described herein to generate an immune response in a subject can be assessed using any approach known to those of skill in the art or described herein. In some embodiments, the ability of a bioconjugate to generate an immune response in a subject can be assessed by immunizing a subject (e.g., a mouse, rat, rabbit, or monkey) or set of subjects with a bioconjugate described herein and immunizing an additional subject (e.g., a mouse, rat, rabbit, or monkey) or set of subjects with a control (e.g., PBS). The subjects or set of subjects can subsequently be challenged with ExPEC and the ability of the ExPEC to cause disease (e.g., UTI, bacteremia, or other disease) in the subjects or set of subjects can be determined. Those skilled in the art will recognize that if the subject or set of subjects immunized with the control suffer(s) from disease subsequent to challenge with the ExPEC but the subject or set of subjects immunized with a bioconjugate(s) or composition thereof described herein suffer less from or do not suffer from disease, then the bioconjugate is able to generate an immune response in a subject. The ability of a bioconjugate(s) or composition thereof described herein to induce antiserum that cross-reacts with an O antigen from ExPEC can be tested by, e.g., an immunoassay, such as an ELISA (see e.g., Van den Dobbelsteen et al, 2016, Vaccine 34: 4152-4160), or an ECL-based immunoassay.

For example, the ability of the bioconjugates described herein to generate an immune response in a subject can be assessed using a serum bactericidal assay (SBA) or opsonophagocytic killing assay (OPK assay, or OPKA), which represents an established and accepted method that has been used to obtain approval of glycoconjugate-based vaccines. Such assays are well-known in the art and, briefly, comprise the steps of generating and isolating antibodies against a target of interest (e.g., an O antigen polysaccharide, e.g., *E. coli* O75 antigen polysaccharide) by administering to a subject (e.g., a mouse, rat, rabbit, or monkey) a compound that elicits such antibodies. Subsequently, the bactericidal capacity of the antibodies can be assessed by, e.g., culturing the bacteria in question (e.g., *E. coli* of the relevant serotype) in the presence of the antibodies and complement and—depending on the assay—neutrophilic cells and assaying the ability of the antibodies to mediate killing and/or neutralization of the bacteria, e.g., using standard microbiological approaches. For an example of OPK assay for *E. coli* bioconjugate vaccines, see e.g. Abbanat et al, 2017, Clin. Vaccine Immunol. 24: e00123-17. An OPK assay can be performed in monoplex or multiplex format, of which multiplex format (e.g. testing multiple serotypes at the same time) is typically preferred. A multiplex OPK assay is sometimes referred to herein as "MOPA".

In particular embodiments, wherein a composition provided herein comprises a bioconjugate of an *E. coli* O75 antigen polysaccharide and at least a bioconjugate of an *E. coli* O6A antigen polysaccharide, an effective amount of the *E. coli* O75 antigen polysaccharide is about 1.2 to 8 times, e.g. about 2 to 4 times higher, such as 1.5, 2, 3, 4, 5, 6, 7 or 8 times higher than the concentration of any of the other bioconjugates present in the composition. In such embodiments, an effective amount of the *E. coli* O75 antigen polysaccharide is for instance about 5 to 18 μg per administration, such as 5, 6, 7, 8, 9, 10, 11, 12, 13, 14, 15, 16, 17, 18 μg per administration. Preferably, about 8-16 μg of the O75 antigen polysaccharide is administered per administration.

In certain embodiments, a composition described herein is administered to a subject in combination with one or more other therapies (e.g., antibacterial or immunomodulatory therapies). The one or more other therapies can be beneficial in the treatment or prevention of an ExPEC infection or can ameliorate a symptom or condition associated with an ExPEC infection. In some embodiments, the one or more other therapies are pain relievers or anti-fever medications. In certain embodiments, the therapies are administered less than 5 minutes apart to less than 1 week apart. Any antibacterial agents known to one of skill in the art (e.g. antibiotics) may be used in combination with a composition described herein.

In certain embodiments, a bioconjugate or composition according to the invention is administered to a subject once. In certain embodiments, a bioconjugate or composition according to the invention is administered to a subject more than once, e.g. in a prime-boost regimen. In certain embodiments, the time between two administrations is at least two weeks, at least one month, at least two months, at least three months, at least six months, at least one year, at least two years, at least five years, at least ten years, or at least fifteen years. In humans, a desired immune response can typically be generated by a single administration of a bioconjugate or composition according to the invention. In certain embodiments, a repeat administration after, for instance ten years, is provided.

The compositions provided herein can be used to induce antibodies against *E. coli* O antigens in a subject, and to vaccinate a subject against *E. coli*, in particular extra-intestinal pathogenic *E. coli* (ExPEC). As used herein, "subject" means any animal, preferably a mammal, to whom will be or has been administered a bioconjugate or composition provided herein. The term "mammal" as used herein, encompasses any mammal. Examples of mammals include, but are not limited to, cows, horses, sheep, pigs, cats, dogs, mice, rats, rabbits, guinea pigs, non-human primates (NHPs) such as monkeys or apes, humans, etc. In certain embodiments, a subject is a human. A human subject may be of any age. In certain embodiments, a subject is a human of about two months to about 18 years old, e.g. of 1 year to 18 years old. In certain embodiments, a subject is a human of at least 18 years old. In certain embodiments, a subject is a human of 15 to 50 years old, e.g. 18 to 45 years old, e.g. 20 to 40 years old. In certain embodiments, a subject is a human male. In certain embodiments, a subject is a human female. In certain embodiments, a subject is immunocompromised. In certain embodiments, a subject is a human of at least 50 years, at least 55 years, at least 60 years, at least 65 years old. In certain embodiments, a subject is a human that is not older than 100 years, not older than 95 years, not older than 90 years, not older than 85 years, not older than 80 years, or not older than 75 years. In certain embodiments, a subject is a human of at least 60 years old, and not older than 85 years old. In certain embodiments, a subject is a human in stable health. In certain embodiments, a subject is a human adult of at least 60 and not more than 85 years old in stable health. In certain embodiments, a subject is a human that has a history of a urinary tract infection (UTI, i.e. a bacterial infection in the urethra, bladder, ureters, and/or kidneys; in some embodiments this includes pyelonephritis), i.e. having had at least one UTI episode in his or her life. In certain embodiments, a subject is a human that has a history of UTI in the past twenty, fifteen, twelve, ten, nine, eight, seven, six, five, four, three, two or one years. In certain embodiments, a subject is a human that has a history of UTI in the past two years. In certain embodiments, a subject is a human subject that has a history of recurrent UTI, i.e. having had at least two UTIs in six months or at least three UTIs in one year. In certain embodiments, a subject is a human subject that has a history of recurrent UTI in the past two years. In certain embodiments, a subject is a human of 60 years or older in stable health. In certain embodiments, a subject is a human of 60 years or older that has a history of UTI in the past two years. In certain embodiments, a subject is a human of at least 60 years and less than 75 years old that has a history of UTI in the past two years. In certain embodiments, a subject is a human subject of 75 years or older that has a history of UTI in the past two years. In certain embodiments, a subject is a patient scheduled for undergoing elective urogenital and/or abdominal procedures or surgeries, e.g. transrectal ultrasound-guided prostate needle biopsy (TRUS-PNB). In certain embodiments, a subject is a human that has a history of prostatitis, including but not limited to an acute bacterial prostatitis (ABP), i.e. a bacterial infection of the prostate, i.e. having had at least one prostatitis episode in his life, e.g. in the last ten, nine, eight, seven, six, five, four, three, two or one years.

In preferred embodiments, the immune response induced by the compositions or methods of inducing an immune response according to the invention includes antibodies that have opsonophagocytic activity. It has been shown that compositions comprising *E. coli* O antigen polysaccharides covalently linked to a carrier protein (i.e. glycoconjugates of *E. coli* O-antigens) can induce this type of functional antibodies in humans, and it has been shown that such antibodies mediate bacterial killing in vivo, and via this mechanism can protect against *E. coli* infections.

In another aspect, provided herein is a method of inducing an immune response to *E. coli*, preferably extra-intestinal pathogenic *E. coli* (ExPEC), in a subject, comprising administering to the subject a composition as described herein.

In another aspect, provided herein is a method of vaccinating a subject against *E. coli*, preferably extra-intestinal pathogenic *E. coli* (ExPEC), comprising administering to the subject a composition as described herein. In certain aspects, provided herein is a composition as described herein, for use in inducing antibodies against *E. coli*, preferably ExPEC. In certain aspects, provided herein is a composition as described herein, for use in vaccination against *E. coli*, preferably ExPEC. In certain aspects, provided herein is the use of a composition as described herein, for the manufacture of a medicament for inducing antibodies in a subject against *E. coli*, preferably ExPEC. In certain aspects, provided herein is the use of a composition as described herein, for the manufacture of a medicament for vaccinating a subject against *E. coli*, preferably ExPEC.

In certain aspects, provided herein is a composition as described herein for use in a method of inducing an immune response to *E. coli*, preferably extra-intestinal pathogenic *E. coli* (ExPEC), in a subject. In certain aspects, provided herein is use of a composition as described herein in the manufacture of a medicament for inducing an immune response to *E. coli*, preferably extra-intestinal pathogenic *E. coli* (ExPEC), in a subject.

In another aspect, provided herein is a method of inducing an immune response to *E. coli*, preferably extra-intestinal pathogenic *E. coli* (ExPEC), in a subject, comprising administering to the subject a first effective amount of *E. coli* O75 antigen polysaccharide, and a second effective amount of *E. coli* O6 antigen polysaccharide, wherein each of the antigen polysaccharides is independently covalently linked to a carrier protein, and wherein the ratio of the first effective amount to the second effective amount is about 1.2:1 to about 8:1, preferably about 1.5:1 to about 4:1, more preferably about 2:1.

In certain embodiments, the immune response limits the severity of or prevents an invasive ExPEC disease in the subject.

In certain embodiments, the invasive ExPEC disease comprises sepsis and/or bacteremia.

In certain embodiments, the method further comprises administering to the subject one or more, preferably all, of *E. coli* O1, O2, O4, O15, O16, O18, O25 antigen polysaccharides, wherein each of the antigen polysaccharides is independently covalently linked to a carrier protein, preferably the O1 antigen is O1A, the O4 is glucosylated, the O6 antigen is O6A, the O18 antigen is O18A, and the O25 antigen is O25B, more preferably wherein each of the O1A, O2, glucosylated O4, O6A, O15, O16, O18A, O25B, and O75 antigen polysaccharides comprise the structures of Formulas (O1A), (O2), (O4-Glc+), (O6A), (O15), (O16), (O18A), (O25B), and (O75), respectively, as shown in Table 1, wherein each n is independently an integer of 1 to 100, preferably of 3 to 50, for example 5 to 40, preferably of 5 to 30, for example 7 to 25, for example 10 to 20, and wherein the ratio of O75 antigen polysaccharide to O6 antigen polysaccharide is about 1.2:1 to about 8:1, preferably about 1.5:1 to about 4:1, more preferably about 2:1.

In certain embodiments, the method further comprises administering to the subject from 1 to 15 additional *E. coli* antigen polysaccharides, each independently covalently linked to a carrier protein.

In a particular embodiment, each of the carrier proteins comprises the amino acid sequence of SEQ ID NO: 3.

In certain embodiments, the subject is a human having or at risk of having an *E. coli* (preferably ExPEC) infection, preferably an invasive ExPEC disease.

In certain embodiments, about 8-16 μg, preferably about 16 μg, of the O75 antigen polysaccharide is administered per administration.

In certain embodiments, the weight ratio of the administered *E. coli* antigen polysaccharides of O1:O2:O4:O6:O15:O16:O18:O25:O75 is 1:1:1:1:1:1:1:2:2.

In certain embodiments, the glucosylated O4 is a bioconjugate of an *E. coli* glucosylated O4 antigen polysaccharide covalently linked to a carrier protein, wherein the *E. coli* glucosylated O4 antigen polysaccharide comprises the structure of Formula (O4-Glc+) shown in Table 1, wherein n is an integer of 3 to 50, for example 5 to 40, preferably of 5 to 30, for example 7 to 25, for example 10 to 20, wherein the bioconjugate of an *E. coli* glucosylated O4 antigen polysaccharide covalently linked to a carrier protein has been produced in an *E. coli* cell that comprises:

(i) a nucleotide sequence of an rfb gene cluster for the *E. coli* O4 antigen polysaccharide;
(ii) a nucleotide sequence encoding a glucosyl transferase having at least 80%, preferably at least 90%, preferably at least 95% sequence identity to SEQ ID NO: 4, wherein the glucosyl transferase is capable of modifying the *E. coli* O4 antigen polysaccharide to produce the *E. coli* glucosylated O4 antigen polysaccharide;
(iii) nucleotide sequences encoding a translocase and a glycosyltransferase having at least 80%, preferably at least 90%, preferably at least 95% sequence identity to SEQ ID NOs: 7 and 8 respectively, wherein the translocase is capable of translocating bactoprenol-linked glucose and the glycosyltransferase is capable of glucosylating bactoprenol;
(iv) a nucleotide sequence encoding the carrier protein; and
(v) a nucleotide sequence encoding an oligosaccharyl transferase capable of covalently linking the *E. coli* glucosylated O4 antigen polysaccharide to the carrier protein, preferably wherein the oligosaccharyl transferase is PglB from *Campylobacter jejuni*.

In one aspect, the invention also provides a composition comprising *E. coli* O1, O2, O4, O6, O15, O16, O18, O25 and O75 antigen polysaccharides (having the structures as indicated above for each antigen respectively), wherein each of the antigen polysaccharides is independently covalently linked to a carrier protein, and which composition does not comprise other *E. coli* O-antigen polysaccharides covalently linked to a carrier protein (i.e. a 9-valent composition). In certain embodiments of this aspect, the carrier protein is EPA. In other embodiments of this aspect, the carrier protein is $CRM_{197}$. In certain embodiments of this aspect, the covalent linkages are the result of chemical conjugation. In other embodiments, the covalent linkages are the result of bioconjugation. In certain embodiments of this aspect, the carrier protein is $CRM_{197}$ and the covalent linkages are the result of chemical conjugation. In other embodiments of this aspect, the carrier protein is EPA and the covalent linkages are the result of bioconjugation. In preferred embodiments of this aspect, the composition comprises an increased amount of *E. coli* O75 antigen polysaccharide as compared to O1, O2, or O6 antigen polysaccharide, preferably as compared to each one of O1, O2, and O6 antigen polysaccharide, preferably an about 1.5-4 times increased, preferably an about two times increased amount.

Embodiments

Embodiment 1 is a composition comprising *E. coli* O75 antigen polysaccharide and at least one additional *E. coli* O-antigen polysaccharide selected from the group consisting of O1, O2, O4, O6, O15, O16, and O18, wherein each of the antigen polysaccharides is independently covalently linked to a carrier protein, and wherein the ratio of concentrations of O75 antigen polysaccharide to the additional O-antigen polysaccharide is about 1.2:1 to about 8:1, preferably about 1.5:1 to about 4:1, preferably about 1.5:1 to about 2.5:1, more preferably about 2:1.

Embodiment 1a is the composition of embodiment 1, wherein the at least one additional O-antigen polysaccharide is O1, preferably O1A.

Embodiment 1a1 is the composition of embodiment 1a, wherein the ratio of concentrations of O75 antigen polysaccharide to O1 antigen polysaccharide is 2:1.

Embodiment 1b is the composition of embodiment 1, wherein the at least one additional O-antigen polysaccharide is O2.

Embodiment 1b1 is the composition of embodiment 1b, wherein the ratio of concentrations of O75 antigen polysaccharide to O1 antigen polysaccharide is 2:1.

Embodiment 1c is the composition of embodiment 1, wherein the at least one additional O-antigen polysaccharide is O4, preferably glucosylated O4.

Embodiment 1c1 is the composition of embodiment 1c, wherein the ratio of concentrations of O75 antigen polysaccharide to O4 antigen polysaccharide is 2:1.

Embodiment 1d is the composition of embodiment 1, wherein the at least one additional O-antigen polysaccharide is O6, preferably O6A.

Embodiment 1d1 is the composition of embodiment 1d, wherein the ratio of concentrations of O75 antigen polysaccharide to O6 antigen polysaccharide is 2:1.

Embodiment 1e is the composition of embodiment 1, wherein the at least one additional O-antigen polysaccharide is O15.

Embodiment 1e1 is the composition of embodiment 1e, wherein the ratio of concentrations of O75 antigen polysaccharide to O15 antigen polysaccharide is 2:1.

Embodiment 1f is the composition of embodiment 1, wherein the at least one additional O-antigen polysaccharide is O16.

Embodiment 1f1 is the composition of embodiment if, wherein the ratio of concentrations of O75 antigen polysaccharide to O16 antigen polysaccharide is 2:1.

Embodiment 1g is the composition of embodiment 1, wherein the at least one additional O-antigen polysaccharide is O18, preferably O18A.

Embodiment 1g1 is the composition of embodiment 1g, wherein the ratio of concentrations of O75 antigen polysaccharide to O18 antigen polysaccharide is 2:1.

Embodiment 1h is the composition of embodiment 1, further comprising an O25 antigen polysaccharide independently covalently linked to a carrier protein, preferably the O25 antigen is O25B.

Embodiment 1h1 is the composition of embodiment 1h, wherein the ratio of concentrations of O75 antigen polysaccharide to O25 antigen polysaccharide is 1:1.

Embodiment 2 is the composition of embodiment 1, wherein the composition comprises the *E. coli* O75 antigen polysaccharide and two or more, preferably all, of *E. coli* O1, O2, O4, O6, O15, O16, O18, O25 antigen polysaccharides, wherein each of the antigen polysaccharides is independently covalently linked to a carrier protein, preferably the O1 antigen is O1A, the O4 is glucosylated, the O6 antigen is O6A, the O18 antigen is O18A, and the O25 antigen is O25B.

Embodiment 3 is the composition of embodiment 2, wherein (i) the *E. coli* O1 antigen polysaccharide comprises the structure of Formula (O1A):

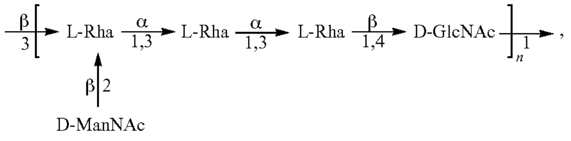

(ii) the *E. coli* O2 antigen polysaccharide comprises the structure of Formula (O2):

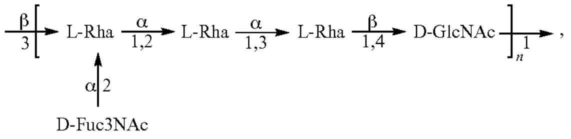

(iii) the *E. coli* O4 antigen polysaccharide comprises the structure of Formula (O4-Glc+):

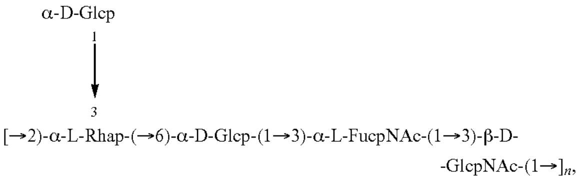

(iv) the *E. coli* O6 antigen polysaccharide comprises the structure of Formula (O6A):

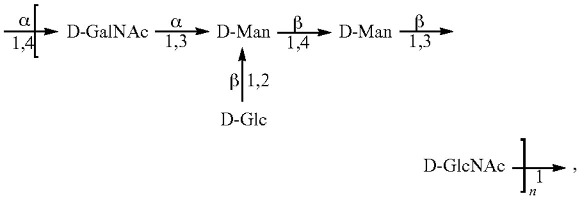

(v) the *E. coli* O15 antigen polysaccharide comprises the structure of Formula (O15):

[→2)-β-D-Galp-(1→3)-α-L-FucpNAc-(1→3)-β-D-GlcpNAc-(1→]$_n$, (vi) the *E. coli* O16 antigen polysaccharide comprises the structure of Formula (O16):

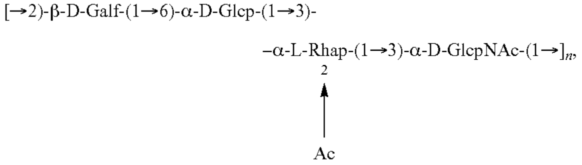

(vii) the *E. coli* O18 antigen polysaccharide comprises the structure of Formula (O18A):

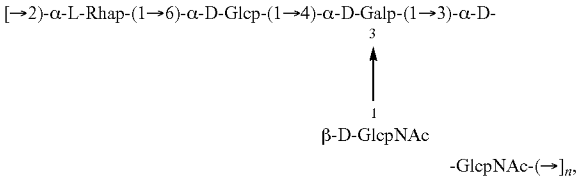

(viii) the *E. coli* O25 antigen polysaccharide comprises the structure of Formula (O25B):

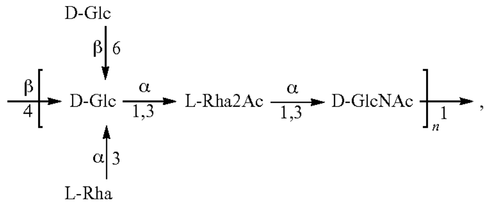

(ix) the *E. coli* O75 antigen polysaccharide comprises the structure of Formula (O75):

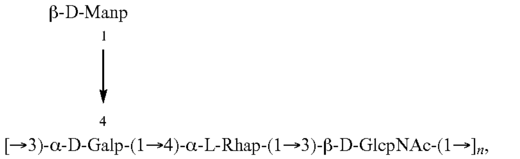

wherein each n is independently an integer of 1 to 100, preferably of 3 to 50, for example 5 to 40, preferably of 5 to 30, for example 7 to 25, for example 10 to 20.

Embodiment 4 is the composition of embodiment 2 or 3, wherein the weight ratio of the *E. coli* antigen polysaccharides of O1:O2:O4:O6:O15:O16:O18:O25:O75 is 1:1:1:1:1:1:1:2:2.

Embodiment 5 is the composition of any one of embodiments 1-4, wherein the concentration of the O75 antigen polysaccharide is from about 8 to about 50 μg/mL, preferably 12 to 40 μg/mL, e.g. 16-32 μg/mL, preferably about 26-38 μg/mL, preferably about 32 μg/mL.

Embodiment 6 is the composition of any one of embodiments 1-5, further comprising at least one other additional *E. coli* antigen polysaccharide covalently linked to a carrier protein.

Embodiment 7 is the composition of embodiment 6, wherein the one other additional *E. coli* antigen polysaccharide comprises O8 antigen polysaccharide with Formula (O8):

α-D-Manp3Me-(1→[3)-β-D-Manp-(1→2)-α-D-Manp-(1→2)-α-D-Manp-(1→]$_n$, wherein n is an integer of 1 to 100, preferably of 3 to 50, for example 5 to 40, preferably of 5 to 30, for example 7 to 25, for example 10 to 20.

Embodiment 8 is the composition of any one of embodiments 1-7, wherein each carrier protein is independently selected from the group consisting of detoxified Exotoxin A of *P. aeruginosa* (EPA), *E. coli* flagellin (FliC), $CRM_{197}$, maltose binding protein (MBP), Diphtheria toxoid, Tetanus toxoid, detoxified hemolysin A of *S. aureus*, clumping factor A, clumping factor B, *E. coli* heat labile enterotoxin, detoxified variants of *E. coli* heat labile enterotoxin, Cholera toxin B subunit (CTB), cholera toxin, detoxified variants of cholera toxin, *E. coli* Sat protein, the passenger domain of *E. coli* Sat protein, *Streptococcus pneumoniae* Pneumolysin, Keyhole limpet hemocyanin (KLH), *P. aeruginosa* PcrV, outer membrane protein of *Neisseria meningitidis* (OMPC), and protein D from non-typeable *Haemophilus influenzae.*

Embodiment 9 is the composition of embodiment 8, wherein the carrier protein is detoxified exotoxin A of *Pseudomonas aeruginosa* (EPA) or $CRM_{197}$.

Embodiment 10 is the composition of any one of embodiments 1-9, wherein the carrier protein comprises 1 to 20, such as 1 to 10, or 2 to 4, glycosylation consensus sequences having the amino acid sequence of SEQ ID NO: 1, such as the consensus sequences having the amino acid sequence of SEQ ID NO: 2, most preferably the carrier protein comprises four of the glycosylation consensus sequences.

Embodiment 11 is the composition of any one of embodiments 1-10, wherein each carrier protein is EPA comprising the amino acid sequence of SEQ ID NO: 3.

Embodiment 12 is the composition of any one of embodiments 1-11, wherein the *E. coli* antigen polysaccharides are covalently linked to the carrier protein by bioconjugation or chemical conjugation, for example reductive amination chemistry (RAC), single-end conjugation, or conjugation with a (2-((2-oxoethyl)thio)ethyl) carbamate (eTEC) spacer.

Embodiment 13 is the composition of embodiment 12, wherein the *E. coli* antigen polysaccharides are covalently linked to the carrier protein by bioconjugation, preferably the polysaccharide is covalently linked to an Asn residue in a glycosylation site in the carrier protein.

Embodiment 14 is a composition comprising:

(i) a bioconjugate of an *E. coli* O1A antigen polysaccharide covalently linked to a detoxified Exotoxin A of *P. aeruginosa* (EPA-4) carrier protein, wherein the *E. coli* O1A antigen polysaccharide comprises the structure of Formula (O1A);

(ii) a bioconjugate of an *E. coli* O2 antigen polysaccharide covalently linked to an EPA-4 carrier protein, wherein the *E. coli* O2 antigen polysaccharide comprises the structure of Formula (O2);

(iii) a bioconjugate of an *E. coli* glucosylated O4 antigen polysaccharide covalently linked to an EPA-4 carrier protein, wherein the *E. coli* glucosylated O4 antigen polysaccharide comprises the structure of Formula (O4-Glc+);

(iv) a bioconjugate of an *E. coli* O6A antigen polysaccharide covalently linked to an EPA-4 carrier protein, wherein the *E. coli* O6A antigen polysaccharide comprises the structure of Formula (O6A);

(v) a bioconjugate of an *E. coli* O15 antigen polysaccharide covalently linked to an EPA-4 carrier protein, wherein the *E. coli* O15 antigen polysaccharide comprises the structure of Formula (O15);

(vi) a bioconjugate of an *E. coli* O16 antigen polysaccharide covalently linked to an EPA-4 carrier protein, wherein the *E. coli* O16 antigen polysaccharide comprises the structure of Formula (O16);

(vii) a bioconjugate of an *E. coli* O18A antigen polysaccharide covalently linked to an EPA-4 carrier protein, wherein the *E. coli* O18A antigen polysaccharide comprises the structure of Formula (O18A);

(viii) a bioconjugate of an *E. coli* O25B antigen polysaccharide covalently linked to an EPA-4 carrier protein, wherein the *E. coli* O25B antigen polysaccharide comprises the structure of Formula (O25B); and (ix) a bioconjugate of an *E. coli* O75 antigen polysaccharide covalently linked to an EPA-4 carrier protein, wherein the *E. coli* O75 antigen polysaccharide comprises the structure of Formula (O75);

wherein the EPA-4 comprises the amino acid sequence of SEQ ID NO: 3, wherein each of the structures of Formulas (O1A), (O2), (O4-Glc+), (O6A), (O15), (O16), (O18A), (O25B), and (O75) is shown in Table 1, wherein each n is independently an integer of 1 to 100, preferably of 3 to 50, for example 5 to 40, more preferably of 5 to 30, for example 7 to 25, for example 10 to 20, and wherein the ratio of O75 antigen polysaccharide to O6A antigen polysaccharide is about 1.2:1 to about 8:1, preferably about 1.5:1 to about 4:1, more preferably about 2:1.

Embodiment 15 is the composition of embodiment 14, further comprising from 1 to 15 additional *E. coli* antigen polysaccharides each independently covalently linked to a carrier protein.

Embodiment 16 is the composition of any one of embodiments 2-15, wherein the glycosylated O4 is a bioconjugate of an *E. coli* glucosylated O4 antigen polysaccharide covalently linked to a carrier protein, wherein the *E. coli* glucosylated O4 antigen polysaccharide comprises the structure of Formula (O4-Glc+) shown in Table 1, wherein n is an integer of 3 to 50, for example 5 to 40, preferably of 5 to 30, for example 7 to 25, for example 10 to 20, wherein the bioconjugate of an *E. coli* glucosylated O4 antigen polysaccharide covalently linked to a carrier protein has been produced in an *E. coli* cell that comprises:

(i) a nucleotide sequence of an rfb gene cluster for the *E. coli* O4 antigen polysaccharide;

(ii) a nucleotide sequence encoding a glucosyl transferase having at least 80%, preferably at least 90%, preferably at least 95% sequence identity to SEQ ID NO: 4, wherein the glucosyl transferase is capable of modifying the *E. coli* O4 antigen polysaccharide to produce the *E. coli* glucosylated O4 antigen polysaccharide;

(iii) nucleotide sequences encoding a translocase and a glycosyltransferase having at least 80%, preferably at least 90%, preferably at least 95% sequence identity to SEQ ID NOs: 7 and 8 respectively, wherein the translocase is capable of translocating bactoprenol-linked glucose and the glycosyltransferase is capable of glucosylating bactoprenol;

(iv) a nucleotide sequence encoding the carrier protein; and (v) a nucleotide sequence encoding an oligosaccharyl transferase capable of covalently linking the *E. coli* glucosylated O4 antigen polysaccharide to the carrier protein, preferably wherein the oligosaccharyl transferase is PglB from *Campylobacter jejuni*.

Embodiment 17 is a method of inducing an immune response to *E. coli* (preferably extra-intestinal pathogenic *E. coli*, ExPEC) in a subject, comprising administering to the subject the composition of any one of embodiments 1-16.

Embodiment 17a is the method of embodiment 17, wherein the subject is in need of said immune response.

Embodiment 18 is a method of inducing an immune response to *E. coli* (preferably extra-intestinal pathogenic *E. coli*, ExPEC) in a subject, comprising administering to the subject a first effective amount of *E. coli* O75 antigen polysaccharide, and a second effective amount of *E. coli* O6 antigen polysaccharide, wherein each of the antigen polysaccharides is independently covalently linked to a carrier protein, and wherein the ratio of the first effective amount to the second effective amount is about 1.2:1 to about 8:1, preferably about 1.5:1 to about 4:1, more preferably about 2:1.

Embodiment 18a is the method of embodiment 18, wherein the subject is in need of said immune response.

Embodiment 19 is the method of any one of embodiments 17-18a, wherein the immune response limits the severity of or prevents an invasive ExPEC disease in the subject.

Embodiment 20 is the method of embodiment 19, wherein the invasive ExPEC disease comprises sepsis and/or bacteremia.

Embodiment 20a is the method of embodiment 20, wherein the invasive ExPEC disease comprises sepsis.

Embodiment 20b is the method of embodiment 20, wherein the invasive ExPEC disease comprises bacteremia.

Embodiment 21 is the method of any one of embodiments 18-20, further comprising administering to the subject one or more, preferably all, of *E. coli O*1, O2, O4, O15, O16, O18, O25 antigen polysaccharides, wherein each of the antigen polysaccharides is independently covalently linked to a carrier protein, preferably the O1 antigen is O1A, the O4 is glucosylated, the O6 antigen is O6A, the O18 antigen is O18A, and the O25 antigen is O25B, more preferably each of the O1A, O2, glucosylated O4, O6A, O15, O16, O18A, O25B, and O75 antigen polysaccharides comprise the structures of Formulas (O1A), (O2), (O4-Glc+), (O6A), (O15), (O16), (O18A), (O25B), and (O75), respectively, as shown in Table 1, wherein each n is independently an integer of 1 to 100, preferably of 3 to 50, for example 5 to 40, preferably of 5 to 30, for example 7 to 25, for example 10 to 20, and wherein the ratio of O75 antigen polysaccharide to O6 antigen polysaccharide is about 1.2:1 to about 8:1, preferably about 1.5:1 to about 4:1, more preferably about 2:1.

Embodiment 22 is the method of any one of embodiments 18-21, further comprising administering to the subject from 1 to 15 additional *E. coli* antigen polysaccharides, each independently covalently linked to a carrier protein.

Embodiment 23 is the method of any one of embodiments 18-22, wherein each of the carrier proteins comprises the amino acid sequence of SEQ ID NO: 3.

Embodiment 24 is the method of any one of embodiments 17-23, wherein the subject is a human having or at risk of having an *E. coli* (preferably ExPEC) infection or an invasive ExPEC disease.

Embodiment 25 is the method of any one of embodiments 17-24, wherein about 8-16 μg, preferably about 16 μg, of the O75 antigen polysaccharide is administered per administration.

Embodiment 26 is the method of any one of embodiments 21-25, wherein the weight ratio of the administered *E. coli* antigen polysaccharides of O1:O2:O4:O6:O15:O16:O18:O25:O75 is 1:1:1:1:1:1:1:2:2.

Embodiment 27 is the method of any one embodiments 21-26, wherein the glycosylated O4 is a bioconjugate of an *E. coli* glucosylated O4 antigen polysaccharide covalently linked to a carrier protein, wherein the *E. coli* glucosylated O4 antigen polysaccharide comprises the structure of Formula (O4-Glc+) shown in Table 1, wherein n is an integer of 3 to 50, for example 5 to 40, preferably of 5 to 30, for example 7 to 25, for example 10 to 20, wherein the bioconjugate of an *E. coli* glucosylated O4 antigen polysaccharide covalently linked to a carrier protein has been produced in an *E. coli* cell that comprises:

(i) a nucleotide sequence of an rfb gene cluster for the *E. coli* O4 antigen polysaccharide;

(ii) a nucleotide sequence encoding a glucosyl transferase having at least 80%, preferably at least 90%, preferably at least 95% sequence identity to SEQ ID NO: 4, wherein the glucosyl transferase is capable of modifying the *E. coli* O4 antigen polysaccharide to produce the *E. coli* glucosylated O4 antigen polysaccharide;

(iii) nucleotide sequences encoding a translocase and a glycosyltransferase having at least 80%, preferably at least 90%, preferably at least 95% sequence identity to SEQ ID NOs: 7 and 8 respectively, wherein the translocase is capable of translocating bactoprenol-linked glucose and the glycosyltransferase is capable of glucosylating bactoprenol;

(iv) a nucleotide sequence encoding the carrier protein; and (v) a nucleotide sequence encoding an oligosaccharyl transferase capable of covalently linking the *E. coli* glucosylated O4 antigen polysaccharide to the carrier protein, preferably wherein the oligosaccharyl transferase is PglB from *Campylobacter jejuni.*

Embodiment 27 is the composition of any one of embodiments 1-16 for use in a method of inducing an immune response to *E. coli* (preferably extra-intestinal pathogenic *E. coli*, ExPEC) in a subject.

Embodiment 28 is the use of the composition of any one of embodiments 1-16 in the manufacture of a medicament for inducing an immune response to *E. coli* (preferably extra-intestinal pathogenic *E. coli*, ExPEC) in a subject.

Embodiment 29 is a combination of a first effective amount of *E. coli* O75 antigen polysaccharide and a second effective amount of *E. coli* O6 antigen polysaccharide for use in a method of inducing an immune response to *E. coli*, preferably extra-intestinal pathogenic *E. coli* (ExPEC), in a subject, wherein each of the antigen polysaccharides is independently covalently linked to a carrier protein, and wherein the ratio of the first effective amount to the second effective amount is about 1.2:1 to about 8:1, preferably about 1.5:1 to about 4:1, more preferably about 2:1.

Embodiment 29a is the combination of embodiment 29, wherein the first effective amount and the second effective amount are in the same composition.

Embodiment 29b is the combination of embodiment 29, wherein the first effective amount and the second effective amount are in separate compositions.

Embodiment 29c is the combination of any one of embodiments 29-29b, wherein the subject is in need of said immune response.

Embodiment 30 is the combination of any one of embodiments 29-29c, wherein the immune response limits the severity of or prevents an invasive ExPEC disease in the subject.

Embodiment 31 is the combination of embodiment 30, wherein the invasive ExPEC disease comprises sepsis and/or bacteremia.

Embodiment 32 is the combination of any one of embodiments 29-31, further comprising one or more, preferably all, of effective amounts of *E. coli* O1, O2, O4, O15, O16, O18, O25 antigen polysaccharides, wherein each of the antigen polysaccharides is independently covalently linked to a carrier protein, preferably the O1 antigen is O1A, the O4 is glucosylated, the O6 antigen is O6A, the O18 antigen is O18A, and the O25 antigen is O25B, preferably each of the O1A, O2, glucosylated O4, O6A, O15, O16, O18A, O25B, and O75 antigen polysaccharides comprise the structures of Formulas (O1A), (O2), (O4-Glc+), (O6A), (O15), (O16), (O18A), (O25B), and (O75), respectively, as shown in Table 1, wherein each n is independently an integer of 1 to 100, preferably of 3 to 50, for example 5 to 40, preferably of 5 to 30, for example 7 to 25, for example 10 to 20, and wherein the ratio of O75 antigen polysaccharide to O6 antigen polysaccharide is about 1.2:1 to about 8:1, preferably about 1.5:1 to about 4:1, more preferably about 2:1.

Embodiment 33 is the combination of any one of embodiments 29-32, further comprising effective amounts of from 1 to 15 additional *E. coli* antigen polysaccharides, each independently covalently linked to a carrier protein.

Embodiment 34 is the combination of any one of embodiments 29-33, wherein each of the carrier proteins comprises the amino acid sequence of SEQ ID NO: 3.

Embodiment 35 is the combination of any one of embodiments 29-34, wherein the subject is a human having or at risk of having an *E. coli* (preferably ExPEC) infection or an invasive ExPEC disease.

Embodiment 36 is the combination of any one of embodiments 29-35, wherein the effective amount of the O75 antigen polysaccharide is about 8-16 μg, preferably about 16 μg.

Embodiment 37 is a combination of a first effective amount of *E. coli* O75 antigen polysaccharide and a second effective amount of *E. coli* O6 antigen polysaccharide in the manufacture of a medicament for inducing an immune response to *E. coli*, preferably extra-intestinal pathogenic *E. coli* (ExPEC), in a subject, wherein each of the antigen polysaccharides is independently covalently linked to a carrier protein, and wherein the ratio of the first effective amount to the second effective amount is about 1.2:1 to about 8:1, preferably about 1.5:1 to about 4:1, more preferably about 2:1.

Embodiment 37a is the combination of embodiment 37, wherein the subject is in need of said immune response.

Embodiment 38 is the combination of embodiment 37 or 37a, wherein the immune response limits the severity of or prevents an invasive ExPEC disease in the subject.

Embodiment 39 is the combination of embodiment 38, wherein the invasive ExPEC disease comprises sepsis and/or bacteremia.

Embodiment 40 is the combination of any one of embodiments 37-39, further comprising one or more, preferably all, of effective amounts of *E. coli* O1, O2, O4, O15, O16, O18, O25 antigen polysaccharides in the manufacture of the medicament, wherein each of the antigen polysaccharides is independently covalently linked to a carrier protein, preferably the O1 antigen is O1A, the O4 is glucosylated, the O6 antigen is O6A, the O18 antigen is O18A, and the O25 antigen is O25B, preferably each of the O1A, O2, glucosylated O4, O6A, O15, O16, O18A, O25B, and O75 antigen polysaccharides comprise the structures of Formulas (O1A), (O2), (O4-Glc+), (O6A), (O15), (O16), (O18A), (O25B), and (O75), respectively, as shown in Table 1, wherein each n is independently an integer of 1 to 100, preferably of 3 to 50, for example 5 to 40, preferably of 5 to 30, for example 7 to 25, for example 10 to 20, and wherein the ratio of O75 antigen polysaccharide to O6 antigen polysaccharide is about 1.2:1 to about 8:1, preferably about 1.5:1 to about 4:1, more preferably about 2:1.

Embodiment 41 is the combination of any one of embodiments 37-40, further comprising effective amounts of from 1 to 15 additional *E. coli* antigen polysaccharides, each independently covalently linked to a carrier protein, in the manufacture of the medicament.

Embodiment 42 is the combination of any one of embodiments 37-41, wherein each of the carrier proteins comprises the amino acid sequence of SEQ ID NO: 3.

Embodiment 43 is the combination of any one of embodiments 37-42, wherein the subject is a human having or at risk of having an *E. coli* (preferably ExPEC) infection or an invasive ExPEC disease.

Embodiment 44 is the combination of any one of embodiments 37-43, wherein the effective amount of the O75 antigen polysaccharide in one dose for administration to the subject is about 8-16 μg, preferably about 16 μg.

EXAMPLES

Example 1: Epidemiological Data of *E. coli* Infections

To determine the O-serotype distribution of bacteremia-causing *E. coli*, global surveillance studies were performed. Between 2011 and 2017, more than 3200 *E. coli* bloodstream isolates were collected from patients ≥60 years of age hospitalized in countries within North America, Europe, the Asia-Pacific region, and South America. Each strain was analyzed for O antigen serotype using classical agglutination techniques and sequence-based O-genotyping. See Table 2 below.

Isolated human blood samples were analyzed to determine the identity of pathogens therein and their antibiotic resistance patterns. *E. coli* isolates were obtained from the samples following the analysis. *E. coli* identity was verified by MALDI-TOF MS. Further analysis on the *E. coli* isolates was performed using an antisera-based agglutination assay to determine their O-antigen serotype (DebRoy et al. (2011) Animal health research reviews/Conference of Research Workers in Animal Diseases 12, 169-185). Isolates un-typeable by the agglutination method, were further analyzed by whole-genome sequencing followed by O-genotyping based on O-serotype specific wzy and wzx gene sequences.

TABLE 2

Distribution of the most common bacteremia-associated *E. coli* O-serotypes from a collection of 3217 blood isolates collected globally between 2011 and 2017, based on O-serotyping by agglutination plus O-genotyping of isolates un-typeable by agglutination. Subjects were hospitalized in the following countries: USA, Canada, Argentina, Brazil, UK, Germany, Spain, Italy, The Netherlands, France, Japan, Thailand, South Korea and Australia.

| O-serotype | Prevalence n (%) |
|---|---|
| O25 | 737 (22.9%) |
| O2 | 268 (8.3%) |
| O6 | 261 (8.1%) |
| O1 | 255 (7.9%) |
| O75 | 145 (4.5%) |
| O15 | 110 (3.4%) |
| O8 | 104 (3.2%) |
| O16 | 103 (3.2%) |
| O4 | 96 (3.0%) |
| O18 | 91 (2.8%) |

Stratification of on geographical location in the global set of bacteremia-associated *E. coli* showed a prevalence of the top 10 O-serotypes independent of location, suggesting these to be the predominant O-serotypes globally associated with bacteremia-causing *E. coli.*

In the global set of bacteremia-associated multi-drug resistant *E. coli* isolates (n=345), i.e. those strains that are resistant to at least three classes of clinically relevant antimicrobial drugs, the prevalence of the top 10 O-serotypes is 75.4%.

All information from epidemiology analysis taken together, the 10 predominant O-serotypes could cover an estimated 60-80% of *E. coli*-associated bacteremia infections, assuming coverage of subportions of the un-typeable strains.

A multivalent vaccine covering a significant proportion of bacteremia-causing *E. coli* serotypes would be very useful. The O-serotypes of Table 2 would thus be good candidates for an O-antigen based multivalent vaccine. Such a vaccine could beneficially be prepared using chemical conjugation or bioconjugation technology.

Example 2: Production of *E. coli* O-Antigen Bioconjugates and Resulting Bioconjugate Products Ten (10) bioconjugates were produced, including *E. coli* O1A-EPA bioconjugate, O2-EPA bioconjugate, O4-Glc+-EPA bioconjugate (also referred to as O4-EPA hereinbelow, i.e. in the examples below the bioconjugate of the O4 antigen polysaccharide is the variant wherein O4 is glucosylated, having glycan structure (O4-Glc+) shown in Table 1; description of making this variant using a novel and hitherto unreported and unknown glucosyltransferase GtrS that is capable of specifically modifying an *E. coli* O4 antigen polysaccharide by addition of glucose to produce the *E. coli* glucosylated O4 antigen was provided in detail in PCT/US20/23404, filed on 18 Mar. 2020, incorporated by reference herein), O6A-EPA bioconjugate, O8-EPA bioconjugate, O15-EPA bioconjugate, O16-EPA bioconjugate, O18A-EPA bioconjugate, O25B-EPA bioconjugate, and O75-EPA bioconjugate. The structures of the glycans of these conjugates can be seen in the respective Formulas in Table 1. A composition comprising the 10 bioconjugates is referred to herein as 'ExPEC10V'. A composition comprising the O1A-EPA, O2-EPA, O6A-EPA and O25B-EPA bioconjugates is referred to as 'ExPEC4V' (and was previously described in, for example, WO 2015/124769 and WO 2017/035181). Production of these ten bioconjugates, and exemplary production strains for these bioconjugates, were described in detail in PCT/US20/23404, filed on 18 Mar. 2020, incorporated by reference herein.

*Escherichia coli* W3110 Parental Strain

The non-pathogenic *E. coli* K12 strain W3110 was used as the parental strain for the construction of all ten production strains. The *E. coli* K12 strain W3110 was obtained from the Coli Genetic Stock Center (Yale University, New Haven (Conn.), USA, product number CGSC #4474). Its relevant genotype was previously described (*E. coli* W3110, F-, lambda-, IN(rrnD-rrnE)1, rph-1) and its genomic sequence was previously published (Hayashi K, et al., 2006, Mol. Syst. Biol. 2006.0007 (doi:10.1038/msb4100049). The *E. coli* W3110 strain was genetically modified to enable production of each of the *E. coli* O-antigen bioconjugates (Table 3).

Bioconjugate Production Strains

The "ExPEC4V" and "ExPEC10V" compositions both comprise the O2-EPA and O25B-EPA bioconjugates from the same production strains. The "ExPEC4V" composition comprises the O1A-EPA bioconjugate from the stGVXN4411 or stLMTB10217 production strains, while the "ExPEC10V" composition comprises the O1A-EPA bioconjugate from the stLMTB10217 production strain. The "ExPEC4V" composition comprises the O6A-EPA bioconjugate from the stGVXN4112 production strain, while the "ExPEC10V" composition comprises the O6A-EPA bioconjugate from the stLMTB10923 production strain. Furthermore, the "ExPEC10V" composition comprises the O4-EPA (i.e. (O4-Glc+)-EPA), O8-EPA, O15-EPA, O16-EPA, O18A-EPA, and O75-EPA bioconjugates from production strains that are not used for "ExPEC4V". Different production strains could vary in the plasmids for expression of the EPA carrier protein and/or the oligosaccharyl transferase PglB, as indicated below. An overview of several exemplary production strains is given in Table 3 below.

TABLE 3

Overview of genetic engineering of *E. coli* production strains for O-antigen bioconjugates for ExPEC4V and ExPEC10V vaccine compositions

| | | Genomic mutations | | | Plasmids | |
|---|---|---|---|---|---|---|
| Serotype | Strain name | rfb gene cluster | waaL | gtrABS | pglB | epa |
| O1A (ExPEC4V) | stGVXN4411 | Δrfb::01A rfb upecGVXN_032 | ΔwaaL | — | pGVXN970 | PGVXN1076 |
| O1A (ExPEC4V; ExPEC10V) | stLMTB10217 | Δrfb::01A rfb upecGVXN_032 | ΔwaaL | — | pGVXN1221 | PGVXN1076 |
| O2 | stGVXN4906 | Δrfb::O2 rfb upecGVXN_116 | Δwaal | — | pGVXN971 | pGVXN1076 |
| O4 | BVEC-L-00684 | Δrfb::O4 rfb CCUG11450 | Δwaal | ΔgtrS::gtrS O4 | pGVXN1217 | pGVXN1076 |
| O6A (ExPEC4V) | stGVXN4112 | Δrfb::O6A rfb CCUG11309 | Δwaal | — | pGVXN114 | pGVXN659 |
| O6A (ExPEC10V) | stLMTB10923 | Δrfb::O6A rfb CCUG11309 | Δwaal | — | pGVXN1221 | pGVXN1076 |
| O8 | stLMTB11734 | Δrfb::O8 rfb E2420 | Δwaal | ΔgtrABS | pGVXN970 | pGVXN1076 |
| O15 | stLMTB11738 | Δrfb::O15 rfb OC24891 | Δwaal | ΔgtrABS | pGVXN1221 | pGVXN1076 |
| O16 | stLMTB11739 | Δrfb::O16 rfb OC24208 | Δwaal | ΔgtrABS | pGVXN2381 | pGVXN1076 |
| O18A | BVEC-L-00559 | Δrfb::O18A rfb OC24255 | Δwaal | ΔgtrABS | pGVXN970 | pGVXN1076 |
| O25B | stGVXN4459 | Δrfb::O25B rfb upecGVXN_138 | Δwaal | ΔgtrABS | pGVXN970 | pGVXN1076 |
| O75 | stLMTB11737 | Δrfb::O75 rfb CCUG31 | Δwaal | ΔgtrABS | pGVXN1217 | pGVXN1076 |

Alternative production strains were also prepared and used for some of the bioconjugates, e.g. to find clones with improved yields and/or changes in certain characteristics of the bioconjugates.

O-Antigen Biosynthesis (Rib) Gene Cluster

In all *E. coli* O-antigen production strains, the naturally occurring *E. coli* W3110 genomic O16::IS5-antigen biosynthesis (rfb) gene cluster was replaced by the selected O-antigen-specific biosynthesis clusters from *E. coli* strains of the selected serotype, encoding for the serotype-specific O-antigen structures (see Table 1 for these O-antigen structures). The ten donor rfb clusters were selected or confirmed after whole-genome analysis of *E. coli* blood isolates. Replacement of the W3110 O16::IS5 rfb gene cluster, which is defective in O-antigen biosynthesis, has been achieved in a single homologous recombination event. In case of the O16 and O18A rfb gene clusters, the donor DNA recombined via the flanking gnd and rmlCA genes, while the rfb gene cluster for the other strains recombined via the flanking gnd and galF genes. Sequences of the rfb clusters in the production strains are provided in SEQ ID NOs: 9 and 11-19.

O-Antigen Ligase (waaL) Gene

All *E. coli* O-antigen production strains carry an artificially introduced deletion of the *E. coli* W3110 genomic O-antigen ligase encoded by the waaL gene. In the ΔwaaL strains the transfer of the O-antigen to lipid A is disrupted, which instead directs transfer of the O-antigen to the carrier protein to increase product yield.

O-Antigen Glucosylation (gtrABS) Genes

In the *E. coli* O8, O15, O16, O18A, O25B, and O75 production strains the *E. coli* W3110 genomic gtrABS genes, which are responsible for O16 O-antigen glucosylation, have been deleted. While the gtrA and gtrB genes in different serotypes are highly homologous and interchangeable, the gtrS gene encodes a serotype-specific O-antigen glycosyl transferase. In *E. coli* W3110 GtrS can transfer a glucose (Glc) residue to the GlcNAc sugar in the α-L-Rha-(1→3)-D-GlcNAc motif of the *E. coli* O16 O-antigen. In the *E. coli* O1A, O2 and O6A production strains no deletion or replacement of the gtrABS gene has occurred. These O-antigens miss the α-L-Rha-(1→3)-D-GlcNAc motif that is the natural substrate for *E. coli* O16 gtrS. In the *E. coli* O4 production strain, the W3110 gtrS gene has been replaced with the *E. coli* O4 gtrS gene to accommodate proper glucosylation of the *E. coli* O4 O-antigen (a coding sequence of the *E. coli* O4 gtrS gene is provided herein as SEQ ID NO: 5 and an amino acid sequence of *E. coli* O4 GtrS protein is provided herein as SEQ ID NO. 4; see e.g. also PCT/US20/23404, filed on 18 Mar. 2020).

Oligosaccharyl transferase PglB

All *E. coli* O-antigen production strains expressed a variant of the *C. jejuni* glycosyl transferase PglB, which can transfer the O-antigen onto an amino acid consensus sequence on a carrier protein by N-glycosylation. PglB has broad substrate recognition, but due to low product yields several production strains were prepared expressing a PglB variant having modified substrate specificities, which resulted in improved product yield (see e.g. WO 2016/107818, WO 2016/107819). The pglB gene was placed behind an Isopropyl β-D-1-thiogalactopyranoside (IPTG) inducible promoter on a plasmid. Table 4 below lists the PglB variants encoded by the plasmids used for production of the *E. coli* O-antigen production strains for the bioconjugates for the ExPEC4V and ExPEC10V compositions described above. Further plasmids with variation in vector backbone, antibiotic resistance marker, and/or alternative PglB variants have also been tested successfully for bioconjugate production.

TABLE 4

PglB and EPA plasmids used in *E. coli* O-antigen Production Strains

| Plasmid name | Gene | Description[1] |
|---|---|---|
| pGVXN114 | pglB | *C. jejuni* codon usage; SpR |
| pGVXN970 | pglB | *E. coli* codon usage optimized; SpR |
| pGVXN971 | $pglB^{N534Q}$ | *E. coli* codon usage optimized; The natural glycosylation site of PglB was inactivated; SpR |
| pGVXN1217 | $pglB^{N311V}$ | *E. coli* codon usage optimized; Substrate optimized PglB; SpR |
| pGVXN1221 | $pglB^{N311V,K482R,D483H,A669V}$ | *E. coli* codon usage optimized; Substrate optimized PglB; SpR |
| pGVXN2381 | $pglB^{Y77H,S80R,Q287P,K289R,N311V}$ | *E. coli* codon usage optimized; Substrate optimized PglB; SpR |
| pGVXN659 | EPA-4 | EPA with four bioconjugation sites; AmpR |
| pGVXN1076 | EPA-4 | EPA with four bioconjugation sites; KanR |

[1]SpR, spectinomycin resistant; AmpR, ampicillin resistant; KanR, kanamycin resistant Optimal PglB variants for each bioconjugate of the ten *E. coli* O-antigens in ExPEC10V were determined as described in more detail in e.g. PCT/US20/23415, filed on 18 Mar. 2020, incorporated in its entirety by reference herein.

Carrier Protein (EPA)

All *E. coli* O-antigen production strains expressed a genetically detoxified *P. aeruginosa* ADP-ribosyltransferase toxoid (EPA) as a carrier protein for the O-antigen. The EPA toxoid differs from wild-type EPA toxin in two residues: Leu552 was changed to Val and Glu553 (in the catalytic domain) was deleted. Glu553 deletions were reported to significantly reduce toxicity. In addition to the detoxification mutation, four (EPA-4) consensus N-glycosylation site motifs were introduced. The epa gene was placed behind a 1-Arabinose (Ara) inducible promoter on a plasmid (Table 4). Table 4 is limited to the plasmids used in production strains for bioconjugates used in the “ExPEC4V” and “ExPEC10V” compositions described above. Plasmids with variation in vector backbone, antibiotic resistance marker, and/or EPA variants, e.g. varying in the number of consensus N-glycosylation site motifs (e.g. having two such motifs, EPA-2), have also been tested successfully for bioconjugate production.

Example 3: Optimizing the Oligosaccharyltransferase for Generation of Bioconjugates of *E. coli* O-Antigens Yield optimization for bioconjugate production can be achieved by modification of the *C. jejuni* oligosaccharyl transferase PglB, which can lead to a more efficient or higher degree of N-glycosylation of the O-antigen of interest to the EPA carrier protein. In an *E. coli* strain for production of bioconjugate with glucosylated O4 (O4-Glc+) O-antigen polysaccharide, such optimization strategy was applied and resulted in an (O4-Glc+)-specific optimized PglB variant improving bioconjugate product yield.

In this approach, an O4-Glc+O-antigen polysaccharide producing strain containing an EPA-expression plasmid was transformed with a variety of different PglB expression plasmids, each of which contained different amino acid substitutions in the PglB protein, altering substrate specificity. Bioconjugate production level and profile of each strain was assessed at shake-flask level in osmotic shock experiments, and readout was performed by capillary electrophoresis immunoassays on the periplasmic extract using O4-Glc+-specific monoclonal antibodies.

One of the tested PglB variants containing an N311V amino acid substitution was found to improve product yield of glucosylated O4 bioconjugates significantly (see PCT/US20/23415, filed on 18 Mar. 2020, incorporated in its entirety by reference herein).

In a further improvement where the N311V PglB-variant was further modified, an Y77H amino acid substitution further enhanced O4-Glc+-specific product yield and showed an increased degree of di- and tri-glycosylated product compared to the N311V PglB-variant, where other modifications were found to be neutral or had a negative effect on product yield (see PCT/US20/23415, filed on 18 Mar. 2020, incorporated in its entirety by reference herein). Plasmid pLMTB4008 (SpR) encodes *E. coli* codon usage optimized, (O4-Glc+)-substrate optimized, PglB variant with mutations Y77H and N311V.

The PglB variant with optimized substrate specificity for O4-Glc+O-antigen polysaccharide, containing N311V and Y77H amino acid substitutions relative to wild-type (wt) *C. jejuni* glycosyl transferase PglB, was found to double bioconjugate yield compared to the first round optimized PglB-N311V variant.

Similarly using screens, the most optimal yielding PglB variants were also determined for *E. coli* O-antigen bioconjugate production of the other nine serotypes in the ExPEC10V composition, see e.g. PCT/US20/23415, filed on 18 Mar. 2020, incorporated in its entirety by reference herein.

For bioconjugates having the O1A, O6A, or O15 antigen polysaccharide, PglB with amino acid mutations N311V, K482R, D483H, and A669V was found to give the highest yields.

For bioconjugates having the O2, O8, O18A, or O25B antigen polysaccharide, wild-type PglB (i.e. not having amino acid mutations at positions 77, 80, 287, 289, 311, 482, 483 and 669) was found to give the highest yields.

For bioconjugates having the O16 antigen polysaccharide, PglB with amino acid mutations Y77H, S80R, Q287P, K289R, and N311V was found to give the highest yields.

For bioconjugates having the O75 antigen polysaccharide, PglB with amino acid mutation N311V was found to give the highest yields.

These results showed that the optimal PglB variant is different for different O-antigens, and that the optimal PglB variant for producing a bioconjugate with a given O-antigen polysaccharide is unpredictable.

Example 4: Quality Attributes of Bioconjugates of O-Antigens from 10 *E. coli* Serotypes O-glycan residues of the target O-antigens are structurally diverse and have variable repeating units. The specificity and affinity of the glycosyl transferase PglB is linked to the glycan structure. Thus, making a bioconjugate that has the desired quality attributes, e.g., purity, glycan/protein ratio, etc., is a challenging, non-straightforward, task. The right combination of PglB and EPA carrier protein determines the yield and may influence glycosylation efficiency. By optimizing the PglB and carrier proteins, bioconjugates having the desired quality attributes were produced. It may be also important to maintain a lower threshold value of total carrier protein, particularly when one or more O-antigen bioconjugates are combined together and administered in a single composition or vaccine, because very high amounts of carrier protein may lead to immunological interference. In order to avoid such a phenomenon, conjugates having a higher glycan/protein ratio are preferred. Hence, for ExPEC10V vaccine, bioconjugates with at least comparable (to the previously described ExPEC4V vaccine that has been subject to clinical trials) glycosylation ratio were developed.

The bioconjugates were each produced by culturing the respective host cells (Example 2, Table 3) in bioreactors (10 L and/or 200 L volumes) and expression of the bioconjugates, following methods previously described. Each drug substance was manufactured batch-wise by bacterial fed-batch fermentation to generate biomass containing the expressed bioconjugates of the corresponding polysaccharide serotype. Cells were cultured and induced with IPTG and arabinose. The bioconjugates were isolated from the periplasm of the cells in the bioreactor cultures by osmotic shock followed by chromatographic purification. This process was performed for each of the 10 bioconjugates.

The *E. coli* O-antigen bioconjugates thus prepared that are drug substances (DSs) for ExPEC10V and ExPEC4V showed comparable critical quality attributes: (1) process-related purity (measured by RP-HPLC) was higher than 95%, (2) polysaccharide/protein ratio ranged between about 0.1-0.5, mostly between 0.15 and 0.45, (3) bacterial endotoxin (Ph. Eur. 2.2.3) was less than 0.5 EU/μg polysaccharide. The average length of the individual polysaccharide chains was typically between about 10-20 repeating units (measured using high resolution SDS-PAGE).

The structures of the polysaccharide repeat units were confirmed (by NMR and MS/MS of the conjugates, intact or trypsin-digested) to be the ones shown in the Formulas for the corresponding serotypes in Table 1, for all ten bioconjugates that are DSs for the ExPEC10V composition described above.

ExPEC10V drug product (DP) comprises a mixture of the ten monovalent DSs described above.

Example 5: Toxicology of ExPEC10V Vaccine

A single-dose pilot toxicity and local tolerance study (non-GLP) with ExPEC10V was conducted in female NZW rabbits. One group (n=2) received an intramuscular (IM) injection (on Day 0) of the control (saline), and a second group (n=4) received an IM injection of ExPEC10V at 105.6 μg total polysaccharide (PS)/dose (9.6:9.6:9.6:9.6:9.6:9.6:9.6:9.6:19.2:9.6 μg PS per dose, for respectively O-serotypes O1A, O2, O4, O6A, O8, O15, O16, O18A, O25B and O75) using a dosing volume of 0.6 mL (176 μg PS/mL). Necropsy was performed on Day 2.

There were no mortalities observed. In addition, there were no vaccine-related effects noted for clinical observations (including injection site effects using Draize scoring), body weight, food consumption, and body temperature. Histopathologically, there were no vaccine-related changes observed at the administration site or draining (iliac) lymph node. A minimal increase in germinal center formation in the spleen was observed in one out of four treated animals (Day 2), and was considered a normal, immunological response to the injected vaccine. Overall, the administration of a single IM dose of ExPEC10V to female rabbits was well-tolerated.

Example 6: Immunogenicity of ExPEC10V Blended Formulation in Rabbits

An ExPEC4V vaccine (comprising bioconjugates of *E. coli* O1A, 02, 06A, and O25B serotypes) has previously been shown to be immunogenic for these four serotypes in rats, rabbits, and humans (see e.g. WO 2015/124769; WO 2017/035181; Huttner et al, 2017, Lancet Infect Dis, [http] hypertext transfer protocol://dx.doi.org/10.1016/S1473-3099 (17) 30108-1; R W Frenck Jr, et al, 2019, Lancet Infect Dis 19 (6): 631-640, hypertext transfer protocol://dx.doi.org/10.1016/S1473-3099 (18) 30803-X). Immunogenicity of the bioconjugates of *E. coli* serotypes O4-Glu+, O8, O15, O16, O18A, and O75 (all having EPA-2 as carrier protein) when separately administered (monovalent) to rats confirmed that also each of these bioconjugates was immunogenic, since ELISA data indicated that each of these bioconjugates could elicit high levels of *E. coli* O-antigen specific antibodies (not shown).

Immunogenicity of the 10-valent vaccine that contained a mixture of the 10 bioconjugates as described above was also tested. New Zealand White (NZW) rabbits (female, 12-16 weeks old) received 3 intramuscular immunizations with ExPEC10V or saline administered 2 weeks apart (Table 5; administration at days 0, 14, and 27). The 10 polysaccharides that are part of the ExPEC10V vaccine used in these experiments were conjugated to the carrier protein EPA containing 4 sites of glycosylation (EPA-4). The vaccine was formulated in 3 different doses: Group 1 ('high dose'): 8 μg/dose of O1A, O2, O6A, O4, O8, O15, O16, O18 and O75 and 16 μg/dose of O25B; Group 2 ('medium dose'): 4 μg/dose of O2, O4, O8, O15, O16, O18 and O75, 8 μg/dose of O1A and O6A and 16 μg/dose of O25B; Group 3 ('low dose'): 0.4 μg/dose of O2, O4, O8, O15, O16, O18 and O75, 0.8 μg/dose of O1A and O6A and 1.6 μg/dose of O25B. Animals from the control group (Group 4) received only saline (0.9% (w/v) sodium chloride solution) (Table 5).

Antibody responses were evaluated at day 0 (pre-immunization) and days 14, 27 and 42 post-immunization. Serum antibody levels induced by each of the bioconjugates included in the vaccine and the carrier protein EPA were measured by ELISA (total IgG), using type-specific LPS as coating material. The antibody titers were reported as EC50 values that correspond to the half maximal effective concentration based on duplicates of 12-step titration curves plotted in a 4-parameter logistic nonlinear regression model. Functional activity was determined by OPK.

TABLE 5

Description of experimental groups.

| Experimental groups | Dosing (μg/PS) O1A:O2:O6A:O25B:O4:O8:O15:O16:O18A:O75 | Sample size |
|---|---|---|
| Group 1 (high dose) | 8:8:8:16:8:8:8:8:8:8 | 7 |
| Group 2 (medium dose) | 8:4:8:16:4:4:4:4:4:4 | 7 |
| Group 3 (low dose) | 0.8:0.4:0.8:1.6:0.4:0.4:0.4:0.4:0.4:0.4 | 7 |
| Group 4 (control) | 0.9% (w/v) sodium chloride solution | 7 |

Figure 1B:
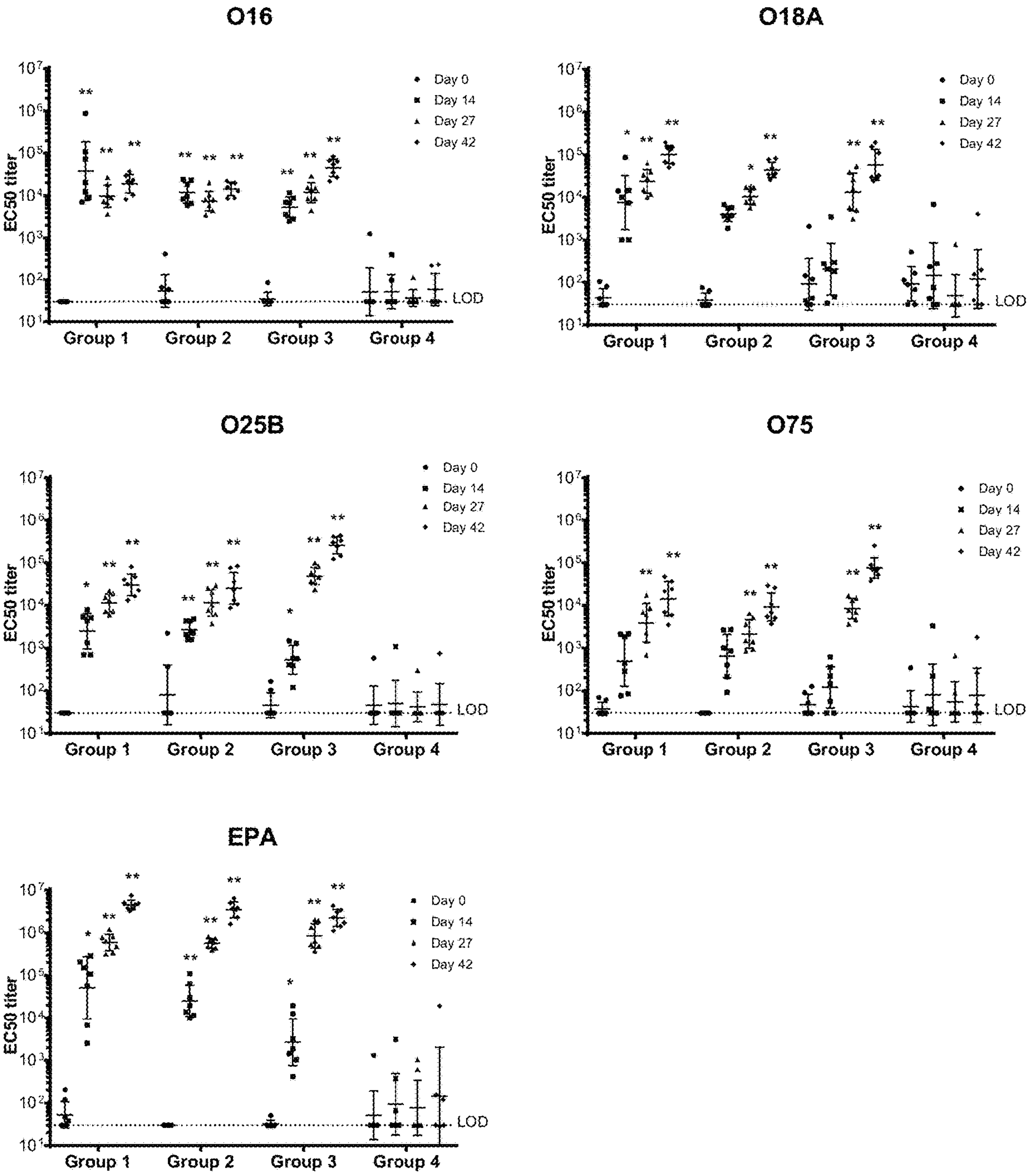

Results are shown in FIG. 1 and summarized in Table 6.

TABLE 6

Summary of *E. coli* O-antigen specific antibody responses induced by ExPEC10V in NZW rabbits.

| ExPEC10V dose | O1A | O2 | O6A | O25B | O4 | O8 | O15[#] | O16 | O18A | O75 |
|---|---|---|---|---|---|---|---|---|---|---|
| | Antibody responses day 14 post-vaccination | | | | | | | | | |
| High | * | ** | ** | * | ** | ns | ** | ** | * | ns |
| Mid | * | ** | ** | ** | ** | ns | ** | ** | ns | ns |
| Low | * | * | * | * | * | ns | ** | ** | ns | ns |
| | Antibody responses day 27 post-vaccination | | | | | | | | | |
| High | ** | ** | ** | ** | ** | * | ** | ** | ** | ** |
| Mid | ** | ** | ** | ** | ** | * | ** | ** | * | ** |
| Low | ** | ** | ** | ** | ** | * | ** | ** | ** | ** |
| | Antibody responses day 42 post-vaccination | | | | | | | | | |
| High | ** | ** | ** | ** | ** | ** | ** | ** | ** | ** |
| Mid | ** | ** | ** | ** | ** | ** | ** | ** | ** | ** |
| Low | ** | ** | ** | ** | ** | ** | ** | ** | ** | ** |

Serotype-specific antibody responses in which p values were statistically significant are shown by asterisks.

Serotype-specific antibody responses in which p values were not statistically significant are designated as ns.

Wilcoxon Rank Sum test with Bonferroni correction for multiple comparisons.

Comparisons ExPEC10V vaccinated animals (Group 1, 2 and 3) versus saline control (Group 4).

* $p \leq 0.05$,

** $p \leq 0.01$.

[#]P values were statistically significant after excluding an outlier animal from the control group (sensitivity analysis).

Figure 2A:
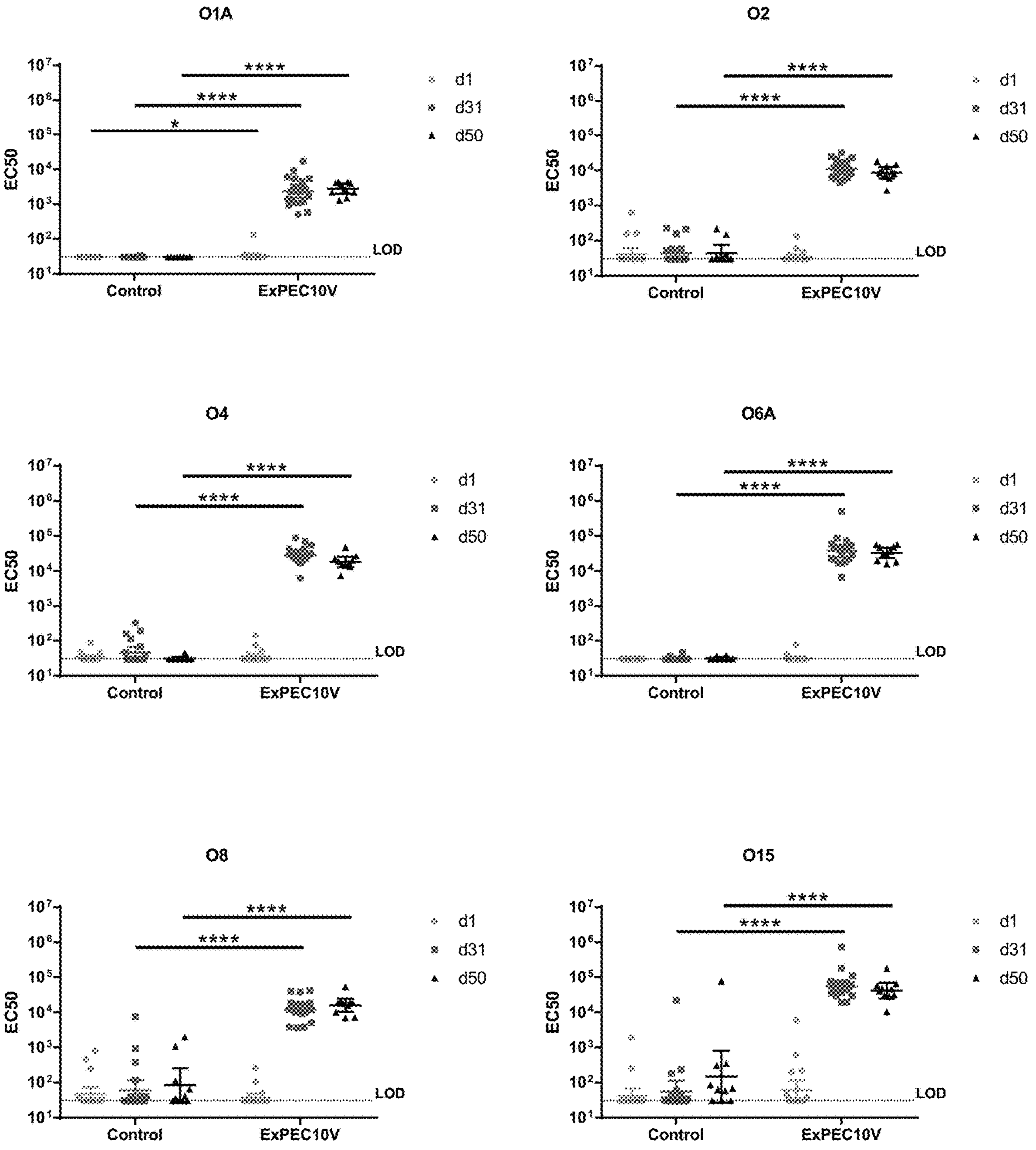
FIG. 2A-2B shows antibody responses induced by ExPEC10V. New Zealand White rabbits received 3 intramuscular immunizations with ExPEC10V (105.6 μg total polysaccharide) or 0.9% w/v sodium chloride solution (control). IgG titers were determined by ELISA at day 1 (pre-immunization, n=20/group), day 31 (post-immunization, n=20/group) and day 50 (post-immunization, n=10/group). Plots show individual titers and geometric mean±95% confidence interval for each group. Differences in IgG titers between the ExPEC10V and control group were analyzed using a Tobit model with a likelihood ratio test. P-values≤0.05 were considered significant. * $P \leq 0.05$, **** $P \leq 0.0001$.
Figure 2B:
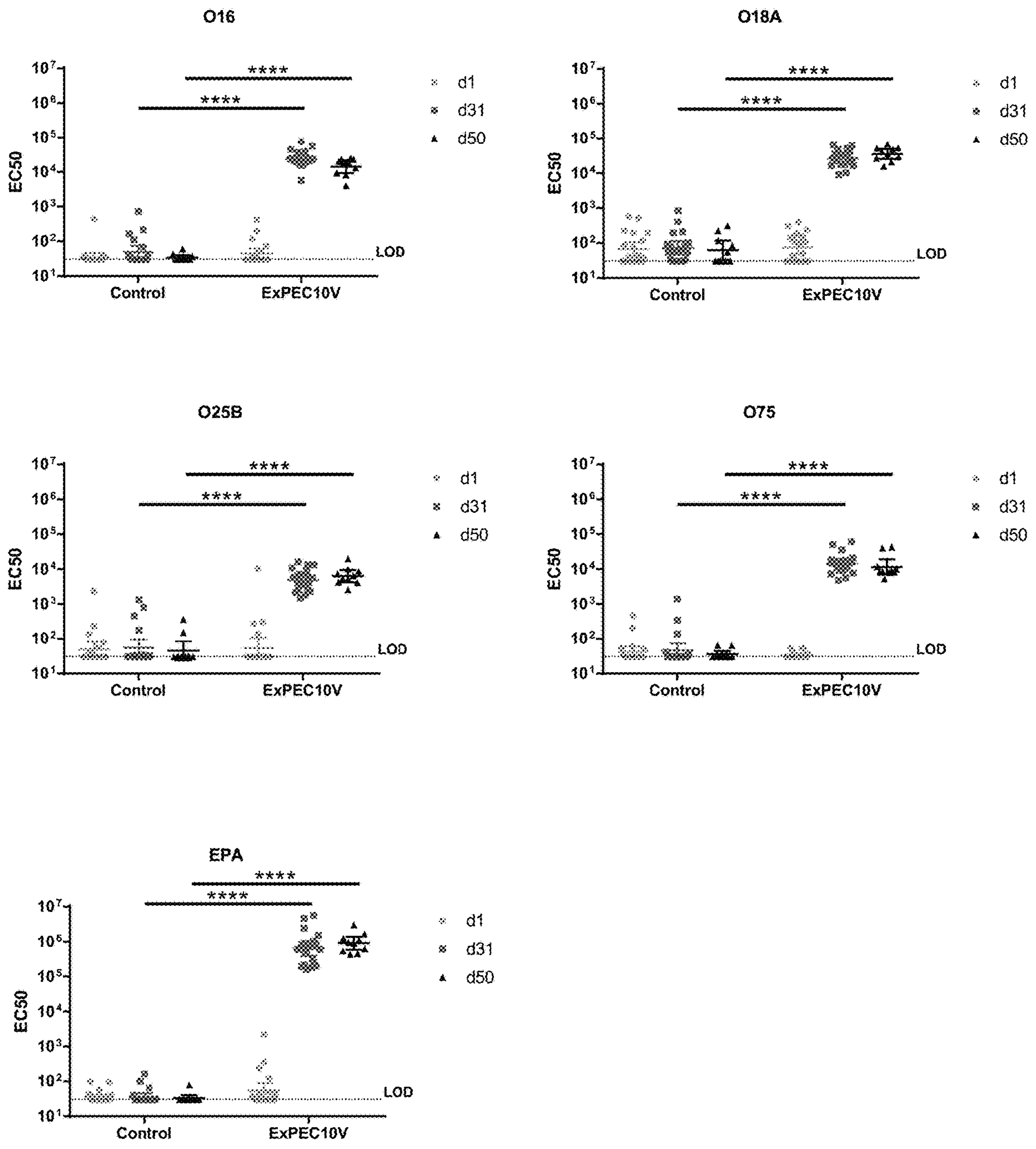

The high dose of ExPEC10V (Group 1) induced significantly higher IgG antibody levels at all time-points investigated (Days 14, 27 and 42 post-immunization) when compared to saline control for O1A, O2, O4, O6A, O16, O18A and O25B (FIG. 2, Table 6). Significantly higher antibody titers induced by O8 and O75 conjugates when compared to saline control were observed at Days 27 and 42 post-immunization (FIG. 1, Table 6).

The medium dose of ExPEC10V (Group 2) and the low dose (Group 3) induced significantly higher antibody levels at all time-points investigated (Days 14, 27 and 42 post-immunization) when compared to saline control for O1A, O2, O4, O6A, O16 and O25B (FIG. 1, Table 6). Significantly higher antibody titers induced by O8, O18A and O75 conjugates when compared to saline control were observed at Days 27 and 42 post-immunization suggesting that the boost dose in rabbits increases the response to these O-serotypes (FIG. 1, Table 6).

For O15 conjugates, sensitivity analysis omitting an outlier animal from the control group showed that all three doses of ExPEC10V vaccine induced a significant increase in antibody responses when compared to saline control at Days 14, 27 and 42 post-immunization (FIG. 1, Table 6).

Antibodies induced by the carrier protein EPA were significantly higher than EPA antibody titers in the saline-treated (control) group for the three doses of ExPEC10V tested (high, medium and low) at all time points investigated (Days 14, 27 and 42) (FIG. 1).

Between dose comparisons (not shown) showed that at Day 14 post-vaccination, the high dose of ExPEC10V induced significantly higher antibody responses when compared to the low dose for most of the conjugates tested (O1A, O2, O4, O6A, O15, O16, O18A and O25B). The medium dose of ExPEC10V also induced significantly higher antibody responses compared to the low dose for O1A, O2, O4, O18A, O25B and O75. For O8 conjugate, all three formulations of ExPEC10V induced similar levels of antibodies at Day 14 post-vaccination.

The low dose of ExPEC10V induced a significant increase in antibody responses at Day 42 post vaccination (after a prime and two boost doses) when compared to the high and medium doses of ExPEC10V for O1A, O2, O4, O16, O25B and O75 conjugates. These findings are in line with other experiences with conjugate vaccines, where for instance no clear relationship between dose and the magnitude of the antibody response to primary vaccination was observed in infants vaccinated with pneumococcal conjugate vaccine (Poolman J T, et al. Expert Rev Vaccines. 2013, 12(12):1379-94).

There were no significant differences between the three doses of ExPEC10V tested at Day 42 post-vaccination for O6A, O8 and O15 conjugates. For the O18A conjugate, the high dose of ExPEC10V induced a significantly higher antibody response when compared to the medium dose at Day 42 post-vaccination.

For the carrier protein (EPA), the high and medium dose of ExPEC10V induced significantly higher antibody responses when compared to the low dose at day 14 post-vaccination. The high dose of the vaccine also induced significantly higher antibody responses when compared to the low dose at day 42 post-vaccination.

In conclusion, the three formulations of ExPEC10V (high, medium and low), administered via intramuscular injection on Days O, 14, 27 are immunogenic in rabbits.

So far, functional antibodies capable of killing *E. coli* strains induced by this vaccine in rabbits were shown for serotypes O1A, O2, O4, O6A, O15, O16 and O25B.

In a further experiment, a GMP batch of the ExPEC10V vaccine (see Example 4 above for production) was prepared and injected into NZW rabbits as part of a toxicology study (Table 7). In this study, NZW rabbits (males and females) received 3 intramuscular injections (0.6 mL) of the ExPEC10V vaccine (day 1, 15 and 29) and a control group received 0.9% (w/v) sodium chloride solution (saline). Each dose of the vaccine contained 9.6 μg polysaccharide (PS) for serotypes O1A, O2, O4, O6A, O8, O15, O16, O18A and O75 and 19.2 μg PS for serotypes O25B, corresponding to 105.6 μg total PS (176 μg total PS/mL) and 382.8 μg of total EPA (638 g EPA/mL). IgG titers against O-antigens and carrier proteins (EPA) were determined from samples collected during the pre-treatment period (day 1) and days 31 and 50 post-immunization.

A significant increase in antibody responses against all O-antigens and the carrier protein EPA were observed at day 31 and 50 post-vaccination in the group that received ExPEC10V when compared to the control group that received only saline (FIG. 2, Table 8). For O1A serotype, a significantly higher antibody response was also observed at day 1 (baseline) when vaccinated animals were compared with the controls. These results suggest that some animals were pre-exposed to *E. coli* or have antibodies that cross-react with O1A-LPS.

TABLE 7

Experimental groups and ExPEC10V dose used in NZW rabbits.

| Groups | Treatment | Dose | Dosing days | Main (day 31) (males/ females) | Recovery (day 50) (males/ females) |
|---|---|---|---|---|---|
| 1 | control | 0 | 1, 15, 29 | 10 | 10 |
| 2 | ExPEC10V | 105.6 μg PS* | 1, 15, 29 | 10 | 10 |

*Each dose (0.6 mL dosing volume) contains 9.6:9.6:9.6:9.6:9.6:9.6:9.6:9.6:19.2:9.6 μg polysaccharide (PS) for serotypes O1A, O2, O4, O6A, O8, O15, O16, O18A, O25B, O75, respectively (176 μg total PS/mL). Each dose contains 382.8 μg EPA protein (638 μg EPA/mL).

TABLE 8

Immunogenicity of ExPEC10V in NZW rabbits as part to a toxicology study.

| Treatment | Antibody responses day 14 post-vaccination | | | | | | | | | |
|---|---|---|---|---|---|---|---|---|---|---|
| ExPEC10V | O1A | O2 | O6A | O25B | O4 | O8 | O15 | O16 | O18A | O75 |
| Day 31 | **** | **** | **** | **** | **** | **** | **** | **** | **** | **** |
| Day 50 | **** | **** | **** | **** | **** | **** | **** | **** | **** | **** |

Antibody responses induced by ExPEC10V. Serotypes in which a significant increase in antibody responses was observed in the vaccine group compared to control are shown by asterisks. Tobit model with a likelihood ratio test.
**** $p \leq 0.0001$.

Example 7: Phase 1/2a Trial with the ExPEC10V Vaccine in Humans

At present, there is no vaccine available to prevent IED. The serotypes comprising the ExPEC10V vaccine (O1A, O2, O4, O6A, O8, O15, O16, O18A, O25B and O75) were selected to address invasive disease caused by the majority of clinically relevant ExPEC strains that also represent the majority of ExPEC isolates causing antimicrobial resistant IED, including ST131. The selected serotypes are representative for the ten prevalent ExPEC O-serotypes causing bloodstream infections in the older population and responsible for approximately 70% of bloodstream infections caused by ExPEC.

Since the mechanism of action of conjugate vaccines in the prevention of invasive disease is not expected to be affected by antibiotic resistance mechanisms, it is believed that ExPEC10V vaccine provides protection against IED caused by drug-resistant- and drug-susceptible O1A, O2, O4, O6A, O8, O15, O16, O18A, O25B and O75 serotypes.

There is preceding clinical experience with ExPEC4V, an earlier vaccine candidate which comprised a subset of four of the *E. coli* O-antigen conjugates (O1A, O2, O6A and O25B) also found in ExPEC10V. Based on the results from four completed clinical studies (two phase 1 studies, two phase 2 studies), ExPEC4V was well-tolerated by the study participants and no vaccine-related safety signals were observed at doses up to 16 μg polysaccharide (PS) per serotype (O1A, O2, O6A and O25B). Most adverse events (AEs) were Grade 1 and 2, very few Grade 3 AEs were reported. Late-onset solicited local AEs (AEs which start after Day 5 post-vaccination) were observed mainly with the higher doses of ExPEC4V. In each study, the ExPEC4V vaccine was shown to be immunogenic, demonstrating a dose-dependent vaccine immune response, and O-antigen specific Immunoglobulin G (IgG) titer increases, as measured by enzyme-linked immunosorbent assay (ELISA). Functional activity of the antibodies was demonstrated with an ExPEC4V-optimized opsonophagocytic killing assay (OPKA). Co-analysis of ELISA and OPKA test results showed correlation between the assay responses (Pearson correlation coefficients ≥0.61 and ≥0.48 for Day 30 and Day 360, respectively in a Phase 2 clinical trial [study 4V-BAC2001]), substantiating the use of ELISA as a primary measure of ExPEC4V antibody titers and to predict functional antibody activity. Analysis of the immunogenicity data has demonstrated the durability of the immune response through three years after vaccination with ExPEC4V. It has now also been observed that sera from humans vaccinated with ExPEC4V and that had high titers of serotype-specific opsonophagocytic antibodies, when passively transferred into mice that were subsequently intraperitoneally challenged with *E. coli* strains of O25B or O2 serotype, were able to mediate protection in vivo, demonstrated by significant reduction in *E. coli* colony counts (CFU) in blood, spleen and liver (data not shown). Hence, ExPEC4V-specific opsonophagocytic human antibodies mediate bacterial killing in vivo, which is in agreement with other conjugate vaccines in which the proposed mechanism of protection is by induction of opsonophagocytic antibodies that mediate bacterial killing.

ExPEC10V includes a total of ten serotypes and increases coverage from about 50% (ExPEC4V) to approximately 70% of bloodstream infections caused by ExPEC in adults aged 60 years and older. Based on the clinical experience with ExPEC4V, and on the pre-clinical data for ExPEC10V as discussed in the examples above, it was expected that administration of ExPEC10V will induce immune responses to *E. coli* serotypes O1A, O2, O4, O6A, O8, O15, O16, O18A, O25B and O75 also in humans. Each of the O-antigen polysaccharides (PSs) are separately bioconjugated to the carrier protein, a genetically detoxified form of exotoxin A (EPA) derived from *Pseudomonas aeruginosa*, and its production has been described above. The O4 PS is the glucosylated form, having the structure of Formula (O4-Glc+) in Table 1.

A randomized, observer-blind, first-in-human phase 1/2a study to evaluate the safety, reactogenicity, and immunogenicity of three different doses of the ExPEC10V vaccine is conducted in humans aged 60 to 85 years in stable health (study 10V-BAC1001). The study design includes 2 cohorts: A total of 824 participants are enrolled in the study with 404 participants (100 participants/ExPEC10V dose) aged ≥60 to ≤85 years in stable health in Cohort 1 and an additional of approximately 420 participants (280 in ExPEC10V group and 140 in placebo group) aged ≥60 years in stable health with a history of UTI in the past 5 years in Cohort 2 (originally it was planned to include 600 participants in Cohort 2, but this number was reduced during the study to approximately 420 with some adaptations to the protocol).

Objectives and Endpoints

Cohort 1—Phase 1/2a Observer-Blind Period with Open-Label Long-Term Follow-Up Period (N=404):

| Objectives | Endpoints |
|---|---|
| **Primary** | |
| To evaluate the safety and reactogenicity of different doses of ExPEC10V in participants ≥60 to ≤85 years of age | Solicited local and systemic adverse events (AEs) collected for 14 days post-vaccination (from Day 1 to Day 15)<br>Unsolicited AEs collected from the administration of the study vaccine until 29 days post-vaccination (from Day 1 to Day 30)<br>Serious adverse events (SAEs) collected from the administration of the study vaccine until Day 181 |
| To evaluate the dose-dependent immunogenicity of ExPEC10V on Day 15 in participants ≥60 to ≤85 years of age | Antibody titers for ExPEC10V, as determined by multiplex electrochemiluminescent (ECL)-based immunoassay and multiplex opsonophagocytic assay (MOPA) on Day 15 |
| **Secondary** | |
| To evaluate the correlation between multiplex ECL-based immunoassay (total antibody) and MOPA (functional antibody) serum titers on Day 15 | Antibody titers for ExPEC10V, as determined by multiplex ECL-based immunoassay and MOPA on Day 15 |
| To evaluate the dose-dependent immunogenicity of ExPEC10V on Days 30 and 181 in participants ≥60 to ≤85 years of age | Antibody titers for ExPEC10V, as determined by multiplex ECL-based immunoassay and MOPA on Days 30 and 181 |
| To evaluate, in the long-term follow-up (LTFU) period, the safety of the ExPEC10V dose selected for further clinical development based on the Day 30 primary analysis in participants ≥60 to ≤85 years of age | SAEs related to the study vaccine or study procedures collected from Day 182 until the end of the study |
| To evaluate, in the LTFU period, the immunogenicity of the ExPEC10V dose selected for further clinical development based on the Day 30 primary analysis | Antibody titers for ExPEC10V, as determined by multiplex ECL-based immunoassay and MOPA at Year 1 (Day 366), Year 2 (Day 731) and Year 3 (Day 1096) |

Cohort 2—Double-Blind Period with Double-Blind Long-Term Follow-Up Period (N=420):

| Objectives | Endpoints |
|---|---|
| Primary | |
| To evaluate the safety and reactogenicity of the selected dose of ExPEC10V in participants ≥60 years of age with a history of UTI in the past 5 years | Solicited local and systemic AEs collected for 14 days post-vaccination (from Day 1 to Day 15) |
| | Unsolicited AEs collected from the administration of the study vaccine until 29 days post-vaccination (from Day 1 to Day 30) |
| | SAEs collected from the administration of the study vaccine until Day 181 |
| To evaluate the immunogenicity of the selected dose of ExPEC10V on Day 30 in participants ≥60 years of age with a history of UTI in the past 5 years | Antibody titers for ExPEC10V, as determined by multiplex ECL-based immunoassay and MOPA on Day 30 |
| Secondary | |
| To evaluate the correlation between multiplex ECL-based immunoassay (total antibody) and MOPA (functional antibody) serum titers on Day 30 in participants ≥60 years of age with a history of UTI in the past 5 years | Antibody titers for ExPEC10V, as determined by multiplex ECL-based immunoassay and MOPA on Day 30 |
| To evaluate the immunogenicity of the selected dose of ExPEC10V on Days 15 and 181 in participants ≥60 years of age with a history of UTI in the past 5 years | Antibody titers for ExPEC10V, as determined by multiplex ECL-based immunoassay on Days 15 and 181 and MOPA on Day 181 |
| To evaluate, in the LTFU period, the safety of the selected dose of ExPEC10V in participants ≥60 years of age with a history of UTI in the past 5 years | SAEs related to the study vaccine or study procedures collected from Day 182 until the end of the study |
| To evaluate, in the LTFU period, the immunogenicity of the selected dose of ExPEC10V in participants ≥60 years of age with a history of UTI in the past 5 years | Antibody titers for ExPEC10V, as determined by multiplex ECL-based immunoassay and MOPA at Year 1 (Day 366), Year 2 (Day 731) (not applicable for MOPA), and Year 3 (Day 1096) |
| Exploratory | |
| To evaluate the effect of ExPEC10V on the intestinal (stool) microbiome by metagenomic analyses | Metagenomics of stool samples from a selected subset of participants to evaluate the effect of ExPEC10V on:<br>Prevalence of pathogens (e.g., *Clostridium difficile*) in the intestinal flora<br>Prevalence of ExPEC10V serotypes in the intestinal flora |

Overall Design

This is a randomized, multicenter, interventional study including two cohorts.

Figure 3A:
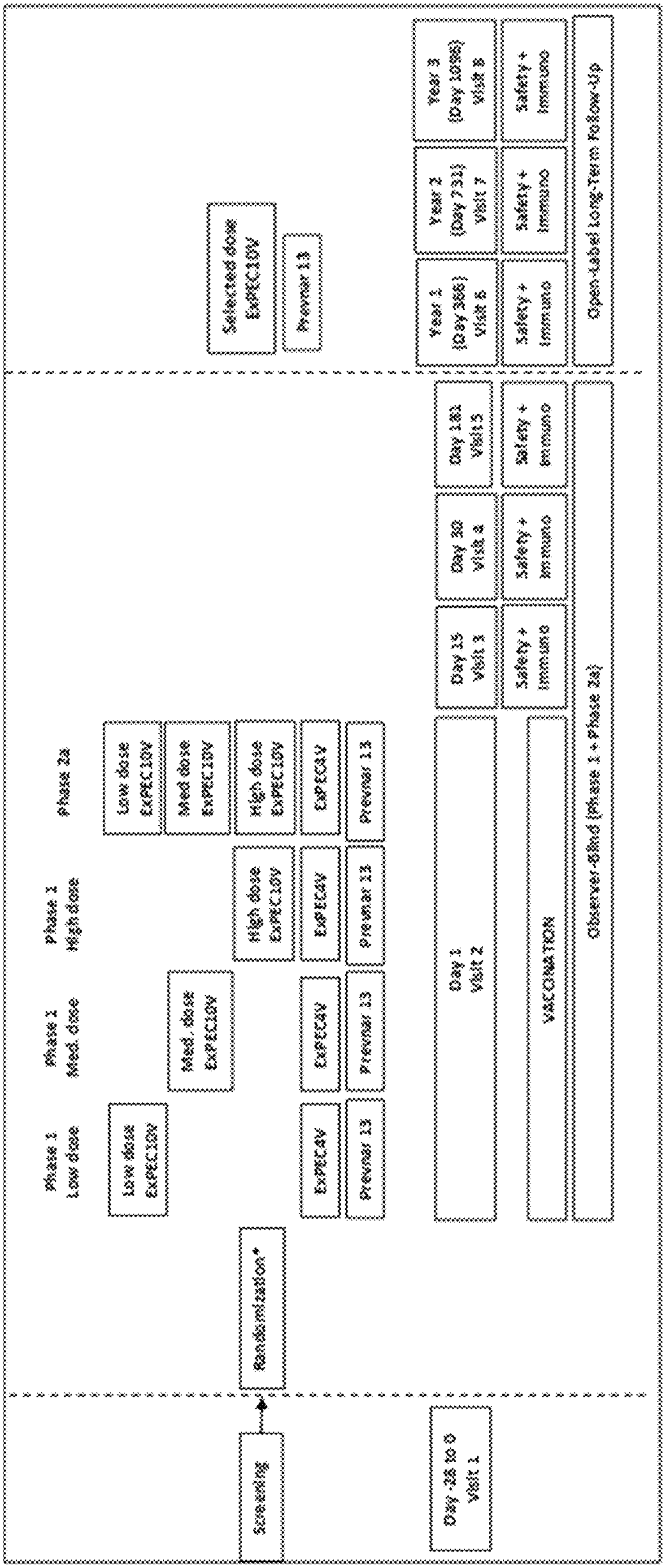
FIG. 3A-FIG. 3B show the overall study design for a phase 1/2a clinical trial with ExPEC10V vaccine in humans.

For Cohort 1, the study has an observer-blind, active-controlled design, and a total of 404 adult participants aged ≥60 to ≤85 years in stable health with or without a history of UTI are included. The study design for Cohort 1 is comprised of three periods: a maximum of 28-day screening period, an observer-blinded 181-day follow-up period with vaccination on Day 1 and an open-label LTFU period which lasts from Day 182 until 3 years (Day 1096) post-vaccination (FIG. 3A). Only participants from the ExPEC10V selected dose group (approximately 100 participants) and participants from the Prevnar 13 group progress to the LTFU period. The end of Cohort 1 is the last participant's Year 3 visit (Day 1096).

Figure 3B:
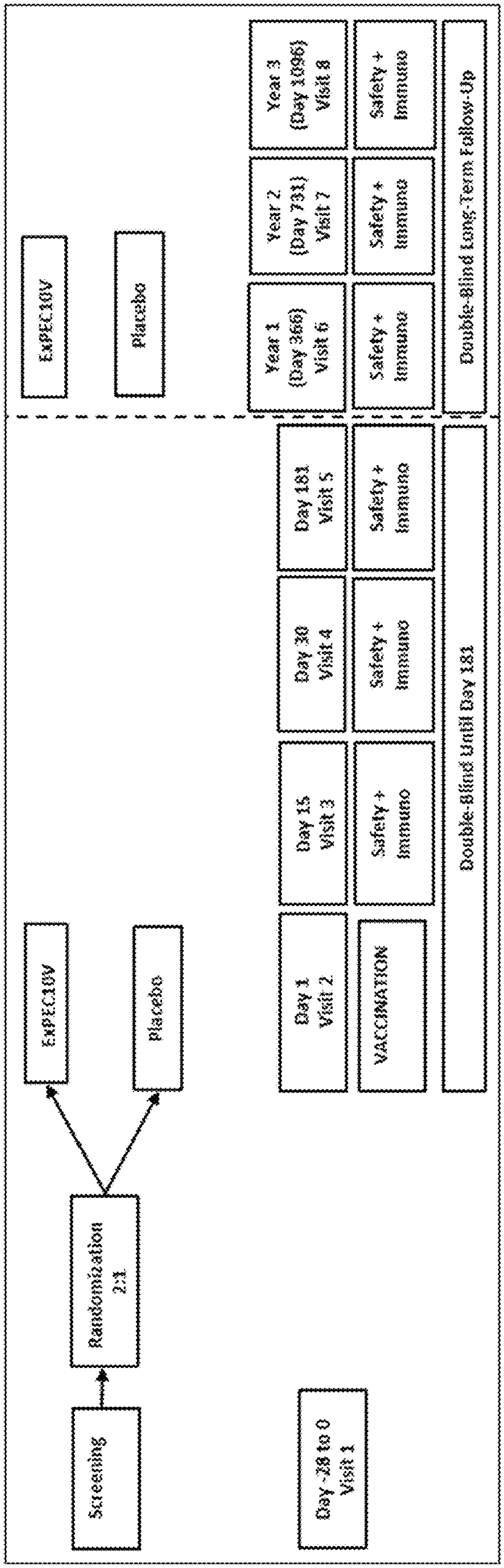

For Cohort 2, the study has a double-blind, placebo-controlled design, and a total of approximately 420 adult participants aged ≥60 years in stable health with a history of UTI in the past 5 years was included. Enrollment commenced after completion of the Phase 1/2a primary analysis and ExPEC10V dose selection from Cohort 1. The study design for Cohort 2 is comprised of three periods: a maximum 28-day screening period, a double-blind 181-day follow-up period with vaccination on Day 1, and a double-blind LTFU period which lasts from Day 182 until 3 years (Day 1096) post-vaccination (FIG. 3B). All participants in Cohort 2 progress to the LTFU period. The end of study is the last participant's Year 3 visit (Day 1096) in Cohort 2.

Cohort 1: Phase 1

In Phase 1 of Cohort 1, a total of 84 participants were enrolled in a staggered approach following stepwise dose-escalating procedures with safety evaluations in place before progressing from one step to the next. An internal Data Review Committee (DRC) was commissioned for this study to review the physical examination data (baseline as well as targeted), baseline demographic data and the 14-day post-vaccination safety data (including solicited local and systemic AEs, unsolicited AEs, SAEs, clinical laboratory data and vital signs) of these 84 Phase 1 participants. In this phase of the study, participants were enrolled and randomized in six steps:

Step 1: Four sentinel participants were enrolled and randomized; two participants in the ExPEC10V low dose group (Table 11), and one participant each in the ExPEC4V and Prevnar 13 groups.

Step 2: Twenty-four participants were enrolled and randomized; 18 participants in the ExPEC10V low dose group (Table 11), and three participants each in the ExPEC4V and Prevnar 13 groups.

Step 3: Four sentinel participants were enrolled and randomized; two participants in the ExPEC10V medium dose group (Table 11), and one participant each in the ExPEC4V and Prevnar 13 groups.

Step 4: Twenty-four participants were enrolled and randomized; 18 participants in the ExPEC10V medium dose group (Table 11), and three participants each in the ExPEC4V and Prevnar 13 groups.

Step 5: Four sentinel participants were enrolled and randomized; two participants in the ExPEC10V high dose group (Table 11), and one participant each in the ExPEC4V and Prevnar 13 groups.

Step 6: Twenty-four participants were enrolled and randomized; 18 participants in the ExPEC10V high dose group (Table 11), and three participants each in the ExPEC4V and Prevnar 13 groups.

All participants received a single intramuscular (IM) injection of either ExPEC10V (1 of 3 doses), ExPEC4V or Prevnar 13 on Day 1 per the assigned study vaccination groups. The four sentinel participants at each of Steps 1, 3 and 5 were contacted by telephone 24 hours post-vaccination to collect safety information. The blinded 24-hour post-vaccination safety data in each group of four sentinel participants were reviewed by the principal investigator (PI), study responsible physician (SRP) and sponsor medical lead (SML). Randomization of additional participants for the next step was halted until this Day 2 sentinel safety evaluation was completed.

In the absence of any clinically significant findings, an additional 24 participants (for Steps 2, 4, and 6) were enrolled and randomized to one of three study vaccination groups (Table 11) to receive a single IM injection of either ExPEC10V (1 of 3 doses), ExPEC4V or Prevnar 13 on Day 1.

After vaccination of an additional 24 participants at each dose level (low dose in Step 2, medium dose in Step 4, and high dose in Step 6), 14-day post-vaccination safety data of all 28 (4+24) participants at each dose level was reviewed by the DRC before progressing to the next dose level or Phase 2a.

Cohort 1: Phase 2a

Based on acceptable safety and reactogenicity (in the absence of any safety concerns or any events meeting a specific study pausing rule) as determined by DRC after the review of 14-day post-vaccination safety data for the initial 84 participants, the remaining 320 participants from Cohort 1 were randomized and dosed in Phase 2a of the study. These additional 320 participants were enrolled and randomized in parallel in a ratio of 2:2:2:1:1 to one of the five study vaccination groups to receive a single IM injection of either ExPEC10V (1 of 3 doses), ExPEC4V or Prevnar 13 on Day 1 (Table 11). In addition to performing the 14-day safety review for the initial 84 participants, the DRC also evaluates safety data of Cohort 1 over the course of the study and reviews any events that meet a specific study vaccination pausing rule or any other safety issue that may arise.

For Cohort 1, the primary analysis occurred when all participants had completed the Day 30 visit (Visit 4) or have discontinued earlier. The final analysis occurs when all participants have completed the Day 181 visit or have discontinued earlier. For participants progressing to the open-label long-term follow-up (LTFU) period (ExPEC10V selected dose group and Prevnar 13 group), yearly follow-up analyses include safety and immunogenicity data (multiplex ECL-based immunoassay and MOPA) collected up to the time of the visit at Year 1 (Day 366), Year 2 (Day 731) and Year 3 (Day 1096) after vaccination.

Cohort 2

In Cohort 2, the safety, reactogenicity, and immunogenicity of the selected dose of ExPEC10V (based on the primary analysis results of Cohort 1 the high dose was selected) is evaluated in participants aged ≥60 years in stable health with a history of UTI in the past 5 years. For Cohort 2, the study has a double-blind, placebo-controlled design, and a total of approximately 420 participants were enrolled and randomized in parallel in a 2:1 ratio (approximately 280 participants in the ExPEC10V group and approximately 140 in the placebo group).

All participants received a single IM injection of either the selected dose of ExPEC10V or placebo on Day 1 per the assigned study vaccination groups (Table 12).

For Cohort 2, the primary analysis includes safety and immunogenicity data and occurs when all participants have completed the Day 30 visit (Visit 4) or have discontinued earlier. The final analysis occurs when all participants have completed the Day 181 visit or have discontinued earlier. For all participants, yearly follow-up analyses include safety and immunogenicity data (multiplex ECL-based immunoassay and MOPA) collected up to the time of the visit at Year 1 (Day 366), Year 2 (Day 731) (not applicable for MOPA), and Year 3 (Day 1096) after vaccination.

A stool sample analysis is performed in a selected subset of participants to evaluate the effect of ExPEC10V on the prevalence of pathogens (eg, *Clostridium difficile*) and ExPEC10V serotypes in the intestinal flora using metagenomics.

Number of Participants

A total of approximately 824 participants was enrolled in the study; 404 participants in Cohort 1 and approximately 420 participants in Cohort 2.

Intervention Groups: Description of Interventions

ExPEC10V: *E. coli* bioconjugate vaccine in phosphate buffered solution containing O-antigen PS of ExPEC serotypes O1A, O2, O4, O6A, O8, O15, O16, O18A, O25B and O75 separately bioconjugated to the EPA carrier protein. Single 0.5 mL IM (deltoid) injection of one of the three doses of ExPEC10V on Day 1.

ExPEC4V: *E. coli* bioconjugate vaccine in saline buffer solution containing O-antigen PS of ExPEC serotypes O1A, O2, O6A, O25B (4:4:4:8 μg PS/ExPEC serotypes) separately bioconjugated to the EPA carrier protein. Single 0.5 mL IM (deltoid) injection of ExPEC4V on Day 1.

Prevnar 13: Sterile suspension of saccharides of the capsular antigens of *Streptococcus pneumoniae* serotypes 1, 3, 4, 5, 6A, 6B, 7F, 9V, 14, 18C, 19A, 19F, and 23F, individually linked to non-toxic Diphtheria $CRM_{197}$ protein. Single 0.5 mL IM (deltoid) injection on Day 1, supplied in a single-dose prefilled syringe.

Placebo: normal saline. Single 0.5 mL IM (deltoid) injection of placebo on Day 1.

The ExPEC study intervention materials are described in Table 9.

TABLE 9

BAC1001MV ExPEC Study Vaccines

| Study Arm | O1A (μg) | O2 (μg) | O4 (μg) | O6A (μg) | O8 (μg) | O15 (μg) | O16 (μg) | O18A (μg) | O25B (μg) | O75 (μg) | EPA (μg) | PS (Total) (μg) |
|---|---|---|---|---|---|---|---|---|---|---|---|---|
| Low dose ExPEC10V | 4 | 4 | 4 | 4 | 4 | 4 | 4 | 4 | 8 | 4 | 160 | 44 |
| Medium dose ExPEC10V | 8 | 4 | 4 | 8 | 4 | 4 | 4 | 4 | 16 | 4 | 221 | 60 |
| High dose ExPEC10V | 8 | 8 | 8 | 8 | 8 | 8 | 8 | 8 | 16 | 8 | 320 | 88 |
| ExPEC4V | 4 | 4 | — | 4 | — | — | — | — | 8 | — | 72 | 20 |

EPA = a genetically detoxified form of exotoxin A derived from *Pseudomonas aeruginosa*;
PS = polysaccharide ExPEC4V consists of the O-antigen polysaccharides (PSs) of the ExPEC serotypes O1A, O2, O6A, and O25B separately bioconjugated to the EPA carrier protein.
ExPEC10V consists of the O-antigen polysaccharides (PSs) of the ExPEC serotypes O1A, O2, O4, O6A, O8, O15, O16, O18A, O25B and O75 separately bioconjugated to the EPA carrier protein.
Dose is based on PS only.
The EPA (μg) are measured values.

ExPEC10V is composed of 10 monovalent drug substances (DSs). For this clinical study, 2 different concentrations (medium and high) of drug product (DP) are produced (Table 10). A third (low) concentration is obtained in the clinic by diluting the high concentration 1:1 with dilution buffer, which is the same as the formulation buffer. Each DP is formulated in Sodium/Potassium phosphate buffer at pH 7.0 (0.02% [w/w] Polysorbate 80, 5% [w/w] sorbitol, 10 mM methionine).

TABLE 10

Composition of ExPEC10V vaccine for phase 1/2a clinical study

| Ingredient Active[a] | Amount (μg/mL)[a] Low Concentration [b] | Medium Concentration | High Concentration |
|---|---|---|---|
| O-antigen polysaccharide | | | |
| EcoO1A | 8 | 16 | 16 |
| EcoO2 | 8 | 8 | 16 |
| EcoO4 | 8 | 8 | 16 |
| EcoO6A | 8 | 16 | 16 |
| EcoO8 | 8 | 8 | 16 |
| EcoO15 | 8 | 8 | 16 |
| EcoO16 | 8 | 8 | 16 |
| EcoO18A | 8 | 8 | 16 |
| EcoO25B | 16 | 32 | 32 |
| EcoO75 | 8 | 8 | 16 |
| Carrier protein | | | |
| EPA | 320 | 441 | 640 |
| Excipients | | | |
| $KH_2PO_4$ | | 6.19 mM | |
| $Na_2HPO_4$ | | 3.81 mM | |
| Sorbitol | | 5% (w/w) | |
| Methionine | | 10 mM | |
| Polysothate 80 | | 0.02% (w/w) | |

EPA = genetically detoxified *P. aeruginosa* exotoxin A used as carrier protein
[a]The active ingredient is a biologically synthesized conjugate composed of the PS antigen and a carrier protein (EPA); the dose is calculated on the PS moiety only.
[b] The "low concentration" is obtained in the clinic by diluting the "high concentration" 1:1 with dilution buffer Safety Evaluations Key safety assessments include solicited local and systemic AEs, unsolicited AEs, SAEs, physical examinations, vital sign measurements, and clinical laboratory tests.

Immunogenicity Evaluations

Key immunogenicity assessments of collected sera include the assessment of ExPEC10V and ExPEC4V serotype-specific total IgG antibody levels elicited by the vaccine as measured by a multiplex ECL-based immunoassay, and ExPEC10V and ExPEC4V serotype-specific functional antibodies as measured by an opsonophagocytic killing assay (OPKA) in multiplex format (MOPA). Immunogenicity assessments of pneumococcal antibody titers elicited by Prevnar 13 are not performed.

The levels of serum antibodies induced by ExPEC10V are measured by a multiplex electrochemiluminescent (ECL)-based immunoassay. This assay combines high binding carbon electrodes in a multi-spot 96-well format microplate that is coated with different *E. coli* O-LPS antigens or the carrier protein EPA. The levels of antigen-specific antibodies present in serum samples are detected using a secondary antibody (anti-human IgG) labeled with SULFO-TAG. The SULFO-TAG emits light in the presence of electrical stimulation at an intensity that increases proportionally to the amount of bound IgG antibodies. This assay was qualified according to International Conference on Harmonisation (ICH) recommendations.

The levels of functional antibodies induced by ExPEC10V are measured by a multiplex opsonophagocytic assay (MOPA). Briefly, heat-inactivated serum samples are serially diluted and incubated with different *E. coli* strains that are specifically resistant to different types of antibiotics. After that, human complement and phagocytic cells (HL60) are added to the reaction and, after a second incubation period, an aliquot of the reaction mix is transferred to different PVDF hydrophilic membrane filter plates containing media supplemented with specific antibiotic that selectively allow growth of a strain that is resistant to that particular antibiotic. After overnight growth, the colony forming units (CFUs) are counted to determine the number of surviving bacteria. This assay was qualified according to ICH recommendations.

For ExPEC10V serotype antibodies as measured by multiplex ECL-based immunoassay and MOPA, and EPA as measured by multiplex ECL-based immunoassay only, the following measures of immunogenicity are evaluated and tabulated by the study vaccination groups, for all immunogenicity time points:

- proportion of participants with a ≥2-fold and ≥4-fold increase in serum antibody titers from Day 1 (pre-vaccination)
- geometric mean titer (GMT)
- GMR: fold change from baseline, calculated from the post-baseline/baseline value.

For the LTFU period, descriptive summaries of immunogenicity are provided for each serotype.

Dose selection for later phases considers the totality of the evidence available at the time of the primary analysis of Cohort 1 (Day 30 results).

TABLE 11

Cohort 1: Vaccination Schedule

| Study Vaccination Group | Vaccination on Day 1 | Phase 1: Step 1 Sentinel participants (Low dose) | Step 2 Additional participants (Low dose) | Step 3 Sentinel participants (Medium dose) | Step 4 Additional participants (Medium dose) | Step 5 Sentinel participants (High dose) | Step 6 Additional participants (High dose) | Phase 2a Step 7 Additional Phase 2a Participants | Total |
|---|---|---|---|---|---|---|---|---|---|
| G1 | Low dose ExPEC10V* | 2 | 18 | | | | | 80 | 100 |
| G2 | Medium dose ExPEC10V* | | | 2 | 18 | | | 80 | 100 |
| G3 | High dose ExPEC10V* | | | | | 2 | 18 | 80 | 100 |
| G4 | ExPEC4V** | 1 | 3 | 1 | 3 | 1 | 3 | 40 | 52 |
| G5 | Prevnar 13*** | 1 | 3 | 1 | 3 | 1 | 3 | 40 | 52 |
| Total | | 4 | 24 | 4 | 24 | 4 | 24 | 320 | 404 |

*ExPEC10V consists of the O-antigen polysaccharides (PSs) of the ExPEC serotypes O1 A, O2, O4, O6A, O8, O15, O16, O18A, O25B and O75 separately bioconjugated to the carrier protein, a genetically detoxified form of exotoxin A (EPA) derived from *Pseudomonas aeruginosa*.
**ExPEC4V consists of the O-antigen polysaccharides (PSs) of the ExPEC serotypes O1A, O2, O6A, and O25B separately bioconjugated to the carrier protein, a genetically detoxified form of exotoxin A (EPA) derived from *Pseudomonas aeruginosa*.
***Prevnar 13, Pneumococcal 13-valent conjugate vaccine (Diphtheria CRM197 protein) is a sterile suspension of saccharides of the capsular antigens of *Streptococcus pneumoniae* serotypes 1, 3, 4, 5, 6A, 6B, 7F, 9V, 14, 18C, 19A, 19F, and 23F, individually linked to non-toxic Diphtheria CRM197 protein.

TABLE 12

Cohort 2: Vaccination Schedule

| Study Vaccination Group | Vaccination on Day 1 | Total |
|---|---|---|
| G6 | ExPEC10V[a] | 280 |
| G7 | Placebo | 140 |
| Total | | 420 |

aExPEC10V consists of the O-antigen polysaccharides (PSs) of the ExPEC serotypes O1A, O2, O4, O6A, O8, O15, O16, O18A, O25B, and O75 separately bioconjugated to the carrier protein, a genetically detoxified form of exotoxin A (EPA) derived from *Pseudomonas aeruginosa*.

The randomization ratio for the participants enrolled in Cohort 2 of the study is 2:1 (ExPEC10V:Placebo). The ExPEC10V dose used in Cohort 2 was based on the primary analysis (Day 30) results of Cohort 1, and this is the high dose that was used in Cohort 1.

Status

Enrollment and vaccination of Cohort 1 of the study described above was completed. No major safety issues were identified, and the ExPEC10V vaccine has an acceptable safety profile.

The analysis of the immunogenicity of the Cohort 1 clinical samples was performed and results are described below.

The Cohort 2 vaccinations were started using the high dose for ExPEC10V, and this part of the study is ongoing.

Cohort 1 Safety and Immunogenicity Results

These results presented here refer to the BAC1001 clinical study (cohort 1). There were 416 participants in the full analysis set. Each participant was randomized to either 1 of 3 single intra-muscular administered doses of ExPEC10V or to 1 of 2 active control doses of ExPEC4V or Prevnar; 104 were vaccinated with the ExPEC10V low dose, 102 with the ExPEC10V medium dose, 104 with the ExPEC10V high dose, 52 with the ExPEC4V (4:4:4:8 μg O1A, O2, O6A and O25B polysaccharide/dose), and 54 with Prevnar. A total of 413 participants completed the Day 30 visit. There were 392 (94.2%) participants included in the Day 15 per protocol immunogenicity analysis.

Safety

Overall, all ExPEC10V doses were well tolerated. There was a trend for increased reactogenicity with high doses, with the ExPEC10V high dose reactogenicity lower or comparable to Prevnar, except for erythema, swelling and nausea. In contrast to Prevnar, more late onset local reactogenicity was observed in ExPEC10V groups with injection site erythema and swelling reported as late onset events in >90% of participants experiencing these local events. However, the reactogenicity profile of ExPEC10V is acceptable when compared to other licensed vaccines used in older adult populations.

Immunogenicity

Vaccine-induced immune responses were assessed at baseline (day 1 pre-vaccination) and at day 15 post-vaccination using a multiplex electrochemiluminescent (ECL)-based immunoassay that measures the levels of serotype-specific serum antibodies (total immunoglobulin G [IgG]) and a multiplex opsonophagocytic killing assay (MOPA) that measures antibody mediated bacterial opsonophagocytic killing.

Levels of Antigen-Specific Serum Antibodies (ECL)

Figure 4:
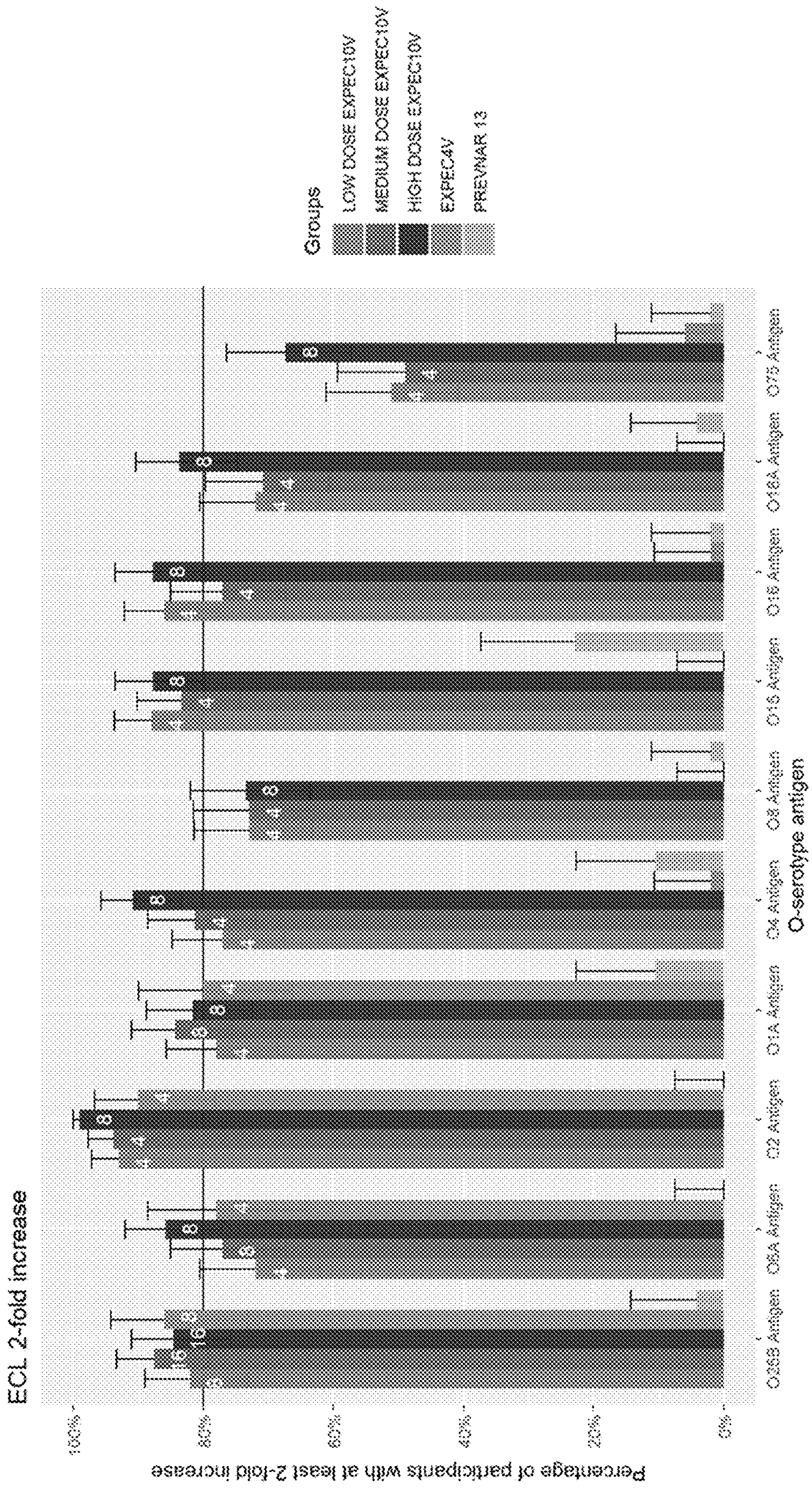
FIG. 4 shows the percentage of participants with at least 2-fold increase in serum O-antigen specific antibody titers at day 15 post-vaccination as measured from baseline (day 1) in the BAC1001 clinical trial (see Example 7 for details). O-antigen specific serum antibody titers were measured by ECL-based immunoassay.

Levels of O-antigen-specific serum antibodies (total IgG) increased significantly on Day 15 post-vaccination for all ExPEC10V doses tested and all vaccine-related serotypes. It was observed that at least 80% of the subjects that received the high dose of the ExPEC10V vaccine showed a two-fold or greater increase in O-antigen-specific antibody titers by Day 15 post-vaccination for 8 out of 10 serotypes that include O25B, O6A, O2, O1A, O4, O15, O16 and O18A. For the ExPEC10V medium dose group, at least 80% of subjects show a two-fold or greater increase in O-antigen specific antibody titers by Day 15 post-vaccination, for 5 out of 10 serotypes that include O25B, O2, O1A, O4 and O15; and for the ExPEC10V low dose group for 4 out of 10 serotypes that include O25B, O2, O15 and O16 (FIG. 4, Table 13). Minimal changes in the GMT from day 1 to day 15 were observed in the group of subjects that received Prevnar or ExPEC4V (for the non-ExPEC4V serotypes) (FIG. 4, Table 13).

For the ECL assay, all subjects were analyzed and included in the all immunogenicity subset. Subjects with major violations according to protocol exclusion criteria were excluded from the per protocol analyses. The geometric mean titer (GMT), GMT FI (geometric mean titer fold-increase) and percentage of participants with at least 2- and 4-fold increases from baseline in the ECL-based immunoassay are summarized in Table 13 below.

TABLE 13

ECL data BAC1001 cohort 1

| Endpoint (95% CI) | Time point | ExPEC10V Low Dose | ExPEC10V Medium Dose | ExPEC10V High Dose | ExPEC4V | Prevnar |
|---|---|---|---|---|---|---|
| Serotype O1A | | | | | | |
| GMTs | Day 1 | 1226879.8 (1030417.6; 1460800.0) | 1193952.5 (978207.8; 1457279.9) | 1202227.3 (999407.5; 1446207.5) | 1072873.1 (798770.8; 1441035.1) | 1310616.9 (1010870.8; 1699244.5) |
| GMTs | Day 15 | 5328463.0 (4620273.9; 6145202.3) | 6351780.5 (5647000.4; 7144521.5) | 6379531.1 (5682021.0; 7162665.7) | 6539744.0 (5315259.2; 8046315.4) | 1650517.3 (1228541.5; 2217432.2) |
| GM FI[1] | Day 15 vs Day 1 | 4.35 (3.646; 5.198) | 5.26 (4.361; 6.345) | 5.19 (4.310; 6.256) | 5.99 (4.459; 8.043) | 1.27 (1.094; 1.485) |
| % 2-fold[2] | Day 15 vs Day 1 | 78.0% (68.61%; 85.67%) | 84.4% (75.54%; 90.98%) | 81.6% (72.53%; 88.74%) | 80.0% (66.28%; 89.97%) | 10.4% (3.47%; 22.66%) |
| % 4-fold[2] | Day 15 vs Day 1 | 56.0% (45.72%; 65.92%) | 61.5% (50.97%; 71.22%) | 64.3% (53.97%; 73.71%) | 66.0% (51.23%; 78.79%) | 6.3% (1.31%; 17.20%) |
| Serotype O2 | | | | | | |
| GMTs | Day 1 | 510014.8 (424544.1; 612692.6) | 465679.8 (393668.5; 550863.6) | 534252.7 (456163.2; 625710.3) | 477186.7 (365264.4; 623403.6) | 467863.4 (354874.1; 616827.7) |
| GMTs | Day 15 | 4846804.8 (4088473.9; 5745791.1) | 4779406.7 (4015130.7; 5689162.0) | 6505196.8 (5820337.7; 7270640.9) | 6174400.7 (4983834.3; 7649376.5) | 431229.4 (334539.7; 555864.6) |
| GM FI[1] | Day 15 vs Day 1 | 9.48 (7.955; 11.306) | 10.09 (8.389; 12.132) | 12.46 (10.686; 14.516) | 12.70 (9.383; 17.196) | 1.01 (0.952; 1.067) |
| % 2-fold[2] | Day 15 vs Day 1 | 93.0% (86.11%; 97.14%) | 93.8% (86.89%; 97.67%) | 99.0% (94.45%; 99.97%) | 90.0% (78.19%; 96.67%) | 0.0% (0.00%; 7.40%) |
| % 4-fold[2] | Day 15 vs Day 1 | 83.0% (74.18%; 89.77%) | 84.4% (75.54%; 90.98%) | 92.9% (85.84%; 97.08%) | 82.0% (68.56%; 91.42%) | 0.0% (0.00%; 7.40%) |
| Serotype O4 | | | | | | |
| GMTs | Day 1 | 461135.6 (394351.8; 539229.2) | 492816.2 (420242.9; 577922.5) | 449573.2 (396266.8; 510050.4) | 462018.9 (378746.2; 563600.3) | 429691.9 (352681.9; 523517.5) |
| GMTs | Day 15 | 2876992.7 (2312781.5; 3578845.2) | 2776953.7 (2271070.8; 3395522.4) | 4135064.0 (3466612.3; 4932410.4) | 479974.7 (389335.0; 591716.0) | 556386.8 (418115.4; 740384.7) |
| GM FI[1] | Day 15 vs Day 1 | 6.26 (5.080; 7.716) | 5.52 (4.543; 6.717) | 9.15 (7.568; 11.063) | 1.06 (1.006; 1.124) | 1.29 (1.085; 1.524) |
| % 2-fold[2] | Day 15 vs Day 1 | 77.0% (67.51%; 84.83%) | 81.3% (72.00%; 88.49%) | 90.8% (83.28%; 95.71%) | 2.0% (0.05%; 10.65%) | 10.4% (3.47%; 22.66%) |
| % 4-fold[2] | Day 15 vs Day 1 | 64.0% (53.79%; 73.36%) | 63.5% (53.09%; 73.13%) | 79.6% (70.26%; 87.07%) | 0.0% (0.00%; 7.11%) | 4.2% (0.51%; 14.25%) |
| Serotype O6A | | | | | | |
| GMTs | Day 1 | 1220500.4 (1060415.0; 1404753.0) | 1143877.4 (965179.1; 1355660.9) | 1127737.5 (987356.6; 1288077.7) | 1178385.6 (934832.4; 1485392.0) | 943745.8 (776652.7; 1146788.3) |
| GMTs | Day 15 | 4314596.8 (3748795.9; 4965793.3) | 5145946.5 (4369752.3; 6060015.3) | 5839456.8 (5126873.3; 6651082.1) | 4930272.7 (3947184.1; 6158210.2) | 1012716.0 (821125.5; 1249009.7) |
| GM FI[1] | Day 15 vs Day 1 | 3.55 (3.033; 4.145) | 4.45 (3.691; 5.370) | 5.06 (4.355; 5.869) | 4.38 (3.407; 5.618) | 1.04 (0.986; 1.088) |
| % 2-fold[2] | Day 15 vs Day 1 | 72.0% (62.13%; 80.52%) | 77.1% (67.39%; 85.05%) | 85.7% (77.19%; 91.96%) | 78.0% (64.04%; 88.47%) | 0.0% (0.00%; 7.40%) |

TABLE 13-continued

| Endpoint (95% CI) | Time point | ExPEC10V Low Dose | ExPEC10V Medium Dose | ExPEC10V High Dose | ExPEC4V | Prevnar |
|---|---|---|---|---|---|---|
| ECL data BAC1001 cohort 1 | | | | | | |
| % 4-fold[2] | Day 15 vs Day 1 | 43.0% (33.14%; 53.29%) | 52.1% (41.64%; 62.39%) | 65.3% (55.02%; 74.64%) | 52.0% (37.42%; 66.34%) | 0.0% (0.00%; 7.40%) |
| Serotype O8 | | | | | | |
| GMTs | Day 1 | 1534906.4 (1315284.3; 1791200.5) | 1732564.1 (1488898.1; 2016107.4) | 1535536.4 (1319371.4; 1787117.9) | 1537793.8 (1250768.0; 1890686.4) | 1339640.3 (1061371.9; 1690864.7) |
| GMTs | Day 15 | 5052165.0 (4405019.0; 5794383.9) | 5600945.1 (4902756.3; 6398561.1) | 6178848.4 (5511236.6; 6927332.3) | 1709293.2 (1392733.5; 2097805.0) | 1374269.5 (1075143.6; 1756617.9) |
| GM FI[1] | Day 15 vs Day 1 | 3.35 (2.896; 3.871) | 3.26 (2.777; 3.832) | 3.94 (3.381; 4.584) | 1.07 (1.034; 1.116) | 1.05 (0.994; 1.111) |
| % 2-fold[2] | Day 15 vs Day 1 | 73.0% (63.20%; 81.39%) | 72.9% (62.89%; 81.48%) | 73.5% (63.59%; 81.88%) | 0.0% (0.00%; 7.11%) | 2.1% (0.05%; 11.07%) |
| % 4-fold[2] | Day 15 vs Day 1 | 42.0% (32.20%; 52.29%) | 39.6% (29.75%; 50.08%) | 52.0% (41.71%; 62.24%) | 0.0% (0.00%; 7.11%) | 0.0% (0.00%; 7.40%) |
| Serotype O15 | | | | | | |
| GMTs | Day 1 | 871316.5 (728072.4; 1042743.2) | 865326.5 (733883.5; 1020311.8) | 869436.4 (742857.9; 1017583.0) | 847989.9 (659076.0; 1091053.0) | 839725.1 (668057.1; 1055505.9) |
| GMTs | Day 15 | 5145327.6 (4381397.1; 6042455.2) | 4658173.1 (3991308.2; 5436457.2) | 5502286.9 (4828131.0; 6270575.8) | 859569.9 (666001.9; 1109397.0) | 1208928.4 (882681.8; 1655758.5) |
| GM FI[1] | Day 15 vs Day 1 | 5.93 (4.945; 7.100) | 5.37 (4.496; 6.408) | 6.24 (5.276; 7.391) | 1.01 (0.973; 1.055) | 1.48 (1.227; 1.797) |
| % 2-fold[2] | Day 15 vs Day 1 | 88.0% (79.98%; 93.64%) | 83.3% (74.35%; 90.16%) | 87.8% (79.59%; 93.51%) | 0.0% (0.00%; 7.11%) | 22.9% (12.03%; 37.31%) |
| % 4-fold[2] | Day 15 vs Day 1 | 61.0% (50.73%; 70.60%) | 63.5% (53.09%; 73.13%) | 68.4% (58.20%; 77.39%) | 0.0% (0.00%; 7.11%) | 10.4% (3.47%; 22.66%) |
| Serotype O16 | | | | | | |
| GMTs | Day 1 | 860263.7 (725964.5; 1019407.5) | 853674.6 (740655.4; 983939.8) | 803233.9 (691840.6; 932562.7) | 675579.3 (572649.9; 797009.5) | 706903.3 (568193.4; 879475.6) |
| GMTs | Day 15 | 4265641.1 (3633602.0; 5007618.8) | 3973364.4 (3373538.4; 4679841.3) | 5630267.2 (4906785.0; 6460423.5) | 750895.2 (615148.2; 916598.0) | 744487.3 (588274.4; 942181.5) |
| GM FI[1] | Day 15 vs Day 1 | 5.00 (4.262; 5.870) | 4.56 (3.794; 5.489) | 6.93 (5.817; 8.249) | 1.11 (0.991; 1.247) | 1.08 (1.002; 1.154) |
| % 2-fold[2] | Day 15 vs Day 1 | 86.0% (77.63%; 92.13%) | 77.1% (67.39%; 85.05%) | 87.8% (79.59%; 93.51%) | 2.0% (0.05%; 10.65%) | 2.1% (0.05%; 11.07%) |
| % 4-fold[2] | Day 15 vs Day 1 | 63.0% (52.76%; 72.44%) | 57.3% (46.78%; 67.34%) | 72.4% (62.50%; 80.99%) | 2.0% (0.05%; 10.65%) | 0.0% (0.00%; 7.40%) |
| Serotype O18A | | | | | | |
| GMTs | Day 1 | 934049.6 (819694.2; 1064358.5) | 963410.7 (838467.8; 1106971.8) | 923828.6 (816988.8; 1044640.1) | 948044.5 (795966.9; 1129178.2) | 979084.2 (788765.0; 1215325.0) |
| GMTs | Day 15 | 3517970.2 (2948912.8; 4196839.6) | 3585716.9 (3003087.3; 4281382.5) | 4539608.6 (3893880.0; 5292419.4) | 972430.2 (803752.4; 1176507.2) | 1087640.8 (828956.9; 1427049.5) |
| GM FI[1] | Day 15 vs Day 1 | 3.79 (3.219; 4.470) | 3.62 (3.020; 4.341) | 4.85 (4.130; 5.702) | 1.04 (0.996; 1.086) | 1.14 (1.029; 1.256) |
| % 2-fold[2] | Day 15 vs Day 1 | 72.0% (62.13%; 80.52%) | 70.8% (60.67%; 79.67%) | 83.7% (74.84%; 90.37%) | 0.0% (0.00%; 7.11%) | 4.2% (0.51%; 14.25%) |
| % 4-fold[2] | Day 15 vs Day 1 | 49.0% (38.86%; 59.20%) | 41.7% (31.68%; 52.18%) | 61.2% (50.85%; 70.90%) | 0.0% (0.00%; 7.11%) | 2.1% (0.05%; 11.07%) |

TABLE 13-continued

| ECL data BAC1001 cohort 1 | | | | | | |
|---|---|---|---|---|---|---|
| Endpoint (95% CI) | Time point | ExPEC10V Low Dose | ExPEC10V Medium Dose | ExPEC10V High Dose | ExPEC4V | Prevnar |
| Serotype O25B | | | | | | |
| GMTs | Day 1 | 246235.1 (205202.9; 295472.1) | 240586.0 (200618.4; 288515.9) | 243305.0 (204854.9; 288972.0) | 189072.4 (149829.5; 238593.9) | 267582.0 (207517.9; 345031.0) |
| GMTs | Day 15 | 1413686.1 (1100919.7; 1815308.2) | 2275453.1 (1768282.1; 2928088.7) | 2047161.5 (1617468.8; 2591005.3) | 2026104.2 (1428854.6; 2872999.1) | 270695.3 (202827.4; 361272.4) |
| GM FI[1] | Day 15 vs Day 1 | 5.78 (4.732; 7.054) | 9.61 (7.509; 12.298) | 8.19 (6.474; 10.363) | 10.36 (7.430; 14.445) | 1.03 (0.929; 1.136) |
| % 2-fold[2] | Day 15 vs Day 1 | 82.0% (73.05%; 88.97%) | 87.5% (79.18%; 93.37%) | 83.7% (74.84%; 90.37%) | 86.0% (73.26%; 94.18%) | 4.2% (0.51%; 14.25%) |
| % 4-fold[2] | Day 15 vs Day 1 | 58.0% (47.71%; 67.80%) | 76.0% (66.25%; 84.17%) | 69.4% (59.26%; 78.30%) | 76.0% (61.83%; 86.94%) | 2.1% (0.05%; 11.07%) |
| Serotype O75 | | | | | | |
| GMTs | Day 1 | 1258387.9 (1054541.9; 1501637.9) | 1329257.4 (1126527.2; 1568471.0) | 1284187.5 (1101597.2; 1497042.2) | 1107038.5 (902508.7; 1357919.5) | 1373337.6 (1061821.6; 1776245.9) |
| GMTs | Day 15 | 2952821.0 (2468576.2; 3532057.1) | 3102330.4 (2620338.5; 3672981.2) | 3923938.0 (3410142.4; 4515145.6) | 1317142.3 (1048701.5; 1654297.0) | 1368220.0 (1042053.0; 1796478.7) |
| GM FI[1] | Day 15 vs Day 1 | 2.34 (2.019; 2.715) | 2.36 (2.039; 2.734) | 3.01 (2.579; 3.510) | 1.14 (1.023; 1.260) | 1.04 (0.942; 1.139) |
| % 2-fold[2] | Day 15 vs Day 1 | 51.0% (40.80%; 61.14%) | 49.0% (38.61%; 59.37%) | 67.3% (57.13%; 76.48%) | 6.0% (1.25%; 16.55%) | 2.1% (0.05%; 11.07%) |
| % 4-fold[2] | Day 15 vs Day 1 | 21.0% (13.49%; 30.29%) | 25.0% (16.72%; 34.88%) | 32.7% (23.52%; 42.87%) | 4.0% (0.49%; 13.71%) | 2.1% (0.05%; 11.07%) |

Cohort 1: output for the primary analysis
[1]= GM of FI from baseline (Day 1)
[2]= percentage of participants with fold increase from baseline (Day 1)
CI = Confidence interval;
GM = Geometric mean,
GMT = Geometric mean titer;
FI = Fold increase
95% CI for GMT and GM FI is based on the t-distribution
95% CI for Percentage of Participants With 2- and 4-Fold Increase is obtained using Clopper-Pearson method.

It can be seen from the data (FIG. 4) that the total IgG response to O75 polysaccharide antigen is lower compared to the other antigens administered in the same amount (e.g. lower percentage of subjects with at least a two-fold increase on day 15 vs day 1), which was a surprising result. The data also show that an increase of the amount of O75 polysaccharide antigen in the composition (i.e. administration of 8 μg in the high dose vs 4 μg in the low and medium doses) increased the induced immune response to O75 polysaccharide antigen.

Serum Antibodies Functionality (MOPA)

Partial data were included in the cohort 1 MOPA analysis. Table 14 shows the number of participants included in the MOPA GMT analysis at Day 15. Although partial data was used for the evaluation of the functionality of the antibody response induced by ExPEC10V, the conclusions of the analysis did not change when the complete data set was available.

TABLE 14

| Number of participants included in the MOPA GMT analysis | | | | | |
|---|---|---|---|---|---|
| Sero-type | Low Dose | Medium Dose | High Dose | ExPEC4V | Prevnar |
| Expected number | 100 | 96 | 98 | 50 | 48 |
| O25B | 93 (93%) | 94 (98%) | 93 (95%) | 48 (96%) | 46 (96%) |
| O6A | 98 (98%) | 94 (98%) | 97 (99%) | 48 (96%) | 48 (100%) |
| O2 | 59 (59%) | 54 (56%) | 44 (45%) | 24 (48%) | 45 (94%) |
| O1A | 92 (92%) | 94 (98%) | 88 (90%) | 40 (80%) | 46 (96%) |
| O4 | 98 (98%) | 93 (97%) | 97 (99%) | 50 (100%) | 47 (98%) |
| O8 | 99 (98%) | 94 (98%) | 96 (98%) | 50 (100%) | 46 (96%) |
| O15 | 85 (85%) | 90 (94%) | 92 (94%) | 49 (98%) | 45 (94%) |
| O16 | 100 (100%) | 94 (98%) | 96 (98%) | 50 (100%) | 48 (100%) |
| O18A | 89 (89%) | 87 (91%) | 92 (94%) | 45 (90%) | 43 (90%) |
| O75 | 95 (95%) | 92 (96%) | 89 (91%) | 47 (94%) | 46 (96%) |

Figure 5:
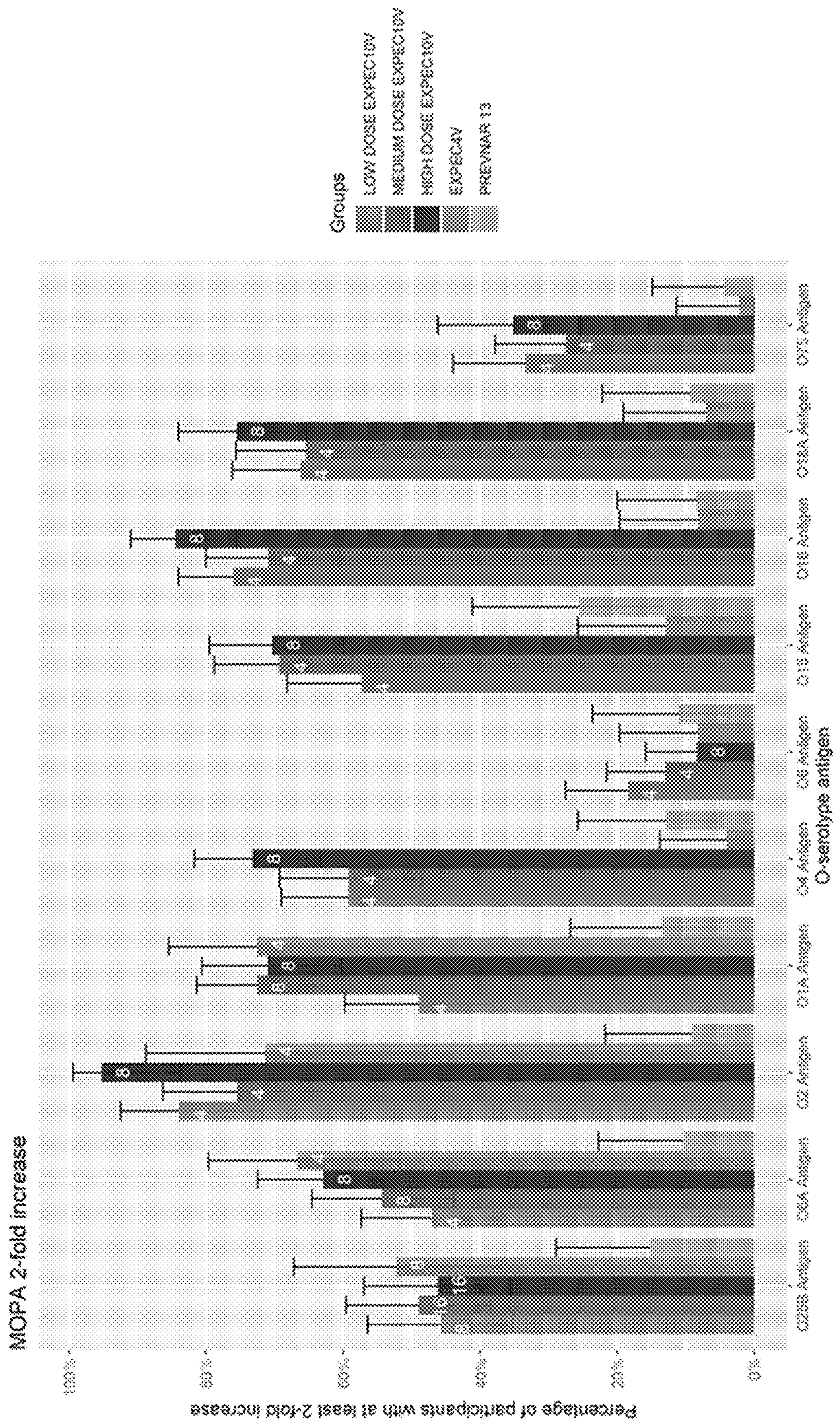
FIG. 5 shows the percentage of participants with at least 2-fold increase in serum opsonophagocytic antibody titers at day 15 post-vaccination as measured from baseline (day 1) in the BAC1001 clinical trial (see Example 7 for details). Levels of serum opsonophagocytic antibodies were measured by MOPA.

Levels of opsonophagocytic antibodies measured by MOPA were generally consistent with the levels of O-antigen-specific antibodies (total IgG) measured by ECL-based immunoassay. Increased levels of functional antibodies were observed on Day 15 for nine out of the ten ExPEC10V serotypes at all dose groups tested (FIG. 5).

In contrast to the other ExPEC10V serotypes, for serotype O8 the qualified MOPA assay was unable to show a vaccine-mediated increase in functional antibodies on day 15 following ExPEC10V vaccination on Day 1 (FIG. 5), although an increase in serotype O8 total IgG titers was observed (FIG. 4). Studies were initiated to distinguish whether the qualified assay was unable to detect functional O8 antibodies. Subsequent experiments with a modified MOPA assay and Day 1 and Day 15 sera successfully showed Day 15 functional antibody increases of 2-fold or more (data not shown), demonstrating that the ExPEC10V vaccine did actually induce functional antibodies also for serotype O8. For clinical development, the modified O8 MOPA would require re-qualification of the assay and retesting of clinical samples, which takes substantial time, and it was decided to initially proceed with development of a vaccine composition that does not include the O8 polysaccharide antigen. However, it is clear from the subsequent experiments that the O8 bioconjugate in the 10-valent ExPEC vaccine composition does induce functional antibodies against the *E. coli* O8 serotype, and hence such bioconjugate can likely be added successfully to the nine-valent vaccine compositions described in the example below.

The highest levels of opsonophagocytic antibodies were observed for the serotype O2; 95% of the subjects that were vaccinated with the high dose of that vaccine showed a 2-fold or greater increase in anti-O2 opsonic antibody titers at day 15 post-vaccination. Excluding O8 serotype, for which limited levels of functional antibodies were detected as discussed above, the lowest levels of opsonophagocytic antibodies were observed for the serotype O75; 36% of the subjects that were vaccinated with the high dose of the vaccine showed a 2-fold or greater increase in anti-O75 opsonic antibody titers at day 15 post-vaccination. The MOPA data for the O75 serotype are thus consistent with the ECL data for this serotype described above, corroborating the relatively lower immunogenicity of conjugates of *E. coli* O75 antigen polysaccharide as compared to several other conjugates in the composition at the same concentration, e.g. of *E. coli* O6, O1, or O2 conjugates. In addition, minimal changes in the GMT from day 1 to day 15 were observed in the group of subjects that received Prevnar or ExPEC4V (for the non-ExPEC4V serotypes) (FIG. 5), which is in line with expectations for serotypes not present in the respective vaccine compositions.

The geometric mean titers (GMT), geometric mean fold increase (GMR FI) and percentage of participants with at least 2- and 4-fold increase from baseline in the MOPA are summarized in Table 15 for each of the 10 serotypes.

TABLE 15

MOPA data BAC1001 cohort 1

| Endpoint (95% CI) | Time point | ExPEC10V Low Dose | ExPEC10V Medium Dose | ExPEC10V High Dose | ExPEC4V | Prevnar |
|---|---|---|---|---|---|---|
| | | Serotype O1A | | | | |
| GMTs | Day 1 | 221.5 (179.7; 272.9) | 154.8 (125.5; 190.8) | 171.3 (136.7; 214.8) | 255.1 (179.2; 363.2) | 201.1 (154.1; 262.5) |
| GMTs | Day 15 | 606.2 (469.6; 782.5) | 748.5 (584.4; 958.8) | 995.9 (738.1; 1343.7) | 974.5 (620.4; 1530.7) | 226.3 (167.0; 306.7) |
| GM FI[1] | Day 15 vs Day 1 | 2.67 (2.068; 3.455) | 4.41 (3.473; 5.589) | 5.63 (4.102; 7.739) | 4.29 (2.868; 6.406) | 1.12 (0.895; 1.413) |
| % 2-fold[2] | Day 15 vs Day 1 | 48.9% (38.05%; 59.75%) | 72.5% (62.17%; 81.37%) | 72.0% (60.94%; 81.32%) | 72.5% (56.11%; 85.40%) | 13.3% (5.05%; 26.79%) |
| % 4-fold[2] | Day 15 vs Day 1 | 28.4% (19.30%; 39.02%) | 48.4% (37.74%; 59.07%) | 51.2% (39.92%; 62.42%) | 47.5% (31.51%; 63.87%) | 2.2% (0.06%; 11.77%) |
| | | Serotype O2 | | | | |
| GMTs | Day 1 | 370.7 (298.5; 460.4) | 305.7 (239.5; 390.2) | 385.2 (312.2; 475.3) | 403.5 (287.3; 566.6) | 370.0 (272.5; 502.5) |
| GMTs | Day 15 | 1951.9 (1436.3; 2652.5) | 1535.4 (1116.0; 2112.5) | 3455.8 (2424.9; 4925.1) | 2810.9 (1502.2; 5259.6) | 349.6 (261.6; 467.2) |
| GM FI[1] | Day 15 vs Day 1 | 5.77 (4.283; 7.778) | 6.38 (4.434; 9.172) | 11.18 (7.676; 16.272) | 8.28 (3.432; 19.966) | 1.05 (0.901; 1.212) |
| % 2-fold[2] | Day 15 vs Day 1 | 83.9% (71.67%; 92.38%) | 75.5% (61.72%; 86.24%) | 95.2% (83.84%; 99.42%) | 71.4% (47.82%; 88.72%) | 9.1% (2.53%; 21.67%) |
| % 4-fold[2] | Day 15 vs Day 1 | 62.5% (48.55%; 75.08%) | 60.4% (46.00%; 73.55%) | 76.2% (60.55%; 87.95%) | 57.1% (34.02%; 78.18%) | 0.0% (0.00%; 8.04%) |
| | | Serotype O4 | | | | |
| GMTs | Day 1 | 116.4 (96.5; 140.4) | 82.1 (66.8; 100.9) | 89.8 (77.2; 104.4) | 101.6 (73.2; 141.0) | 93.8 (72.9; 120.8) |
| GMTs | Day 15 | 359.7 (269.3; 480.5) | 296.9 (222.6; 395.8) | 458.3 (350.9; 598.5) | 104.1 (75.4; 143.8) | 98.4 (75.1; 129.0) |

TABLE 15-continued

MOPA data BAC1001 cohort 1

| Endpoint (95% CI) | Time point | ExPEC10V Low Dose | ExPEC10V Medium Dose | ExPEC10V High Dose | ExPEC4V | Prevnar |
|---|---|---|---|---|---|---|
| GM FI[1] | Day 15 vs Day 1 | 3.22 (2.526; 4.114) | 3.20 (2.557; 3.993) | 4.96 (3.915; 6.283) | 1.00 (0.874; 1.140) | 1.09 (0.916; 1.294) |
| % 2-fold[2] | Day 15 vs Day 1 | 59.2% (48.79%; 69.01%) | 59.1% (48.46%; 69.23%) | 73.2% (63.24%; 81.68%) | 4.0% (0.49%; 13.71%) | 12.8% (4.83%; 25.74%) |
| % 4-fold[2] | Day 15 vs Day 1 | 35.7% (26.29%; 46.03%) | 37.6% (27.79%; 48.28%) | 55.7% (45.23%; 65.76%) | 2.0% (0.05%; 10.65%) | 4.3% (0.52%; 14.54%) |
| Serotype O6A | | | | | | |
| GMTs | Day 1 | 632.8 (489.5; 818.0) | 559.0 (431.0; 724.9) | 628.0 (505.0; 781.0) | 495.8 (338.8; 725.6) | 623.6 (458.6; 848.1) |
| GMTs | Day 15 | 1454.0 (1109.3; 1905.8) | 2146.6 (1651.0; 2791.0) | 2227.9 (1685.7; 2944.7) | 1984.9 (1335.8; 2949.3) | 695.0 (489.5; 986.7) |
| GM FI[1] | Day 15 vs Day 1 | 2.24 (1.833; 2.733) | 3.74 (2.764; 5.069) | 3.59 (2.798; 4.597) | 4.11 (2.773; 6.084) | 1.20 (1.023; 1.397) |
| % 2-fold[2] | Day 15 vs Day 1 | 46.9% (36.78%; 57.29%) | 54.3% (43.66%; 64.58%) | 62.9% (52.48%; 72.48%) | 66.7% (51.59%; 79.60%) | 10.4% (3.47%; 22.66%) |
| % 4-fold[2] | Day 15 vs Day 1 | 23.5% (15.50%; 33.11%) | 41.5% (31.41%; 52.12%) | 41.2% (31.33%; 51.69%) | 39.6% (25.77%; 54.73%) | 2.1% (0.05%; 11.07%) |
| Serotype O8 | | | | | | |
| GMTs | Day 1 | 967.6 (764.2; 1225.1) | 699.2 (538.5; 907.9) | 896.3 (714.1; 1125.1) | 710.0 (535.1; 941.9) | 891.8 (684.4; 1162.1) |
| GMTs | Day 15 | 1205.4 (945.7; 1536.5) | 859.9 (657.8; 1124.2) | 937.3 (748.9; 1173.0) | 758.4 (558.5; 1029.9) | 930.0 (698.3; 1238.6) |
| GM FI[1] | Day 15 vs Day 1 | 1.22 (1.055; 1.422) | 1.22 (1.102; 1.346) | 1.09 (0.961; 1.226) | 1.04 (0.845; 1.271) | 1.03 (0.846; 1.242) |
| % 2-fold[2] | Day 15 vs Day 1 | 18.4% (11.26%; 27.47%) | 12.9% (6.85%; 21.45%) | 8.3% (3.67%; 15.76%) | 8.2% (2.27%; 19.60%) | 10.9% (3.62%; 23.57%) |
| % 4-fold[2] | Day 15 vs Day 1 | 4.1% (1.12%; 10.12%) | 3.2% (0.67%; 9.14%) | 3.1% (0.65%; 8.86%) | 4.1% (0.50%; 13.98%) | 2.2% (0.06%; 11.53%) |
| Serotype O15 | | | | | | |
| GMTs | Day 1 | 579.8 (443.0; 758.7) | 440.5 (322.1; 602.5) | 517.6 (394.8; 678.6) | 720.2 (472.1; 1098.6) | 528.0 (370.3; 752.9) |
| GMTs | Day 15 | 2509.1 (1742.6; 3612.8) | 2747.1 (1887.8; 3997.5) | 3355.7 (2272.3; 4955.5) | 641.2 (432.6; 950.4) | 777.6 (498.7; 1212.6) |
| GM FI[1] | Day 15 vs Day 1 | 4.30 (2.989; 6.199) | 6.40 (4.355; 9.408) | 6.70 (4.508; 9.948) | 0.96 (0.697; 1.331) | 1.54 (1.077; 2.206) |
| % 2-fold[2] | Day 15 vs Day 1 | 57.3% (45.91%; 68.18%) | 69.3% (58.58%; 78.71%) | 70.3% (59.84%; 79.45%) | 13.0% (4.94%; 26.26%) | 25.6% (13.52%; 41.17%) |
| % 4-fold[2] | Day 15 vs Day 1 | 39.0% (28.44%; 50.43%) | 54.5% (43.58%; 65.20%) | 56.0% (45.25%; 66.44%) | 8.7% (2.42%; 20.79%) | 14.0% (5.30%; 27.93%) |
| Serotype O16 | | | | | | |
| GMTs | Day 1 | 215.7 (170.2; 273.4) | 186.7 (149.3; 233.6) | 173.0 (139.4; 214.6) | 227.6 (164.3; 315.4) | 189.2 (146.1; 244.9) |
| GMTs | Day 15 | 1367.2 (1005.3; 1859.5) | 942.6 (697.1; 1274.4) | 1591.7 (1190.4; 2128.3) | 217.7 (150.4; 315.2) | 175.7 (130.1; 237.3) |
| GM FI[1] | Day 15 vs Day 1 | 5.90 (4.428; 7.852) | 5.00 (3.655; 6.845) | 9.12 (6.807; 12.223) | 0.92 (0.778; 1.092) | 0.99 (0.832; 1.175) |
| % 2-fold[2] | Day 15 vs Day 1 | 76.0% (66.43%; 83.98%) | 71.0% (60.64%; 79.92%) | 84.4% (75.54%; 90.98%) | 8.2% (2.27%; 19.60%) | 8.3% (2.32%; 19.98%) |

TABLE 15-continued

| Endpoint (95% CI) | Time point | ExPEC10V Low Dose | ExPEC10V Medium Dose | ExPEC10V High Dose | ExPEC4V | Prevnar |
|---|---|---|---|---|---|---|
| MOPA data BAC1001 cohort 1 | | | | | | |
| % 4-fold[2] | Day 15 vs Day 1 | 55.0% (44.73%; 64.97%) | 50.5% (39.97%; 61.07%) | 75.0% (65.12%; 83.28%) | 2.0% (0.05%; 10.85%) | 4.2% (0.51%; 14.25%) |
| Serotype O18A | | | | | | |
| GMTs | Day 1 | 65.6 (51.3; 83.9) | 51.8 (39.0; 68.9) | 52.7 (42.1; 66.1) | 63.6 (42.2; 95.8) | 52.8 (39.4; 70.8) |
| GMTs | Day 15 | 251.0 (180.9; 348.1) | 248.8 (184.9; 334.7) | 310.0 (221.7; 433.4) | 68.3 (45.2; 103.4) | 62.4 (40.1; 97.1) |
| GM FI[1] | Day 15 vs Day 1 | 3.91 (2.946; 5.193) | 4.52 (3.259; 6.256) | 5.65 (4.190; 7.624) | 1.10 (0.930; 1.309) | 1.24 (0.961; 1.609) |
| % 2-fold[2] | Day 15 vs Day 1 | 66.3% (55.28%; 76.12%) | 65.4% (54.04%; 75.66%) | 76.4% (66.22%; 84.76%) | 7.1% (1.50%; 19.48%) | 9.5% (2.66%; 22.62%) |
| % 4-fold[2] | Day 15 vs Day 1 | 44.2% (33.48%; 55.30%) | 46.9% (35.73%; 58.33%) | 55.1% (44.14%; 65.62%) | 4.8% (0.58%; 16.16%) | 7.1% (1.50%; 19.48%) |
| Serotype O25B | | | | | | |
| GMTs | Day 1 | 157.9 (121.4; 205.3) | 145.0 (109.6; 191.8) | 149.8 (117.6; 191.0) | 147.1 (105.5; 204.9) | 162.2 (115.8; 227.2) |
| GMTs | Day 15 | 399.1 (303.8; 524.2) | 497.4 (375.7; 658.4) | 387.9 (295.5; 509.2) | 460.1 (312.1; 678.3) | 245.0 (154.5; 388.6) |
| GM FI[1] | Day 15 vs Day 1 | 2.23 (1.792; 2.768) | 2.70 (2.117; 3.453) | 2.28 (1.833; 2.826) | 2.83 (1.932; 4.143) | 1.42 (1.004; 2.015) |
| % 2-fold[2] | Day 15 vs Day 1 | 45.7% (35.22%; 56.37%) | 48.9% (38.34%; 59.56%) | 46.2% (35.64%; 56.92%) | 52.2% (36.95%; 67.11%) | 15.2% (6.34%; 28.87%) |
| % 4-fold[2] | Day 15 vs Day 1 | 23.9% (15.63%; 33.94%) | 31.5% (22.23%; 42.04%) | 26.4% (17.69%; 36.65%) | 39.1% (25.09%; 54.63%) | 4.3% (0.53%; 14.84%) |
| Serotype O75 | | | | | | |
| GMTs | Day 1 | <LLOQ (<LLOQ; 39.3) | <LLOQ (<LLOQ; <LLOQ) | <LLOQ (<LLOQ; <LLOQ) | <LLOQ (<LLOQ; 37.2) | <LLOQ (<LLOQ; 40.1) |
| GMTs | Day 15 | 77.1 (60.6; 98.1) | 55.6 (44.6; 69.4) | 71.0 (53.9; 93.7) | <LLOQ (<LLOQ; 37.2) | <LLOQ (<LLOQ; 44.0) |
| GM FI[1] | Day 15 vs Day 1 | 1.88 (1.548; 2.275) | 1.65 (1.404; 1.941) | 2.10 (1.700; 2.596) | 1.04 (0.944; 1.147) | 1.04 (0.945; 1.156) |
| % 2-fold[2] | Day 15 vs Day 1 | 33.7% (24.17%; 44.30%) | 27.5% (18.63%; 37.83%) | 36.0% (25.97%; 47.12%) | 2.3% (0.06%; 12.02%) | 4.4% (0.54%; 15.15%) |
| % 4-fold[2] | Day 15 vs Day 1 | 15.2% (8.58%; 24.21%) | 15.4% (8.67%; 24.46%) | 22.1% (13.86%; 32.33%) | 2.3% (0.06%; 12.02%) | 0.0% (0.00%; 7.87%) |

Cohort 1: output for the primary analysis

[1]= GM of FI from baseline (Day 1)

[2]= percentage of participants with fold increase from baseline (Day 1)

CI = Confidence interval;

GM = Geometric mean,

GMT = Geometric mean titer;

FI = Fold increase

95% CI for GMT and GM FI is based on the t-distribution

95% CI for Percentage of Participants With 2- and 4-Fold Increase is obtained using Clopper-Pearson method.

Dose Selection

The immunogenicity dose selection algorithm based on the mean of the log 10 fold increase from baseline to Day 15 of each dose group identified the ExPEC10V high dose for cohort 2 of this trial considering the two analysis sets (PPI and FAS) and the two assays (ECL and MOPA).

For serotypes O2, O4, O15, O16 and O18A, the high dose group had higher GMT, GMR and percentage of participants with 2-fold and 4-fold increases at Day 15 compared to the other 2 ExPEC10V doses in both assays. For serotype O25B, the medium dose group generally had higher GMT, GMR and percentage of participants with 2-fold and 4-fold increases among the 3 ExPEC10V dose groups; for this serotype the O-antigen dose was the same (16 μg) for both the medium and the high ExPEC10V dose groups. For both serotype O1A and O6A, the results were mixed between the high and the medium dose. In serotype O75, there was a measurable functional antibody response for the ExPEC10V doses. Measurable functional antibody responses were not detected in the qualified assay for serotype O8, as discussed above. In the non-ExPEC4V serotypes, low functional antibody responses were observed in the 2 active controls; the antibody response came from pre-existing antibodies rather than from vaccine-induced response. Based on these results, the high dose of ExPEC10V was selected for the cohort 2 of BAC1001 clinical trial.

CONCLUSION

ExPEC10V vaccine induced robust antibody responses, an increase in O-antigen specific serum antibodies were observed for all vaccine-related serotypes at day 15 post-vaccination when compared to baseline titers (day 1). ExPEC10V-induced functional antibodies that mediated *E. coli* opsonophagocytic killing were detected in a qualified MOPA for all vaccine-related serotypes, except for the serotype O8. For serotype O8, subsequent studies with a modified MOPA did measure a functional antibody response. Notably, the O75 response was weaker at 4 μg and 8 μg doses than for the other serotypes at the same dose, which was a surprising and unpredictable finding from this study. To improve the immune response to *E. coli* O75 serotype generated by multivalent glycoconjugate compositions, in one aspect the instant invention increases the dose of serotype O75 antigen polysaccharide, e.g., to about 1.2 to 8 times the dose of some of the other serotypes, e.g. about 1.5 to 4 times, e.g. about 1.5 to 2.5 times, e.g. about 2 times the dose of some of the other serotypes such as O6 or O1, e.g. to about 16 μg, which is higher than for instance three of the most relevant and prevalent serotypes O1A, O2, and O6A, and similar to serotype O25B antigen polysaccharide. It is noted that in earlier experiments (see e.g. above in this example as well as examples 5 and 6, i.e. before the clinical data with the ExPEC10V vaccine disclosed herein were available) the dose of O75 antigen polysaccharide was at best as high as the doses of O1A, O2 and O6A antigen polysaccharides, or actually in certain tested groups even two times lower than O1A and O6A antigen polysaccharides, and even 2 to 4 times lower than O25B antigen polysaccharide. In contrast, in certain aspects of the instant invention the dose of O75 is thus actually increased compared to the dose of O1, O2, and/or O6.

Cohort 2 Safety and Immunogenicity Results

In Cohort 2 of this study, a total of approximately 420 participants aged ≥60 year in stable health with a history of UTI in the past 5 year were enrolled and randomized in parallel in a 2:1 ratio (the set on which a full results analysis was performed included 278 participants in the ExPEC10V (high dose) group and 138 in the placebo group).

Safety

Overall, the ExPEC10V vaccine was well tolerated. The reactogenicity profile was generally comparable to that observed with medium and high doses of ExPEC10V in Cohort 1. The most frequent local solicited AE was pain/tenderness and the most frequently reported systemic AEs were myalgia, headache, and fatigue. Injection site erythema and swelling were the most common late-onset events (time to first onset >5 days after vaccination). The reactogenicity profile of ExPEC10V is acceptable when compared to other licensed vaccines used in older adult populations.

Immunogenicity

Vaccine-induced antibody responses were assessed at baseline (day 1 pre-vaccination) and at day 15 and day 30 post-vaccination using a multiplex ECL-based immunoassay that measures the levels of serotype-specific serum antibodies (total IgG).

Levels of Antigen-Specific Serum Antibodies (ECL, Day 1, Day 15 and Day 30)

The ExPEC10V vaccine was immunogenic for all serotypes based on the increasing value of the GMT, GMT FI and percentage of participants with at least 2-fold increase in titer from baseline from Day 1 to Day 15. There were minimal changes in all three measures from Day 15 to Day 30. The highest antibody responses were observed for the serotypes O2, O4, O15 and O16 with at least 80% of the participants vaccinated with ExPEC10V showing a two-fold or greater increase in antibody responses by Day 15 and Day 30 post-vaccination. For the serotypes O1A, O6A and O25B, at least 70% of participants show a two-fold or greater increase in antibody response and for the serotypes O8 and O18A at least 60% of the participants show a two-fold or greater increase in antibody response. Lower antibody responses were observed for the serotype O75, nevertheless, a two-fold or greater increase in antigen-specific antibody response was observed in at least 50% of the participants. Minimal changes in the GMT from day 1 to day 15 and day 30 were observed in the group of subjects that received placebo (Table 16).

The geometric mean titer (GMT), GMT FI (geometric mean titer fold-increase) and percentage of participants with at least 2- and 4-fold increases from baseline in the ECL-based immunoassay are summarized in Table 16 below.

TABLE 16

ECL data BAC1001 cohort 2 (day 1, day 15 and day 30)

| Endpoint (95% CI) | Time point | ExPEC10V | Placebo |
|---|---|---|---|
| | | Serotype O1A | |
| GMTs | Day 1 | 1466300.6 (1309861.4; 1641423.6) | 1714154.2 (1463104.9; 2008280.3) |
| GMTs | Day 15 | 6474621.3 (5996773.2; 6990546.4) | 1696032.9 (1445852.1; 1989503.3) |
| GMTs | Day 30 | 6363928.5 (5918207.5; 6843218.4) | 1773323.4 (1515713.5; 2074716.7) |
| GM FI[1] | Day 15 vs Day 1 | 4.38 (3.908; 4.902) | 0.99 (0.966; 1.023) |
| GM FI[1] | Day 30 vs Day 1 | 4.35 (3.915; 4.843) | 1.02 (0.954; 1.094) |
| % 2-fold[2] | Day 15 vs Day 1 | 75.9% (70.13%; 81.03%) | 0.0% (0.00%; 2.84%) |
| % 2-fold[2] | Day 30 vs Day 1 | 77.6% (72.04%; 82.46%) | 1.5% (0.19%; 5.45%) |
| % 4-fold[2] | Day 15 vs Day 1 | 54.5% (48.19%; 60.79%) | 0.0% (0.00%; 2.84%) |
| % 4-fold[2] | Day 30 vs Day 1 | 54.4% (48.14%; 60.50%) | 0.8% (0.02%; 4.21%) |

TABLE 16-continued

ECL data BAC1001 cohort 2 (day 1, day 15 and day 30)

| Endpoint (95% CI) | Time point | ExPEC10V | | Placebo | |
|---|---|---|---|---|---|
| Serotype O2 | | | | | |
| GMTs | Day 1 | 739313.9 | (659799.6; 828410.8) | 768325.6 | (648274.3; 910608.6) |
| GMTs | Day 15 | 6001149.0 | (5522390.3; 6521413.2) | 759366.1 | (637561.8; 904440.8) |
| GMTs | Day 30 | 5995886.9 | (5530975.6; 6499876.9) | 747487.9 | (627602.8; 890273.4) |
| GM FI[1] | Day 15 vs Day 1 | 8.02 | (7.105; 9.043) | 1.00 | (0.933; 1.061) |
| GM FI[1] | Day 30 vs Day 1 | 8.16 | (7.244; 9.182) | 0.98 | (0.910; 1.054) |
| % 2-fold[2] | Day 15 vs Day 1 | 88.9% | (84.40%; 92.52%) | 0.8% | (0.02%; 4.28%) |
| % 2-fold[2] | Day 30 vs Day 1 | 89.4% | (84.98%; 92.81%) | 1.5% | (0.19%; 5.45%) |
| % 4-fold[2] | Day 15 vs Day 1 | 78.7% | (73.09%; 83.54%) | 0.8% | (0.02%; 4.28%) |
| % 4-fold[2] | Day 30 vs Day 1 | 77.6% | (72.04%; 82.46%) | 1.5% | (0.19%; 5.45%) |
| Serotype O4 | | | | | |
| GMTs | Day 1 | 678578.0 | (616370.1; 747064.4) | 744119.6 | (646038.0; 857092.0) |
| GMTs | Day 15 | 3746755.5 | (3336959.5; 4206876.5) | 760274.2 | (652833.0; 885397.7) |
| GMTs | Day 30 | 3570627.3 | (3188275.4; 3998832.6) | 806768.3 | (691960.6; 940624.6) |
| GM FI[1] | Day 15 vs Day 1 | 5.60 | (4.965; 6.309) | 1.03 | (0.992; 1.067) |
| GM FI[1] | Day 30 vs Day 1 | 5.31 | (4.743; 5.955) | 1.09 | (1.014; 1.166) |
| % 2-fold[2] | Day 15 vs Day 1 | 82.6% | (77.37%; 87.07%) | 1.6% | (0.19%; 5.53%) |
| % 2-fold[2] | Day 30 vs Day 1 | 81.7% | (76.54%; 86.23%) | 2.3% | (0.48%; 6.60%) |
| % 4-fold[2] | Day 15 vs Day 1 | 62.1% | (55.77%; 68.06%) | 0.8% | (0.02%; 4.28%) |
| % 4-fold[2] | Day 30 vs Day 1 | 58.9% | (52.73%; 64.94%) | 1.5% | (0.19%; 5.45%) |
| Serotype O6A | | | | | |
| GMTs | Day 1 | 1491643.9 | (1353036.8; 1644450.1) | 1836907.8 | (1582827.3; 2131774.0) |
| GMTs | Day 15 | 5624986.5 | (5131740.4; 6165641.6) | 1881936.5 | (1613534.0; 2194986.4) |
| GMTs | Day 30 | 5516879.9 | (5049584.3; 6027419.7) | 1934121.0 | (1657028.0; 2257550.3) |
| GM FI[1] | Day 15 vs Day 1 | 3.92 | (3.548; 4.339) | 1.03 | (0.991; 1.073) |
| GM FI[1] | Day 30 vs Day 1 | 3.64 | (3.295; 4.026) | 1.06 | (0.991; 1.135) |
| % 2-fold[2] | Day 15 vs Day 1 | 74.7% | (68.88%; 79.94%) | 0.8% | (0.02%; 4.28%) |
| % 2-fold[2] | Day 30 vs Day 1 | 73.0% | (67.21%; 78.27%) | 2.3% | (0.48%; 6.60%) |
| % 4-fold[2] | Day 15 vs Day 1 | 50.2% | (43.87%; 56.52%) | 0.0% | (0.00%; 2.84%) |
| % 4-fold[2] | Day 30 vs Day 1 | 44.5% | (38.38%; 50.72%) | 0.8% | (0.02%; 4.21%) |
| Serotype O8 | | | | | |
| GMTs | Day 1 | 2145103.2 | (1937289.9; 2375208.6) | 2335274.5 | (2038224.0; 2675617.0) |
| GMTs | Day 15 | 6281926.9 | (5810107.0; 6792061.6) | 2380959.0 | (2063441.9; 2747334.9) |
| GMTs | Day 30 | 6286969.0 | (5832409.6; 6776955.4) | 2303456.2 | (2002524.6; 2649610.7) |
| GM FI[1] | Day 15 vs Day 1 | 2.95 | (2.669; 3.253) | 1.03 | (0.992; 1.073) |
| GM FI[1] | Day 30 vs Day 1 | 2.94 | (2.676; 3.239) | 1.01 | (0.965; 1.058) |
| % 2-fold[2] | Day 15 vs Day 1 | 62.8% | (56.57%; 68.82%) | 1.6% | (0.19%; 5.53%) |
| % 2-fold[2] | Day 30 vs Day 1 | 64.6% | (58.53%; 70.41%) | 1.5% | (0.19%; 5.45%) |
| % 4-fold[2] | Day 15 vs Day 1 | 37.5% | (31.56%; 43.83%) | 1.6% | (0.19%; 5.53%) |
| % 4-fold[2] | Day 30 vs Day 1 | 38.4% | (32.50%; 44.58%) | 1.5% | (0.19%; 5.45%) |
| Serotype O15 | | | | | |
| GMTs | Day 1 | 1178299.6 | (1056703.9; 1313887.4) | 1188287.9 | (1014882.9; 1391321.1) |
| GMTs | Day 15 | 5790439.7 | (5353107.3; 6263500.7) | 1198106.9 | (1021376.8; 1405416.7) |
| GMTs | Day 30 | 5728512.6 | (5308296.8; 6181993.5) | 1204454.0 | (1026963.7; 1412620.0) |
| GM FI[1] | Day 15 vs Day 1 | 4.97 | (4.461; 5.545) | 1.02 | (0.974; 1.070) |
| GM FI[1] | Day 30 vs Day 1 | 4.98 | (4.477; 5.544) | 1.02 | (0.961; 1.075) |
| % 2-fold[2] | Day 15 vs Day 1 | 82.6% | (77.37%; 87.07%) | 0.8% | (0.02%; 4.28%) |
| % 2-fold[2] | Day 30 vs Day 1 | 84.0% | (79.03%; 88.24%) | 1.5% | (0.19%; 5.45%) |
| % 4-fold[2] | Day 15 vs Day 1 | 59.3% | (52.96%; 65.40%) | 0.8% | (0.02%; 4.28%) |
| % 4-fold[2] | Day 30 vs Day 1 | 58.6% | (52.34%; 64.57%) | 0.8% | (0.02%; 4.21%) |
| Serotype O16 | | | | | |
| GMTs | Day 1 | 1040760.3 | (957123.1; 1131706.2) | 1089930.0 | (964478.4; 1231699.4) |
| GMTs | Day 15 | 5395867.2 | (4945129.5; 5887688.6) | 1068317.6 | (948255.2; 1203581.7) |
| GMTs | Day 30 | 5148889.9 | (4731805.0; 5602738.7) | 1119689.3 | (994125.9; 1261112.1) |
| GM FI[1] | Day 15 vs Day 1 | 5.20 | (4.673; 5.785) | 1.03 | (0.987; 1.083) |
| GM FI[1] | Day 30 vs Day 1 | 5.03 | (4.565; 5.539) | 1.06 | (0.992; 1.124) |
| % 2-fold[2] | Day 15 vs Day 1 | 86.6% | (81.73%; 90.51%) | 0.8% | (0.02%; 4.28%) |
| % 2-fold[2] | Day 30 vs Day 1 | 86.3% | (81.56%; 90.23%) | 1.5% | (0.19%; 5.45%) |
| % 4-fold[2] | Day 15 vs Day 1 | 63.2% | (56.97%; 69.19%) | 0.8% | (0.02%; 4.28%) |
| % 4-fold[2] | Day 30 vs Day 1 | 62.0% | (55.81%; 67.87%) | 1.5% | (0.19%; 5.45%) |
| Serotype O18A | | | | | |
| GMTs | Day 1 | 1190203.0 | (1087258.8; 1302894.3) | 1302260.8 | (1143295.8; 1483328.6) |
| GMTs | Day 15 | 4279941.4 | (3862457.1; 4742550.6) | 1343837.5 | (1178013.2; 1533004.1) |
| GMTs | Day 30 | 4072329.3 | (3684419.9; 4501079.2) | 1356020.6 | (1188694.1; 1546900.9) |
| GM FI[1] | Day 15 vs Day 1 | 3.65 | (3.282; 4.058) | 1.06 | (1.025; 1.097) |
| GM FI[1] | Day 30 vs Day 1 | 3.41 | (3.095; 3.758) | 1.07 | (1.014; 1.128) |
| % 2-fold[2] | Day 15 vs Day 1 | 69.2% | (63.08%; 74.80%) | 0.8% | (0.02%; 4.28%) |
| % 2-fold[2] | Day 30 vs Day 1 | 69.2% | (63.24%; 74.73%) | 1.5% | (0.19%; 5.45%) |

TABLE 16-continued

ECL data BAC1001 cohort 2 (day 1, day 15 and day 30)

| Endpoint (95% CI) | Time point | ExPEC10V | Placebo |
|---|---|---|---|
| % 4-fold[2] | Day 15 vs Day 1 | 47.8% (41.53%; 54.17%) | 0.0% (0.00%; 2.84%) |
| % 4-fold[2] | Day 30 vs Day 1 | 43.0% (36.90%; 49.19%) | 0.8% (0.02%; 4.21%) |
| | | Serotype O25B | |
| GMTs | Day 1 | 386797.7 (340192.1; 439788.2) | 374962.9 (316641.9; 444025.8) |
| GMTs | Day 15 | 2214631.7 (1915515.0; 2560457.0) | 362651.4 (304024.4; 432583.7) |
| GMTs | Day 30 | 2124158.2 (1851850.8; 2436507.4) | 372616.7 (314118.4; 442009.2) |
| GM FI[1] | Day 15 vs Day 1 | 5.96 (5.129; 6.937) | 1.02 (0.965; 1.073) |
| GM FI[1] | Day 30 vs Day 1 | 5.57 (4.851; 6.389) | 1.04 (0.963; 1.114) |
| % 2-fold[2] | Day 15 vs Day 1 | 77.9% (72.24%; 82.83%) | 0.8% (0.02%; 4.28%) |
| % 2-fold[2] | Day 30 vs Day 1 | 77.9% (72.44%; 82.81%) | 2.3% (0.48%; 6.60%) |
| % 4-fold[2] | Day 15 vs Day 1 | 58.9% (52.56%; 65.02%) | 0.8% (0.02%; 4.28%) |
| % 4-fold[2] | Day 30 vs Day 1 | 56.7% (50.43%; 62.73%) | 1.5% (0.19%; 5.45%) |
| | | Serotype O75 | |
| GMTs | Day 1 | 1610037.7 (1463566.9; 1771167.0) | 1522567.0 (1323219.9; 1751946.3) |
| GMTs | Day 15 | 3874235.9 (3529397.7; 4252766.2) | 1527849.3 (1311522.5; 1779857.8) |
| GMTs | Day 30 | 3753012.6 (3419195.0; 4119421.0) | 1572632.2 (1362470.9; 1815211.0) |
| GM FI[1] | Day 15 vs Day 1 | 2.44 (2.236; 2.671) | 1.02 (0.977; 1.073) |
| GM FI[1] | Day 30 vs Day 1 | 2.32 (2.136; 2.526) | 1.04 (0.979; 1.109) |
| % 2-fold[2] | Day 15 vs Day 1 | 53.0% (46.61%; 59.25%) | 1.6% (0.19%; 5.53%) |
| % 2-fold[2] | Day 30 vs Day 1 | 51.0% (44.74%; 57.14%) | 2.3% (0.48%; 6.60%) |
| % 4-fold[2] | Day 15 vs Day 1 | 25.3% (20.06%; 31.12%) | 1.6% (0.19%; 5.53%) |
| % 4-fold[2] | Day 30 vs Day 1 | 23.6% (18.58%; 29.18%) | 2.3% (0.48%; 6.60%) |

Cohort 2: output for the primary analysis
1 = GM of FI from baseline (Day 1)
2 = percentage of participants with fold increase from baseline (Day 1)
CI = Confidence interval;
GM = Geometric mean,
GMT = Geometric mean titer;
FI = Fold increase
95% CI for GMT and GM FI is based on the t-distribution
95% CI for Percentage of Participants With 2- and 4-Fold Increase is obtained using Clopper-Pearson method.

The magnitude of response at day 15 (GMTs) was similar between cohort 1 and 2 for all serotypes.

Example 8: Novel ExPEC Compositions and Immunogenicity in Rabbits

A new study was designed, which included 2 adapted compositions (also referred to herein as adapted formulations) of ExPEC vaccine (ExPEC9V a and b, Table 17). These adapted formulations are depleted of the serotype O8 polysaccharide and have increased polysaccharide content for the *E. coli* serotype O75 (ExPEC9V b), since low immunogenicity was observed for these antigens during the analysis of the cohort 1 from the Ph1/2a clinical trial. As a control to verify earlier experiments described above, an ExPEC10V composition was also evaluated. A saline control (unvaccinated group) was also included.

The overall aim of the study was to evaluate whether the changes in the vaccine composition as compared to ExPEC10V described above (depletion of O8 polysaccharide and dose increase specifically for O75 antigen polysaccharide) have any impact on the vaccine-induced immune response. In particular, the aim was to see if increasing the amount of conjugate of *E. coli* O75 antigen polysaccharide as compared to e.g. conjugate of *E. coli* O6 antigen polysaccharide in multivalent conjugate vaccine compositions indeed selectively improves the immune response to *E. coli* of serotype O75, and thus results in a more uniformly elevated immune response across the constituent *E. coli* serotypes. For that, the antibody responses induced by different formulations of ExPEC vaccine were evaluated in an established pre-clinical model of immunogenicity using New Zealand White rabbits (NZW).

Experimental Design

New Zealand White rabbits (NZW, 13 weeks of age at start of the study) received 3 intramuscular immunizations (500 μL/injection) with different formulations of ExPEC vaccine or saline administered 2 weeks apart (Table 17). The study contained 4 different groups (Table 18): Group 1 (ExPEC10V) received 8 μg/dose of O1A, O2, O6A, O4, O8, O15, O16, O18 and O75, and 16 μg/dose of O25B (i.e. 0.5 mL of a composition comprising 16 μg/mL of each of O1A, O2, O6A, O4-Glc+, O8, O15, O16, O18A and O75 antigen polysaccharides, and 32 μg/mL of O25B antigen polysaccharide, each antigen polysaccharide separately bioconjugated to EPA carrier protein, see examples above); Group 2 (ExPEC9V a) received 8 μg/dose of O1A, O2, O6A, O4, O15, O16, O18A and O75, and 16 μg/dose of O25B (i.e. 0.5 mL of a composition comprising 16 μg/mL of each of O1A, O2, O6A, O4-Glc+, O15, O16, O18A and O75 antigen polysaccharides, and 32 μg/mL of O25B antigen polysaccharide, each antigen polysaccharide separately bioconjugated to EPA carrier protein, see examples above); Group 3 (ExPEC9V b) received 8 μg/dose of O1A, O2, O6A, O4, O15, O16 and O18A, and 16 μg/dose of O75 and O25B (i.e. 0.5 mL of a composition comprising 16 μg/mL of each of O1A, O2, O6A, O4-Glc+, O15, O16, and O18A antigen polysaccharides, and 32 μg/mL of O25B and O75 antigen polysaccharides, each antigen polysaccharide separately bioconjugated to EPA carrier protein, see examples above).

The buffer used for compounding contained 6.19 mM KH2PO4, 3.81 mM Na2HPO4, 5% sorbitol (w/w), 10 mM Methionine, 0.02% PS80 (w/w), pH 7.0. Animals from the control group (Group 4) received saline (0.9% (w/v) sodium chloride solution). Each experimental group contained 10 animals. Serum antibody levels measured by ELISA (total IgG) were evaluated pre-immunization (day 0) and post-immunization (day 14, 28 and 42).

TABLE 17

Different multivalent ExPEC vaccine compositions.

| Serotypes | ExPEC10V | ExPEC9V a | ExPEC9V b |
|---|---|---|---|
| O1A | 8 | 8 | 8 |
| O2 | 8 | 8 | 8 |
| O4 | 8 | 8 | 8 |
| O6A | 8 | 8 | 8 |
| O8 | 8 | 0 | 0 |
| O15 | 8 | 8 | 8 |
| O16 | 8 | 8 | 8 |
| O18A | 8 | 8 | 8 |
| O25B | 16 | 16 | 16 |
| O75 | 8 | 8 | 16 |
| Total PS (μg) | 88 | 80 | 88 |

TABLE 18

Experimental groups.

| Groups | Treatment | Dosing at days | Number of animals |
|---|---|---|---|
| 1 | ExPEC10V | 0, 14, 28 | 10 |
| 2 | ExPEC9V a (O75:O6 in 1:1 ratio) | 0, 14, 28 | 10 |
| 3 | ExPEC9V b (O75:O6 in 2:1 ratio) | 0, 14, 28 | 10 |
| 4 | Saline | 0, 14, 28 | 10 |

Potential injection site reactions were monitored using Draize scoring system before each dose, approximately 6 hours post-dose on each dosing day, and daily for 7 days after the injection. If case injection site effects were observed, the daily observations were continued until scores returned to 0.

Animals were individually weighed (in grams) once during pre-treatment, daily for 3 days post each dose, once weekly thereafter. Animals were observed at least once daily for ill health, or untoward clinical effects. On dosing days, animals were examined for reaction to treatment before dosing and approximately 6h after treatment (at same time as injection site examination). Body temperature was monitored using a rectal digital thermometer and recorded pre-dose, 6 h and 24 h after each dose. Where a temperature falls outside the normal range for rabbits of 38-40° C., additional measurements were conducted daily until body temperature returned to be within these values.

Animals received 3 intramuscular immunizations with ExPEC10V, ExPEC9V a, ExPEC9V b, or saline, administered 2 weeks apart. Antibody levels were measured by ELISA at day 0 (pre-vaccination) and days 14, 28 and 42 (post-vaccination).

Serum antibody levels induced by each of the O-antigens included in ExPEC vaccine compositions were analyzed by ELISA using Gen 5 software. OD at 450 nm was analyzed in a 4 parameter (4PL) nonlinear regression model. Half maximal effective concentration (EC50) was calculated for each individual sample based on duplicate 12 step titration curves. Sample results are expressed as EC50 titers.

Figure 6A:
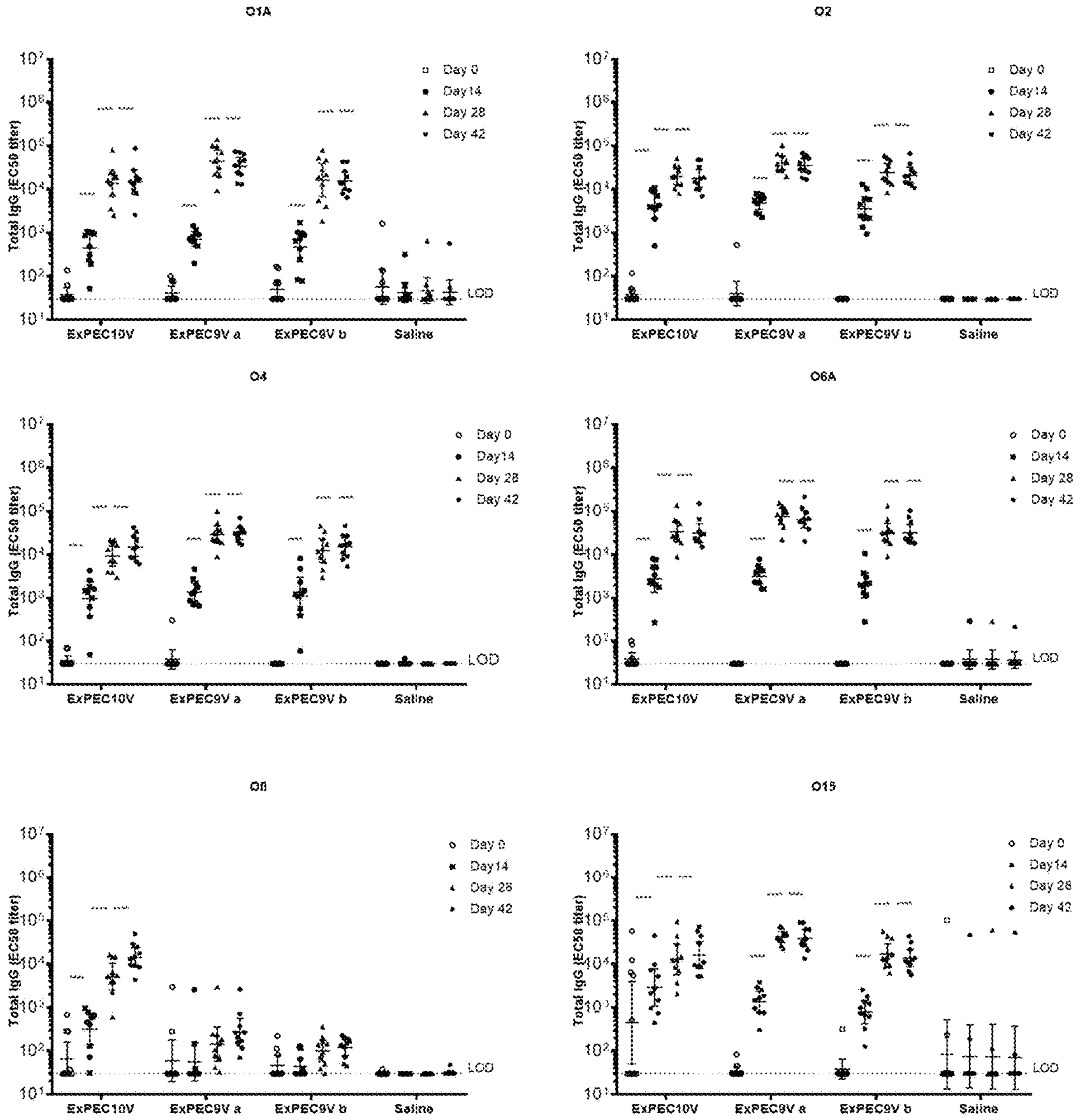
FIG. 6A-6B shows serum antibody levels (total IgG) induced by different compositions of ExPEC vaccine in New Zealand White rabbits. See Example 8 for details. Graphs show individual titers (EC50 titer) and geometric mean titers (GMT)+95% confidence intervals. Comparison between vaccine groups versus saline control were statistically evaluated using a Tobit model with likelihood ratio test and a Bonferroni correction for multiple comparisons was used. p values ≤0.05 were considered statistically significant. **** $p \leq 0.0001$.
Figure 6B:
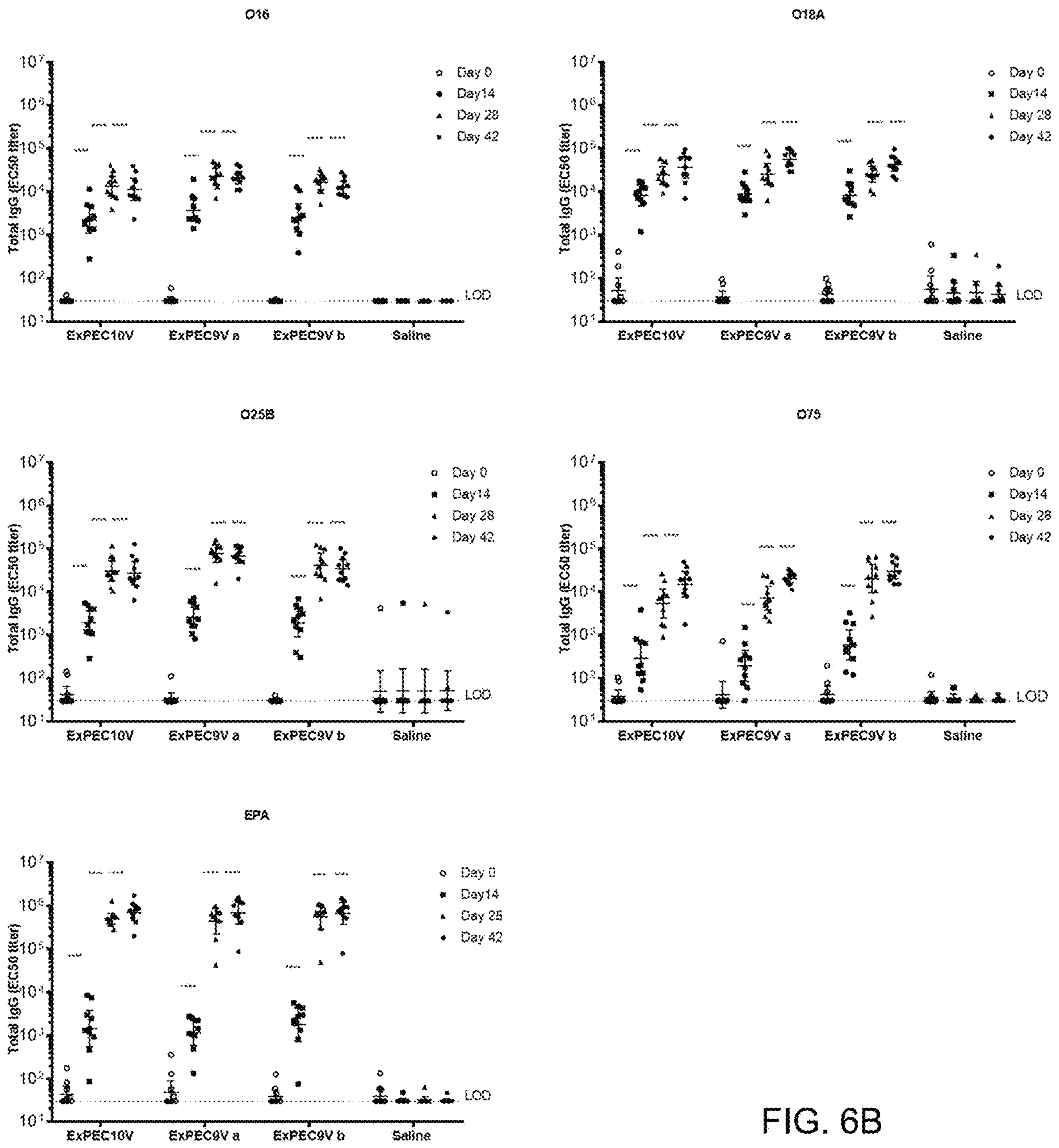

Evaluation of antigen-specific serum antibody responses in NZW rabbits showed that all ExPEC vaccine compositions tested (ExPEC10V, ExPEC9V a and ExPEC9V b) induced a significant increase in antibody responses to all vaccine antigens at day 14, 28 and 42 post-vaccination when compared to the saline control (FIG. 6). The second dose of all ExPEC vaccine compositions tested boosted antibody responses as demonstrated by a significant increase in antigen specific antibody responses from day 14 to day 28 post-vaccination. A further boost effect of the third dose of ExPEC vaccine was evident for certain antigens and compositions.

The geometric mean antibody titers (GMT) of O75 antigen increased with increased concentration of O75 polysaccharide (FIG. 6). ExPEC9V b composition, containing increased concentration of the polysaccharide O75 (16 μg), induced higher O75 GMT and GMT fold-increase at day 14, 28 and 42 post-vaccination when compared to ExPEC9V a and ExPEC10V compositions that contain only 8 μg of O75 polysaccharide (Table 19).

TABLE 19

Evaluation of O75 antibody responses in different ExPEC vaccine compositions.

| Treatment | O75 antibody responses | Time-point post-vaccination Day 0 | Day 14 | Day 28 | Day 42 |
|---|---|---|---|---|---|
| ExPEC10V | GMT | 38 | 288 | 5322 | 15052 |
| | 95% CI | 26.7-53.2 | 115.0-720.4 | 2430.2-11653.4 | 7569.2-29930.8 |
| | GMT fold increase | na | 7.6 | 141.2 | 399.4 |
| ExPEC9V a | GMT | 41 | 192 | 7116 | 20798 |
| | 95% CI | 20.1-84.5 | 83.9-439.6 | 3769.1-13436.4 | 16368.0-26425.8 |
| | GMT fold increase | na | 4.7 | 172.7 | 504.7 |
| ExPEC9V b | GMT | 42 | 585 | 20303 | 30269 |
| | 95% CI | 26.7-65.2 | 264.3-1296.6 | 9403.1-43836.5 | 20294.9-45146.3 |
| | GMT fold increase | na | 14.0 | 486.9 | 726.0 |

n.a.: not applicable;
GMT: geometric mean antibody titers;
CI: confidence interval;
fold-increase GMT compared to day 0 (baseline pre-vaccination).

Evaluation of body weight, body temperature and injection site reactions show that all ExPEC vaccine compositions tested were well tolerated by the animals (data not shown).

In conclusion, all ExPEC vaccine compositions tested were immunogenic in NZW rabbits, significant increase in antigen-specific serum antibody responses were observed at day 14, 28 and 42 post-vaccination when compared to saline control. All ExPEC vaccine compositions tested were able to boost polysaccharide specific-antibody responses. In addition, all ExPEC vaccine compositions tested were well tolerated by the animals, no vaccine-related adverse events were observed. Importantly, ExPEC9V b composition, containing increased concentration of O75 polysaccharide, induced higher O75 antibody responses (GMT and GMT fold-increase) when compared to compositions that contain lower concentration of O75 polysaccharide (ExPEC9Va and ExPEC10V). The increased dose of O75 in the ExPEC9V b composition thus improves the immune response to the O75 serotype, and therefore such a composition leads to a more uniformly elevated immune response across the serotypes in the ExPEC9V b composition.

Example 9. Phase 3 Efficacy Trial in Humans with Novel ExPEC9V Composition

An efficacy study in humans is conducted with the 9-valent ExPEC vaccine composition that has an increased concentration of O75 antigen polysaccharide. The title of the study is: "Randomized, Double-blind, Placebo-controlled, Multicenter Phase 3 Study to Assess the Efficacy, Safety And Immunogenicity of Vaccination With ExPEC9V in the Prevention of Invasive Extraintestinal Pathogenic *Escherichia coli* Disease in Adults Aged 60 Years And Older with a History of Urinary Tract Infection in the Past 2 Years.", and it will be referred to as the 'BAC3001' study herein.

ExPEC9V is a 9-valent vaccine candidate in development for the prevention of invasive extraintestinal pathogenic *Escherichia coli* (ExPEC) disease (IED) in adults 60 years of age and older. ExPEC9V consists of the O-antigen polysaccharides (PSs) of the ExPEC serotypes O1A, O2, O4, O6A, O15, O16, O18A, O25B, and O75 separately bioconjugated to the carrier protein, a genetically detoxified form of exotoxin A (EPA) derived from *Pseudomonas aeruginosa*, as described in detail in the previous examples. ExPEC9V vaccine covers the 9 indicated *E. coli* serotypes, which are among the most prevalent O-serotypes of ExPEC that are responsible for about 65% of all IED.

Objectives and Endpoints

| Objectives | Endpoints |
|---|---|
| **Primary** | |
| To demonstrate the efficacy of ExPEC9V compared to placebo in the prevention of the first IED event, with microbiological confirmation from blood, other sterile sites, or urine, caused by ExPEC9V O-serotypes O1A, O2, O4, O6A, O15, O16, O18A, O25B, and O75 | First IED event, with microbiological confirmation from blood, other sterile sites, or urine, caused by ExPEC9V O-serotypes O1A, O2, O4, O6A, O15, O16, O18A, O25B, and O75 |
| To demonstrate the efficacy of ExPEC9V compared to placebo in the prevention of the first IED event, with microbiological confirmation from blood or other sterile sites, caused by ExPEC9V O-serotypes | First IED event, with microbiological confirmation from blood or other sterile sites, caused by ExPEC9V O-serotypes |
| **Secondary** | |
| To demonstrate the efficacy of ExPEC9V compared to placebo in the prevention of all IEDs (including multiple IEDs per participant) caused by ExPEC9V O-serotypes | All IEDs (including multiple IEDs per participant) caused by ExPEC9V O-serotypes |
| To demonstrate the efficacy of ExPEC9V compared to placebo in the prevention of the first hospitalized IED event caused by ExPEC9V O-serotypes | First hospitalized IED event caused by ExPEC9V O-serotypes |
| To demonstrate the efficacy of ExPEC9V compared to placebo in the prevention of the first IED event meeting criteria for sepsis caused by ExPEC9V O-serotypes | First IED event meeting criteria for sepsis caused by ExPEC9V O-serotypes |
| To demonstrate the efficacy of ExPEC9V compared to placebo in the prevention of the first bacteremic (ie, microbiological confirmation from blood) IED event caused by ExPEC9V O-serotypes | First bacteremic IED event caused by ExPEC9V O-serotypes |
| To demonstrate the efficacy of ExPEC9V compared to placebo in the prevention of the first pyelonephritis event caused by ExPEC9V O-serotypes | First pyelonephritis event caused by ExPEC9V O-serotypes |
| To demonstrate the efficacy of ExPEC9V compared to placebo in the prevention of the first UTI event caused by ExPEC9V O-serotypes | First UTI event caused by ExPEC9V O-serotypes |
| To demonstrate the efficacy of ExPEC9V compared to placebo in the prevention of all UTIs (including multiple UTIs per participant) caused by ExPEC9V O-serotypes | All UTIs (including multiple UTIs per participant) caused by ExPEC9V O-serotypes |
| To demonstrate the efficacy of ExPEC9V compared to placebo in the prevention of the first IED event caused by any ExPEC O-serotype | First IED event caused by any ExPEC O-serotype |
| To demonstrate the efficacy of ExPEC9V compared to placebo in the prevention of the first pyelonephritis event caused by any ExPEC O-serotype | First pyelonephritis event caused by any ExPEC O-serotype |
| To demonstrate the efficacy of ExPEC9V compared to placebo in the prevention of the first UTI event caused by any ExPEC O-serotype | First UTI event caused by any ExPEC O-serotype |
| To evaluate the immunogenicity of ExPEC9V in the Immunogenicity Subset | Antibody titers to vaccine O-serotype antigens in the Immunogenicity Subset, as determined by multiplex electrochemiluminescent (ECL)-based immunoassay and multiplex |

-continued

| Objectives | Endpoints |
|---|---|
| | opsonophagocytic killing assay (MOPA) on Day 30, Day 181, Year 1, Year 2, and Year 3 |
| To evaluate the safety and reactogenicity of ExPEC9V | Solicited local and systemic AEs (collected until 14 days post-vaccination [from Day 1 to Day 15] in the Safety Subset)<br>Unsolicited AEs (collected until 29 days post-vaccination [from Day 1 to Day 30] in all participants)<br>Serious adverse events (SAEs) in all participants |
| To evaluate the preservation of health status and health-related quality of life (HRQoL) of ExPEC9V compared to placebo as measured by the Short Form-36 (SF-36) survey and the 5-level EuroQol 5-Dimension questionnaire (EQ-5D-5L) Descriptive System | SF-36 and EQ-5D-5L responses at scheduled timepoints |
| To evaluate the impact of IED, caused by ExPEC9V O-serotypes, on physical and mental health, and overall HRQoL as measured by the SF-36 | |
| To evaluate the impact of UTI, caused by ExPEC9V O-serotypes, on physical and mental health, and overall HRQoL, as measured by the SF-36 | |
| To assess the degree of frailty in participants who received ExPEC9V versus placebo at baseline, Year 1, Year 2, Year 3, and at the time of an IED | Frailty index as a measure of frailty at baseline, Year 1, Year 2, Year 3, and at the time of an IED |
| To determine the medical resource utilization for IED and UTI events caused by any ExPEC O-serotype | Medical resource utilization for IED events<br>Medical resource utilization for UTI events (Immunogenicity Subset only) and acute bacterial prostatitis (ABP) events (Immunogenicity Subset only)<br>Hospitalization and length of stay in hospital for IED, UTI, or ABP events |
| To determine the mortality associated with IED | IED-related and all-cause mortality |
| Exploratory | |
| To evaluate the efficacy of ExPEC9V compared to placebo in the prevention of the first IED event caused by ExPEC9V O-serotypes resistant to ≥1, ≥2, and ≥3 antibiotics | First IED event caused by ExPEC9V O-serotypes showing resistance to ≥1, ≥2, and ≥3 antibiotics in the microbiological profile |
| To evaluate the efficacy of ExPEC9V compared to placebo in the prevention of first uncomplicated, complicated, and recurrent UTI events caused by ExPEC9V O-serotypes | First uncomplicated UTI event caused by ExPEC9V O-serotypes<br>First complicated UTI event caused by ExPEC9V O-serotypes<br>First recurrent UTI (rUTI) event caused by ExPEC9V O-serotypes<br>First recurrent uncomplicated UTI event caused by ExPEC9V O-serotypes |
| To evaluate the efficacy of ExPEC9V compared to placebo in the prevention of the first ABP event caused by ExPEC9V O-serotypes | First ABP event caused by ExPEC9V O-serotypes |
| To evaluate antibody titers to vaccine O-serotype antigens in participants with IED | Antibody titers for ExPEC9V, determined by multiplex ECL-based immunoassay and MOPA assays in participants with IED, with sera obtained at the time of diagnosis of the suspected IED |
| To evaluate the severity of IED | Severity of IED (presence of sepsis or septic shock) in participants with IED |
| To identify a correlate of protection for the vaccine-mediated immune response associated with vaccine efficacy | Antibody titers for ExPEC9V determined by multiplex ECL-based immunoassay and MOPA assays at Day 1 pre-vaccination, Day 30 and at the time of diagnosis of the suspected IED (all participants) or at the time of a UTI or ABP event (Immunogenicity Subset only), in association with vaccine efficacy |
| To evaluate the efficacy of ExPEC9V compared to placebo in the prevention of the first invasive disease event caused by *P. aeruginosa* and first *P. aeruginosa* UTI | First invasive disease event caused by *P. aeruginosa*<br>First *P. aeruginosa* UTI event |

Overall Design

This is a randomized, double-blind, placebo-controlled, parallel-group, multicenter, interventional Phase 3 study to be conducted in approximately 18,556 medically stable adults aged ≥60 years and with a history of UTI in the past 2 years.

All participants are enrolled and randomized in parallel in a 1:1 ratio to either ExPEC9V or placebo and receive the study vaccine (0.5 mL intramuscular injection (in deltoid)) on Day 1. The final analysis for the first primary endpoint (with microbiological confirmation from blood, other sterile sites, or urine) occurs when 72 vaccine serotype TED events have been observed in the study or at the latest when the last participant has been followed up for 36 months post-vaccination. The second primary endpoint (with microbiological confirmation from blood or other sterile sites) is tested in a hierarchical manner when the first primary endpoint has shown statistical significance. For the final analysis of the second primary endpoint (with microbiological confirmation from blood or other sterile sites), 53 vaccine serotype IED events according to the second primary endpoint have to be observed. The ExPEC9V vaccine composition comprises 16 μg/mL of each of O1A, O2, O6A, O4-Glc+, O15, O16, and O18A antigen polysaccharides and 32 μg/mL of O25B and O75 antigen polysaccharides, each antigen polysaccharide separately bioconjugated to EPA carrier protein, see examples above (e.g. this is the same composition used in group 3 of the rabbit immunizations of example 8 above; the excipients are the same as described for the ExPEC10V vaccine used in the BAC1001 study of example 7). Placebo is 0.9% w/v sodium chloride.

Safety Evaluations

Key safety assessments include SAEs, physical examination, and vital signs. In addition, solicited local and systemic AEs and unsolicited AEs are recorded for participants in the "Safety Subset", ie, approximately 4,000 participants from selected study sites who have given informed consent prior to randomization for the additional assessments.

Immunogenicity Evaluations

For assessment of immunogenicity, IgG antibody levels elicited by the vaccine against each of the 9 vaccine O-serotypes and the carrier protein EPA are measured by a multiplex ECL-based immunoassay and serotype-specific functional antibodies are measured by a MOPA. Immunogenicity analysis is performed for participants in the "Immunogenicity Subset", ie, for approximately 1,200 participants from selected study sites who have given informed consent prior to randomization for additional immunogenicity assessments, and for all participants with a confirmed IED event, and for participants in the Immunogenicity Subset with a UTI or acute bacterial prostatitis (ABP) event.

Efficacy Evaluations

The primary objective is to demonstrate efficacy of ExPEC9V compared to placebo in the prevention of the first IED events caused by ExPEC serotypes O1A, O2, O4, O6A, O15, O16, O18A, O25B, and O75. Events defined as IED, UTI, or ABP are collected for all participants for the entire study duration (1,096 days; 3 years). During study follow-up, participants are expected to inform the study site, as soon as possible, if they experience any signs or symptoms of UTI or ABP, or if they experience any new onset or worsening of symptoms that could be caused by a systemic infection. In addition, all participants will be questioned about past hospitalizations or medical events that could have been UTIs, ABPs, or potential IEDs, and that were not captured by the site in real time. Medical resource utilization data associated with medical encounters related to IED (all participants) and for UTI or ABP (Immunogenicity Subset only) are collected. Two patient-reported outcome (PRO) instruments are used to measure Health-Related Quality of Life: the SF-36 version 2 and the EQ-5D-5L. In addition, frailty is assessed using the SPPB and the Frailty Index Score.

Immunogenicity Evaluations

For assessment of immunogenicity, IgG antibody levels elicited by the vaccine against each of the 9 vaccine O-serotypes and the carrier protein EPA is measured by a multiplex ECL-based immunoassay and serotype-specific functional antibodies is measured by a MOPA. Immunogenicity analysis is performed for participants in the "Immunogenicity Subset", ie, for approximately 1,200 participants from selected study sites who have given informed consent prior to randomization for additional immunogenicity assessments, and for all participants with a confirmed IED and for participants in the Immunogenicity Subset with an UTI or an ABP event. Day 1 and Day 30 immunogenicity blood samples are collected from all participants.

Safety Evaluations

Key safety assessments include SAEs, physical examination, and vital signs. In addition, solicited local and systemic AEs and unsolicited AEs are recorded for participants in the "Safety Subset", ie, approximately 4,000 participants from selected study sites who have given informed consent prior to randomization for the additional assessments.

Efficacy Analyses

The primary analysis of the first primary endpoint evaluates the number of participants with at least 1 IED event caused by ExPEC serotypes O1A, O2, O4, O6A, O15, O16, O18A, O25B, and O75 with onset at least 29 days after vaccination in the active vaccine (ExPEC9V) group compared to the placebo group in the per protocol efficacy (PPE) population. The primary analysis of the second primary endpoint evaluates the number of participants with at least 1 IED event with microbiological confirmation in blood or other sterile sites caused by ExPEC serotypes O1A, O2, O4, O6A, O15, O16, O18A, O25B, and O75 with onset at least 29 days after vaccination (from Day 30) in the active vaccine (ExPEC9V) group compared to the placebo group in the PPE population. The follow-up time is also taken into account. For participants with an IED event, the follow-up time is defined as the time between vaccination and the occurrence of the first event. For participants without an IED event, it is the time between vaccination and last visit (or last contact for participants that discontinued the study). The null hypothesis of VE≤20% is tested versus the alternative hypothesis VE >20%.

A stagewise hierarchical testing strategy is applied to the following endpoints:

Primary:

- First IED, with microbiological confirmation from blood, other sterile sites, or urine, caused by ExPEC9V O-serotypes
- First IED with microbiological confirmation from blood or other sterile sites caused by ExPEC9V O-serotypes Secondary:

- All IEDs (including multiple IEDs per participant) caused by ExPEC9V O-serotypes
- First hospitalized IED event caused by ExPEC9V O-serotypes
- First IED event meeting criteria for sepsis caused by ExPEC O-serotypes
- First bacteremic IED event caused by ExPEC9V O-serotypes
- First pyelonephritis event caused by ExPEC9V O-serotypes
- First UTI caused by ExPEC9V O-serotypes
- All UTIs (including multiple UTIs per participant) caused by ExPEC9V O-serotypes
- First IED event caused by any ExPEC O-serotype
- First pyelonephritis event caused by any ExPEC O-serotype
- First UTI caused by any ExPEC O-serotype In this testing strategy, the second primary endpoint is only tested when the first primary endpoint showed statistical significance. When the first primary endpoint has shown statistical significance with 72 events, an interim analysis is performed for the second primary endpoint (with microbiological confirmation from blood or other sterile sites) if less than 53 events are observed at that time. If the second primary endpoint is not significant, the final analysis of the second primary endpoint is performed when 53 vaccine serotype IED events according to the second primary endpoint definition have been observed. Further, the first key secondary endpoint is only tested when both primary endpoints showed statistical significance. The first key secondary endpoint includes all ExPEC9V IED events with onset of at least 29 days after vaccination (PPE) until the end of the follow-up period.

A participant is considered to have IED if the below criteria are met and confirmed by the independent endpoint adjudication committee (IEAC).

An adult participant diagnosed with IED is any participant with:

- signs and symptoms of systemic bacterial infection as indicated by the presence of any of the following:
  - temperature <36.0° C. (96.8° F.) or >38.0° C. (100.4° F.),
  - tachycardia (HR) >90 bpm,
  - tachypnoea (RR) >20 breaths/minute, or
  - WBC count <4 or $>12\times10^9$/L or 10% immature (band) forms, AND
- microbiological confirmation by culture of:
  - *E. coli* in blood or in any other sterile site (e.g. cerebrospinal fluid [CSF], pleura), AND/OR
  - *E. coli* in urine (colony forming units/mL $\geq10^5$) with UTI sign/symptoms and with no other identifiable site of infection and with an acute change in total sequential organ failure assessment (SOFA) score ≥2 points from baseline.

For the primary and secondary endpoints, with IED caused by any of the ExPEC9V O-serotypes (ie, O1A, O2, O4, O6A, O15, O16, O18A, O25B, or O75), the O-serotyping has to be available and the IED has to be confirmed as being O1A, O2, O4, O6A, O15, O16, O18A, O25B, or O75 positive. For the secondary endpoints related to any ExPEC O-serotype, no O-serotyping has to be available. Cases with multiple pathogens in the culture results are not considered for the primary or secondary endpoints if the systemic infection cannot be attributed only to *E. coli*, as per IEAC judgment. Cases with mixed pathogens and the presence of *E. coli* are included in sensitivity analyses.

If a participant has contacted their physician and/or study site with signs and symptoms of UTI, the participant is defined as having a symptomatic UTI if the below criteria are met and confirmed by the IEAC for cases of pyelonephritis.

An adult with documented pyuria (white blood cell (WBC) count ≥10 cells/$mm^3$) and microbiological confirmation by culture of *E. coli* in urine (colony forming units $\geq10^5$/mL) with one of the following definitions for signs and symptoms:

- for uncomplicated UTI, at least 2 of the following signs or symptoms:
  - dysuria,
  - urinary frequency,
  - urinary urgency, or
  - suprapubic pain.
- for complicated UTI (cUTI):
  - at least 2 of the following signs or symptoms:
    - chills, rigors or warmth associated with fever (eg, temperature≥38.0° C.),
    - dysuria, urinary frequency or urinary urgency,
    - lower abdominal pain or pelvic pain, or
    - nausea or vomiting,
  - AND,
  - at least 1 of the following complicating factors:
    - history of urinary retention (in male participants),
    - current indwelling urinary catheter,
    - obstructive uropathy, or
    - any relevant functional or anatomical abnormality.
- for pyelonephritis (regardless of underlying abnormality of the urinary tract) with at least 2 of the following symptoms:
  - chills, rigors, or warmth associated with fever (eg, temperature ≥38.0° C.), or
  - flank pain or tenderness in the costovertebral angle on physical examination, or
  - nausea or vomiting.
- for recurrent UTI (rUTI):
  - recurrence of uncomplicated and/or complicated UTIs with a frequency of two UTIs in the last six months, or
  - recurrence of uncomplicated and/or complicated UTIs with a frequency of at least three UTIs per year.

For the secondary endpoints, with UTI caused by any of the ExPEC9V O-serotypes (ie, O1A, O2, O4, O6A, O15, O16, O18A, O25B, or O75), the O-serotyping has to be available and the UTI has to be confirmed as being O1A, O2, O4, O6A, O15, O16, O18A, O25B, or O75 positive. For the secondary endpoints, related to any ExPEC O-serotype, no O-serotyping has to be available. Cases with multiple pathogens in the culture results and with the presence of *E. coli* are not considered for the secondary endpoints. These cases are included in sensitivity analyses.

As an exploratory endpoint, participants meeting the above definition of IED (except the microbiological confirmation of *E. coli*) or UTI but with (urine in case of UTI) samples positive for *P. aeruginosa* (colony forming units $\geq10^5$/mL in case of UTI) are reported to have invasive disease due to *P. aeruginosa*, or *P. aeruginosa* UTI, respectively. No serotyping is performed for *P. aeruginosa*. Samples with mixed pathogens with the presence of *P. aeruginosa* are not considered for this exploratory endpoint.

As an exploratory efficacy endpoint for ABP, events caused by ExPEC serotypes O1A, O2, O4, O6A, O15, O16, O18A, O25B, and O75 are reported.

If a participant contacts their physician and/or study site with signs and symptoms of ABP, the participant is defined as having a symptomatic ABP if the below criteria are met.

An adult with documented pyuria (WBC count ≥10 cells/$mm^3$) and microbiological confirmation by culture of *E. coli* in urine (colony forming units $\geq10^5$/mL) with fever and an acute onset of the following:

- irritative voiding symptoms:
  - dysuria,
  - urinary frequency,
  - urinary urgency, or
- obstructive voiding symptoms:
  - hesitancy,
  - incomplete voiding,
  - straining to urinate,
  - weak stream, and
- suprapubic, rectal, or perineal pain.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the present description.

Sequences (Glycosylation consensus sequence)

SEQ ID NO: 1

Asn-X-Ser(Thr),
wherein X can be any amino acid except Pro (Optimized glycosylation consensus sequence)

SEQ ID NO: 2

Asp(Glu)-X-Asn-Z-Ser(Thr),
wherein X and Z are independently selected from any amino acid except Pro (EPA carrier protein comprising 4 glycosylation consensus sequences (EPA-4)

SEQ ID NO: 3

G SGGGDQNATG SGGGKLAEEA FDLWNECAKA CVLDLKDGVR SSRMSVDPAI ADTNGQGVLH

YSMVLEGGND ALKLAIDNAL SITSDGLTIR LEGGVEPNKP VRYSYTRQAR GSWSLNWLVP IGHEKPSNIK

VFIHELNAGN QLSHMSPIYT IEMGDELLAK LARDATFFVR AHESNEMQPT LAISHAGVSV VMAQAQPRRE

KRWSEWASGK VLCLLDPLDG VYNYLAQQRC NLDDTWEGKI YRVLAGNPAK HDLDIKDNNN STPTVISHRL

HFPEGGSLAA LTAHQACHLP LEAFTRHRQP RGWEQLEQCG YPVQRLVALY LAARLSWNQV DQVIRNALAS

PGSGGDLGEA IREQPEQARL ALTLAAAESE RFVRQGTGND EAGAASADVV SLTCPVAKDQ NRTKGECAGP

ADSGDALLER NYPTGAEFLG DGGDVSFSTR GTQNWTVERL LQAHRQLEER GYVFVGYHGT FLEAAQSIVF

GGVRARSQDL DAIWRGFYIA GDPALAYGYA QDQEPDARGR IRNGALLRVY VPRWSLPGFY RTGLTLAAPE

AAGEVERLIG HPLPLRLDAI TGPEEEGGRV TILGWPLAER TVVIPSAIPT DPRNVGGDLD PSSIPDKEQA

ISALPDYASQ PGKPPREDLK LGSGGGDQNA T

(O4 GtrS amino acid sequence)

SEQ ID NO: 4

MNNLIMNNWCKLSIFIIAFILLWLRRPDILTNAQFWAEDSVFWYKDAYENGFLSSLTTPRNGYFQTVSTFIVGLTAL

LNPDYAPFVSNFFGIMIRSVIIWFLFTERFNFLTLTTRIFLSIYFLCMPGLDEVHANITNAHWYLSLYVSMILIARN

PSSKSWRFHDIFFILLSGLSGPFIIFILAASCFKFINNCKDHISVRSFINFYLRQPYALMIVCALIQGTSIILTFNG

TRSSAPLGFSFDVISSIISSNIFLFTFVPWDIAKAGWDNLLLSYFLSVSILSCAAFVFVKGTWRMKVFATLPLLIII

FSMAKPQLTDSAPQLPTLINGQGSRYFVNIHIAIFSLLCVYLLECVRGKVATLFSKTYLTILLFVMGCLNFVITPLP

NMNWREGATLINNAKTGDVISIQVLPPGLTLELRKK (Example O4 gtrS nucleic acid sequence)

SEQ ID NO: 5

ATGAATAATTTAATTATGAATAACTGGTGTAAATTATCTATATTTATTATTGCATTTATTTTGCTATGGCTTAGAAG

GCCGGATATACTCACAAACGCACAATTTTGGGCAGAAGATTCCGTTTTCTGGTATAAGGACGCCTATGAGAACGGAT

TCTTAAGTTCACTAACAACGCCTAGGAATGGGTATTTCCAGACTGTTTCTACATTTATAGTTGGTCTGACTGCTTTA

TTAAATCCAGATTATGCACCTTTTGTTTCTAATTTTTTTGGCATAATGATTCGCTCAGTAATTATATGGTTTTTATT

TACAGAAAGATTCAACTTCCTCACATTGACTACTAGGATTTTCTTATCTATTTATTTTCTATGCATGCCTGGATTGG

ATGAAGTTCATGCAAATATAACAAATGCACATTGGTATTTGTCATTATATGTATCAATGATCCTGATAGCTCGCAAT

CCAAGTTCAAAATCATGGAGGTTTCATGATATATTCTTTATCTTGCTATCCGGGCTCAGTGGCCCATTTATAATTTT

CATTTTAGCAGCTTCATGCTTTAAATTTATAAATAATTGTAAAGATCATATTAGTGTAAGATCTTTCATAAATTTCT

ACTTGCGTCAGCCATACGCATTAATGATTGTTTGCGCTTTAATTCAAGGAACTTCTATAATTCTAACTTTCAATGGC

ACACGTTCCTCAGCACCGCTAGGATTCAGTTTTGATGTGATTTCGTCTATTATATCATCGAATATTTTTTTATTTAC

ATTTGTCCCATGGGATATTGCAAAGGCTGGGTGGGATAATTTACTGTTATCTTATTTTTTGTCTGTTTCGATTTTGT

CGTGTGCGGCCTTTGTTTTTGTTAAAGGTACGTGGCGAATGAAAGTATTTGCAACTTTACCATTGCTAATTATAATA

TTTTCAATGGCAAAACCACAATTGACAGACTCGGCACCTCAATTGCCAACACTTATTAATGGGCAAGGTTCAAGATA

CTTCGTAAATATACATATTGCGATATTCTCTTTGCTATGTGTTTACTTACTTGAGTGCGTCAGGGGGAAAGTGGCAA

CTTTATTTTCCAAAATATACTTAACAATTTTGCTATTCGTGATGGGATGTTTGAATTTTGTTATCACCCCACTCCCA

-continued

AACATGAACTGGAGGGAAGGTGCTACTTTGATTAATAATGCAAAAACTGGTGATGTCATTTCGATTCAAGTGCTACC

ACCTGGCCTAACACTTGAACTAAGGAAAAAATAA (Example PglB sequence ('wild-type')

SEQ ID NO: 6

MLKKEYLKNPYLVLFAMITLAYVFSVFCRFYWVWWASEFNEYFFNNQLMIISNDGYAFAEGARDMIAGFHQPNDLSY

YGSSLSALTYWLYKITPFSFESIILYMSTFLSSLVVIPTILLANEYKRPLMGFVAALLASIANSYYNRTMSGYYDTD

MLVIVLPMFILFFMVRMILKKDFFSLIALPLFIGIYLWWYPSSYTLNVALIGLFLIYTLIFHRKEKIFYIAVILSSL

TLSNIAWFYQSAIIVILFALFALEQKRLNFMIIGILGSATLIFLILSGGVDPILYQLKFYIFRSDESANLTQGFMYF

NVNQTIQEVENVDLSEFMRRISGSEIVFLFSLFGFVWLLRKHKSMIMALPILVLGFLALKGGLRFTIYSVPVMALGF

GFLLSEFKAIMVKKYSQLTSNVCIVFATILTLAPVFIHIYNYKAPTVFSQNEASLLNQLKNIANREDYVVTWWDYGY

PVRYYSDVKTLVDGGKHLGKDNFFPSFALSKDEQAAANMARLSVEYTEKSFYAPQNDILKTDILQAMMKDYNQSNVD

LFLASLSKPDFKIDTPKTRDIYLYMPARMSLIFSTVASFSFINLDTGVLDKPFTFSTAYPLDVKNGEIYLSNGVVLS

DDFRSFKIGDNVVSVNSIVEINSIKQGEYKITPIDDKAQFYIFYLKDSAIPYAQFILMDKTMFNSAYVQMFFLGNYD

KNLFDLVINSRDAKVFKLKI (example gtrA amino acid sequence; *E. coli* W3110 yfdG, GenBank: BAA16209.1)

SEQ ID NO: 7

MLKLFAKYTSIGVLNTLIHWVVFGVCIYVAHTNQALANFAGFVVAVSFSFFANAKFTFKASTTTMRYMLYVGFMGTL

SATVGWAADRCALPPMITLVTFSAISLVCGFVYSKFIVFRDAK (example gtrB amino acid sequence-*E. coli* W3110 yfdH, GenBank: BAA16210.1)

SEQ ID NO: 8

MKISLVVPVFNEEEAIPIFYKTVREFEELKSYEVEIVFINDGSKDATESIINALAVSDPLVVPLSFTRNFGKEPALF

AGLDHATGDAIIPIDVDLQDPIEVIPHLIEKWQAGADMVLAKRSDRSTDGRLKRKTAEWFYKLHNKISNPKIEENVG

DFRLMSRDVVENIKLMPERNLFMKGILSWVGGKTDIVEYVRAERIAGDTKFNGWKLWNLALEGITSFSTFPLRIWTY

IGLVVASVAFIYGAWMILDTIIFGNAVRGYPSLLVSILFLGGIQMIGIGVLGEYIGRTYIETKKRPKYIIKRVKK (example O4 rfb locus nucleotide sequence-O4-EPA production strain BVEC-L-00684f)

SEQ ID NO: 9

ATGACGAATTTAAAAGCAGTTATTCCTGTAGCGGGTCTCGGGATGCATATGTTGCCTGCCACTAAGGCGATACCCAA

AGAGATGCTACCAATCGTCGACAAGCCAATGATTCAGTACATTGTTGACGAGATTGTGGCTGCAGGGATCAAAGAAA

TCCTCCTGGTAACTCACGCGTCCAAGAACGCGGTCGAAAACCACTTCGACACCTCTTATGAGTTAGAATCACTCCTT

GAGCAGCGCGTGAAGCGTCAACTGCTGGCGGAAGTACAGTCCATCTGTCCGCCGGGCGTGACCATTATGAACGTGCG

TCAGGGCGAACCTTTAGGTTTAGGCCACTCCATTTTGTGTGCGCGACCTGCCATTGGTGACAACCCATTTGTCGTGG

TACTGCCAGACGTTGTGATCGACGATGCCAGCGCCGACCCGCTACGTTACAACCTTGCTGCCATGATTGCACGTTTC

AACGAAACGGGCCGCAGCCAGGTGCTGGCAAAACGTATGCCGGGTGACCTCTCTGAATACTCCGTCATCCAGACTAA

AGAGCCGCTGGACCGTGAGGGTAAAGTCAGCCGCATTGTTGAATTTATCGAAAAACCGGATCAGCCGCAGACGCTGG

ACTCAGACATCATGGCCGTAGGTCGCTATGTGCTTTCTGCCGATATTTGGCCGGAACTGGAACGTACTCAGCCTGGT

GCATGGGGACGTATTCAGCTGACTGATGCTATTGCCGAGCTGGCGAAAAAACAATCCGTTGATGCAATGCTGATGAC

CGGCGACAGTTACGACTGCGGCAAAAAAATGGGCTATATGCAGGCGTTTGTGAAGTATGGCCTACGCAACCTGAAAG

AAGGGGCGAAGTTCCGTAAAGGTATTGAGAAGCTGTTAAGCGAATAATGAAAATCTGACCGGATGTAACGGTTGATA

AGAAAATTATAACGGCAGTGAAAATTCGCAGCAAAAGTAATTTGTTGCGAATCTTCCTGCCGTTGTTTTATATAAAC

CATCAGAATAACAACGAGTTAGCAGTAGGGTTTTATTCAAAGTTTTCCAGGATTTTCCTTGTTTCCAGAGCGGATTG

GTAAGACAATTAGCGTTTGAATTTTTCGGGTTTAGCGCGAGTGGGTAACGCTCGTCACATCATAGGCATGCATGCAG

TGCTCTGGTAGCTGTAAAGCCAGGGGCGGTAGCGTGCATTAATACCTCTATTAATCAAACTGAGAGCCGCTTATTTC

ACAGCATGCTCTGAAGTAATATGGAATAAATTAAGTGAAAATACTTGTTACTGGTGGCGCAGGATTTATTGGTTCAG

CTGTAGTTCGTCACATTATAAATAATACGCAGGATAGTGTTGTTAATGTCGATAAATTAACGTACGCCGGAAACCGG

-continued

GAATCACTTGCTGATGTTTCTGATTCTGAACGCTATGTTTTTGAACATGCGGATATTTGCGATGCACCTGCAATGGC
ACGGATTTTTGCTCAGCATCAGCCGGATGCAGTGATGCACCTGGCTGCTGAAAGCCATGTTGACCGTTCAATTACAG
GCCCTGCGGCATTTATTGAAACCAATATTGTTGGTACTTATGTCCTTTTGGAAGCCGCTCGCAATTACTGGTCTGCT
CTTGATAGCGACAAGAAAAATAGCTTCCGTTTTCATCATATTTCTACTGACGAAGTATATGGTGATTTGCCTCATCC
TGACGAGGTAAATAATACAGAAGAATTACCCTTATTTACTGAGACAACAGCTTACGCGCCAAGCAGCCCTTATTCCG
CATCCAAAGCATCCAGCGATCATTTAGTCCGCGCGTGGAAACGTACCTATGGTTTACCGACCATTGTGACTAATTGC
TCTAACAATTATGGTCCTTATCATTTCCCGGAAAAATTGATTCCATTGGTTATTCTCAATGCTCTGGAAGGTAAAGC
ATTACCTATTTATGGTAAAGGGGATCAAATTCGCGACTGGCTGTATGTTGAAGATCATGCGCGTGCGTTATATACCG
TCGTAACCGAAGGTAAAGCGGGTGAAACTTATAACATTGGTGGGCACAACGAAAAGAAAAACATAGATGTAGTGCTC
ACTATTTGTGATTTGCTGGATGAGATTGTACCGAAAGAGAAATCTTATCGTGAGCAAATCACTTATGTTGCCGATCG
TCCGGGACACGATCGCCGTTATGCGATTGATGCTGAGAATATTGGTCGCGAATTGGGATGGAAACCACAGGAAACGT
TTGAGAGCGGGATTCGGAAGACAGTGGAATGGTATCTGTCCAATACAAAATGGGTTGATAATGTGAAAAGTGGTGCC
TATCAATCGTGGATTGAAGAGAACTATGAGGGCCGCCAGTAATGAATATCCTCCTTTTTGGCAAAACAGGGCAGGTA
GGTTGGGAACTACAGCGTGCTCTGGCACCTCTGGGTAACTTGATTGCTCTTGATGTTCATTCCACTGATTATTGTGG
CGATTTCAGTAACCCCGAAGGTGTGGCTGAAACCGTCAAAAAAATTCGCCCAGATGTTATTGTTAATGCTGCTGCTC
ATACCGCGGTAGATAAGGCTGAGTCAGAACCAGAATTTGCACAATTACTCAATGCGACCAGCGTTGAAGCAATTGCA
AAAGCGGCTAATGAAGTTGGGGCTTGGGTAATTCATTACTCAACTGACTACGTCTTCCCTGGAAATGGCGACATGCC
ATGGCTCGAGACTGATGTAACCGCTCCGCTCAATGTTTATGGCAAAACCAAATTGGCTGGAGAAAGAGCATTACAAG
AACATTGCGCAAAGCATCTTATTTTCCGTACCAGCTGGGTATATGCAGGTAAAGGAAATAACTTTGCCAAAACAATG
TTACGTCTGGCAAAAGAGCGCGAAGAACTGGCTGTGATAAACGATCAGTTTGGCGCACCAACAGGTGCTGAATTGCT
GGCTGATTGCACCGCTCATGCCATTCGCGTGGCATTAAAAAAACCAGAAGTTGCTGGCTTGTACCATCTGGTAGCAA
ATGGCACAACAACCTGGCACGATTACGCCGCGCTAGTATTCGAAGAAGCCCGTAAAGCAGGGATTGACCTTGCACTT
AACAAACTCAACGCCGTACCAACAACGGCTTATCCTACTCCAGCCCGCCGTCCTCATAATTCTCGCCTCAATACCGA
AAAGTTTCAGCAGAACTTTGCGCTTGTCTTGCCTGACTGGCAGGTGGGCGTGAAACGTATGCTCAACGAATTATTTA
CGACTACGGCAATTTAACAAATTTTTGCATCTCGCTCATGATGCCAGAGCGGGATGAATTAAAAGGAATGGTGAAAT
GAAAACGCGTAAAGGTATTATTCTGGCTGGTGGTTCCGGCACTCGTCTTTATCCTGTGACGATGGCAGTGAGTAAAC
AACTGCTGCCGATTTATGATAAGCCGATGATTTATTATCCGCTTTCAACGCTTATGTTAGCGGGTATTCGCGATATT
CTTATTATCAGTACGCCACAGGATACACCGCGTTTCCAACAATTGTTGGGGGACGGGAGTCAGTGGGGGCTTAATCT
ACAGTATAAAGTACAACCGAGTCCGGATGGCCTGGCGCAAGCGTTTATTATTGGTGAAGACTTTATTGGTGGTGATG
ATTGTGCACTCGTACTTGGCGATAATATCTTCTATGGACACGACTTGCCGAAATTAATGGAAGCTGCTGTTAACAAA
GAAATCGGTGCAACGGTATTTGCTTATCACGTCAATGATCCTGAACGTTATGGTGTCGTGGAGTTTGATAATAACGG
TACTGCAATTAGCCTGGAAGAAAAACCGCTGGAACCAAAAAGTAACTATGCGGTTACTGGGCTTTATTTCTATGACA
ATGATGTTGTAGAAATGGCGAAAAACCTTAAGCCTTCTGCCCGTGGCGAACTGGAAATTACCGATATTAACCGTATT
TATATGGAGCAGGGACGTTTGTCTGTCGCTATGATGGGGCGTGGTTATGCCTGGTTGGATACTGGTACACATCAAAG
TCTTATTGAAGCAAGTAACTTCATTGCCACCATTGAAGAGCGTCAGGGATTAAAGGTATCTTGCCCGGAAGAGATTG
CTTACCGTAAAGGGTTTATTGATGCTGAGCAGGTGAAAGTATTAGCCGAACCGCTGAAGAAAAATGATTATGGTCAG
TATCTGCTAAAAATGATTAAAGGTTATTAATAAAATGAACGTAATTAAAACTGAAATTCCTGATGTGCTGATTTTTG
AACCAAAAGTTTTTGGTGATGAACGTGGCTTCTTTTTTGAGAGTTTTAACCAGAAAGTATTTGAAGAAGCTGTAGGA
CGGAAGGTTGAATTTGTTCAGGATAACCATTCTAAGTCTAAAATAAATGTATTGCGTGGGATGCATTATCAAACACA
AAATACTCAAGGAAAACTGGTTCGGGTAATTTCTGGTTCAGTATATGATGTTGCCGTAGATTTAAGAGAAAAATCAA

-continued

AGACATTTGGCAAATGGGTGGGTGTAGAATTATCTGGGAATAATAAAAGACAATTGTGGATCCCCGAAGGTTTTGCC

CATGGTTTTTATGTGTTGGAGGAGAATACCGAATTTGTTTATAAATGTACCGATACTTATAACCCTGCTCATGAACA

CACATTGCTATGGAATGATCCAACTATCAATATAAGTTGGCCAATCATACAAAACTGCAAGCCAATTATTTCTGAAA

AAGATGCTAATGGACATCTTTTTTCACATAAAACCTATTTCTGAAATGCAATATTATGAGTTTAATTAGAAACAGTT

TCTATAATATTGCTGGTTTTGCTGTGCCGACATTAGTTGCAGTCCCTGCTTTGGGGATTCTTGCCAGGCTGCTTGGA

CCGGAGAATTTTGGACTTTTCACACTAGCATTCGCTTTGATAGGATATGCAAGTATTTTCGACGCCGGGATTAGTCG

AGCTGTAATCAGAGAAATCGCTCTTTATCGAGAAAGTGAAAAAGAGCAAATACAAATTATTTCGACAGCAAGTGTAA

TCGTACTATTCTTAGGGGTGGTTGCAGCTTTGTTACTTTATTTTAGTAGTAATAAAGTTGTTGAGTTATTGAATGTT

AGTTCCGTTTATATTGAAACAGCAGTGCGTGCATTCTCTGTTATTTCATTTATAATACCTGTGTATCTGATTAACCA

GATTTGGCTTGGTTATCTGGAAGGGCTAGAAAAATTTGCAAATATAAATGTTCAGAGAATGATTTCTAGCACAAGCT

TGGCTATATTACCAGTGATATTTTGTTATTACAATCCCTCGTTGCTTTATGCTATGTATGGGTTGGTGGTTGGGCGT

GTGATTTCATTTTTGATTAGCGCAATAATTTGTCGAGATATTATTCTTAAAAGTAAACTTTACTTTAATGTGGCAAC

TTGCAATCGTCTTATCTCTTTTGGTGGATGGATAACAGTTAGTAATATCATAAGCCCAATCATGGCATATTTCGACC

GCTTTATCATCTCTCATATTATGGGGGCTTCGAGAATTGCATTTTATACAGCGCCCTCAGAGGGTGTATCAAGGTTA

ATTAATATCCCATATGCTTTGGCAAGAGCTCTATTTCCTAAATTGGCATATAGCAATAATGATGATGAACGAAAAAA

ATTACAACTACAGAGCTACGCAATTATAAGCATTGTATGTCTACCCATAGTTGTTATTGGTGTCATTTTTGCCTCAT

TCATAATGACAACATGGATGGGACCTGATTATGCCTTAGAAGCAGCAACTATCATGAAAATACTTCTTGCTGGTTTT

TTCTTTAACTCTTTAGCGCAAATACCTTATGCATACTTGCAATCTATCGGAAAGTCAAAAATTACCGCATTTGTGCA

TCTCATAGAACTTGCGCCATACTTATTATTATTGTATTACTTCACAATGCATTTCGGCATAATTGGCACGGCAATCG

CTTGGTCACTTAGAACATTTTGTGATTTTGTTATACTACTTTCGATATCGAGAAGAAAATGATTGCGGTTGATATTG

CGCTTGCAACCTACAATGGTGCTAATTTTATTCGGCAACAGATTGAATCTATCCAGAAACAAACTTATAGAAATTGG

CGTCTTATAATAAGTGATGATAACTCGAGTGATGATACTGTTGATATTATTAAGGATATGATGTCTAACGACAGTCG

TATCTATTTGGTAGGAAATAAAAGACAAGGAGGGGTTATTCAGAACTTTAATTATGCTCTTTCACAAACTACATCTG

AAATTGTGTTACTATGTGACCAGGATGACATTTGGCCGGAGGAGCGTCTGGAAATTCTTATAGATAAATTTAAGGCC

TTGCAGCGTAATGATTTTGTTCCGGCAATGATGTTTACTGATTTGAAATTAGTAGACGAAAATAATTGTTTGATTGC

AGAAAGTTTTTATCGAACGAATAATATTAATCCACAAGATAATCTGAAAAATAATAATCTTCTCTGGCGTTCAACGG

TATATGGCTGTACTTGCATCATGAATAAGAAACTTGTTGATATTGCATTGCCTATACCTACATATGCACATATGCAT

GATCAATGGTTGGCATTATTAGCGAAGCAATATGGTAACATTTTTTATTTCGACTATGCGTCTGTTCGTTATAGGCA

ACATTCTACAAATGTTGTTGGTGGTAGAAATAAAACGCCATTTCAAAAATTTAATTCCATACAAAAAAACCTAAAAA

GGATTAATTTGCTAGTGGATAGAACTGTTGCTTTAATTAAATCAAATAACGATTTCTATCCAGGGAATAAAATGGAA

AATAAAATTGATTACTTAAAATTTGGAGTGAATGAAGTATTACCTTATCTTTTTAAAGGAAACAAGAAAGTTTTTTC

ACTTTGTGTATTAATTAGTTTGGCATTACAAAAATGATATATTTATTATTTTTTTTTGCACTGTTTATGATCTGTAC

GTTTTTAACACACAGGCGACAGGCATTATATGTTGTATCTGCGTTAGTATTTCTTTTTTTGGCTTTAACCTATCCAT

CAGGAGGGGACTGGATAGGTTATTTTCTCCATTATGACTGCATGGTTAATGAGCAGTGTAATAATGGTTTTATAATG

TTTGAACCTGGATATGAATTAATTGTTTCCTTATTTGGATATTTGGGATTTCAGACAATTATTATTTTTATAGCCGC

TGTAAATGTAATTCTAATATTAAATTTTGCAAAGCATTTTGAAAACGGAAGTTTTGTTATTGTTGCGATAATGTGCA

TGTTCCTTTGGAGTGTTTATGTTGAGGCGATTAGACAGGCTCTGGCCTTATCTATAGTTATATTTGGGATTCATTCT

CTTTTTTTGGGTAGAAAAAGGAAATTTATAACATTAGTATTATTTGCGTCAACTTTCCATATAACTGCTTTGATTTG

TTTTCTTCTAATGACTCCTCTATTTTCAAAGAAATTAAGCAAGATAATAAGTTATAGCCTATTAATTTTCAGTAGCT

TCTTTTTCGCTTTTTCTGAAACCATATTAAGTGCACTCCTTGCAATTTTGCCAGAAGGATCCATTGCCAGTGAAAAA

TTAAGTTTTTACTTAGCAACCGAGCAATACAGGCCACAGTTATCTATTGGGAGTGGCACTATTCTTGACATTATACT

-continued

TATTTTTCTGATATGTGTAAGTTTTAAACGAATAAAGAAATATATGCTCGCTAATTATAATGCTGCAAATGAGATAT

TGCTTATTGGTTGCTGTCTTTATATTTCTTTCGGTATTTTTATCGGGAAAATGATGCCAGTTATGACTCGCATTGGT

TGGTATGGTTTTCCATTTGTTATAGTACTTCTTTATATTAACTTGGGTTATTCAGAATATTTTAAGAGGTATATAAA

TAAAAGAGGGTGTGGGTATAGCAAATTATTAATTGCTTTTTATTTTTTGCTACAAATTTTGCGACCATTAACATATG

ATTATAGCTATTATAATATAATGCACCAGGATACTTTGCTGAATAGGTTTGATGCATTAGATGATGCATCATTAAGA

CAATCAGCGAAGAGAAAATGTTTCGATTTGGGAAAGATAGGATATGGTTTCTTATGTAGTATATAATATCCTGCATT

CATTCGGATAATTTCCTATGGAAGTGTCCTTTGCTCTGTCTGTCCTCATTTGTTGAAATTTTATGTTAATAAGAAGC

TTTAGATAACCACTTAGGAACTGTATGTTTGATCTGTCCAAAAATTATATTATTGTAAGTGCGACGGCGCTGGCTTC

CGGAGGTGCATTAACTATATTAAAGCAATTTATAAAACATGCATCACAAAATTCAAATGACTATATTATGTTTGTAT

CTGCGGGATTGGAGTTGCCGGTCTGTGATAACATCATTTACATAGAAAACACACCAAAAGGATGGTTGAAAAGAATA

TATTGGGATTGGTTCGGTTGTCGGAAGTTTATCTCGGAACATAAGATTAACGTTAAGAAAGTAATTTCTCTACAAAA

TTCCAGTTTGAATGTTCCTTACGAACAGATTATTTACTTGCACCAGCCAATTCCTTTTAGTAAAGTTGATTCTTTTT

TAAAAAATATCACATCCGATAACGTAAAGCTTTTTTTATATAAAAAGTTTTATTCCTATTTTATATTTAAATATGTG

AATGCCAATACAACCATCGTAGTGCAAACGAATTGGATGAAAAAAGGAGTGCTGGAGCAATGTGATAAAATTAGTAC

CGAAAGGGTCCTTGTTATAAAACCTGATATCAAAGCATTTAATAATACTAATTTTGATGTAGATATGGATGTATCTG

CAAAAACACTCTTATATCCAGCGACACCACTTACCTATAAAAATCATTTGGTCATTCTGAAGGCGTTGGTTATTTTA

AAGAAAAAGTATTTTATAGATGATCTGAAATTCCAAGTGACTTTTGAAAAGAATAGGTACAAAAATTTTGATAAGTT

TGTGCAATTAAATAACTTAAGCAAAAACGTTGATTATCTCGGCGTTCTTTCATACTCGAACTTGCAAAAAAAATATA

TGGCGGCATCTTTAATCGTTTTTCCTAGCTATATCGAATCATATGGGTTACCACTCATCGAAGCTGCTAGTTTAGGA

AAAAAAATCATTAGTAGTGATCTTCCTTATGCCCGGGATGTTTTAAAGGATTATAGCGGCGTAGATTTTGTAATTTA

CAATAATGAAGATGGCTGGGCTAAGGCGTTGTTTAATGTTTTAAATGGCAATTCGAAGCTCAATTTTAGGCCTTATG

AAAAAGATAGTCGTTCATCTTGGCCACAGTTCTTCTCTATTTTGAAATAAGGTGTATTATGTTTAATGGTAAAATAT

TGTTAATTACTGGTGGTACGGGGTCTTTCGGTAATGCTGTTCTAAGACGTTTTCTTGACACTGATATCAAAGAAATA

CGTATTTTTTCCCGGGATGAAAAAAAACAAGATGACATGAGGAAAAAATATAATAATCCGAAACTTAAGTTCTATAT

AGGTGATGTTCGCGACTATTCGAGTATCCTCAATGCTTCTCGAGGTGTTGATTTTATTTATCATGCTGCAGCTCTGA

AGCAAGTACCTTCCTGCGAATTCCACCCAATGGAAGCTGTAAAAACGAATGTTTTAGGTACGGAAAACGTACTGGAA

GCGGCAATAGCTAATGGAGTTAGGCGAATTGTATGTTTGAGTACAGATAAAGCTGTATATCCTATCAATGCAATGGG

TATTTCCAAAGCGATGATGGAAAAAGTAATGGTAGCAAAATCGCGCAATGTTGACTGCTCTAAAACGGTTATTTGCG

GTACACGTTATGGCAATGTAATGGCATCTCGTGGTTCAGTTATCCCATTATTTGTCGATCTGATTAAATCAGGTAGA

CCAATGACGATAACAGACCCTAATATGACTCGTTTCATGATGACTCTCGAAGACGCTGTTGATTTGGTTCTTTACGC

ATTTGAACATGGCAATAATGGTGATATTTTTGTCCAAAAGGCACCTGCGGCTACCATCGAAACGTTGGCTATTGCAC

TCAAAGAATTACTTAATGTAAACCAACACCCTGTAAATATAATCGGCACCCGACACGGGGAAAAACTGTACGAAGCG

TTATTGAGCCGAGAGGAAATGATTGCAGCGGAGGATATGGGTGATTATTATCGTGTTCCACCAGATCTCCGCGATTT

GAACTATGGAAAATATGTGGAACATGGTGACCGTCGTATCTCGGAAGTGGAAGATTATAACTCTCATAATACTGATA

GGTTAGATGTTGAGGGAATGAAAAAATTACTGCTAAAACTTCCTTTTATCCGGGCACTTCGGTCTGGTGAAGATTAT

GAGTTGGATTCATAATATGAAAATTTTAGTTACTGGCGCTGCAGGGTTTATCGGTCGAAATTTGGTATTCCGGCTTA

AGGAAGCTGGATATAACGAACTCATTACGATAGATCGTAACTCTTCTTTGGCGGATTTAGAGCAGGGACTTAAGCAG

GCAGATTTTATTTTTCACCTTGCTGGGGTAAATCGTCCCGTGAAGGAGTGTGAATTTGAAGAGGGAAATAGTAATCT

AACTCAACAGATTGTTGATATCCTGAAAAAAAACAATAAAAATACTCCTATCATGCTGAGTTCTTCCATCCAGGCTG

AATGTGATAACGCTTATGGAAAGAGTAAAGCAGCTGCGGAAAAAATCATTCAGCAGTATGGGGAAACGACAAACGCT

-continued

AAATATTATATTTATCGCTTGCCGAATGTATTCGGTAAGTGGTGTCGACCAAATTATAACTCCTTTATAGCAACTTT

CTGCCATCGCATTGCAAATGATGAAGCTATTACAATTAATGATCCTTCAGCAGTTGTAAATCTGGTGTATATAGATG

ACTTTTGTTCTGACATATTAAAGCTATTAGAAGGAGCGAACGAAACTGGTTACAGGACATTTGGTCCAATTTATTCT

GTTACTGTTGGTGAAGTGGCACAATTAATTTACCGGTTTAAAGAAAGTCGCCAAACATTAATCACCGAAGATGTAGG

TAATGGATTTACACGTGCATTGTACTCAACATGGTTAAGTTACCTGTCTCCTGAACAGTTTGCGTATACGGTTCCTT

CTTATAGTGATGACAGAGGGGTATTCTGTGAAGTATTGAAAACGAAAAACGCGGGCCAGTTTTCGTTCTTTACTGCG

CATCCAGGAATTACTCGGGGTGGTCATTATCATCATTCCAAAAATGAGAAATTTATTGTCATCCGAGGAAGTGCTTG

TTTCAAATTTGAAAATATTGTCACGAGTGAACGATATGAACTTAATGTTTCCTCTGATGATTTTAAAATTGTTGAAA

CAGTTCCGGGATGGACGCATAACATTACTAATAATGGCTCGGATGAGCTAGTTGTTATGCTTTGGGCAAATGAAATA

TTTAATCGTTCTGAACCAGATACTATAGCGAGAGTTTTATCGTGAAAAAATTGAAAGTCATGTCGGTTGTTGGGACT

CGTCCAGAAATTATTCGACTCTCGCGTGTCCTTGCAAAATTAGATGAATATTGTGACCACCTTATTGTTCATACCGG

GCAAAACTACGATTATGAACTGAATGAAGTTTTTTTCAAAGATTTGGGTGTTCGCAAACCTGATTATTTTCTTAATG

CCGCAGGTAAAAATGCAGCAGAGACTATTGGACAAGTTATCATTAAAGTTGATGAGGTCCTTGAACAGGAAAAACCA

GAAGCCATGTTAGTACTTGGCGATACTAACTCCTGTATTTCAGCAATACCAGCAAAGCGTCGAAGAATTCCGATCTT

CCATATGGAGGCTGGGAATCGTTGTTTTGACCAACGCGTACCGGAAGAAACTAACAGAAAAATAGTTGATCATACCG

CTGATATCAATATGACATATAGTGATATCGCGCGTGAATATCTTCTGGCTGAAGGTGTACCAGCCGATAGAATTATT

AAAACCGGTAGCCCAATGTTTGAAGTACTCACTCATTATATGCCGCAGATTGATGGTTCCGATGTACTTTCTCGCCT

GAATTTAACACCTGGGAATTTCTTTGTGGTAAGTGCCCACAGAGAAGAAAATGTTGATACCCCTAAACAACTTGTGA

AACTGGCGAATATACTTAATACCGTGGCTGAAAAATATGATGTCCCGGTAGTTGTTTCTACTCATCCTCGCACTCGT

AACCGCATCAACGAAAACGGTATTCAATTCCATAAAAATATCTTGCTTCTTAAGCCATTAGGATTTCACGATTACAA

CCATCTGCAAAAAAATGCACGTGCTGTTTTATCGGATAGTGGGACTATTACAGAAGAGTCCTCCATTATGAACTTCC

CTGCACTCAATATACGAGAAGCGCACGAACGCCCGGAAGGCTTCGAAGAAGGGGCAGTAATGATGGTCGGTCTTGAA

TCTGATCGCGTTTTACAGGCATTAGAAATTATTGCAACACAGCCTCGTGGAGAAGTACGCTTACTTCGTCAGGTTAG

TGACTATAGCATGCCAAATGTTTCAGATAAAGTTCTGCGTATTATCCATTCATATACTGACTACGTTAAACGGGTTG

TCTGGAAGCAATACTAATGAAACTTGCATTAATCATTGATGATTATTTGCCCCATAGCACACGCGTTGGGGCTAAAA

TGTTTCATGAGTTAGGCCTTGAATTACTGAGCAGAGGCCATGATGTAACTGTAATTACGCCTGACATCTCATTACAA

GCAATTTATTCTATTAGTATGATTGATGGTATAAAGGTTTGGCGTTTCAAAAGTGGACCTTTAAAGGATGTAGGTAA

GGCTAAACGTGCCATAAATGAAACTCTTTTATCTTTTCGCGCATGGCGCGCATTTAAGCACCTCATTCAACATGATA

CATTTGATGGTATCGTTTATTATTCCCCCTCTATTTTTTGGGGCGACTTGGTTAAAAAAATAAAACAACGATGCCAG

TGCCCAAGCTATCTGATCCTAAGGGATATGTTTCCACAGTGGGTCATTGATGCAGGTATGTTGAAAGCCGGTTCACC

AATTGAAAAAATATTTTAGGTATTTTGAAAAAAAGTCATATCAGCAGGCTGGCCGGATAGGGGTAATGTCTGATAAGA

ATCTTGAGATATTTCGCCAGACCAATAAAGGTTATCCGTGTGAAGTTTTACGTAATTGGGCCTCAATGACTCCTGTG

TCTGCCAGCGATGATTATCATTCACTTCGTCAAAAATACGATCTAAAAGATAAAGTCATTTTTTTCTATGGCGGTAA

TATTGGGCATGCTCAGGATATGGCAAACTTAATGCGCCTTGCGCGTAATATGATGCGTTATCATGATGCTCATTTCC

TGTTTATAGGGCAGGGTGATGAAGTTGAGCTGATAAAATCTCTTGCTGCAGAATGGAATTTAACTAATTTCACTCAT

CTACCTTCAGTGAACCAGGAAGAGTTTAAATTAATTTTATCTGAAGTTGATGTCGGCCTGTTCTCCCTTTCATCTCG

CCATTCTTCACATAATTTCCCCGGAAAATTACTAGGGTATATGGTTCAATCAATCCCGATCCTTGGGAGTGTGAATG

GCGGCAATGATTTAATGGATGTAATTAATAAGCACAGAGCCGGTTTCATTCATGTTAATGGTGAAGATGATAAACTG

TTTGAATCTGCACAATTGCTTCTTAGTGATTCAGTTTTAAGAAAACAGCTAGGTCAGAACGCTAATGTGTTGTTAAA

GTCTCAATTTTCGGTTGAATCGGCGGCACATACTATCGAAGTCCGACTGGAGGCTGGAGAATGCGTTTAGTTGATGA

CAATATTCTGGATGAACTTTTTCGCACTGCAGCAAATTCTGAACGTTTGCGCGCTCATTATTTATTGCACGCATCTC

-continued

ATCAGGAGAAGGTTCAACGTTTACTTATTGCATTTGTACGCGACAGCTATGTTGAACCCCATTGGCATGAGTTACCG

CATCAGTGGGAAATGTTTGTCGTCATGCAAGGGCAATTAGAAGTTTGTTTGTATGAGCAAAATGGTGAGATCCAAAA

ACAGTTTGTTGTTGGAGACGGTACGGGAATAAGCGTCGTGGAATTTTCCCCAGGAGATATACATAGTGTCAAATGCC

TGTCACCAAAAGCCCTTATGTTGGAGATAAAGGAGGGGCCATTTGACCCACTCAAAGCTAAGGCTTTTTCTAAGTGG

TTATAGGGCGATACACCACCGTTTATTCTTCTATCTTATTCTATACATGCTGGGTTACCATCTTAGCTTCTTCAAGC

CGCGCAACCCCGCGGTGACCACCCCTGACAGGAGTAGCTAGCATTTGACCACCCCTGACAGGATTAGCTAGCATATG

AGCTCGAGGATATCTACTGTGGGTACCCGGGATCCGTGTAGGCTGGAGCTGCTTCGAAGTTCCTATACTTTCTAGAG

AATAGGAACTTCGGAATAGGAACTAAGGAGGATATTCATAT (example signal sequence for EPA carrier protein)

SEQ ID NO: 10

MKKIWLALAG LVLAFSASA (example O1A rfb locus nucleotide sequence-O1A-EPA production strain stGVXN4411 and stLMTB10217)

SEQ ID NO: 11

ATGACGAATTTAAAAGCAGTTATTCCTGTAGCGGGTCTCGGGATGCATATGTTGCCTGCCACTAAGGCGATACCCAA

AGAGATGCTACCAATCGTCGACAAGCCAATGATTCAGTACATTGTTGACGAGATTGTGGCTGCAGGGATCAAAGAAA

TCCTCCTGGTAACTCACGCGTCCAAGAACGCGGTCGAAAACCACTTCGACACCTCTTATGAGTTAGAATCACTCCTT

GAGCAGCGCGTGAAGCGTCAACTGCTGGCGGAAGTACAGTCCATCTGTCCGCCGGGCGTGACCATTATGAACGTGCG

TCAGGGCGAACCTTTAGGTTTAGGCCACTCCATTTTGTGTGCGCGACCTGCCATTGGTGACAACCCATTTGTCGTGG

TACTGCCAGACGTTGTGATCGACGATGCCAGCGCCGACCCGCTACGTTACAACCTTGCTGCCATGATTGCACGTTTC

AACGAAACGGGCCGCAGCCAGGTGCTGGCAAAACGTATGCCGGGTGACCTCTCTGAATACTCCGTCATCCAGACTAA

AGAGCCGCTGGACCGTGAGGGTAAAGTCAGCCGCATTGTTGAATTTATCGAAAAACCGGATCAGCCGCAGACGCTGG

ACTCAGACATCATGGCCGTAGGTCGCTATGTGCTTTCTGCCGATATTTGGCCGGAACTGGAACGTACTCAGCCTGGT

GCATGGGGACGTATTCAGCTGACTGATGCTATTGCCGAGCTGGCGAAAAAACAATCCGTTGATGCAATGCTGATGAC

CGGCGACAGTTACGACTGCGGCAAAAAAATGGGCTATATGCAGGCGTTTGTGAAGTATGGCCTACGCAACCTGAAAG

AAGGGGCGAAGTTCCGTAAAGGTATTGAGAAGCTGTTAAGCGAATAATGAAAATCTGACCGGATGTAACGGTTGATA

AGAAAATTATAACGGCAGTGAAAATTCGCAGCAAAAGTAATTTGTTGCGAATCTTCCTGCCGTTGTTTTATATAAAC

CATCAGAATAACAACGAGTTAGCAGTAGGGTTTTATTCAAAGTTTTCCAGGATTTTCCTTGTTTCCAGAGCGGATTG

GTAAGACAATTAGCGTTTGAATTTTTCGGGTTTAGCGCGAGTGGGTAACGCTCGTCACATCATAGGCATGCATGCAG

TGCTCTGGTAGCTGTAAAGCCAGGGGCGGTAGCGTGCATTAATACCTCTATTAATCAAACTGAGAGCCGCTTATTTC

ACAGCATGCTCTGAAGTAATATGGAATAAATTAAGCTAGCGTGAAGATACTTGTTACTAGGGGCGCAGGATTTATTG

GTTCTGCTGTAGTTCGTCACATTATAAATAATACGCAGGATAGTGTTGTTAATGTCGATAAATTAACGTACGCCGGA

AACCTGGAATCACTTGCTGATGTTTCTGACTCTGAACGCTATGTTTTTGAACATGCGGATATTTGCGATGCTGCTGC

AATGGCGCGGATTTTTGCTCAGCATCAGCCGGATGCAGTGATGCACCTGGCTGCTGAAAGCCATGTGGATCGTTCAA

TTACAGGCCCTGCGGCATTTATTGAAACCAATATTGTTGGTACTTATGTCCTTTTGGAAGCGGCTCGCAATTACTGG

TCTGCTCTTGATGGCGACAAGAAAAATAGCTTCCGTTTTCATCATATTTCTACTGACGAAGTCTATGGTGATTTGCC

TCATCCTGACGAAGTAAATAATAAAGAACAATTACCCCTCTTTACTGAGACGACAGCTTACGCGCCTAGTAGTCCTT

ATTCCGCATCAAAAGCATCCAGCGATCATTTAGTCCGCGCGTGGAAACGTACCTATGGTTTACCGACTATTGTGACT

AACTGTTCGAATAACTACGGTCCTTATCACTTTCCGGAAAAATTGATTCCACTAGTAATTCTTAATGCTCTGGAAGG

TAAGGCATTACCTATTTATGGCAAAGGGGATCAAATTCGTGACTGGCTGTATGTTGAAGATCATGCGCGTGCGTTAT

ATACCGTAGTTACTGAAGGTCAAGCGGGTGAAACCTATAACATTGGCGGACACAACGAAAAGAAAAACATCGATGTT

GTGCTGACTATTTGTGATTTGTTGGACGAGATAGTCCCGAAAGAGAAATCTTATCGTGAGCAAATTACTTATGTTGC

TGATCGCCCAGGGCATGATCGCCGTTATGCGATTGATGCTGAGAAGATTGGTCGCGAATTGGGATGGAAACCACAGG

-continued

AAACGTTTGAGAGTGGGATTCGTAAAACGGTGGAATGGTATTTGGCTAATGCAAAATGGGTTGATAATGTGAAAAGT

GGTGCCTATCAATCGTGGATTGAACAGAACTATGAGGGCCGCCAGTAATGAATATCCTCCTTTTTGGCAAAACAGGG

CAGGTAGGTTGGGAACTACAGCGTGCTCTGGCACCTCTGGGTAATTTGATTGCTCTTGATGTTCACTCCACTGATTA

CTGTGGTGATTTTAGTAACCCTGAAGGTGTGGCTGAAACAGTCAAAAGAATTCGACCTGATGTTATTGTTAATGCTG

CGGCTCACACCGCAGTAGATAAGGCTGAGTCAGAACCCGAATTTGCACAATTACTCAATGCGACTAGCGTTGAATCA

ATTGCAAAAGCGGCAAATGAAGTTGGGGCTTGGGTAATTCATTACTCAACTGACTACGTATTCCCTGGAAATGGCGA

CACGCCATGGCTGGAGATGGATGCAACCGCACCGCTAAATGTTTACGGTGAAACCAAGTTAGCTGGAGAAAAAGCAT

TACAAGAGCATTGTGCGAAGCACCTAATTTTCCGTACCAGCTGGGTCTATGCAGGTAAAGGAAATAATTTCGCCAAA

ACGATGTTGCGTCTGGCAAAAGAGCGTGAAGAACTAGCCGTTATTAATGATCAGTTTGGTGCGCCAACAGGTGCTGA

ACTGCTGGCTGATTGTACGGCACATGCCATTCGTGTCGCACTGAATAAACCGGATGTCGCAGGCTTGTACCATTTGG

TAGCCAGTGGTACCACAACCTGGTACGATTATGCTGCGCTGGTTTTTGAAGAGGCGCGCAATGCAGGCATTCCTCTT

GCACTCAACAAGCTCAACGCAGTACCAACAACTGCCTATCCTACACCAGCTCGTCGTCCACATAACTCTCGCCTTAA

TACAGAAAAAATTTCAGCAGAATTTTGCGCTTGTATTGCCTGACTGGCAGGTTGGTGTGAAACGCATGCTCAACGAAT

TATTTACGACTACAGCAATTTAATAGTTTTTGCATCTTGTTCGTGATGGTGGAGCAAGATGAATTAAAAGGAATGAT

GAAATGAAAACGCGTAAAGGTATTATTTTAGCGGGTGGTTCTGGTACTCGTCTTTATCCTGTGACTATGGTCGTCAG

TAAACAGCTATTACCTATATATGATAAACCGATGATCTATTATCCGCTTTCTACACTGATGTTAGCGGGTATTCGCG

ATATTCTGATTATTAGTACGCCACAGGATACTCCTCGTTTTCAACAACTGCTGGGTGACGGTAGCCAGTGGGGCCTG

AATCTTCAGTACAAAGTGCAACCGAGTCCGGATGGTCTTGCGCAGGCATTTATTATCGGTGAAGAGTTTATTGGTGG

TGATGATTGTGCTTTGGTACTTGGTGATAATATCTTCTACGGTCACGACCTGCCTAAGTTAATGGATGCCGCTGTTA

ACAAAGAAAGTGGTGCAACGGTATTTGCCTATCACGTTAATGATCCTGAACGCTATGGTGTCGTTGAGTTTGATAAA

AACGGTACGGCGATCAGCCTGGAAGAAAAACCGCTACAACCAAAAAGTAATTATGCGGTAACCGGGCTTTATTTTTA

TGATAACGACGTTGTCGAAATGGCGAAAAATCTTAAGCCTTCTGCCCGCGGTGAACTGGAAATTACCGATATTAACC

GTATCTATATGGAACAAGGGCGTTTATCTGTTGCCATGATGGGGCGTGGTTATGCGTGGTTAGACACGGGGACACAT

CAGAGCCTGATTGAGGCAAGCAACTTTATTGCAACAATTGAAGAGCGTCAGGGGCTGAAAGTTTCCTGCCCGGAAGA

AATTGCTTACCGTAAAGGGTTTGTTGATGCTGAGCAGGTGAAAGTATTAGCTGAACCTCTGAAAAAAAATGCTTATG

GTCAGTATCTGCTGAAAATGATTAAAGGTTATTAATAAAATGAACGTAATTAAAACAGAAATTCCTGATGTACTGAT

TTTTGAACCGAAAGTTTTTGGTGATGAGCGTGGTTTCTTTTTTGAGAGCTTTAACCAGAAGGTTTTTGAGGAAGCTG

TAGGCCGCAAAGTTGAATTTGTTCAGGATAACCATTCGAAGTCTAGTAAAGGTGTTTTACGCGGGCTGCATTATCAG

TTGGAACCTTATGCACAAGGAAAATTGGTGCGTTGCGTTGTCGGTGAAGTTTTTGACGTAGCTGTTGATATTCGTAA

ATCGTCATCGACTTTTGGCAAATGGGTTGGGGTGAATTTATCTGCTGAGAATAAGCGGCAATTGTGGATTCCTGAGG

GATTTGCACATGGTTTTTTAGTGCTGAGTGAGACGGCGGAGTTTTTGTATAAGACGACAAATTATTATCATCCTCAG

AGTGATAGAGGAATAAAATGGGATGATCCAAGCATCAATATTTCATGGCCAGTCGATTCACAAGTGCTGCTATCAGC

TAAAGATAATAAGCATCCTCCATTAACAAAGATTGAAATGTATAGTTAAGATCACGATAAATCTTGGAAGGGTTGCA

AAATTGAATAAAATAGTGAGCAAAAGTGAAATAAGGAACGTAATCCACAATGCTGGCTATATGATGATTACTCAGAT

AGCTTTATATGTTGCACCATTATTTATACTGAGTTATCTGTTAAAAACACTGGGGGTTGCACAGTTTGGTAATTATG

CCTTAATACTATCAATCGTTGCATATTTACAGATTATAACGGATTATGGTTTTTCTTTTAGTGCAAGTCGTGCGATC

TCACAGAATAGAGAGGACAAAGAATATATATCAAAAATTTATCTGTCAACTATGACTATCAAGTTGGCGATATGCGC

TTTCTTATTCTTATTGCTCATGCTATTTTTAAATCTTTTGCCTGTGCAAGCTGAATTAAAACAAGGAATATTATATG

GATATCTTCTTGTAATAGGAAATACTTTCCAACCACAATGGTTTTTCCAAGGTATCGAAAAAATTAAAAATCATAGCC

CTTTCTAATGTTATATCAAGATGCGCCGCGTGTTTACTTGTATTTATCTATGTGAGGAATAGCGAGGATTTACAAAA

-continued

AGCACTTTTAGTACAGTCACTTCCATTAGTAATTTCTGCGATTGGATTAAATATATTTATATTGAAATATATCAATA

TTATTTTTCCGGAAAAAAAATTATTTAAGGTAATTTTAAAAGAAGGTAAGGATTTTTTTCTTGCATCACTTTATTCT

GTTATTCTCAATAATAGTGGCATTTTTCTATTAGGGATTTTTACTAATCCTGTTATTGTTGGTGTATATGCCGCCGC

TGAAAAGATAGTCAAGGCCGTATTGTCGCTATTTACACCACTGACGCAAGCTATATATCCTTATAATTGTCGTAAGT

TTTCACTATCCGTATTTGACGGCATTGAGGCAGCAAAAAAAACTGGTATACCAATTATAATTTTAGCATTTATAGCT

GCTGTTATCGTTGCAATTACCTTACCTGTTGCAATCGACTATCTTAATTTTCCAAAAGAAACAATTTTTGTAGGTCA

AATATTAAGTGCATGGATCTTTTTTGGTGTTCTTAATAATGTATTCGGCATTCAGATATTGAGTGCATCAGGAAGAA

GTAAAATATATAGTAGGATGGTATTCGTATCAGCGCTTATAACATTACTTTTGATTACTCTATTATTGCAGTTTTGT

AACGCCACTGGAGTGGCATGTGCAATATTATTGGGTGAAATGTTCTTATCAATATTGTTACTTAAGCGATATAAAAA

AATAATTTAAGGAATAGTTATGAAGAAGTTATTATTAGTGTTCGGTACTAGGCCTGAAGCAATAAAGATGGCCTCTA

TCATTGAATTATTAAAAAAAGATTGTAGATTCGAATATAAAATATGTGTGACAGGCCAACATAAAGAGATGCTTGAT

CAAGTTATGCAAGTATTTGATGTTAAACCTGATTATAATTTACGGATTATGCAGCCTGGGCAAACATTAGTATCTAT

AGCAACAAATATACTCTCACGGTTAAGTGAAGTTTTAATTATAGAAAAGCCAGATATTATACTTGTGCATGGGGATA

CAACGACTACCCTTGCTGCTACTTTAGCTGGGTATTACCACCAAATAAAAGTTTGTCATGTGGAAGCAGGATTAAGA

ACAGGGGATATTTACTCTCCTTGGCCTGAAGAGGGCAATCGTAAAGTTACAGGGGCATTAGCATGTATTCATTTCGC

CCCAACAGAGAGATCAAAAGATAATCTCCTGAGGGAGGGGGTCAAAGTAAATAATATATTTGTAACGGGTAATACCG

TCATCGACTCTTTATTTATTGCAAAAGATATCATAGATAATGACCCTAATATAAAGAACGCTTTACATAATAAATTT

AATTTTCTTGATAAAAGCCGACGAGTAGTACTTATAACAGGTCATCGAAGAGAAAATTTCGGGAAAGGTTTTGAAGA

TATATGCTTTGCAATAAAGGAATTAGCTTTCATTTATCCTAATGTAGATTTTATTTATCCGGTGCATCTTAATCCCA

ATGTAATGGAACCAGTACATCGTATATTAGATAATATATGTAATATTTACCTTATTGAGCCCTTGGATTATTTGCCT

TTTGTTTATTTAATGAATGAGTCATATTTAATATTGACTGATTCAGGGGGGATACAAGAAGAAGCGCCTTCGTTAGG

TAAACCGGTTTTGGTTATGCGTGATACTACTGAACGCCCTGAGGCGGTTGAGGCTGGTACTGTTGTATTAGTGGGGA

CTTCTAAGATAAAAATAGTAAATAAAGTAACGGAGCTATTAAACAATGCTGATATCTACAATGCTATGTCTCTGTTA

CATAATCCATATGGCGATGGAACAGCTGCTCAAAAAATTCTTAATGTGCTCGCCCAAGAGCTAATTTAATTTAAGCT

AAAAATATGTTATTAATTATTGCTGATTATCCAAACGAAATGAATATGCGCGAGGGAGCTATGCAACGAATAGATGC

GATAGACTCTCTCATTCGAGATCGCAAGCGAGTGTATTTGAATATTTCATTCAAAAAGCATCTAGTTCGCTCAAATA

GTTCCTTTAATAATGTTATAGTTGAAAATCTAAATGCAATTATTCACAGAAACATCATAAAACAGTACATGCAAAAA

TCAACAACTATATATGTTCATTCTGTTTATAATTTATTAAAGGTTATAACGCTCATTGATCTAAAAAAAACAATTCT

TGATATACATGGTGTTGTACCGGAAGAACTTTTGGCAGATAATAAAAAATTACTTAGTAAAGTATATAACATGGTGG

AAAAAAAAGGTGTCCTTGGATGCAAAAAATTAATACACGTCAGTACAGAAATGCAAAAACACTATGAAGCAAAATAT

GGAGTAAACTTGGCTGAAAGGTCAATAGTGCTCCCGATTTTTGAATATAAAAATATAACCCAATCGCAAAACAAATG

GACAGAAAATAAAATACGAAGTATCTATCTTGGAGGATTACAAACATGGCAAAATATTGATAAAATGATTCAAGTTT

GTGATGACACAGTGATAAACAATGAAGCAGGTAAGTATGAATTCAACTTTTTCATCCCACAGAGTAACTTGGAAGGG

TTTATAGATAAATATTCGTTAAAATTACATAATATCAATGCTAATGCATCTACGCTATCACGTGATGAAGTAATTCC

CTTTCTAAAAGAATGTCATATTGGTTTTGTATTGCGCGATGATATAATAGTAAACAGAGTTGCGTGCCCTACAAAAT

TGGTTGAATATTTAGAGTGTGGTGTCGTTCCAGTTGTGCTCTCCCCACTTATAGGTGATTTTTATTCGATGGGATAT

CAATACATTACTACAGAGGAAATGGCTAACAGAAGTATAAGTTTGTTGGATCTTGAAAAAATGGCTGCACATAATTT

ACAAATTTTGACTTCTTATCAGAAGAGAACCTACAAGGCACAGAAAGAACTTATTGCTCAACTGTGCTGAATTTTTT

ACATATATAAAATTATGTAAGCATATCGCGGGTCAGGTAATTGTATGCGTATCAAATATAAAGATAACGGTTATATA

TTATGTTTTCTATTATGTTTCATTTTGAGCTACTTAGTTTTACTCAAATCTGACTACTTTCCTGCTGATTTTCTGCC

ATATACAGAAATATACGATGGGACATACGGAGAAATCAATAATATTGAGCCTGCCTTTTTATATTTAACACGGTTGT

-continued

TTCATTATTTAAATTTCCCCTATATATTTTTTGCAATGTTAGTTTGTGCCTTATGTTTAAGTTGGAAAATAAAATAT

GCAAGAAAAATAATTAAAGATAGTTATATATATTTGTTCTTGTATGTATATGTATCATTTTATGTGTTTTTGCATGA

AATGACTCAATTGCGCATAGCAATTGCAGTCACTATGTGCTATGTGTCGGTTTATTATTACTTTTATAAAAATTGTA

TTAAACATGCACTGCCATGGATGGTGTTGGCTATTTTGTTTCATTACAGCGCCTTGCTTTTATTTATGTCATTATTT

ATATACAGTTATAGGAGGTTATTAATAGTAATTATAGGGTTTGTAATATGTATGAGCTTTTTAAACGTGTATGCAGA

TACAATTGCACTATATTTGCCAAATGAAAAAATAGTAAATTATTTATATAGTATTTCATCATCATTAGACAATAGAA

ATGATTTGGCAATATTCAACCTGAATAATATAATATTTTTATCAATATTTATTTGATCTTTTATCTTAGCCGATAT

ATAAAATTAAATGATAATGAGGCGAAGTTTATTAAGTATGTGCAATGTTCAGGAATATTAGCCTTTTGTATTTTCTT

TCTGGCTAGTGGAGTCCCGGTCATTGCTTATCGAACTGCAGAGTTGCTGCGAATATTTTATCCGATGGCTTTAGTAT

TAATCCTTTCGCATATAAAAAATAATAATATGCGTTATTTTATTGCAGTCATTATAGTTATCCTTTCAGGCTTAATG

TTGTTTATAACACTAAGGGCTGTATCAATAGTTGGTCAAGGATTATAAAATGAATGTTGCTATTTTGTTGTCTACGT

ATAATGGCGAAAAATATTTAGAGGAACAACTGGATTCATTGCTGCTTCAAAGTTATCAGGATTTTGTAGTGTATATC

CGTGATGACGGATCATCTGATAGAACTGTAAATATAATAAACCAATACGTAATGAAAGATAACAGATTTATTAACGT

GGGTAATTCAGAAAATCTTGGTTGTGCTGCTTCGTTTATTAATTTATTAAGAAATGCTTCAGCCGATATTTATATGT

TTTGTGACCAAGATGATTATTGGCTTCCGAATAAATTACAGCGTGCTGTGGATTATTTTTCGGCTATTGATCCTTTA

CAACCTACCTTGTATCATTGCGATCTAAGCGTTGTTGATGAAAAACTTAATATTATACAAAATTCATTTTTGCAGCA

TCAGAAAATGTCAGCGTATGATTCAATGAGAAAAAATAATCTTTTCATACAAAATTTTGTTGTTGGTTGTTCATGTG

CTGTTAATGCTTCACTTGCGGAATTTGTTCTTTCGCGAATTGGAGAGCAGCATGTAAAAATGATAGCTATGCATGAC

TGGTGGTTAGCCGTGACTGCAAAACTTTTTGGTCGAATCCATTTTGATAATACTCAAACGATTCTTTATCGACAACA

TCAGGGCAATGTATTAGGTGCAAAATCATCAGGTATGATGCGTTTTATTCGATTAGGATTAAATGGGCAAGGGATTT

CGCGAGTAGTATCTTTTAGAAAAAAAGTTTGTGCGCAAAATAAGCTTCTTTTAGATGTCTATGATAAAGATTTAAAT

CTTGAGCAAAAAAAATCTATCAGGCTTGTAATTGAGGGCCTTAAAGAGAACTCTTCAATTGCTGACCTTTTAAAATG

TTTCTATCATGGTAGCTATATGCAAGGTTTTAAACGTAATCTTGCCTTAATATATTCAGTTCTTTACACAAAAAAAA

GAAGATAGTGTATCCTTATGAAAAAAATTGCTATTATCGGTACTGTTGGCATACCAGCATCATATGGCGGATTTGAA

ACATTAGTTGAAAATTTAACAAGATACAATTCCTCGGGAGTTGAATATAATGTTTTTTGTTCATCGTTTCACTACAA

ATCCCACCAAAAAAAACATAATGGGGCCCGTTTAATTTATATTCCGCTTAAAGCCAATGGATGGCAGAGCATTGCGT

ATGACATAATTTCGTTAGCATATTCTATTTTTTTGAAGCCTGATGTGATTCTGATTTTAGGGGTTTCTGGTTGTTCA

TTTTTGCCTTTCTTCAAACTCTTAACACGCGCTAAGTTTATTACTAATATTGATGGCCTGGAATGGCGAAGAGATAA

ATGGAATTCAAAAGTGAAACGTTTCTTAAAATTTTCAGAAAAAATCGCAGTTCAATATTCGGATGTCGTTATTACGG

ATAATGAGGCAATTTCTGAGTACGTTTTTAACGAGTATAATAAAGATAGCCGAGTTATTGCCTATGGAGGGGATCAT

GCATGGTTAAATACTGAGGATGTATTTACAACAAGAAATTATAAAAGCGATTACTACCTTTCTGTATGTCGTATCGA

ACCCGAAAACAATGTAGAATTAATTTTAAAAACATTTTCAAAGCTAAAATATAAAATAAAATTTATTGGAAATTGGA

ATGGCAGCGAGTTTGGAAAGAAACTTAGGCTGCATTATTCTAACTATCCAAATATTGAAATGATTGATCCGATTTAT

GATCTTCAACAATTATTTCACTTACGAAATAATTGCATAGGATATATACATGGTCATTCGGCTGGAGGAACAAACCC

TTCTTTAGTCGAGGCAATGCATTTTAGTAAACCTATATTTGCATATGATTGTAAGTTTAATAGGTACACTACTGAAA

ATGAAGCATGTTATTTTTCTAATGAATCTGACCTCGCAGAGAAAATCATAATGCATTGTGAGCTATCATTAGGTGTC

TCTGGCACGAAAATGAAAGAAATTGCTAACCAGAAATACACTTGGAGACGAATAGCAGAAATGTATGAGGATTGCTA

TTAACTCTGTTAAACTTCAAATCTTTTACAATATATGGCATGACTATAAGCGCATTAATTGTTTTTCAAGCCGCTCT

CGCGGTGACCACCCCCTGACAGGGGATCCGTGTAGGCTGGAGCTGCTTCGAAGTTCCTATACTTTCTAGAGAATAGG

AACTTCGGAATAGGAACTAAGGAGGATATTCATATGGATAAAGCCGTAAGCATATAAGCATGGATAAGCTATTTATA

-continued

CTTTAATAAGTACTTTGTATACTTATTTGCGAACATTCCAGGCCGCGAGCATTCAGCGCGGTGATCACACCTGACAG

GAGTATGTAATGTCCAAGCAACAGATCGGCGTAGTCGGTATGGCAGTGATGGGACGCAACCTTGCGCTCAACATCGA

AAGCCGTGGTTATACCGTCTCTATTTTCAACCGTTCCCGTGAGAAGACGGAAGAAGTGATTGCCGAAAATCCAGGCA

AGAAACTGGTTCCTTACTATACGGTGAAAGAGTTTGTCGAATCTCTGGAAACGCCTCGTCGCATCCTGTTAATGGTG

AAAGCAGGTGCAGGCACGGATGCTGCTATTGATTCCCTCAAACCATATCTCGATAAAGGAGACATCATCATTGATGG

TGGTAACACCTTCTTCCAGGACACTATTCGTCGTAATCGTGAGCTTTCAGCAGAGGGCTTTAACTTCATCGGTACCG

GTGTTTCTGGCGGTGAAGAGGGGGCGCTGAAAGGTCCTTCTATTATGCCTGGTGGCCAGAAAGAAGCCTATGAATTG

GTAGCACCGATCCTGACCAAAATCGCCGCCGTAGCTGAAGACGGTGAACCATGCGTTACCTATATTGGTGCCGATGG

CGCAGGTCACTATGTGAAGATGGTTCACAACGGTATTGAATACGGCGATATGCAGCTGATTGCTGAAGCCTATTCTC

TGCTTAAAGGTGGCCTGAACCTCACCAACGAAGAACTGGCGCAGACCTTTACCGAGTGGAATAACGGTGAACTGAGC

AGTTACCTGATCGACATCACCAAAGATATCTTCACCAAAAAAGATGAAGACGGTAACTACCTGGTTGATGTGATCCT

GGATGAAGCGGCTAACAAAGGTACCGGTAAATGGACCAGCCAGAGCGCGCTGGATCTCGGCGAACCGCTGTCGCTGA

TTACCGAGTCTGTGTTTGCACGTTATATCTCTTCTCTGAAAGATCAGCGTGTTGCCGCATCTAAAGTTCTCTCTGGT

CCGCAAGCACAGCCAGCAGGCGACAAGGCTGAGTTCATCGAAAAAGTTCGTCGTGCGCTGTATCTGGGCAAAATCGT

TTCTTACGCCCAGGGCTTCTCTCAGCTGCGTGCTGCGTCTGAAGAGTACAACTGGGATCTGAACTACGGCGAAATCG

CGAAGATTTTCCGTGCTGGCTGCATCATCCGTGCGCAGTTCCTGCAGAAAATCACCGATGCTTATGCCGAAAATCCA

CAGATCGCTAACCTGTTGCTGGCTCCGTACTTCAAGCAAATTGCCGATGACTACCAGCAGGCGCTGCGTGATGTCGT

TGCTTATGCAGTACAGAACGGTATTCCGGTTCCGACCTTCTCCGCAGCGGTTGCCTATTACGACAGCTACCGTGCTG

CTGTTCTGCCTGCGAACCTGATCCAGGCACAGCGTGACTATTTTGGTGCGCATACTTATAAGCGTATCGATAAAGAA

GGTGTGTTCCATACCGAATGGCTGGATTAA (example O2 rfb locus nucleotide sequence-O2-EPA production strain stGVXN4906)

SEQ ID NO: 12

ATGACGAATTTAAAAGCAGTTATTCCTGTAGCGGGTCTCGGGATGCATATGTTGCCTGCCACTAAGGCGATACCCAA

AGAGATGCTACCAATCGTCGACAAGCCAATGATTCAGTACATTGTTGACGAGATTGTGGCTGCAGGGATCAAAGAAA

TCCTCCTGGTAACTCACGCGTCCAAGAACGCGGTCGAAAACCACTTCGACACCTCTTATGAGTTAGAATCACTCCTT

GAGCAGCGCGTGAAGCGTCAACTGCTGGCGGAAGTACAGTCCATCTGTCCGCCGGGCGTGACCATTATGAACGTGCG

TCAGGGCGAACCTTTAGGTTTAGGCCACTCCATTTTGTGTGCGCGACCTGCCATTGGTGACAACCCATTTGTCGTGG

TACTGCCAGACGTTGTGATCGACGATGCCAGCGCCGACCCGCTACGTTACAACCTTGCTGCCATGATTGCACGTTTC

AACGAAACGGGCCGCAGCCAGGTGCTGGCAAAACGTATGCCGGGTGACCTCTCTGAATACTCCGTCATCCAGACTAA

AGAGCCGCTGGACCGTGAGGGTAAAGTCAGCCGCATTGTTGAATTTATCGAAAAACCGGATCAGCCGCAGACGCTGG

ACTCAGACATCATGGCCGTAGGTCGCTATGTGCTTTCTGCCGATATTTGGCCGGAACTGGAACGTACTCAGCCTGGT

GCATGGGGACGTATTCAGCTGACTGATGCTATTGCCGAGCTGGCGAAAAAACAATCCGTTGATGCAATGCTGATGAC

CGGCGACAGTTACGACTGCGGCAAAAAAATGGGCTATATGCAGGCGTTTGTGAAGTATGGCCTACGCAACCTGAAAG

AAGGGGCGAAGTTCCGTAAAGGTATTGAGAAGCTGTTAAGCGAATAATGAAAATCTGACCGGATGTAACGGTTGATA

AGAAAATTATAACGGCAGTGAAAATTCGCAGCAAAAGTAATTTGTTGCGAATCTTCCTGCCGTTGTTTTATATAAAC

CATCAGAATAACAACGAGTTAGCAGTAGGGTTTTATTCAAAGTTTTCCAGGATTTTCCTTGTTTCCAGAGCGGATTG

GTAAGACAATTAGCGTTTGAATTTTTCGGGTTTAGCGCGAGTGGGTAACGCTCGTCACATCATAGGCATGCATGCAG

TGCTCTGGTAGCTGTAAAGCCAGGGGCGGTAGCGTGCATTAATACCTCTATTAATCAAACTGAGAGCCGCTTATTTC

ACAGCATGCTCTGAAGTAATATGGAATAAATTAAGTGAAAATACTTGTTACTGGTGGCGCAGGATTTATTGGTTCAG

CTGTAGTTCGTCACATTATAAATAATACGCAGGATAGTGTTGTTAATGTCGATAAATTAACGTACGCCGGAAACCGG

GAATCACTTGCTGATGTTTCTGATTCTGAACGCTATGTTTTTGAACATGCGGATATTTGCGATGCACCTGCAATGGC

-continued

ACGGATTTTTGCTCAGCATCAGCCGGATGCAGTGATGCACCTGGCTGCTGAAAGCCATGTTGACCGTTCAATTACAG

GCCCTGCGGCATTTATTGAAACCAATATTGTTGGTACTTATGTCCTTTTGGAAGCCGCTCGCAATTACTGGTCTGCT

CTTGATAGCGACAAGAAAAATAGCTTCCGTTTTCATCATATTTCTACTGACGAAGTCTATGGTGATTTGCCTCATCC

AGATGAAGTAAATAATACAGAAGAATTACCCTTATTTACTGAGACGACAGCTTACGCGCCAAGCAGCCCTTATTCCG

CATCCAAAGCATCCAGCGATCATTTAGTCCGCGCATGGAAACGTACGTATGGTTTACCGACCATTGTGACTAATTGC

TCGAACAACTATGGTCCGTATCACTTCCCGGAAAAGCTTATTCCATTGGTTATTCTTAATGCACTGGAAGGTAAGGC

ATTACCTATTTATGGCAAAGGGGATCAAATTCGCGACTGGTTGTATGTAGAGGATCATGCTCGTGCGTTATATACCG

TCGTAACCGAAGGTAAAGCGGGTGAAACTTATAACATTGGCGGACACAACGAAAAGAAAAACATCGATGTTGTGCTG

ACTATTTGTGATTTGTTGGATGAGATTGTACCGAAAGAGAAATCTTATCGTGAGCAAATTACTTATGTTGCTGATCG

CCCAGGGCATGATCGCCGTTATGCAATTGATGCCGATAAAATTAGCCGCGAATTGGGCTGGAAACCACAGGAAACGT

TTGAGAGCGGGATTCGCAAAACGGTGGAATGGTATCTGGCTAATACAAATTGGGTTGAGAATGTGAAAAGCGGTGCT

TATCAGTCATGGATCGAACAAAACTATGAGGGCCGTCAGTAATGAATATCCTGCTTTTCGGCAAAACAGGGCAGGTG

GGTTGGGAACTGCAGCGTGCTCTGGCGCCGCTGGGTAATCTGATCGCTCTTGATGTTCACTCCACTAATTATTGTGG

AGATTTCAGCAACCCCGAAGGTGTGGCAGAAACCGTCAAAAAAATTCGTCCTGACGTTATTGTTAATGCTGCTGCTC

ACACTGCAGTAGATAAAGCAGAATCAGAACCGGATTTCGCACAATTACTTAACGCGACAAGCGTCGAAGCGATTGCA

AAAGCTGCTAATGAAGTCGGGGCCTGGGTTATACACTACTCTACTGATTATGTTTTCCCAGGCAGTGGTGACGCGCC

ATGGCTGGAAACGGATGCAACAGCACCGCTAAATGTTTACGGTGAAACAAAATTAGCTGGGGAAAAGGCATTACAAG

AACATTGCGCAAAGCATCTTATTTTCCGTACCAGCTGGGTATACGCTGGTAAAGGAAATAACTTTGCTAAAACGATG

TTGCGTTTGGCAAAAGAACGCGAAGAACTGGCTGTGATAAACGATCAGTTTGGCGCACCAACAGGTGCTGAATTGCT

GGCTGATTGCACCGCTCATGCCATTCGCGTGGCATTAAAAAAACCAGAAGTCGCTGGCTTGTACCATCTGGTAGCAA

GTGGCACAACAACCTGGCACGATTATGCTGCGCTGGTTTTTGAAGAGGCGCGCAAAGCAGGGATTAATCTTGCACTT

AACAAACTTAACGCCGTGCCAACAACGGCCTATCCCACACCAGCCCGTCGACCCCATAACTCTCGCCTCAATACAGA

AAAGTTTCAGCAGAACTTTGCGCTTGTCTTGCCTGACTGGCAGGTGGGCGTGAAACGTATGCTCAACGAATTATTTA

CGACTACGGCAATTTAACAAATTTTTGCATCTCGCTCATGATGCCAGAGCGGGATGAATTAAAAGGAATGGTGAAAT

GAAAACGCGTAAAGGTATTATTCTGGCTGGTGGTTCCGGCACTCGTCTTTATCCTGTGACGATGGCAGTGAGTAAAC

AATTGCTGCCGATTTATGATAAGCCGATGATTTATTATCCGCTTTCAACGCTTATGTTAGCGGGTATTCGCGATATT

CTTATTATTAGTACGCCACAGGATACACCGCGTTTCCAACAATTATTGGGGGACGGGAGCCAGTGGGGTCTTAATCT

ACAGTATAAAGTACAACCGAGTCCGGATGGCCTGGCGCAAGCGTTTATTATTGGCGAAGACTTTATTGGTGGTGATG

ATTGTGCACTCGTACTTGGCGATAATATCTTCTATGGACACGACTTGCCGAAATTGATGGAAGCTGCTGTTAACAAA

GAAAGCGGTGCAACGGTATTTGCTTATCACGTTAATGATCCTGAACGCTATGGTGTCGTGGAGTTTGATAATAACGG

TACGGCAATTAGCCTGGAAGAAAAACCGCTGGAGCCAAAAAGCAACTATGCGGTTACTGGGCTTTATTTCTATGACA

ATGACGTTGTGGAAATGGCTAAAAACCTTAAGCCTTCTGCCCGTGGCGAACTGGAAATTACCGATATTAACCGTATT

TATATGGAACAAGGACGTTTGTCTGTAGCCATGATGGGGCGTGGCTATGCATGGTTGGATACAGGGACGCATCAAAG

CCTTATTGAAGCAAGTAACTTCATTGCAACAATTGAAGAGCGTCAGGGATTAAAGGTATCTTGCCCGGAAGAGATTG

CTTACCGTAAAGGGTTTATTGATGCCGAGCAGGTGAAAGTATTAGCCGAACCGCTTATCAAGAATCAATATGGTCAA

TATTTGCTGAAAATGATCAGCGAATAGTATATGGGAACTCAATGATGGATATTAAATTAATCTCTTTGCAAAAACAT

GGGGATGAGCGCGGTGCATTAATTGCTCTTGAAGAGCAACGAAATATACCTTTCGAAGTCAAAAGAATATATTACAT

ACTTGAGACTCTTAATGGAGTAAGACGCGGATTTCATGCGCACAAGGTTACTCGTCAGTTAGCTATTGTAGTCAAGG

GAGCTTGTAAATTTCATCTGGATAATGGTAAAGAAACAAAGCAGGTGGAACTTAATGATCCAACAATTGCGTTGCTG

ATAGAACCCTATATATGGCATGAAATGTATGATTTTAGTGATGATTGTGTGCTGCTTGTAATTGCGGATGATTTCTA

TAAAGAGTCTGATTATATCCGCAATTATGATGATTTTATTAGAAGAGTAAATTCAATTGAGAATTCATAAGCTAAGT

-continued

GACGTCCAGACAACATCAATTGGTGATGGAACAACTATCTGGCAGTTTGTTGTGATACTAAAAGGTGCTGTAATTGG

TAATAATTGCAACATCTGTGCAAATACCTTAATTGAAAATAACGTTGTAATTGGTAACAATGTCACAGTCAAAAGCG

GTGTGTATATTTGGGATGGCGTTAAAATAGAGGATAATGTTTTTATTGGTCCTTGTGTAGCATTTACAAATGATAAG

TATCCTCGCTCTAAAGTCTATCCTGATGAATTTTTGCAAACAATAATACGCAAAGGAGCATCAATAGGTGCTAACGC

AACCATCCTGCCAGGAATTGAAATTGGTGAAAAAGCAATCGTTGGTGCGGGGAGTGTTGTAACCAAAAATGTACCGC

CATGCGCAATAGTAGTAGGTAATCCAGCTCGATTTATTAAATGGGTAGAGGATAATGAATAAAATTGATTTTTTAGA

TCTTTTTGCAATTAACCAGCGACAGCACAAAGAATTAGTCTCTGCGTTTAGTAGGGTGCTAGATTCTGGTTGGTATA

TCATGGGCGAAGAACTTGAGCAGTTCGAGAAAGAGTTCGCAGAATACTGTGGAGTTAAGTATTGCATTGGTGTAGCA

AATGGCCTTGATGCGTTGATACTAGTATTGAGGGCATGGAAAGAACTTGGCTATCTTGAAGACGGTGACGAGGTATT

AGTACCGGCAAATACATATATTGCTTCTATTCTTGCTATAACAGAGAACAAACTTGTTCCTGTTCTTGTTGAACCAG

ATATAGAAACTTATAATATTAATCCTGCTTTAATTGAAAATTACATTACGGAAAAAACTAAAGCAATATTACCGGTT

CACTTATATGGTCTATTGTGCAATATGCCAGAAATTAGTGCAATCGCCAGAAAATATAATCTGTTGATTCTTGAAGA

TTGTGCACAAGCACATGGTGCAATACGTGATGGTCGCAAAGCTGGAGCTTGGGGGGATGCTGCAGGATTTAGTTTTT

ATCCAGGAAAAAACCTTGGAGCTTTGGGGGATGCGGGAGCTGTTACTACAAATAATGCAGAATTATCCTCAACTATA

AAAGCTTTGCGAAATTATGGGTCACATAAGAAATATGAAAATATTTATCAGGGATTGAATAGTCGATTGGATGAACT

GCAAGCAGCCTTATTGCGTGTAAAAATCCATACATTACCGGAAGATACTGCGATTCGGCAAAGGATTGCTGAAAAAT

ATATTCGTGAAATAAAAAACCCTGCGATTACGTTACCAGTGTACGAAGGCCAAGGTGCGCATGTTTGGCATTTATTT

GTAGTAAGAATCGCTAATCGTGAAAAATTCCAGTCATACTTATTAGAGAAGGGTATCAAAACCTTAATTCACTATCC

ATTACCACCCCATAAGCAGCAAGCATATCAAAATATGTCTAGCCTTAGCCTTCCAATTACTGAGCAAATTCATGATG

AAGTCATTTCTTTACCTATAAGTCCGGTAATGAGTGAAGATGATGTCAATTATGTAATCAAAATGGTCAATGATTAC

AAGTAATGAAAAAATTTCTTCAGGTAACTATATTATCCGCTATCTATACATTCATTAAAATGATTGCGGGTTTTATC

ATCGGTAAGGTAGTAGCAATTTATACAGGGCCATCAGGGGTAGCAATGCTTGGCCAAGTGCAAAGTTTAATCACAAT

AGTTGCAGGTACTACCTCTGCACCTGTAAGCACAGGCCTTGTTCGATATACTGCGGAAAATTGGCAAGAAGGACAAG

AAGCATGCGCGCCATGGTGGCGCGCATGCTTAAGGGTTACTCTGTTTTTATTCTTGCTTATTATTCCCGTTGTTATT

ATATTGTCGAAAAATATTAGTGAGTTACTTTTTAGCGATGGACAATACACATGGTTAATCATTTTCGCATGTTGTAT

ATTGCCATTCTCCATTATAAATACATTGATCGCTTCAGTTTTAAATGGTCAACAATTTTATAAGCAATATATATTGG

TTGGGATGTTTTCTGTATTCATTTCTACTATGTTTATGATTTTGTTGATTGTAGCTTATAATCTTAAAGGTGCATTG

ATTGCCACAGCTATAAATAGTGCTATTGCTGGTCTTGTATTGGTTTTATTTTGTCTCAATAAATCTTGGTTTAGATT

TAAATATTGGTGGGGTAAAACGGATAAAGACAAAATTATAAAAATTATTCATTATACTCTGATGGCTCTGGTTTCTG

TTATCTCCATGCCTACAGCATTGATGTGTATTAGAAAAATATTGATTGCTAAAACTGGTTGGGAGGATGCAGGGCAA

TGGCAGGCCGTATGGAAGATATCTGAGGTTTATCTTGGTGTTGTGACAATTGCTTTGTCAACATATTTCTTACCAAG

ATTGACAATTATAAAAACAAGTTTCCTTATAAAAAAAGAAGTAAATAGTACTATATTATACATAATATCTATTACTT

CATTCATGGCGTTGAGTATCTATTTATTCCGCGATTTGGTAATAACAGTTTTATTTACTGAACAGTTTCGCTCAGCT

CGTGAATTATTTTTATTACAACTTATAGGGGATGTAATAAAAATTGCTGGGTTTCTTTATGCATACCCTCTTCAAAG

TCAGGGGCATACTAAACTATTCATCAGTTCAGAAGTGATTTTTTCTATGCTCTTTATCATTACCACCTATATTTTTG

TTGTAAATTATGGAGTACATGGTGCTAACATAAGTTATGTCATTACATATAGTTTATATTTTGTGTTTGCATTTGTG

TTTACTAATTTTATTAATGTTAGAAGAAATAATTAAAAACAGAGGTTGAATTTTGAAAATAATTATACCTGTCTTAG

GATTTGGCAGGGCTGGTGGTGAAAGAGTTCTTTCTAAGCTGGCAACTGAATTGATGAATTATGGACATGATGTAAGT

TTTGTTGTTCCAGATAATAGAACTAATCCATATTATGCTACCACAGCAAAAATTGTCACGAGTAAATCTAGTCAAAA

CCGTGTAAAAATATTGAGAATCATTAAAAATTACTATAATCTGTGGCGTAAATGCATAGAGTTAAATCCTGATGCTG

-continued

TAGTTGCTAGTTTTCATTTGACTGCCTATCTTGTCGCATTATTACCAATCACCCGTCGTAAGAAATATTATTATATT

CAGGCGTATGAAGTTAATTTTTTTGATAATATAATATGGAAATTAATAGCGGGTTTAACATATTATTTACCGCTTAA

AAAAATACTAAATAGTCCTAATTTGCTTCCTCATAAACATGATGATTTTATAGGAGTAGTTCCTGCAGGAGTAGATT

TAAACGTTTTCTATCCGAAACCATCAAATAGGTTATTAAATGGTCACACATCAATAGGGATTATTGGTAGAAAAGAG

AAGCACAAAGGAACTAGCGAAATTATTTCAGTATTGTGTTCACTGGAAAATAAAGCTGGAATTATAATCAATATTGC

GATCTATCTTGAAGAAGTTGATAAGCAGCGTTTAATCGCTGCCGGGTTTCAGGTTAATTTTTTTCCGATTACTTCTG

ATTTAGAATTGGCATCCTTTTATCGAAGCAATGACATCATGATTGCTGTTGGGTTAATTGAAGATGGCGCTTTCCAT

TATCCTTGTGCTGAATCAATGGCTTGTGGTTGTCTTGTTATTTCAAATTATGCGCCACTTACTGAAACTAACAGTGT

ACTTAAATTAGTCAAGTTTGATGCTTGCAAACTTGGTGAAGCAATTAATCTTTGTCTCAATCTTGACCTAGAAGAAA

AAAGCAAAGAAATCCAATCTAATATTTCTGTGTTGAATAAATATGACTGGAAAATTGTTGGTGAAACTTTCAATAGT

TTATTGTTAGATGCAAATAAATAGTATACGTTGATGGGGAAAATATGAATATTGTTAAAACTGATATTCCAGATCTG

ATCGTTCTTGAACCAAAAGTGTTTAGTGATGAACGCGGCTTTTTTATGGAGAGTTATAATCAGATTGAATTTGAGAA

GGCAATAGGAAGGCACGTAAATTTTGTTCAGGATAATCATTCAAAATCTAGTAAAGGCGTACTACGTGGGTTGCATT

ATCAATTAGCACCGTATGCACAGGCTAAATTAGTTCGATGTGTTGTAGGTCAGGTATTTGATGTTGCTGTTGATCTT

AGAAAAAATTCACCAACGTTCAAAAAATGGTTTGGAATAACCCTTTCCGCAGAAAATAAACGACAATTATGGATACC

CGAAGGATTTGCTCATGGTTTCTTGGTGACCAGTGATGAAGCTGAGTTCATTTATAAGACAACTAACTACTATGCTC

CTGGTCATCAGCAAGCAATTATTTACAATGATCCTATTTTAAACATCGATTGGCCTTTCTGCAGTAGTGCTCTGTCA

TTATCACAAAAAGATCAAGAAGCAAAATTATTTTCAGAATTATTGGACAGTGAACTGTTCTAATAAAGTGTGCCACC

TTATCCGTCTGAAGGATAGGTGGTTGCTTATATTTTTTTGAGTATGTTTGTATAATGACAGAAAATAGTCCGAAATA

TAAACACGATAAAAGCTTAATAAGTTTTATCTACTTATTTTTTATATTTACACTTATTGTAGGCTTTATTATCGCAA

ATACCCAGTTTTTGGGGCGAAGTAGAGACTATGATAATTATATACAGATCTTTTCTGGTAAAGAAGGGGAGGGGGTT

CTTGAATTATTTTATCGCGGATTGATGTTAATAACGACCAGCTATGAAACTATCATTTTTATAATTTTAACATGTTC

TTTTTTTATAAAGGCAAGGTTTCTCGCTAACTATTCGCGTAATTTTTCAGGCTTGACCTTATTCTTTATTTATTATG

CAAGCGTTGCACTTTGGGTTTTAGATTATACTCAATTCAGAAATGGTCTATGTATTTCCATTTTAATGTTTTCCGTA

TACTATTTATTTATAAATAAACCGACTTATTTTTATTTCTCGGTATTATGTGCAATTGCAACTCATTGGTCTGCTTT

GCCTTTTTTGCTTTTATATCCTTTTGTCTATTCAACAAAAATAAGACGCCTTGGTTATTTTTGTTTCAGTATTCTTG

TTTTGATTGCGATCTCAGGAGAAGGAAAAGAGATCATATCTTTTATAAGAAATTTTGGAGTGGGACAAAAAATAGGA

AATGAAGCTGGTGTAAATTTAATAAATTCATTATCCCTTACCGCTATTTCCTGGTTTATTATTAGTTACATATCAAG

CATTGGAAATGAAAGGAGAAATTTAAGGCTTTTCTTTTGTTATGGTGTCATGCAATACGTGACTTTTAGCCTTTTCT

CTCTACCTGTTATGGCTTTCCGTATTTTGGAAATGTATTTTTTCCTTATGCTAACCATTGGGGTGTTTATTAAGCAA

AAAAAGAATTATTATTTTATTTTTTGCAAAGTGTTAATTTTATTGTATCTAACATACTATTATCATATGGTCTTTGG

AGTGATTAATGTGTAAGGCTAAGGTGTTGGCTATAATTGTTACTTACAACCCGGAAATTATTCGATTGACGGAATGT

ATTAACTCTTTAGCCCCACAAGTTGAGAGAATAATTCTTGTAGATAATGGCTCAAATAATAGTGATTTGATAAAAAA

TATCAGTATTAATAACCTTGAAATTATTTTACTTTCGGAAAACAAAGGCATTGCATTTGCTCAGAACCATGGTGTTA

AGAAGGGCCTGGAAGCAAAAGAGTTTGACTATTTATTTTTCTCAGATCAGGATACTTGCTTTCCTAGCGATGTTATT

GAAAAACTTAAGAGTACATTTACGAAAAATAATAAAAAAGGTAAAAATGTTGCTTGTGCTTCTCCTTTTTTTAAAGA

CCATCGTTCAAATTATATGCATCCGTCAGTCAGCCTAAATATTTTTACGAGTACAAAAGTTATATGTAGTGAAGTAG

ACGATGATCTTTATCCCTCGCATGTTATTGCTTCTGGGATGTTAATGTCTCGTGAAGCATGGCGCGTCGTCGGACCA

TTTTGTGAAAAACTCTTTATAGACTGGGTTGATACAGAATGGTGTTGGCGTGCATTAGCTAATAATATGATTATTGT

TCAGACACCATCAGTCATCATTTCTCATGAACTTGGGTATGGGCAGAAAATTTTTGCTGGTCGATCTGTTACAATAC

ATAATTCTTTCAGAAATTTTTATAAAATACGCAATGCAATATACTTAATGCTGCATTCAAATTATAGCTTCAAGTAT

-continued

CGTTATCATGCTTTTTTTCATGCGACAAAGAATGTTGTATTTGAAATTTTATATTCGAAAGAAAAATTAAATTCACT

GAAGGTTTGTTTTAAAGCTGTACGTGATGGTATGTTCAATAATTTTTAATACGAAAATAGTTAGGCTCAAGGTGTTT

AAATGGAAGAAAATAATATGAAGACGGTCGCTGTAGTTGGCACAGTGGGTGTTCCTGCTTGTTATGGTGGGTTCGAA

TCACTTGTTCAGAATCTAATTGATTATCAATCTGATGGTATACAATATCAGATATTTTGCTCTTCAAAAAAATATGA

TAAAAAATTTAAAAATTATAAAAATGCAGAATTAATCTATTTGCCGATAAATGCCAATGGCGTCTCTAGCATAATTT

ATGATATTATGTGTTTAATTATTTGTTTATTCAAAAGGCCAGATGTTGTTTTAATATTGGGGGTGTCTGGTTGTTTA

TTTCTACCAATTTATAAACTATTTTCAAAATCAAAGATTATTGTCAATATTGATGGGCTTGAATGGCGTAGAAATAA

ATGGGGAACGTTTGCTAAGAAATTTCTTAAAATATCTGAGGCGATATCTATTAGAATAGCTGATATTATCATTTCAG

ATAATCAAGCAATAGCTGATTATGTGGAAAATAAGTACAAGAAAAAAAGTGTAGTTATAGCTTATGGCGGAGATCAT

GCCACTAATCTTAGTACACCGATAGACAATGATCAAAAAAAAGAAGGTTATTATTTGGGGCTTTGTAGGATAGAGCC

TGAGAATAATATAGAAATGATTCTGAATGCCTTCATTAATACAGATAAAAAAATTAAATTTATGGGTAATTGGGATA

ACAGCGAGTATGGACGCCAGCTAAAAAAATATTATTCAAACTATCCAAATATCACCCTACTAGAACCTAACTATAAT

ATTGAAGAGCTTTATAAACTAAGAAAAAATTGTCTTGCATACATTCATGGACACTCGGCTGGTGGAACAAACCCTTC

TTTAGTTGAAGCGATGCATTTTAATATTCCTATTTTTGCTTTCGATTGTGACTTTAATCGTTACACAACTAACAATT

TAGCTCATTACTTTAATGATTCTGAACAACTTAGCTTATTAGCAGAAAGTTTGTCTTTTGGAAATCTTAAATGTCGA

GTATTAGATTTAAAAAATTATGCTGAAGATATGTATAACTGGAGGCATATAGCTGCTATGTATGAATCTATTTATTA

AACGCATTAACAATAATATAATTGACCTTATATAGCAGGGAAAGATCACGTAACGCTGCGGCGCGCCGATCCCCATA

TGAATATCCTCCTTAGTTCCTATTCCGAAGTTCCTATTCTTTCTAGAGAATAGGAACTTCGGAATAGGAACTAAGGA

GGATATTCATATGGATAAAGCCGTAAGCATATAAGCATGGATAAGCTATTTATACTTTAATAAGTACTTTGTATACT

TATTTGCGAACATTCCAGGCCGCGAGCATTCAGCGCGGTGATCACACCTGACAGGAGTATGTAATGTCCAAGCAACA

GATCGGCGTAGTCGGTATGGCAGTGATGGGACGCAACCTTGCGCTCAACATCGAAAGCCGTGGTTATACCGTCTCTA

TTTTCAACCGTTCCCGTGAGAAGACGGAAGAAGTGATTGCCGAAAATCCAGGCAAGAAACTGGTTCCTTACTATACG

GTGAAAGAGTTTGTCGAATCTCTGGAAACGCCTCGTCGCATCCTGTTAATGGTGAAAGCAGGTGCAGGCACGGATGC

TGCTATTGATTCCCTCAAACCATATCTCGATAAAGGAGACATCATCATTGATGGTGGTAACACCTTCTTCCAGGACA

CTATTCGTCGTAATCGTGAGCTTTCAGCAGAGGGCTTTAACTTCATCGGTACCGGTGTTTCTGGCGGTGAAGAGGGG

GCGCTGAAAGGTCCTTCTATTATGCCTGGTGGCCAGAAAGAAGCCTATGAATTGGTAGCACCGATCCTGACCAAAAT

CGCCGCCGTAGCTGAAGACGGTGAACCATGCGTTACCTATATTGGTGCCGATGGCGCAGGTCACTATGTGAAGATGG

TTCACAACGGTATTGAATACGGCGATATGCAGCTGATTGCTGAAGCCTATTCTCTGCTTAAAGGTGGCCTGAACCTC

ACCAACGAAGAACTGGCGCAGACCTTTACCGAGTGGAATAACGGTGAACTGAGCAGTTACCTGATCGACATCACCAA

AGATATCTTCACCAAAAAAGATGAAGACGGTAACTACCTGGTTGATGTGATCCTGGATGAAGCGGCTAACAAAGGTA

CCGGTAAATGGACCAGCCAGAGCGCGCTGGATCTCGGCGAACCGCTGTCGCTGATTACCGAGTCTGTGTTTGCACGT

TATATCTCTTCTCTGAAAGATCAGCGTGTTGCCGCATCTAAAGTTCTCTCTGGTCCGCAAGCACAGCCAGCAGGCGA

CAAGGCTGAGTTCATCGAAAAAGTTCGTCGTGCGCTGTATCTGGGCAAAATCGTTTCTTACGCCCAGGGCTTCTCTC

AGCTGCGTGCTGCGTCTGAAGAGTACAACTGGGATCTGAACTACGGCGAAATCGCGAAGATTTTCCGTGCTGGCTGC

ATCATCCGTGCGCAGTTCCTGCAGAAAATCACCGATGCTTATGCCGAAAATCCACAGATCGCTAACCTGTTGCTGGC

TCCGTACTTCAAGCAAATTGCCGATGACTACCAGCAGGCGCTGCGTGATGTCGTTGCTTATGCAGTACAGAACGGTA

TTCCGGTTCCGACCTTCTCCGCAGCGGTTGCCTATTACGACAGCTACCGTGCTGCTGTTCTGCCTGCGAACCTGATC

CAGGCACAGCGTGACTATTTTGGTGCGCATACTTATAAGCGTATCGATAAAGAAGGTGTGTTCCATACCGAATGGCT

GGATTAA

-continued (example O6A rfb locus nucleotide sequence-O6A-EPA production strain stGVXN4112 and stLMTB10923)

SEQ ID NO: 13

ATGACGAATTTAAAAGCAGTTATTCCTGTAGCGGGTCTCGGGATGCATATGTTGCCTGCCACTAAGGCGATACCCAA

AGAGATGCTACCAATCGTCGACAAGCCAATGATTCAGTACATTGTTGACGAGATTGTGGCTGCAGGGATCAAAGAAA

TCCTCCTGGTAACTCACGCGTCCAAGAACGCGGTCGAAAACCACTTCGACACCTCTTATGAGTTAGAATCACTCCTT

GAGCAGCGCGTGAAGCGTCAACTGCTGGCGGAAGTACAGTCCATTTGCCCGCCGGGCGTGACAATTATGAACGTGCG

TCAGGGCGAACCTTTAGGTTTGGGCCACTCCATTTTATGTGCACGACCTGCCATTGGTGACAATCCATTTGTCGTGG

TGCTGCCAGACGTTGTGATCGACGACGCCAGCGCCGACCCGCTGCGCTACAACCTTGCTGCCATGATTGCGCGCTTC

AACGAAACGGGCCGCAGCCAGGTGCTGGCAAAACGTATGCCGGGTGACCTCTCTGAATACTCTGTCATCCAGACCAA

AGAGCCGCTGGACCGCGAAGGTAAAGTCAGCCGCATTGTTGAATTCATCGAAAAACCGGATCAGCCGCAGACGCTGG

ACTCAGACATCATGGCCGTTGGTCGCTATGTGCTTTCTGCCGATATTTGGCCGGAACTTGAACGCACTCAGCCTGGT

GCATGGGGGCGTATTCAGCTGACTGATGCCATTGCCGAACTGGCGAAAAAACAGTCCGTTGATGCCATGCTGATGAC

CGGCGACAGCTACGACTGCGGTAAAAAAATGGGTTATATGCAAGCGTTCGTGAAGTATGGACTACGCAACCTCAAAG

AAGGGGCGAAGTTCCGTAAAGGGATTGAGAAGCTGTTAAGCGAATAATGAAAATCTGACCGGATGTAACGGTTGATA

AGAAAATTATAACGGCAGTGAAGATTAGCGGCGAAAGTAATTTGTTGCGAATTTTCCTGCCGTTGTTTTATATAAAC

AATCAGAATAACAACGACTTAGCAATAGGATTTTCGTCAAAGTTTTCCAGGATTTTCCTTGTTTCCAGAGCGGATTG

GTAAGACAATTAGCATTTGAATTTTACGGGTTTAGCGCGAGTGGGTAACGCTCGTCACATCGTAGACATGCATGCAG

TGCTCTGGTAGCTGTAAAGCCAGGGGCGGTAGCGTGCTGAAATTATAAAGTCATTCTTATAGAACATCGCATTTCAA

TAATATAATTACACCTAAATGAATAGGATACAACGTGTGCACAATTATTTAAGGCTTAAAGATAAAATAAAAAACGT

ATTTTTAGGGTTGTATATATTGCAGTTATTTAATTATATCGCGCCATTGGTAATTATCCCTATCCTGATAAAATATA

TTGGGTTGGGGGAATATGGGGAATTGGTCTATATTACATCTATTTATCAAATAGTGGCTTTGATTATTGATTTTGGC

TTTACTTACACAGGACCTGTGGTTGCTGCGAGACATAGATGTGAGACCCAAAATTTACAGCGCTATTACTCAATAGT

TGTTCTTTTAAAATCATTGCTTTTTATAATTGCATTAACATGTGTATTTTTATTGTGCAGATTAAATATAGTCCACT

TGTCATTTTTTGGGTTTTTGTCAATTTTTCTATGCACTATTGGTAATATATTATCGCCCAATTGGTTTTTGCAGGGG

ATTGGTGATTTTAAAAAACTTTCATACTCACAAGTAATAGTGAGAATAACATTGTTTATCATACTTCTTGTTTATGT

CTGTAGTGGCGGAGATAATGTTTTTATCCTAAGTTTTTTGCAAAATGCAACATTACTCATATGCTGTATATACTTAT

GGCCAAATATTCATATTAGCCATGTTGTTCATCTTAAACCTAATGAATGCATTGTGGAATTTAAGAAGGCAGGAAAT

GTTTTTATTGGCGTAATAGGTACGATTGGTTACAATGGTCTAATTCCTGTGTTAATTGGAAACCTTTGCGGTAATAC

GAGTCTTGGTGTTTTTTCAATCGTTCAAAAAATGACAACAGCATGTCAAAGTCTAATTAATCCAATATCACAGTATA

TGTTATCTCAAGTTTCAGAAATTAAACCTCAAGATAAACTGTTTTATTATAGAATTAAAAAAAGTTTTTTTGTGCAT

TTAACAATTAGCATAATTGCATGTTTATGTTATATGGGGTTAGGGCAATATGTGGCGACTTTTATAGGTAAAGTTGA

CGTTTCATTTGTTATTATTTTATTTGCGTCAATAATTACCATTTTTTCATCTTTAAATAATGTCCTTGGTATACAGT

TTCTTATACCGACAGATAATGTAAAAATACTACGAAGTATAAATGTTATGGCGGGAATTATTGTTGTTAGTTTGTCC

TGGCTGTTAATATCACGCTTTGACATTCTGGGGGGGGTTTTATTAAACCTAATTGGTGAGTTTCTTGTATTCAGTAT

GCTAGCTTTTATTGCCCATCGAAAGTGGGGAGCGAGAGTATAATGAAAGTGAAGGCGGTTCCTGCTATTACATTCTA

TTTAAGTTTAATGCTGACAATTTTAGTGTTACTGTTTGGTAATGAACCAAATAAATCACAATATATCCTTGTTATAG

CAACGATAACAGTTTTTTATATCGCATATATCACTAATAAAATAACTTCTCCGGCCAGCCTTCTCGTTATATCATCT

TTTGTGTTTTTAGGTTGTCGCCCTTTATTATCTTTGTTTGCAAACTATGATTATAGGATTGCCGATTGGTTTATTGA

AGGATATATGGATGACGATGTGATTTTGGCTAACTATGCTATAACACTAATGTATTATGGTTATACATTGGGACTAA

-continued

TTCTATGCAAAAATACTGAAAAATTTTATCCGCATGGTCCTTATCCTGAAAAACAATTGCTAAAAATAAAGTTTCTT
TTGACTTTATTTTTTCTGGGTTCGATAGGTATGGTTGTAAAAGGGATATTCTTTTTTAACTTTATAGAATCTAATAG
TTATGTTGATATTTATCAATCAAATATAACAACGCCAATAGGTTATGATTTTCTATCTTATTTATTTTATTGTTCTT
TTTTCCTTATATGTGCGTTTCATATACAGTTCAGAACAAATAAAAAATTTCTTTTTATTGCGATATGCATTGCTGCA
TTTAGCACCTTGAAGGGTAGTCGTAGTGAAGCTATAACGTTTCTTTTAACGGTTACATGTATATATTTTAATGAAGT
AAAGACAAGAAACTTACGTCTGCTGATTACAATGATTTTTGTTTTTAGCGTCATTTTTGTGATTAGTGAATTTATCT
CAATGTGGCGCACTGGAGGGAGTTTTTTTCAATTAATGCAGGGTAATAATCCTGTTATAAACTTTGTATACGGCATG
GGAGTATCATATCTTTCCATTTATCAATCAGTAAAACTACAACTATTGTCAGGGGGATATAATGTTACCTATCTATT
CAGCCAGTTAATAATAACTTGCTCGTCAATATTTAATGTCAAATTGAGCTTGCCGGAAATAAGCTATAGCCATTTGG
CCTCATACACAGCAAACCCAGAACTATATAATCTTGGGTTCGGACTTGGGGGGAGTTATTTAGCAGAATCGTTTTTA
GCATTTGGTCTGATTGGATGTTTCATTATACCCTTTTTACTTTTACTTAATTTAAATGTATTGGAAAAATATACAAA
AAACAAACCAATTATATATTTTGTTTATTATAGTGTGTTGCCACCTATATTATTCACACCAAGAGAGACTTTGTTCT
ATTTCTTCCCCTATCTTGTCAAAAGTATATTTGTTGCTTTTTTAGTTACATTATACATCCAGTATAAAAAGGATTGA
CCAAAATGTCAGAAAAAAATGTCAGCATAATAATCCCAAGTTATAACAGGGCTCATATTCTTAAGGAGGTCATACCA
AGTTATTTTCAGGATGAGACTTTAGAGGTTATAGTTATCAATGATGGATCAACAGATAATACAAATAGTGTATTAGC
TGAACTGAAGGAAAAATATTCTCAGTTAGTTATTTTAGAAAATGAAACGAATAAAAAACAGATGTATTCTAAAAACC
GAGGGATTGAAATAGCCAAAGGGAAATATATTTTTTTTGGTGATGATGACTCTTACCTCTTACCCGGTGTTATATCT
CGGTTATTGGCTACAAAATATGAGACAGGCGCTGATGTAATCGGCGCAAGAATACTTTATATGAATAATAACGAGAA
AACAATTGAAGATTGCATAAATCGACATAAAAAAGAGGGGCGTTTTGTTAGTGATCTAAATAGATTGGATTTTAGTT
ATACATGTGATTTGGACCATCCGATTGAATGTTTTTATGCACAGCCTTTTGTTCTAGCTGAAAGGGAACTAATATCG
AAATATCGATTTGATATATCTTATACGGGAAACTGCTATCGTGAGGAAACTGATTTCATGCTATCTCTATTTATTAA
AAATAAAAAATTTATATATGATTCAAAGGCTTTGTTAATAAATTTACCTCCAAGAAAAGCGACGGGAGGGGCAAGAA
CAGCTAATCGATTAAAATATCATTACGAAAGTTGCATAAATAATTATAGATTTTTAAAAAAATATAATGATAATTTG
AATCTTCTTTCAGGACAAAAGCATGCTATATTTTACCGACAGTGTCAATTCGTTCTGCTAAAAATGAAGTCGTTTAT
CGGGAAGTTTTTAAAATGATTATATATATCGCCGCGTATAATGGTTCAGGAGGGCAAGGTGGGGTGGAAAGGGTTGT
TGCCCAACAATGTAACATTCTTAAAAATTTGGGGGTTAAAGTCATTATACTTGATAAAACATACTTCAAAATTTCTA
ACAAAATTCGTAACAAAAAAATACAAGTAGCACTTTATCCAATATTAGTTTCTCTTTATTTAACCTTACAAAAATTA
CGTGGCGTGACGTTTAAAGTTATTGCACATGGCTATTGTTCTCCTTTTTATAGGAATGACATCTTAATAGCTCATGG
CAATATGAAATGTTATTTTCAAACAGTCATGAATAAAAAACCTAATCGGTTGTCTGGCAGTGGTCTTTTATCTTTCT
ATGAGCGTTGGGCTGGAGCATTTTCAAAAAATATCTGGGCTGTTTCAAATAAGGTTAAAAGTGAATGGAATGAGCTT
TACAATATTAATTCACATAAAATCAAAGTTGTTCGAAATTTTATAAATCTTGCACAATTTGATTACACTGATGTTAA
TGAAGCAGAATATGTGACATTTGTCGGGCGATTGGAAAAAGGAAAAGGAATAGATGATCTGTATTACATATGTAAAA
ATCTGCCAGATACTTCCTTCCATTTAGTTTCAAGTATTCCCGCCCCACAAAATTTTGCTTCGCTAAATAATGTTCTG
ACCAGCATTGCTGTCCCCTATGCGAAAATGCCAGAAATATTTAAGAAATCCAGAGTACTTATTTTACCGTCCTATTA
TGAAGGATATGAGCTGGTTACTATTGAAGCGCTATGCTGTGGTTGCCCTGTGATAGGCTATAATGTTGGTGCAATTA
GAGAGTTGTATGCAGAAAGTTTTCCTGGCGTATTTATTGCCAATAATAAAGAAGATTTAGCACAAGTAGCCTACAAA
TTAATTAGTCTTGATAATGAAAAATATTATCATTTGAGACAAACTATTTATAGCAAGCGTGAGCTTTTTTCTGAAGA
GAGATATGCGGAAATTTTAACGGCGGCATTTAATGAAAAAAAATAAGAAACTCTGTCTCATTTCAATTAACTCATAT
AATGAACTTACCGGAGGAGGAGTATATTTACGTACGCTTGTTAGTTTTCTACAAAAACAGAATGTTAATTTAACACT
TATTGATAAAAAATCCTCAGGTAAACTATTCGAAGACAATACTTTTCAACATATATCATTTATTAAAGGTAAACGTC

-continued

AGGATATAATATCCAGGCTTTTTTTATACCATCATTTTATGTCCCTTATATTTTCTCAATAATTAAAATTTTACGG

AAGCAAGATATTCTTGCTTTTCACAACTCTCGGCTTGGATTGTTATGTCTGCTTTTTAGAATACTCATGCCCCACAA

AAAGATCATATTGTTTACGGATAACTTCGAATATGACTTAATAAGACAAAAAGATAAAAACATAACTACTTTTATTG

AAAAATTAATTGTTTATCTCAATGAATTTATCGGGCTTAAGAATTCAGATTTAGTTAGCTATATTACCCGGCAAGAT

AAAAATGCAATGGATAAATTTTATGGGATTAAAAAAAGCAGAAATTTAATTCTCCCTGTGATATTTAGTAGAGAAAA

ACCAACTGATGTATTGTCAGCTCACTTTATTAATGAGTATAATCGATTGAATAATGATAATAGGAAAAAAGTAGTAT

TTACTGCATCTTTTGATTTTTTTCCAAATATAGATGCTGCCAACTATGTTTTAAATGCAGCAAAGTCTAATAATGAT

TATTGCTATATTTTGGCAGGTAGGAAAAGTACTACTTTGAATCTTCCTGATTTGGATAATTTATTTTTTTTCGATAA

TCTATCTAATAGTGAAATGTCATATTTATTATCTGCTTGTGATGTTTTTTATTCTCCTATAGTTTTAGGAAGTGGAA

TGAAAACAAAAATTGCAGAAGCACTATCATATGGATTATATATTTATGCGACAGAGCATTCCTTAATCGGCTATGAT

GAAATTATACACAATAAGGAGTGTGTTAAAAAAATCTCACATTTGGATGAGGAATTTCCTAAAGATTTCAAGATGAA

AAGTATCAATAAACAGCTAATAATGTCTTATCAGCAAAAATATTATTCACATTATCGGTTTAATGGCCATGAACTTG

ATATAATAAATTTTGACGATTAGTTAGTGGAGATATAATATGAACATATTAGTAACTGGTGGTGCTGGATATATCGG

ATCTCATACGGCTATTGAATTACTGAATGCAGGTCATGAGATTATCGTTCTGGACAATTTCAGTAATGCTTCATACA

AGTGTATCGAAAAAATAAAAGAAATTACTCGACGTGATTTTATAACAATTACTGGAGATGCTGGGTGTAGGAAGACA

CTCTCCGCTATTTTCGAGAAACACGCCATAGATATAGTTATTCATTTTGCTGGCTTTAAATCTGTTTCAGAGTCTAA

AAGTGAACCCTTAAAGTATTACCAGAATAATGTTGGAGTGACCATTACTTTATTACAGGTAATGGAAGAGTACAGAA

TTAAAAAATTTATCTTTAGTTCATCTGCGACAGTCTATGGTGAACCAGAGATAATTCCAATTCCAGAAACAGCTAAA

ATTGGAGGAACTACGAATCCATATGGCACATCGAAGTATTTTGTTGAAAAAATTCTAGAGGATGTTAGTTCCACGGG

AAAACTGGATATAATTTGCTTGAGATATTTTAATCCTGTCGGTGCTCATTCTAGTGGTAAAATAGGTGAGGCTCCAT

CTGGTATCCCTAATAATCTTGTTCCTTATTTATTGGATGTTGCGAGTGGTAAACGTGATAAATTATTTATTTATGGC

AATGATTACCCTACTAATGATGGAACAGGTGTAAGGGATTTTATTCATGTTGTTGACTTAGCGAAAGGTCATTTGGC

TGCAATGAATTATTTAAGTATCAATTCGGGATATAATATCTTTAATCTTGGTACAGGAAAAGGTTATTCGGTACTTG

AATTAATCACTACATTTGAAAAATTAACAAACATTAAGGTCAATAAATCTTTTATAGAGAGAAGGGCAGGGGATGTT

GCGTCTTGTTGGGCTGATGCAGATAAAGCTAATTCTTTATTGGACTGGCAAGCCGAACAAACTCTAGAACAGATGTT

ATTGGACTCGTGGCGTTGGAAAAAAAATTATCCAGACGGATTCTGAATATAAAAGGTTTCAGTTTTATGAATCAATC

AGAGCAGAGAAAAAAAATACTGGTTCTTACACCTCGCTTTCCCTACCCTGTCATTGGAGGGGATAGATTAAGAGTCT

ATATGTTATGTAAAGAACTTTCCAAAAAATATGATCTTATTCTTCTGAGCTTATGTGATCAACCACTAGAACTTGAA

ATAAATATAAATGACTCGGTCTTCAAAGAAATTCATCGTGTCTATCTACCAAAATATAAATCATATTATAATGTATT

AAAAGCTTTGGTTACGCAAAAACCGTTGCAAATTGCTTATTATCAATCGGACACATTTAAGAATAAATACAATAAAT

TAATTAAACAATGCGATGCAGTATTTTGTCATCTGATAAGAGTTGCTGATTATGTTAAGGATACAGACAAGTTCAAA

ATTCTTGATATGACAGATGCAATATCTTTGAATTACAGTCGCGTTAAAAAATTAGCAAGTAAAAAAAGTTTGCGTGC

AATTATTTATTCTCTGGAACAAAAAAGATTAGAATCATATGAACGTTCTGTGGCGAATCTTTTTGATTTGACCACTT

TTATTTCATCCGTAGACCGTGACTATCTCTACCCTAATCTGGGCAGTAATATCCATATAGTCAATAATGGGGTTGAT

ACATCAGCCTTGAGATATATAAAAAGAGAAATAAAAATCGATAAGCCTGTGGAACTTATATTTATCGGAAATATGTA

TTCTTTACAAAATATGGATGCTGCAAAACATTTTGCTAAGAATATTTTACCTTGCTTGTATGATGAGTTTAATATTA

TTTTTAAAGTGATTGGTAAGATCTCAGAAACTAATAAAAATATATTAAATTCATTTAAAAATACAATTGCTTTAGGT

ACTGTTGATGATATCAATTCTTCCGCTTCTACAGGGCATATAGGTATATGTCCTGTTCGTCTTGGAGCAGGCGTACA

AAATAAAATTCTTGAATACATGGCTTTAGGTTTACCATGTATTACATCTAGCATTGGTTATGAAGGTATTAATGCAA

AATCAGGTAGCGAAATTTTTGTTGCAGATACAGTAGAGCAATATAAAAACGTACTAAGAGAAATAATTTACGATTAT

AATCGTTATACTGAAGTGGCTGAAAATGCCCGTAGTTTTGTAGAAAATAATTTTTCTTGGGAATCAAAAGTTGCCAA

-continued

TTTAATGAATACATTAGATGAGAAATTATATGAACAATAATAAAATTATTACACCTATCATTATGGCTGGTGGTTCA

GGCAGTCGGTTGTGGCCACTATCAAGAATTCTCTATCCGAAACAATTTCTTAGCCTAATCGGTAGTCATACCATGCT

TCAAACAACGGCTAATCGTCTGGATGGTTTGGATTGTACCAACCCTTATGTCATTTGTAATGAACAATACCGCTTTA

TAGTTGCTGAACAGCTTAGAAAAATCGATAGATTGACTTCAAAGAATATCATCCTTGAGCCTGTTGGGCGTAACACT

GCCCCTGCAATTGCATTAGCGGCGTTGCTGATGTCTAAGTCTGATAAAAGTGCAGATGATCTTATGCTCGTACTGGC

TGCAGATCACGTTATACACGATGAAGAAAAATTTTGTAACGCTGTTAGATCGGCAATTCCATACGCTGCTGATGGGA

AATTGGTAACATTTGGTATAATTCCAGACAAAGCAGAAACTGGTTATGGTTATATACATCGAGGACAATATATTAAT

CAGGAAGATTCGGATGCATTTATAGTGTCATCATTTGTTGAAAAGCCAAATCATGAGACAGCCACTAAATATCTTGC

TTCCGGTGAGTATTATTGGAATAGCGGTATGTTTTTGTTTAGTGCAAATCGTTATATAGAGGAACTTAAACAATTTC

GGCCTGATATTTTATCCGCTTGTGAAAAAGCAATTGCTTCAGCGAACTTTGACCTTGATTTTGTGCGTTTAGATGAA

AGTTCTTTCTCTAAGTGCCCTGAAGAATCAATTGATTACGCTGTAATGGAAAAAACAAAAGACGCAATTGTTATTCC

AATGGATGCTGGCTGGAGTGATGTCGGTTCATGGTCTTCTCTTTGGGAAATTAATGATAAAGACTCAGACGGCAACG

TAATAGTTGGGGATATTTTCTCTCATGAAACAAAGAATTCTTTCATATATGCCGAATCGGGAATTGTTGCTACAGTT

GGAGTGGAAAATTTAGTTGTTGTCCAAACAAAGGATGCTGTTCTTGTCTCAGAGAGAAATAAAGTTCAGGATGTAAA

GAAAATAGTAGAACAAATTAAAAATTCAGGTCGTAGCGAGCATTATGTTCATCGCGAAGTATATCGTCCTTGGGGTA

AATATGATTCCATTGACACAGGGGAGCGTTATCAGGTCAAACGTATAACAGTAAATCCTGGTGAAGGACTTTCTTTA

CAAATGCACCATCATAGGGCAGAACATTGGATCATAGTTTCTGGAACTGCAAGGGTGACTATAGGTTCTGAAACTAA

GATTCTTAGCGAAAATGAATCTGTTTACATACCTCTTGGTGTAATACACTGCTTGGAAAATCCAGGGAAAATTCCTC

TTGATTTAATTGAAGTTCGTTCTGGATCTTATTTAGAAGAAGACGATGTTATCCGTTTTCAGGACCGATATGGTCGT

AGCTAAATTTTTGATAATGTAACGTTAGTAGAAGAGCGCTAATATTTTTAGTTAATCTGTAATAAGTATTATTTGTT

TAAGGTATATCATGTCGAGTTTACCCTGCTTTAAAGCCTATGATATTCGCGGGAAATTAGGCGAAGAACTGAATGAA

GATATTGCCTGGCGCATTGGTCGCGCTTATGGCGAATTTCTCAAACCGAAAACCATTGTGTTAGGCGGTGACGTCCG

ACTCACCAGCGAAACCTTAAAACTGGCGCTGGCGAAGGGGTTACAGGATGCGGGCGTCGATGTGCTGGATATTGGCA

TGTCCGGCACCGAAGAGATCTATTTCGCCACGTTCCATCTCGGCGTGGATGGCGGCATCGAAGTTACCGCCAGCCAT

AACCCGATGGATTACAACGGCATGAAACTGGTGCGCGAAGGGGCTCGCCCGATCAGCGGTGATACCGGACTGCGCGA

CATCCAGCGTCTGGCAGAAGCCAACGACTTTCCTCCCGTTGATGAAACCAAACGCGGTCGCTATCAGCAAATCAATC

TGCGTGACGCTTACGTTGATCACCTGTTCGGTTATATCAACGTCAAAAACCTCACGCCGCTCAAGCTGGTGATTAAC

TCCGGGAACGGCGCGGCGGGTCCGGTGGTGGACGCCATTGAAGCCCGCTTTAAAGCCCTCGGCGCACCCGTGGAATT

AATCAAAGTGCACAACACGCCGGACGGCAATTTCCCCAACGGTATTCCTAACCCGCTACTGCCGGAATGTCGCGACG

ACACCCGCAATGCGGTCATCAAACACGGCGCGGATATGGGCATTGCCTTTGATGGCGATTTTGACCGCTGTTTCCTG

TTTGACGAAAAAGGGCAGTTTATTGAGGGCTACTACATTGTCGGCCTGCTGGCAGAAGCGTTCCTCGAAAAAAATCC

CGGCGCGAAGATCATCCACGATCCACGTCTCTCCTGGAACACCGTTGATGTGGTGACTGCCGCAGGCGGCACCCCGG

TAATGTCGAAAACCGGACACGCCTTTATTAAAGAACGTATGCGCAAGGAAGACGCTATCTACGGTGGCGAAATGAGC

GCCCACCATTACTTCCGTGATTTCGCTTACTGCGACAGCGGCATGATCCCGTGGCTGCTGGTCGCCGAACTGGTGTG

CCTGAAAGGAAAAACGCTGGGCGAACTGGTGCGCGACCGGATGGCAGCGTTTCCGGCAAGCGGTGAGATCAACAGCA

AACTGGCACACCCCGTTGAGGCGATTAACCGCGTGGAACAGCACTTTAGCCGCGAGGCGCTGGCGGTGGATCGCACC

GATGGCATCAGCATGACCTTTGCCGACTGGCGCTTTAACCTGCGCTCCTCTAACACCGAACCGGTGGTGCGGTTGAA

TGTGGAATCGCGCGGCGATGTACCGCTGATGGAAGAAAAGACAAAACTTATCCTTGAGTTACTGAACAAGTAATTCA

GTAATTTCATATAAATGGGTTTTAAAAAACGGAAAAGATGAGATATCCGGTGTGGTATATCCAAGGTAATGCTATTC

AGTATCTCTATGAGTGAGTTAACATCTATACCACATTTAAGCCGCACACTTCGGATCCCCATATGAATATCCTCCT

-continued

TAGTTCCTATTCCGAAGTTCCTATTCTTTCTAGAGAATAGGAACTTCGGAATAGGAACTAAGGAGGATATTCATATG

GATAAAGCCGTAAGCATATAAGCATGGATAAGCTATTTATACTTTAATAAGTACTTTGTATACTTATTTGCGAACAT

TCCAGGCCGCGAGCATTCAGCGCGGTGATCACACCTGACAGGAGTATGTAATGTCCAAGCAACAGATCGGCGTAGTC

GGTATGGCAGTGATGGGACGCAACCTTGCGCTCAACATCGAAAGCCGTGGTTATACCGTCTCTATTTTCAACCGTTC

CCGTGAGAAGACGGAAGAAGTGATTGCCGAAAATCCAGGCAAGAAACTGGTTCCTTACTATACGGTGAAAGAGTTTG

TCGAATCTCTGGAAACGCCTCGTCGCATCCTGTTAATGGTGAAAGCAGGTGCAGGCACGGATGCTGCTATTGATTCC

CTCAAACCATATCTCGATAAAGGAGACATCATCATTGATGGTGGTAACACCTTCTTCCAGGACACTATTCGTCGTAA

TCGTGAGCTTTCAGCAGAGGGCTTTAACTTCATCGGTACCGGTGTTTCTGGCGGTGAAGAGGGGGCGCTGAAAGGTC

CTTCTATTATGCCTGGTGGCCAGAAAGAAGCCTATGAATTGGTAGCACCGATCCTGACCAAAATCGCCGCCGTAGCT

GAAGACGGTGAACCATGCGTTACCTATATTGGTGCCGATGGCGCAGGTCACTATGTGAAGATGGTTCACAACGGTAT

TGAATACGGCGATATGCAGCTGATTGCTGAAGCCTATTCTCTGCTTAAAGGTGGCCTGAACCTCACCAACGAAGAAC

TGGCGCAGACCTTTACCGAGTGGAATAACGGTGAACTGAGCAGTTACCTGATCGACATCACCAAAGATATCTTCACC

AAAAAAGATGAAGACGGTAACTACCTGGTTGATGTGATCCTGGATGAAGCGGCTAACAAAGGTACCGGTAAATGGAC

CAGCCAGAGCGCGCTGGATCTCGGCGAACCGCTGTCGCTGATTACCGAGTCTGTGTTTGCACGTTATATCTCTTCTC

TGAAAGATCAGCGTGTTGCCGCATCTAAAGTTCTCTCTGGTCCGCAAGCACAGCCAGCAGGCGACAAGGCTGAGTTC

ATCGAAAAAGTTCGTCGTGCGCTGTATCTGGGCAAAATCGTTTCTTACGCCCAGGGCTTCTCTCAGCTGCGTGCTGC

GTCTGAAGAGTACAACTGGGATCTGAACTACGGCGAAATCGCGAAGATTTTCCGTGCTGGCTGCATCATCCGTGCGC

AGTTCCTGCAGAAAATCACCGATGCTTATGCCGAAAATCCACAGATCGCTAACCTGTTGCTGGCTCCGTACTTCAAG

CAAATTGCCGATGACTACCAGCAGGCGCTGCGTGATGTCGTTGCTTATGCAGTACAGAACGGTATTCCGGTTCCGAC

CTTCTCCGCAGCGGTTGCCTATTACGACAGCTACCGTGCTGCTGTTCTGCCTGCGAACCTGATCCAGGCACAGCGTG

ACTATTTTGGTGCGCATACTTATAAGCGTATCGATAAAGAAGGTGTGTTCCATACCGAATGGCTGGATTAA (example O8 rfb locus nucleotide sequence-O8-EPA production strain stLMTB11734)

SEQ ID NO: 14

ATGACGAATTTAAAAGCAGTTATTCCTGTAGCGGGTCTCGGGATGCATATGTTGCCTGCCACTAAGGCGATACCCAA

AGAGATGCTACCAATCGTCGACAAGCCAATGATTCAGTACATTGTTGACGAGATTGTGGCTGCAGGGATCAAAGAAA

TCCTCCTGGTAACTCACGCGTCCAAGAACGCGGTCGAAAACCACTTCGACACCTCTTATGAGTTAGAATCACTCCTT

GAGCAGCGCGTGAAGCGTCAACTGCTGGCGGAAGTACAGTCCATCTGTCCGCCGGGCGTGACCATTATGAACGTGCG

TCAGGGCGAACCTTTAGGTTTAGGCCACTCCATTTTGTGTGCGCGACCTGCCATTGGTGACAACCCATTTGTCGTGG

TACTGCCAGACGTTGTGATCGACGATGCCAGCGCCGACCCGCTACGTTACAACCTTGCTGCCATGATTGCACGTTTC

AACGAAACGGGCCGCAGCCAGGTGCTGGCAAAACGTATGCCGGGTGACCTCTCTGAATACTCCGTCATCCAGACTAA

AGAGCCGCTGGACCGTGAGGGTAAAGTCAGCCGCATTGTTGAATTTATCGAAAAACCGGATCAGCCGCAGACGCTGG

ACTCAGACATCATGGCCGTAGGTCGCTATGTGCTTTCTGCCGATATTTGGCCGGAACTGGAACGTACTCAGCCTGGT

GCATGGGGACGTATTCAGCTGACTGATGCTATTGCCGAGCTGGCGAAAAAACAATCCGTTGATGCAATGCTGATGAC

CGGCGACAGTTACGACTGCGGCAAAAAAATGGGCTATATGCAGGCGTTTGTGAAGTATGGCCTACGCAACCTGAAAG

AAGGGGCGAAGTTCCGTAAAGGTATTGAGAAGCTGTTAAGCGAATAATGAAAATCTGACCGGATGTAACGGTTGATA

AGAAAATTATAACGGCAGTGAAAATTCGCAGCAAAAGTAATTTGTTGCGAATCTTCCTGCCGTTGTTTTATATAAAC

CATCAGAATAACAACGAGTTAGCAGTAGGGTTTTATTCAAAGTTTTCCAGGATTTTCCTTGTTTCCAGAGCGGATTG

GTAAGACAATTAGCGTTTGAATTTTTCGGGTTTAGCGCGAGTGGGTAACGCTCGTCACATCATAGGCATGCATGCAG

TGCTCTGGTAGCTGTAAAGCCAGGGGCGGTAGCGTGCATTAATACCTCTATTAATCAAACTGAGAGCCGCTTATTTC

ACAGCATGCTCTGAAGTAATATGGAATAAATTAAGCTAGCGATCGCTTAAGATCTAGGATTTCATTATGTTACTTCC

TGTAATTATGGCTGGTGGTACCGGCAGTCGTCTCTGGCCGATGTCACGCGAGCTTTATCCGAAACAGTTCCTCCGCC

-continued

TGTTCGGGCAGAACTCCATGCTGCAGGAAACCATCACCCGACTCTCGGGCCTTGAAATCCATGAACCGATGGTCATC

TGTAACGAAGAGCACCGCTTCCTGGTGGCTGAACAGCTACGCCAGCTCAATAAGCTGTCGAATAATATTATTCTTGA

GCCGGTCGGGCGCAACACCGCCCCGGCCATCGCCCTGGCAGCCCTTCAGGCCACCCGCGACGGCGACGACCCGCTGA

TGCTGGTTCTCGCCGCTGACCATATCATCAATAACCAGTCGGCCTTCCACGACGCCATCCGGGTCGCCGAGCAGTAT

GCTGATGAAGGTCATCTGGTCACCTTCGGTATCGTGCCGAATGCCCCGGAAACTGGCTACGGTTACATTCAGCGCGG

CGTGGCGCTCACCGATAGTGCCCATTCCGCGTACCAGGTGGCCCGCTTTGTGGAGAAGCCGGATCGCGAGCGCGCCG

AGGCTTACCTCGCCTCCGGGGAGTACTACTGGAACAGCGGCATGTTTATGTTCCGCGCCAAGAAATACCTCATCGAG

CTGGCCAAATACCGTCCGGATATCCTGGAAGCCTGCCAGGCTGCGGTGAATGCCGCCGATAATGGCAGCGATTTCAT

CAATATCCCGCATGATATTTTCTGCGAGTGCCCGGATGAGTCCGTGGACTATGCCGTTATGGAGAAAACCGCCGATG

CGGTGGTGGTCGGTCTCGATGCTGACTGGAGCGACGTCGGCTCCTGGTCCGCACTATGGGAGGTCAGCCCGAAAGAC

GAGCAGGGCAATGTCCTCAGCGGTGACGCGTGGGTACACAACAGCGAAAACTGCTACATCAACAGCGACGAGAAGCT

AGTGGCGGCCATTGGCGTAGAGAATCTGGTGATTGTCAGCACTAAGGACGCCGTGCTGGTGATGAATCGCGAGCGTT

CCCAGGACGTGAAGAAGGCGGTCGAGTTCCTCAAGCAGAACCAGCGCAGCGAGTACAAGCGCCACCGTGAGATTTAC

CGCCCCTGGGGCCGTTGCGACGTAGTGGTCCAGACCCCGCGCTTCAACGTCAACCGCATCACGGTGAAACCAGGCGG

TGCCTTCTCGATGCAGATGCACCACCATCGCGCCGAGCATTGGGTTATTCTCGCCGGCACCGGTCAGGTGACTGTCA

ACGGTAAGCAGTTCCTGTTGTCCGAGAACCAGTCCACCTTTATTCCGATTGGCGCCGAGCACTGCCTGGAAAACCCT

GGCTGTATTCCGCTGGAAGTGCTGGAGATCCAGTCGGGGGCGTACCTTGGCGAGGACGACATTATTCGTATTAAAGA

CCAGTATGGTCGTTGCTAATTATTTTCGGGACAAGACGCAGAATGACACAGTTAACTTGTTTTAAAGCTTATGACAT

CCGTGGTGAACTGGGTGAGGAACTGAACGAGGACATCGCCTACCGTATCGGTCGCGCCTACGGCGAATTTCTGAAAC

CCGGGAAGATAGTGGTGGGGGGCGATGTGCGCCTCACAAGCGAGTCGCTGAAGCTGGCGCTGGCCCGCGGGTTAATG

GACGCCGGTACCGACGTGCTGGACATCGGCCTGAGCGGTACCGAAGAGATTTACTTTGCCACCTTCCACCTTGGGGT

AGATGGTGGCATCGAGGTGACCGCGAGCCACAATCCTATGAACTACAACGGCATGAAGCTGGTGCGCGAGAATGCGA

AGCCCATCAGCGGCGACACCGGCCTGCGGGATATCCAGCGCCTGGCGGAGGAAAACCAGTTCCCGCCAGTGGACCCG

GCGCGTCGCGGGACCCTGAGCAAGATATCGGTACTGAAGGAGTATGTTGACCATCTGATGAGCTACGTGGACTTCTC

GAACTTCACCCGTCCACTGAAGTTGGTGGTGAACTCCGGAAACGGGGCTGCGGGGCACGTGATTGATGAGGTGGAGA

AACGCTTCGCGGCGGCTGGGGTGCCGGTAACCTTTATCAAGGTGCATCACCAGCCGGATGGCCATTTCCCTAACGGT

ATCCCGAATCCGCTGCTGCCGGAGTGCCGCCAGGATACCGCCGACGCGGTGCGCGAGCATCAGGCCGACATGGGGAT

TGCCTTTGACGGCGACTTCGATCGCTGCTTCCTGTTCGATGACGAAGCTTCGTTTATCGAGGGGTATTACATTGTCG

GCCTGCTGGCTGAGGCGTTCCTGCAGAAGCAGCCGGGAGCGAAAATCATTCACGACCCGCGCTTGACGTGGAACACG

GTAGACATCGTGACCCGCAACGGCGGCCAGCCGGTGATGTCGAAGACGGGGCATGCGTTCATCAAGGAGCGGATGCG

TCAGGAAGACGCTATCTACGGCGGGGAGATGAGTGCGCACCATTACTTCCGCGATTTCGCCTACTGCGATAGCGGGA

TGATCCCGTGGCTGCTGGTGGCGGAGCTGCTGTGTCTGAAGAACAGCTCGCTGAAATCGCTGGTGGCGGACCGCCAG

AAGGCGTTCCCTGCGTCGGGAGAGATCAACCGCAAGCTAAGTAATGCTGCTGAGGCGATCGCCCGCATCCGGGCGCA

GTATGAGCCGGCGGCTGCACACATCGACACAACGGACGGGATCAGTATTGAATACCCTGAATGGCGCTTTAACCTGC

GCACGTCTAACACCGAGCCGGTGGTGCGTCTGAACGTTGAGTCCAGAGCTGATGTGGCGCTTATGAATGAAAAAACG

ACCGAGCTGTTACACCTGTTAAGCGGGGAATAAGGTGAGAGATTTACTAACGACGATTTATCGTTATCGGGGATTTA

TCTGGAGCAGTGTTAAACGTGATTTTCAGGCACGCTATCAAACTAGTATGCTGGGCGCACTATGGCTCGTTTTACAA

CCGCTCTCTATGATTCTGGTCTATACCCTGGTTTTTTCCGAGGTGATGAAGGCAAGAATGCCCGATAATACCGGGTC

GTTTGCCTATAGTATTTATCTCTGTTCCGGGGTACTGACCTGGGGATTATTTACTGAGATGCTGGATAAAGGTCAGA

GCGTATTTATTAACAATGCTAATCTGATCAAGAAACTCAGTTTTCCGAAAATCTGTCTGCCGATCATCGTGACGTTA

TCGGCGGTGCTAAATTTCGCGATTATTTTCAGTCTGTTTCTAATTTTTATCATTGTCACCGGTAACTTCCCCGGCTG

-continued

GCTCTTTCTCTCGGTGATACCGGTCCTGCTTTTGCAGATCCTGTTTGCCGGTGGGCTGGGGATGATCCTTGGTGTCA

TGAACGTCTTTTTCAGGGATGTGGGGCAACTGGTTGGCGTTGCGCTGCAATTCTGGTTTTGGTTCACACCCATTGTT

TATGTACTGAATTCATTACCTGCATGGGCAAAAAATCTGATGATGTATAACCCGATGACTCGGATCATGCAATCTTA

TCAGTCCATCTTCGCCTATCATCTGGCCCCCAACTGGTATTCGCTATGGCCAGTATTGGCTCTCGCCATTATTTTCT

GCGTCATCGGTTTCAGGATGTTCCGCAAGCATGCGGCGGATATGGTGGATGAATTATAATGAGTTATATCAGAGTAA

ATAATGTCGGTAAGGCGTATCGCCAGTATCACTCAAAGACCGGGAGACTGATCGAATGGTTATCCCCTCTGAATACC

AAACGCCATAATTTGAAATGGATCCTCCGCGATATTAATTTCGAAGTCGCTCCGGGCGAGGCTGTCGGTATTATCGG

TATCAACGGTGCAGGCAAGAGTACCCTGCTTAAACTCATAACCGGGACGTCCAGGCCGACGACTGGAGAAATTGAAA

TCTCCGGACGTGTCGCTGCATTACTCGAATTGGGGATGGGGTTTCATTCTGATTTCACTGGTCGGCAGAATGTTTAT

ATGTCTGGGCAACTGTTGGGGTTATCGTCAGAGAAAATAACTGAACTGATGCCGCAAATTGAAGAGTTTGCTGAGAT

TGGGGACTATATCGATCAACCTGTGCGCGTCTACTCCAGTGGGATGCAAGTTCGATTAGCTTTTAGTGTAGCGACGG

CTATCCGTCCTGATGTGCTAATTATCGATGAGGCATTATCTGTTGGGGATGCATATTTCCAGCATAAAAGCTTTGAG

CGTATTCGAAAATTTCGTCAGGAAGGGACCACGCTGTTGCTGGTATCCCATGATAAACAAGCGATCCAAAGCATTTG

CGACCGGGCCATTTTATTGAATAAAGGCCAAATTGAAATGGAAGGTGAACCTGAAGCAGTGATGGATTATTACAATG

CTCTTCTGGCCGATAAACAAAATCAGTCCATTAAACAAGTTGAGCATAATGGTAAAACGCAAACTGTTTCAGGCACT

GGTGAGGTGACTATCTCTGAGGTTCATCTTCTCGATGAACAGGGCAATGTGACTGAATTTGTTTCGGTAGGGCATCG

TGTCAGCTTGCAGGTCAACGTTGAGGTCAAGGACGATATTCCTGAGCTTGTTGTCGGATATATGATTAAGGATCGAC

TTGGGCAGCCGATTTTCGGGACCAATACGTACCATCTCAATCAGACACTCACCTCCCTGAAAAAAGGAGAAAAGCGT

TCGTTCTTATTTTCTTTCGATGCGAGATTGGGGGTTGGCTCCTATTCTGTCGCTGTCGCGTTGCATACTTCCAGTAC

GCACCTCGGCAAAAACTATGAATGGCGCGATCTGGCCGTGGTATTCAACGTCGTTAACACGGAACAACAAGAGTTTG

TCGGCGTGTCCTGGTTGCCGCCTGAACTGGAGATTTCTTAATGGGTTCGTCGTTTTATCGTTCATTTGAAGAACGAC

ACAGAGGTTCGGTTGAAGAAATCAAGCGCCGCTTGAGTTTTTATTTACCTTTTCTTGCAGGTCTGAAGGACATTTAT

CCTGATGGCGTGATTGCGGATATTGGTTGCGGACGTGGCGAATGGTTGGAGATCCTGACTGAAAATGGCATTGCGAA

CATCGGCGTCGATCTCGATGATGGCATGCTGGCGCGCGCCAGGGAGGCCGGACTGAATGTGCAGAAAATGGATTGTC

TGCAGTTTTTGCAAAGTCAGGCGGATCAGAGCCTGATAGCGTTGACCGGTTTTCATATTGCTGAGCATTTGCCGTTT

GAGGTCCTGCAGCAACTCGCCATGCATACCCTACGGGTGCTGAAACCAGGTGGTTTGCTGATCCTCGAAACGCCGAA

CCCGGAGAATGTAAGCGTCGGCACCTGTTCATTTTATATGGATCCAACGCATAATCATCCTCTGCCACCGCCACTGC

TTGAGTTTTTACCTATTCATTATGGTTTTACCCGAGCAATTACCGTTCGTCTGCAGGAAAAAGAGGTTCTTCAATCT

CCGGATGCAGCCGTTAATTTGGTCGATGTACTCAAAGGGGTGAGCCCCGACTACAGCATCATTGCTCAGAAAGCAGC

GCCAACAGATATTCTTGAACGCTTTGACACCCTGTTTACCCAGCAGTACGGTCTGACGCTGGATGCTCTGAGCAACC

GTTACGATGCGATTTTGCGCCAACAGTTTTCGTCCGTTGTCTCACGGCTGGAGACGTTGAACCAAACCTATATGCAA

CAGATAAGCCAAATGTCAGAGACTATTCAGACGTTGCAAGGTGAGGTTGACGATCTGAGTCATGTCATCGATCAGAA

CCATCAGCTTCATCAGCAAATGGCGGATTTACATAACAGTCGTTCATGGCGTATTACTCAACCACTACGCTGGTTGT

CTTTGCAACGTCAATTATTACGTCAGGAAGGGGCTAAAGTGCGAGCCCGTAGGGCTGGGAAAAAAATATTGCGCAAA

GGGATGGCGCTCTCGCTGGTCTTTTTCCATCGTTACCCTAAGTCTAAGGTTTATCTGTTTAAGGTTCTGAGAAAAAC

TGGCTGCTATACATTGCTACAACGTTTGTTCCAACGCGTAATGCTGGTGCAATCTGACACGATGATGATGCAGTCCA

GAAGATATGATGTGGGTACTGAAGAAATGACAAGTCGCGCGATGAGTATTTATAACGAATTAAAAAATAAAAATACG

GAGAAATAACGATGCGTATTGTCATAGATTTACAAGGCGCACAGACGGAAAGCCGCTTTCGTGGCATCGGTCGTTAT

AGTATCGCAATCGCCAGAGGCATAATCAGAAATAACAGCCGGCATGAGATTTTCATCGCGCTATCCGCCATGCTGGA

TGAGTCGATTGCAAATATTAAGGCGCAATTTGCCGATCTCCTGCCGGCAGAAAATATAGTCGTATGGCATGCCGTAG

-continued

GCCCTGTTCGTGCGATGGACCAAGGTAATGAATGGCGTCGGGAGAGCGCAGAACTGATTCGGGAAGCGTTTCTTGAA

TCATTGTGTCCAGATGTCGTTTTCATTACGAGTTTGTTTGAAGGTCATGTCGACGATGCGGCTACATCGGTACACAA

ATTTAGTCGTCAGTATAAAGTAGCCGTACTGCACCACGATCTTATCCCCCTCGTGCAGGCGGAAACCTATCTGCAGG

ACGATGTATACAAACCCTACTATTTACAGAAAGTTGAGTGGTTAAAAAACGCTGACCTTTTGTTGACTAACTCTGCT

TATACCGCACAGGAAGCGATCGAGCATCTGCATTTACAGGGCGATCATGTGCAGAATATTGCAGCCGCAGTCGATTC

TCAGTTTTGTATGGCGGAGGTGGCAGCGAGCGAAAAAGAGACCGTCCTTGGCCATTACGGTATTCAGCGCGAGTTCA

TGTTGTATGCGCCCGGAGGATTTGACTCAAGGAAAAACTTTAAACGGTTGATTGAGGCCTATGCCGGGCTCAGTGAT

GCCTTACGTCGCAGTCATCAACTGGTCATCGTCAGTAAGCTTTCCATCGGTGATCGTCAGTATCTGGAATCCCTTGC

GTCAGGTAATGGTTTACAGCAGGGCGAACTGGTACTCACTGGTTATGTGCCGGAAGATGAGCTGATCCAGCTCTATC

GCCTATGTAAGCTGTTCATCTTTGCTTCACTACATGAAGGTTTTGGGTTGCCGGTTCTGGAAGCAATGTCGTGCGGT

GCGCCGGTGATTGGCTCAAATGTCACCAGTATTCCTGAAGTCATCGGTAATCCTGAGGCATTATTCGACCCGTATTC

TGTCTCTTCCATGAGGGATAAGATCGCGCAATGTTTGACTGATGATACCTTCCTCGCGCGTCTGAAAGAAATGGCGC

AGCAGCAAGCGCGTAATTTCTCTTGGGATAAAGCTGCGGTGACTGCTCTGGAAGCTTTCGAAAAGATCGCGGTAGAA

GACACCGGTACTGCGCAGGTTTTGCCTGAAGCTTTGATTCAGAAGATCCTTGCTATCTCACAAGGGCAGCCAGATGA

CCGCGATCTGCGCTTGTGCGCAACGGCCATTGATTACAATCTGAAAACGGCAGAACTTTATCAAATCGACGATAAAT

CGCTGAACTGGCGTGTGGAAGGCCCATTCGATAGCTCATATAGTCTGGCGTTGGTCAACCGCGAATTTGCCCGGGCA

CTCTCAGCCGATGGTGTAGAGGTTTTATTGCATTCCACTGAAGGACCAGGTGATTTTGCCCCAGATGCCTCGTTTAT

GGCACAGTCGGAAAATAGTGATCTTCTGGCATTTTATAATCAATGTCAGACCCGCAAGAGTAACGAAAAGATAGATA

TTATTAGCAGAAATATCTATCCACCGCGGGTTACCAAAATGGATGCCAAAGTAAAATTCCTTCATTGTTATGCTTGG

GAAGAAACGGGCTTTCCGCAACCGTGGATCAATGAATTTAATCGGGAACTTGACGGAGTGCTGTGTACTTCGGAACA

TGTTCGTAAAATACTGATTGATAACGGACTGAATGTGCCCGCATTTGTTGTTGGCAATGGCTGTGACCATTGGCTCA

ATATCCCAGCCGAGACGACAAAAGATGTGGATCACGGAACATTCCGTTTCCTGCACGTCTCTTCTTGTTTCCCACGC

AAAGGGATACAGGCAATGCTTCAGGCTTGGGGGAAGGCGTTCACTCGTCGTGACAATGTTATCTTAATCATTAAGAC

TTTTAACAATCCGCACAATGAAATTGACGCATGGCTGGCTCAGGCCCAGGCTCAATTCATAGACTATCCCAAAGTTG

AAGTGATCAAAGAGGATATGTCAGCCACCGAGCTTAAAGGGCTTTATGAAAGCTGTGATGTTTTGGTTGCTCCAGGT

TGCGCTGAAGGCTTTGGTTTACCTATTGCTGAAGCAATGCTGAGTGGGCTACCGGCTATCGTCACCAATTGGAGCGG

GCAACTTGATTTTGTTAATTCACAAAATTCATGGCTGGTTGACTATCAGTTCACTCGGGTAAAAACGCACTTTGGTC

TGTTTTCCTCAGCCTGGGCCAGTGTGGATATTGACAACTTAACAGATGCATTAAAAGCGGCAGCCTCAACCGATAAA

TCAGTGCTGCGTGACATGGCCAATGCTGGTCGCGAGCTTCTTCTGCAGCAGTTTACCTGGAAAGCGGTGGCTGATCG

TTCTTGCCAGGCGGTCAAGACTCTGCGTGCGCATATTGATATTGCACAGCATCGGGCGCGCATTGGCTGGGTGACGA

CCTGGAACACGAAATGTGGGATCGCAACCTATTCCCAGCATCTGGTGGAAAGCGCACCTCATGGCGCGGATGTTGTT

TTTGCTCCCCAGGTCAGCGCTGGCGATCTTGTGTGTGCAGACGAAGAGTTTGTACTTCGCAACTGGATTGTAGGTAA

AGAGAGCAACTATCTGGAAAACCTCCAGCCACACATTGATGCTCTGAGACTCGATGTCATTGTGATCCAATTCAACT

ATGGATTCTTTAATCATCGAGAACTGTCGGCGTTTATTCGTCGCCAGCATGACGCCGGTCGTTCAGTTGTTATGACG

ATGCACTCAACTGTGGATCCGCTGGAAAAAGAGCCGAGCTGGAATTTCCGTCTTGCTGAAATGAAAGAGGCGCTGGC

ACTTTGCGACCGGTTGTTGGTGCATTCGATTGCCGATATGAACCGCCTTAAAGATTTAGGCTTAACTGCGAATGTTG

CTTTATTCCCGCACGGTGTTATCAACTACTCCGCAGCGAGCGTCACACGTCAACAGCAGTCTTTACCGCTAATTGCG

AGCTATGGCTTCTGCTTACCGCATAAGGGCCTGATGGAACTAGTAGAATCCGTCCATAGACTCAAGCAAGCCGGTAA

ACCGGTTCGTTTACGACTGGTGAACGCAGAGTATCCTGTTGGGGAGTCACGCGATCTGGTGGCAGAGCTTAAAGCTG

CTGCTCAGCGGTTAGGTGTTACCGATCTGATTGAGATGCATAATGATTTCCTACCTGATGCGGAGAGTCTGCGGTTG

CTTTCAGAAGCCGATCTTCTGATTTTTGCTTATCAGAATACTGGGGAGTCTGCTAGCGGGGCGGTACGTTATGGTAT

-continued

GGCGACTCAAAAACCTGTTGCGGTAACGCCCCTGGCGATATTTGATGATTTGGACGATGCCGTCTTTAAATTTGATG

GATGCAGCGTCGATGATATCAGTCAGGGGATTGACCGGATCCTGAATTCCATCCGTGAACAGAACTCTTGGGCAACC

AGGACTCAACAACGTGCCGATGCATGGCGGGAACAACATGATTATCAAGCTGTTTCACGCCGTCTGGTTAATATGTG

TCAAGGCTTAGCTAAAGCTAAATATTTTAAATAAAAATATCTCTCTTGTATTTTTTGCCTTTGAATACAAGAGGGGT

TAGATAATGTGTCATTTATTATGAAAATTATTTTTGCTACTGAGCCAATTAAATACCCATTAACGGGCATCGGTCGG

TATTCCCTGGAGCTGGTTAAGCGGCTGGCGGTCGCCCGCGAAATTGAAGAATTAAAGCTATTTCACGGTGCGTCGTT

TATAGAACAGATCCCTTTGGTGGAGAATAAAAGCGATACCAAAGCCAGCAATCATGGTCGTCTGTCGGCGTTTCTAC

GCCGACAGACGCTGTTGATTGAGGCTTATCGCTTGCTGCATCCGCGGCGCCAGGCGTGGGCATTGCGCGACTATAAG

GATTATATCTACCATGGCCCCAATTTTTATCTGCCGCATAAACTGGAACGCGCCGTGACCACGTTTCATGACATATC

CATTTTTACCTGCCCGGAATATCATCCAAAAGATCGGGTTCGCTATATGGAGAAGTCCCTGCATGAGAGTCTGGATT

CGGCAAAGCTGATCCTGACCGTTTCTGATTTCTCGCGCAGTGAAATTATCCGCTTGTTCAACTATCCGGCGGAGCGG

ATCGTAACCACCAAGCTAGCCTGCAGCAGTGACTATATCCCACGCAGCCCGGCAGAGTGTCTGCCGGTACTGCAGAA

ATATCAGCTGGCGTGGCAGGCCTACGCGCTATATATCGGCACTATGGAGCCACGTAAAAATATCCGAGGCCTGCTGC

ATGCCTATCAGCTGCTACCGATGGAGATCCGCATGCGCTATCCGCTAATCCTTAGCGGCTATCGCGGCTGGGAAGAC

GATGTGCTGTGGCAGTTAGTCGAGCGCGGTACTCGGGAAGGCTGGATCCGTTACCTCGGATATGTTCCGGATGAAGA

CCTGCCGTATCTGTACGCAGCGGCCAGAGTCTTTGTTTATCCCTCCTTCTACGAGGGATTCGGTTTACCTATTCTTG

AAGCGATGTCTTGCGGTGTGCCGGTAGTATGCTCCAATGTCACCTCTTTGCCTGAGGTTGTTGGCGATGCCGGCCTC

GTTGCCGATCCTAATGATATAGACGCGATTAGCGCGCAAATTTTGCAGAGCCTGCAAGATGATAGCTGGCGGGAAAT

CGCCACCGCGCGCGGTCTTGCTCAGGCGAAACAGTTTTCGTGGGAGAACTGTGCGACACAGACCATTAACGCCTATA

AATTACTCTAAGGGTGTCAGTTGAGAGTTCTACACGTCTATAAGACTTACTATCCCGATACCTACGGCGGTATTGAG

CAGGTCATTTATCAGCTAAGTCAGGGCTGCGCCCGCCGGGGAATCGCAGCCGATGTTTTCACTTTTAGCCCGGACAA

AGATACAGGTCCTGTCGCTTACGAAGATCATCGGGTCATTTATAATAAACAGCTTTTTGAAATTGCCTCCACGCCGT

TTTCGCTGAAAGCGTTAAAGCGTTTTAAGCTGATTAAAGATGACTACGATATCATCAACTACCATTTTCCGTTTCCC

TTTATGGATATGCTGCATCTTTCGGCGCGGCCTGACGCCAGGACTGTGGTGACCTATCACTCTGATATAGTGAAACA

AAAACGGTTAATGAAGCTGTACCAGCCGCTGCAGGAGCGATTTCTCAGCGGCGTAGATTGCATCGTTGCCTCGTCGC

CCAATTACGTGGCTTCCAGCCAGACCCTGAAAAAATATCTGGATAAAACGGTGGTGATCCCGTTTGGTCTGGAGCAG

CAGGACGTGCAGCACGATCCGCAGAGGGTCGCGCACTGGCGGGAAACTGTCGGCGATAAGTTCTTTCTCTTCGTCGG

CACTTTCCGCTACTACAAAGGGCTGCATATTCTGATGGATGCCGCTGAGCGTAGCCGACTGCCAGTGGTGGTTGTAG

GGGGCGGGCCGCTGGAATCGGAAGTGCGGCGTGAAGCGCAGCAGCGCGGGCTGAGCAATGTGATGTTTACCGGCATG

CTCAACGACGAAGATAAGTACATTCTCTTCCAGCTCTGCCGGGGCGTGGTATTCCCCTCGCATCTGCGCTCTGAGGC

GTTTGGCATTACGTTATTGGAAGGCGCACGCTTTGCAAGGCCGCTGATCTCTTGCGAGATCGGTACAGGTACCTCTT

TCATTAACCAGGACAAAGTGAGTGGTTGCGTGATTCCGCCGAATGATAGCCAGGCGCTGGTGGAGGCGATGAATGAG

CTCTGGAATAACGAGGAAACCTCCAACCGCTATGGCGAAAACTCGCGTCGTCGTTTTGAAGAGATGTTTACTGCCGA

CCATATGATTGACGCCTATGTCAATCTCTACACTACATTGCTGGAAAGCAAATCCTGAGCGGCCGCGAGCTCGTCGA

CTCGAGGATCCGTGTAGGCTGGAGCTGCTTCGAAGTTCCTATACTTTCTAGAGAATAGGAACTTCGGAATAGGAACT

AAGGAGGATATTCATATGGATAAAGCCGTAAGCATATAAGCATGGATAAGCTATTTATACTTTAATAAGTACTTTGT

ATACTTATTTGCGAACATTCCAGGCCGCGAGCATTCAGCGCGGTGATCACACCTGACAGGAGTATGTAATGTCCAAG

CAACAGATCGGCGTAGTCGGTATGGCAGTGATGGGACGCAACCTTGCGCTCAACATCGAAAGCCGTGGTTATACCGT

CTCTATTTTCAACCGTTCCCGTGAGAAGACGGAAGAAGTGATTGCCGAAAATCCAGGCAAGAAACTGGTTCCTTACT

ATACGGTGAAAGAGTTTGTCGAATCTCTGGAAACGCCTCGTCGCATCCTGTTAATGGTGAAAGCAGGTGCAGGCACG

-continued

GATGCTGCTATTGATTCCCTCAAACCATATCTCGATAAAGGAGACATCATCATTGATGGTGGTAACACCTTCTTCCA

GGACACTATTCGTCGTAATCGTGAGCTTTCAGCAGAGGGCTTTAACTTCATCGGTACCGGTGTTTCTGGCGGTGAAG

AGGGGGCGCTGAAAGGTCCTTCTATTATGCCTGGTGGCCAGAAAGAAGCCTATGAATTGGTAGCACCGATCCTGACC

AAAATCGCCGCCGTAGCTGAAGACGGTGAACCATGCGTTACCTATATTGGTGCCGATGGCGCAGGTCACTATGTGAA

GATGGTTCACAACGGTATTGAATACGGCGATATGCAGCTGATTGCTGAAGCCTATTCTCTGCTTAAAGGTGGCCTGA

ACCTCACCAACGAAGAACTGGCGCAGACCTTTACCGAGTGGAATAACGGTGAACTGAGCAGTTACCTGATCGACATC

ACCAAAGATATCTTCACCAAAAAAGATGAAGACGGTAACTACCTGGTTGATGTGATCCTGGATGAAGCGGCTAACAA

AGGTACCGGTAAATGGACCAGCCAGAGCGCGCTGGATCTCGGCGAACCGCTGTCGCTGATTACCGAGTCTGTGTTTG

CACGTTATATCTCTTCTCTGAAAGATCAGCGTGTTGCCGCATCTAAAGTTCTCTCTGGTCCGCAAGCACAGCCAGCA

GGCGACAAGGCTGAGTTCATCGAAAAAGTTCGTCGTGCGCTGTATCTGGGCAAAATCGTTTCTTACGCCCAGGGCTT

CTCTCAGCTGCGTGCTGCGTCTGAAGAGTACAACTGGGATCTGAACTACGGCGAAATCGCGAAGATTTTCCGTGCTG

GCTGCATCATCCGTGCGCAGTTCCTGCAGAAAATCACCGATGCTTATGCCGAAAATCCACAGATCGCTAACCTGTTG

CTGGCTCCGTACTTCAAGCAAATTGCCGATGACTACCAGCAGGCGCTGCGTGATGTCGTTGCTTATGCAGTACAGAA

CGGTATTCCGGTTCCGACCTTCTCCGCAGCGGTTGCCTATTACGACAGCTACCGTGCTGCTGTTCTGCCTGCGAACC

TGATCCAGGCACAGCGTGACTATTTTGGTGCGCATACTTATAAGCGTATTGATAAAGAAGGTGTGTTCCATACCGAA

TGGCTGGATTAA (example O15 rfb locus nucleotide sequence-O15-EPA production strain stLMTB11738)

SEQ ID NO: 15

ATGACGAATTTAAAAGCAGTTATTCCTGTAGCGGGTCTCGGGATGCATATGTTGCCTGCCACTAAGGCGATACCCAA

AGAGATGCTACCAATCGTCGACAAGCCAATGATTCAGTACATTGTTGACGAGATTGTGGCTGCAGGGATCAAAGAAA

TCCTCCTGGTAACTCACGCGTCCAAGAACGCGGTCGAAAACCACTTCGACACCTCTTATGAGTTAGAATCACTCCTT

GAGCAGCGCGTGAAGCGTCAACTGCTGGCGGAAGTACAGTCCATCTGTCCGCCGGGCGTGACCATTATGAACGTGCG

TCAGGGCGAACCTTTAGGTTTAGGCCACTCCATTTTGTGTGCGCGACCTGCCATTGGTGACAACCCATTTGTCGTGG

TACTGCCAGACGTTGTGATCGACGATGCCAGCGCCGACCCGCTACGTTACAACCTTGCTGCCATGATTGCACGTTTC

AACGAAACGGGCCGCAGCCAGGTGCTGGCAAAACGTATGCCGGGTGACCTCTCTGAATACTCCGTCATCCAGACTAA

AGAGCCGCTGGACCGTGAGGGTAAAGTCAGCCGCATTGTTGAATTTATCGAAAAACCGGATCAGCCGCAGACGCTGG

ACTCAGACATCATGGCCGTAGGTCGCTATGTGCTTTCTGCCGATATTTGGCCGGAACTGGAACGTACTCAGCCTGGT

GCATGGGGACGTATTCAGCTGACTGATGCTATTGCCGAGCTGGCGAAAAAACAATCCGTTGATGCAATGCTGATGAC

CGGCGACAGTTACGACTGCGGCAAAAAAATGGGCTATATGCAGGCGTTTGTGAAGTATGGCCTACGCAACCTGAAAG

AAGGGGCGAAGTTCCGTAAAGGTATTGAGAAGCTGTTAAGCGAATAATGAAAATCTGACCGGATGTAACGGTTGATA

AGAAAATTATAACGGCAGTGAAAATTCGCAGCAAAAGTAATTTGTTGCGAATCTTCCTGCCGTTGTTTTATATAAAC

CATCAGAATAACAACGAGTTAGCAGTAGGGTTTTATTCAAAGTTTTCCAGGATTTTCCTTGTTTCCAGAGCGGATTG

GTAAGACAATTAGCGTTTGAATTTTTCGGGTTTAGCGCGAGTGGGTAACGCTCGTCACATCATAGGCATGCATGCAG

TGCTCTGGTAGCTGTAAAGCCAGGGGCGGTAGCGTGCATTAATACCTCTATTAATCAAACTGAGAGCCGCTTATTTC

ACAGCATGCTCTGAAGTAATATGGAATAAATTAAGCTAGCATGAGCAAAACTAAACTAAATGTTCTTTACCTTGCAA

TAAGTCAGGGTGCCAATTACCTACTGCCATTATTAATTTTTCCTTATCTTGTTAGAGTCATTGGTGTATCGAATTTT

GGTGATCTGAGTTTTTCATTGATAACTATACAAGTGTTGTTAATGGTTGTTGAATATGGTTTTGGATATAGTGGGAC

AAGAGAAATAGCACTAAATAACGATAAAAAATACCATTCTGAATTTTTTTGCGGTGTGGTGCTTGCTCGTTTTATAT

TAATGCTAATTGCAGCTATAATACTCATAATACTCTGTTTTTTTTATGTTTTTAACGACGTTAAGTCTTTGTTATGT

GTTGGTTTTCTGTCCGTAATTGCAGGTGTTTTCAATCCAAATTGGTTTTTGCAAGGTAAGGAAATGATGAGTGTGAT

GGCTGTGCTGTCACTATTTTCACGAGGCATAGCAGTCGTTGCAGTTTATCTAATTATAAAACCCGCAACGCCGATGT

-continued

ACATCAGTGCCTTATTATTGAGCATGCCATATATTTGTATTCATTCTGTGGCGTTGCCTACTTACTTATTATCAAG

GAGATTTTTTTATGTAGGCCACCGATAAAGAAAATTCAAGTAATTTTAAAAAATGGATTTCATTTTTTTTGTTCAAC

ACTTGCGACTAGTGCATACACAATGTTGACCCCTCTTGTATTGGGTGGCGTATCTGGAAAGTTTGATGTAGGCATCT

TTAACTCAGCTAACATGATCAAACAAGGTTTGGCTGGACTTGCATCACCATTAGTCCAAGCTTTTTATCCAAGAATT

AACATTTTGCAAAGAGAGAATCCATATATTGCAAACTTAAAATCTAGAATGATTCTTAAATACTTGCTTGTTTTTTA

CATGGCTTTAGCAATACCATTTTTACTTTTTGCCAACCAATTATCATTATTAATATTCGGCATGAAAGGTGAAGTAA

TTGCAGGTGCAATGCAATTAATGACATTGCTTCCTATATTCATAGGTTTTAATACAGTTGTCGGGTTACTTGTATTA

GTACCTAATGGGATGCAAAAACAGTATTTCAAATCTATTTTCCTAGGAACTATTACTTGTTTAAGCATAGTTTATCC

AGCATGTAAATATTATGGAGCAACGGGTGCGATTGTGAGTCTTATTGTAGCTGAAATTTTCGTTGGCATGGGAATGC

TTAAACAATTCATTAAAGTAAATAAAACCGTATGTAGGCCTCATAAATTATGAATATCTCGGTAATAATATCTGTTT

GGAAACGCCCAGTTCAATTAGAATTGATTCTCTCTGAGCTCGATTCTCAGGCTAAAGACAATAGTCTACACCTAGAA

GTAATTGTTTCCGATAGTCATAGTGGTAAAGAAATTGATGATGTAGTTGCTGATAATATTCATAAAAAGAAAAATAT

TAATATTATCCATCAACATACTAAAAATATACTCTCCGCTAAGCGCAATTTCGGAGCATCCCTAGCCCATGGGGATT

ATTTAATATTTCTTGATGATGATTGTATACCCGCAAGTGGATATATATCATCGTTGCTGAACTATTTAAAAAAAATG

AATAGTAAAAGCGTTTTATGTGGGGAAGTTAGATTCGAAAATGAACTCATTGAGACCAGCAATTACTATCGCTACAG

GAACTCTTTACACCCTAAGTTTAGTGATAGTCCTGATATCTCTATGAATGCCTGGACTTTTGTCGCAATGAATTGTG

TTCTTGATAGAAAGGCATTTTCATCAGGTATAGTTTCATATAATGAAAATTTTATTGGTTATGGTTGTGAAGATCAT

GAGTTTGGGTGGCAACTTGAAAAAAATGACTTCAAAATTATTTTTGCTGATTTTAAAATATTACATCACGAATACAG

TGGCGATATAGAAGGATATACAAAAAAAATTCGTGCTACAGCACGTGATGGTATGAATGTATTAAGCAAAGTAAGGC

CTGAAATGTTTTCTACTAATAAAAAATTATTCCTAGTTGAGAAAATATTTAGTAAACACAAAACGTTTAGTAAAATA

TGCCAATCAATATTTTTCAATAAATTTATTTTTAAAAAAATAATACAATTTTTAAAAAAAACAGATGCAAATAAAAA

ACTCTATTTCCCAATTCTTTACAGATATGTGTTGATTTCGGCATATATACATGGTATTGGAGAGCGTGGCACCTCAA

AAACAGATGATTTGCTTAAGAACTGGTATATATAGATGATGCTATCTTCATTTATTAAGACATTTGTATGGAAGGTA

AAAAACAATGAAGTATAATGCATTGATGGCTTTTTTATTATTTTTTGTTGTTTTTTTAGATTGTCGCTGATAATAC

CTTTCTTATATTTGGCATTTATTCCTGCATTTTTTGGTATTATGTATTTAGTGCGTAATTTTATGATTACTATGGGC

AATGGATTGGTATCTATAGATCGTAAAAATTTGTTGCTGTTATCTATATTCATAATTATTTTTTTATTTTGTTTGGT

TTTCGATTTGTTTCAAAAAAGCCATTCTTTTCAAAGTTATTTTACCGTTAGATTATTTATGTTGTTTTTATTTTCAT

TTGTTCCTGCGTATTATTTAGTAAATAGATTCATAAAGGGTGACTTGAAATTAATGGAGCGAATATTAGTGTATTCT

CTCTGGGTTCAAATAGTTATTTTTTTTGGTATGTATATAAGTCCAGAGTTAAAAAGATTGTTATATACTTTCTTTGG

TATGTCTGACTCTGTTAATCTTTGGGAACAAAATGCTAAAGTAAGAGGATTTGGGTTGTCGGGTGAAATAAATTTCA

TGACACCATTTTTGATGATCTATATGTCATTTTTTATGATGAAAAGGCGTTATGCTTTAATTACTTTAATTTGTCTG

ACTCAAATCGTAAATTCTAACATGGCTGTGATTGCAGCCATTATTGGTATCGGTTGCTCTAGACTTAATATTAATAT

AAAAATTGCAACAGTATTGATTTTGGGAGTTTTAGTTTATAGCTTAGGAGCGGTGTTCTTTCCTCGATTTTATGATG

AGTTCGTTTCTGGAGATGGCACAAGAACTCTGGATATCTTATTACAGCAACATGTGTTTGTTGTAGGTAATTTAGAT

TTTTTTAATATTATATTTGGATTACAGCAAAACATATCTTCATCAATCCCCGATATTAAACAAAGTTCGGATATGGG

CTGGGTTATACTGTTTAATTACGGTGGGTTAACATTTATTACACTCTTTTTATTTTTAATCTTTACTATTTCTATTG

CGACATTTGGAATGACATATCAAGCAATTATATGGATGTTAATTGGGATAATTTTCAATACCAAAGGTTTAGTTTTA

GGATCTAACGGCTATTTCTTTCTATCTTTTATATATATGTTTTGAATAGAGTAACACTTAGTGGACAGAGTTCAAT

TACTAATAAGTTAGGTCAAGTAAGTAAATAGCTTCCAGAGTATATTTGTCAATGATTTGAGGTTCGGTTATTATGTT

TTCATCTAAAACACTGTTAATTACTGGTGGTACTGGCTCTTTCGGGAATGCTGTATTAAATAGATTTCTTGATACAG

ATATTGCAGAAATCCGTATATTTAGTCGTGATGAAAAAAAACAAGATGATATGCGGAAAAAAATACAATAATCAAAAA

-continued

TTAAAGTTCTATATTGGTGATGTCAGAGATTACCGTAGTATTTTGAATGCGACTCGCGGTGTTGATTTTATATATCA

TGCAGCGGCACTTAAGCAAGTTCCATCATGTGAATTTCATCCTATGGAAGCCGTTAAAACTAATATCCTTGGTACGG

AAAATGTTCTTGAAGCAGCTATAGCGAATGAAGTGAAGAGGGTTGTATGCCTAAGTACTGATAAAGCTGTATACCCG

ATTAACGCAATGGGTATTTCAAAAGCTATGATGGAAAAGGTCATGGTCGCGAAATCCCGTAATGTTGATCGCAATAA

AACAGTAATATGTGGTACCCGTTATGGGAATGTTATGGCATCTCGCGGTTCAGTTATTCCATTATTTGTTGATCTTA

TTAGAGCGGGCAAGCCACTCACAATAACTGATCCTAATATGACCCGCTTTATGATGACTCTTGAGGATGCGGTAGAT

TTAGTTCTTTATGCGTTTGAACATGGTAATAATGGTGATATCTTTGTGCAAAAAGCACCTGCAGCAACTATTGACAC

ATTAGCTATTGCTTTAAAGGAATTACTAAATGTTCCTGACCATCCGGTAAATGTCATTGGAACGCGTCATGGCGAGA

AATTATATGAAGCTCTACTTAGTCGTGAGGAAATGATCGCTGCTATAGATATGGGCGATTATTACCGTGTCCCGCCA

GATCTTCGTGACCTTAATTATGGCAAATATGTTGAGCAAGGTGATAGCCGAATATCTGAAATAGAAGATTATAACTC

TCATAATACTCAACGGTTAGATGTTGAAGGCATGAAAGAGCTCTTGCTAAAATTAGCCTTTATTCGAGCAATTCGTG

CTGGTGAAAAATATAATCTGGATTCATGATATGAAAATATTAGTTACTGGTGCAAATGGTTTTATTGGTCGTAATTT

ATGTTTGAGGCTTGAGGAACTTGGTTATAAAGATCTTATTAGAATTGATCGAGAATCAACGAAGCAAGATCTTGAAC

AAGGCTTACAGGATGCCGATTTTATTTATCACTTAGCTGGTATCAATAGACCTAAGACTGATGATGAGTTTATTTCT

GGAAACAGTGATTTAACAAAGCATATAGTTGAGTATCTCCTTTCTATTGGTAAGAATACACCAATTATGCTAAGTTC

TTCGATACAAGCTGAACTTAATAATGCTTATGGGGTTAGCAAAGCTGTAGCTGAAAGCTATGTCGAAAAATATGCTG

CTGCTAGTGGTTCTTCGTATTATATTTTCAGATATCCAAACGTTTTTGGTAAATGGTGTAAGCCAAACTATAATTCT

TTTATAGCAACTTTTTGCTACAATATTTCCAATGATATTGAGATTACTATCAATGATGCAGCAGCGCCAGTCAATCT

GGTCTATATTGATGATGTTTGTACTGATGCTATAGCTCTTCTCTCTGGGACGGTTGAAAGTGGATATAAAGTTGTTG

CACCAATTTATTCAACAACAGTTGGTGAAGTTGCAGAATTAATTTATAGCTTCAAAAATAGCCGTTCCACCCTGATC

ACAGAGGCTGTCGGGGCGGGATTTACCCGTGCATTGTATTCTACATGGCTGAGTTATTTACCAGCAGAGAAGTTTGC

GTACAAGGTACCTTTTTATGGGGATGCCCGCGGAGTCTTTTGTGAGATGTTGAAAACGCCTTCAGCGGGGCAGTTTT

CATTTTTTACTGCTCACCCTGGTATTACGCGTGGCGGACATTACCATCACAGTAAAAATGAGAAGTTTTTGGTCATT

CGAGGTCAGGCATGCTTTAAATTTGAACATGTGATTACCGGTGAGCGATATGAACTGAAAGTTTCATCGGGTGAGTT

TAAGATTGTTGAAACAGTTCCTGGTTGGACACATGACATTACAAATATTGGAACTGATGAATTAATAGTCATGCTCT

GGGCAAATGAAATTTTCAACCGTGATGAGCCCGATACTATTGCGAGACCTCTATAATGAAAAAATTAAAAGTTATGT

CTGTTGTTGGAACCCGTCCTGAGATTATCCGTTTGTCGAGGGTTCTTGCTAAGTTTGATGAATACTGCGAGCATATT

ATTGTCCATACTGGTCAAAATTATGATTACGAATTAAATGAAGTGTTCTTCAATGACTTGGGTGTTCGAAAACCTGA

TTATTTTTTAAATGCAGCGGGTAAAAATGCGGCGGAAACCATTGGTCAGGTTATTATTAAGGTAGATGAAGTATTAG

AAATCGAAAAACCTGAAGCAATACTGGTATTGGGCGATACGAATTCATGTATTTCTGCCATTCCGGCCAAACGCCGT

AAAGTGCCTATATTTCATATGGAAGCAGGTAACCGTTGTTTCGATCAACGCGTGCCTGAAGAAACCAACAGACGTAT

TGTTGACCATACGGCTGATATCAATATGACCTACAGTGATATTGCTCGTGAATATCTCTTGGCTGAAGGTATCCCAG

CTGATCGGATCATAAAAACTGGTAGCCCTATGTTTGAGGTTCTTTCATATTATATGCCCCAAATTGATGGTTCAGAT

GTGCTATCGCGTTTGAATCTACAGTCTGGTGAGTTTTTTGTAGTAAGTGCGCATCGTGAAGAGAATGTTGATTCTCC

AAAACAGCTCGTAAAGCTTGCGAACATTCTAAATACTGTTGCTGAAAAATATAATCTTCCAGTTATTGTCTCCACAC

ACCCAAGGACACGTAACCGAATCCGTGAGCAAGGAATTGAATTTCATTCAAATATAAATCTACTGAAACCATTGGGT

TTCCATGATTATAACCACTTGCAGAAGAACTCACGAGCTGTGCTTTCAGATAGCGGTACTATCACTGAAGAGTCATC

CATCATGAATTTCCCAGCGGTAAACATCCGGGAAGCGCATGAGCGTCCGGAAGGCTTTGAGGAAGCATCCGTCATGA

TGGTGGGGTTAGAGTGTGAACGCGTATTACAAGCGCTGGATATTCTGGCAACACAACCGCGAGGTGAAGTCCGTCTT

TTACGTCAGGTTAGTGATTACAGCATGCCAAATGTGTCGGATAAAGTTGTCAGAATTGTTCACTCTTACACAGATTA

-continued
TGTTAAGAGAGTCGTCTGGAAAGAATATTGATGAAACTTGCTTTAATCATAGATGATTACCTGCCCAACAGTACTCG

TGTTGGTGCAAAAATGTTTCATGAACTTGCTCAAGAATTTATCCAGCGTGGGCACGATGTTACGGTAATTACTCCTG

GTACGGGCATGCAAGAAGAGATTTCTTTTGATACCTTTCAGGGGGTAAAAACATGGCGTTTTAAAAGCGGGCCGCTC

AAGGATGTAAGTAAAATTCAGCGAGCGGTCAATGAAACGCTTTTGTCCTATCGGGCGTGGAAAGCCATCAAAAAATG

GGTAAAAAAAGAGACCTTTGAGGGGGTGATTTATTATTCACCTTCCATATTCTGGGGGCCTTTAGTTAAAAAAATTA

AAGCTCGTTGCCAATGTCCTGCTTATCTTATTTTAAGAGATATGTTTCCACAATGGGTAATTGATGCAGGAATGCTT

AATGCTGGTTCCCCAATAGAACGCTACTTTCGTCTTTTTGAAAAAATATCTTATCGTCAGGCAAATCGTATTGGACT

TATGTCTGATAAGAATCTTGATGTTTTTCGGAAAGATAATAAAGGCTATCCGTGCGAAGTTTTGCGTAATTGGGCAT

CCCTAACACCAACGATCATACCCAAGGATTATATACCACTACGTAAGCGACTTGGCCTAGAGGATAAAACCATTTTC

TTCTATGGTGGAAACATAGGTCATGCACAGGACATGACAAACTTGATGCGACTTGTGAGAAACATGGCAGCATATCC

TCAAGCTCATTTCCTATTTATTGGCCAGGGGGATGAAGTTGAATTAATTAATTCATTAGCATCTGAGTGGGCATTGA

CGAATTTCACCTATTTGCCCTCGGTTAACCAAGATGAATTTAAGTTCATTTTGTCGGAAATGGATATCGGCTTGTTT

TCTCTTTCCGCTAGACACTCTTCCCATAATTTTCCTGGTAAGTTATTAGGCTATATGGTTCAGTCGCTACCTATTTT

AGGTAGCGTAAATGCCGGAAATGATTTGCTCGACATTGTCAATCAAAATAATGCGGGATTAATCCATGTCAATGGTG

AGGACGATAAATTATGTCAATCTGCGCTATTAATGTTGCATGATATTGATGTGCGCCGGCAACTTGGTTCGGGGGCG

AATATATTGTTGAAAGAACAATTCTCCGTTGAGTCTGCGGCACAGACGATAGAAATGAGGTTGGAGGCATGCAATGC

GATTAATTGATAATGACCAACTCGACGAATTATATGATCAAGCCGGGCAATCGGAACGTTTACGTTCCCACCTTATG

ATGCACGGCTCGCATCAAGAAAAGGTACAGCGTTTACTTATTGCATTAGTAAAGGGCAGCTATGTTGAACCGCATTA

TCACGAACTTCCTCATCAGTGGGAAATGTTCATTGTTATGGAGGGGCAACTTCAGGTTTGTTTGTATGGTAGAAATG

GTGAGGTTATAAAGCAATTTATAGCAGGAGATAATACTGGAATGAGCATTGTGGAGTTTTCTCCGGGCGATATACAC

AGTGTCGAATGCCTATCTCCGCGTGCTCTTATGGTGGAAGTTAAGGAGGGGCCATTTGACCCTTCTTTTGCAAAATC

GTTCGTGTGAGCGGCCGCGAGCTCGTCGACTCGAGGATCCGTGTAGGCTGGAGCTGCTTCGAAGTTCCTATACTTTC

TAGAGAATAGGAACTTCGGAATAGGAACTAAGGAGGATATTCATATGGATAAAGCCGTAAGCATATAAGCATGGATA

AGCTATTTATACTTTAATAAGTACTTTGTATACTTATTTGCGAACATTCCAGGCCGCGAGCATTCAGCGCGGTGATC

ACACCTGACAGGAGTATGTAATGTCCAAGCAACAGATCGGCGTAGTCGGTATGGCAGTGATGGGACGCAACCTTGCG

CTCAACATCGAAAGCCGTGGTTATACCGTCTCTATTTTCAACCGTTCCCGTGAGAAGACGGAAGAAGTGATTGCCGA

AAATCCAGGCAAGAAACTGGTTCCTTACTATACGGTGAAAGAGTTTGTCGAATCTCTGGAAACGCCTCGTCGCATCC

TGTTAATGGTGAAAGCAGGTGCAGGCACGGATGCTGCTATTGATTCCCTCAAACCATATCTCGATAAAGGAGACATC

ATCATTGATGGTGGTAACACCTTCTTCCAGGACACTATTCGTCGTAATCGTGAGCTTTCAGCAGAGGGCTTTAACTT

CATCGGTACCGGTGTTTCTGGCGGTGAAGAGGGGGCGCTGAAAGGTCCTTCTATTATGCCTGGTGGCCAGAAAGAAG

CCTATGAATTGGTAGCACCGATCCTGACCAAAATCGCCGCCGTAGCTGAAGACGGTGAACCATGCGTTACCTATATT

GGTGCCGATGGCGCAGGTCACTATGTGAAGATGGTTCACAACGGTATTGAATACGGCGATATGCAGCTGATTGCTGA

AGCCTATTCTCTGCTTAAAGGTGGCCTGAACCTCACCAACGAAGAACTGGCGCAGACCTTTACCGAGTGGAATAACG

GTGAACTGAGCAGTTACCTGATCGACATCACCAAAGATATCTTCACCAAAAAAGATGAAGACGGTAACTACCTGGTT

GATGTGATCCTGGATGAAGCGGCTAACAAAGGTACCGGTAAATGGACCAGCCAGAGCGCGCTGGATCTCGGCGAACC

GCTGTCGCTGATTACCGAGTCTGTGTTTGCACGTTATATCTCTTCTCTGAAAGATCAGCGTGTTGCCGCATCTAAAG

TTCTCTCTGGTCCGCAAGCACAGCCAGCAGGCGACAAGGCTGAGTTCATCGAAAAAGTTCGTCGTGCGCTGTATCTG

GGCAAAATCGTTTCTTACGCCCAGGGCTTCTCTCAGCTGCGTGCTGCGTCTGAAGAGTACAACTGGGATCTGAACTA

CGGCGAAATCGCGAAGATTTTCCGTGCTGGCTGCATCATCCGTGCGCAGTTCCTGCAGAAAATCACCGATGCTTATG

CCGAAAATCCACAGATCGCTAACCTGTTGCTGGCTCCGTACTTCAAGCAAATTGCCGATGACTACCAGCAGGCGCTG

CGTGATGTCGTTGCTTATGCAGTACAGAACGGTATTCCGGTTCCGACCTTCTCCGCAGCGGTTGCCTATTACGACAG

-continued

CTACCGTGCTGCTGTTCTGCCTGCGAACCTGATCCAGGCACAGCGTGACTATTTTGGTGCGCATACTTATAAGCGTA

TTGATAAAGAAGGTGTGTTCCATACCGAATGGCTGGATTAA (example O16 rfb locus nucleotide sequence-O16-EPA production strain stLMTB11739)

SEQ ID NO: 16

ATGACGAATTTAAAAGCAGTTATTCCTGTAGCGGGTCTCGGGATGCATATGTTGCCTGCCACTAAGGCGATACCCAA

AGAGATGCTACCAATCGTCGACAAGCCAATGATTCAGTACATTGTTGACGAGATTGTGGCTGCAGGGATCAAAGAAA

TCCTCCTGGTAACTCACGCGTCCAAGAACGCGGTCGAAAACCACTTCGACACCTCTTATGAGTTAGAATCACTCCTT

GAGCAGCGCGTGAAGCGTCAACTGCTGGCGGAAGTACAGTCCATCTGTCCGCCGGGCGTGACCATTATGAACGTGCG

TCAGGGCGAACCTTTAGGTTTAGGCCACTCCATTTTGTGTGCGCGACCTGCCATTGGTGACAACCCATTTGTCGTGG

TACTGCCAGACGTTGTGATCGACGATGCCAGCGCCGACCCGCTACGTTACAACCTTGCTGCCATGATTGCACGTTTC

AACGAAACGGGCCGCAGCCAGGTGCTGGCAAAACGTATGCCGGGTGACCTCTCTGAATACTCCGTCATCCAGACTAA

AGAGCCGCTGGACCGTGAGGGTAAAGTCAGCCGCATTGTTGAATTTATCGAAAAACCGGATCAGCCGCAGACGCTGG

ACTCAGACATCATGGCCGTAGGTCGCTATGTGCTTTCTGCCGATATTTGGCCGGAACTGGAACGTACTCAGCCTGGT

GCATGGGGACGTATTCAGCTGACTGATGCTATTGCCGAGCTGGCGAAAAAACAATCCGTTGATGCAATGCTGATGAC

CGGCGACAGTTACGACTGCGGCAAAAAAATGGGCTATATGCAGGCGTTTGTGAAGTATGGCCTACGCAACCTGAAAG

AAGGGGCGAAGTTCCGTAAAGGTATTGAGAAGCTGTTAAGCGAATAATGAAAATCTGACCGGATGTAACGGTTGATA

AGAAAATTATAACGGCAGTGAAAATTCGCAGCAAAAGTAATTTGTTGCGAATCTTCCTGCCGTTGTTTTATATAAAC

CATCAGAATAACAACGAGTTAGCAGTAGGGTTTTATTCAAAGTTTTCCAGGATTTTCCTTGTTTCCAGAGCGGATTG

GTAAGACAATTAGCGTTTGAATTTTTCGGGTTTAGCGCGAGTGGGTAACGCTCGTCACATCATAGGCATGCATGCAG

TGCTCTGGTAGCTGTAAAGCCAGGGGCGGTAGCGTGCATTAATACCTCTATTAATCAAACTGAGAGCCGCTTATTTC

ACAGCATGCTCTGAAGTAATATGGAATAAATTAAGTGAAAATACTTGTTACTGGTGGCGCAGGATTTATTGGTTCAG

CTGTAGTTCGTCACATTATAAATAATACGCAGGATAGTGTTGTTAATGTCGATAAATTAACGTACGCCGGAAACCGG

GAATCACTTGCTGATGTTTCTGATTCTGAACGCTATGTTTTTGAACATGCGGATATTTGCGATGCACCTGCAATGGC

ACGGATTTTTGCTCAGCATCAGCCGGATGCAGTGATGCACCTGGCTGCTGAAAGCCATGTTGACCGTTCAATTACAG

GCCCTGCGGCATTTATTGAAACCAATATTGTTGGTACTTATGTCCTTTTGGAAGCCGCTCGCAATTACTGGTCTGCT

CTTGATAGCGACAAGAAAAATAGCTTCCGTTTTCATCATATTTCTACTGACGAAGTCTATGGTGATTTGCCTCATCC

AGATGAAGTAAATAATACAGAAGAATTACCCTTATTTACTGAGACGACAGCTTACGCGCCAAGCAGCCCTTATTCCG

CATCCAAAGCATCCAGCGATCATTTAGTCCGCGCGTGGAAACGTACATATGGTTTACCGACAATTGTGACTAATTGC

TCGAACAACTATGGTCCTTATCATTTCCCGGAAAAGCTTATTCCACTGGTTATTCTTAATGCACTGGAAGGTAAGGC

ATTACCTATTTATGGCAAAGGAGATCAGATCCGCGACTGGTTGTATGTTGAAGATCATGCGCGTGCGTTATATACCG

TCGTAACCGAAGGTAAAGCGGGTGAAACTTATAACATTGGTGGGCACAACGAAAAGAAAAACATCGATGTAGTGCTC

ACTATTTGTGATTTGCTGGATGAGATTGTACCGAAAGAGAAATCTTATCGTGAGCAAATCACTTATGTTGCTGATCG

TCCGGGACACGATCGCCGCTATGCTATTGATGCTGAGAAGATTGGTCGCGCATTGGGATGGAAACCACAGGAAACGT

TTGAGAGCGGGATTCGTAAAACGGTGGAATGGTACCTGTCCAATACAAAATGGGTTGATAATGTGAAAAGTGGTGCC

TATCAATCGTGGATTGAACAGAACTATGAGGGCCGCCAGTAATGAATATCCTCCTTTTTGGCAAAACAGGGCAGGTA

GGTTGGGAACTACAGCGTGCTCTGGCACCTTTGGGTAATTTGATTGCTTTTGATGTTCACTCTACTGATTATTGCGG

TGATTTTAGTAATCCTGAAGGTGTAGCTGAAACCGTAAGAAGCATTCGGCCGGATATTATTGTCAATGCAGCCGCTC

ACACCGCAGTAGACAAAGCAGAATCAGAACCGGAGTTTGCACAATTAATTAACGCAACAAGTGTCGAAGCGATTGCG

AAAGCAGCAAATGAAGTTGGAGCCTGGGTTATCCATTACTCGACTGATTACGTCTTCCCTGGAAATGGCGATATGCC

ATGGCTGGAGACGGATGCAACCGCACCACTAAATGTTTACGGTGAAACCAAGTTAGCCGGAGAAAAAGCGTTACAGG

AATATTGCGCGAAGCATCTTATTTTCCGGACCAGCTGGGTCTATGCAGGAAAAGGAAATAACTTCGCCAAAACGATG

-continued

TTACGTCTGGCAAAAGAGCGTGAAGAATTAGCGGTTATTAACGATCAGTTTGGTGCGCCAACAGGTGCTGAACTGCT

GGCTGATTGTACAGCACATGCCATTCGTGTCGCACTGAATAAACCGGATGTCGCAGGCTTGTACCATTTGGTAGCCA

GTGGTACCACAACCTGGTACGATTATGCTGCGCTGGTTTTTGAAGAGGCGCGCAAAGCAGGCATTCCCCTTGCACTC

AACAAGCTCAACGCAGTACCAACAACAGCCTATCCTACACCAGCTCGTCGTCCACATAACTCTCGCCTTAATACAGA

AAAATTTCAGCAGAACTTTGCGCTTGTCTTGCCTGACTGGCAGGTTGGCGTGAAACGAATGCTCAATGAATTATTTA

CGACTACAGCAATTTAATAGTTTTTGCATCTTGTTCGTGATGGTGGAGCAAGATGAATTAAAAGGAATGATGAAATG

AAAATGCGTAAAGGTATTATTTTAGCGGGTGGTTCTGGTACACGTCTTTATCCTGTGACTATGGCTGTCAGTAAACA

GCTATTACCTATTTATGATAAACCGATGATCTATTACCCGCTCTCTACACTGATGTTGGCGGGTATTCGCGATATTT

TGATTATCAGTACACCTCAGGATACTCCTCGTTTTCAACAATTGCTGGGTGACGGTAGCCAGTGGGGCCTGAATCTT

CAGTACAAAGTGCAACCTAGCCCAGATGGCCTCGCGCAGGCATTTATCATCGGTGAAGAGTTTATTGGTGGTGATGA

TTGTGCTTTGGTTCTTGGTGATAATATCTTTTACGGTCACGATCTGCCGAAGCTAATGGAGGCCGCTGTTAACAAAG

AAAGTGGTGCAACGGTATTTGCCTATCACGTTAATGATCCAGAACGCTATGGTGTCGTTGAGTTTGATAAAAACGGT

ACGGCAATCAGTCTGGAAGAAAAACCGTTAGAACCAAAGAGTAATTACGCCGTTACAGGTCTGTACTTTTATGATAA

CGACGTGGTTCAGATGGCGAAAAACTTGAAGCCGTCTGCACGTGGTGAGTTAGAAATTACAGATATTAACCGTATTT

ATCTTGAGCAGGGACGTCTGTCTGTCGCGATGATGGGGCGTGGCTACGCGTGGCTGGACACGGGGACTCATCAGAGT

CTGATAGAAGCAAGTAATTTTATTGCGACAATTGAAGAGCGCCAGGGATTGAAGGTTTCCTGTCCTGAAGAGATTGC

ATTTCGTAAAGGTTTTATTGATGTTGAGCAAGTAAGAAAATTAGCTGTACCACTAATAAAGAATAATTATGGGCAGT

ATCTTTATAAAATGACGAAGGATTCAAATTAATGAATGTGATTAGAACTGAAATTGAAGATGTGCTAATTCTGGAGC

CAAGAGTATTTGGTGATGATAGAGGTTTCTTTTATGAGAGCTTTAATCAATCAGCATTTGAACATATTCTAGGCTAT

CCGGTCAGCTTTGTTCAAGACAATCACTCACGTTCATCAAAAAATGTACTCAGAGGCCTTCACTTTCAACGCGGCGA

GTACGCACAAGATAAACTTGTACGCTGCACTCATGGAGCAGTTTTTGATGTTGCTGTTGATATTCGACCCAATTCGG

TATCCTTTGGTAAATGGGTTGGTGTTCTGCTTTCAGCTGATAATAAGCAGCAGTTGTGGATACCAAAAGGGTTTGCT

CATGGCTTTTTGGTTCTGTCTGATATCGCTGAATTTCAATATAAAACTACAAACTATTATCATCCTGAAAGCGATTG

TGGAATATGTTGGAATGATGAACGCATTGCAATTGATTGGCCCCAAACATCAGGGTTAATCCTTTCGCCAAAAGATG

AAAGGCTCTTTACGTTAGATGAGCTTATCAGATTAAAATTAATTGCATGAATACGAATAAATTATCTTTAAGAAGAA

ACGTTATATATCTGGCTGTCGTTCAAGGTAGCAATTATCTTTTACCATTGCTTACATTTCCATATCTTGTAAGAACA

CTTGGTCCTGAAAATTTCGGTATATTCGGTTTTTGCCAAGCGACTATGCTATATATGATAATGTTTGTTGAATATGG

TTTCAATCTCACAGCAACTCAGAGTATTGCCAAAGCAGCAGATAGTAAAGATAAAGTAACGTCTATTTTTTGGGCGG

TGATATTTTCAAAAATAGTTCTTATCGTCATTACATTGATTTTCTTAACGTCGATGACCTTGCTTGTTCCTGAATAT

AACAAGCATGCCGTAATTATATGGTCGTTTGTTCCTGCATTAGTCGGGAATTTAATCTACCCTATCTGGCTGTTTCA

GGGAAAAGAAAAAATGAAATGGCTGACTTTAAGTAGTATTTTATCCCGCTTGGCTATTATCCCTCTAACATTTATTT

TTGTGAACACAAAGTCAGATATAGCAATTGCCGGTTTTATTCAGTCAAGTGCAAATCTGGTTGCTGGAATTATTGCA

CTAGCTATCGTTGTTCATGAAGGTTGGATTGGTAAAGTTACGCTATCATTACATAATGTGCGTCGATCTTTAGCAGA

CGGTTTTCATGTTTTTATTTCCACATCTGCTATTAGTTTATATTCTACGGGAATAGTTATTATCCTGGGATTTATAT

CTGGACCAACGTCCGTAGGGAATTTTAATGCGGCCAATACTATAAGAAACGCGCTTCAAGGGCTATTAAATCCTATC

ACCCAAGCAATATACCCAAGAATATCAAGTACGCTTGTTCTTAATCGTGTGAAGGGTGTGATTTTAATTAAAAAATC

ATTGACCTGCTTGAGTTTGATTGGTGGTGCTTTTTCATTAATTCTGCTCTTGGGTGCATCTATACTAGTAAAAATAA

GTATAGGGCCGGGATATGATAATGCAGTGATTGTGCTAATGATTATATCGCCTCTGCCTTTTCTTATTTCATTAAGT

AATGTCTATGGCATTCAAGTTATGCTGACCCATAATTATAAGAAAGAATTCAGTAAGATTTTAATCGCTGCGGGTTT

GTTGAGTTTGTTGTTGATTTTTCCGCTAACAACTCTTTTTAAAGAGATTGGTGCAGCAATAACATTGCTTGCAACAG

-continued

AGTGCTTAGTTACGTCACTCATGCTGATGTTCGTAAGAAATAATAAATTACTGGTTTGCTGAGGATTTTATGTACGA

TTATATCATTGTTGGTTCTGGTTTGTTTGGTGCCGTTTGTGCGAATGAGTTAAAAAAGCTAAACAAAAAAGTTTTAG

TGATTGAGAAAAGAAATCATATCGGTGGAAATGCGTACACAGAGGACTGTGAGGGTATCCAGATTCATAAATATGGT

GCACATATTTTTCATACCAATGATAAATATATATGGGATTACGTTAATGATTTAGTAGAATTTAATCGTTTTACTAA

TTCTCCACTGGCGATTTATAAAGACAAATTATTCAACCTTCCTTTTAATATGAATACTTTCCACCAAATGTGGGGAG

TTAAAGATCCTCAAGAAGCTCAAAATATCATTAATGCTCAGAAAAAAAAGTATGGTGACAAGGTACCTGAAAATTTG

GAGGAGCAGGCGATTTCATTAGTTGGGGAGGACTTATACCAAGCATTGATAAAGGGTTATACGGAGAAGCAGTGGGG

AAGAAGTGCAAAAGAATTGCCTGCATTTATTATTAAGCGAATCCCAGTGAGATTTACGTTTGATAACAATTATTTTT

CCGATCGCTATCAAGGTATTCCGGTGGGAGGCTACACTAAGCTTATTGAAAAAATGCTTGAAGGTGTGGACGTAAAA

TTAGGCATTGATTTTTTGAAAGACAAAGATTCTCTAGCGAGTAAAGCCCATAGAATCATCTACACTGGACCCATTGA

TCAGTACTTCGACTATAGGTTTGGAGCGTTAGAATATCGCTCTTTAAAATTTGAGACGGAACGCCATGAATTTCCAA

ACTTCCAAGGGAATGCAGTAATAAATTTCACTGATGCTAATGTACCATATACCAGAATAATTGAGCATAAACATTTT

GACTATGTTGAGACAAAGCATACGGTTGTTACAAAAGAATATCCATTAGAGTGGAAAGTTGGCGACGAACCCTACTA

TCCAGTTAATGATAATAAAAACATGGAGCTTTTTAAGAAATATAGAGAGTTAGCTAGCAGAGAAGACAAGGTTATAT

TTGGCGGGCGTTTGGCCGAGTATAAATATTATGATATGCATCAAGTGATATCTGCCGCTCTTTATCAAGTGAAAAAT

ATAATGAGTACGGATTAATGATCTATCTTGTAATTAGTGTCTTTCTCATTACAGCATTTATCTGTTTATATCTTAAG

AAGGATATATTTTATCCAGCCGTATGCGTTAATATCATCTTCGCACTGGTCTTATTGGGATATGAAATAACGTCAGA

TATATATGCTTTTCAGTTAAATGACGCTACGTTGATTTTTCTACTTTGCAATGTTTTGACATTTACCCTGTCATGTT

TATTGACGGAAAGTGTATTAGATCTAAATATCAGAAAAGTCAATAATGCTATTTATAGCATACCATCGAAGAAAGTG

CATAATGTAGGCTTGTTAGTTATTTCTTTTTCGATGATATATATATGCATGAGGTTAAGTAACTACCAGTTCGGGAC

TAGCTTACTTAGCTATATGAATTTGATAAGAGATGCTGATGTTGAAGACACATCAAGAAATTTCTCAGCATACATGC

AGCCAATCATTCTAACTACTTTTGCTTTATTTATTTGGTCTAAAAAATTTACTAATACAAAGGTAAGTAAAACATTT

ACTTTACTTGTTTTTATTGTATTCATCTTTGCAATTATACTGAATACTGGTAAGCAAATTGTCTTTATGGTTATCAT

CTCTTATGCATTCATCGTAGGTGTTAATAGAGTAAAACATTATGTTTATCTTATTACAGCTGTAGGTGTTCTATTCT

CCTTGTATATGCTCTTTTTACGTGGACTGCCTGGGGGGATGGCATATTATCTATCCATGTATTTGGTCAGCCCTATA

ATCGCGTTTCAGGAGTTTTATTTTCAGCAAGTATCTAACTCTGCCAGTTCTCATGTCTTTTGGTTTTTTGAAAGGCT

GATGGGGCTATTAACAGGTGGAGTCTCTATGTCGTTGCATAAAGAATTTGTGTGGGTGGGTTTGCCAACAAATGTTT

ATACTGCTTTTTCGGATTATGTTTATATTTCCGCGGAGCTAAGCTATTTGATGATGGTTATTCATGGCTGTATTTCA

GGTGTTTTATGGAGATTGTCTCGAAATTACATATCTGTGAAAATATTTTATTCATATTTTATTTATACCTTTTCTTT

CATTTTTTATCATGAAAGCTTCATGACTAATATTAGCAGTTGGATACAAATAACTCTTTGTATCATAGTATTCTCTC

AATTTCTTAAGGCCCAGAAAATAAAGTGAAAATGTATTTTTTGAATGATTTAAATTTCTCTAGACGCGATGCTGGAT

TTAAAGCAAGAAAAGATGCACTGGACATTGCTTCAGATTATGAAAACATTTCTGTTGTTAACATTCCTCTATGGGGT

GGAGTAGTCCAGAGAATTATTAGTTCTGTTAAGCTTAGTACATTTCTCTGCGGTCTTGAAAATAAAGATGTTTTAAT

TTTCAATTTCCCGATGGCCAAACCATTTTGGCATATATTGTCATTCTTTCACCGCCTTCTAAAATTTAGAATAGTAC

CTCTGATTCATGATATTGATGAATTAAGAGGAGGAGGGGGTAGTGATTCTGTGCGGCTTGCTACCTGTGATATGGTC

ATAAGTCACAATCCACAAATGACAAAGTACCTTAGTAAATATATGTCTCAGGATAAAATCAAAGACATAAAAATATT

TGATTACCTCGTCTCATCTGATGTGGAGCATCGAGATGTTACGGATAAGCAACGAGGGGTCATATATGCTGGCAACC

TTTCTAGGCATAAATGTTCTTTCATATATACTGAAGGATGCGATTTTACTCTCTTTGGTGTCAACTATGAAAATAAA

GATAATCCTAAATATCTTGGAAGTTTTGATGCTCAATCTCCGGAAAAGATTAACCTCCCAGGCATGCAATTTGGACT

CATTTGGGATGGAGATTCTGTCGAAACCTGTAGTGGTGCCTTTGGCGACTATTTAAAGTTTAATAACCCTCATAAGA

CATCTCTTTATCTTTCAATGGAACTTCCAGTATTTATATGGGATAAAGCCGCCCTTGCGGATTTCATTGTAGATAAT

-continued

AGAATAGGATATGCAGTGGGATCAATCAAAGAAATGCAAGAGATTGTTGACTCCATGACAATAGAAACTTATAAGCA

AATTAGTGAGAATACAAAAATTATTTCTCAGAAAATTCGAACAGGAAGTTACTTCAGGGATGTTCTTGAAGAGGTGA

TCGATGATCTTAAAACTCGCTAAACGATATGGTCTCTGTGGTTTTATTCGGCTTGTTAGAGATGTCTTATTGACTCG

TGTATTTTACCGGAACTGTAGAATTATTCGATTTCCCTGCTATATTCGCAATGATGGTAGCATTAATTTTGGTGAAA

ATTTCACAAGTGGAGTCGGTCTCAGGCTGGATGCATTTGGACGTGGCGTGATTTTTTTTTCCGATAATGTGCAAGTT

AACGACTATGTTCATATCGCCTCAATTGAGAGCGTTACGATAGGTCGGGATACGCTTATTGCAAGTAAAGTATTTAT

TACCGATCATAATCACGGTTCCTTTAAGCACTCTGATCCAATGAGTTCGCCAAATATACCTCCAGACATGCGCACGT

TGGAATCTTCAGCTGTTGTAATTGGCCAGAGGGTTTGGTTGGGTGAGAATGTGACGGTTTTGCCTGGAACAATTATT

GGTAATGGAGTCGTAGTCGGCGCCAATTCTGTTGTTAGAGGTTCTATTCCCGAAAATACTGTCATTGCGGGAGTACC

AGCAAAAATCATAAAGAAATACAATCATGAGACCAAATTATGGGAAAAAGCATAGTCGTTGTTTCTGCGGTCAATTT

TACCACTGGCGGTCCATTTACCATTTTGAAAAAATTTTTGGCAGCAACTAATAATAAAGAAAATGTCAGTTTTATCG

CATTAGTCCATTCTGCTAAAGAGTTAAAAGAAAGTTATCCATGGGTTAAATTCATTGAGTTTCCTGAGGTTAAAGGG

TCGTGGCTAAAACGTTTGCACTTTGAATATGTAGTTTGTAAAAAACTTTCAAAAGAGCTGAATGCTACGCATTGGAT

TTGTCTGCATGATATTACGGCCAATGTCGTCACTAAAAAAAGATATGTGTATTGTCATAACCCTGCCCCTTTTTATA

AAGGAATTTTATTCCGTGAAATTCTTATGGAGCCTAGCTTTTTCTTATTTAAAATGCTATACGGGCTGATATATAAA

ATAAACATTAAAAAAAATACTGCAGTGTTTGTTCAACAATTCTGGATGAAAGAAAAATTTATCAAGAAATATTCTAT

AAATAACATCATTGTCAGTCGGCCAGAAATTAAATTATCTGATAAAAGCCAACTTACTGATGATGATTCTCAATTTA

AGAATAACCCTTCTGAGTTGACAATATTTTACCCTGCTGTTCCACGAGTATTTAAAAATTACGAGCTTATTATTAGT

GCAGCAAGGAAATTGAAAGAACAATCCAATATTAAATTTCTGCTTACTATCAGTGGTACAGAAAATGCGTATGCAAA

ATATATTATCAGTCTTGCAGAAGGACTGGATAATGTTCATTTCCTCGGGTACTTGGATAAAGAAAAAATCGATCATT

GTTATAATATTTCAGATATAGTTTGTTTTCCCTCTAGGTTAGAAACATGGGGATTGCCGTTGTCTGAGGCTAAAGAG

CGAGGTAAGTGGGTATTAGCATCAGATTTCCCATTTACTAGAGAAACTCTTGGTAGTTATGAAAAGAAAGCTTTTTT

TGATTCTAATAACGATGACATGTTAGTTAAACTTATTATTGACTTCAAAAAAGGTAACCTCAAAAAAGATATCTCTG

ATGCAAATTTCATTTATCGTAATGAAAATGTATTAGTTGGGTTTGATGAACTAGTTAATTTTATTACTGAAGAACAT

TGAAATGGTATATATAATAATCGTTTCCCACGGACATGAAGACTACATCAAAAAATTACTCGAAAATCTTAATGCTG

ACGATGAGCACTACAAGATTATCGTACGCGACAACAAAGACTCTCTATTATTGAAACAAATATGCCAGCATTATGCA

GGCCTGGACTATATTAGTGGAGGTGTATACGGCTTTGGTCATAATAATAATATTGCGGTGGCGTATGTAAAGGAAAA

ATATAGACCCGCAGATGATGATTACATTTTGTTTTTGAATCCCGATATCATCATGAAGCATGATGATTTGCTGACAT

ATATTAAATATGTCGAAAGTAAGCGTTATGCTTTTAGTACATTATGCCTGTTCCGAGATGAAGCGAAATCTTTACAT

GATTATTCCGTAAGAAAATTTCCTGTGCTTTCTGATTTTATTGTGTCATTTATGTTAGGGATTAATAAAACAAAAAT

TCCTAAAGAAAGTATCTATTCTGATACGGTTGTTGATTGGTGCGCAGGATCATTTATGCTGGTACGTTTTTCAGATT

TTGTGCGTGTAAATGGCTTCGATCAAGGTTACTTTATGTACTGTGAAGATATTGACCTGTGCTTGAGGCTTAGCCTG

GCTGGTGTCAGACTTCATTATGTTCCCGCTTTTCATGCGATACATTATGCTCATCATGACAATCGAAGTTTTTTTTC

AAAAGCCTTCAGATGGCACTTAAAAAGTACTTTTAGATATTTAGCCAGAAAACGTATTTTATCAAATCGCAACTTTG

ATCGAATTTCATCAGTTTTTCACCCGTAAGAGCTCGGTACCCGGGCCTAGGGTGTAGGCTGGAGCTGCTTCGAAGTT

CCTATACTTTCTAGAGAATAGGAACTTCGGAATAGGAACTAAGGAGGATATTCATATCCGTCGACGGCGGCCGCCCT

GCAGGCATGCAAGCTTGATCCATATGGATCGCTAGCTTAATTAAATAAAGCCGTAAGCATATAAGCATGGATAAGCT

ATTTATACTTTAATAAGTACTTTGTATACTTATTTGCGAACATTCCAGGCCGCGAGCATTCAGCGCGGTGATCACAC

CTGACAGGAGTATGTAATGTCCAAGCAACAGATCGGCGTAGTCGGTATGGCAGTGATGGGACGCAACCTTGCGCTCA

ACATCGAAAGCCGTGGTTATACCGTCTCTATTTTCAACCGTTCCCGTGAGAAGACGGAAGAAGTGATTGCCGAAAAT

-continued

CCAGGCAAGAAACTGGTTCCTTACTATACGGTGAAAGAGTTTGTCGAATCTCTGGAAACGCCTCGTCGCATCCTGTT

AATGGTGAAAGCAGGTGCAGGCACGGATGCTGCTATTGATTCCCTCAAACCATATCTCGATAAAGGAGACATCATCA

TTGATGGTGGTAACACCTTCTTCCAGGACACTATTCGTCGTAATCGTGAGCTTTCAGCAGAGGGCTTTAACTTCATC

GGTACGGGTGTTTCTGGCGGTGAAGAGGGGGCGCTGAAAGGTCCTTCTATTATGCCTGGTGGCCAGAAAGAAGCCTA

TGAATTGGTAGCACCGATCCTGACCAAAATCGCCGCCGTAGCTGAAGACGGTGAACCATGCGTTACCTATATTGGTG

CCGATGGCGCAGGTCACTATGTGAAGATGGTTCACAACGGTATTGAATACGGCGATATGCAGCTGATTGCTGAAGCC

TATTCTCTGCTTAAAGGTGGCCTGAACCTCACCAACGAAGAACTGGCGCAGACCTTTACCGAGTGGAATAACGGTGA

ACTGAGCAGTTACCTGATCGACATCACCAAAGATATCTTCACCAAAAAAGATGAAGACGGTAACTACCTGGTTGATG

TGATCCTGGATGAAGCGGCTAACAAAGGTACGGGTAAATGGACCAGCCAGAGCGCGCTGGATCTCGGCGAACCGCTG

TCGCTGATTACCGAGTCTGTGTTTGCACGTTATATCTCTTCTCTGAAAGATCAGCGTGTTGCCGCATCTAAAGTTCT

CTCTGGTCCGCAAGCACAGCCAGCAGGCGACAAGGCTGAGTTCATCGAAAAAGTTCGTCGTGCGCTGTATCTGGGCA

AAATCGTTTCTTACGCCCAGGGCTTCTCTCAGCTGCGTGCTGCGTCTGAAGAGTACAACTGGGATCTGAACTACGGC

GAAATCGCGAAGATTTTCCGTGCTGGCTGCATCATCCGTGCGCAGTTCCTGCAAAAAATCACCGATGCTTATGCCGA

AAATCCACAGATCGCTAACCTGTTGCTGGCTCCGTACTTCAAGCAAATTGCCGATGACTACCAGCAGGCGCTGCGTG

ATGTCGTTGCTTATGCAGTACAGAACGGTATTCCGGTTCCGACCTTCTCCGCAGCGGTTGCCTATTACGACAGCTAC

CGTGCTGCTGTTCTGCCTGCGAACCTGATCCAGGCACAGCGTGACTATTTTGGTGCGCATACTTATAAGCGTATTGA

TAAAGAAGGTGTGTTCCATACCGAATGGCTGGATTAA (example O18A rfb locus nucleotide sequence-O18A-EPA production strain BVEC-L-00559)

SEQ ID NO: 17

ATGACGAATTTAAAAGCAGTTATTCCTGTAGCGGGTCTCGGGATGCATATGTTGCCTGCCACTAAGGCGATACCCAA

AGAGATGCTACCAATCGTCGACAAGCCAATGATTCAGTACATTGTTGACGAGATTGTGGCTGCAGGGATCAAAGAAA

TCCTCCTGGTAACTCACGCGTCCAAGAACGCGGTCGAAAACCACTTCGACACCTCTTATGAGTTAGAATCACTCCTT

GAGCAGCGCGTGAAGCGTCAACTGCTGGCGGAAGTACAGTCCATCTGTCCGCCGGGCGTGACCATTATGAACGTGCG

TCAGGGCGAACCTTTAGGTTTAGGCCACTCCATTTTGTGTGCGCGACCTGCCATTGGTGACAACCCATTTGTCGTGG

TACTGCCAGACGTTGTGATCGACGATGCCAGCGCCGACCCGCTACGTTACAACCTTGCTGCCATGATTGCACGTTTC

AACGAAACGGGCCGCAGCCAGGTGCTGGCAAAACGTATGCCGGGTGACCTCTCTGAATACTCCGTCATCCAGACTAA

AGAGCCGCTGGACCGTGAGGGTAAAGTCAGCCGCATTGTTGAATTTATCGAAAAACCGGATCAGCCGCAGACGCTGG

ACTCAGACATCATGGCCGTAGGTCGCTATGTGCTTTCTGCCGATATTTGGCCGGAACTGGAACGTACTCAGCCTGGT

GCATGGGGACGTATTCAGCTGACTGATGCTATTGCCGAGCTGGCGAAAAAACAATCCGTTGATGCAATGCTGATGAC

CGGCGACAGTTACGACTGCGGCAAAAAAATGGGCTATATGCAGGCGTTTGTGAAGTATGGCCTACGCAACCTGAAAG

AAGGGGCGAAGTTCCGTAAAGGTATTGAGAAGCTGTTAAGCGAATAATGAAAATCTGACCGGATGTAACGGTTGATA

AGAAAATTATAACGGCAGTGAAAATTCGCAGCAAAAGTAATTTGTTGCGAATCTTCCTGCCGTTGTTTTATATAAAC

CATCAGAATAACAACGAGTTAGCAGTAGGGTTTTATTCAAAGTTTTCCAGGATTTTCCTTGTTTCCAGAGCGGATTG

GTAAGACAATTAGCGTTTGAATTTTTCGGGTTTAGCGCGAGTGGGTAACGCTCGTCACATCATAGGCATGCATGCAG

TGCTCTGGTAGCTGTAAAGCCAGGGGCGGTAGCGTGCATTAATACCTCTATTAATCAAACTGAGAGCCGCTTATTTC

ACAGCATGCTCTGAAGTAATATGGAATAAATTAAGTGAAAATACTTGTTACTGGTGGCGCAGGATTTATTGGTTCAG

CTGTAGTTCGTCACATTATAAATAATACGCAGGATAGTGTTGTTAATGTCGATAAATTAACGTACGCCGGAAACCGG

GAATCACTTGCTGATGTTTCTGATTCTGAACGCTATGTTTTTGAACATGCGGATATTTGCGATGCACCTGCAATGGC

ACGGATTTTTGCTCAGCATCAGCCGGATGCAGTGATGCACCTGGCTGCTGAAAGCCATGTTGACCGTTCAATTACAG

GCCCTGCGGCATTTATTGAAACCAATATTGTTGGTACTTATGTCCTTTTGGAAGCCGCTCGCAATTACTGGTCTGCT

CTTGATAGCGACAAGAAAAATAGCTTCCGTTTTCATCATATTTCTACTGACGAAGTCTATGGTGATTTGCCTCATCC

-continued

AGATGAAGTAAATAATACAGAAGAATTACCCTTATTTACTGAGACGACAGCTTACGCGCCAAGCAGCCCTTATTCCG

CATCCAAAGCATCCAGCGATCATTTAGTCCGCGCGTGGAAACGTACATATGGTTTACCGACAATTGTGACTAATTGC

TCGAACAACTATGGTCCTTATCATTTCCCGGAAAAGCTTATTCCACTGGTTATTCTTAATGCACTGGAAGGTAAGGC

ATTACCTATTTATGGCAAAGGAGATCAGATCCGCGACTGGTTGTATGTTGAAGATCATGCGCGTGCGTTATATACCG

TCGTAACCGAAGGTAAAGCGGGTGAAACTTATAACATTGGTGGGCACAACGAAAAGAAAAACATCGATGTAGTGCTC

ACTATTTGTGATTTGCTGGATGAGATTGTACCGAAAGAGAAATCTTATCGTGAGCAAATCACTTATGTTGCTGATCG

TCCGGGACACGATCGCCGCTATGCTATTGATGCTGAGAAGATTGGTCGCGCATTGGGATGGAAACCACAGGAAACGT

TTGAGAGCGGGATTCGTAAAACGGTGGAATGGTACCTGTCCAATACAAAATGGGTTGATAATGTGAAAAGTGGTGCC

TATCAATCGTGGATTGAACAGAACTATGAGGGCCGCCAGTAATGAATATCCTCCTTTTTGGCAAAACAGGGCAGGTA

GGTTGGGAACTACAGCGTGCTCTGGCACCTTTGGGTAATTTGATTGCTTTTGATGTTCACTCTACTGATTATTGCGG

TGATTTTAGTAATCCTGAAGGTGTAGCTGAAACCGTAAGAAGCATTCGGCCGGATATTATTGTCAATGCAGCCGCTC

ACACCGCAGTAGACAAAGCAGAATCAGAACCGGAGTTTGCACAATTAATTAACGCAACAAGTGTCGAAGCGATTGCG

AAAGCAGCAAATGAAGTTGGAGCCTGGGTTATCCATTACTCGACTGATTACGTCTTCCCTGGAAATGGCGATATGCC

ATGGCTGGAGACGGATGCAACCGCACCACTAAATGTTTACGGTGAAACCAAGTTAGCCGGAGAAAAAGCGTTACAGG

AATATTGCGCGAAGCATCTTATTTTCCGGACCAGCTGGGTCTATGCAGGAAAAGGAAATAACTTCGCCAAAACGATG

TTACGTCTGGCAAAAGAGCGTGAAGAATTAGCGGTTATTAACGATCAGTTTGGTGCGCCAACAGGTGCTGAACTGCT

GGCTGATTGTACAGCACATGCCATTCGTGTCGCACTGAATAAACCGGATGTCGCAGGCTTGTACCATTTGGTAGCCA

GTGGTACCACAACCTGGTACGATTATGCTGCGCTGGTTTTTGAAGAGGCGCGCAAAGCAGGCATTCCCCTTGCACTC

AACAAGCTCAACGCAGTACCAACAACAGCCTATCCTACACCAGCTCGTCGTCCACATAACTCTCGCCTTAATACAGA

AAAATTTCAGCAGAACTTTGCGCTTGTCTTGCCTGACTGGCAGGTTGGCGTGAAACGAATGCTCAATGAATTATTTA

CGACTACAGCAATTTAATAGTTTTTGCATCTTGTTCGTGATGGTGGAGCAAGATGAATTAAAAGGAATGATGAAATG

AAAATGCGTAAAGGTATTATTTTAGCGGGTGGTTCTGGTACACGTCTTTATCCTGTGACTATGGCTGTCAGTAAACA

GCTATTACCTATTTATGATAAACCGATGATCTATTACCCGCTCTCTACACTGATGTTGGCGGGTATTCGCGATATTT

TGATTATCAGTACACCTCAGGATACTCCTCGTTTTCAACAATTGCTGGGTGACGGTAGCCAGTGGGGCCTGAATCTT

CAGTACAAAGTGCAACCTAGCCCAGATGGCCTCGCGCAGGCATTTATCATCGGTGAAGAGTTTATTGGTGGTGATGA

TTGTGCTTTGGTTCTTGGTGATAATATCTTTTACGGTCACGATCTGCCGAAGCTAATGGAGGCCGCTGTTAACAAAG

AAAGTGGTGCAACGGTATTTGCCTATCACGTTAATGATCCAGAACGCTATGGTGTCGTTGAGTTTGATAAAAACGGT

ACGGCAATCAGTCTGGAAGAAAAACCGTTAGAACCAAAGAGTAATTACGCCGTTACAGGTCTGTACTTTTATGATAA

CGACGTGGTTCAGATGGCGAAAAACTTGAAGCCGTCTGCACGTGGTGAGTTAGAAATTACAGATATTAACCGTATTT

ATCTTGAGCAGGGACGTCTGTCTGTCGCGATGATGGGGCGTGGCTACGCGTGGCTGGACACGGGGACTCATCAGAGT

CTGATAGAAGCAAGTAATTTTATTGCGACAATTGAAGAGCGCCAGGGATTGAAGGTTTCCTGTCCTGAAGAGATTGC

ATTTCGTAAAGGTTTTATTGATGTTGAGCAAGTAAGAAAATTAGCTGTACCACTAATAAAGAATAATTATGGGCAGT

ATCTTTATAAAATGACGAAGGATTCAAATTAATGAATGTGATTAGAACTGAAATTGAAGATGTGCTAATTCTGGAGC

CAAGAGTATTTGGTGATGATAGAGGTTTCTTTTATGAGAGCTTTAATCAATCAGCATTTGAACATATTCTAGGCTAT

CCGGTCAGCTTTGTTCAAGACAATCACTCACGTTCATCAAAAAATGTACTCAGAGGCCTTCACTTTCAACGCGGCGA

GTACGCACAAGATAAACTTGTACGCTGCACTCATGGAGCAGTTTTTGATGTTGCTGTTGATATTCGACCCAATTCGG

TATCCTTTGGTAAATGGGTTGGTGTTCTGCTTTCAGCTGATAATAAGCAGCAGTTGTGGATACCAAAAGGGTTTGCT

CATGGCTTTTTGGTTCTGTCTGATATCGCTGAATTTCAATATAAAACTACAAACTATTATCATCCTGAAAGCGATTG

TGGAATATGTTGGAATGATGAACGCATTGCAATTGATTGGCCCCAAACATCAGGGTTAATCCTTTCGCCAAAAGATG

AAAGGCTCTTTACGTTAGATGAGCTTATCAGATTAAAATTAATTGCATGAGGCCGGCCTTAAGGAGGACTAGTCCCG

GCGCGCCATGAGTTTAATCAAAAACAGTTTTTGGAACCTTTGCGGGTATGTACTTCCAGCTATTGTGACACTACCAG

-continued

CTTTGGGTATTATGGGGCGAAAATTAGGCCCAGAATTATTTGGTGTATTCACTTTGGCATTAGCTGTTGTGGGTTAT

GCAAGCATTTTTGATGCAGGCCTTACTCGCGCAGTGATACGAGAAGTCGCAATTGAAAAAGATAATGAAGAAAATAA

GTTGAAAATTATTTCTTCAGCGACAGTTGTAATTATTTATTTGAGTTTGGCCGCCTCACTCTTATTATTTTTTTTA

GTGGTCATATCGCATTGCTACTGAACATTAGTGAGACTTTTTTTCATAATGTAAGTGTCTCGCTTAAAATTCTCGCA

GCATCCATACCATTATTTTTGATTACTCAAATATGGTTGTCAATTTTAGAAGGTGAAGAAAGATTTGGTTTACTTAA

TATCTACAAATCAATTACGGGAGTGATATTAGCAATCTCACCGGCATTATTTATACTTATTAAACCCTCTTTGATGT

ATGCGATAATAGGCTTAGTTCTAGCAAGGTTTTTATGTTTTATTTTGGCTTTTATAATTTGTCACGATAAAGTGCTT

AAAGCTAAACTAACAATCGATATACCAACAATTAAAAGATTGTTTATGTTCGGTGGTTGGATTACAGTAAGTAATAT

CATCAGCCCTGTGCTATCATATTTTGATAGGTTTATTGTTTCAAATCAACTTGGGGCTGCTAATGTTGCTTTTTATA

CTGCACCATCAGAAATTATTTCTCGGCTTAGTATAATTCCAGGTGCGTTTTCAAGAGCCTTATTTCCAAGATTAGCT

AATGCAAATAATTCCGCTGAAAGATATAAAACGAAAAGATTAATTACAATTTCACTTTTAATAATCATCACCCCTAT

TTTTTGTATTGGCGTGTTATTTTCAGAGAAGATAATGGTTTTATGGATGGGGGCATCATTTTTTGGTGAGCCTGGTT

TGGTATTATCAATATTACTGATTGGCTTTATTTTTAATGGATTGGCACAAGTACCATTTGCCAGTATTCAATCCCGA

GGTCATGCTAAGATAACTGCATTTGTTCATCTCTTAGAGTTGTTTCCTTATTTATTACTTTTATTTTACCTCATAAA

AGCACATGGGGTTGTTGGCGCGGGTATTGCGTGGTCAGTGAGGATGATAGTAGATTATATAGCATTAAGTCTTTTGG

ACGGTAAGTATATTAATAAATAAAATTCAAAATGCAAGTTAATAACTCATGGCTTTATTTGGGTAGGTGACAATTTA

TAATGATATATATATTAACTTTAACTCTTCTTCTAGTTATAGCCATAATGTTTTCTCTTCTCGGCACAAAAAGTAGG

ATCACATCTCCATTACCTTTGCATTTTTTACCATGGTTACTAACTTTAATTGTCGGGATAAGTAATTACGATCAATT

TTACGAGTTTAATGAAAGAAGCTTTTACTCTTTGTTGATTTGGTTTACAGTTATTTTTATATTTTATTTCATAGGGG

AACTGGTTAATTATAAACGTGAAAATATAAATGTTTATTATGGTCTTTCACATATTAAATATGAATGTAAAAAATAT

TGGATCATTGTCATCCCAATTTCATTATATACCATTTTCGAAATATATATGGTTGGTATGGGGGGAGCAGATGGATT

CTTTCTCAATTTACGTCTTGCAAATACATTGGAGGGCTATACGGGTAAAAAATTTATCTTAATGCCTGCTGTATATC

CTCTAATGATGGCTATGTTCGCAATTGTTTGTCTAACAAAAACTTCCAAATTAAATAAATACTCCATTTATTTCTGG

ATGTTTTTGTATTGTATTGGCACAATGGGAAAAATTTTCAATATTAACGCCAATATTGACATATTTAATTATTTATGA

CTTCAAACATAGATTAAAAGTAAAAAAAACAATAAAGTTTACATTGTTGATAATTATATTAGCTTTAACTTTGCATT

TTACACGTATGGCTGAGAATGACCACTCAACATTTTTATCTATTTTAGGGCTCTATATTTATTCACCAATAATTGCT

TTAGGCCAGTTGAATGAAGTAAATAGTAGTCATTTTGGTGAGTATACGTTTAGATTCATATATGCTATAACTAATAA

AATTGGCCTTATTAAAGAATTGCCAGTAAATACTATTCTTGACTATTCATACGTTCCTGTACCAACAAATGTATATA

CTGCACTTCAACCATTTTACCAGGATTTTGGTTATACTGGCATCATATTTGGAGCAGTATTATACGGACTAATATAT

GTGAGTTTATACACGGCCGGTGTTCGTGGAAATAATACACAGGCATTACTGATTTACGCATTGTTTTCAGTTAGCAG

TGCAACGGCTTTCTTCGCTGAAACGCTAGTAACGAATTTAGCTGGAAATGTGATGTTAGTATTATGTACCATCTTAC

TATGGCGATTTACAGTAATATGCAAACCAGTACAGTAACCATTCTAATGGCCACCTACAATGGCGAGGCCTTCATCA

AAAATCAGATTTTGTCACTACAACAACAAACATTTTCTAACTGGCGGTTATTTATTCAGGATGATGGGTCTACAGAC

AATACTATATCTATAATAAAAAACTTCCAAAAATCTGACTCCAGAATTCGGCTAGTTGATGATAATTTGAAAGGTCA

AGGTGCAGGAAAAAATTTTTTATCGCTGATAAAGTACAGCGAGACAGATTATACAATTTATTGTGACCAAGATGATA

TTTGGTTAGAAAACAAAATATTTGAATTAGTAAAGTATGCAAATGAAATTAAATTGAATGTATCAGATGCGCCTTCG

CTAGTTTATGCTGATGGCTATGCTTATATGGATGGTGAGGGTACAATCGATTTTTCTGGGATATCTAACAATCATGC

TGATCAATTAAAGGATTTTCTTTTTTTTAATGGTGGATACCAAGGATGTTCTATTATGTTCAATCGTGCAATGACCA

AATTTCTTCTGAATTATCGAGGATTTGTATATCTACATGACGATATCACAACATTAGCTGCATACGCTCTTGGTAAA

GTTTATTTTCTCCCGAAATACCTTATGTTATATAGACAGCACACGAATGCGGTAACTGGTATCAAAACATTCCGCAA

-continued

TGGATTGACTTCTAAATTTAAATCACCAGTAAACTATCTTTTATCACGAAAACATTATCAGGTAAAAAAATCTTTTT

TTGAATGTAACAGCTCTATCTTATCAGAGACGAATAAAAAAGTTTTTTTGGATTTTATTTCATTTTGTGAATCAAAT

AATAAATTTACAGATTTTTTTAAGTTATGGCGAGGTGGGTTTAGATTAAATAACAGTAGAACTAAATTATTATTAAA

ATTCTTAATACGGAGAAAATTTAGCGAATGATTTCAATACTTACACCTACTTTTAATCGGCAACATACTTTATCAAG

GCTATTCAATTCTCTTATATTACAAACTGATAAAGATTTTGAGTGGATAATAATTGATGATGGTAGTATAGATGCAA

CAGCGGTACTTGTAGAAGATTTTAGAAAAAAATGTGATTTTGACTTGATTTATTGCTATCAGGAAAATAATGGTAAG

CCCATGGCTTTAAACGCTGGTGTTAAAGCTTGTAGAGGCGATTATATCTTTATTGTTGACAGTGATGATGCACTAAC

TCCCGATGCCATAAAATTAATTAAAGAATCAATACATGATTGCTTATCTGAGAAGGAAAGTTTCAGCGGAGTCGGTT

TTAGAAAAGCATATATAAAAGGGGGGATTATTGGTAATGATTTAAATAATTCTTCAGAACATATATACTATTTAAAT

GCGACTGAGATTAGCAATTTAATAAATGGTGATGTTGCATATTGTTTTAAAAAAGAAAGTTTGGTAAAAAAATCCATT

CCCCCGTATAGAAGATGAAAAATTTGTTCCAGAATTATATATTTGGAATAAAATAACTGACAAGGCGAAGATTCGAT

TTAACATAAGCAAAGTTATATATCTTTGTGAGTATCTTGATGATGGTCTTTCTAAAAATTTCCATAACCAGCTTAAA

AAATACCCAAAGGGGTTTAAGATTTATTACAAAGATCAAAGAAAACGAGAGAAAACTTATATAAAAAAAACAAAGAT

GCTAATTAGATATTTGCAATGTTGTTATTATGAGAAAATAAAATGAAAATACTATTTGTCATTACAGGTTTAGGCCT

TGGAGGTGCTGAGAAGCAGGTTTGTCTTTTAGCTGATAAATTAAGTTTAAGCGGGCACCATGTAAAGATTATTTCAC

TTGGACATATGTCTAATAATAAAGTCTTTCCTAGCGAAAATAATGTTAATGTCATTAATGTAAATATGTCAAAAAAC

ATTTCTGGAGTTATAAAAGGTTGTGTCAGAATTAGAGATGTTATAGCTAATTTCAAACCAGACATTGTACACAGTCA

TATGTTTCATGCAAACATTATCACTAGATTGTCTGTAATTGGAATCAAAAACAGACCTGGTATTATATCAACTGCAC

ATAATAAAAATGAAGGTGGGTATTTCAGAATGCTCACATATAGAATAACCGATTGTTTAAGTGATTGTTGTACAAAT

GTTAGCAAAGAAGCAGTGGATGAGTTTTTACGGATAAAAGCCTTTAATCCCGCTAAAGCAATTACTATGTATAATGG

GATAGATACCAATAAATTTAAATTTGATTTATTGGCAAGGAGGGAAATTCGAGACGGTATTAATATAAAAAATGATG

ATATATTATTACTTGCTGCAGGTCGTTTAACGTTAGCTAAAGATTATCCTAATTTATTGAATGCAATGACTCTGCTT

CCTGAACACTTTAAACTTATTATTATTGGTGATGGTGAATTGCGTGACGAAATTAATATGCTTATAAAAAAATTGCA

ATTATCTAATAGGGTGTCCTTGTTGGGAGTTAAAAAAAATATTGCTCCCTATTTTTCTGCATGTGATATTTTTGTTC

TCTCTTCTCGTTGGGAAGGATTTGGATTAGTCGTGGCAGAAGCTATGTCATGTGAGCGAATTGTTGTTGGCACGGAT

TCAGGGGGAGTAAGAGAAGTTATTGGTGACGATGATTTTCTTGTACCCATATCTGATTCAACACAACTTGCAAGCAA

AATTGAAAAATTGTCTTTGAGCCAGATACGTGATCACATTGGTTTTCGGAATCGTGAGCGTATTTTAAAAAATTTCT

CAATAGATACTATTATTATGCAGTGGCAAGAACTCTATGGAACTATAATTTGCTCAAAACATGAAAGGTAGATTTAT

ATTTGGAACGTGTCTTTTGTTTGAATTTAATTCAATCTCAATTGAGATTTTTGTATTTCAAAAATACCATCATAGCT

AACGATGATTGGTATTTATTTTAAGATGCTTTCTATAAATATATTGACGTTTTTAATGCGCCGAAACGATTGGGCTG

GGAACAGAGAAGTAAAACTGTTTTGAGAATGAAGAGTTTTTGAGATGTTTATGGATATTAAAAATTGATCCAGTGAA

TTAATTATTTATAATAAATCAAGATTTAATGTTAATAAATGATAATCTTTTCTGACACTCATATTAATTATGAGTGG

TACGTTTGGTAAACGGTAAACTATTATATGACAGCTAGAACAACTAAAGTTTTGCACTTACAATTACTCCCACTCTT

AAGTGGCGTTCAAAGGGTAACATTAAACGAAATTAGTGCGTTATATACTGATTATGATTATACACTAGTTTGCTCAA

AAAAAGGTCCACTAACAAAAGCATTGCTGGAATATGATGTCGATTGTCATTGTATCCCCGAACTTACGAGAGAAATT

ACCGTAAAGAATGATTTTAAAGCATTGTTCAAGCTTTATAAGTTCATAAAAAAAGAAAAATTTGACATTGTGCATAC

ACATTCTTCAAAAACAGGTATTTTGGGGCGAGTTGCTGCCAAATTAGCACGTGTTGGAAAGGTGATCCACACTGTAC

ATGGTTTTTCTTTTCCAGCCGCATCTAGTAAAAAAAGTTATTACCTTTATTTTTTCATGGAATGGATAGCAAAGTTC

TTTACGGATAAGTTAATCGTCTTGAATGTAGATGATGAATATATAGCAATAAACAAATTAAAATTCAAGCGGGATAA

AGTTTTTTTAATTCCTAATGGAGTAGACACTGATAAGTTTTCTCCTTTAGAAAATAAAATTTATAGTAGCACCTTGA

ATCTAGTAATGGTTGGTAGATTATCCAAGCAAAAAGATCCTGAGACATTATTGCTTGCTGTTGAAAAACTGCTGAAT

-continued

GAAAATGTTAATGTTAAGCTGACACTTGTAGGAGATGGTGAACTAAAAGAACAGTTAGAAAGCAGGTTCAAACGGCA

AGATGGACGTATAATTTTTCATGGATGGTCAGATAACATTGTTAATATTTTAAAAGTTAATGATCTTTTTATATTAC

CTTCTCTTTGGGAGGGTATGCCATTAGCAATTTTAGAAGCATTGAGCTGTGGACTTCCATGTATAGTCACTAATATT

CCAGGTAATAATAGCTTAATAGAAGATGGCTATAATGGTTGTTTGTTTGAAATTAGAGATTGTCAGTTATTATCTCA

AAAAATCATGTCATATGTTGGTAAGCCAGAACTGATTGCACAGCAATCTACCAATGCACGATCATTTATTCTGAAAA

ATTATGGATTAGTTAAAAGAAATAATAAGGTCAGACAGCTATATGATAATTAAGAGCTCGGTACCCGGGCCTAGGGT

GTAGGCTGGAGCTGCTTCGAAGTTCCTATACTTTCTAGAGAATAGGAACTTCGGAATAGGAACTAAGGAGGATATTC

ATATCCGTCGACGGCGGCCGCCCTGCAGGCATGCAAGCTTGATCCATATGGATCGCTAGCTTAATTAAATAAAGCCG

TAAGCATATAAGCATGGATAAGCTATTTATACTTTAATAAGTACTTTGTATACTTATTTGCGAACATTCCAGGCCGC

GAGCATTCAGCGCGGTGATCACACCTGACAGGAGTATGTAATGTCCAAGCAACAGATCGGCGTAGTCGGTATGGCAG

TGATGGGACGCAACCTTGCGCTCAACATCGAAAGCCGTGGTTATACCGTCTCTATTTTCAACCGTTCCCGTGAGAAG

ACGGAAGAAGTGATTGCCGAAAATCCAGGCAAGAAACTGGTTCCTTACTATACGGTGAAAGAGTTTGTCGAATCTCT

GGAAACGCCTCGTCGCATCCTGTTAATGGTGAAAGCAGGTGCAGGCACGGATGCTGCTATTGATTCCCTCAAACCAT

ATCTCGATAAAGGAGACATCATCATTGATGGTGGTAACACCTTCTTCCAGGACACTATTCGTCGTAATCGTGAGCTT

TCAGCAGAGGGCTTTAACTTCATCGGTACCGGTGTTTCTGGCGGTGAAGAGGGGGCGCTGAAAGGTCCTTCTATTAT

GCCTGGTGGCCAGAAAGAAGCCTATGAATTGGTAGCACCGATCCTGACCAAAATCGCCGCCGTAGCTGAAGACGGTG

AACCATGCGTTACCTATATTGGTGCCGATGGCGCAGGTCACTATGTGAAGATGGTTCACAACGGTATTGAATACGGC

GATATGCAGCTGATTGCTGAAGCCTATTCTCTGCTTAAAGGTGGCCTGAACCTCACCAACGAAGAACTGGCGCAGAC

CTTTACCGAGTGGAATAACGGTGAACTGAGCAGTTACCTGATCGACATCACCAAAGATATCTTCACCAAAAAAGATG

AAGACGGTAACTACCTGGTTGATGTGATCCTGGATGAAGCGGCTAACAAAGGTACGGGTAAATGGACCAGCCAGAGC

GCGCTGGATCTCGGCGAACCGCTGTCGCTGATTACCGAGTCTGTGTTTGCACGTTATATCTCTTCTCTGAAAGATCA

GCGTGTTGCCGCATCTAAAGTTCTCTCTGGTCCGCAAGCACAGCCAGCAGGCGACAAGGCTGAGTTCATCGAAAAAG

TTCGTCGTGCGCTGTATCTGGGCAAAATCGTTTCTTACGCCCAGGGCTTCTCTCAGCTGCGTGCTGCGTCTGAAGAG

TACAACTGGGATCTGAACTACGGCGAAATCGCGAAGATTTTCCGTGCTGGCTGCATCATCCGTGCGCAGTTCCTGCA

AAAAATCACCGATGCTTATGCCGAAAATCCACAGATCGCTAACCTGTTGCTGGCTCCGTACTTCAAGCAAATTGCCG

ATGACTACCAGCAGGCGCTGCGTGATGTCGTTGCTTATGCAGTACAGAACGGTATTCCGGTTCCGACCTTCTCCGCA

GCGGTTGCCTATTACGACAGCTACCGTGCTGCTGTTCTGCCTGCGAACCTGATCCAGGCACAGCGTGACTATTTTGG

TGCGCATACTTATAAGCGTATTGATAAAGAAGGTGTGTTCCATACCGAATGGCTGGATTAA (example O25B rfb locus nucleotide sequence-O25B-EPA production strain stGVXN4459)

SEQ ID NO: 18

ATGACGAATTTAAAAGCAGTTATTCCTGTAGCGGGTCTCGGGATGCATATGTTGCCTGCCACTAAGGCGATACCCAA

AGAGATGCTACCAATCGTCGACAAGCCAATGATTCAGTACATTGTTGACGAGATTGTGGCTGCAGGGATCAAAGAAA

TCCTCCTGGTAACTCACGCGTCCAAGAACGCGGTCGAAAACCACTTCGACACCTCTTATGAGTTAGAATCACTCCTT

GAGCAGCGCGTGAAGCGTCAACTGCTGGCGGAAGTACAGTCCATCTGTCCGCCGGGCGTGACCATTATGAACGTGCG

TCAGGGCGAACCTTTAGGTTTAGGCCACTCCATTTTGTGTGCGCGACCTGCCATTGGTGACAACCCATTTGTCGTGG

TACTGCCAGACGTTGTGATCGACGATGCCAGCGCCGACCCGCTACGTTACAACCTTGCTGCCATGATTGCACGTTTC

AACGAAACGGGCCGCAGCCAGGTGCTGGCAAAACGTATGCCGGGTGACCTCTCTGAATACTCCGTCATCCAGACTAA

AGAGCCGCTGGACCGTGAGGGTAAAGTCAGCCGCATTGTTGAATTTATCGAAAAACCGGATCAGCCGCAGACGCTGG

ACTCAGACATCATGGCCGTAGGTCGCTATGTGCTTTCTGCCGATATTTGGCCGGAACTGGAACGTACTCAGCCTGGT

GCATGGGGACGTATTCAGCTGACTGATGCTATTGCCGAGCTGGCGAAAAAACAATCCGTTGATGCAATGCTGATGAC

CGGCGACAGTTACGACTGCGGCAAAAAAATGGGCTATATGCAGGCGTTTGTGAAGTATGGCCTACGCAACCTGAAAG

-continued

AAGGGGCGAAGTTCCGTAAAGGTATTGAGAAGCTGTTAAGCGAATAATGAAAATCTGACCGGATGTAACGGTTGATA

AGAAAATTATAACGGCAGTGAAAATTCGCAGCAAAAGTAATTTGTTGCGAATCTTCCTGCCGTTGTTTTATATAAAC

CATCAGAATAACAACGAGTTAGCAGTAGGGTTTTATTCAAAGTTTTCCAGGATTTTCCTTGTTTCCAGAGCGGATTG

GTAAGACAATTAGCGTTTGAATTTTTCGGGTTTAGCGCGAGTGGGTAACGCTCGTCACATCATAGGCATGCATGCAG

TGCTCTGGTAGCTGTAAAGCCAGGGGCGGTAGCGTGCATTAATACCTCTATTAATCAAACTGAGAGCCGCTTATTTC

ACAGCATGCTCTGAAGTAATATGGAATAAATTAAGCTAGCAGTGAAGATACTTGTTACTGGTGGCGCAGGATTTATT

GGTTCTGCTGTTGTTCGTCACATAATAAATAATACGCAAGATAGTGTTGTTAATGTCGATAAATTAACATACGCCGG

AAACCTGGAATCACTTGCAGATGTTTCTGATTCTGAACGCTATTTCTTTGAACATGCGGATATTTGTGATGCAGCTG

CAATGGCACGGATTTTTGCTCAGCATCAGCCGGATGCAGTGATGCACCTGGCAGCTGAAAGCCATGTTGACCGTTCA

ATTACAGGCCCTGCGGCATTTATTGAAACCAATATTGTGGGTACTTATGTCCTTTTAGAAGCGGCTCGGAATTATTG

GTCTGGTCTGGATGATGAAAAGAAAAAAAACTTCCGTTTTCATCATATTTCTACTGATGAGGTGTATGGTGACTTAC

CCCATCCGGATGAAGTAAATAGCAATGAAACGTTGCCGCTATTTACGGAAACGACAGCATACGCGCCAAGTAGTCCA

TATTCTGCTTCTAAAGCTTCCAGCGATCATTTGGTTCGCGCATGGAAACGTACTTATGGTTTACCGACCATTGTGAC

TAATTGCTCGAACAACTATGGTCCTTATCATTTCCCGGAAAAGCTTATTCCACTGGTTATTCTTAATTCACTGGAAG

GTAAGGCATTACCTATTTATGGCAAAGGAGATCAGATCCGCGACTGGTTGTATGTAGAGGATCATGCTCGAGCGTTA

TATACCGTCGTAACCGAAGGTAAAGCGGGCGAAACTTATAACATTGGTGGACACAACGAAAAGAAAAACATCGACGT

AGTGTTCACTATTTGTGATTTGTTGGATGAGATAGTCCCGAAAGAGAAATCTTACCGCGAGCAAATTACTTATGTTA

CCGATCGTCCGGGACACGATCGCCGTTATGCGATTGATGCTGAGAAGATTGGTCGCGAATTGGGATGGAAACCACAG

GAAACGTTTGAGAGTGGGATTCGTAAAACGGTGGAATGGTACCTGTCCAATACAAAATGGGTTGATAATGTGAAAAG

TGGTGCCTATCAATCGTGGATTGAACAGAACTATGAGGGCCGCCAGTAATGAATATCCTCCTTTTTGGCAAAACAGG

GCAGGTAGGTTGGGAACTACAGCGTGCTCTGGCACCTCTGGGTAATTTGATTGCTCTTGATGTTCACTCCACTGATT

ACTGTGGTGATTTTAGTAATCCTGAAGGTGTAGCTGAAACCGTAAGAAGCATTCGGCCTGATATTATTGTCAACGCA

GCCGCTCACACCGCAGTAGACAAAGCAGAATCAGAACCGAAGTTTGCACAATTACTGAACGCGACGAGTGTCGAAGC

GATCGCGAAAGCAGCCAATGAAGTCGGCGCCTGGGTTATTCACTACTCTACTGACTACGTATTTCCGGGGACCGGTG

AAATACCATGGCAGGAGGAGGATGCAACCGCACCGCTAAATGTTTACGGTGAAACCAAGTTAGCGGGAGAAAAAGCA

TTACAAGAGCATTGTGCGAAGCACCTTATTTTCCGGACCAGCTGGGTCTATGCAGGTAAAGGAAATAACTTCGCCAA

AACAATGTTGCGTCTGGCAAAAGAGCGTGAAGAATTAGCCGTTATTAATGATCAGTTTGGTGCGCCAACTGGCGCAG

AGTTACTGGCTGATTGTACGGCACATGCTATTCGTGTGGCACTGAATAAACCGGAAGTCGCAGGCTTGTACCATCTG

GTAGCTAGTGGTACCACAACGTGGCACGATTATGCTGCGCTGGTTTTTGAAGAGGCGCGCAAAGCAGGCATTCCCCT

TGCACTCAACAAGCTCAACGCAGTACCAACAACAGCCTATCCTACACCAGCTCGTCGTCCACATAACTCTCGCCTTA

ATACAGAAAAATTTCAGCAGAACTTTGCGCTTGTCTTGCCTGACTGGCAGGTTGGCGTGAAACGAATGCTTAACGAA

TTATTTACGACTACAGCAATTTAATAGTTTTTGCATCTTGTTCGTAATGGTGGAGCAAGATGTATTAAAAGGAATGA

TGAAATGAAAACGCGTAAAGGTATTATTTTGGCGGGTGGTTCTGGTACTCGTCTTTATCCTGTGACGATGGCCGTCA

GTAAACAGCTGTTACCGATTTATGATAAACCGATGATCTATTACCCGCTCTCTACACTGATGTTAGCGGGTATTCGC

GATATTCTGATTATCAGTACACCACAGGATACTCCTCGTTTTCAACAACTGCTGGGTGACGGGAGCCAGTGGGGCCT

GAATCTTCAGTACAAAGTGCAACCGAGTCCGGATGGTCTTGCGCAGGCGTTTATTATCGGTGAAGAGTTTATTGGTG

GTGATGATTGTGCTTTGGTACTTGGTGATAATATCTTCTACGGCCACGACCTGCCGAAGTTAATGGACGTAGCTGTT

AACAAAGAAAGTGGTGCAACGGTATTTGCCTATCACGTTAATGATCCTGAACGTTATGGTGTCGTGGAGTTTGATAA

TAACGGTACTGCAATTAGCCTGGAAGAAAAACCGCTGGAACCAAAAAGTAACTATGCGGTTACTGGGCTTTATTTCT

ATGACAATGACGTTGTGGAAATGGCGAAAAACCTTAAGCCTTCTGCCCGAGGTGAACTGGAAATTACCGATATTAAC

-continued
CGTATTTATATGGAACAAGGACGTTTGTCTGTCGCTATGATGGGGCGTGGCTATGCATGGCTGGATACAGGGACGCA

TCAAAGTCTTATTGAAGCAAGCAACTTCATTGCCACCATTGAAGAGCGCCAGGGACTAAAGGTTTCCTGTCCGGAAG

AAATTGCTTATCGTAAAGGGTTTATTGATGCTGAGCAGGTAAAAGTATTAGCCGAACCGTTGAAGAAAAAATGCTTAT

GGTCAGTATCTGCTCAAAATGATTAAAGGTTATTAATAAGATGAACGTAATTAAAACTGAAATTCCTGATGTGCTGA

TTTTTGAACCAAAAGTTTTTGGGGATGAACGTGGCTTCTTTTTTGAGAGTTTTAATCAGAGGATTTTTGAAGAAGCA

GTAGGTCGTAAGGTTGAGTTTGTTCAGGATAACCATTCTAAGTCCAGTAAAGGTGTTTTACGTGGTCTTCATTATCA

GTTAGAACCTTATGCTCAAGGAAAACTGGTGCGCTGTGTTGTTGGCGAGGTTTTTGATGTTGCGGTTGATATTCGTA

AATCGTCACCTACATTTGGGAAATGGGTTGGGGTGAATTTGTCTGCTGAGAATAAGCGTCAGTTGTGGATTCCTGAG

GGATTTGCACATGGTTTTTTGGTGCTGAGTGATTTAGCAGAAGTTTTATATAAAACGAATCAATATTATGCTCCATC

ACATGAAAAAAATATTATATGGAATGACCTCTTGCTTAATATTAAATGGCCGAGCACAGCACTGATCACTCTGTCTG

ATAAGGATGCAAATGGGGAAAGATTTGAACTAAGTGAGTTTTGAAATGTCTCTCTTAAAACATAGTATATGGAATGT

TGCGGGCTACTTTATACCAACATTAATTGCAATTCCCGCCTTTGGATTAATTGCGAGGAAAATTGGTGTAGAACTAT

TTGGTTTGTATACGTTAGCAATGATTTTTATAGGGTATGCAAGTATATTTGATGCTGGGTTAACAAGAGCTGTTGTG

CGTGAAATAGCATTACTAAAAAACAGAGTGGACGATTGTAATACGATAATAGTAACTTCTATTATCGCTGTGATATT

TTTAGGGTTTATCGGAGGCGGGGGAGTGTTTCTGCTTAAAGGCGATATTATTGAACTGTTAAATATCTCACCAATAT

ATTACGCCGATTCGATAAAGTCTCTAGTATTATTATCATCTCTGATACCTGTATTCTTAGTCACGCAAATACTATTA

GCAGAGCTTGAGGGTCGGGAATATTTTGGGATTCTAAATATACAAAAAAGTGTAGGGAATTCTTTAATTGCAGGGTT

ACCTGCATTATTTGTTTTAATTAATCAAACGCTTTTTTCTGCAATTATTGGTGTAGCGATTGCAAGAGTTATATGCT

TGTGGTTAAGCTACATTATGAGCAGGGAAAGAATAACTATCGATATCTCATTTTTTTCAATAACTGTTTTAAAGCGG

TTATTTAGATATGGCGGGTGGGTAACTATAAGTAACATAATATCTCCTATATTAGCGAGTATGGATAGATTTATTCT

ATCCCATATCCAGGGAGCATCAAAAATATCATTCTATACAGTCCCTAATGAGCTGGTAACTAGGCTTGGAATAGTTC

CAGGCTCTCTTGGGAAAGCTGTTTTTCCAAAATTAAGTCATGCAAGGAATTTTACAGCGTCATATGCAGAGCAAAAA

AAAGCTTATATATTAATGACTGTCATTGTAATGCCTTTGGTTTTATTTGTATATTATTACGCAAAGTTTATTTTAAC

ATTGTGGATGGGGGCTGAGTATGCAGGGATTTCGGTCGAAATATTACGGATTATGCTTATAGGGTATATTTTTAACT

GTTATTCACAAATCTCTTTTGCCAACATACAGGCCTTTGGAAAAGCAAAATACACTGCATACATCCATATGATGGAA

TTTATTCCTTATTTGATAATGTTATATATAATTTCAAAGGAATATGGGGTTATTGGTGTTGCGTGGTTATGGACAAT

TCGAGTAATAATTGATTTTTTGATGCTTTTATATATGAGTTATCGTTGTAATAATCTTATGAAAAAAGGGTAGCCTG

ATGATATATATTGTGGTATTAAATTGGAATGGGGCTATAGATACCATTAATTGTGTTAAAAGTTTAATGGATTTAAA

TGTTAGCGATTATAAAATTATCATTGTTGATAACTGTTCTATGGATAACTCATATGATACTATAAAAGAAAATCTTA

ATTCATTATATATTGCTGATAAAAGTATCATTGAGGTGAAGTATGAGGATAGAAATAAATATAAAACCTTAGAAAAC

GATAAAATCATATTAATACAATCTCCGCAAAATAATGGGTACGCAAGTGGTAATAATATTGGCATAGAGTTCGCTCT

TAATCAGGAGAATATGAAATACGTCTGGGTTCTGAATAATGATACTGAAGTGGATAAAGAGGCTTTAACTCATTTAA

TTAGTAAATGTGATTCAGATAAAAGTATAGGGATTTGCGGTTCTCGTTTAGTCTATTTTGCCGACAGAGAGATGCAG

CAAGGACTAGGTGGGGTGCATAACAAATGGTTATGCACTACAAAAAATTATGAAATGGGAAGATTAGTTTCCAAAAA

ATATGATGATGAAGTCATTAGTAATGATATAGATTATATAATTGGCGCATCGATGTTTTTCTCTAGAGAATGTTTGG

AAACAGTTGGATTGATGAATGAAGAATATTTTTTATACTATGAAGAGTTAGATATTTGCCTCAGAGCAAAAGCAAAG

AACTTTAAATTAGGTATTTGCTCAGAAAGTTTGGTTTATCATAAAATAGGTGCAAGTACTGATGGGGGAAAGAGCAT

GATGGCTGATCTTTGCTCAATAAAAAATAGGCTGGTCATTACAGAAAGGTTTTATCCCCAATATTATTGGACGGTAT

GGTTGTCACTTTTTGTTGTAGCATTTAACCGTGCTAGAAGAGGTGAGTTTAATAAGATGAAAAGATGTTTGAATGTT

ATGTTTAACTTCAAACGAAACAAAGGTAGCAAATGCCATTAGAATATGCACTTAATCATGGTGTTAATAAATCTATA

GTTTGATATGTTATTAAAGGGTATTTAATGAAAGTGGCTTTTTTATCTGCTTATGATCCACTATCTACATCCAGTTG

-continued

GTCTGGCACACCTTATTATATGCTAAAGGCATTATCGAAGAGAAATATTTCCATTGAAATATTAGGACCGGTAAATA

GCTATATGATATACATGTTAAAAGTATATAAATTAATATTAAGGTGTTTCGGAAAAGAATATGATTATAGTCATTCG

AAGTTGCTTTCCAGGTATTACGGTAGAATATTCGGTAGGAAATTAAAAAAAATTGATGGTTTGGATTTTATTATCGC

ACCTGCAGGTTCCTCACAAATTGCTTTTTTAAAAACAACCATACCAATAATATATCTATCGGATACAACATATGATC

AATTAAAAAGCTATTATCCGAATTTAAATAAAAAAACAATTATAAATGATGAGGATGCAAGTTTAATCGAACGCAAG

GCTATTGAAAAAGCAACAGTAGTATCTTTCCCATCTAAATGGGCAATGGATTTTTGCAGGAATTATTACAGATTAGA

TTTTGATAAATTAGTTGAAATACCATGGGGGGCTAATTTATTTGATGATATTCACTTTGCTAATAAAAATATAATTC

AAAAGAATAGTTATACTTGTCTTTTCTTGGGAGTTGATTGGGAAAGAAAAGGTGGGAAAAACAGCCTTGAAAGCAATT

GAATATGTAAGGCAGTTATATGGGATCGATGTTAGACTAAAAATTTGTGGATGTACTCCGAATCAAAAGATTTTACC

TACTTGGGTTGAATTAATTGATAAAGTAGATAAAAATAACGTTGACGAATATCAGAAATTCATCGATGTGTTATCTA

ACGCTGATATACTTCTTTTACCAACCATTGCTGAATGTTATGGAATGGTATTTTGTGAAGCTGCTGCTTTTGGATTG

CCTGTTGTCGCTACAGATACAGGTGGAGTCAGTTCTATAGTTATCAACGAAAGGACGGGGATATTAATTAAAGACCC

GTTAGACTATAAGCACTTTGGAAATGCAATTCATAAAATAATTAGTTCCGTAGAGACTTATCAAAACTACTCCCAAA

ACGCAAGAATTAGATATAATAATATATTGCATTGGGACAATTGGGCTAAAAAGATAATTGAGATTATGTATGAGCAT

AAGAATAGAAGAATCAAATAGCACAAAAAGAATTATATGTTTATTTATACTTTTTCTTGTTTTCCCTGATTTTTTGT

TTTATACATTAGGGGTTGATAATTTTAGCATTTCAACGATAATCTCAATTACATTGCTTTTTGTTTTTTTAAGAGCT

AAAAATATTTGCAAAGATAATTTTCTAATAATAGTAGCGTTATTCATATTGTTGTGTTTTAACTGTTTGTTAAGTAT

GCTATTTAATATTGAACAGGCTTTAACATTTAAAGTTGTACTTTCAATATATAGCATCTTAATAATGGCATACGTCT

CCTCTTGTTATGCACAGACGTTGTGGTTATGTTCTGAAGAAATACTTAAGAGATCCGTCTTTTATTTGTTCGCATTT

CTTTGCCTTATTGGCATTATAAGTATTCTTTTACAGAAGACTGAGATTATACATGATAAAAGTATGATTCTTTTTCC

TGAACCATCAGCATTTGCATTGGTTTTTATACCTATCTTTTCATTTTGTTTATACTATACAAGAGGGGGGGGGCTAC

TATTGCTCTATATATTATCTTTGGGTATTGCGTTAGGTATCCAGAATTTAACAATGTTGGTAGGCATTGTGATTAGT

GTTTTTGTGATGAAAAAAAATAACTATAAGGCAAACTATTGTTATACTTTTGGGGGCATGGATTTTTTCCATGATATT

AAGTGATTTAGACATTTCTTACTATACATCGCGGCTTGATTTTAAAAATACTACGAACCTATCAGTGCTTGTATATC

TTTCAGGAATTGAAAGAGCTTTCTTGAATTTTATTACAAGTTATGGTCTTGGTATTGGTTTTCAACAAATGGGAGTG

AATGGGGAGATAGGAATATATCAACAAATTTTAGCTGAACTTGATGCCCCTATGTTAAATATATACGATGGCTCATT

TATTTCTTCTAAGTTAATATCTGAGTTTGGGGTTATTGGTGCATTAATGTGTATTTTCTATTTTTTTTATTTTTCCC

GATTTTATCTGCGTTTCAAAAAAAGTAAGAGATATTCACCGCAGTATATTTTAGCATATAGCTTCTACATGTGTTTC

TTCATCCCTCTTTTTATACGTGGTGCTGGTTATATAAACCCCTATGTGTTTATGTTATTTTCATCAATATTTTTGTG

CAAATATCACGCTAAAAATATCTTGATGAAATCTAATGTCCAGATAGCTATATAATAGTAGATTATATTATCATTAT

CACGTAAATTACATATTAATAGCATATATGATAACTAGGACATAAATAATGTGCATTAAAAAAAAACTTAAGTTAAT

TAAACGATATGGCCTTTATGGTGGTCTTAGGCTTCTTAAAGATATATTCTTAACAAAATTTTTATTTTGTTCAAATG

TTAGGATTATTAGATTTCCATGTTATATTAGAAAAGATGGAAGTGTTAGTTTTGGAAAAGGTTTTACATCAGGTGTA

GGATTACGAGTTGATGCATTTATGGATGCCGTAGTTTCCATTGGAGAAAATGTTCAAATTAATGACTATGTTCACAT

CGCGGCTATTAATAATGTCATTATTGGTAGAGATACATTAATAGCAAGTAAAGTATTTATTAGTGATCATAATCATG

GTATTTTTTCTAAATCCGATATCCATAGTTCACCAACTATTATTCCTTCGTCTAGGCCCCTTGAATCTGCACCTGTG

TATATTGGAGAGCGTGTGTGGATTGGCGAAAATGTGACAATATTACCAGGTGCGTGTATAGGTAATGGTGTAGTTAT

TGGCGCAAACAGTGTTGTTCGTGGTGAGATTCCTAATAATGTGATCATTGCTGGTGTTCCAGCTAAAATTGTTAAAA

AATATAACTATGAGCGTATGCAATGGGAAAGAATATAGTTGTAATATCGGCTGTTAATTTTACAACCGGAGGCCCCT

TTACCGTACTAAAAAATGTGCTTACAGCAACTAAAGATAGAGCCGAATGTAAATTTATTGCACTGGTTCATAGCTCT

-continued

GCTGAACTAATGGAATTATTTCCGTGGGTTGAATTTATAGAGTATCCAGAAGTCAAGTCTTCGTGGGTTAAAAGATT

ATATTTCGAATATATAACTTGCAATAGATTATCTAAGGTGATTAAGGCAACTCATTGGGTATGCTTACATGATATTA

CAGCAAATGTTAGTGTACCCTATAGATTTGTTTATTGCCACAATCCTGCACCGTTCTATAAATATTTAAGCTATCGA

GATATTATAGGAGAACCTAAATTTTATCTTTTTTATCTTTTTTATGGGCTTTTATACAATATCAATATAAAAAAGAA

CACAGCAGTTTTTGTTCAGCAGCAGTGGCTAAAAAAAGAATTCGAAAAAAAATATAAGTTAAAGAATGTTGTTGTTA

GTCGCCCTGAAGATATTTGCCCTTTTGAAAGTGATGGTTTGGTAAGAAATAATAATAAAAAGGATGTGAGGATATTT

TACCCAGCAGTGCCCCGTATATTTAAAAACTTTGAAGTTATCATACGTGCTGCACAAATATTACAAGATAAAAATAT

TCATTTTTATCTTACTTTTGATGGTACTGAAAATAAGTATGCAAAAGAATATATAAATTAGCTTCCGAACTGAAAA

ATGTACATTTCCTCGGTTACCTTAATGCAACCGAGATGGTTAACTTTTATCAAGATTCAGATATTATTTGTTTCCCA

TCGAAACTAGAAACGTGGGGATTACCATTATCAGAAGCTAAAACATACAAAAAATGGATATTTGCGGCAGACTTACC

TTATGCTCATGAAGTTTTATATAACTATTCAAAAACTAGATATTTTCCATTTGACGATGAGAAAATACTTGTTCGCT

ACATATTAGAGTACACAAGTAAAAATATGCATGAAGATATAAAAAATAGTAGGGTGAATTTTAATAATGATGCATTG

ACTGGTTTTGAACAGTTTATTGAATATATCCTCAAGGGGAACTGACGTGGTTTATATTATAATCGTTTCACATGGCC

ATGATGACTATATAGAAAATCTTTTATTAAATTTAAAGTTGCCCTCTGGAAGATTTAAAATAATAGTTCGTGATAAC

AAAAGTTCAATGGTTTTAAAAAAAACATGCGAAAAAAATTGCGTAACCTATTTGCATGGAGGGCAATATGGATTTGG

ACATAATAATAACATAGCAGTGTCATATATAATTAATAACTTCATGATTATGAATAATGATTATTTTCTCTTTCTTA

ACCCCGATGTATTCATAACCAGTGAAAGTTTGATTAATTATGTTGATTATATAATTAGTAATGATTATAAGTTTAGC

ACATTATGTCTTTATCGAGATTTTACTAAAAGCAAACATGATTATTCAATACGGAGTTTTCCAACTTTATATGATTT

TCTTTGTTCTTTTTTATTGGGGGTGAATAAAAGTAAAATTAAGAAGGAAAATATACTTTCTGATACTGTAGTTGATT

GGTGTGCTGGCTCATTTATGCTTATTCATGCTTTAAGTTTCTTAAATGTGAATGGTTTTGATCAAAAATATTTTATG

TATTGTGAAGATATTGACCTTTGTATGCGTTTAAAATTAAGTGGAGTAGATCTTTACTATACTCCCCATTTTGATGC

TATTCATTATGCGCAGCATGAAAATAGAAGAATATTTACTAAAGCATTTCGATGGCATATAAGGAGTATTACGCGCT

ACATATTACGGAAACCAATTCTTTCTTATAAAAACTATAGAAAAATTACATCCGAACTGGTAAAGTGATTAAGGATC

CGTGTAGGCTGGAGCTGCTTCGAAGTTCCTATACTTTCTAGAGAATAGGAACTTCGGAATAGGAACTAAGGAGGATA

TTCATATGGATAAAGCCGTAAGCATATAAGCATGGATAAGCTATTTATACTTTAATAAGTACTTTGTATACTTATTT

GCGAACATTCCAGGCCGCGAGCATTCAGCGCGGTGATCACACCTGACAGGAGTATGTAATGTCCAAGCAACAGATCG

GCGTAGTCGGTATGGCAGTGATGGGACGCAACCTTGCGCTCAACATCGAAAGCCGTGGTTATACCGTCTCTATTTTC

AACCGTTCCCGTGAGAAGACGGAAGAAGTGATTGCCGAAAATCCAGGCAAGAAACTGGTTCCTTACTATACGGTGAA

AGAGTTTGTCGAATCTCTGGAAACGCCTCGTCGCATCCTGTTAATGGTGAAAGCAGGTGCAGGCACGGATGCTGCTA

TTGATTCCCTCAAACCATATCTCGATAAAGGAGACATCATCATTGATGGTGGTAACACCTTCTTCCAGGACACTATT

CGTCGTAATCGTGAGCTTTCAGCAGAGGGCTTTAACTTCATCGGTACCGGTGTTTCTGGCGGTGAAGAGGGGGCGCT

GAAAGGTCCTTCTATTATGCCTGGTGGCCAGAAAGAAGCCTATGAATTGGTAGCACCGATCCTGACCAAAATCGCCG

CCGTAGCTGAAGACGGTGAACCATGCGTTACCTATATTGGTGCCGATGGCGCAGGTCACTATGTGAAGATGGTTCAC

AACGGTATTGAATACGGCGATATGCAGCTGATTGCTGAAGCCTATTCTCTGCTTAAAGGTGGCCTGAACCTCACCAA

CGAAGAACTGGCGCAGACCTTTACCGAGTGGAATAACGGTGAACTGAGCAGTTACCTGATCGACATCACCAAAGATA

TCTTCACCAAAAAAGATGAAGACGGTAACTACCTGGTTGATGTGATCCTGGATGAAGCGGCTAACAAAGGTACCGGT

AAATGGACCAGCCAGAGCGCGCTGGATCTCGGCGAACCGCTGTCGCTGATTACCGAGTCTGTGTTTGCACGTTATAT

CTCTTCTCTGAAAGATCAGCGTGTTGCCGCATCTAAAGTTCTCTCTGGTCCGCAAGCACAGCCAGCAGGCGACAAGG

CTGAGTTCATCGAAAAAGTTCGTCGTGCGCTGTATCTGGGCAAAATCGTTTCTTACGCCCAGGGCTTCTCTCAGCTG

CGTGCTGCGTCTGAAGAGTACAACTGGGATCTGAACTACGGCGAAATCGCGAAGATTTTCCGTGCTGGCTGCATCAT

CCGTGCGCAGTTCCTGCAGAAAATCACCGATGCTTATGCCGAAAATCCACAGATCGCTAACCTGTTGCTGGCTCCGT

-continued

ACTTCAAGCAAATTGCCGATGACTACCAGCAGGCGCTGCGTGATGTCGTTGCTTATGCAGTACAGAACGGTATTCCG

GTTCCGACCTTCTCCGCAGCGGTTGCCTATTACGACAGCTACCGTGCTGCTGTTCTGCCTGCGAACCTGATCCAGGC

ACAGCGTGACTATTTTGGTGCGCATACTTATAAGCGTATTGATAAAGAAGGTGTGTTCCATACCGAATGGCTGGATT

AA (example O75 rfb locus nucleotide sequence-O75-EPA production strain stLMTB11737)

SEQ ID NO: 19

ATGACGAATTTAAAAGCAGTTATTCCTGTAGCGGGTCTCGGGATGCATATGTTGCCTGCCACTAAGGCGATACCCAA

AGAGATGCTACCAATCGTCGACAAGCCAATGATTCAGTACATTGTTGACGAGATTGTGGCTGCAGGGATCAAAGAAA

TCCTCCTGGTAACTCACGCGTCCAAGAACGCGGTCGAAAACCACTTCGACACCTCTTATGAGTTAGAATCACTCCTT

GAGCAGCGCGTGAAGCGTCAACTGCTGGCGGAAGTACAGTCCATCTGTCCGCCGGGCGTGACCATTATGAACGTGCG

TCAGGGCGAACCTTTAGGTTTAGGCCACTCCATTTTGTGTGCGCGACCTGCCATTGGTGACAACCCATTTGTCGTGG

TACTGCCAGACGTTGTGATCGACGATGCCAGCGCCGACCCGCTACGTTACAACCTTGCTGCCATGATTGCACGTTTC

AACGAAACGGGCCGCAGCCAGGTGCTGGCAAAACGTATGCCGGGTGACCTCTCTGAATACTCCGTCATCCAGACTAA

AGAGCCGCTGGACCGTGAGGGTAAAGTCAGCCGCATTGTTGAATTTATCGAAAAACCGGATCAGCCGCAGACGCTGG

ACTCAGACATCATGGCCGTAGGTCGCTATGTGCTTTCTGCCGATATTTGGCCGGAACTGGAACGTACTCAGCCTGGT

GCATGGGGACGTATTCAGCTGACTGATGCTATTGCCGAGCTGGCGAAAAAACAATCCGTTGATGCAATGCTGATGAC

CGGCGACAGTTACGACTGCGGCAAAAAAATGGGCTATATGCAGGCGTTTGTGAAGTATGGCCTACGCAACCTGAAAG

AAGGGGCGAAGTTCCGTAAAGGTATTGAGAAGCTGTTAAGCGAATAATGAAAATCTGACCGGATGTAACGGTTGATA

AGAAAATTATAACGGCAGTGAAAATTCGCAGCAAAAGTAATTTGTTGCGAATCTTCCTGCCGTTGTTTTATATAAAC

CATCAGAATAACAACGAGTTAGCAGTAGGGTTTTATTCAAAGTTTTCCAGGATTTTCCTTGTTTCCAGAGCGGATTG

GTAAGACAATTAGCGTTTGAATTTTTCGGGTTTAGCGCGAGTGGGTAACGCTCGTCACATCATAGGCATGCATGCAG

TGCTCTGGTAGCTGTAAAGCCAGGGGCGGTAGCGTGCATTAATACCTCTATTAATCAAACTGAGAGCCGCTTATTTC

ACAGCATGCTCTGAAGTAATATGGAATAAATTAAGCTAGCAGTGAAGATACTTGTTACTGGTGGCGCAGGATTTATT

GGTTCTGCTGTTGTTCGTCACATAATAAATAATACGCAAGATAGTGTTGTTAATGTCGATAAATTAACATACGCCGG

AAACCTGGAATCGCTCGCTGAAATTTCTGATTCTGAACGTTATTCATTTGAGCATGCAGATATCTGCGATGCCGAAG

CGATGGCTCGTATTTTCGCACAGCACCAGCCAGACGCGGTGATGCACCTGGCAGCAGAGAGCCACGTTGACCGCTCA

ATAACTGGCCCTGCGGCATTTATTGAAACCAATATTGTGGGTACTTATGTTCTTTTAGAAGCGGCGCGCAATTATTG

GTCTGGTCTGGATGATGAAAAGAAAAAAAACTTCCGCTTTCATCATATTTCTACTGATGAGGTGTATGGTGACTTAC

CCCATCCGGATGAAGTAAATAGCAATGAAACGTTGCCGCTATTTACGGAAATGACAGCATACGCGCCAAGTAGTCCA

TATTCTGCTTCTAAAGCTTCCAGCGATCATTTGGTTCGCGCATGGAAACGTACTTATGGTTTACCGACCATTGTGAC

TAATTGCTCGAACAACTATGGTCCTTATCATTTCCCGGAAAAGCTTATTCCACTGGTTATTCTTAATGCACTGGAAG

GTAAGGCATTACCTATTTATGGCAAAGGAGATCAGATCCGCGACTGGTTGTATGTAGAGGATCATGCTCGAGCGTTA

TATACCGTCGTAACCGAAGGTAAAGCGGGCGAAACTTATAACATTGGTGGACACAACGAAAAGAAAAACATCGACGT

AGTGTTCACTATTTGTGATTTGTTGGATGAGATAGTCCCGAAAGAGAAATCTTATCGTGAGCAAATTACCTATGTTG

CTGATCGCCCAGGGCATGATCGCCGTTATGCAATTGATGCCGATAAAATTAGCCGCGAATTGGGCTGGAAACCACAG

GAAACGTTTGAGAGCGGGATTCGTAAAACTGTGGAATGGTATCTGTCCAATACAAAATGGGTTGATAATGTGAAAAG

TGGTGCCTATCAATCGTGGATTGAACAGAACTATGGGGGCCGCCACTAATGAATATCCTCCTTTTTGGCAAAACAGG

GCAGGTTGGTTGGGAACTACAGCGTGCTCTGGCACCTCTGGGTAATTTGATTGCTCTTGATGTTCACTCCACTGATT

ACTGTGGTGATTTTAGTAACCCTGAAGGTGTGGCTGAAACCGTTAGAAGCATTCGGCCTGATATTATTGTCAACGCA

GCCGCTCACACCGCAGTAGACAAAGCAGAATCAGAACCGGAGTTTGCACAATTACTGAACGCGACGAGTGTCGAAGC

GATCGCGAAAGCAGCCAATGAAGTCGGCGCTTGGGTTATTCACTACTCTACTGACTACGTATTTCCGGGGACCGGTG

-continued

AAATACCATGGCAGGAGGAGGATGCAACCGCACCGCTAAATGTTTACGGTGAAACCAAGTTAGCAGGAGAAAAAGCA

TTACAAGAGCATTGTGCGAAGCACCTTATTTTCCGGACCAGCTGGGTCTATGCAGGTAAAGGAAATAACTTCGCCAA

AACGATGTTGCGTCTGGCAAAAGAGCGTGAAGAATTAGCCGTTATTAATGATCAGTTTGGTGCGCCAACTGGCGCAG

AGTTGCTGGCTGATTGTACGGCACATGCCATTCGTGTGGCACTGAATAAACCGGAAGTCGCAGGTTTGTACCATCTG

GTAGCCAGTGGTACCACAACCTGGCACGATTATGCTGCGCTGGTTTTTGAAGAGGCGCGCAAAGCAGGCATTCCCCT

TGCACTCAACAAGCTCAACGCAGTACCAACAACAGTCTATCCTACACCAGCTCGTCGTCCACATAACTCTCGCCTTA

ATACAGAAAAATTTCAGCAGAACTTTGCGCTTGTCTTGCCTGACTGGCAGGTTGGTGTGAAACGCATGCTCAACGAA

TTATTTACGACTACAGCAATTTAATAGTTTTTGCATCTTGTTCGTGATGGTGGAACAAGATGAATTAAAAGGAATGA

TGGAATGAATACGCGTAAAGGTATTATTTTAGCGGGTGGTTCTGGTACACGTCTTTATCCTGTGACTATGGCTGTCA

GTAAACAGCTGTTACCGATTTATGATAAACCGATGATCTATTACCCGCTCTCTACACTGATGTTGGCGGGTATTCGC

GATATTTTGATTATCAGCACGCCACAGGATACTCCTCGTTTTCAACAACTGCTGGGTGATGGGAGCCAGTGGGGGCT

AAATCTTCACTACAAAGTGCAACCGAGTCCGGATGGTCTTGCGCAGGCATTTATCATCGGTGAAGAGTTTATCGGTG

GTGATGATTGTGCTTTGGTACTTGGTGATAATATCTTCTACGGTCACGACCTGCCTAAGTTAATGGATGCCGCTGTT

AACAAAGAAAGTGGTGCAACGGTATTTGCCTATCACGTTAATGATCCTGAACGCTATGGTGTCGTTGAGTTTGATAA

AAACGGTACTGCAATCAGCCTGGAAGAAAAACCGTTACAACCAAAAAGTAATTATGCGGTAACCGGGCTTTATTTCT

ATGATAACTACGTTGTGGAAATGGCGAAAAATCTTAAGCCTTCTGCCCGCGGTGAACTGGAAATTACCGATATTAAC

CGTATCTATATGGAACAGGGGCATTTATCTGTTGCCATGATGGGACGTGGATATGCCTGGCTGGACACGGGGACACA

TCAAAGTCTTATTGAAGCAAGCAACTTCATTGCCACCATTGAAGAGCGCCAGGGCTTGAAAGTTTCCTGCCCGGAAG

AAATTGCTTACCGTAAAGGGTTTATTGATGCTGAGCAGGTGAAAGTATTAGCTAAACCGCTGAAAAAAAATGCTTAT

GGTCAGTATCTGCTAAAAATGATTAAAGGTTATTAATAAAATGAATGTTATTAAAACAGAAATTCCAGATGTACTGA

TTTTTGAACCGAAAGTTTTTGGTGATGAGCGTGGTTTCTTTATGGAAAGCTTTAATCAGAAAGTTTTCGAAGAGGCT

GTAGGGCGGAAGGTTGAATTTGTTCAGGATAATCATTCTAAATCGTGTAAAGGTGTACTTAGAGGTTTACACTTTCA

GCTTCCTCCCTTTGAGCAGGCAAAATTAGTAAGGTGTATAGTTGGCGAGGTATTTGATGTTGCAGTAGACATTAGAC

CTAATTCTGAAACATTTGGTTCATGGGTTGGAGTAACTCTTTCGTCAGAAAATAAAAGGCAGCTATGGATTCCAGAA

GGATTCGCCCATGGTTTTTTAACTTTAAGTGATATTGCAGAGTTTGTTTATAAAACTAACAACTATTATTCTTTAAA

TCATGAAAGGGGAGTCATTTGGAACGATGAGGAAATTAACATTGCCTGGCCCTCTCAATCAGAGAAGATTCTGTCAC

AGAAAGATATTAATTTACCATCATTTAGATTTGTTCAAATGTTTAGCAAGTAGTGTTATCTTTACACTGCACATAGT

CATCATTTTTTATGCTTTAAGTAAATTATATTGCACATCTATAACACAAAGCGCAATAATATTTCGACCTGATGAAG

GTTTGTGGTTATTTATCTTTCTAGGCGTTTTTTATGACTAAAATAGTTGTGGTTTCTACAGCTCCAATATTCCCGAC

AAATAATGGGTACAAAAGTTCTGTATTAGGAAGAATTGATGAGTTATTAAATGAGGATAATGAGGTCGTTTTGATTG

AAATAAACCTTGAAAATGTTACGGAAAAGAAAGATGAATTAATACCAACAAGATTTAATAATATTCAAAGATATGAA

GTAAAAAAAAATATCTAGATCATTTATTGCCGAGTTACAAATATTATTTGATATCAGAACTCGGTATGAACAATTATT

TTCTTCTGCTGACATTAGAGATAACATAAAAAAGATAATTGATTTAGAAAAACCTTCTATTATTATTGCTGAGTCTA

TATGGGCGTTGCAAGCATTGCCTATTGAAATTAGTGCGAGAATACACTGTGTTATTCATGATGTGGCAACTGATTTC

TTTAAAGAAATGTTTGTATCTCATAATGAGGTTGTACGAAAAAATTTTGTTTTTTAATGATTACCTAAAGTTGAAAAT

TACTGAAGAAAATATTATCAAACGTTTGAGAGTTGAGCAATTTATCTTTCTGACAGAAGAAGATAAATGTTGGTATA

AAACAAGATACAATATTGATGAGGGTTGTTGTTCCTTAGCGAGCAATCATCTTTATGTAGAAAAGATTAAGAGAACT

ATCAATTTCCAAACCCCTTTCCTGCTTATTCCCGGTAGCATTGAATTTTCACAAAATTTTTACGGCTTAAATTGGTT

TATAAAAAATATATATCCTGGATTAAATAGGAAAATAAGAATAGTTGTAACAGGAAAGGCATCAGATAAAAAAATAA

AGATGTTAAACTGTGGAGAGGAAATTACCTTTACGGGAGAGCTTGACTTTTCCACATATAATAAACTTAGCTCAACA

-continued

TGCTTGTGTGTTATTGCACCGATTACAACGGGCACTGGAATTAAAATAAAAATATTAGAAGCTGTACAAAAAGGTAT

TCCTGTACTTACAACAAAATTTGCTTCAAAAGGAATATGTTCCGATTTATGTTTTTATTGCGAGGAGGATACTGACA

CAAACTTTGTCAATTTAATTAACAGTTTTCTTGAAACGACATTAAGAGTCCAAGAATGAATTTATTGCTTTTTTCAG

TCCTTGCGTTTGGTTTAATATTGGCTTTGGCCCATAATAATAAAAGTGGAGATATTAACGCATACTTAATGTTTTTT

CTCGTGGTCCTAATGGTATTAATATCAGGGCTGCGTATGAATGATAGTGATTATATCGAATACAGGAAAATGTATAA

TGAAGTGCCTATTTTATGTGACTTTAGTCTCGCATCTATAAGAGATATACATGGGGAGGTAGGCTATCTATTCTTAT

CATCAATCTTTAAAACTTTATGCTTGCCATTTCAATTATTTCTTTTTTTTATTGCTTTTTTATCACTCCTGCTTACA

TATTTTTCATTCAGAAAAATAAGTTTAATACCGATACTATCGTTAGTTTTTTATTTAAGCCATGCTTTTATAGTTAG

AGATTTGATTCAAATTAGGGCAGGATTAGCTGTTAGCATATCATTATATTCAATAATTAAATTTAAAGGAAATAAAA

GTATAATTACAGGAGTTTTATTTGCTTCTTTGATTCATTCTGGGGCGCTTATTATTGCTCTTTGTTATCCTTTTTTC

AAAAAAAAATACATAACATTAAAAATGATGTTGTTTTTATTTTTAGTGTCAATTATTTTTTCTTATTTGAATGGGCT

TAATTTATCGATACAACTCTTATCTCAATATAGTTTGCTTCCAACTGCAATTTCGAATTATGTTGGTTGGGAAGAAT

ATGATTATCGGGTGAGTATATTTACTAATCCGGTTTTTATTAAAGGTGTTTTTTTAATTGTCTTAATGCACAAATAT

GTACTTTCAGATATTAAAAATGAGAAAATTATAGTGCTTTATAACTTATATGTTTTAGGTGTATTAGCTATGGTTGC

ATTGAGTGGGATGGCTATTCTTTCAGGCCGTCTTTCATCCTTTCTGACACTAGGTGAAAGCATTTTAATTGTATATG

CTCTGTTCTACAAAAGAAATACACCTCTGGCGTTTCTAATTTTTTCTTTTTTAACAATTGTGCAATTAGGATATGAT

CTATTTATTTCTAATGTGCATCCTGAGCTTACTCTGATTATATTTGGGTGAATCTAAGTGAAAAATAATAAAATAGG

CATACTTATCTCTAAAATACAAAATCTTGGACCTGTGAATGTAGTACGAGGATTGATAAAAGAAAATAAAAAATATG

CTTTTACTGTTTTTTGTTTAACAAATAGCGTAGATAAAAATATATATGATGAGTTATGCTGTTTAGGAGCCAAGGTT

ATATTAATACCAGATGGTACTTGGTTCAGCAAAATTTTATTTGTGAGAAGTTTTTTAAAGGAACATCCACATAATAT

CTTACATTCACATGGGATCACGGCCGATATGTTTTCTTACTTTCTGAATGGCGTGAAAATATCTACTATTCACAATA

GACTAGATGAGGATTATATCCCATTATTTGGCGCGGTTAAAGGGAATGCTATATATTATCTTCATCGTTTTATATTA

CGAAGATTTAATCATATCGTTGCTTGCTCAGCAGCGGTCCAATCAAAACTGAAACAATCGAAAGTAAAAACTAAAAT

AACCACCATCCAGAATGGGATTGATATAACTAGGTTTAAGACACTTGAGTCTGATAAAAAAAAATTATTGAGGGAAA

AACACGGATTTGATAGTGAAAAAAGAATATTTATATATTGTGGCTCGTTATCATTAAGGAAAAATATTGCTTACCTC

TTGGAACACTTAGCCATCGAAGAAAATGATATATTTTTAATTCTAGGTGATGGTGAACTTTTTAGATATTGTAAGGA

TAAATATTCTAAAGATTTACGGTATATATTTATGGGGAAAGTTGAATGCCCTCTTGAATATTATCAATTATCAGATA

TTTTTGTTTCCGCTTCTTTATCGGAAGGGCTCCCCTTGGCACTATTAGAAGCTGCCTCTACTGGGTGCTATTTATAT

GTTAGCGATATAGAGCCCCATAGAGAAATTGCATCTCTATTAGGAGAGGAAAATATTTCTATGTTTAAAATTAAGGA

TGGATCATATAATTATTTGCAACCTAAAATAAAAAAAGCTGACTATAACGCTCTTTCTGACGATAAACTTTACAATA

TATCCGATAAAAAAATGTCAAATCTTTATGACAAACTTTTTGTTTCTTTATTAGAGCAGAGGCACTAATATAATGAT

TTATGTTTCGGTAATTTCTCATGGTCATTTCAAAACTCTTAAGGAATTAGGAGCAGTATCAAAATTAAATAATCACA

GCAGAATTAAAGTTATCATCAAAGATAATTTAGGAGAGAGCGAGCTTTTGGATTTTTGTCAGGAAAACAAAATAACT

TATTTAAGGTCTAAAGAGAAAAAAGGATTTGGAGAGAATAATAATGAAGTTTTTTCCTCTATATCCTCCTTAATTAC

TAAGGAAGATTTTTTTGTGGTTATGAATCCTGATATATATATTGAGTGCTCTGATCTATTAGATGTCGTAGATGAGT

GTGGTTCAGCGAATGTTAATCTAGCAACGATAAATTTATACAGGGATTTTGATAAAAAAACATATGATAACTCAGTA

AGGAAATTTCCCTCGGCAATTGATTTTTTTATGTCATTTTTATTTAAGAAAAATGACTGTGTAGTAAATAAGAACAA

AATAACGAAACCAACATATGTTGATTGGGCTGCAGGTTCTTTTCTAATATTTAATGCCTTCTTTTATTCAAAACTCA

ACGGATTCAACGAAAAGTATTTTATGTATTGCGAAGATATTGATATATGTTGGCGAGCTAAAAAACACTTCAATACT

TCAGTTTTATACTATCCATGCTATGCAGCAATTCATTTGGCACAATTTAACAATCGTAGGATTTTTAGTAGACATTT

CATTTGGCATATAAAAAGTATTATCCTTTTTTTATTATATAAAAATGGTATGCTGCGTTCTAGTAAGTTGCTTTAAT

-continued

GCTAATATTCTTTTAAGAGGTGAGAATGATACCTGTTATTTTGGCTGGTGGTTCGGGAAGTCGCTTGTGGCCACTTT

CACGAGAAAAGTTCCCCAAGCAGTTTTTAAAGTTGACTGGCAGTTTGACAATGTTGCAGTCAACATTGTCACGTCTT

AATAATTTAAATGCTGATGATTCAATAGTTATATGCAACGAAGAGCATAGATTTATTGTTGCAGAACAATTAAGAGA

GTTAGGCAAACTTTCAAATAACATTATTCTTGAACCCAAAGGTCGTAATACAGCCCCTGCTATAACACTCGCAGCAT

TAGCAGCAAAAAGAAAATTCGCTGATGAAGATCCATTGATTCTTATTTTAGCTGCAGATCACAACATCCAAGACGAA

CATGTTTTCTGTGAGGCAATTAATAAGGCGTCATCTTTAGCTAGTTATGGAAAACTAGTGACTTTTGGTATCGTTCC

ATTCAAACCTGAAACTGGGTATGGCTATATTCGTCGCGGTGATGAAGTGCCTGTAGATGAGCAGCATGCGGTGGCCT

TTGAAGTGGCGCAGTTTGTCGAAAAACCGAATCTGGAAACCGCGCAGGCCTATGTGGCAAGCGGCGAATATTACTGG

AACAGCGGTATGTTCCTGTTCCGTGCCGGACGCTATCTCGAAGAACTGAAAAAGTATCGTCCGGATATTCTCGATGC

CTGTGAAAAAGCGATGAGCGCCGTCGATCCGGATCTCGATTTTATTCGTGTGGATGAAGAGGCGTTTCTCGCTTGTC

CGGAAGAGTCGGTGGATTACGCGGTCATGGAATGCACGGCAGATGCCGTTGTGGTGCCGATGGATGCGGGCTGGAGC

GATGTCGGTTCCTGGTCTTCATTATGGGAGATCAGCGCCCACACCGCCGAGGGCAACGTTTGCCACGGCGATGTGAT

TAATCACAAAACTGAAAACAGCTATGTGTACGCCGAATCTGGCCTGGTCACCACCGTCGGGGTGAAAGATTTGGTGG

TAGTGCAGACCAAAGATGCAGTGCTGATTGCCGACCGTAATGCGGTGCAGGATGTGAAGAAAGTGGTCGAGCAGATC

AAAGCTGATGGTCGCCATGAGCATCGGGTGCATCGCGAAGTGTATCGTCCGTGGGGCAAATATGACTCTATCGACGC

GGGCGACCGCTACCAGGTGAAACGCATCACCGTGAAACCGGGCGAAGGTTTGTCGGTACAGATGCATTATCATCGCG

CGGAACACTGGGTGGTTGTCGCGGGAACGGCAAAAGTCACTATCAACGGTGATATCAAACTGCTTGGTGAAAACGAG

TCCATTTATATTCCGCTGGGGGCGATGCACTGCCTGGAAAACCCGGGGAAAATAGATTTAGAATTAATTGAAGTTCG

CTCTGGTGCATATCTTGAAGAAGATGATGTTATTAGATGTTATGATCGCTATGGACGAAAGTAATATATAATAATTA

TTTCAGAATTAGAAATGATAATTATAAGTTTTCGTCTGGATAAACAATAGATAGTATGGGTTGGAAAATATGAGTTC

TTTAACTTGTTTTAAAGCTTACGACATTCGCGGGAAATTAGGTGAAGAACTGAATGAAGATATCGCCTGGCGCATTG

GTCGCGCCTATGGCGAATTTCTCAAACCGAAAACCATTGTGTTAGGCGGTGATGTCCGTCTCACCAGCGAAACCTTA

AAACTGGCGCTGGCAAAAGGTTTACAGGATGCGGGCGTCGATGTGCTGGATATTGGCATGTCCGGCACCGAAGAGAT

TTATTTCGCCACGTTCCATCTCGGCGTGGATGGCGGCATTGAAGTTACCGCCAGCCATAATCCGATGGATTACAACG

GCATGAAGCTGGTGCGCGAAGGGGCTCGCCCGATCAGCGGTGATACCGGACTGCGCGACGTCCAGCGTCTGGCAGAA

GCTAACGACTTTCCTCCCGTCGATGAAACCAAACGCGGTCGCTATCAGCAAATCAATCTGCGTGACGCTTACGTTGA

TCACCTGTTCGGTTATATCAATGTCAAAAACCTTACGCCGCTCAAGCTGGTGATCAACTCCGGGAATGGCGCAGCGG

GTCCGGTGGTGGACGCTATCGAAGCCCGCTTTAAAGCCCTCGGCGCACCGGTGGAGTTAATCAAAGTGCATAACACG

CCGGACGGCAATTTCCCCAACGGTATTCCTAACCCGTTGCTGCCGGAATGTCGCGACGACACCCGCAATGCGGTCAT

CAAACACGGCGCGGATATGGGCATTGCCTTTGATGGCGATTTTGACCGCTGTTTCCTGTTTGACGAAAAAGGGCAGT

TTATTGAGGGCTACTACATTGTCGGCCTGCTGGCAGAAGCGTTCCTCGAAAAAAATCCCGGCGCGAAGATCATCCAC

GATCCACGTCTCTCCTGGAACACCATTGATGTGGTGACGGCCGCGGGCGGCACGCCGGTGATGTCGAAAACAGGACA

CGCCTTTATTAAAGAACGTATGCGCAAGGAAGACGCCATCTACGGTGGCGAAATGAGCGCTCACCATTACTTCCGCG

ATTTCGCTTACTGTGACAGCGGCATGATCCCGTGGCTGCTGGTCGCCGAACTGGTGTGCCTGAAAGGAAAAACGCTG

GGCGAACTGGTGCGCGACCGGATGGCGGCGTTTCCGGCAAGCGGTGAGATCAACAGAAAACTGGCGCACCCTGTTGA

GGCGATTAACCGCGTGGAACAGCATTTTAGCCGTGAGGTGCTGGCGGTGGATCGCACCGATGGCATCAGCATGACCT

TTGCCGACTGGCGCTTTAACCTGCGCTCTTCCAACACCGAACCGGTGGTGCGCCTGAATGTGGAATCTCGCGGTGAT

GTTCAGGTTATGGTAATCCATACTCAAGAAATATTATCAATTTTGACGTCATAAAGAATAAGCCCTGACAAGTTAGG

GCTTAATTAATATATATATTTTTTTGAATTGGGGATTTGTGGTAAGATTTTTAATATGTTATTTAATGTGGTTGAATT

AATGTTGACTGGAAAATAATAATGAGAACGAAAAAAGCATTACACAACTTTAAAGTTGATTTATTAATTACTTTTTT

-continued

ATTGGTTTTGCTAGGGTTTTATATTCGAACTGTTTTTGTTTCAAAAATGGGAAGTGATATTACTGGAGTGATGTTAC

TATTCACACAGTTGACAGCATATCTCAATTTGGCAGAATTAGGTATTGGAATTGCAGCTGCCAGCGTATTATATAAA

CCGCTCAGCGAGAATGAATACAATAAAATAACTTACATAATATCTTTGCTCTCAGTCATATACAAATATATATTTGT

GTTTGTTTTGATTCTTGGCGTTGTTATAGGTATCTGTATTTATTACTTTATTGATTCTGTAAAGGTTGTAAATGGCG

TTTTTTTATATTGGGCTTTGTTCGTTTTTAATACATCGTTGACATATAGTTATGCTAAATACTCCACATTATTAACT

GCTAATCAGCGGTACTCAGCAGTAAGAAAAATTCAAGGTGGCGGAAAAGTTATAATAATTGTATTTCAGATATTAAT

TTTGTGCTTTACGCAAAGTTTCATACTTTATTTGTTAGTTGAGACTTTAGGTATTTTTTCTCAATATTTGATTTTTA

AAAAAATAATTGGGAACGGAAATCAATATCTCAGTAATGAGGTTTTACTTATTGAAAGCGATAAACTTTTGATAAAA

AAAGAATTAAAAATAAGAATAAAAAATATGTTCTTCCATAAAATAGGTGCTGTGCTTGTCCTTAATACAGACTACCT

GCTTGTATCAAAGTTTCTGACATTAAGTTATGTGACAATTTTTGGCAGCTATATGATGGTATTTCAGATAGTAACTG

TTTTGATGTCAAGTTTTGTTAATGCTATTACTGCAGGAATGGGTAATTACTTAATTAATAAAAGTAATTTAGAAATT

AAGGAAATTACACGTCAATTTTATGTGATATTTATCGCCTTTGCAACATTCATATCACTAAATATGTTTTTTCTTGT

TAATGATTTTATCGCAAAATGGATAGGTGTTAATTATACATTAAGTAACACCCTAGTTGCATTAATGATTGTTAACG

TATTCATTAGTGTTGTCAGGGTACCTTCTGATATATTAAAAAACGCAAGTGGACATTTTGGTGATATTTATTATCCA

TTATTAGAAGGTGTGCTGAATATTACGATATCCATCATTTTGGCTATCATTATTGGATTACCTGGCATTATTATAGG

GACAATAGTATCTAACTTAATAGTAATAATGCTTGCGAAACCATTATATCTTTACTCTAAGTTATTTAATCTTAGAA

ATCCGACGAGGGTTTATTTTGAATTTATTTCTCGGCCTATGTTATATTCATTATGTGTGATTGGGGTGAGCTATTTA

TTGCGCGATGAAATATATTCATTTAAAGTAAGTACATGGTTGGATTTTATTAACAAGCTACTCTTAGTCTCTACTCC

TAGCATATTGGTAATATGTGCTATTTTCTCTACGGATAGTGACTTTAGATTATTTTTCAGAAAAATTATATATGTGA

TTATGAAGAAATAAAAATTTCGAAAATGTATTAATCGAAATTATGCAACGAGCTTTATTTTTATAAATGATATGTGA

TCTTTTCGCGAATAGGAGTAAGGATCCGTGTAGGCTGGAGCTGCTTCGAAGTTCCTATACTTTCTAGAGAATAGGAA

CTTCGGAATAGGAACTAAGGAGGATATTCATATGGATAAAGCCGTAAGCATATAAGCATGGATAAGCTATTTATACT

TTAATAAGTACTTTGTATACTTATTTGCGAACATTCCAGGCCGCGAGCATTCAGCGCGGTGATCACACCTGACAGGA

GTATGTAATGTCCAAGCAACAGATCGGCGTAGTCGGTATGGCAGTGATGGGACGCAACCTTGCGCTCAACATCGAAA

GCCGTGGTTATACCGTCTCTATTTTCAACCGTTCCCGTGAGAAGACGGAAGAAGTGATTGCCGAAAATCCAGGCAAG

AAACTGGTTCCTTACTATACGGTGAAAGAGTTTGTCGAATCTCTGGAAACGCCTCGTCGCATCCTGTTAATGGTGAA

AGCAGGTGCAGGCACGGATGCTGCTATTGATTCCCTCAAACCATATCTCGATAAAGGAGACATCATCATTGATGGTG

GTAACACCTTCTTCCAGGACACTATTCGTCGTAATCGTGAGCTTTCAGCAGAGGGCTTTAACTTCATCGGTACCGGT

GTTTCTGGCGGTGAAGAGGGGGCGCTGAAAGGTCCTTCTATTATGCCTGGTGGCCAGAAAGAAGCCTATGAATTGGT

AGCACCGATCCTGACCAAAATCGCCGCCGTAGCTGAAGACGGTGAACCATGCGTTACCTATATTGGTGCCGATGGCG

CAGGTCACTATGTGAAGATGGTTCACAACGGTATTGAATACGGCGATATGCAGCTGATTGCTGAAGCCTATTCTCTG

CTTAAAGGTGGCCTGAACCTCACCAACGAAGAACTGGCGCAGACCTTTACCGAGTGGAATAACGGTGAACTGAGCAG

TTACCTGATCGACATCACCAAAGATATCTTCACCAAAAAAGATGAAGACGGTAACTACCTGGTTGATGTGATCCTGG

ATGAAGCGGCTAACAAAGGTACCGGTAAATGGACCAGCCAGAGCGCGCTGGATCTCGGCGAACCGCTGTCGCTGATT

ACCGAGTCTGTGTTTGCACGTTATATCTCTTCTCTGAAAGATCAGCGTGTTGCCGCATCTAAAGTTCTCTCTGGTCC

GCAAGCACAGCCAGCAGGCGACAAGGCTGAGTTCATCGAAAAAGTTCGTCGTGCGCTGTATCTGGGCAAAATCGTTT

CTTACGCCCAGGGCTTCTCTCAGCTGCGTGCTGCGTCTGAAGAGTACAACTGGGATCTGAACTACGGCGAAATCGCG

AAGATTTTCCGTGCTGGCTGCATCATCCGTGCGCAGTTCCTGCAGAAAATCACCGATGCTTATGCCGAAAATCCACA

GATCGCTAACCTGTTGCTGGCTCCGTACTTCAAGCAAATTGCCGATGACTACCAGCAGGCGCTGCGTGATGTCGTTG

CTTATGCAGTACAGAACGGTATTCCGGTTCCGACCTTCTCCGCAGCGGTTGCCTATTACGACAGCTACCGTGCTGCT

GTTCTGCCTGCGAACCTGATCCAGGCACAGCGTGACTATTTTGGTGCGCATACTTATAAGCGTATTGATAAAGAAGG

-continued

TGTGTTCCATACCGAATGGCTGGATTAA (Example CRM197 sequence)

SEQ ID NO: 20

GADDVVDSSKSFVMENFSSYHGTKPGYVDSIQKGIQKPKSGTQGNYDDDWKEFYSTDNKYDAAGYSVDNENPLSGKA

GGVVKVTYPGLTKVLALKVDNAETIKKELGLSLTEPLMEQVGTEEFIKRFGDGASRVVLSLPFAEGSSSVEYINNWE

QAKALSVELEINFETRGKRGQDAMYEYMAQACAGNRVRRSVGSSLSCINLDWDVIRDKTKTKIESLKEHGPIKNKMS

ESPNKTVSEEKAKQYLEEFHQTALEHPELSELKTVTGTNPVFAGANYAAWAVNVAQVIDSETADNLEKTTAALSILP

GIGSVMGIADGAVHHNTEEIVAQSIALSSLMVAQAIPLVGELVDIGFAAYNFVESIINLFQVVHNSYNRPAYSPGHK

TQPFLHDGYAVSWNTVEDSIIRTGFQGESGHDIKITAENTPLPIAGVLLPTIPGKLDVNKSKTHISVNGRKIRMRCR

AIDGDVTFCRPKSPVYVGNGVHANLHVAFHRSSSEKIHSNEISSDSIGVLGYQKTVDHTKVNSKLSLFFEIKS

The embodiments described herein are intended to be merely exemplary, and those skilled in the art will recognize, or be able to ascertain using no more than routine experimentation, numerous equivalents to the specific procedures described herein. All such equivalents are considered to be within the scope of the present invention and are covered by the following claims.

All references (including patent applications, patents, and publications) cited herein are incorporated herein by reference in their entirety and for all purposes to the same extent as if each individual publication or patent or patent application was specifically and individually indicated to be incorporated by reference in its entirety for all purposes.

The invention claimed is:

1. A composition comprising an *E. coli* O1 antigen polysaccharide covalently linked to a carrier protein, an *E. coli* O2 antigen polysaccharide covalently linked to a carrier protein, an *E. coli* O4 antigen polysaccharide covalently linked to a carrier protein, an *E. coli* O15 antigen polysaccharide covalently linked to a carrier protein, an *E. coli* O16 antigen polysaccharide covalently linked to a carrier protein, an *E. coli* O18 antigen polysaccharide covalently linked to a carrier protein, an *E. coli* O25 antigen polysaccharide covalently linked to a carrier protein, an *E. coli* O75 antigen polysaccharide covalently linked to a carrier protein and an *E. coli* O6 antigen polysaccharide covalently linked to a carrier protein, wherein:

(i) the *E. coli* O1 antigen polysaccharide is O1A antigen polysaccharide comprising the structure of Formula (O1A):

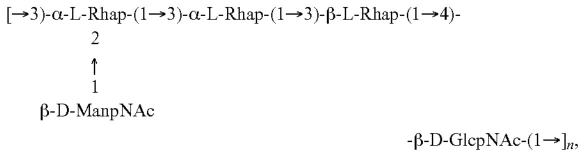

(ii) the *E. coli* O2 antigen polysaccharide comprises the structure of Formula (O2):

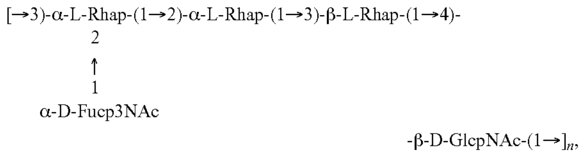

(iii) the *E. coli* O4 antigen polysaccharide is O4-Glc+ antigen polysaccharide comprising the structure of Formula (O4-Glc+):

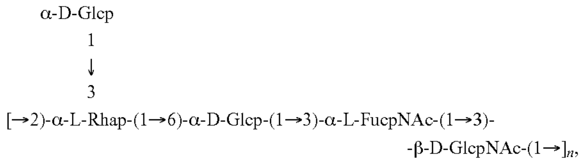

(iv) the *E. coli* O6 antigen polysaccharide is O6A antigen polysaccharide comprising the structure of Formula (O6A):

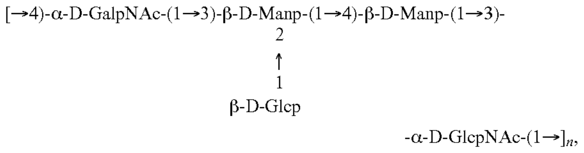

(v) the *E. coli* O15 antigen polysaccharide comprises the structure of Formula (O15):

[→2)-β-D-Galp-(1→3)-α-L-FucpNAc-(1→3)-β-D-GlcpNAc-(1→]$_n$, (vi) the *E. coli* O16 antigen polysaccharide comprises the structure of Formula (O16):

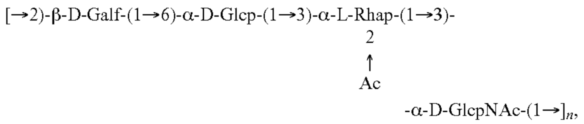

(vii) the *E. coli* O18 antigen polysaccharide is O18A antigen polysaccharide comprising the structure of Formula (O18A):

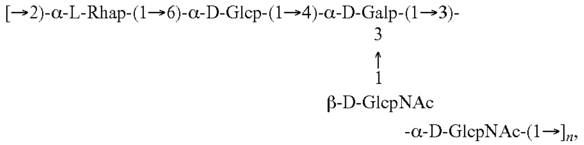

(viii) the *E. coli* O25 antigen polysaccharide is O25B antigen polysaccharide comprising the structure of Formula (O25B):

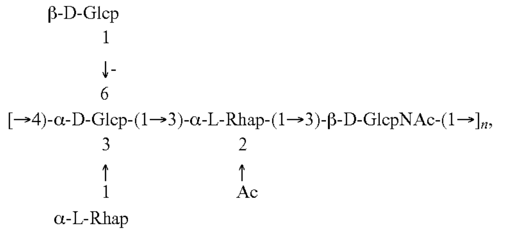

and (ix) the *E. coli* O75 antigen polysaccharide comprises the structure of Formula (O75):

β-D-Manp
1
↓
4
[→3)-α-Galp-(1→4)-α-L-Rhap-(1→3)-β-D-GlcpNAc-(1→]*n*, wherein the weight ratio of the *E. coli* antigen polysaccharides O1:O2:O4:O6:O15:O16:O18:O25:O75 is about 1:1:1:1:1:1:1:2:2 and wherein each n is independently an integer of 1 to 100.

2. The composition of claim 1, wherein the weight ratio of the *E. coli* antigen polysaccharides O1:O2:O4:O6:O15:O16:O18:O25:O75 is 1:1:1:1:1:1:1:2:2.

3. The composition of claim 1, wherein the concentration of the *E. coli* O75 antigen polysaccharide is from about 8 to about 64 μg/mL.

4. The composition of claim 1, wherein the *E. coli* O antigen polysaccharides present in the composition consist of the *E. coli* O1, O2, O4, O6, O15, O16, O18, O25, and O75 antigen polysaccharides, wherein each of the polysaccharides is covalently linked to its carrier protein.

5. The composition of claim 1, further comprising at least one additional *E. coli* O antigen polysaccharide covalently linked to a carrier protein.

6. The composition of claim 1, wherein each of the carrier proteins is a detoxified exotoxin A of *Pseudomonas aeruginosa* (EPA) or $CRM_{197}$.

7. The composition of claim 1, wherein each of the *E. coli* antigen polysaccharides O1, O2, O4, O6, O15, O16, O18, O25, and O75 is covalently linked to its carrier protein by bioconjugation or by chemical conjugation.

8. A method of inducing an immune response to *E. coli* in a mammalian subject, the method comprising administering to the subject an effective amount of the composition of claim 1.

9. The method of claim 8, wherein the *E. coli* O antigen polysaccharides administered to the subject consist of the *E. coli* O1, O2, O4, O6, O15, O16, O18, O25, and O75 antigen polysaccharides, wherein each of the polysaccharides is covalently linked to its carrier protein.

10. The method of claim 8, wherein the subject is a human having or at risk of having an *E. coli* infection.

11. The method of claim 8, wherein 16 μg of the *E. coli* O75 antigen polysaccharide is administered per administration.

12. The composition of claim 1, wherein each n is independently an integer of 5 to 30.

13. The composition of claim 3, wherein the concentration of the *E. coli* O75 antigen polysaccharide is from about 28 to about 36 μg/mL.

14. The composition of claim 2, wherein the concentration of the *E. coli* O75 antigen polysaccharide is about 32 μg/mL.

15. The composition of claim 6, wherein each of the carrier proteins is EPA comprising 1 to 20 glycosylation sequences having the amino acid sequence of SEQ ID NO: 1.

16. The composition of claim 1, wherein each of the carrier proteins comprises the amino acid sequence of SEQ ID NO: 3.

17. The composition of claim 2, wherein each of the carrier proteins comprises the amino acid sequence of SEQ ID NO: 3.

18. The composition of claim 7, wherein each of the *E. coli* O antigen polysaccharides is covalently linked by bioconjugation to an Asn residue in a glycosylation site in its carrier protein.

19. The composition of claim 2, wherein each of the *E. coli* O antigen polysaccharides is covalently linked to its carrier protein by bioconjugation.

20. A method of inducing an immune response to *E. coli* in a mammalian subject, the method comprising administering to the subject an effective amount of the composition of claim 2.

21. The method of claim 20, wherein the *E. coli* is extra-intestinal pathogenic *E. coli* (ExPEC).

22. The composition of claim 2, wherein each n is independently an integer of 5 to 30, wherein each of the carrier proteins comprises the amino acid sequence of SEQ ID NO: 3, and wherein the concentration of the *E. coli* O75 antigen polysaccharide is about 32 μg/mL.

23. The method of claim 9, wherein the composition administered to the subject further comprises from 1 to 15 additional *E. coli* O antigen polysaccharides, each independently covalently linked to a carrier protein.

24. The composition of claim 18, wherein the polysaccharide to the carrier protein ratio by weight/weight (w/w) of each of the *E. coli* O antigen polysaccharides covalently linked to its carrier protein is about 0.1 to 0.5.

25. The composition of claim 22, wherein the polysaccharide to the carrier protein ratio by weight/weight (w/w) of each of the *E. coli* O antigen polysaccharides covalently linked to its carrier protein is about 0.1 to 0.5.

* * * * *